United States Patent
Ikuma et al.

(10) Patent No.: US 9,758,480 B2
(45) Date of Patent: Sep. 12, 2017

(54) 1-(CYCLOALKYL-CARBONYL)PROLINE DERIVATIVE

(71) Applicant: SUMITOMO DAINIPPON PHARMA CO., LTD., Osaka-shi, Osaka (JP)

(72) Inventors: Yohei Ikuma, Osaka (JP); Nobuhisa Fukuda, Osaka (JP); Masato Iwata, Osaka (JP); Hidenori Kimura, Osaka (JP); Kuniko Suzuki, Osaka (JP)

(73) Assignee: SUMITOMO DAINIPPON PHARMA CO., LTD., Osaka-shi (JP)

( * ) Notice: Subject to any disclaimer, the term of this patent is extended or adjusted under 35 U.S.C. 154(b) by 0 days.

(21) Appl. No.: 14/414,838

(22) PCT Filed: Jul. 18, 2013

(86) PCT No.: PCT/JP2013/069499
§ 371 (c)(1),
(2) Date: Jan. 14, 2015

(87) PCT Pub. No.: WO2014/014050
PCT Pub. Date: Jan. 23, 2014

(65) Prior Publication Data
US 2015/0210640 A1    Jul. 30, 2015

(30) Foreign Application Priority Data
Jul. 19, 2012 (JP) ................. 2012-160745

(51) Int. Cl.
| C07D 207/16 | (2006.01) |
| C07D 401/12 | (2006.01) |
| C07D 403/12 | (2006.01) |
| C07D 405/12 | (2006.01) |
| C07D 405/14 | (2006.01) |
| C07D 409/12 | (2006.01) |
| C07D 413/12 | (2006.01) |
| C07D 417/12 | (2006.01) |
| C07D 417/14 | (2006.01) |
| C07D 471/04 | (2006.01) |

(Continued)

(52) U.S. Cl.
CPC ......... *C07D 207/16* (2013.01); *C07D 401/12* (2013.01); *C07D 403/12* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 417/14* (2013.01); *C07D 471/04* (2013.01); *C07D 491/048* (2013.01)

(58) Field of Classification Search
CPC .. C07D 207/16; C07D 401/12; C07D 403/12; C07D 405/12; C07D 405/14; C07D 409/12; C07D 413/12; C07D 413/14; C07D 417/12; C07D 417/14; C07D 471/04; C07D 491/048
See application file for complete search history.

(56) References Cited

U.S. PATENT DOCUMENTS

| 5,484,772 A | 1/1996 | Sall et al. |
| 5,488,037 A | 1/1996 | Sall et al. |

(Continued)

FOREIGN PATENT DOCUMENTS

| EP | 0671390 A2 | 9/1995 |
| EP | 0673936 A1 | 9/1995 |

(Continued)

OTHER PUBLICATIONS

X. Wang, et al., "Effects of factor XI deficiency on ferric chloride-induced vena cava thrombosis in mice", Journal of Thrombosis and Haemostasis, vol. 4, 2006, pp. 1982-1988.
William A. Schumacher, et al., "Inhibition of Factor XIa as a New Approach to Anticoagulation", Arterioscler Thromb Vasc Biol., 2010, vol. 30, pp. 388-392.
Jonas Emsley, et al., "Structure and function of factor XI", Blood, vol. 115, No. 13, 2010, pp. 2569-2577.
International Search Report issued Oct. 15, 2013 in International Application No. PCT/JP2013/069499.
Written Opinion of the International Searching Authority issued Oct. 15, 2013 in International Application No. PCT/JP2013/069499.
International Preliminary Report on Patentability issued Jan. 20, 2015 in International Application No. PCT/JP2013/069499.

(Continued)

*Primary Examiner* — Rebecca Anderson
(74) *Attorney, Agent, or Firm* — Sughrue Mion, PLLC

(57) ABSTRACT

A compound represented by formula (1) (in the formula: ring-D represents a three- to eight-membered hydrocarbon ring; $R^a$ represents an optionally substituted amino $C_{1-6}$ alkyl group or the like; $R^{b1}$ and $R^{b2}$ each independently represent a hydrogen atom, a halogen atom, or the like; $R^c$ represents an optionally substituted $C_{6-10}$ aryl group or the like; $R^d$ represents a hydrogen atom or the like; and ring-Q represents a (hetero)aryl group or the like which may be substituted with a carboxyl group or the like) or a pharmaceutically acceptable salt thereof exhibits an excellent FXIa inhibitory activity, and is useful as a therapeutic agent against thrombosis or the like.

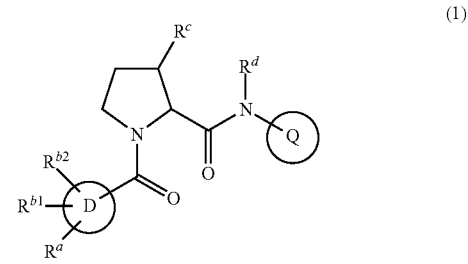

(1)

39 Claims, 1 Drawing Sheet

(51) Int. Cl.
*C07D 491/048* (2006.01)
*C07D 413/14* (2006.01)

(56) References Cited

U.S. PATENT DOCUMENTS

| | | |
|---|---|---|
| 2003/0139597 A1 | 7/2003 | Xue et al. |
| 2006/0183739 A1 | 8/2006 | Tsaklakidis et al. |
| 2008/0003214 A1 | 1/2008 | Cezanne et al. |
| 2010/0173899 A1 | 7/2010 | Pinto et al. |
| 2010/0256131 A1 | 10/2010 | Tsaklakidis et al. |

FOREIGN PATENT DOCUMENTS

| | | |
|---|---|---|
| EP | 1087937 A1 | 12/1999 |
| EP | 1720844 | 10/2004 |
| EP | 1791597 | 3/2006 |
| JP | S63233963 A | 9/1988 |
| JP | S63238051 A | 10/1988 |
| JP | S63239256 A | 10/1988 |
| JP | 7-278091 A | 10/1995 |
| JP | H08-41095 A | 2/1996 |
| JP | 2002-518368 A | 6/2002 |
| JP | 2006-522033 A | 9/2006 |
| JP | 2008-513387 A | 5/2008 |
| WO | 2004/087646 A2 | 10/2004 |
| WO | 2008/157162 A1 | 12/2008 |
| WO | 2013/056034 A1 | 4/2013 |
| WO | 2013/056060 A1 | 4/2013 |
| WO | 2013/093484 A1 | 6/2013 |
| WO | 2013/118805 A1 | 8/2013 |
| WO | 2013/174937 A1 | 11/2013 |

OTHER PUBLICATIONS

Communication dated Dec. 16, 2015, issued by the European Patent Office in corresponding European Application No. 13819255.4.
Okada et al., "Development of Plasma Kallikrein Selective Inhibitors", Biopolymers, 1999, vol. 51, pp. 41-50.
Tsuda et al., "Design of Plasma Kallikrein Inhibitors: Functional and Structural Requirements of Plasma Kallikrein Inhibitors", Chem. Pharm. Bull., 1998, vol. 46, No. 3, pp. 452-457.
Second Office Action dated Sep. 7, 2016 in corresponding Chinese Patent Application No. 201380048531.1 with translation.
First Office Action dated Nov. 25, 2015 in corresponding Chinese Patent Application No. 201380048531.1 with translation.
Cover letter and Office Action dated Dec. 12, 2016 in corresponding Taiwanese Patent Application No. 102125743.
Examination Report No. 1 dated Dec. 21, 2016 in corresponding Australian Patent Application No. 2013291098.
English translation of Office Action dated Jun. 2, 2017 in counterpart Japanese Patent Application No. 2014-525859.

DATA ARE SHOWN AS MEAN VALUE ± STANDARD DEVIATION.

1-(CYCLOALKYL-CARBONYL)PROLINE DERIVATIVE

CROSS REFERENCE TO RELATED APPLICATIONS

This application is a National Stage of International Application No. PCT/JP2013/069499, filed Jul. 18, 2013, claiming priority based on Japanese Patent Application No. 2012-160745, filed Jul. 19,2012.

TECHNICAL FIELD

The present invention relates to a 1-(cycloalkylcarbonyl) proline derivative having anticoagulant activity or a salt thereof. Specifically, the present invention relates to a 1-(cycloalkylcarbonyl)proline derivative that is useful as an activated factor XI (FXIa) inhibitor. Moreover, the present invention relates to medicinal use of the 1-cycloalkylcarbonyl)proline derivative that is useful as an FXIa inhibitor.

BACKGROUND ART

Atherothrombosis, which is caused by arteriosclerosis and induces myocardial infarction, cerebral infarction and the like, and deep vein thrombosis, which induces pulmonary embolism, accounts for a majority of causes of death for human beings. Warfarin, which is currently most frequently used as an anticoagulant agent having the efficacy and effect of the "treatment and prevention of thromboembolism such as vein thrombosis, myocardial infarction, pulmonary embolism, cerebral embolism, slowly progressive cerebral thrombosis, and the like", exhibits excellent antithrombotic activity. On the other hand, warfarin has problems of causing difficult hemostasis during bleeding and thus severe side effects of hemorrhagic complication. Under such circumstances, it has been strongly desired to develop a therapeutic agent and a preventive agent for thrombosis or thromboembolism, which have a novel action mechanism that suppresses the pathological growth of thrombus while having no influence on hemostasis of blood vessels.

It has been known that many blood-coagulating factors (cascade) are involved in hemostasis and thrombus formation. Hence, if the action mechanism of each blood-coagulating factor was elucidated and a specific blood-coagulating factor of interest could be controlled, it would provide a powerful approach for solving the aforementioned problems. In recent years, it has been found that the factor XI (FXI), one of endogenous blood-coagulating factors, is closely involved in the pathological growth of thrombus (see, for example, Non Patent Literatures 1 and 2). That is to say, it has been revealed that accelerating the step of the blood coagulation cascade, in which activated factor XI (FXIa) is generated from FXI, plays an important role in the pathological growth process of thrombus. Moreover, it has also been revealed that FXI is not involved in the hemostatic process during bleeding. In fact, in a study using FXI knock-out mice, an inhibitory activity against the generation of thrombus has been confirmed to be in a venous thrombus model, but it has been proved that hemostatic time is not affected in the same model (see, for example, Non Patent Literature 3). Therefore, inhibition of FXIa activity will be an extremely appealing approach for solving the aforementioned problem.

Protease inhibitors comprising, as active ingredients, phenylalanine derivatives represented by Formula 1 and Formula 2 are disclosed in Patent Literatures 1 and 2, respectively.

[Formula 1]

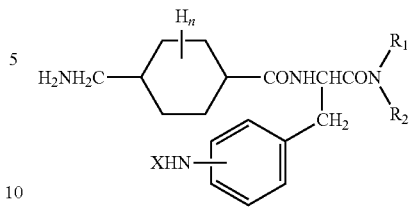

wherein X represents —COY wherein Y represents a lower alkyl group optionally substituted with a specific substituent or the like; $R^1$ and $R^2$ each represent a hydrogen atom, with the proviso that $R^1$ and $R^2$ do not simultaneously represent hydrogen atoms, an alkyl group optionally substituted with a specific substituent, a cycloalkyl group, a phenyl group optionally substituted with a specific substituent, or a pyridyl group optionally substituted with a specific substituent, or $R^1$ and $R^2$ represent, together with a nitrogen atom to which they bind, a cyclic piperidyl group optionally substituted with a specific group; and n represents 4 or 10.

[Formula 2]

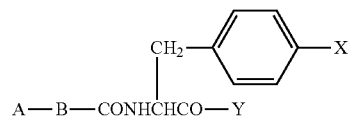

wherein A represents $H_2N$— or the like; B represents —$CH_2$-cyclohexane ring- or the like; X represents a hydrogen atom or the like; and Y represents —$NR^1R^2$, wherein $R^1$ and $R^2$ each independently represent a hydrogen atom, with the proviso that $R^1$ and $R^2$ do not simultaneously represent hydrogen atoms, a phenyl group optionally substituted with a specific substituent, a pyridyl group optionally substituted with a specific substituent, a $C_1$ to $C_4$ alkyl group optionally substituted with a specific substituent, or a $C_5$ to $C_7$ cycloalkyl group, or $R^1$ and $R^2$ represent, together with a nitrogen atom to which they bind, a piperidino group optionally substituted with a specific group, or a pyrrolidyl group optionally substituted with a specific group.

These patent literatures describe that an antiplasmin agent, which is one of protease inhibitors, is useful as a hemostatic agent, and that an anti-urokinase agent is useful for suppressing bleeding symptoms during application of thrombolytic therapy (see the "Prior Art" and "Technical Problem" sections in both publications).

Furthermore, a protease inhibitor comprising, as an active ingredient, a phenylalanine derivative represented by the following [Formula 3] is disclosed in Patent Literature 3.

[Formula 3]

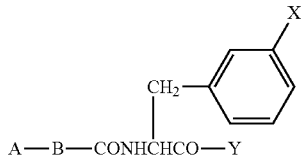

wherein A represents $H_2N$— or the like; B represents —$CH_2$-cyclohexane ring- or the like; X represents a hydroxyl group or the like; and Y represents —$NR^1R^2$, wherein $R^1$ and $R^2$ each independently represent a hydrogen atom, a phenyl group optionally substituted with a specific group, a pyridyl group optionally substituted with a specific group, an imidazolyl group, a pyrimidyl group, a tetrazolyl group, a thiazolyl group optionally substituted with a specific group, a $C_1$ to $C_6$ alkyl group optionally substituted with a specific substituent, or a $C_5$ to $C_7$ cycloalkyl group optionally substituted with a specific group, or $R^1$ and $R^2$ represent, together with a nitrogen atom to which they bind, a piperazyl group optionally substituted with a specific group, a piperidino group optionally substituted with a specific group, a pyrrolidyl group optionally substituted with a specific group, or a morpholino group, or represent —$OR^3$ wherein $R^3$ represents a hydrogen atom or the like, or a pyridyl group.

This patent literature describes that a kallikrein inhibitor, which is one of protease inhibitors, is useful as a blood pressure regulator or the like (see the "Prior Art" and "Technical Problem" sections).

Patent Literature 1: JP 63-233963 A
Patent Literature 2: JP 63-238051 A
Patent Literature 3: JP 63-239256 A
Non Patent Literature 1: Blood 2010, 115, 2569.
Non Patent Literature 2: Arterioscler Thromb Vasc Biol 2010, 30, 388.
Non Patent Literature 3: J. Thromb. Haemost. 2006, 4, 1982.

SUMMARY OF INVENTION

Technical Problem

It is an object of the present invention to provide a novel compound which has excellent FXIa inhibitory activity and anticoagulant action and is useful as a therapeutic agent for thrombosis, thromboembolism and the like. It is another object of the present invention to provide use as a medicament of the novel compound.

Solution to Problem

As a result of intensive studies directed towards achieving the aforementioned objects, the present inventors have found that a compound represented by Formula (1) below and a pharmaceutically acceptable salt thereof, which are hereinafter abbreviated as "the compound of the present invention" if necessary, are novel compounds having different chemical structures from those of the phenylalanine derivatives represented by the above formulae, described in Patent Literatures 1 to 3, in that the phenylalanine derivatives disclosed in Patent Literatures 1 to 3 do not have a pyrrolidine ring in the central portion thereof. It has been found that these novel compounds have FXIa inhibitory activity and anticoagulant action and are therefore useful as an FXIa inhibitor or an anticoagulant agent. Based on these findings, the present invention has been completed.

Specifically, the present invention provides as follows.

[1] A compound represented by formula (1) or a pharmaceutically acceptable salt thereof:

[Formula 4]

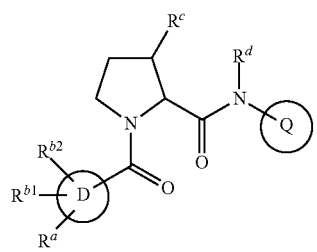

(1)

wherein
ring D represents a 3- to 8-membered hydrocarbon ring;

$R^a$ represents an optionally substituted amino group, an optionally substituted amidino group, an optionally substituted guanidino group, an optionally substituted aminocarbonyl group, an optionally substituted aminosulfonyl group, an optionally substituted $C_{1-6}$ alkoxycarbonylamino group, an optionally substituted amino $C_{1-6}$ alkyl group, an optionally substituted amidino $C_{1-6}$ alkyl group, an optionally substituted imino $C_{1-6}$ alkyl group, an optionally substituted amino $C_{3-10}$ cycloalkyl group, an optionally substituted amidino $C_{3-10}$ cycloalkyl group, an optionally substituted imino $C_{3-10}$ cycloalkyl group, an optionally substituted $C_{1-6}$ alkoxy $C_{1-6}$ alkyl group, an optionally substituted $C_{1-6}$ alkylthio $C_{1-6}$ alkyl group, an optionally substituted mercapto $C_{1-6}$ alkyl group, an optionally substituted hydroxy $C_{1-6}$ alkyl group, an optionally substituted carboxyl $C_{1-6}$ alkyl group, an optionally substituted alkoxycarbonylamino $C_{1-6}$ alkyl group, or a carboxyl group;

$R^{b1}$ and $R^{b2}$ each independently represent a hydrogen atom, a halogen atom, a hydroxy group, an optionally substituted $C_{1-6}$ alkyl group, or an optionally substituted $C_{1-6}$ alkoxy group;

$R^c$ represents a halogen atom, a cyano group, a carboxyl group, a hydroxy group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{3-10}$ cycloalkyl group, an optionally substituted $C_{3-10}$ cycloalkoxy group, an optionally substituted $C_{1-6}$ alkylthio group, an optionally substituted $C_{1-6}$ alkoxycarbonyl group, an optionally substituted $C_{6-10}$ aryl group, an optionally substituted 5- to 10-membered heteroaryl group, an optionally substituted 4- to 10-membered saturated heterocyclic group, an optionally substituted $C_{6-10}$ aryloxy group, an optionally substituted 5- to 10-membered heteroaryloxy group, an optionally substituted 4- to 10-membered saturated heterocyclic oxy group, an optionally substituted amino group, an optionally substituted 4- to 10-membered cyclic amino group, an optionally substituted $C_{1-6}$ alkylcarbonylamino group, an optionally substituted $C_{3-10}$ cycloalkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted aminocarbonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered saturated heterocyclic oxycarbonylamino group, or an optionally substituted 4- to 10-membered cyclic aminocarbonyl group;

$R^d$ represents a hydrogen atom, an optionally substituted $C_{1-6}$ alkyl group, or an optionally substituted $C_{3-10}$ cycloalkyl group; and ring Q is a group represented by any one of formulae (2a) to (2d):

[Formula 5]

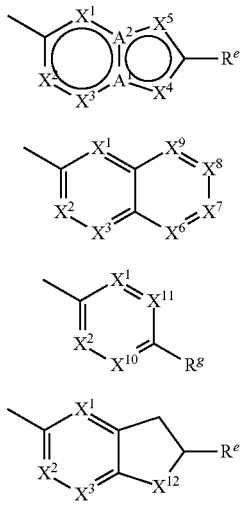

wherein
$X^1$, $X^2$, and $X^3$ each independently represent N or $CR^1$;
$X^4$ and $X^5$ each independently represent $CR^2$, O, S, N or $NR^3$;
$A^1$ and $A^2$ each independently represent N or C; wherein $X^1$, $X^2$, $X^3$, $X^4$, $X^5$, $A^1$ and $A^2$ are selected in such a manner that a ring containing these can form a bicyclic aromatic heterocyclic group;
$X^6$ and $X^9$ each independently represent N or $CR^4$;
$X^7$ and $X^8$ each independently represent N or $CR^f$;
$X^{10}$ and $X^{11}$ each independently represent N or $CR^5$;
$X^{12}$ represents O, S or $NR^3$;
$R^1$ represents a hydrogen atom, a halogen atom, a cyano group, an optionally substituted $C_{1-6}$ alkyl group, an optionally substituted $C_{1-6}$ alkoxy group, or an optionally substituted $C_{3-10}$ cycloalkyl group, wherein when two or three $R^1$ are present in the formula, these $R^1$ groups represent groups identical to or different from one another;
$R^2$ represents a hydrogen atom, a halogen atom, a cyano group, a hydroxy group, an optionally substituted $C_{2-6}$ alkenyl group, an optionally substituted $C_{2-6}$ alkynyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group, an optionally substituted $C_{1-6}$ alkoxy group, or a carboxyl group, wherein when two $R^2$ are present in the formula, these $R^2$ groups represent groups identical to or different from each other;

$R^3$ represents a hydrogen atom, an optionally substituted $C_{1-6}$ alkyl group, an optionally substituted $C_{3-10}$ cycloalkyl group, an optionally substituted $C_{2-6}$ alkenyl group, an optionally substituted $C_{2-6}$ alkynyl group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkylcarbonyl group, an optionally substituted $C_{3-10}$ cycloalkylcarbonyl group, an optionally substituted $C_{1-6}$ alkoxycarbonyl group, an optionally substituted aminocarbonyl group, an optionally substituted 4- to 10-membered cyclic aminocarbonyl group, an optionally substituted aminosulfonyl group, an optionally substituted 4- to 10-membered cyclic aminosulfonyl group, an optionally substituted $C_{3-10}$ cycloalkylsulfonyl group, or an optionally substituted $C_{1-6}$ alkylsulfonyl group;

$R^4$ represents a hydrogen atom, a halogen atom, a cyano group, a carboxyl group, a 4- to 10-membered saturated heterocyclic oxycarbonyl group, a $C_{1-6}$ alkoxycarbonyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted aminocarbonyl group, an optionally substituted 4- to 10-membered cyclic aminocarbonyl group, or an optionally substituted $C_{1-6}$ alkoxy group, wherein when two $R^4$ are present in the formula, these $R^4$ groups represent groups identical to or different from each other;

$R^5$ represents a hydrogen atom, a halogen atom, a cyano group, a hydroxy group, an optionally substituted $C_{1-6}$ alkyl group, an optionally substituted $C_{3-10}$ cycloalkyl group, an optionally substituted $C_{1-6}$ alkoxy group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group, or a carboxyl group, wherein when two $R^5$ are present in the formula, these $R^5$ groups represent groups identical to or different from each other;

$R^e$ and $R^f$ each independently represent a hydrogen atom, a halogen atom, a cyano group, a carboxyl group, a hydroxy group, an optionally substituted $C_{3-10}$ cycloalkyl group, an optionally substituted $C_{1-6}$ alkoxy group, an optionally substituted $C_{3-10}$ cycloalkoxy group, an optionally substituted $C_{6-10}$ aryloxy group, an optionally substituted 5- to 10-membered heteroaryloxy group, an optionally substituted 4- to 10-membered saturated heterocyclic oxy group, an optionally substituted $C_{1-6}$ alkylthio group, an optionally substituted $C_{3-10}$ cycloalkylthio group, an optionally substituted $C_{6-10}$ arylthio group, an optionally substituted 5- to 10-membered heteroarylthio group, an optionally substituted 4- to 10-membered saturated heterocyclic thio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted $C_{1-6}$ alkylcarbonylamino group, an optionally substituted $C_{3-10}$ cycloalkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted $C_{1-6}$ alkylsulfonyl group, an optionally substituted $C_{3-10}$ cycloalkylsulfonyl group, an optionally substituted $C_{6-10}$ arylsulfonyl group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkyl group, an optionally substituted $C_{2-6}$ alkenyl group, an optionally substituted $C_{2-6}$ alkenyloxy group, an optionally substituted $C_{2-6}$ alkynyl group, an optionally substituted $C_{1-6}$ alkylsulfonylaminocarbonyl group, an optionally substituted $C_{3-10}$ cycloalkylsulfonylaminocarbonyl group, an optionally substituted $C_{6-10}$ arylsulfonylaminocarbonyl group, an optionally substituted 4- to 10-membered saturated heterocyclic sulfonylaminocarbonyl group, an optionally substituted 5- to 10-membered heteroarylsulfonylaminocarbonyl group, an optionally substituted aminosulfonylaminocarbonyl group, an optionally substituted 4- to 7-membered cyclic aminosulfonylaminocarbonyl group, an optionally substituted $C_{4-7}$ cycloalkoxycarbonyl group, an optionally substituted 4- to 10-membered saturated heterocyclic oxycarbonyl group, or an optionally substituted $C_{1-6}$ alkoxycarbonyl group, wherein when two $R^f$ are present in the formula, these $R^f$ groups represent groups identical to or different from each other; and $R^g$ represents a hydrogen atom, a halogen atom, a cyano group, a carboxyl group, a hydroxy group, an optionally substituted $C_{3-10}$ cycloalkyl group, an optionally substituted $C_{1-6}$ alkoxy group, an optionally substituted $C_{3-10}$ cycloalkoxy group, an optionally substituted $C_{6-10}$ aryloxy group, an optionally substituted 4- to 10-membered heteroaryloxy group, an optionally substituted 4- to 10-membered saturated heterocyclic oxy group, an optionally substituted $C_{1-6}$ alkylthio group, an optionally substituted $C_{3-10}$ cycloalkylthio group, an optionally substituted 5- to 10-membered heteroarylthio group, an optionally substituted 4- to 10-membered saturated heterocyclic thio group, an optionally substituted $C_{6-10}$ arylthio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted $C_{1-6}$ alkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted $C_{1-6}$ alkylsulfonyl group, an optionally substituted $C_{3-10}$ cycloalkylsulfonyl group, an optionally substituted $C_{6-10}$ arylsulfonyl group, an optionally substituted 4- to 10-membered saturated heterocyclic group, an optionally substituted $C_{1-6}$ alkyl group, an optionally substituted $C_{2-6}$ alkenyl group, an optionally substituted $C_{2-6}$ alkenyloxy group, an optionally substituted $C_{2-6}$ alkynyl group, an optionally substituted $C_{1-6}$ alkylsulfonylaminocarbonyl group, an optionally substituted $C_{3-10}$ cycloalkylsulfonylaminocarbonyl group, an optionally substituted $C_{6-10}$ arylsulfonylaminocarbonyl group, an optionally substituted 5- to 10-membered heteroarylsulfonylaminocarbonyl group, an optionally substituted 4- to 10-membered saturated heterocyclic sulfonylaminocarbonyl group, an optionally substituted aminosulfonylaminocarbonyl group, an optionally substituted 4- to 7-membered cyclic aminosulfonylaminocarbonyl group, an optionally substituted $C_{4-7}$ cycloalkoxycarbonyl group, an optionally substituted saturated heterocyclic oxycarbonyl group, or an optionally substituted $C_{1-6}$ alkoxycarbonyl group.

[2] The compound according to [1] or a pharmaceutically acceptable salt thereof, wherein
ring D represents a cyclobutane ring, a cyclopentane ring, a cyclohexane ring, or a cycloheptane ring;
$R^a$ represents
(1) an amino $C_{1-6}$ alkyl group, wherein the amino may be optionally substituted with one or two, same or different $C_{1-6}$ alkyl groups which may be optionally substituted with one to three halogen atoms, and the $C_{1-6}$ alkyl may be optionally substituted with one to three halogen atoms,
(2) a hydroxy $C_{1-6}$ alkyl group wherein the $C_{1-6}$ alkyl may be optionally substituted with one to three halogen atoms,
(3) a group represented by formula (2e):

[Formula 6]

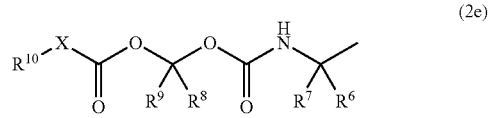

(2e)

wherein X represents a single bond or an oxygen atom;
$R^6$, $R^7$, $R^8$, and $R^9$ each independently represent a hydrogen atom or a $C_{1-4}$ alkyl group which may be optionally substituted with one to three halogen atoms, and
$R^{10}$ represents a $C_{1-4}$ alkyl group or a $C_{4-7}$ cycloalkyl group,
(4) an amino $C_{3-10}$ cycloalkyl group, wherein the amino may be optionally substituted with one or two, same or different $C_{1-6}$ alkyl groups which may be optionally substituted with one to three halogen atoms, and the $C_{3-10}$ cycloalkyl may be optionally substituted with one to three halogen atoms, or
(5) an amidino group which may be optionally substituted with one or two, same or different $C_{1-6}$ alkyl groups which may be optionally substituted with one to three halogen atoms;

$R^{b1}$ and $R^{b2}$ each independently represent a hydrogen atom, a halogen atom, a hydroxy group, a $C_{1-6}$ alkyl group which may be optionally substituted with one to three halogen atoms or a $C_{1-6}$ alkoxy group, or a $C_{1-6}$ alkoxy group which may be optionally substituted with one to three halogen atoms or a $C_{1-6}$ alkoxy group; and $R^d$ represents a hydrogen atom, a $C_{1-6}$ alkyl group which may be optionally substituted with one to three halogen atoms or a $C_{1-6}$ alkoxy group, or a $C_{3-10}$ cycloalkyl group which may be optionally substituted with one to three halogen atoms or a $C_{1-6}$ alkoxy group).

[3] The compound according to [1] or [2], or a pharmaceutically acceptable salt thereof, wherein
ring D represents a cyclohexane ring;
$R^a$ represents
(1) an amino $C_{1-4}$ alkyl group wherein the $C_{1-4}$ alkyl may be optionally substituted with one to three halogen atoms,
(2) a hydroxy $C_{1-4}$ alkyl group wherein the $C_{1-4}$ alkyl may be optionally substituted with one to three halogen atoms, or
(3) a group represented by formula (2e):

[Formula 7]

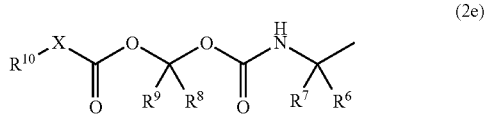

(2e)

wherein X represents a single bond or an oxygen atom;
$R^6$, $R^7$, $R^8$ and $R^9$ each independently represent a hydrogen atom or a $C_{1-4}$ alkyl group which may be optionally substituted with one to three halogen atoms; and
$R^{10}$ represents a $C_{1-4}$ alkyl group or a $C_{4-7}$ cycloalkyl group;
$R^{b1}$ and $R^{b2}$ each represent a hydrogen atom; and
$R^d$ represents a hydrogen atom or a $C_{1-4}$ alkyl group.

[4] The compound according to any one of [1] to [3], or a pharmaceutically acceptable salt thereof, wherein
$R^c$ represents
(1) a $C_{1-6}$ alkyl group which may be optionally substituted with one to three halogen atoms, a phenyl group, a $C_{3-10}$ cycloalkyl group or a $C_{1-6}$ alkoxy group,
(2) a $C_{1-6}$ alkoxy group which may be optionally substituted with one to three halogen atoms, a phenyl group, a $C_{3-10}$ cycloalkyl group or a $C_{1-6}$ alkoxy group,
(3) a $C_{3-10}$ cycloalkyl group which may be optionally substituted with one or two, same or different groups selected from the group consisting of:
 (a) a halogen atom,
 (b) a $C_{1-6}$ alkyl group which may be optionally substituted with one to three halogen atoms,
 (c) a $C_{1-6}$ alkoxy group which may be optionally substituted with one to three halogen atoms,
 (d) a hydroxyl group,
 (e) an amino group which may be optionally substituted with one or two groups selected from the group consisting of a $C_{1-6}$ alkyl group which may be optionally substituted with one to three halogen atoms, and a $C_{3-7}$ cycloalkyl group, and
 (f) an oxo group,
(4) a $C_{3-10}$ cycloalkoxy group which may be optionally substituted with one to four, same or different groups selected from the group consisting of (a) to (f) in (3) above, (5) a phenyl group which may be optionally substituted with
 (a) a halogen atom,
 (b) a cyano group,
 (c) a hydroxy group,
 (d) a carboxyl group,
 (e) a $C_{1-6}$ alkyl group which may be optionally substituted with one to three halogen atoms,
 (f) a $C_{1-6}$ alkoxy group which may be optionally substituted with one to three halogen atoms or a $C_{1-6}$ alkoxy group,
 (g) a $C_{1-6}$ alkoxycarbonylamino group,
 (h) a $C_{1-6}$ alkylsulfonylamino group, wherein the alkyl may be optionally substituted with one to three halogen atoms,
 (i) a $C_{3-10}$ cycloalkyl group which may be optionally substituted with one to three halogen atoms, a $C_{1-6}$ alkoxy group or a $C_{1-6}$ alkyl group,
 (j) a $C_{1-6}$ alkylcarbonylamino group, wherein the alkyl may be optionally substituted with one to three halogen atoms,
 (k) an amino group which may be optionally substituted with one or two, same or different groups selected from the group consisting of:
  (i) a $C_{1-6}$ alkyl group which may be optionally substituted with one to three halogen atoms, a cyano group, a hydroxyl group, a $C_{1-6}$ alkoxy group, a $C_{3-10}$ cycloalkyl group or a $C_{1-6}$ alkoxycarbonylamino group,
  (ii) a $C_{3-10}$ cycloalkyl group which may be optionally substituted with one to three halogen atoms, a $C_{1-6}$ alkoxy group, or a $C_{1-6}$ alkyl group, and
  (iii) a phenyl group which may be optionally substituted with one to four, same or different groups selected from the group consisting of a halogen atom, a cyano group, a $C_{1-6}$ alkyl group, a $C_{3-10}$ cycloalkyl group, a $C_{1-6}$ alkoxycarbonylamino group, and a $C_{1-6}$ alkoxy group,
 (l) an aminocarbonyl group which may be optionally substituted with one or two, same or different groups selected from the group consisting of (i) to (iii) in (k) above,
 (m) a 4- to 10-membered cyclic amino group which may be optionally substituted with one to four, same or different groups selected from the group consisting of:
  (i) a halogen atom,
  (ii) a $C_{1-6}$ alkyl group which may be optionally substituted with a $C_{1-6}$ alkoxy group, a hydroxy group, or one to three halogen atoms,
  (iii) a $C_{1-6}$ alkoxy group which may be optionally substituted with one to three halogen atoms, and
  (iv) a $C_{1-6}$ alkoxycarbonylamino group, and
 (n) a 4- to 10-membered cyclic aminocarbonyl group which may be optionally substituted with one to four, same or different groups selected from the group consisting of (i) to (iv) in (m) above,
(6) a 5- or 6-membered heteroaryl group which may be optionally substituted with one to four, same or different groups selected from the group consisting of (a) to (n) in (5) above,
(7) a 4- to 10-membered saturated heterocyclic group which may be optionally substituted with one to four, same or different groups selected from the group consisting of:
 (a) a halogen atom,
 (b) a $C_{1-6}$ alkyl group which may be optionally substituted with one to three halogen atoms or a $C_{1-6}$ alkoxy group,
 (c) a $C_{1-6}$ alkoxy group which may be optionally substituted with one to three halogen atoms,
 (d) a $C_{1-6}$ alkoxycarbonyl group which may be optionally substituted with one to three halogen atoms, and
 (e) a $C_{3-10}$ cycloalkyl group which may be optionally substituted with one to three halogen atoms, a $C_{1-6}$ alkyl group, or a $C_{1-6}$ alkoxy group, (8) a phenoxy group which may be optionally substituted with one to four, same or different groups selected from the group consisting of (a) to (n) in (5) above,
(9) a 5- or 6-membered heteroaryloxy group which may be optionally substituted with one to four, same or different groups selected from the group consisting of (a) to (n) in (5) above,
(10) a 4- to 10-membered saturated heterocyclic oxy group which may be optionally substituted with one to four, same or different groups selected from the group consisting of (a) to (e) in (7) above,
(11) an amino group which may be optionally substituted with one or two, same or different groups selected from the group consisting of:
    (a) a $C_{1-6}$ alkyl group which may be optionally substituted with one to three halogen atoms, a cyano group, a hydroxy group, a $C_{1-6}$ alkoxy group, a $C_{3-10}$ cycloalkyl group, a phenyl group, a 5- or 6-membered heteroaryl group, a 4- to 7-membered saturated heterocyclic group, or a $C_{1-6}$ alkoxycarbonylamino group,
    (b) a $C_{3-10}$ cycloalkyl group which may be optionally substituted with one to three halogen atoms, a $C_{1-6}$ alkoxy group, or a $C_{1-6}$ alkyl group, and
    (c) a phenyl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group, or
(12) a 4- to 10-membered cyclic amino group which may be optionally substituted with one to four, same or different groups selected from the group consisting of (i) to (iv) in (m) of (5) above.

[5] The compound according to any one of [1] to [4], or a pharmaceutically acceptable salt thereof, wherein $R^c$ represents
(1) a cyclohexyl group which may be optionally substituted with one or two, same or different groups selected from the group consisting of:
    (a) a halogen atom,
    (b) a $C_{1-6}$ alkyl group which may be optionally substituted with one to three halogen atoms or a $C_{1-6}$ alkoxy group,
    (c) a $C_{1-6}$ alkoxy group which may be optionally substituted with one to three halogen atoms or a $C_{1-6}$ alkoxy group,
    (d) a hydroxyl group, and
    (e) an oxo group,
(2) a phenyl group which may be optionally substituted with one to four, same or different groups selected from the group consisting of (a) to (d) in (1) above,
(3) a pyridyl group which may be optionally substituted with one to four, same or different groups selected from the group consisting of (a) to (d) in (1) above, or
(4) a 4- to 7-membered cyclic amino group which may be optionally substituted with one or two, same or different groups selected from the group consisting of (a) to (e) in (1) above.

[6] The compound according to any one of [1] to [5], or a pharmaceutically acceptable salt thereof, wherein ring Q is a group represented by any one of formulae (3a) to (3v):

[Formula 8]

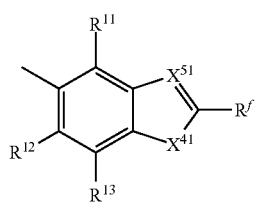
(3a)

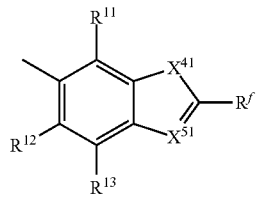
(3b)

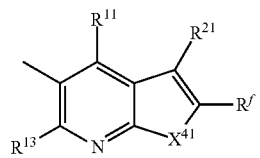
(3c)

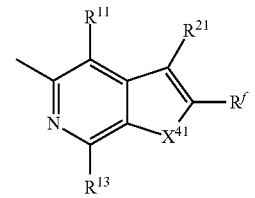
(3d)

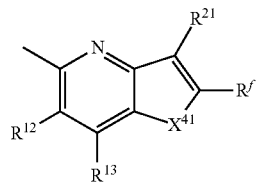
(3e)

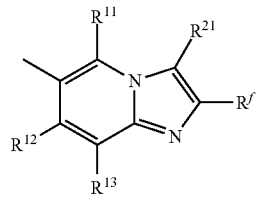
(3f)

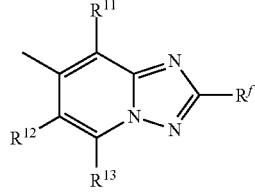
(3g)

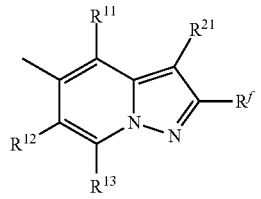
(3h)

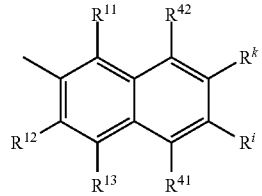
(3i)

-continued

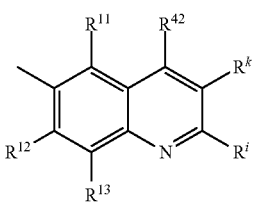
(3j)

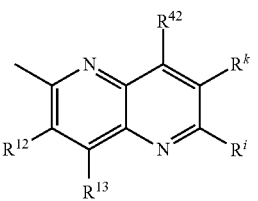
(3k)

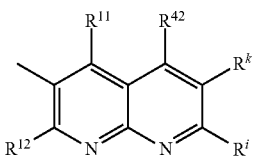
(3l)

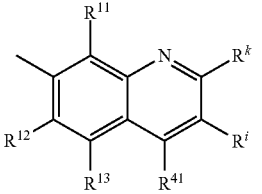
(3m)

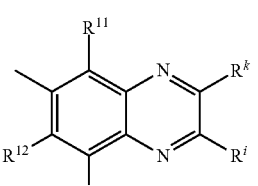
(3n)

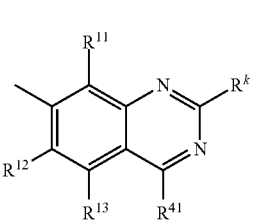
(3o)

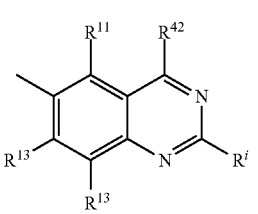
(3p)

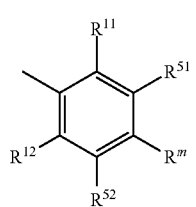
(3q)

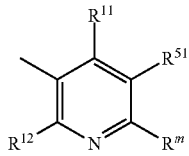
(3r)

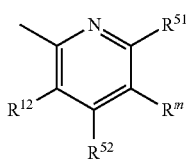
(3s)

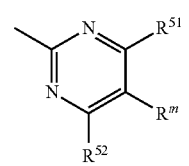
(3t)

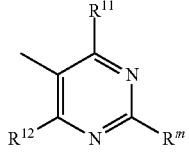
(3u)

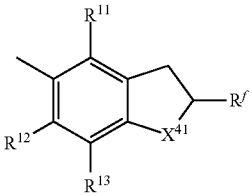
(3v)

wherein
$X^{51}$ represents $CR^{21}$ or N;
$X^{41}$ represents $NR^{31}$, O or S;
$R^{11}$, $R^{12}$ and $R^{13}$ each independently represent a hydrogen atom, a halogen atom, a cyano group, an optionally substituted $C_{1-6}$ alkyl group, an optionally substituted $C_{1-6}$ alkoxy group, or an optionally substituted $C_{3-10}$ cycloalkyl group;
$R^{21}$ represents a hydrogen atom, a halogen atom, a cyano group, a hydroxy group, an optionally substituted $C_{2-6}$ alkenyl group, an optionally substituted $C_{2-6}$ alkynyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group, or a carboxyl group;
$R^{31}$ represents a hydrogen atom, an optionally substituted $C_{1-6}$ alkyl group, an optionally substituted $C_{3-10}$ cycloalkyl group, an optionally substituted $C_{2-6}$ alkenyl group, an optionally substituted $C_{2-6}$ alkynyl group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkylcarbonyl group, an optionally substituted $C_{1-6}$ alkoxycarbonyl group, an optionally substituted aminocarbonyl group, an optionally substituted 4- to 10-membered cyclic aminocarbonyl group, an optionally substituted aminosulfonyl group, an optionally substituted 4- to 10-membered cyclic aminosulfonyl group, an optionally substituted $C_{3-10}$ cycloalkylsulfonyl group, or an optionally substituted $C_{1-6}$ alkylsulfonyl group;

$R^{41}$ and $R^{42}$ each independently represent a hydrogen atom, a halogen atom, a cyano group, a carboxyl group, an optionally substituted 4- to 10-membered saturated heterocyclic oxycarbonyl group, an optionally substituted $C_{1-6}$ alkoxycarbonyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted aminocarbonyl group, an optionally substituted 4- to 10-membered cyclic aminocarbonyl group, or an optionally substituted $C_{1-6}$ alkoxy group;

$R^{51}$ and $R^{52}$ each independently represent a hydrogen atom, a halogen atom, a cyano group, an optionally substituted $C_{1-6}$ alkyl group, an optionally substituted $C_{3-10}$ cycloalkyl group, an optionally substituted $C_{1-6}$ alkoxy group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group, or a carboxyl group;

$R^f$, $R^i$ and $R^k$ each independently represent a hydrogen atom, a halogen atom, a cyano group, a carboxyl group, a hydroxy group, an optionally substituted $C_{3-10}$ cycloalkyl group, an optionally substituted $C_{1-6}$ alkoxy group, an optionally substituted $C_{3-10}$ cycloalkoxy group, an optionally substituted $C_{6-10}$ aryloxy group, an optionally substituted 5- to 10-membered heteroaryloxy group, an optionally substituted 4- to 10-membered saturated heterocyclic oxy group, an optionally substituted $C_{1-6}$ alkylthio group, an optionally substituted $C_{3-10}$ cycloalkylthio group, an optionally substituted $C_{6-10}$ arylthio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted $C_{1-6}$ alkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted $C_{1-6}$ alkylsulfonyl group, an optionally substituted $C_{3-10}$ cycloalkylsulfonyl group, an optionally substituted $C_{6-10}$ arylsulfonyl group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkyl group, an optionally substituted $C_{2-6}$ alkenyl group, an optionally substituted $C_{2-6}$ alkenyloxy group, an optionally substituted $C_{2-6}$ alkynyl group, an optionally substituted $C_{1-6}$ alkylsulfonylaminocarbonyl group, an optionally substituted $C_{3-10}$ cycloalkylsulfonylaminocarbonyl group, an optionally substituted $C_{6-10}$ arylsulfonylaminocarbonyl group, an optionally substituted 4- to 10-membered saturated heterocyclic sulfonylaminocarbonyl group, an optionally substituted $C_{6-10}$ heteroarylsulfonylaminocarbonyl group, an optionally substituted aminosulfonylaminocarbonyl group, an optionally substituted 4- to 7-membered cyclic aminosulfonylaminocarbonyl group, an optionally substituted $C_{4-7}$ cycloalkoxycarbonyl group, an optionally substituted 4- to 10-membered saturated heterocyclic oxycarbonyl group, or an optionally substituted $C_{1-6}$ alkoxycarbonyl group; and $R^m$ represents a hydrogen atom, a halogen atom, a cyano group, a carboxyl group, a hydroxy group, an optionally substituted $C_{3-10}$ cycloalkyl group, an optionally substituted $C_{1-6}$ alkoxy group, an optionally substituted $C_{3-10}$ cycloalkoxy group, an optionally substituted $C_{6-10}$ aryloxy group, an optionally substituted 4- to 10-membered heteroaryloxy group, an optionally substituted 4- to 10-membered saturated heterocyclic oxy group, an optionally substituted $C_{1-6}$ alkylthio group, an optionally substituted $C_{3-10}$ cycloalkylthio group, an optionally substituted $C_{6-10}$ arylthio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted $C_{1-6}$ alkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted $C_{1-6}$ alkylsulfonyl group, an optionally substituted $C_{3-10}$ cycloalkylsulfonyl group, an optionally substituted $C_{6-10}$ arylsulfonyl group, an optionally substituted 4- to 10-membered saturated heterocyclic group, an optionally substituted $C_{1-6}$ alkyl group, an optionally substituted $C_{2-6}$ alkenyl group, an optionally substituted $C_{2-6}$ alkenyloxy group, an optionally substituted $C_{2-6}$ alkynyl group, an optionally substituted $C_{1-6}$ alkylsulfonylaminocarbonyl group, an optionally substituted $C_{3-10}$ cycloalkylsulfonylaminocarbonyl group, an optionally substituted $C_{6-10}$ arylsulfonylaminocarbonyl group, an optionally substituted 4- to 10-membered saturated heterocyclic sulfonylaminocarbonyl group, an optionally substituted $C_{6-10}$ heteroarylsulfonylaminocarbonyl group, an optionally substituted aminosulfonylaminocarbonyl group, an optionally substituted 4- to 7-membered cyclic aminosulfonylaminocarbonyl group, an optionally substituted $C_{4-7}$ cycloalkoxycarbonyl group, an optionally substituted 4- to 10-membered saturated heterocyclic oxycarbonyl group, or an optionally substituted $C_{1-6}$ alkoxycarbonyl group.

[7] The compound according to [6] or a pharmaceutically acceptable salt thereof, wherein ring Q is a group represented by formula (3a), (3b), (3c), (3d), (3e), (3f), (3j), (3q), (3r), (3s) or (3v).

[8] The compound according to [7] or a pharmaceutically acceptable salt thereof, wherein ring Q is a group represented by formula (3a), (3b), (3f), (3j), (3q), (3r) or (3s).

[9] The compound according to [8] or a pharmaceutically acceptable salt thereof, wherein ring Q is a group represented by formula (3a), (3j), (3q) or (3s), and $X^{51}$ is $CR^{21}$.

[10] The compound according to [9] or a pharmaceutically acceptable salt thereof, wherein ring Q is a group represented by formula (3a) or (3q).

[11] The compound according to any one of [1] to [10], or a pharmaceutically acceptable salt thereof, wherein $R^{11}$, $R^{12}$, $R^{13}$, $R^{41}$ and $R^{42}$ each independently represent a hydrogen atom, a halogen atom, a cyano group, a $C_{1-6}$ alkyl group which may be optionally substituted with one to three halogen atoms, a $C_{1-6}$ alkoxy group which may be optionally substituted with one to three halogen atoms, or a $C_{3-10}$ cycloalkyl group which may be optionally substituted with one to three halogen atoms;

$R^{21}$ represents (1) a hydrogen atom,
(2) a halogen atom,
(3) a cyano group,
(4) a $C_{1-6}$ alkyl group which may be optionally substituted with one to three halogen atoms or a $C_{1-6}$ alkoxy group,
(5) a $C_{3-10}$ cycloalkyl group which may be optionally substituted with one to three halogen atoms or a $C_{1-6}$ alkoxy group,
(6) an amino group which may be optionally substituted with one or two, same or different $C_{1-6}$ alkyl groups which may be optionally substituted with one to three halogen atoms,
(7) a $C_{1-6}$ alkylcarbonyl group which may be optionally substituted with one to three halogen atoms,
(8) a $C_{1-6}$ alkylcarbonylamino group which may be optionally substituted with one to three halogen atoms,
(9) a $C_{1-6}$ alkoxycarbonylamino group,
(10) a phenyl group which may be optionally substituted with
  (a) a halogen atom,
  (b) a cyano group,
  (c) a hydroxy group,
  (d) a carboxyl group,
  (e) a $C_{1-6}$ alkyl group which may be optionally substituted with one to three halogen atoms,
  (f) a $C_{1-6}$ alkoxy group which may be optionally substituted with one to three halogen atoms,
  (g) a $C_{1-6}$ alkoxycarbonylamino group which may be optionally substituted with one to three halogen atoms,
  (h) a $C_{1-6}$ alkylsulfonylamino group which may be optionally substituted with one to three halogen atoms,
  (i) a $C_{3-10}$ cycloalkyl group which may be optionally substituted with one to three halogen atoms or a $C_{1-6}$ alkyl group,
  (j) a $C_{1-6}$ alkylcarbonylamino group which may be optionally substituted with one to three halogen atoms,
  (k) an amino group which may be optionally substituted with one or two, same or different groups selected from the group consisting of:
    (i) a $C_{1-6}$ alkyl group which may be optionally substituted with one to three halogen atoms, a cyano group, a hydroxy group, a $C_{1-6}$ alkoxy group, a $C_{3-10}$ cycloalkyl group, or a $C_{1-6}$ alkoxycarbonylamino group,
    (ii) a $C_{3-10}$ cycloalkyl group which may be optionally substituted with one to three halogen atoms or a $C_{1-6}$ alkyl group,
    (iii) a phenyl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group,
    (iv) a 5- or 6-membered heteroaryl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group, and
    (v) a 5- or 6-membered saturated heterocyclic group which may be optionally substituted with one to three halogen atoms, a $C_{1-6}$ alkyl group, or a $C_{1-6}$ alkoxy group,
  (l) an aminocarbonyl group which may be optionally substituted with one or two, same or different groups selected from the group consisting of (i) to (v) in (k) above,
  (m) a 4- to 10-membered cyclic amino group which may be optionally substituted with one to four, same or different groups selected from the group consisting of:
    (i) a $C_{1-6}$ alkyl group which may be optionally substituted with a hydroxy group, a $C_{1-6}$ alkoxy group, or one to three halogen atoms,
    (ii) a $C_{1-6}$ alkoxy group which may be optionally substituted with one to three halogen atoms or a $C_{1-6}$ alkoxy group,
    (iii) a $C_{1-6}$ alkoxycarbonylamino group, and
    (iv) a halogen atom, or
  (n) a 4- to 10-membered cyclic aminocarbonyl group which may be optionally substituted with one to four, same or different groups selected from the group consisting of (i) to (iv) in (m) above,
(11) a 5- or 6-membered heteroaryl group which may be optionally substituted with one to four, same or different groups selected from the group consisting of (a) to (n) in (10) above,
(12) a 5- or 6-membered saturated heterocyclic group which may be optionally substituted with one to four, same or different groups selected from the group consisting of (a) to (n) in (10) above,
(13) a $C_{1-6}$ alkoxycarbonyl group,
(14) an aminocarbonyl group which may be optionally substituted with one or two, same or different groups selected from the group consisting of (i) to (v) in (k) of (10) above,
(15) a 4- to 10-membered cyclic aminocarbonyl group which may be optionally substituted with one to four, same or different groups selected from the group consisting of (i) to (iv) in (m) of 10) above, or

(16) a carboxyl group;

$R^{31}$ represents (1) a hydrogen atom, (2) a $C_{1-6}$ alkyl group which may be optionally substituted with
- (a) a carboxyl group,
- (b) an aminocarbonyl group, wherein the amino may be optionally substituted with one or two, same or different groups selected from the group consisting of:
  - (i) a $C_{1-6}$ alkyl group which may be optionally substituted with one to three halogen atoms, a cyano group, a hydroxy group, a $C_{1-6}$ alkoxy group, a $C_{3-10}$ cycloalkyl group, or a $C_{1-6}$ alkoxycarbonylamino group, and
  - (ii) a $C_{3-10}$ cycloalkyl group which may be optionally substituted with one to three halogen atoms or a $C_{1-6}$ alkyl group,
- (c) a $C_{1-6}$ alkoxy group which may be optionally substituted with one to three halogen atoms,
- (d) a 4- to 10-membered cyclic aminocarbonyl group which may be optionally substituted with one to four, same or different groups selected from the group consisting of:
  - (i) a $C_{1-6}$ alkyl group which may be optionally substituted with a halogen atom, a hydroxy group, a $C_{1-6}$ alkoxy group, or one to three halogen atoms,
  - (ii) a $C_{1-6}$ alkoxy group which may be optionally substituted with one to three halogen atoms, and
  - (iii) a $C_{1-6}$ alkoxycarbonylamino group,
- (e) a $C_{3-10}$ cycloalkyl group which may be optionally substituted with one to three halogen atoms, a $C_{1-6}$ alkoxy group or a $C_{1-6}$ alkyl group, or
- (f) one to three halogen atoms, (3) a $C_{3-10}$ cycloalkyl group which may be optionally substituted with one to three halogen atoms or a $C_{1-6}$ alkyl group, (4) a $C_{1-6}$ alkylcarbonyl group which may be optionally substituted with one to three halogen atoms, or (5) a $C_{1-6}$ alkylsulfonyl group which may be optionally substituted with one to three halogen atoms; and $R^{51}$ and $R^{52}$ each independently represent (1) a hydrogen atom, (2) a halogen atom, (3) a cyano group, (4) a $C_{1-6}$ alkyl group which may be optionally substituted with
- (a) a halogen atom,
- (b) a cyano group,
- (c) a hydroxy group,
- (d) a carboxyl group,
- (e) a $C_{1-6}$ alkoxy group which may be optionally substituted with one to three halogen atoms,
- (f) a $C_{1-6}$ alkoxycarbonylamino group,
- (g) a $C_{1-6}$ alkylsulfonylamino group which may be optionally substituted with one to three halogen atoms,
- (h) a $C_{3-10}$ cycloalkyl group which may be optionally substituted with one to three halogen atoms or a $C_{1-6}$ alkyl group,
- (i) a $C_{1-6}$ alkylcarbonylamino group which may be optionally substituted with one to three halogen atoms,
- (j) an amino group which may be optionally substituted with one or two, same or different $C_{1-6}$ alkyl groups which may be optionally substituted with one to three halogen atoms,
- (k) an aminocarbonyl group which may be optionally substituted with one or two, same or different $C_{1-6}$ alkyl groups which may be optionally substituted with one to three halogen atoms,
- (l) a 4- to 10-membered cyclic amino group which may be optionally substituted with one to four, same or different groups selected from the group consisting of:
  - (i) a $C_{1-6}$ alkyl group which may be optionally substituted with a hydroxy group, a $C_{1-6}$ alkoxy group, or one to three halogen atoms,
  - (ii) a $C_{1-6}$ alkoxy group which may be optionally substituted with one to three halogen atoms,
  - (iii) a $C_{1-6}$ alkoxycarbonylamino group, and
  - (iv) a halogen atom, or
- (m) a 4- to 10-membered cyclic aminocarbonyl group which may be optionally substituted with one to four, same or different groups selected from the group consisting of:
  - (i) a $C_{1-6}$ alkyl group which may be optionally substituted with a $C_{1-6}$ alkoxy group, a hydroxy group, or one to three halogen atoms,
  - (ii) a $C_{1-6}$ alkoxy group which may be optionally substituted with one to three halogen atoms,
  - (iii) a $C_{1-6}$ alkoxycarbonylamino group, and
  - (iv) a halogen atom, (5) a $C_{3-10}$ cycloalkyl group which may be optionally substituted with one to three halogen atoms or a $C_{1-6}$ alkyl group, (6) an amino group which may be optionally substituted with one or two, same or different $C_{1-6}$ alkyl groups, wherein the alkyl may be optionally substituted with one to three halogen atoms, (7) a $C_{1-6}$ alkylcarbonyl group which may be optionally substituted with one to three halogen atoms, (8) an aminocarbonyl group which may be optionally substituted with one or two, same or different $C_{1-6}$ alkyl groups, (9) a 4- to 10-membered cyclic aminocarbonyl group which may be optionally substituted with one to four, same or different groups selected from the group consisting of:
- (a) a $C_{1-6}$ alkyl group which may be optionally substituted with a $C_{1-6}$ alkoxy group, a hydroxy group, or one to three halogen atoms,
- (b) a $C_{1-6}$ alkoxy group which may be optionally substituted with one to three halogen atoms,
- (c) a $C_{1-6}$ alkoxycarbonylamino group, and
- (d) a halogen atom,

(10) a $C_{1-6}$ alkylcarbonylamino group which may be optionally substituted with one to four, same or different groups selected from the group consisting of:
- (a) a halogen atom,
- (b) a cyano group,
- (c) a hydroxy group,
- (d) a carboxyl group,
- (e) a $C_{1-6}$ alkoxy group which may be optionally substituted with one to three halogen atoms,
- (f) a $C_{1-6}$ alkoxycarbonylamino group,
- (g) a $C_{1-6}$ alkylsulfonylamino group which may be optionally substituted with one to three halogen atoms,
- (h) a $C_{3-10}$ cycloalkyl group which may be optionally substituted with one to three halogen atoms or a $C_{1-6}$ alkyl group,
- (i) a $C_{1-6}$ alkylcarbonylamino group which may be optionally substituted with one to three halogen atoms,
- (j) an amino group which may be optionally substituted with one or two, same or different $C_{1-6}$ alkyl groups,
- (k) an aminocarbonyl group which may be optionally substituted with one or two, same or different $C_{1-6}$ alkyl groups, (l) a 4- to 10-membered cyclic amino group which may be optionally substituted with one to four, same or different groups selected from the group consisting of:
  (i) a $C_{1-6}$ alkyl group which may be optionally substituted with a $C_{1-6}$ alkoxy group, a hydroxy group, or one to three halogen atoms,
  (ii) a $C_{1-6}$ alkoxy group which may be optionally substituted with one to three halogen atoms,
  (iii) a $C_{1-6}$ alkoxycarbonylamino group, and
  (iv) a halogen atom, and
(m) a 4- to 10-membered cyclic aminocarbonyl group which may be optionally substituted with (a) to (d) in (9) above,
(11) a $C_{1-6}$ alkoxycarbonylamino group,
(12) a saturated heterocyclic oxycarbonyl group which may be optionally substituted with one to four, same or different groups selected from the group consisting of (a) to (m) in (10) above,
(13) a 5- or 6-membered saturated heterocyclic group which may be optionally substituted with one to four, same or different groups selected from the group consisting of (a) to (m) in (10) above,
(14) a $C_{1-6}$ alkoxy group which may be optionally substituted with one to three halogen atoms, or
(15) a carboxyl group.

[12] The compound according to any one of [1] to [11], or a pharmaceutically acceptable salt thereof, wherein $R^{11}$, $R^{12}$, $R^{13}$, $R^{41}$ and $R^{42}$ each independently represent a hydrogen atom, a halogen atom, a $C_{1-6}$ alkyl group which may be optionally substituted with one to three halogen atoms, or a $C_{1-6}$ alkoxy group which may be optionally substituted with one to three halogen atoms;

$R^{21}$ represents a hydrogen atom, a halogen atom, a cyano group or a $C_{1-6}$ alkyl group which may be optionally substituted with one to three halogen atoms;

$R^{31}$ represents a hydrogen atom, a $C_{1-6}$ alkyl group which may be optionally substituted with one to three halogen atoms, a $C_{1-6}$ alkoxy group or a carboxyl group, a $C_{3-10}$ cycloalkyl group which may be optionally substituted with one to three halogen atoms or a $C_{1-6}$ alkyl group, a $C_{1-6}$ alkylsulfonyl group or a $C_{1-6}$ alkylcarbonyl group; and $R^{51}$ and $R^{52}$ each independently represent a hydrogen atom, a halogen atom, a cyano group, a $C_{1-6}$ alkyl group which may be optionally substituted with one to three halogen atoms, a $C_{1-6}$ alkoxy group which may be optionally substituted with one to three halogen atoms; or a carboxyl group.

[13] The compound according to any one of [1] to [12], or a pharmaceutically acceptable salt thereof, wherein $R^{11}$, $R^{12}$, $R^{13}$, $R^{41}$, $R^{42}$, $R^{51}$ and $R^{52}$ each independently represent a hydrogen atom, a halogen atom, a $C_{1-6}$ alkyl group or a $C_{1-6}$ alkoxy group;

$R^{21}$ represents a hydrogen atom, a halogen atom or a $C_{1-6}$ alkyl group; and $R^{31}$ represents a hydrogen atom or a $C_{1-6}$ alkyl group which may be optionally substituted with one to three halogen atoms.

[14] The compound according to any one of [1] to [13], or a pharmaceutically acceptable salt thereof, wherein $R^f$, $R^i$ and $R^k$ each independently represent
(1) a hydrogen atom,
(2) a cyano group,
(3) a carboxyl group,
(4) an amino group which may be optionally substituted with one or two, same or different groups selected from the group consisting of:
  (a) a $C_{1-6}$ alkyl group which may be optionally substituted with one to three halogen atoms, a cyano group, a hydroxy group, a carboxyl group, a $C_{1-6}$ alkoxy group, a $C_{3-10}$ cycloalkyl group, or a $C_{1-6}$ alkoxycarbonylamino group,
  (b) a $C_{3-10}$ cycloalkyl group which may be optionally substituted with one to three halogen atoms or a $C_{1-6}$ alkyl group,
  (c) a phenyl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group,
  (d) a 5- or 6-membered heteroaryl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group, and
  (e) a 4- to 6-membered saturated heterocyclic group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group,
(5) an aminocarbonyl group, wherein the amino may be optionally substituted with one or two, same or different groups selected from the group consisting of (a) to (e) in (4) above,
(6) a 4- to 10-membered cyclic amino group which may be optionally substituted with one to four, same or different groups selected from the group consisting of:
  (a) a halogen atom,
  (b) a cyano group,
  (c) a hydroxy group,
  (d) a $C_{1-6}$ alkyl group which may be optionally substituted with
    (i) one to three halogen atoms,
    (ii) a carboxyl group,
    (iii) an aminocarbonyl group, wherein the amino may be optionally substituted with one or two, same or different groups selected from the group consisting of (a) to (e) in (4) above,
    (iv) a 4- to 10-membered cyclic aminocarbonyl group which may be optionally substituted with one to four, same or different groups selected from the group consisting of a halogen atom, a cyano group, a hydroxy group, a $C_{1-6}$ alkyl group, a $C_{1-6}$ alkoxy group, and a $C_{1-6}$ alkoxycarbonylamino group, or
    (v) a $C_{1-6}$ alkoxycarbonylamino group,
  (e) a $C_{1-6}$ alkoxy group which may be optionally substituted with
    (i) one to three halogen atoms,
    (ii) a carboxyl group,
    (iii) an aminocarbonyl group, wherein the amino may be optionally substituted with one or two, same or different groups selected from the group consisting of (a) to (e) in (4) above,
    (iv) a 4- to 10-membered cyclic aminocarbonyl group which may be optionally substituted with one to four, same or different groups selected from the group consisting of a halogen atom, a cyano group, a hydroxy group, a $C_{1-6}$ alkyl group, a $C_{1-6}$ alkoxy group, and a $C_{1-6}$ alkoxycarbonylamino group, (v) a $C_{1-6}$ alkoxycarbonylamino group, or
(vi) a $C_{1-6}$ alkoxycarbonyl group, and
(f) a $C_{1-6}$ alkoxycarbonylamino group,
(7) a 4- to 10-membered cyclic aminocarbonyl group which may be optionally substituted with one to four, same or different groups selected from the group consisting of (a) to (f) in (6) above,
(8) a phenyl group which may be optionally substituted with one to four, same or different groups selected from the group consisting of:
(a) a halogen atom,
(b) a cyano group,
(c) a hydroxy group,
(d) a carboxyl group,
(e) a $C_{1-6}$ alkyl group which may be optionally substituted with
(i) one to three halogen atoms,
(ii) a carboxyl group,
(iii) an aminocarbonyl group, wherein the amino may be optionally substituted with one or two, same or different groups selected from the group consisting of (a) to (e) in (4) above,
(iv) a 4- to 10-membered cyclic aminocarbonyl group which may be optionally substituted with one to four, same or different groups selected from the group consisting of a halogen atom, a cyano group, a hydroxy group, a $C_{1-6}$ alkyl group, a $C_{1-6}$ alkoxy group, and a $C_{1-6}$ alkoxycarbonylamino group, or
(v) a $C_{1-6}$ alkoxycarbonylamino group,
(f) a $C_{1-6}$ alkoxy group which may be optionally substituted with
(i) one to three halogen atoms,
(ii) a carboxyl group,
(iii) an aminocarbonyl group, wherein the amino may be optionally substituted with one or two, same or different groups selected from the group consisting of (a) to (e) in (4) above,
(iv) a 4- to 10-membered cyclic aminocarbonyl group which may be optionally substituted with one to four, same or different groups selected from the group consisting of (a) to (f) in (6) above, or
(v) a $C_{1-6}$ alkoxycarbonylamino group,
(g) a $C_{1-6}$ alkoxycarbonylamino group which may be optionally substituted with one to three halogen atoms,
(h) a $C_{1-6}$ alkylsulfonylamino group which may be optionally substituted with one to three halogen atoms,
(i) a $C_{3-10}$ cycloalkyl group which may be optionally substituted with one to three halogen atoms or a $C_{1-6}$ alkyl group,
(j) a $C_{1-6}$ alkylcarbonylamino group which may be optionally substituted with one to three halogen atoms,
(k) an amino group which may be optionally substituted with one or two different groups selected from the group consisting of (a) to (e) in (4) above,
(l) an aminocarbonyl group, wherein the amino which may be optionally substituted with one or two different groups selected from the group consisting of (a) to (e) in (4) above,
(m) a 4- to 10-membered cyclic amino group which may be optionally substituted with one to four, same or different groups selected from the group consisting of (a) to (f) in (6) above,
(n) a 4- to 10-membered cyclic aminocarbonyl group which may be optionally substituted with one to four, same or different groups selected from the group consisting of (a) to (f) in (6) above, and
(o) a $C_{1-6}$ alkoxycarbonyl group, (9) a 5- or 6-membered heteroaryl group which may be optionally substituted with one to four, same or different groups selected from the group consisting of (a) to (o) in (8) above,
(10) a 4- to 10-membered saturated heterocyclic group which may be optionally substituted with one to four, same or different groups selected from the group consisting of (a) to (o) in (8) above,
(11) a $C_{1-6}$ alkyl group which may be optionally substituted with
(a) one to three halogen atoms,
(b) a carboxyl group,
(c) a cyano group,
(d) a $C_{1-6}$ alkoxy group,
(e) a phenyl group which may be optionally substituted with one to four, same or different groups selected from the group consisting of (a) to (o) in (8) above,
(f) a 5- or 6-membered heteroaryl group which may be optionally substituted with one to four, same or different groups selected from the group consisting of (a) to (o) in (8) above,
(g) a 4- to 10-membered saturated heterocyclic group which may be optionally substituted with one to four, same or different groups selected from the group consisting of (a) to (o) in (8) above,
(h) a hydroxy group,
(i) an aminocarbonyl group, wherein the amino may be optionally substituted with one or two different groups selected from the group consisting of (a) to (e) in (4) above,
(j) a 4- to 10-membered cyclic aminocarbonyl group which may be optionally substituted with one to four, same or different groups selected from the group consisting of (a) to (f) in (6) above,
(k) a $C_{1-6}$ alkoxycarbonylamino group,
(l) a $C_{1-6}$ alkoxycarbonyl group which may be optionally substituted with one or two, same or different groups selected from the group consisting of:
(l1) a $C_{1-6}$ alkoxy group which may be optionally substituted with one to three halogen atoms,
(l2) a $C_{3-7}$ cycloalkoxy group which may be optionally substituted with one to three halogen atoms,
(l3) a mono- or di-$C_{1-6}$ alkylamino group wherein the alkyl may be optionally substituted with one to three halogen atoms,
(l4) a 4- to 7-membered cyclic amino group which may be optionally substituted with one to three halogen atoms, a $C_{1-6}$ alkyl group, or a $C_{1-6}$ alkoxy group,
(l5) a mono- or di-$C_{1-6}$ alkylaminocarbonyl group, wherein the alkyl may be optionally substituted with one to three halogen atoms,
(l6) a 4- to 7-membered cyclic aminocarbonyl group which may be optionally substituted with one to three halogen atoms, a $C_{1-6}$ alkyl group, or a $C_{1-6}$ alkoxy group, and
(l7) a $C_{3-7}$ cycloalkyl group which may be optionally substituted with one to three halogen atoms,
(m) a group represented by formula (4a):

[Formula 9]

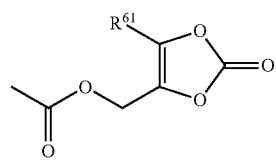

(4a)

wherein $R^{61}$ represents
  (m1) a hydrogen atom,
  (m2) a $C_{1-4}$ alkyl group which may be optionally substituted with one to three halogen atoms or a $C_{1-4}$ alkoxy group,
  (m3) a $C_{3-6}$ cycloalkyl group which may be optionally substituted with a $C_{1-4}$ alkoxy group, or
  (m4) a $C_{6-10}$ aryl group which may be optionally substituted with a $C_{1-4}$ alkyl group, one to three halogen atoms, or a $C_{1-4}$ alkoxy group, or
  (n) a group represented by the following formula (5a):

[Formula 10]

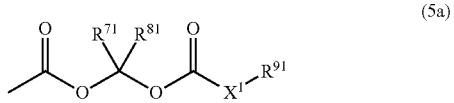

(5a)

wherein $X^1$ represents a single bond or an oxygen atom; $R^{71}$ and $R^{81}$ each independently represent
  (n11) a hydrogen atom,
  (n12) a $C_{1-4}$ alkyl group which may be optionally substituted with one to three halogen atoms; a $C_{3-6}$ cycloalkyl group which may be optionally substituted with a $C_{1-4}$ alkoxy group; a 5- or 6-membered saturated heterocyclic group, or a 5- or 6-membered saturated heterocyclic oxy group,
  (n13) a $C_{3-10}$ cycloalkyl group which may be optionally substituted with one to three halogen atoms or a $C_{1-4}$ alkoxy group,
  (n14) a $C_{6-10}$ aryl group which may be optionally substituted with one to four, same or different groups selected from the group consisting of a halogen atom and a $C_{6-10}$ aryl group wherein the aryl may be optionally substituted with one to four, same or different groups selected from the group consisting of a halogen atom and a $C_{1-4}$ alkoxy group,
  (n15) a 5- or 6-membered saturated heterocyclic group which may be optionally substituted with one to three halogen atoms, or
  (n16) a 5- to 10-membered heteroaryl group which may be optionally substituted with one to four, same or different groups selected from the group consisting of a $C_{1-4}$ alkyl group and a $C_{1-4}$ alkoxy group; and
$R^{91}$ represents
  (n21) a $C_{1-6}$ alkyl group which may be optionally substituted with one to three halogen atoms, a hydroxy group, a $C_{1-4}$ alkoxy group, a carboxyl group, a 5- or 6-membered saturated heterocyclic group, a $C_{3-6}$ cycloalkyl group, a $C_{1-4}$ alkoxycarbonyl group, a $C_{1-4}$ alkoxycarbonylamino group, an amino group, a mono- or di-$C_{1-6}$ alkylamino group, a 4- to 7-membered cyclic amine group, one or two nitrooxy groups, an aminocarbonyl group, or a 4- to 7-membered cyclic aminocarbonyl group,
  (n22) a $C_{3-10}$ cycloalkyl group which may be optionally substituted with a hydroxy group,
  (n23) a $C_{6-10}$ aryl group which may be optionally substituted with a halogen atom, a $C_{1-4}$ alkyl group, a $C_{1-4}$ alkoxy group, or a $C_{1-4}$ alkylcarbonyloxy group,
  (n24) a 5- to 10-membered heteroaryl group, or
  (n25) a 5- or 6-membered saturated heterocyclic group which may be optionally substituted with a $C_{1-4}$ alkyl group or a $C_{1-4}$ alkoxy group,

(12) a $C_{2-6}$ alkenyl group which may be optionally substituted with (a) to (n) in (11) above,
  (13) a $C_{1-6}$ alkoxy group which may be optionally substituted with (a) to (n) in (11) above,
  (14) a $C_{1-6}$ alkoxycarbonylamino group which may be optionally substituted with one to three halogen atoms,
  (15) a $C_{1-6}$ alkylsulfonylamino group which may be optionally substituted with one to three halogen atoms,
  (16) a $C_{1-6}$ alkylsulfonylaminocarbonyl group which may be optionally substituted with one to three halogen atoms,
  (17) a $C_{3-10}$ cycloalkylsulfonylaminocarbonyl group which may be optionally substituted with one to three halogen atoms,
  (18) a phenylsulfonylaminocarbonyl group which may be optionally substituted with one to four, same or different groups selected from the group consisting of (a) to (o) in (8) above,
  (19) a 5- or 6-membered heteroarylsulfonylaminocarbonyl group which may be optionally substituted with one to four, same or different groups selected from the group consisting of (a) to (o) in (8) above,
  (20) a 4- to 10-membered saturated heterocyclic sulfonylaminocarbonyl group which may be optionally substituted with one to four, same or different groups selected from the group consisting of (a) to (o) in (8) above,
  (21) an aminosulfonylaminocarbonyl group wherein the amino may be optionally substituted with one or two, same or different $C_{1-6}$ alkyl groups which may be optionally substituted with one to three halogen atoms,
  (22) a 4- to 7-membered cyclic aminosulfonylaminocarbonyl group which may be optionally substituted with one to four, same or different groups selected from the group consisting of (a) to (o) in (8) above,
  (23) a $C_{4-7}$ cycloalkoxycarbonyl group which may be optionally substituted with one to four, same or different groups selected from the group consisting of (a) to (o) in (8) above,
  (24) a 4- to 10-membered saturated heterocyclic oxycarbonyl group which may be optionally substituted with one to four, same or different groups selected from the group consisting of (a) to (o) in (8) above,
  (25) a $C_{1-6}$ alkoxycarbonyl group which may be optionally substituted with
    (a) a $C_{1-6}$ alkoxy group which may be optionally substituted with one to three halogen atoms or a $C_{1-6}$ alkoxy group,
    (b) a $C_{3-7}$ cycloalkoxy group which may be optionally substituted with one to three halogen atoms,
    (c) a mono- or di-$C_{1-6}$ alkylamino group wherein the alkyl may be optionally substituted with one to three halogen atoms,
    (d) a 4- to 7-membered cyclic amino group which may be optionally substituted with one to three halogen atoms, a $C_{1-6}$ alkyl group, or a $C_{1-6}$ alkoxy group,
    (e) a mono- or di-$C_{1-6}$ alkylaminocarbonyl group wherein the alkyl may be optionally substituted with one to three halogen atoms,
    (f) a 4- to 7-membered cyclic aminocarbonyl group which may be optionally substituted with one to three halogen atoms, a $C_{1-6}$ alkyl group, or a $C_{1-6}$ alkoxy group,
    (g) a $C_{3-7}$ cycloalkyl group which may be optionally substituted with one to three halogen atoms, or
    (h) a 4- to 10-membered saturated heterocyclic group which may be optionally substituted with one to four, same or different groups selected from the group consisting of (a) to (o) in (8) above,

(26) a group represented by formula (4a):

[Formula 11]

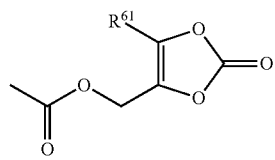

wherein $R^{61}$ represents
  (a) a hydrogen atom,
  (b) a $C_{1-4}$ alkyl group which may be optionally substituted with one to three halogen atoms or a $C_{1-4}$ alkoxy group,
  (c) a $C_{3-6}$ cycloalkyl group which may be optionally substituted with a $C_{1-4}$ alkoxy group, or
  (d) a $C_{6-10}$ aryl group which may be optionally substituted with a $C_{1-4}$ alkoxy group, or
(27) a group represented by the following formula (5a):

[Formula 12]

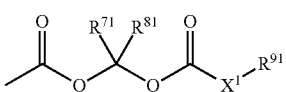

wherein X represents a single bond or an oxygen atom; $R^{71}$ and $R^{81}$ each independently represent
  (a) a hydrogen atom,
  (b) a $C_{1-4}$ alkyl group which may be optionally substituted with one to three halogen atoms; a $C_{3-6}$ cycloalkyl group which may be optionally substituted with a $C_{1-4}$ alkoxy group; a 5- or 6-membered saturated heterocyclic group, or a 5- or 6-membered saturated heterocyclic oxy group,
  (c) a $C_{3-10}$ cycloalkyl group which may be optionally substituted with one to three halogen atoms or a $C_{1-4}$ alkoxy group,
  (d) a $C_{6-10}$ aryl group which may be optionally substituted with one to four, same or different groups selected from the group consisting of a halogen atom and a $C_{6-10}$ aryl group wherein the aryl may be optionally substituted with one to four, same or different groups selected from the group consisting of a halogen atom and a $C_{1-4}$ alkoxy group,
  (e) a 5- or 6-membered saturated heterocyclic group which may be optionally substituted with one to three halogen atoms, or
  (f) a 5- to 10-membered heteroaryl group which may be optionally substituted with one to four, same or different groups selected from the group consisting of a $C_{1-4}$ alkyl group and a $C_{1-4}$ alkoxy group; and
$R^{91}$ represents
  (a) a $C_{1-6}$ alkyl group which may be optionally substituted with one to three halogen atoms, a hydroxy group, a $C_{1-4}$ alkoxy group, a carboxyl group, a 5- or 6-membered saturated heterocyclic group, a $C_{3-6}$ cycloalkyl group, a $C_{1-4}$ alkoxycarbonyl group, a $C_{1-4}$ alkoxycarbonylamino group, an amino group, a mono- or di-$C_{1-6}$ alkylamino group, a 4- to 7-membered cyclic amine group, one or two nitrooxy groups, an aminocarbonyl group, or a 4- to 7-membered cyclic aminocarbonyl group,
  (b) a $C_{3-10}$ cycloalkyl group which may be optionally substituted with a hydroxy group,
  (c) a $C_{6-10}$ aryl group which may be optionally substituted with a halogen atom, a $C_{1-4}$ alkyl group, a $C_{1-4}$ alkoxy group, or a $C_{1-4}$ alkylcarbonyloxy group,
  (d) a 5- to 10-membered heteroaryl group, or
  (e) a 5- or 6-membered saturated heterocyclic group which may be optionally substituted with a $C_{1-4}$ alkyl group or a $C_{1-4}$ alkoxy group.

[15] The compound according to any one of [1] to [14], or a pharmaceutically acceptable salt thereof, wherein $R^f$, $R^i$ and $R^k$ each independently represent
  (1) a hydrogen atom,
  (2) a cyano group,
  (3) a carboxyl group,
  (4) an aminocarbonyl group which may be optionally substituted with one or two, same or different $C_{1-6}$ alkyl groups which may be optionally substituted with one to three halogen atoms or a $C_{1-6}$ alkoxy group,
  (5) a 4- to 6-membered cyclic aminocarbonyl group which may be optionally substituted with one to four, same or different groups selected from the group consisting of one to three halogen atoms, a $C_{1-6}$ alkyl group, a $C_{1-6}$ alkoxy group, a $C_{1-6}$ alkoxycarbonyl group, and a $C_{1-6}$ alkoxycarbonylamino group,
  (6) a tetrazolyl group,
  (7) a 5-oxo-1,2,4-oxadiazol-3-yl group,
  (8) a $C_{1-6}$ alkyl group which may be optionally substituted with
    (a) a hydroxy group,
    (b) a carboxyl group,
    (c) a $C_{1-6}$ alkoxycarbonyl group,
    (d) a group represented by formula (4b):

[Formula 13]

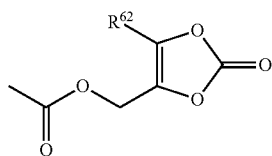

wherein $R^{62}$ represents a hydrogen atom or a $C_{1-4}$ alkyl group, or,
    (e) a group represented by formula (5b):

[Formula 14]

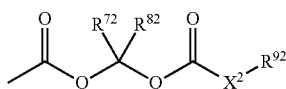

wherein $X^2$ represents a single bond or an oxygen atom; $R^{72}$ and $R^{82}$ each independently represent a hydrogen atom or a $C_{1-4}$ alkyl group; and $R^{92}$ represents a $C_{1-4}$ alkyl group or a $C_{4-7}$ cycloalkyl group,
  (9) a $C_{1-6}$ alkoxycarbonylamino group,
  (10) a $C_{1-6}$ alkylsulfonylamino group,
  (11) a $C_{1-6}$ alkylsulfonylaminocarbonyl group which may be optionally substituted with one to three halogen atoms,
  (12) a pyridylsulfonylaminocarbonyl group,
  (13) a mono- or di-$C_{1-6}$ alkylaminosulfonylaminocarbonyl group,

(14) a 4- to 7-membered cyclic aminosulfonylaminocarbonyl group,
(15) a 4- to 10-membered saturated heterocyclic oxycarbonyl group,
(16) a $C_{1-6}$ alkoxycarbonyl group which may be optionally substituted with
    (a) a $C_{1-6}$ alkoxy group which may be optionally substituted with a $C_{1-6}$ alkoxy group,
    (b) a $C_{3-7}$ cycloalkoxy group,
    (c) a mono- or di-$C_{1-6}$ alkylamino group,
    (d) a 4- to 7-membered cyclic amino group,
    (e) a mono- or di-$C_{1-6}$ alkylaminocarbonyl group, or
    (f) a 4- to 7-membered cyclic amino group,
    (g) a $C_{3-7}$ cycloalkyl group which may be optionally substituted with one to three halogen atoms, or
    (h) a 4- to 7-membered saturated heterocyclic group which may be optionally substituted with one to four, same or different groups selected from the group consisting of a halogen atom and a $C_{1-6}$ alkyl group,
(17) a group represented by formula (4b):

[Formula 15]

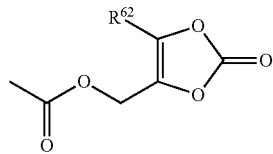

(4b)

wherein $R^{62}$ represents a hydrogen atom or a $C_{1-4}$ alkyl group, or
(18) a group represented by the following formula (5b):

[Formula 16]

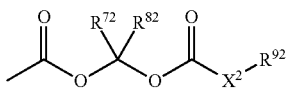

(5b)

wherein $X^2$ represents a single bond or an oxygen atom;
$R^{72}$ and $R^{82}$ each independently represent a hydrogen atom or a $C_{1-4}$ alkyl group; and
$R^{92}$ represents a $C_{1-4}$ alkyl group or a $C_{4-7}$ cycloalkyl group.

[16] The compound according to any one of [1] to [15], or a pharmaceutically acceptable salt thereof, wherein
$R^m$ represents
(1) a hydrogen atom,
(2) a cyano group,
(3) a carboxyl group,
(4) an amino group which may be optionally substituted with one or two, same or different groups selected from the group consisting of:
    (a) a $C_{1-6}$ alkyl group which may be optionally substituted with one to three halogen atoms, a cyano group, a hydroxy group, a carboxyl group, a $C_{1-6}$ alkoxy group, a $C_{3-10}$ cycloalkyl group, or a $C_{1-6}$ alkoxycarbonylamino group,
    (b) a $C_{3-10}$ cycloalkyl group which may be optionally substituted with one to three halogen atoms or a $C_{1-6}$ alkyl group,
    (c) a phenyl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group,
    (d) a 5- or 6-membered heteroaryl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group, and
    (e) a 4- to 6-membered saturated heterocyclic group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group,
(5) an aminocarbonyl group wherein the amino may be optionally substituted with one or two, same or different groups selected from the group consisting of (a) to (e) in (4) above,
(6) a 4- to 10-membered cyclic amino group which may be optionally substituted with one to four, same or different groups selected from the group consisting of:
    (a) a halogen atom,
    (b) a cyano group,
    (c) a hydroxy group,
    (d) a $C_{1-6}$ alkyl group which may be optionally substituted with
        (i) one to three halogen atoms,
        (ii) a carboxyl group,
        (iii) an aminocarbonyl group wherein the amino may be optionally substituted with one or two, same or different groups selected from the group consisting of (a) to (e) in (4) above,
        (iv) a 4- to 10-membered cyclic aminocarbonyl group which may be optionally substituted with a halogen atom, a cyano group, a hydroxy group, a $C_{1-6}$ alkyl group, a $C_{1-6}$ alkoxy group, or a $C_{1-6}$ alkoxycarbonylamino group, or
        (v) a $C_{1-6}$ alkoxycarbonylamino group,
    (e) a $C_{1-6}$ alkoxy group which may be optionally substituted with
        (i) one to three halogen atoms,
        (ii) a carboxyl group,
        (iii) an aminocarbonyl group, wherein the amino may be optionally substituted with one or two, same or different groups selected from the group consisting of (a) to (e) in (4) above,
        (iv) a 4- to 10-membered cyclic aminocarbonyl group which may be optionally substituted with a halogen atom, a cyano group, a hydroxy group, a $C_{1-6}$ alkyl group, a $C_{1-6}$ alkoxy group, or a $C_{1-6}$ alkoxycarbonylamino group, or
        (v) a $C_{1-6}$ alkoxycarbonylamino group, and
    (f) a $C_{1-6}$ alkoxycarbonylamino group,
(7) a 4- to 10-membered cyclic aminocarbonyl group which may be optionally substituted with one to four, same or different groups selected from the group consisting of (a) to (f) in (6) above,
(8) a 4- to 10-membered saturated heterocyclic group which may be optionally substituted with one to four, same or different groups selected from the group consisting of:
    (a) a halogen atom,
    (b) a cyano group,
    (c) a hydroxy group,
    (d) a carboxyl group,
    (e) a $C_{1-6}$ alkyl group which may be optionally substituted with
        (i) one to three halogen atoms,
        (ii) a carboxyl group, (iii) an aminocarbonyl group wherein the amino may be optionally substituted with one or two, same or different groups selected from the group consisting of (a) to (e) in (4) above, (iv) a 4- to 10-membered cyclic aminocarbonyl group which may be optionally substituted with one to four, same or different groups selected from the group consisting of a halogen atom, a cyano group, a hydroxy group, a $C_{1-6}$ alkyl group, a $C_{1-6}$ alkoxy group, and a $C_{1-6}$ alkoxycarbonylamino group, or (v) a $C_{1-6}$ alkoxycarbonylamino group, (f) a $C_{1-6}$ alkoxy group which may be optionally substituted with (i) one to three halogen atoms, (ii) a carboxyl group, (iii) an aminocarbonyl group, wherein the amino may be optionally substituted with one or two, same or different groups selected from the group consisting of (a) to (e) in (4) above, (iv) a 4- to 10-membered cyclic aminocarbonyl group which may be optionally substituted with one to four, same or different groups selected from the group consisting of (a) to (f) in (6) above, or (v) a $C_{1-6}$ alkoxycarbonylamino group, (g) a $C_{1-6}$ alkoxycarbonylamino group which may be optionally substituted with one to three halogen atoms, (h) a $C_{1-6}$ alkylsulfonylamino group which may be optionally substituted with one to three halogen atoms or a $C_{1-6}$ alkyl group, (i) a $C_{3-10}$ cycloalkyl group which may be optionally substituted with one to three halogen atoms or a $C_{1-6}$ alkyl group, (j) a $C_{1-6}$ alkylcarbonylamino group which may be optionally substituted with one to three halogen atoms, (k) an amino group which may be optionally substituted with one or two different groups selected from the group consisting of (a) to (e) in (4) above, (l) an aminocarbonyl group, wherein the amino may be optionally substituted with one or two different groups selected from the group consisting of (a) to (e) in (4) above, (m) a 4- to 10-membered cyclic amino group which may be optionally substituted with one to four, same or different groups selected from the group consisting of (a) to (f) in (6) above, (n) a 4- to 10-membered cyclic aminocarbonyl group which may be optionally substituted with one to four, same or different groups selected from the group consisting of (a) to (f) in (6) above, and (o) a $C_{1-6}$ alkoxycarbonyl group, (9) a $C_{1-6}$ alkyl group which may be optionally substituted with (a) one to three halogen atoms, (b) a carboxyl group, (c) a cyano group, (d) a $C_{1-6}$ alkoxy group, (e) a phenyl group which may be optionally substituted with one to four, same or different groups selected from the group consisting of (a) to (o) in (8) above, (f) a 5- to 6-membered heteroaryl group which may be optionally substituted with one to four, same or different groups selected from the group consisting of (a) to (o) in (8) above, (g) a 4- to 10-membered saturated heterocyclic group which may be optionally substituted with one to four, same or different groups selected from the group consisting of (a) to (o) in (8) above, (h) a hydroxy group, (i) an aminocarbonyl group wherein the amino may be optionally substituted with one or two different groups selected from the group consisting of (a) to (e) in (4) above, (j) a 4- to 10-membered cyclic aminocarbonyl group which may be optionally substituted with one to four, same or different groups selected from the group consisting of (a) to (f) in (6) above, (k) a $C_{1-6}$ alkoxycarbonylamino group, (l) a $C_{1-6}$ alkoxycarbonyl group which may be optionally substituted with one or two, same or different groups selected from the group consisting of:

(l1) a $C_{1-6}$ alkoxy group which may be optionally substituted with one to three halogen atoms, (l2) a $C_{3-7}$ cycloalkoxy group which may be optionally substituted with one to three halogen atoms, (l3) a mono- or di-$C_{1-6}$ alkylamino group wherein the alkyl may be optionally substituted with one to three halogen atoms, (l4) a 4- to 7-membered cyclic amino group which may be optionally substituted with one to three halogen atoms, a $C_{1-6}$ alkyl group, or a $C_{1-6}$ alkoxy group, (l5) a mono- or di-$C_{1-6}$ alkylaminocarbonyl group, wherein the alkyl may be optionally substituted with one to three halogen atoms, (l6) a 4- to 7-membered cyclic aminocarbonyl group which may be optionally substituted with one to three halogen atoms, a $C_{1-6}$ alkyl group, or a $C_{1-6}$ alkoxy group, and (l7) a $C_{3-7}$ cycloalkyl group which may be optionally substituted with one to three halogen atoms, (m) a group represented by formula (4c):

[Formula 17]

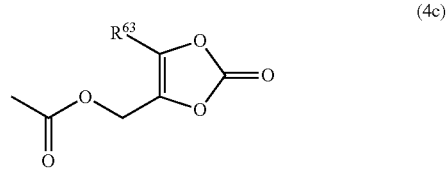

(4c)

wherein $R^{63}$ represents (m1) a hydrogen atom, (m2) a $C_{1-4}$ alkyl group which may be optionally substituted with one to three halogen atoms or a $C_{1-4}$ alkoxy group, (m3) a $C_{3-6}$ cycloalkyl group which may be optionally substituted with a $C_{1-4}$ alkoxy group, or (m4) a $C_{6-10}$ aryl group which may be optionally substituted with a $C_{1-4}$ alkyl group, one to three halogen atoms, or a $C_{1-4}$ alkoxy group, or (n) a group represented by formula (5c):

[Formula 18]

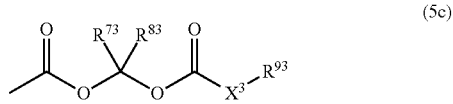

(5c)

wherein $X^3$ represents a single bond or an oxygen atom; $R^{73}$ and $R^{83}$ each independently represent (n11) a hydrogen atom, (n12) a $C_{1-4}$ alkyl group which may be optionally substituted with one to three halogen atoms; a $C_{3-6}$ cycloalkyl group which may be optionally substituted with a $C_{1-4}$ alkoxy group; a 5- or 6-membered saturated heterocyclic group, or a 5- or 6-membered saturated heterocyclic oxy group, (n13) a $C_{3-10}$ cycloalkyl group which may be optionally substituted with one to three halogen atoms or a $C_{1-4}$ alkoxy group, (n14) a $C_{6-10}$ aryl group which may be optionally substituted with one to four, same or different groups selected from the group consisting of a halogen atom and a $C_{6-10}$ aryl group which may be optionally substituted with one to four, same or different groups selected from the group consisting of a halogen atom and a $C_{1-4}$ alkoxy group, (n15) a 5- or 6-membered saturated heterocyclic group which may be optionally substituted with one to three halogen atoms, (n16) a 5- to 10-membered heteroaryl group which may be optionally substituted with one to four, same or different groups selected from the group consisting of a $C_{1-4}$ alkyl group and a $C_{1-4}$ alkoxy group; and $R^{93}$ represents (n21) a $C_{1-6}$ alkyl group which may be optionally substituted with one to three halogen atoms, a hydroxy group, a $C_{1-4}$ alkoxy group, a carboxyl group, a 5- or 6-membered saturated heterocyclic group, a $C_{3-6}$ cycloalkyl group, a $C_{1-4}$ alkoxycarbonyl group, a $C_{1-4}$ alkoxycarbonylamino group, an amino group, a mono- or di-$C_{1-6}$ alkylamino group, a 4- to 7-membered cyclic amine group, one or two nitrooxy groups, an aminocarbonyl group, or a 4- to 7-membered cyclic aminocarbonyl group, (n22) a $C_{3-10}$ cycloalkyl group which may be optionally substituted with a hydroxy group, (n23) a $C_{6-10}$ aryl group which may be optionally substituted with a halogen atom, a $C_{1-4}$ alkyl group, a $C_{1-4}$ alkoxy group, or a $C_{1-4}$ alkylcarbonyloxy group, (n24) a 5- to 10-membered heteroaryl group, or (n25) a 5- or 6-membered saturated heterocyclic group which may be optionally substituted with a $C_{1-4}$ alkyl group or a $C_{1-4}$ alkoxy group,

(10) a $C_{2-6}$ alkenyl group which may be optionally substituted with (a) to (n) in (9) above,

(11) a $C_{1-6}$ alkoxy group which may be optionally substituted with (a) to (n) in (9) above,

(12) a $C_{1-6}$ alkoxycarbonylamino group which may be optionally substituted with one to three halogen atoms,

(13) a $C_{1-6}$ alkylsulfonylamino group which may be optionally substituted with one to three halogen atoms,

(14) a $C_{1-6}$ alkylsulfonylaminocarbonyl group which may be optionally substituted with one to three halogen atoms,

(15) a $C_{3-10}$ cycloalkylsulfonylaminocarbonyl group which may be optionally substituted with one to three halogen atoms,

(16) a phenylsulfonylaminocarbonyl group which may be optionally substituted with one to four, same or different groups selected from the group consisting of (a) to (o) in (8) above,

(17) a 5- or 6-membered heteroarylsulfonylaminocarbonyl group which may be optionally substituted with one to four, same or different groups selected from the group consisting of (a) to (o) in (8) above,

(18) a 4- to 10-membered saturated heterocyclic sulfonylaminocarbonyl group which may be optionally substituted with one to four, same or different groups selected from the group consisting of (a) to (o) in (8) above,

(19) an aminosulfonylaminocarbonyl group, wherein the amino may be optionally substituted with one or two, same or different $C_{1-6}$ alkyl groups which may be optionally substituted with one to three halogen atoms,

(20) a 4- to 7-membered cyclic aminosulfonylaminocarbonyl group which may be optionally substituted with one to four, same or different groups selected from the group consisting of (a) to (o) in (8) above,

(21) a $C_{4-7}$ cycloalkoxycarbonyl group which may be optionally substituted with one to four, same or different groups selected from the group consisting of (a) to (o) in (8) above,

(22) a 4- to 10-membered saturated heterocyclic oxycarbonyl group which may be optionally substituted with one to four, same or different groups selected from the group consisting of (a) to (o) in (8) above,

(23) a $C_{1-6}$ alkoxycarbonyl group which may be optionally substituted with one or two, same or different groups selected from the group consisting of:

(a) a $C_{1-6}$ alkoxy group which may be optionally substituted with one to three halogen atoms or a $C_{1-6}$ alkoxy group, (b) a $C_{3-7}$ cycloalkoxy group which may be optionally substituted with one to three halogen atoms, (c) a mono- or di-$C_{1-6}$ alkylamino group wherein the alkyl may be optionally substituted with one to three halogen atoms, (d) a 4- to 7-membered cyclic amino group which may be optionally substituted with one to three halogen atoms, a $C_{1-6}$ alkyl group or a $C_{1-6}$ alkoxy group, (e) a mono- or di-$C_{1-6}$ alkylaminocarbonyl group wherein the alkyl may be optionally substituted with one to three halogen atoms, (f) a 4- to 7-membered cyclic aminocarbonyl group which may be optionally substituted with one to three halogen atoms, a $C_{1-6}$ alkyl group or a $C_{1-6}$ alkoxy group, (g) a $C_{3-7}$ cycloalkyl group, and (h) a 4- to 10-membered saturated heterocyclic group which may be optionally substituted with one to four, same or different groups selected from the group consisting of (a) to (o) in (8) above,

(24) a group represented by the following formula (4c):

[Formula 19]

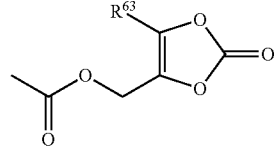

(4c)

wherein $R^{63}$ represents (a) a hydrogen atom, (b) a $C_{1-4}$ alkyl group which may be optionally substituted with one to three halogen atoms, a $C_{1-4}$ alkyl group or a $C_{1-4}$ alkoxy group, (c) a $C_{3-6}$ cycloalkyl group which may be optionally substituted with a $C_{1-4}$ alkyl group or a $C_{1-4}$ alkoxy group, or (d) a $C_{6-10}$ aryl group which may be optionally substituted with one to three halogen atoms, a $C_{1-4}$ alkyl group, or a $C_{1-4}$ alkoxy group, or

(25) a group represented by the following formula (5c):

[Formula 20]

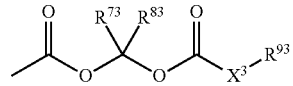

(5c)

wherein $X^3$ represents a single bond or an oxygen atom; $R^{73}$ and $R^{83}$ each independently represent (a) a hydrogen atom, (b) a $C_{1-4}$ alkyl group which may be optionally substituted with one to three halogen atoms; a $C_{3-6}$ cycloalkyl group which may be optionally substituted with a $C_{1-4}$ alkoxy group; a 5- or 6-membered saturated heterocyclic group, or a 5- or 6-membered saturated heterocyclic oxy group, (c) a $C_{3-10}$ cycloalkyl group which may be optionally substituted with one to three halogen atoms or a $C_{1-4}$ alkoxy group,
(d) a $C_{6-10}$ aryl group which may be optionally substituted with one to four, same or different groups selected from the group consisting of a halogen atom and a $C_{6-10}$ aryl group which may be optionally substituted with one to four, same or different groups selected from the group consisting of a halogen atom and a $C_{1-4}$ alkoxy group,
(e) a 5- or 6-membered saturated heterocyclic group which may be optionally substituted with one to three halogen atoms, and
(f) a 5- to 10-membered heteroaryl group which may be optionally substituted with one to four, same or different groups selected from the group consisting of a $C_{1-4}$ alkyl group and a $C_{1-4}$ alkoxy group; and
$R^{93}$ represents
(a) a $C_{1-6}$ alkyl group which may be optionally substituted with one to three halogen atoms, a hydroxy group, a $C_{1-4}$ alkoxy group, a carboxy group, a 5- or 6-membered saturated heterocyclic group, a $C_{3-6}$ cycloalkyl group, a $C_{1-4}$ alkoxycarbonyl group, a $C_{1-4}$ alkoxycarbonylamino group, an amino group, a mono- or di-$C_{1-6}$ alkylamino group, a 4- to 7-membered cyclic amine group, one or two nitrooxy groups, an aminocarbonyl group, or a 4- to 7-membered cyclic aminocarbonyl group,
(b) a $C_{3-10}$ cycloalkyl group which may be optionally substituted with a hydroxy group,
(c) a $C_{6-10}$ aryl group which may be optionally substituted with a $C_{1-4}$ alkyl group, a $C_{1-4}$ alkoxy group, or a $C_{1-4}$ alkylcarbonyloxy group,
(d) a 5- to 10-membered heteroaryl group, or
(e) a 5- or 6-membered saturated heterocyclic group which may be optionally substituted with a $C_{1-4}$ alkyl group or a $C_{1-4}$ alkoxy group.
[17] The compound according to any one of [1] to [16], or a pharmaceutically acceptable salt thereof, wherein
$R^m$ represents
(1) a cyano group,
(2) a carboxyl group,
(3) an aminocarbonyl group which may be optionally substituted with one or two, same or different $C_{1-6}$ alkyl groups which may be optionally substituted with one to three halogen atoms or a $C_{1-6}$ alkoxy group,
(4) a 4- to 6-membered cyclic aminocarbonyl group which may be optionally substituted with one to four, same or different groups selected from the group consisting of one to three halogen atoms, a $C_{1-6}$ alkyl group, a $C_{1-6}$ alkoxy group, a $C_{1-6}$ alkoxycarbonyl group and a $C_{1-6}$ alkoxycarbonylamino group,
(5) a tetrazolyl group,
(6) a 5-oxo-1,2,4-oxadiazol-3-yl group,
(7) a $C_{1-6}$ alkyl group which may be optionally substituted with
(a) a hydroxy group,
(b) a carboxyl group,
(c) a $C_{1-6}$ alkoxycarbonyl group,
(d) a group represented by formula (4d):

[Formula 21]

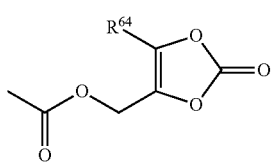

(4d)

wherein $R^{64}$ represents a hydrogen atom or a $C_{1-4}$ alkyl group, or
(e) a group represented by formula (5d):

[Formula 22]

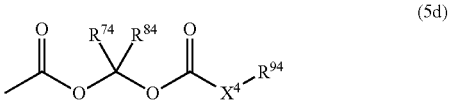

(5d)

wherein $X^4$ represents a single bond or an oxygen atom; $R^{74}$ and $R^{84}$ each independently represent a hydrogen atom or a $C_{1-4}$ alkyl group; and
$R^{94}$ represents a $C_{1-4}$ alkyl group or a $C_{4-7}$ cycloalkyl group,
(8) a $C_{1-6}$ alkoxycarbonylamino group,
(9) a $C_{1-6}$ alkylsulfonylamino group,
(10) a $C_{1-6}$ alkylsulfonylaminocarbonyl group which may be optionally substituted with one to three halogen atoms,
(11) a pyridylsulfonylaminocarbonyl group,
(12) a mono- or di-$C_{1-6}$ alkylaminosulfonylaminocarbonyl group,
(13) a 4- to 7-membered cyclic aminosulfonylaminocarbonyl group,
(14) a 4- to 10-membered saturated heterocyclic oxycarbonyl group,
(15) a $C_{1-6}$ alkoxycarbonyl group which may be optionally substituted with
(a) a $C_{1-6}$ alkoxy group which may be optionally substituted with a $C_{1-6}$ alkoxy group,
(b) a $C_{3-7}$ cycloalkoxy group,
(c) a mono- or di-$C_{1-6}$ alkylamino group,
(d) a 4- to 7-membered cyclic amino group,
(e) a mono- or di-$C_{1-6}$ alkylaminocarbonyl group,
(f) a 4- to 7-membered cyclic aminocarbonyl group,
(g) a $C_{3-7}$ cycloalkyl group, or
(h) a 4- to 7-membered saturated heterocyclic group which may be optionally substituted with one to four, same or different groups selected from the group consisting of a halogen atom and a $C_{1-6}$ alkyl group,
(16) a group represented by formula (4d):

[Formula 23]

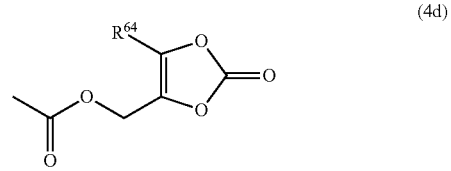

(4d)

wherein $R^{64}$ represents a hydrogen atom or a $C_{1-4}$ alkyl group, or
(19) a group represented by formula (5d):

[Formula 24]

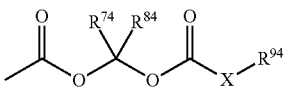

(5d)

wherein X represents a single bond or an oxygen atom; $R^{74}$ and $R^{84}$ each independently represent a hydrogen atom or a $C_{1-4}$ alkyl group; and
$R^{94}$ represents a $C_{1-4}$ alkyl group or a $C_{4-7}$ cycloalkyl group.

[18] The compound according to [1] or a pharmaceutically acceptable salt thereof, represented by formula (6):

[Formula 25]

(6)

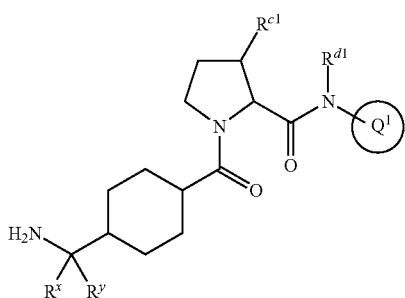

wherein $R^x$ and $R^y$ each independently represent a hydrogen atom or an optionally substituted $C_{1-6}$ alkyl group, or these may together form an optionally substituted 3- to 6-membered cycloalkane ring;

$R^{c1}$ represents an optionally substituted 4- to 7-membered cycloalkyl group, an optionally substituted phenyl group, an optionally substituted pyridyl group, an optionally substituted phenoxy group, an optionally substituted 4- to 7-membered cyclic amino group or an optionally substituted $C_{1-6}$ alkoxy group;

$R^{d1}$ represents a hydrogen atom or an optionally substituted $C_{1-6}$ alkyl group; and ring $Q^1$ is a group represented by any one of formulae (7a) to (7i):

[Formula 26]

(7a)

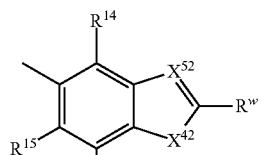

(7b)

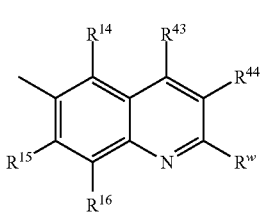

(7c)

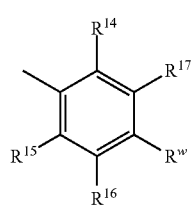

(7d)

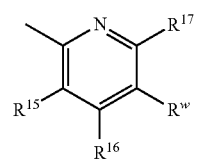

(7e)

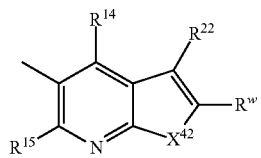

(7f)

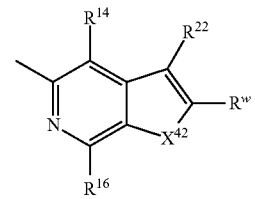

(7g)

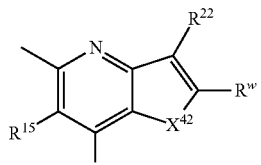

(7h)

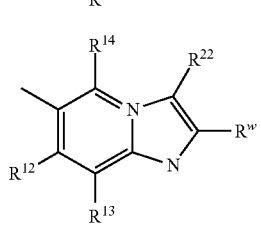

(7i)

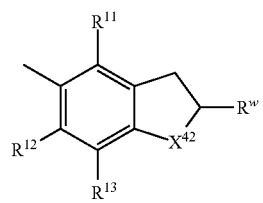

wherein $X^{52}$ represents $CR^{22}$ or N;

$X^{42}$ represents $NR^{32}$, O, or S;

$R^{14}, R^{15}, R^{16}, R^{17}, R^{43}$ and $R^{44}$ each independently represent a hydrogen atom, a halogen atom, an optionally substituted $C_{1-6}$ alkyl group or an optionally substituted $C_{1-6}$ alkoxy group;

$R^{22}$ represents a hydrogen atom, a halogen atom, a cyano group or an optionally substituted $C_{1-6}$ alkyl group;

$R^{32}$ represents a hydrogen atom or an optionally substituted $C_{1-6}$ alkyl group;

$R^w$ represents a hydrogen atom, a carboxyl group, a cyano group, an optionally substituted aminocarbonyl group, an optionally substituted 4- to 7-membered cyclic aminocarbonyl group, a tetrazolyl group, a 5-oxo-1,2,4-oxadiazol-3-yl group, an optionally substituted $C_{1-6}$ alkylsulfonylaminocarbonyl group, an optionally substituted 5- to 10-membered heteroarylsulfonylaminocarbonyl group, an optionally substituted aminosulfonylaminocarbonyl group, an optionally substituted 4- to 7-membered cyclic aminosulfonylaminocarbonyl group, an optionally substituted 4- to 7-membered saturated heterocyclic oxycarbonyl group or an optionally substituted $C_{1-6}$ alkoxycarbonyl group.

[19] The compound according to [18] or a pharmaceutically acceptable salt thereof, wherein $R^x$ and $R^y$ each independently represent a hydrogen atom or a $C_{1-6}$ alkyl group which may be optionally substituted with one to three halogen atoms, or these may together form a 3- to 6-membered cycloalkane ring which may be optionally substituted with one to three halogen atoms;

$R^{c1}$ represents
(1) a cyclohexyl group which may be optionally substituted with one to four, same or different groups selected from the group consisting of:
   (a) a halogen atom,
   (b) a $C_{1-6}$ alkyl group which may be optionally substituted with one to three halogen atoms, and
   (c) a $C_{1-6}$ alkoxy group which may be optionally substituted with one to three halogen atoms,
(2) a phenyl group which may be optionally substituted with one to four, same or different groups selected from the group consisting of (a) to (c) in (1) above,
(3) a pyridyl group which may be optionally substituted with one to four, same or different groups selected from the group consisting of (a) to (c) in (1) above,
(4) a 4- to 7-membered cyclic amino group which may be optionally substituted with one to four, same or different groups selected from the group consisting of (a) to (c) in (1) above, or
(5) a benzyloxy group which may be optionally substituted with one to four, same or different groups selected from the group consisting of (a) to (c) in (1) above;

$R^{d1}$ represents a hydrogen atom or a $C_{1-6}$ alkyl group;
$X^{52}$ represents $CR^{22}$;
$X^{42}$ represents $NR^{32}$, S or O;
$R^{14}$, $R^{15}$, $R^{16}$, $R^{17}$, $R^{43}$ and $R^{44}$ each independently represent a hydrogen atom, a halogen atom, a $C_{1-6}$ alkyl group which may be optionally substituted with one to three halogen atoms, or a $C_{1-6}$ alkoxy group which may be optionally substituted with one to three halogen atoms;
$R^{22}$ represents a hydrogen atom, a halogen atom or a $C_{1-6}$ alkyl group;
$R^{32}$ represents a hydrogen atom or a $C_{1-6}$ alkyl group which may be optionally substituted with one to three halogen atoms; and $R^w$ represents
(1) a hydrogen atom,
(2) a carboxyl group,
(3) a cyano group,
(4) an aminocarbonyl group which may be optionally substituted with one or two, same or different $C_{1-6}$ alkyl groups which may be optionally substituted with one to three halogen atoms,
(5) a 4- to 7-membered cyclic aminocarbonyl group which may be optionally substituted with one to four, same or different groups selected from the group consisting of:
   (a) a halogen atom,
   (b) a $C_{1-6}$ alkyl group which may be optionally substituted with one to three halogen atoms, and
   (c) a $C_{1-6}$ alkoxy group which may be optionally substituted with one to three halogen atoms,
(6) a tetrazolyl group,
(7) a 5-oxo-1,2,4-oxadiazol-3-yl group,
(8) a $C_{1-6}$ alkylsulfonylaminocarbonyl group which may be optionally substituted with one to three halogen atoms,
(9) a pyridylsulfonylaminocarbonyl group,
(10) a mono- or di-$C_{1-6}$ alkylaminosulfonylaminocarbonyl group,
(11) a 4- to 7-membered cyclic aminosulfonylaminocarbonyl group,
(12) a 4- to 7-membered saturated heterocyclic oxycarbonyl group,
(13) a $C_{1-6}$ alkoxycarbonyl group which may be optionally substituted with
   (a) a $C_{1-6}$ alkoxy group which may be optionally substituted with a $C_{1-6}$ alkoxy group,
   (b) a $C_{3-7}$ cycloalkoxy group,
   (c) a mono- or di-$C_{1-6}$ alkylamino group,
   (d) a 4- to 7-membered cyclic amino group,
   (e) a mono- or di-$C_{1-6}$ alkylaminocarbonyl group,
   (f) a 4- to 7-membered cyclic aminocarbonyl group,
   (g) a $C_{3-7}$ cycloalkyl group, or
   (h) a 4- to 7-membered saturated heterocyclic group which may be optionally substituted with one to four, same or different groups selected from the group consisting of a halogen atom and a $C_{1-6}$ alkyl group,
(14) a group represented by formula (4e):

[Formula 27]

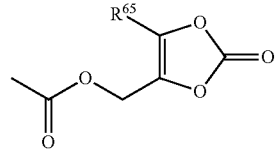

(4e)

wherein $R^{65}$ represents a hydrogen atom or a $C_{1-4}$ alkyl group, or
(15) a group represented by formula (5e):

[Formula 28]

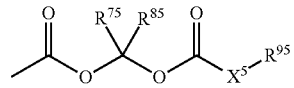

(5e)

wherein $X^5$ represents a single bond or an oxygen atom; $R^{75}$ and $R^{85}$ each independently represent a hydrogen atom or a $C_{1-4}$ alkyl group; and
$R^{95}$ represents a $C_{1-4}$ alkyl group or a $C_{4-7}$ cycloalkyl group.

[20] The compound according to [18] or [19], or a pharmaceutically acceptable salt thereof, wherein
ring $Q^1$ is a group represented by formula (7a) or (7c).

[21] The compound according to [20] or a pharmaceutically acceptable salt thereof, wherein
ring $Q^1$ is a group represented by formula (7a); $X^{52}$ represents $CR^{22}$; $X^{42}$ represents NH or O; and $R^{14}$, $R^{15}$, $R^{16}$ and $R^{22}$ each independently represent a hydrogen atom or a halogen atom.

[22] The compound according to any one of [18] to [21], or a pharmaceutically acceptable salt thereof, wherein
$R^x$ and $R^y$ each independently represent a hydrogen atom or a methyl group which may be optionally substituted with one to three fluorine atoms.

[23] The compound according to any one of [18] to [22], or a pharmaceutically acceptable salt thereof, wherein
$R^{c1}$ represents
(1) a cyclohexyl group which may be optionally substituted with one to four, same or different groups selected from the group consisting of:
   (a) a halogen atom,
   (b) a $C_{1-6}$ alkyl group which may be optionally substituted with one to three halogen atoms, and
   (c) a $C_{1-6}$ alkoxy group which may be optionally substituted with one to three halogen atoms, (2) a phenyl group which may be optionally substituted with one to four, same or different groups selected from the group consisting of (a) to (c) in (1) above, or (3) a 4- to 7-membered cyclic amino group which may be optionally substituted with one to four, same or different groups selected from the group consisting of (a) to (c) in (1) above.

[24] The compound according to [23] or a pharmaceutically acceptable salt thereof, wherein $R^{c1}$ represents a cyclohexyl group which may be optionally substituted with one to four, same or different groups selected from the group consisting of:

(a) a halogen atom, (b) a $C_{1-6}$ alkyl group which may be optionally substituted with one to three halogen atoms, and (c) a $C_{1-6}$ alkoxy group which may be optionally substituted with one to three halogen atoms.

[25] The compound according to any one of [18] to [24], or a pharmaceutically acceptable salt thereof, wherein $R^w$ represents (1) a carboxyl group, (2) a tetrazolyl group, (3) a 5-oxo-1,2,4-oxadiazol-3-yl group, (4) a $C_{1-6}$ alkylsulfonylaminocarbonyl group which may be optionally substituted with one to three halogen atoms, (5) a pyridylsulfonylaminocarbonyl group, (6) a mono- or di-$C_{1-6}$ alkylaminosulfonylaminocarbonyl group, (7) a 4- to 7-membered cyclic aminosulfonylaminocarbonyl group, (8) a $C_{1-6}$ alkoxycarbonyl group which may be optionally substituted with (a) a $C_{1-6}$ alkoxy group which may be optionally substituted with a $C_{1-6}$ alkoxy group, (b) a $C_{3-7}$ cycloalkoxy group, (c) a mono- or di-$C_{1-6}$ alkylamino group, (d) a 4- to 7-membered cyclic amino group, (e) a mono- or di-$C_{1-6}$ alkylaminocarbonyl group, (f) a 4- to 7-membered cyclic aminocarbonyl group, (g) a $C_{3-7}$ cycloalkyl group, or (h) a 4- to 7-membered saturated heterocyclic group which may be optionally substituted with one to four, same or different groups selected from the group consisting of a halogen atom and a $C_{1-6}$ alkyl group, (9) a group represented by the following formula (4e):

[Formula 29]

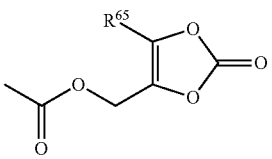

(4e)

wherein $R^{65}$ represents a hydrogen atom or a $C_{1-4}$ alkyl group, or

(10) a group represented by formula (5e):

[Formula 30]

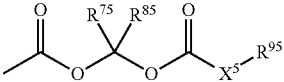

(5e)

wherein $X^5$ represents a single bond or an oxygen atom; $R^{75}$ and $R^{85}$ each independently represent a hydrogen atom or a $C_{1-4}$ alkyl group; and $R^{95}$ represents a $C_{1-4}$ alkyl group or a $C_{4-7}$ cycloalkyl group.

[26] The compound according to any one of [18] to [23], which is represented by any one of the following formulae, or a pharmaceutically acceptable salt thereof:

[Formula 31]

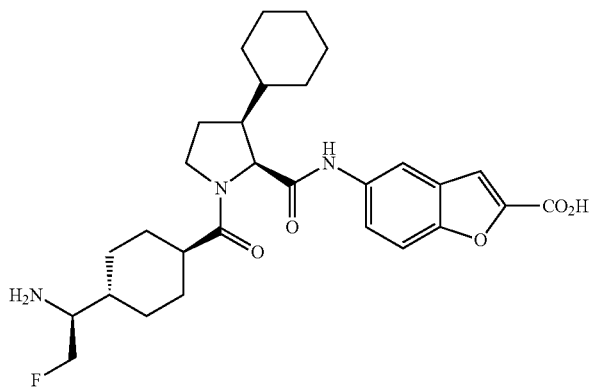

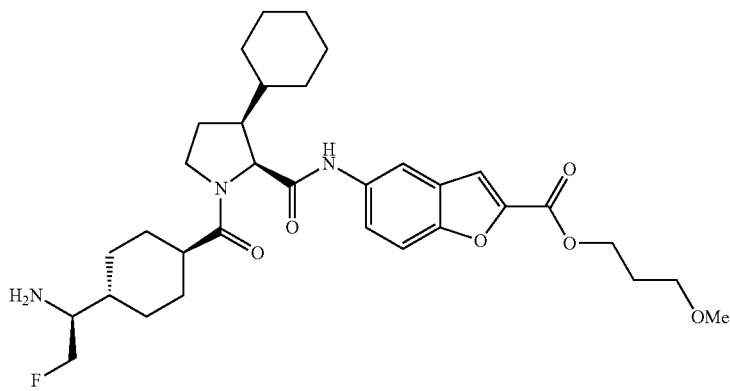

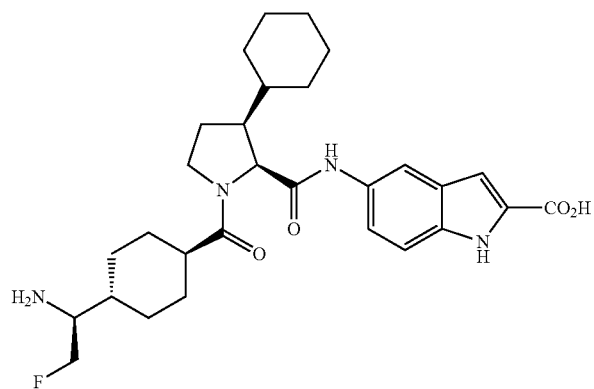
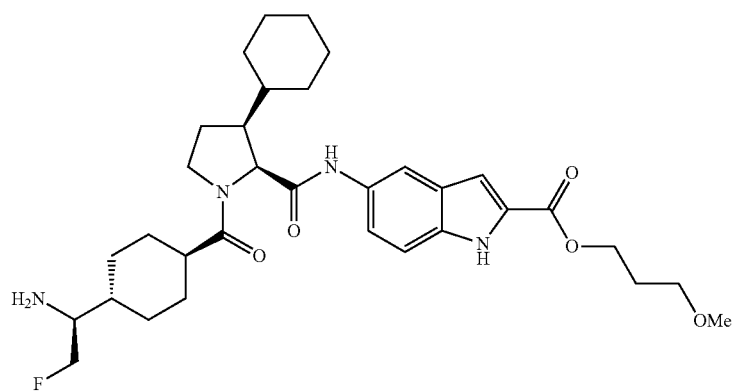
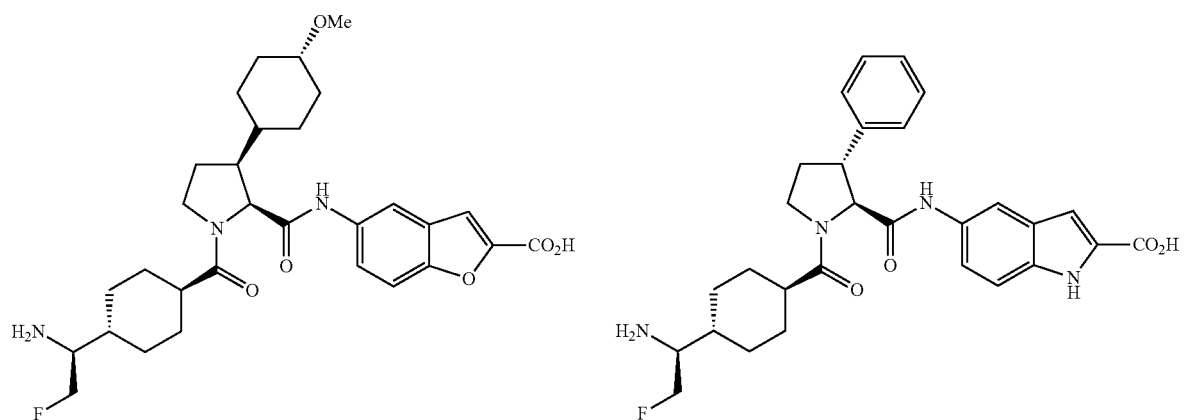
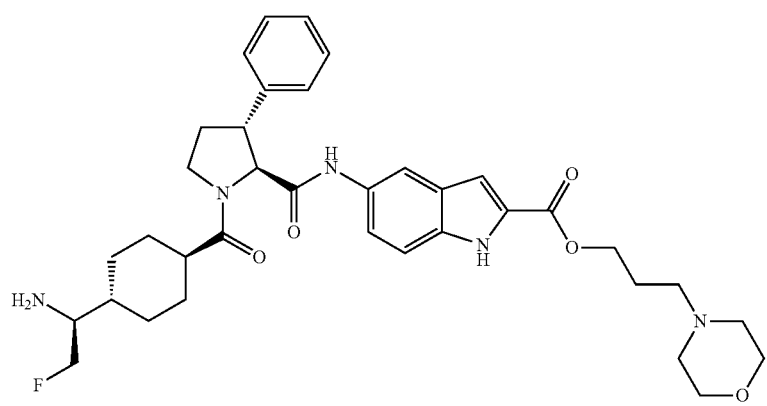

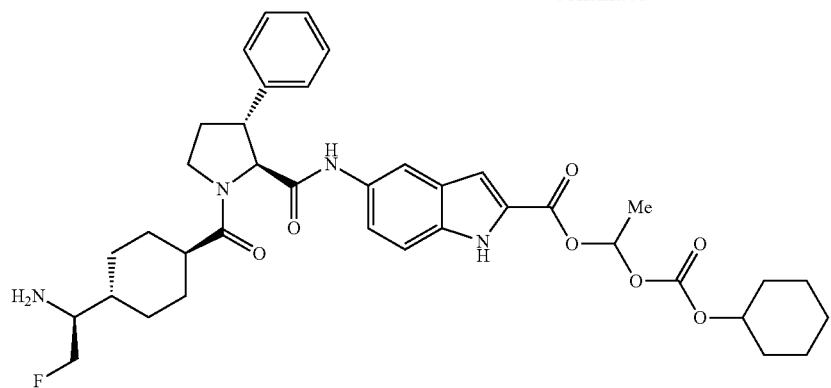
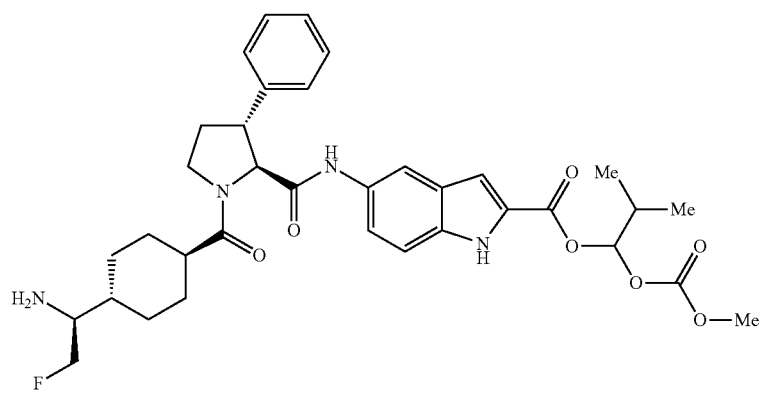
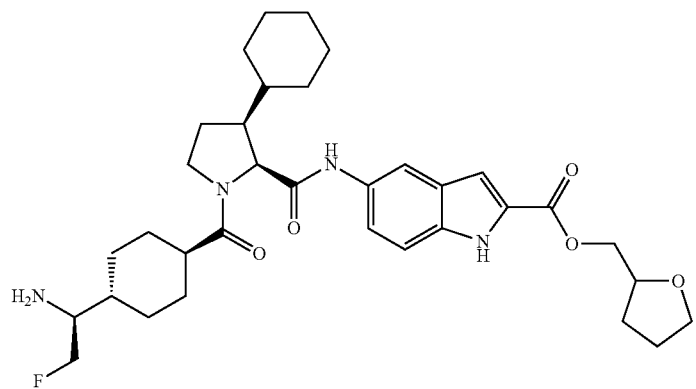
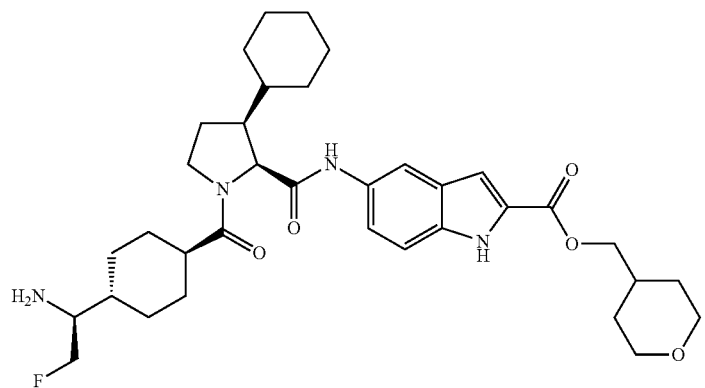

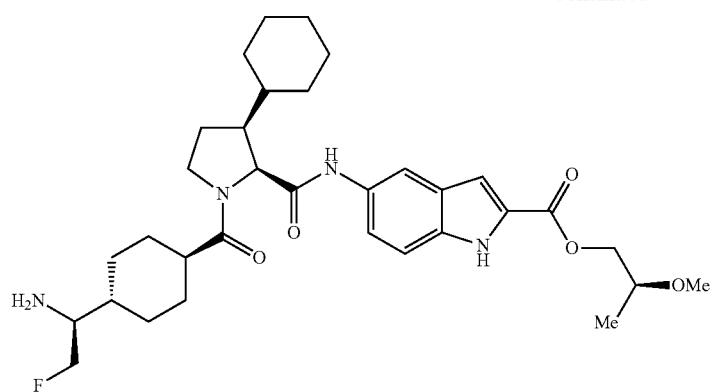
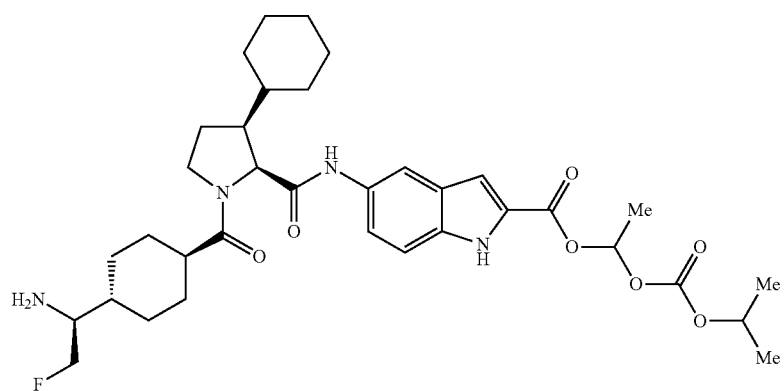
[Formula 32]
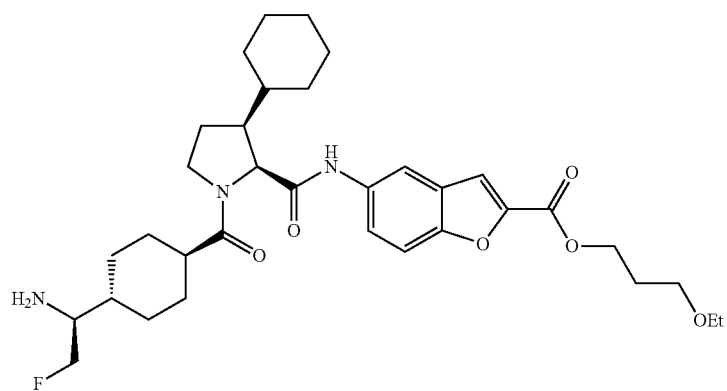

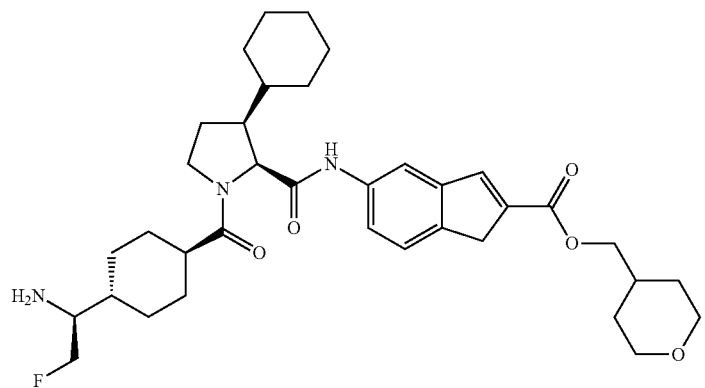
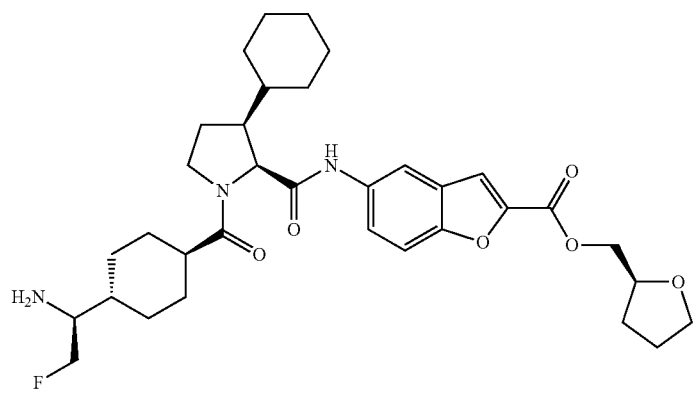
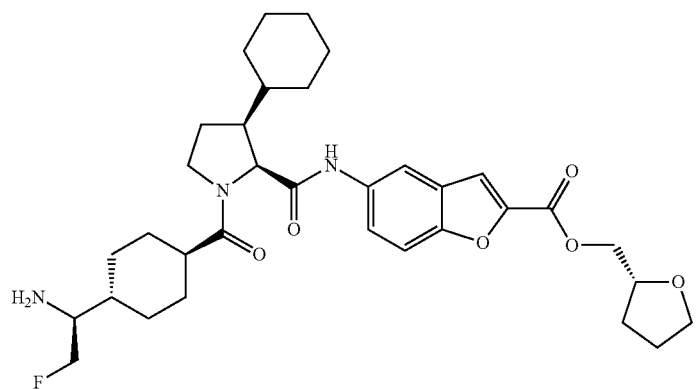
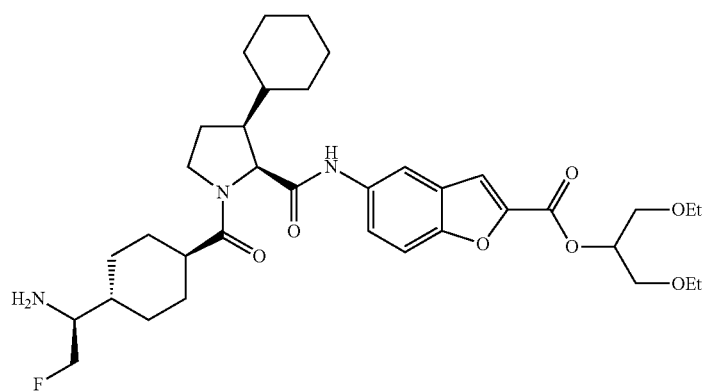

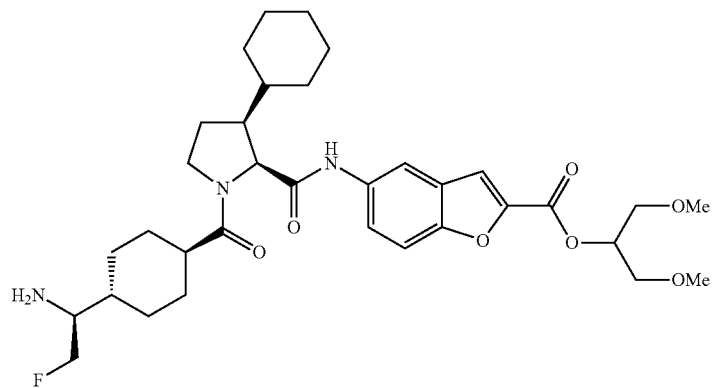
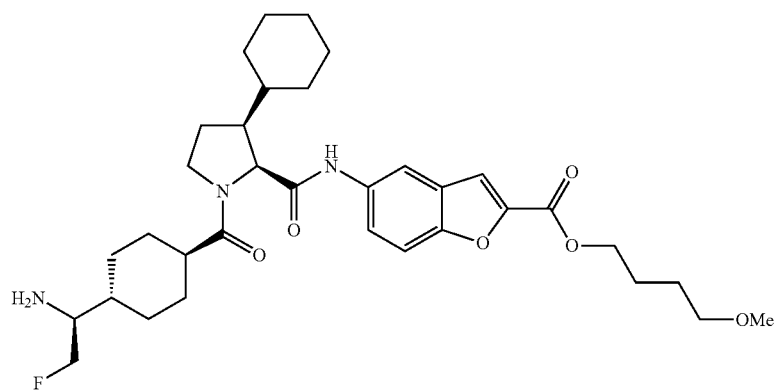
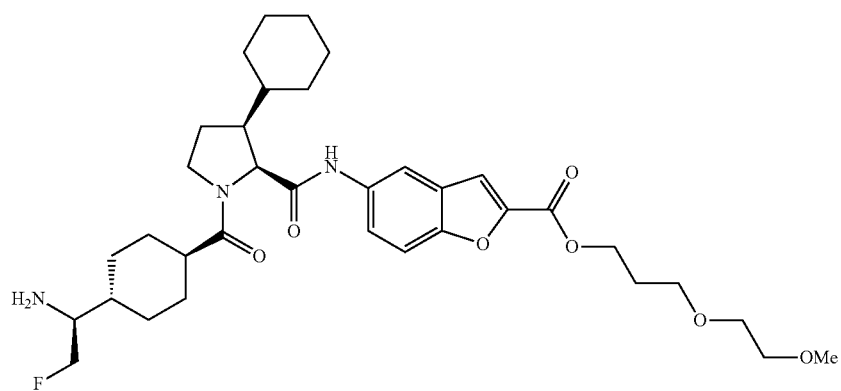
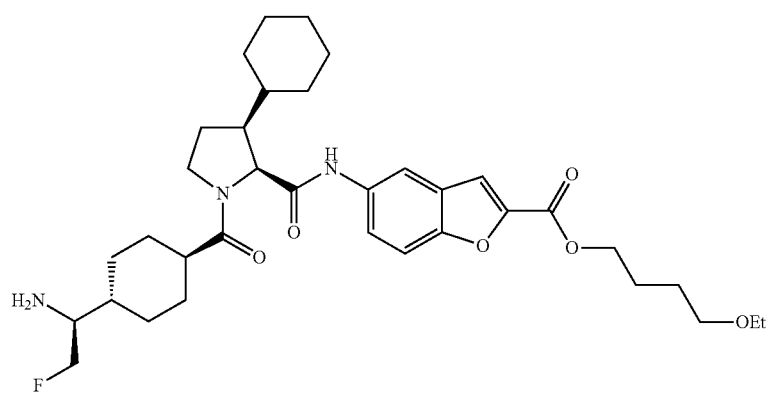

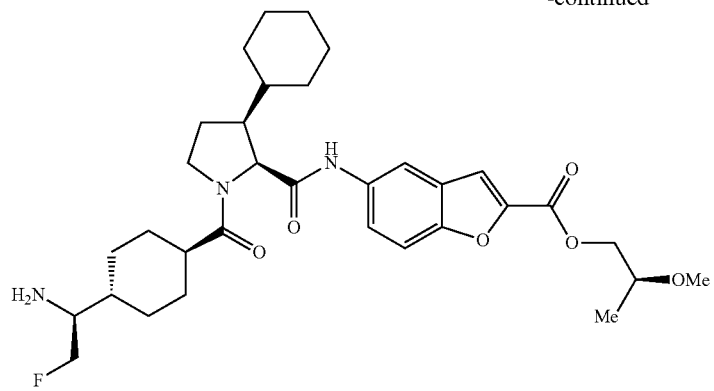
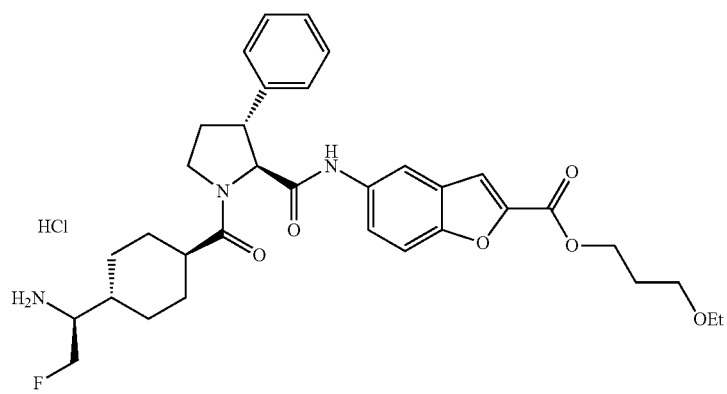
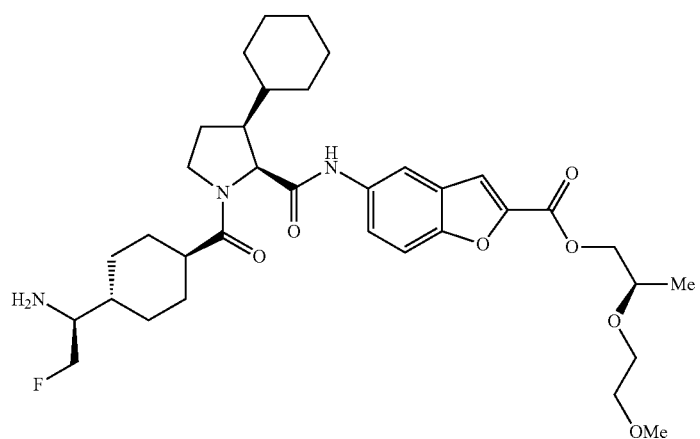
[Formula 33]
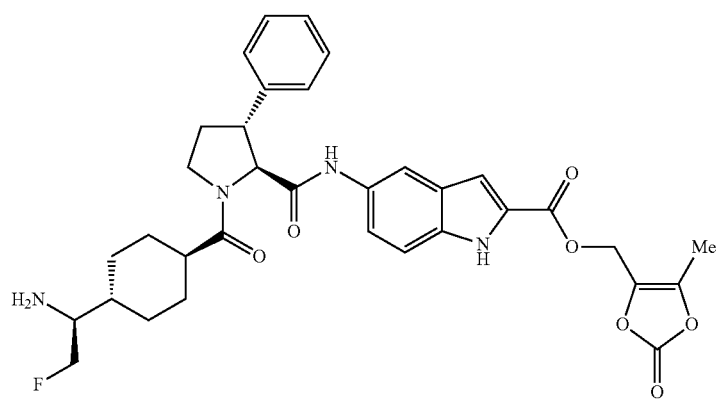

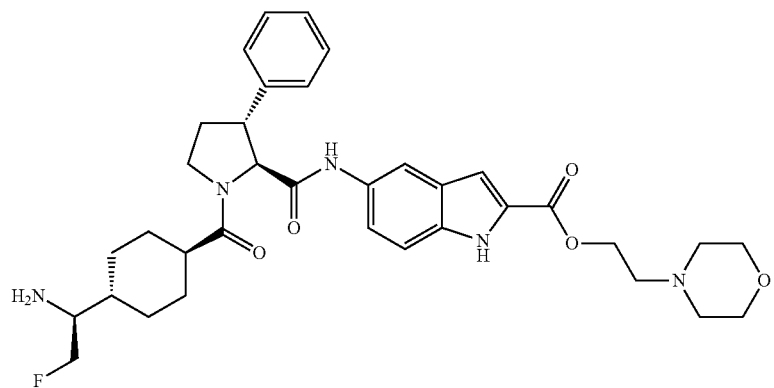
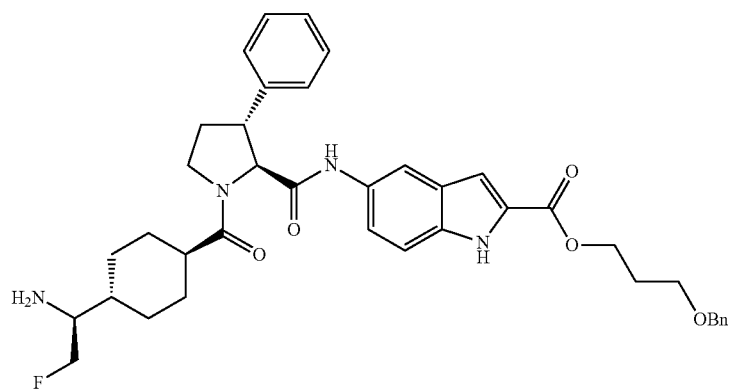
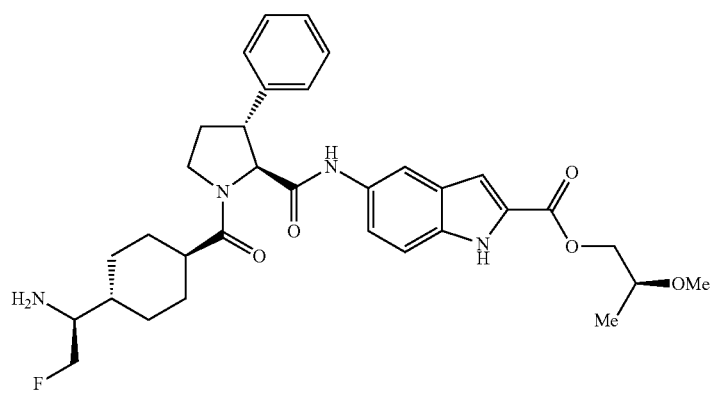
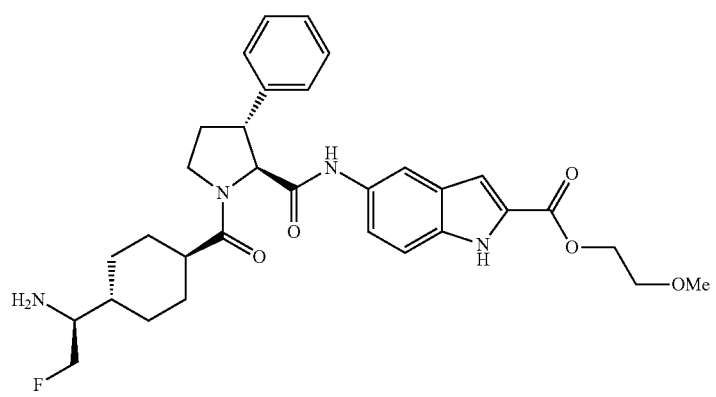

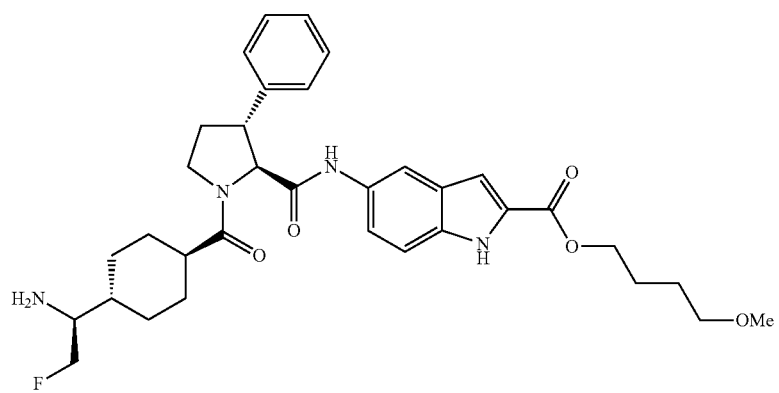
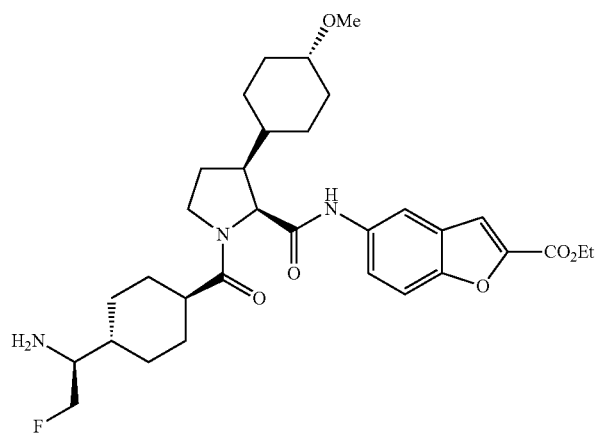
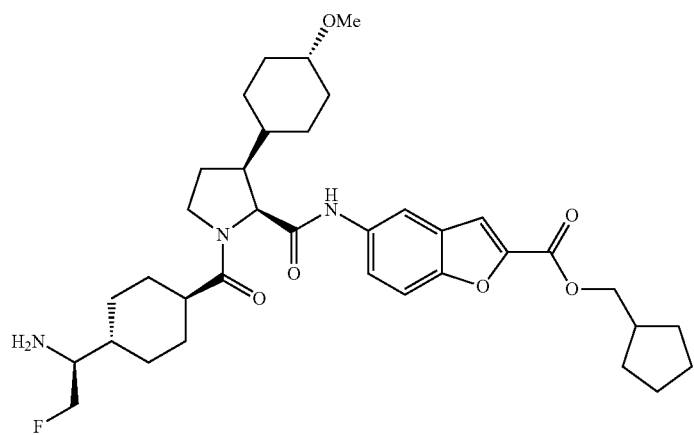
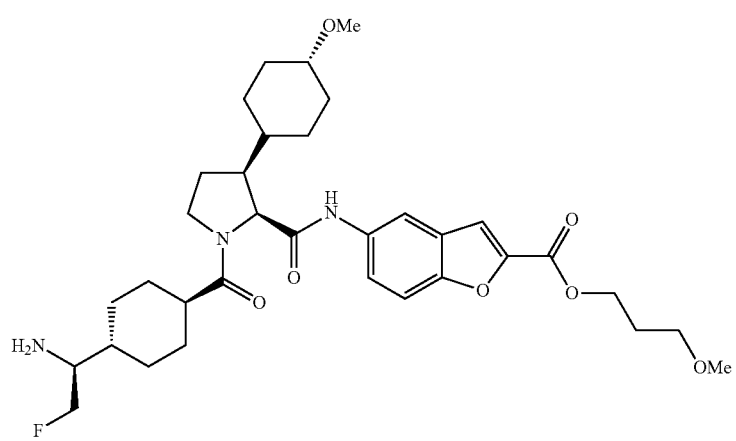

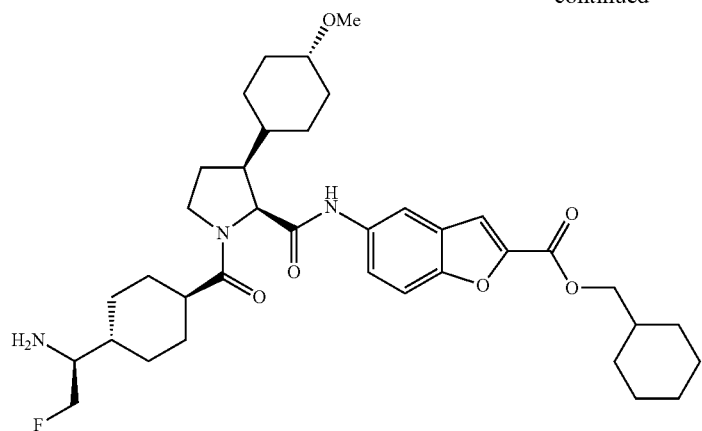
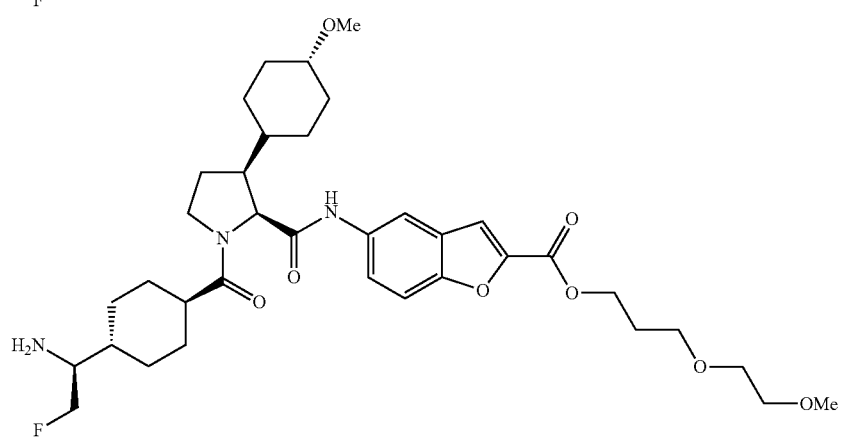
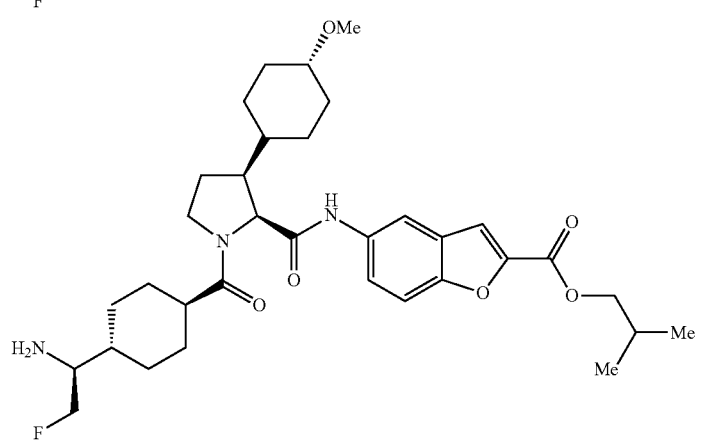
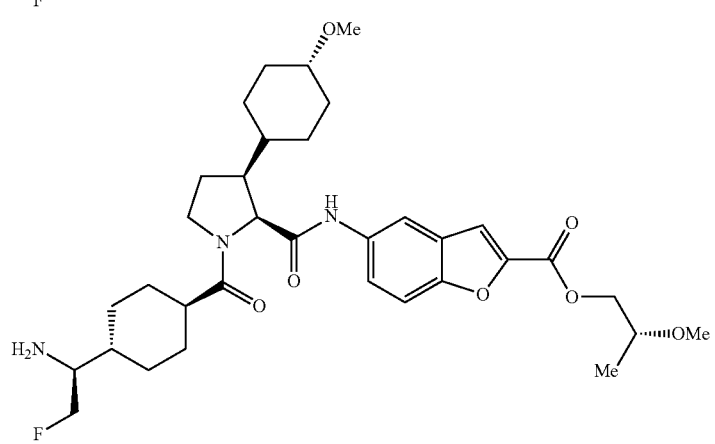

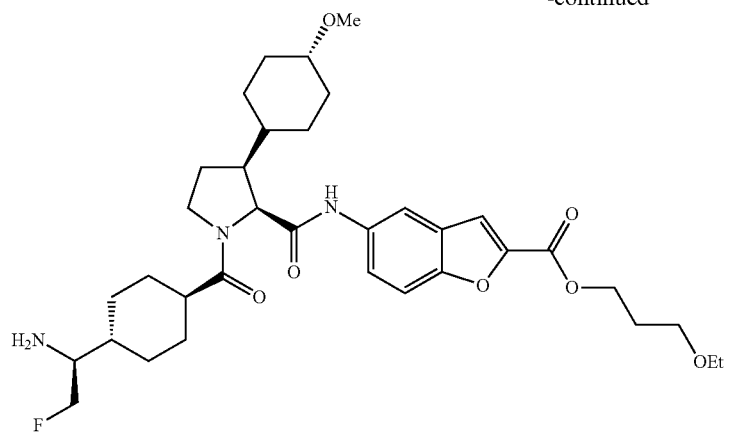
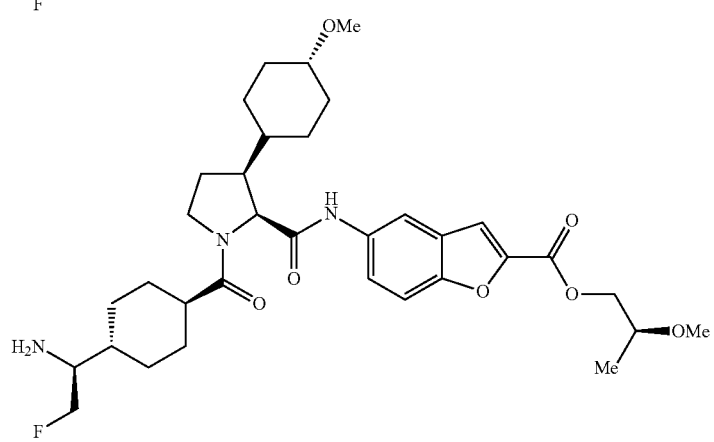
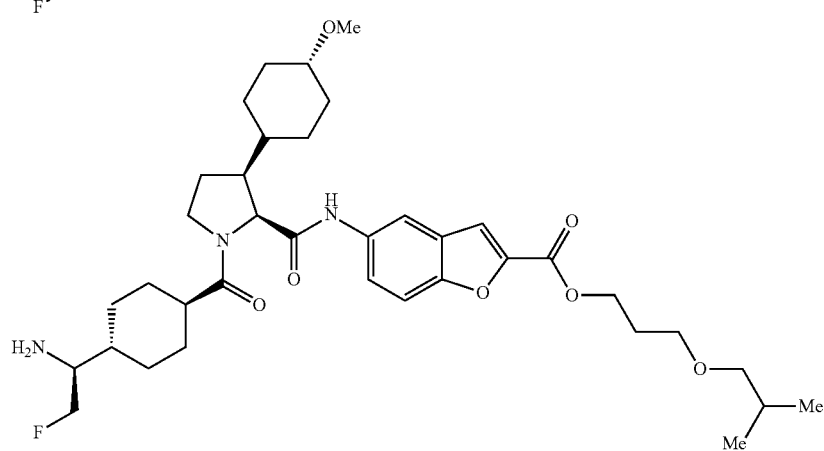
[Formula 34]
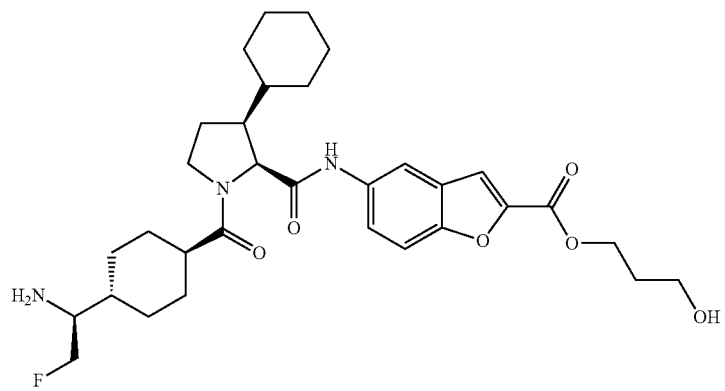

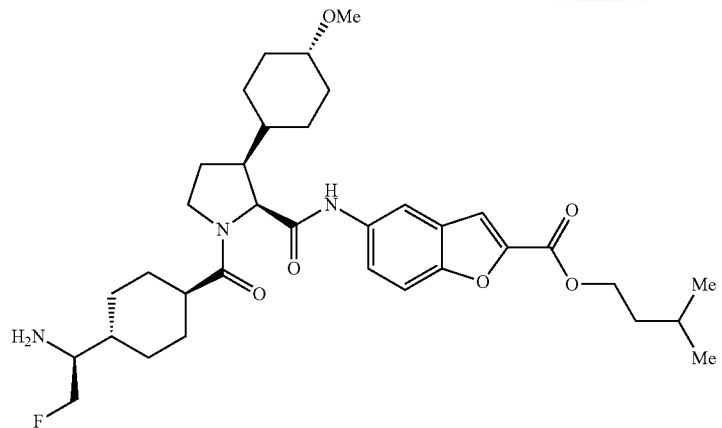
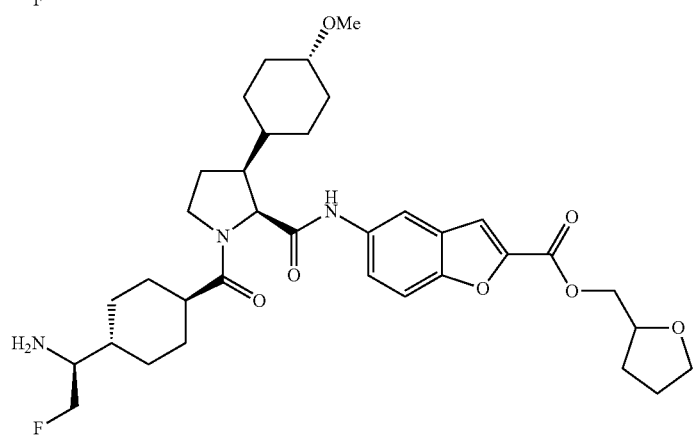
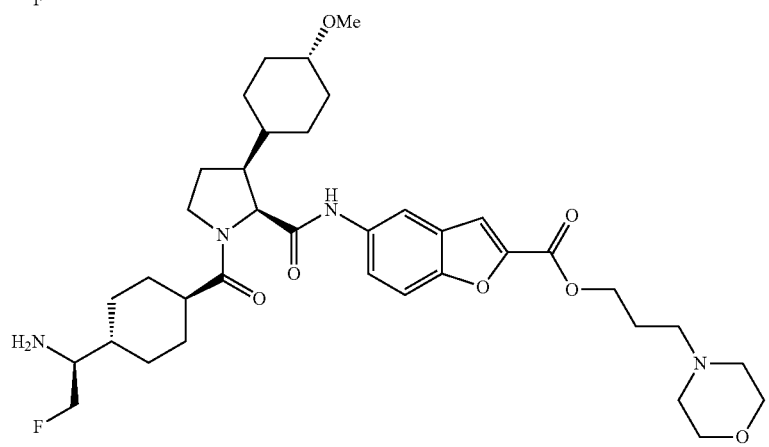
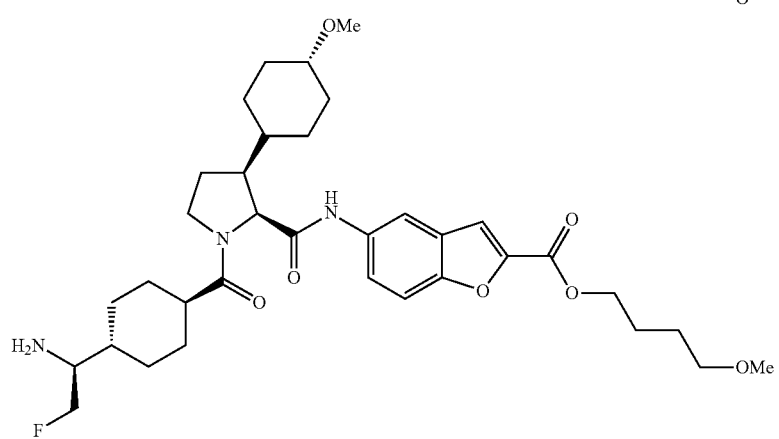

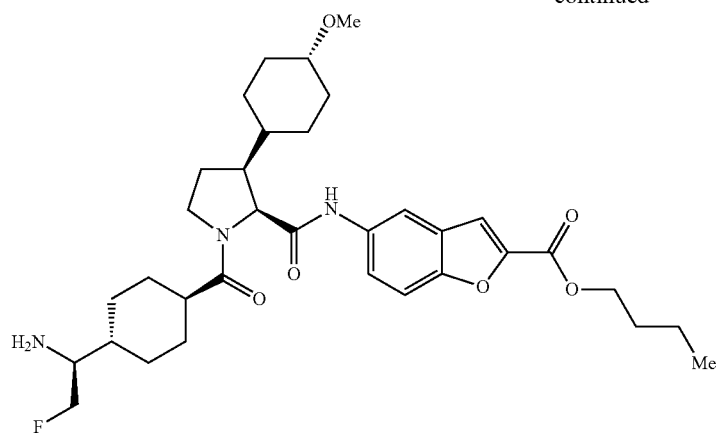
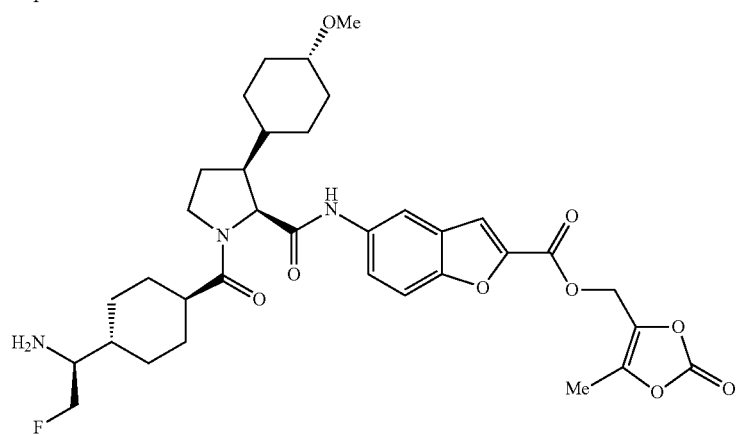
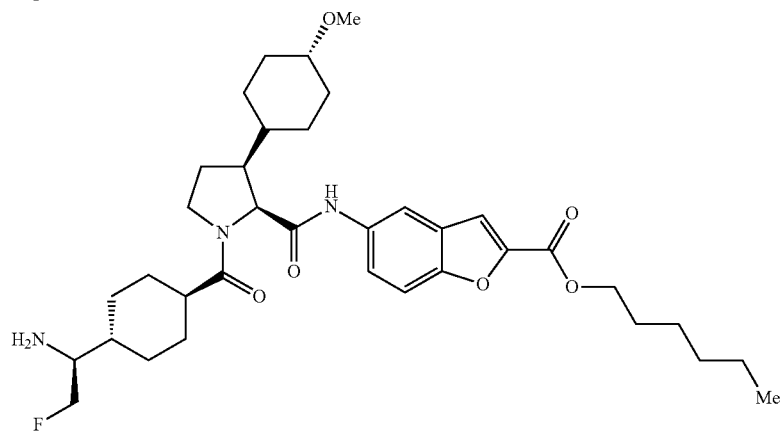
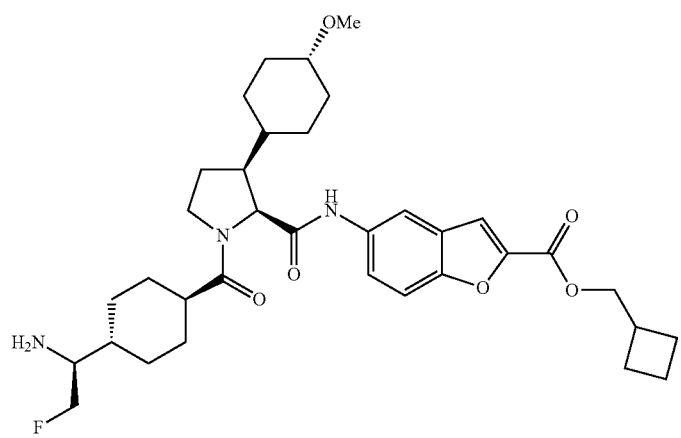

-continued
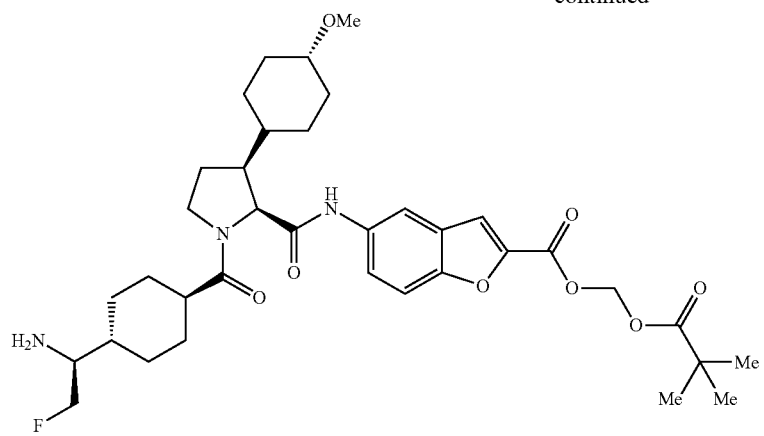
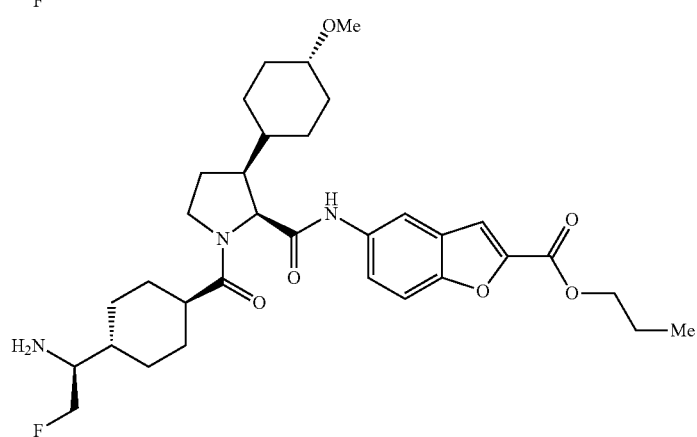
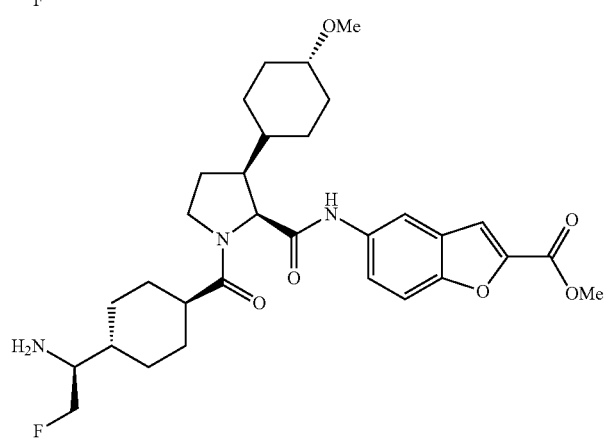
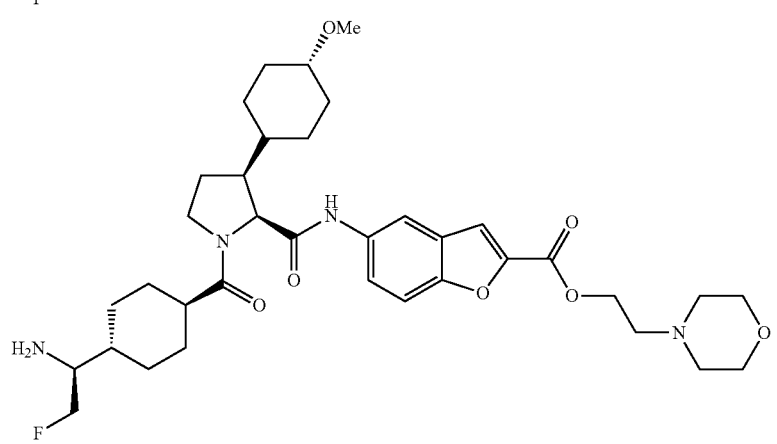

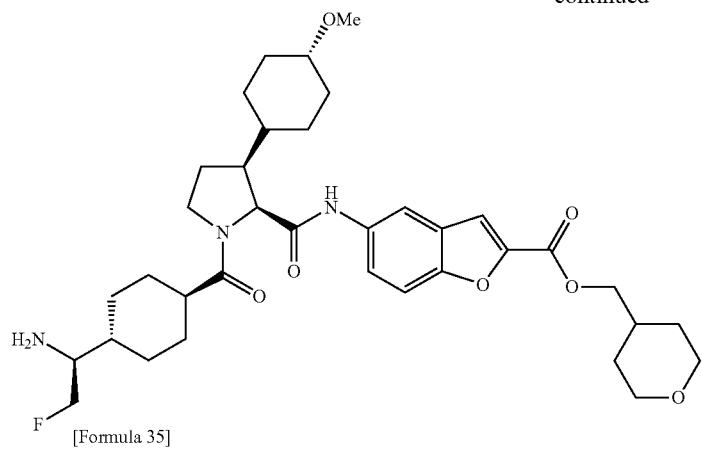
[Formula 35]
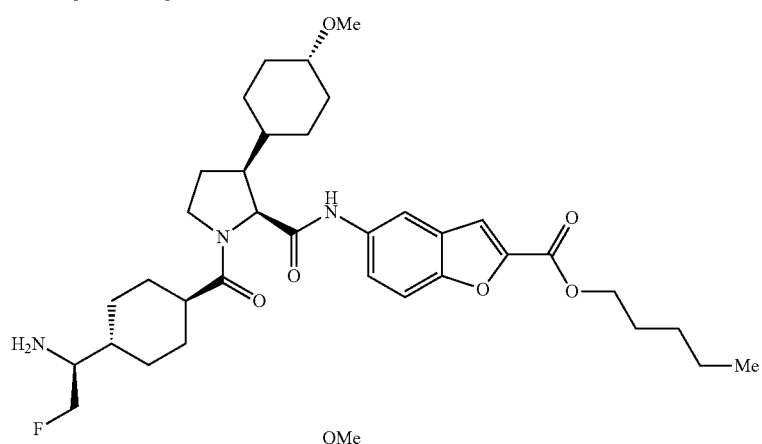
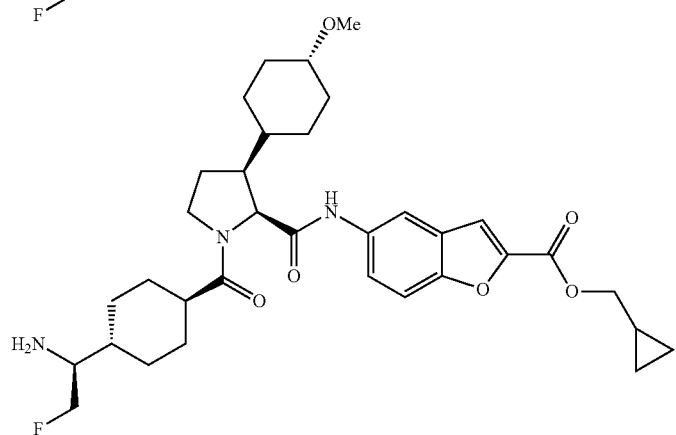
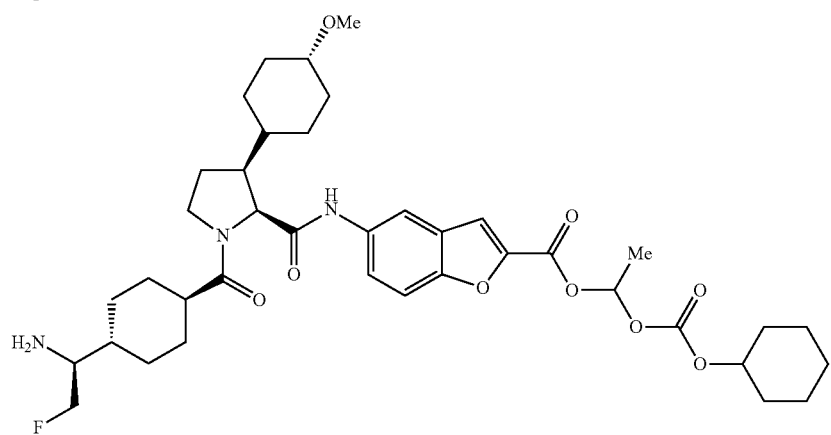

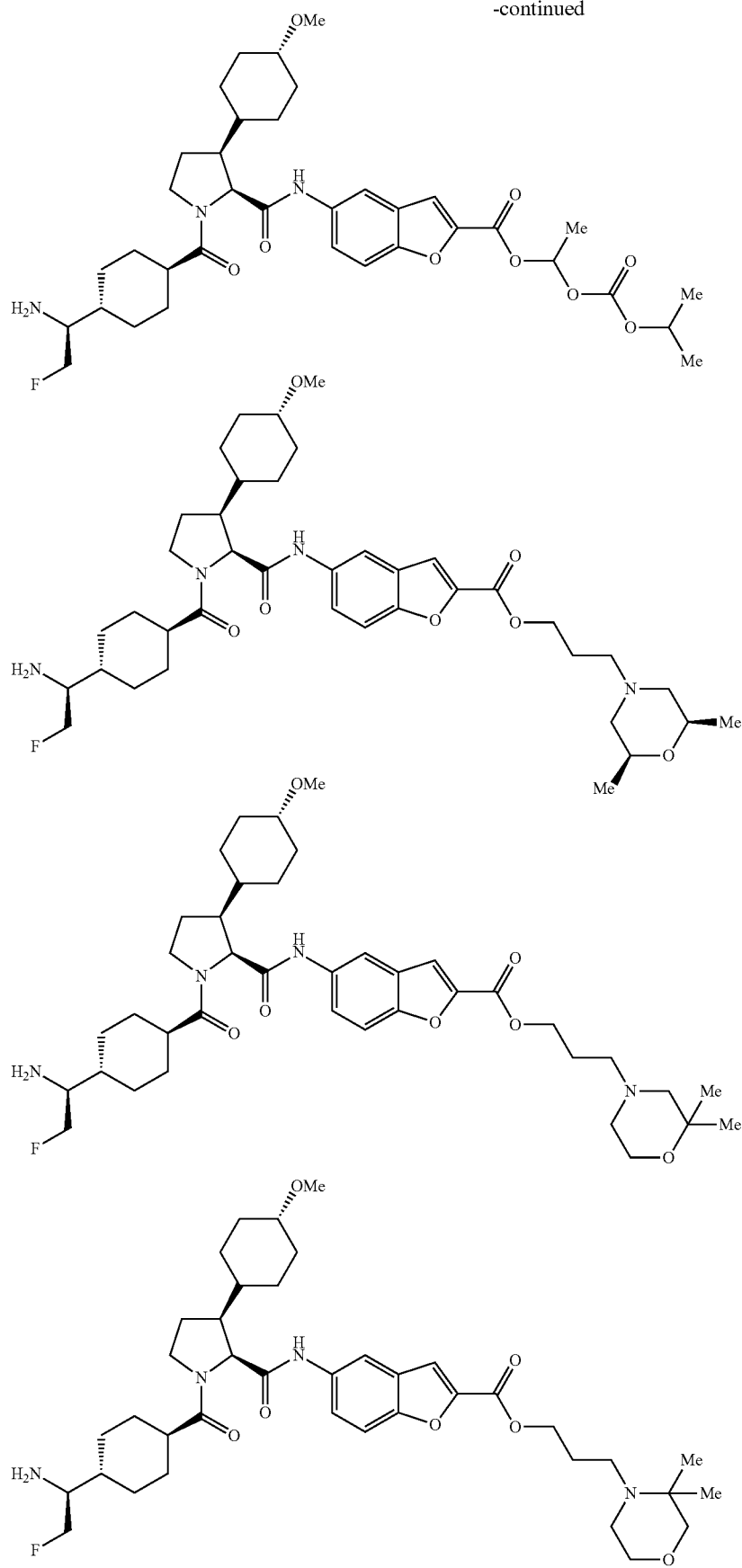

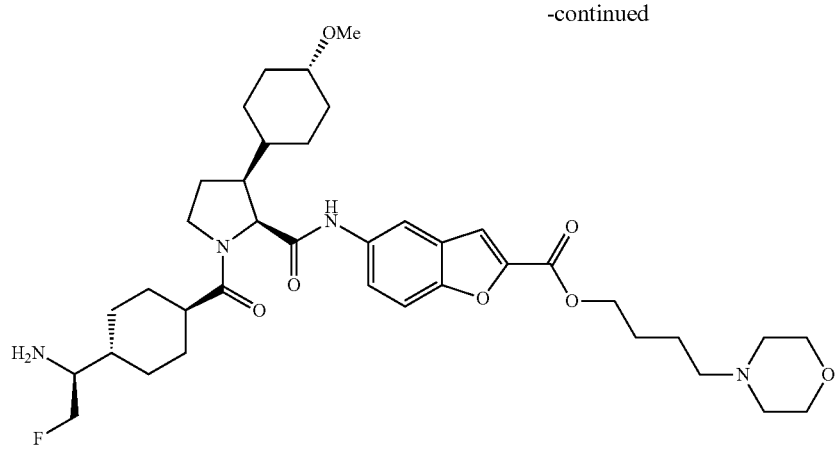
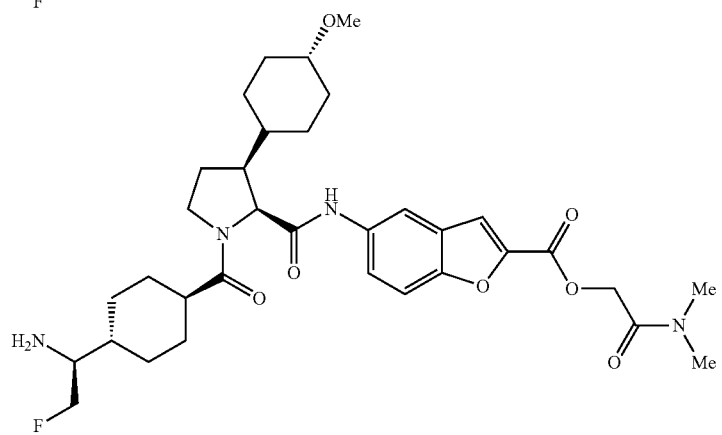
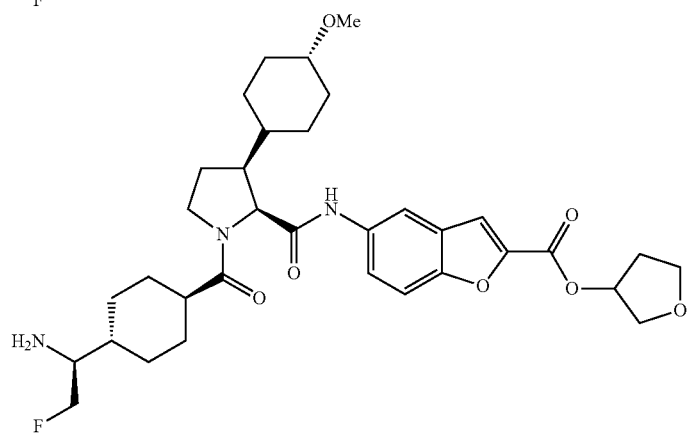
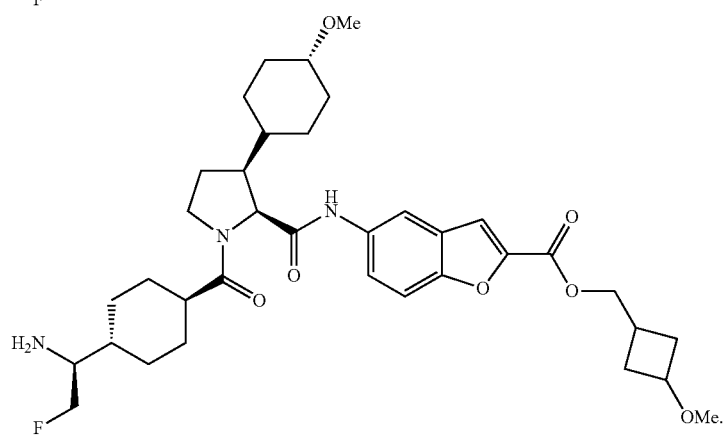

[27] A medicament comprising, as an active ingredient, the compound according to any one of [1] to [26] or a pharmaceutically acceptable salt thereof.

[28] An FXIa inhibitor comprising, as an active ingredient, the compound according to any one of [1] to [26] or a pharmaceutically acceptable salt thereof.

[29] An anticoagulant agent comprising, as an active ingredient, the compound according to any one of [1] to [26] or a pharmaceutically acceptable salt thereof.

[30] A therapeutic agent for thrombosis comprising, as an active ingredient, the compound according to any one of [1] to [26] or a pharmaceutically acceptable salt thereof.

[31] A therapeutic agent for thromboembolism comprising, as an active ingredient, the compound according to any one of [1] to [26] or a pharmaceutically acceptable salt thereof.

[32] Use of the compound according to any one of [1] to [26] or a pharmaceutically acceptable salt thereof for use in the manufacture of an FXIa inhibitor.

[33] Use of the compound according to any one of [1] to [26] or a pharmaceutically acceptable salt thereof for use in the manufacture of an anticoagulant agent.

[34] Use of the compound according to any one of [1] to [26] or a pharmaceutically acceptable salt thereof for use in peparing a therapeutic agent for thrombosis.

[35] Use of the compound according to any one of [1] to [26] or a pharmaceutically acceptable salt thereof for use in the manufacture of a therapeutic agent for thromboembolism.

[36] A method for inhibiting FXIa activity, which comprises administering the compound according to any one of [1] to [26] or a pharmaceutically acceptable salt thereof to a subject in need thereof.

[37] A method for suppressing blood coagulation, which comprises administering the compound according to any one of [1] to [26] or a pharmaceutically acceptable salt thereof to a subject in need thereof.

[38] A method for treating thrombosis, which comprises administering the compound according to any one of [1] to [26] or a pharmaceutically acceptable salt thereof to a subject in need thereof.

[39] A method for treating thromboembolism, which comprises administering the compound according to any one of [1] to [26] or a pharmaceutically acceptable salt thereof to a subject in need thereof.

Advantageous Effects of Invention

The compound of the present invention has FXIa-inhibitory activity and anticoagulant activity and is therefore useful as a therapeutic agent for thrombosis, thromboembolism or the like.

DESCRIPTION OF EMBODIMENTS

Figure 1:
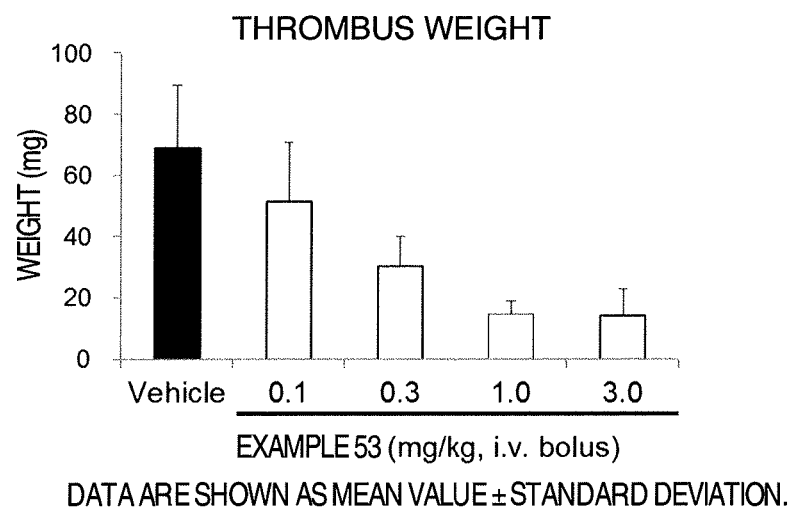
FIG. 1 is a view showing a change in thrombus weight by administration of the compound of Example 53 (Test Example 2).

Hereinafter, the present invention will be described more in detail. As described herein, the number of carbon atoms referred to in the definition of a "substituent" is expressed, for example, as "$C_{1-6}$". Specifically, the term "$C_{1-6}$ alkyl" has the same meaning as an alkyl group containing 1 to 6 carbon atoms.

A group defined as an "optionally substituted" group can be substituted with a possible number of substitute groups in a substitutable position(s), unless otherwise specified. For example, when an optionally substituted $C_{1-6}$ alkyl group is a methyl group, the number of possible substituents can be from 1 to 3. When an optionally substituted $C_{6-10}$ aryl group is a phenyl group, the number of possible substituents can be from 1 to 5. If there are two or more substituted groups, they may be identical to or different from one another. Moreover, unless otherwise specified, the explanation of each group is applicable to a case in which the group constitutes a part or a substituent of a different group.

The "halogen atom" includes a fluorine atom, a chlorine atom, a bromine atom or an iodine atom.

The term "$C_{1-6}$ alkyl group" means a linear or branched saturated hydrocarbon group containing 1 to 6 carbon atoms. It is preferably a "$C_{1-4}$ alkyl group". Examples of the "$C_{1-6}$ alkyl group" specifically include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

The term "$C_{2-6}$ alkenyl group" means a linear or branched unsaturated hydrocarbon group containing 2 to 6 carbon atoms and having one or two double bonds. Examples of the "$C_{2-6}$ alkenyl group" specifically include vinyl, propenyl, methylpropenyl, butenyl and methylbutenyl.

The term "$C_{2-6}$ alkynyl group" means a linear or branched unsaturated hydrocarbon group containing 2 to 6 carbon atoms and having one or two triple bonds. Examples of the "$C_{2-6}$ alkynyl group" specifically include ethynyl, 1-propynyl, 2-propynyl, 2-butynyl, pentynyl and hexynyl. In these groups, carbon atoms constituting triple bonds do not have a bond with a "group".

The term "$C_{3-10}$ cycloalkyl group" means a 3- to 10-membered, monocyclic- or polycyclic, saturated or partially unsaturated hydrocarbon group. It is preferably a "$C_{3-6}$ cycloalkyl group". Examples of the "$C_{3-10}$ cycloalkyl group" specifically include cyclopropyl, cyclobutyl, cyclopentyl, cyclohexyl, cyclopentenyl, cyclohexenyl, decalinyl, adamantyl and norbornyl.

The "$C_{3-10}$ cycloalkyl group" encompasses a group which is formed by condensing the "$C_{3-10}$ cycloalkyl" with a phenyl or a 5- or 6-membered ring containing one or more (e.g., one to four), same or different heteroatoms selected from a nitrogen atom, a sulfur atom and an oxygen atom. Examples of this group specifically include those represented by the formulae below. The phenyl and 5- or 6-membered ring containing one or more (e.g., one to four), same or different heteroatoms selected from a nitrogen atom, a sulfur atom and an oxygen atom may be optionally substituted, and examples of such a substituent include those mentioned in the "optionally substituted $C_{6-10}$ aryl group" and "optionally substituted heteroaryl group".

[Formula 36]

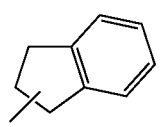

The "$C_{3-10}$ cycloalkyl group" encompasses a saturated bicyclo ring. Examples specifically include the following groups.

[Formula 37]

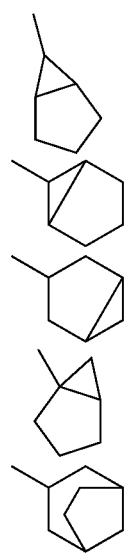

The term "$C_{6-10}$ aryl group" means an aromatic hydrocarbon group containing 6 to 10 carbon atoms. It is preferably a "$C_6$ aryl group" phenyl. Examples of the "$C_{6-10}$ aryl group" specifically include a phenyl group, a 1-naphthyl group and a 2-naphthyl group.

The "$C_{6-10}$ aryl group" encompasses a group formed by condensing a phenyl with a 5- to 7-membered ring containing one or more (e.g., one to four) same or different heteroatoms selected from a nitrogen atom, a sulfur atom and an oxygen atom, or with a 5- to 7-membered saturated hydrocarbon ring (cyclopentane or cyclohexane). Examples of this group specifically include groups represented by the following formulae.

[Formula 38]

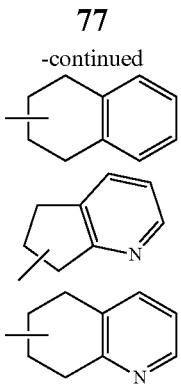

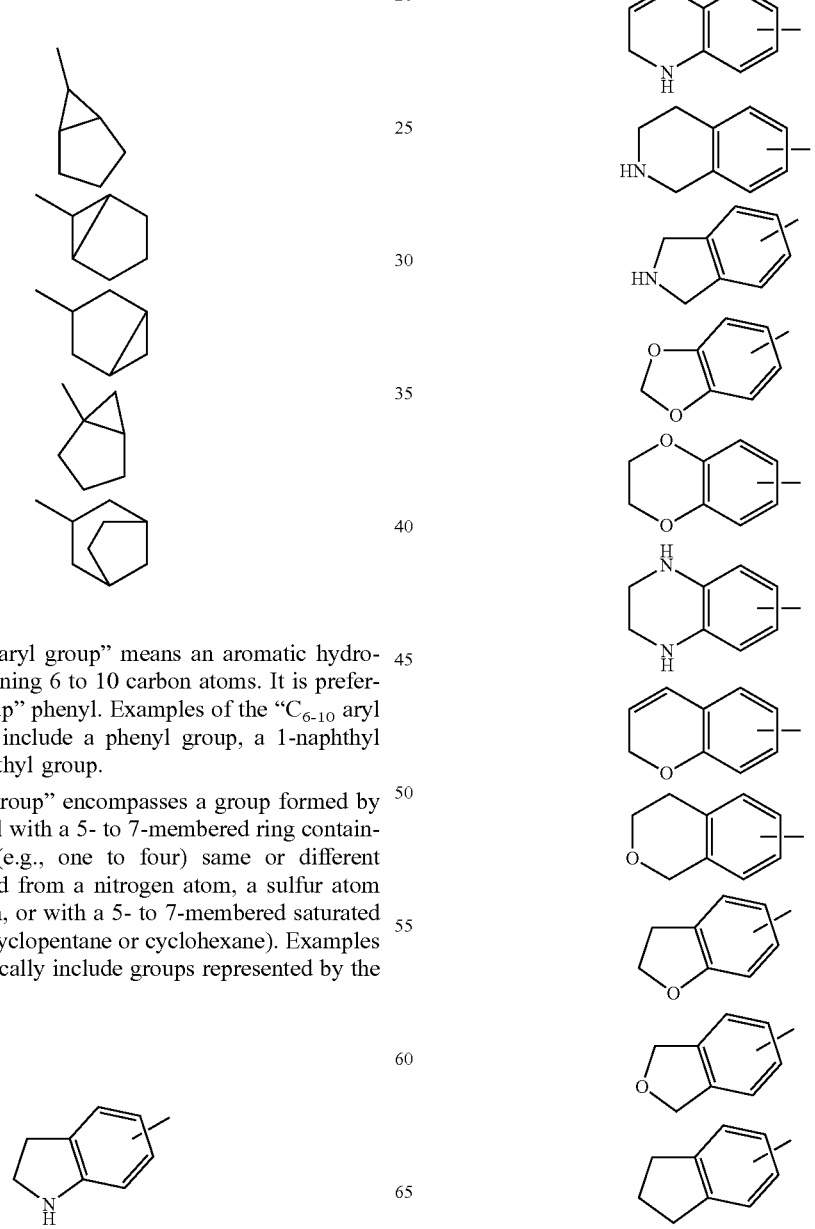

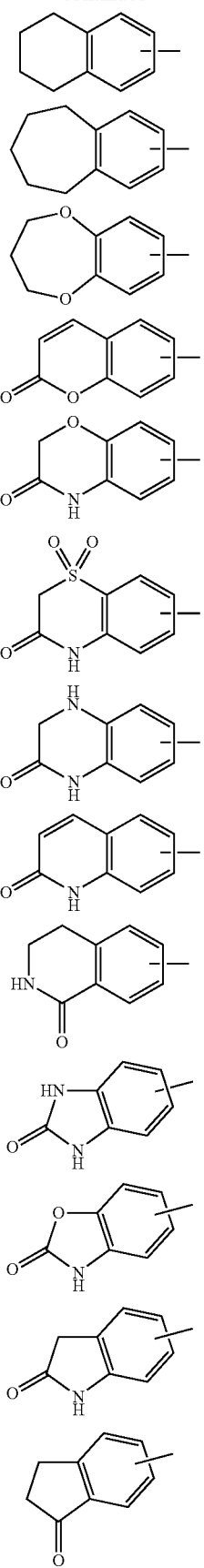

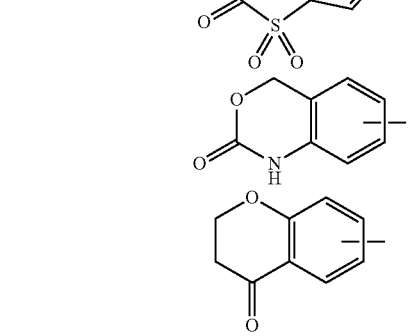

In the case of a condensed aryl group, however, only the aromatic ring has a bond with a "group". For instance, in the case of the "$C_{6-10}$ aryl group" represented by the following formula:

[Formula 39]

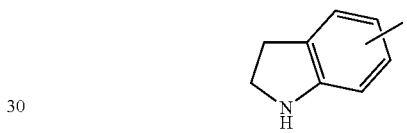

a "group" binds in the 4-, 5-, 6-, or 7-position.

Examples of the "heteroaryl group" include a 5- to 10-membered monocyclic or polycyclic aromatic group. This group may contain one or more (e.g., one to four) same or different heteroatoms selected from a nitrogen atom, a sulfur atom and an oxygen atom. The "polycyclic heteroaryl group" is preferably a bi- or tri-cyclic group and more preferably a bicyclic group. The polycyclic heteroaryl group encompasses a group formed by condensing the above-mentioned monocyclic heteroaryl group with an aromatic ring (benzene, pyridine, etc.) or with a non-aromatic ring (cyclohexyl, piperidine, etc.). Examples of the "heteroaryl group" specifically include groups represented by the following formulae.

[Formula 40]

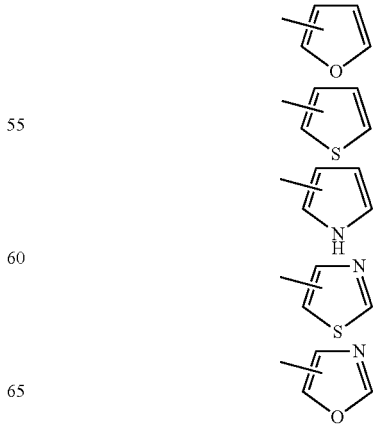

81
-continued
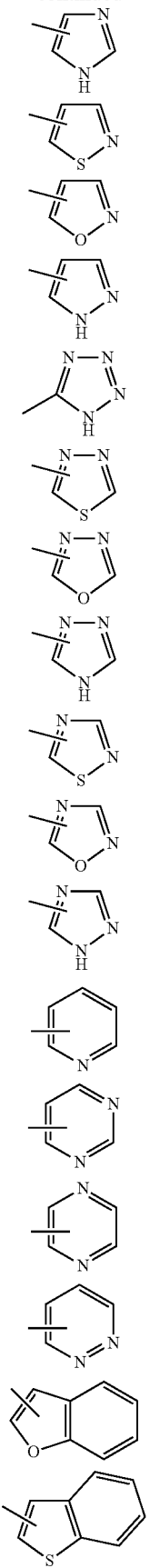
82
-continued
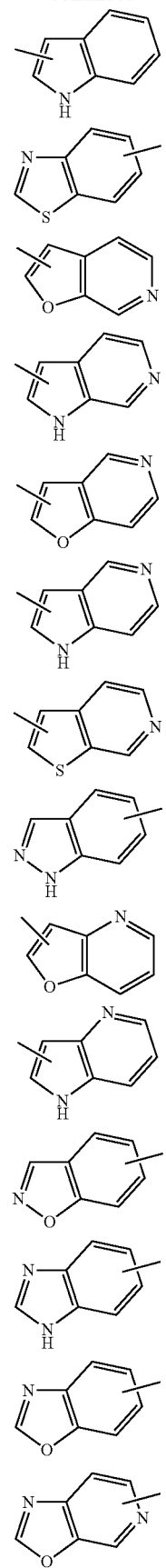

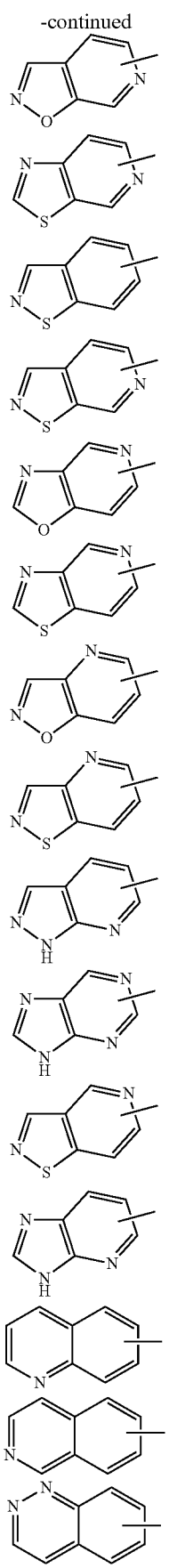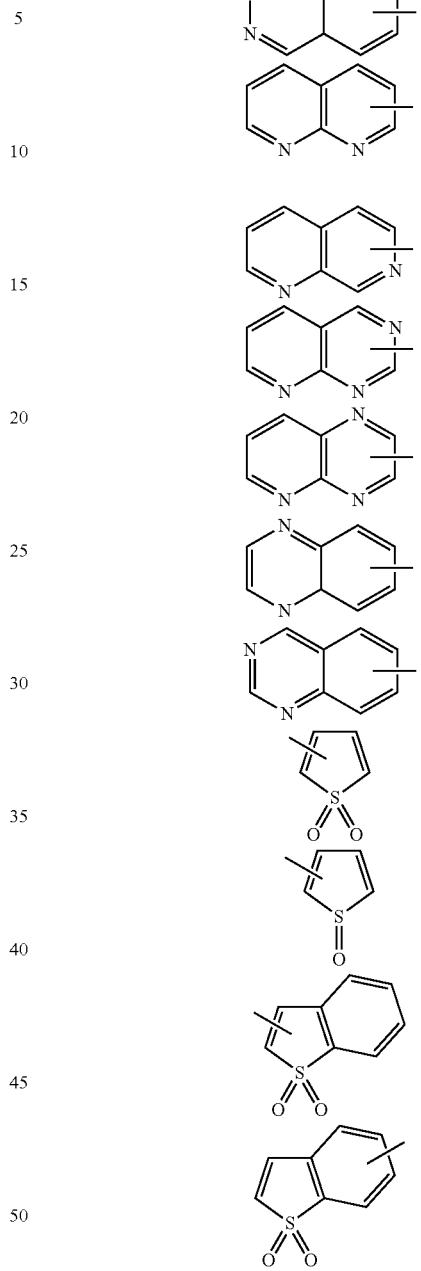
The bond traversing the ring in each of the above formulae means that a "group" binds the ring in a substitutable position. For instance, the heteroaryl group represented by the following formula:
[Formula 41]
may be a 2-furyl group or a 3-furyl group.

Moreover, where the "heteroaryl group" is a polycyclic group, for example, the group represented by the following formula:

[Formula 42]

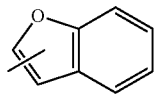

may be 4-, 5-, 6- or 7-benzofuryl, as well as 2-benzofuryl or 3-benzofuryl.

In the case of a polycyclic heteroaryl group in which an aromatic ring and a non-aromatic ring (a cyclohexane ring, a piperidine ring, etc.) are condensed, however, only the aromatic ring can have a bond with a "group". For example, in the case of the "polycyclic heteroaryl group" represented by the following formula:

[Formula 43]

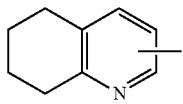

a "group" may bind in the 2-, 3- or 4-position. The "heteroaryl group" is preferably a 5- to 10-membered monocyclic or polycyclic aromatic group, and more preferably a 5- or 6-membered monocyclic aromatic group.

The "3- to 8-membered hydrocarbon ring" in ring D means a 3- to 8-membered monocyclic saturated or partially unsaturated hydrocarbon ring. It is preferably a saturated hydrocarbon ring, and more preferably a 5- or 6-membered saturated hydrocarbon ring. Examples of the "3- to 8-membered hydrocarbon ring" specifically include a cyclopropane ring, a cyclobutane ring, a cyclopentane ring, a cyclohexane ring, a cycloheptane ring, a cyclooctane ring, a cyclopentene ring and a cyclohexene ring. Examples of the saturated hydrocarbon ring specifically include a cyclopropane ring, a cyclobutane ring, a cyclopentane ring, a cyclohexane ring, a cycloheptane ring and a cyclooctane ring.

Examples of the "saturated heterocyclic group" include a 4- to 10-membered monocyclic or polycyclic saturated heterocyclic group containing one to three, same or different atoms selected from a nitrogen atom, an oxygen atom and a sulfur atom. The nitrogen atom, oxygen atom and sulfur atom can all constitute a ring. The heterocyclic group may be either a saturated or a partially unsaturated group. It is preferably a saturated heterocyclic group, and more preferably a 5- or 6-membered saturated heterocyclic group. Examples of the heterocyclic group specifically include pyranyl, dihydropyranyl, tetrahydropyranyl, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, tetrahydrofuranyl, oxooxazolidyl, dioxooxazolidinyl, dioxothiazolidinyl, tetrahydropyranyl, 5-oxo-1,2,4-oxadiazol-3-yl, 5-oxo-1,2,4-thiadiazol-3-yl and 5-thioxo-1,2,4-oxadiazol-3-yl. In the case of this group, a nitrogen atom constituting a ring does not have a bond with a "group". That is, this group does not embrace a concept of a 1-pyrrolidino group.

The "4- to 6-membered saturated heterocyclic group" encompasses a saturated bicyclo ring group and a saturated spiro ring group, which both comprise a "4- to 6-membered saturated heterocyclic group" as a basic skeleton. Examples of the 4- to 6-membered saturated heterocyclic group specifically include the following "groups".

[Formula 44]

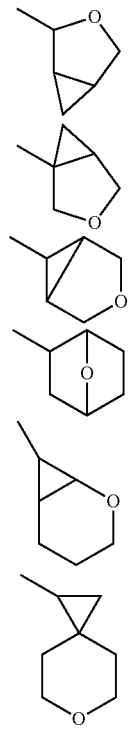

The "saturated heterocyclic group" may form a condensed ring containing a phenyl or a 6-membered heteroaryl. For example, the saturated heterocyclic group encompasses a group formed by condensing the above-mentioned 4- to 6-membered saturated heterocyclic group with a phenyl or a 6-membered heteroaryl. Examples of the 6-membered heteroaryl include pyridine, pyrimidine and pyridazine. Examples of the saturated heterocyclic group include dihydroindolyl, dihydroisoindolyl, dihydropurinyl, dihydrothiazolopyrimidinyl, dihydrobenzodioxanyl, isoindolinyl, tetrahydroquinolinyl, decahydroquinolinyl, tetrahydroisoquinolinyl, decahydroisoquinolinyl, tetrahydronaphthyridinyl and tetrahydropyridoazepinyl. The phenyl or 6-membered heteroaryl may be optionally substituted, and examples of such a substituent include those mentioned in the "optionally substituted $C_{6-10}$ aryl group" and the "optionally substituted heteroaryl group".

The term "$C_{1-6}$ alkoxy group" is synonymous with a "$C_{1-6}$ alkyloxy group", and the "$C_{1-6}$ alkyl" portion has the same definitions as those of the above described "$C_{1-6}$ alkyl". It is preferably a "$C_{1-4}$ alkoxy group". Examples of the "$C_{1-6}$ alkoxy group" specifically include methoxy, ethoxy, propoxy, isopropoxy, butoxy, isobutoxy, sec-butoxy and tert-butoxy.

The "$C_{1-6}$ alkyl" portion of the "$C_{1-6}$ alkylthio group" has the same definitions as those of the above described "$C_{1-6}$ alkyl". It is preferably a "$C_{1-4}$ alkylthio group". Examples of the "$C_{1-6}$ alkylthio group" specifically include methylthio, ethylthio, propylthio, isopropylthio, butylthio, pentylthio and hexylthio.

The "$C_{1-6}$ alkyl" portion of the "$C_{1-6}$ alkylsulfonyl group" has the same definitions as those of the above described "$C_{1-6}$ alkyl". It is preferably a "$C_{1-4}$ alkylsulfonyl group". Examples of the "$C_{1-6}$ alkylsulfonyl group" specifically include methylsulfonyl, ethylsulfonyl, propylsulfonyl, isopropylsulfonyl, butylsulfonyl, pentylsulfonyl and hexylsulfonyl.

The "$C_{3-10}$ cycloalkyl" portion of the "$C_{3-10}$ cycloalkylsulfonyl group" has the same definitions as those of the above described "$C_{3-10}$ cycloalkyl". Examples of the "$C_{3-10}$ cycloalkylsulfonyl group" include cyclopropylsulfonyl, cyclobutylsulfonyl, cyclopentylsulfonyl and cyclohexylsulfonyl.

The "$C_{6-10}$ aryl" portion of the "$C_{6-10}$ arylsulfonyl group" has the same definitions as those of the above described "$C_{6-10}$ aryl". Examples of the "$C_{6-10}$ arylsulfonyl group" include phenylsulfonyl, 1-naphthylsulfonyl and 2-naphthylsulfonyl.

The "$C_{3-10}$ cycloalkoxy group" is synonymous with a "$C_{3-10}$ cycloalkyloxy group", and the "$C_{3-10}$ cycloalkyl" portion has the same definitions as those of the above described "$C_{3-10}$ cycloalkyl". Examples of the "$C_{3-10}$ cycloalkoxy group" include cyclopropyloxy, cyclobutyloxy, cyclopentyloxy and cyclohexyloxy.

The "$C_{6-10}$ aryl" portion of the "$C_{6-10}$ aryloxy group" has the same definitions as those of the above described "$C_{6-10}$ aryl". It is preferably "$C_6$ aryloxy" (phenoxy). Examples of the "$C_{6-10}$ aryloxy group" specifically include phenoxy, 1-naphthyloxy and 2-naphthyloxy.

The "heteroaryl" portion of the "5 to 10-membered heteroaryloxy group" has the same definitions as those of the above described "heteroaryl". Examples of the "5 to 10-membered monocyclic or polycyclic heteroaryloxy group" specifically include pyridyloxy, imidazolyloxy and thiazolyloxy.

The "saturated heterocyclic" portion of the "4 to 10-membered saturated heterocyclic oxy group" has the same definitions as those of the above described "saturated heterocyclic group". It is preferably a "5- or 6-membered saturated heterocyclic oxy group". Examples of the "4 to 10-membered saturated heterocyclic oxy group" specifically include tetrahydropyranyloxy, tetrahydrofuryloxy, pyrrolidinyloxy, imidazolidinyloxy, piperidinyloxy and morpholinyloxy.

The "$C_{3-10}$ cycloalkyl" portion of the "$C_{3-10}$ cycloalkylthio group" has the same definitions as those of the above described "$C_{3-10}$ cycloalkyl". Examples of the "$C_{3-10}$ cycloalkylthio group" include cyclopropylthio, cyclobutylthio, cyclopentylthio and cyclohexylthio.

The "$C_{6-10}$ aryl" portion of the "$C_{6-10}$ arylthio group" has the same definitions as those of the above described "$C_{6-10}$ aryl". It is preferably "$C_6$ arylthio" (phenylthio). Examples of the "$C_{6-10}$ arylthio group" specifically include phenylthio, 1-naphthylthio and 2-naphthylthio.

The "$C_{1-6}$ alkyl" portion of the "$C_{1-6}$ alkylcarbonyl group" has the same definitions as those of the above described "$C_{1-6}$ alkyl". It is preferably a "$C_{1-4}$ alkylcarbonyl group". Examples of the "$C_{1-6}$ alkylcarbonyl group" specifically include methylcarbonyl, ethylcarbonyl, propylcarbonyl, isopropylcarbonyl, pentylcarbonyl, isobutylcarbonyl and butylcarbonyl.

The "$C_{1-6}$ alkoxy" portion of the "$C_{1-6}$ alkoxycarbonyl group" has the same definitions as those of the above described "$C_{1-6}$ alkoxy". It is preferably a "$C_{1-4}$ alkoxycarbonyl group". Examples of the "$C_{1-6}$ alkoxycarbonyl group" specifically include methoxycarbonyl, ethoxycarbonyl, tert-butoxycarbonyl and isobutoxycarbonyl.

The "$C_{1-6}$ alkyl" portion of the "$C_{1-6}$ alkylcarbonylamino group" has the same definitions as those of the above described "$C_{1-6}$ alkyl". It is preferably a "$C_{1-4}$ alkylcarbonylamino group". Examples of the "$C_{1-6}$ alkylcarbonylamino group" specifically include methylcarbonylamino, ethylcarbonylamino, propylcarbonylamino and tert-butylcarbonylamino.

The "$C_{3-10}$ cycloalkyl" portion of the "$C_{3-10}$ cycloalkylcarbonylamino group" has the same definitions as those of the above described "$C_{3-10}$ cycloalkyl". Examples of the "$C_{3-10}$ cycloalkylcarbonylamino group" specifically include cyclopropylcarbonylamino, cyclobutylcarbonylamino, cyclopentylcarbonylamino and cyclohexylcarbonylamino.

The "$C_{6-10}$ aryl" portion of the "$C_{6-10}$ arylcarbonylamino group" has the same definitions as those of the above described "$C_{6-10}$ aryl". It is preferably "$C_6$ arylcarbonylamino" (phenylcarbonylamino). Examples of the "$C_{6-10}$ arylcarbonylamino group" specifically include phenylcarbonylamino, 1-naphthylcarbonylamino and 2-naphthylcarbonylamino.

The "heteroaryl" portion of the "5 to 10-membered heteroarylcarbonylamino group" has the same definitions as those of the above described "heteroaryl". Examples of the "5 to 10-membered heteroarylcarbonylamino group" specifically include pyridylcarbonylamino, imidazolylcarbonylamino and thiazolylcarbonylamino.

The "saturated heterocyclic" portion of the "4 to 10-membered saturated heterocyclic carbonylamino group" has the same definitions as those of the above described "saturated heterocyclic group". It is preferably a "5- or 6-membered saturated heterocyclic carbonylamino group". Examples of the "4 to 10-membered saturated heterocyclic carbonylamino group" specifically include tetrahydropyranylcarbonylamino, tetrahydrofurylcarbonylamino, pyrrolidinylcarbonylamino, imidazolidinylcarbonylamino, piperidinylcarbonylamino and morpholinylcarbonylamino.

The "$C_{1-6}$ alkoxy" portion of the "$C_{1-6}$ alkoxycarbonylamino group" has the same definitions as those of the above described "$C_{1-6}$ alkoxy". It is preferably a "$C_{1-4}$ alkoxycarbonylamino group". Examples of the "$C_{1-6}$ alkoxycarbonylamino group" specifically include methoxycarbonylamino, ethoxycarbonylamino, propoxycarbonylamino and tert-butoxycarbonylamino.

The "$C_{3-10}$ cycloalkyl" portion of the "$C_{3-10}$ cycloalkoxycarbonylamino group" has the same definitions as those of the above described "$C_{3-10}$ cycloalkyl". Examples of the "$C_{3-10}$ cycloalkoxycarbonylamino group" specifically include cyclopropyloxycarbonylamino, cyclobutyloxycarbonylamino, cyclopentyloxycarbonylamino and cyclohexyloxycarbonylamino.

The "$C_{6-10}$ aryl" portion of the "$C_{6-10}$ aryloxycarbonylamino group" has the same definitions as those of the above described "$C_{6-10}$ aryl". It is preferably "$C_6$ aryloxycarbonylamino" (phenoxycarbonylamino). Examples of the "$C_{6-10}$ aryloxycarbonylamino group" specifically include phenoxycarbonylamino, 1-naphthyloxycarbonylamino and 2-naphthyloxycarbonylamino.

The "heteroaryl" portion of the "5 to 10-membered heteroaryloxycarbonylamino group" has the same definitions as those of the above described "heteroaryl". Examples of the "5 to 10-membered heteroaryloxycarbonylamino group" specifically include pyridyloxycarbonylamino, imidazolyloxycarbonylamino and thiazolyloxycarbonylamino.

The "saturated heterocyclic" portion of the "4 to 10-membered saturated heterocyclic oxycarbonylamino group" has the same definitions as those of the above described "saturated heterocyclic group". It is preferably a "5- or 6-membered saturated heterocyclic oxycarbonylamino group". Examples of the "4 to 10-membered saturated heterocyclic oxycarbonylamino group" specifically include tetrahydropyranyloxycarbonylamino, tetrahydrofuryloxycarbonylamino, pyrrolidinyloxycarbonylamino, imidazolidinyloxycarbonylamino, piperidinyloxycarbonylamino and morpholinyloxycarbonylamino.

The "C$_{1-6}$ alkyl" portion of the "C$_{1-6}$ alkylsulfonylamino group" has the same definitions as those of the above described "C$_{1-6}$ alkyl". It is preferably a "C$_{1-4}$ alkylsulfonylamino group". Examples of the "C$_{1-6}$ alkylsulfonylamino group" specifically include methoxysulfonylamino, ethoxysulfonylamino, propoxysulfonylamino and tert-butoxysulfonylamino.

The "C$_{3-10}$ cycloalkyl" portion of the "C$_{3-10}$ cycloalkylsulfonylamino group" has the same definitions as those of the above described "C$_{3-10}$ cycloalkyl". Examples of the "C$_{3-10}$ cycloalkylsulfonylamino group" specifically include cyclopropylsulfonylamino, cyclobutylsulfonylamino, cyclopentylsulfonylamino and cyclohexylsulfonylamino.

The "C$_{6-10}$ aryl" portion of the "C$_{6-10}$ arylsulfonylamino group" has the same definitions as those of the above described "C$_{6-10}$ aryl". It is preferably "C$_6$ arylsulfonylamino" (phenylsulfonylamino). Examples of the "C$_{6-10}$ arylsulfonylamino group" specifically include phenylsulfonylamino, 1-naphthylsulfonylamino and 2-naphthylsulfonylamino.

The "heteroaryl" portion of the "5 to 10-membered heteroarylsulfonylamino group" has the same definitions as those of the above described "heteroaryl". Examples of the "5 to 10-membered heteroarylsulfonylamino group" specifically include pyridylsulfonylamino, imidazolylsulfonylamino and thiazolylsulfonylamino.

The "saturated heterocyclic" portion of the "4 to 10-membered saturated heterocyclic sulfonylamino group" has the same definitions as those of the above described "saturated heterocyclic group". It is preferably a "5- or 6-membered saturated heterocyclic sulfonylamino group". Examples of the "4 to 10-membered saturated heterocyclic sulfonylamino group" specifically include tetrahydropyranylsulfonylamino, tetrahydrofurylsulfonylamino, pyrrolidinylsulfonylamino, imidazolidinylsulfonylamino, piperidinylsulfonylamino and morpholinylsulfonylamino.

The "C$_{1-6}$ alkyl" portion of the "C$_{1-6}$ alkylsulfonylaminocarbonyl group" has the same definitions as those of the above described "C$_{1-6}$ alkyl". It is preferably a "C$_{1-4}$ alkylsulfonylaminocarbonyl group". Examples of the "C$_{1-6}$ alkylsulfonylaminocarbonyl group" specifically include methoxysulfonylaminocarbonyl, ethoxysulfonylaminocarbonyl, propoxysulfonylaminocarbonyl and tert-butoxysulfonylaminocarbonyl.

The term "4- to 10-membered cyclic amino group" means a 4- to 10-membered monocyclic or polycyclic amino group. In this group, a nitrogen atom constituting the ring has a direct bond with a "group". It is preferably a 5- to 7-membered group. Examples of the "4- to 10-membered cyclic amino group" include azetidino, pyrrolidino, piperidino, morpholino, thiomorpholino, thiomorpholinooxide, thiomorpholinodioxide, piperazino and the "groups" shown below. It is to be noted that this group may have a ring containing a partially unsaturated portion.

[Formula 45]

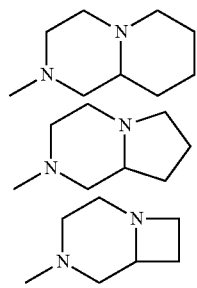

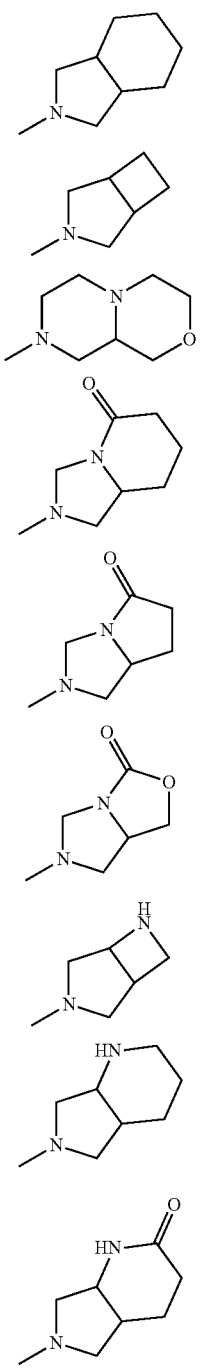

The "4- to 10-membered cyclic amino group" may form a condensed ring containing a phenyl or a 5- or 6-membered monocyclic heteroaryl. Examples of the "4- to 10-membered cyclic amino group" specifically include the following "groups". The phenyl or 5- or 6-membered heteroaryl may be optionally substituted, and examples of such a substituent include those mentioned in the "optionally substituted C$_{6-10}$ aryl group" and the "optionally substituted heteroaryl group".

[Formula 46]
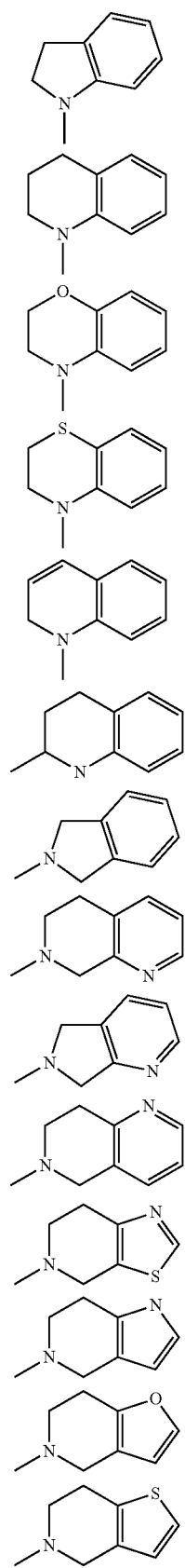
-continued
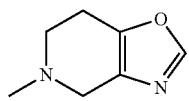
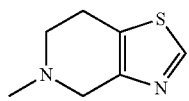
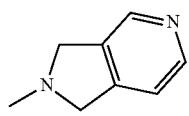
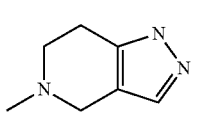
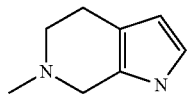
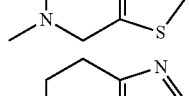

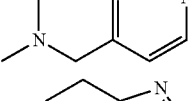
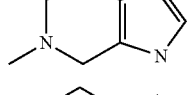
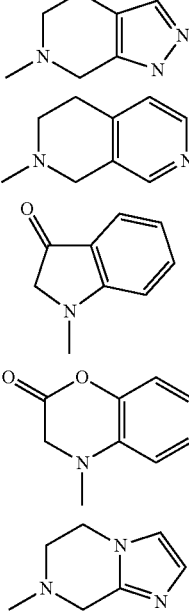

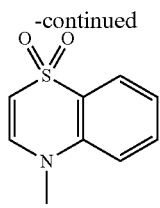

The term "5- or 6-membered cyclic amino group" encompasses a saturated bicyclo ring group and a saturated spiro ring group, which both comprise a "5- or 6-membered saturated heterocyclic group" as a basic skeleton. Examples of the "5- or 6-membered cyclic amino group" specifically include the following "groups".

[Formula 47]

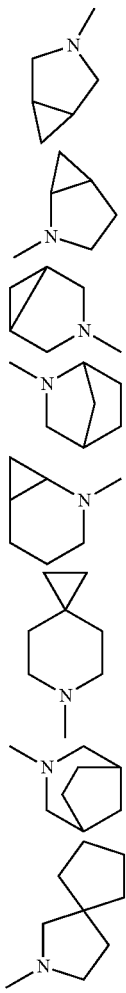

The "cyclic amino" portion of the "4- to 10-membered cyclic aminocarbonyl group" has the same definitions as those of the above described "cyclic amino". It is preferably a "5 to 6-membered cyclic aminocarbonylamino group". Examples of the "4- to 10-membered cyclic aminocarbonyl group" specifically include azetidinocarbonyl, pyrrolidinocarbonyl, piperidinocarbonyl, morpholinocarbonyl, thiomorpholinocarbonyl and piperazinocarbonyl.

The "cyclic amino" portion of the "4- to 10-membered cyclic aminosulfonyl group" has the same definitions as those of the above described "cyclic amino". It is preferably a "5 to 6-membered cyclic aminosulfonylamino group". Examples of the "4- to 10-membered cyclic aminosulfonyl group" specifically include azetidinosulfonyl, pyrrolidinosulfonyl, piperidinosulfonyl, morpholinosulfonyl, thiomorpholinosulfonyl and piperazinosulfonyl.

The "cyclic amino" portion of the "4- to 7-membered cyclic aminosulfonylaminocarbonyl group" has the same definitions as those of the above described "cyclic amino". It is preferably a "5 to 6-membered cyclic aminosulfonylaminocarbonylamino group". Examples of the "4- to 7-membered cyclic aminocarbonyl group" specifically include azetidinosulfonylaminocarbonyl, pyrrolidinosulfonylaminocarbonyl, piperidinosulfonylaminocarbonyl, morpholinosulfonylaminocarbonyl, thiomorpholinosulfonylaminocarbonyl and piperazinosulfonylaminocarbonyl.

The term "$C_{1-6}$ alkoxy $C_{1-6}$ alkyl group" means a "$C_{1-6}$ alkyl" group substituted with a "$C_{1-6}$ alkoxy" group. Examples of the "$C_{1-6}$ alkoxy $C_{1-6}$ alkyl group" specifically include methoxymethyl, ethoxymethyl, propoxymethyl, isopropoxymethyl, butylmethyl, methoxyethyl, ethoxyethyl, methoxypropyl and methoxybutyl.

The term "$C_{1-6}$ alkylthio $C_{1-6}$ alkyl group" means a "$C_{1-6}$ alkyl" group substituted with a "$C_{1-6}$ alkylthio" group. Examples of the "$C_{1-6}$ alkylthio $C_{1-6}$ alkyl group" specifically include methylthiomethyl, ethylthiomethyl, propylthiomethyl, isopropylthiomethyl, butylthiomethyl, methylthioethyl, ethylthioethyl, methylthiopropyl and methylthiobutyl.

The term "amino $C_{1-6}$ alkyl group" means a "$C_{1-6}$ alkyl" group substituted with an amino group. Examples of the "amino $C_{1-6}$ alkyl group" specifically include aminomethyl, 1-aminoethyl, 1-aminopropyl, 2-aminoethyl and 2-aminopropyl.

It is preferably an aminomethyl group wherein the methyl may be optionally substituted with one or two fluorine atoms, or a 1-aminoethyl group wherein the ethyl may be optionally substituted with one to three fluorine atoms. It is more preferably a 1-amino-2-fluoroethyl group.

The term "amidino $C_{1-6}$ alkyl group" means a "$C_{1-6}$ alkyl" group substituted with an amidino group. Examples of the "amidino $C_{1-6}$ alkyl group" specifically include amidinomethyl, 1-amidinoethyl, 1-amidinopropyl, 2-amidinoethyl and 2-amidinopropyl.

The term "imino $C_{1-6}$ alkyl group" is a "$C_{1-6}$ alkyl" group substituted with an imino group. Examples of the "imino $C_{1-6}$ alkyl group" specifically include iminomethyl, 1-iminoethyl, 1-iminopropyl, 2-iminoethyl and 2-iminopropyl.

The term "$C_{1-6}$ alkoxycarbonylamino $C_{1-6}$ alkyl group" means a "$C_{1-4}$ alkyl" group substituted with "$C_{1-6}$ alkoxycarbonylamino". Examples of the "$C_{1-6}$ alkoxycarbonylamino $C_{1-6}$ alkyl group" specifically include methoxycarbonylaminomethyl, ethoxycarbonylaminomethyl and tert-butoxycarbonylaminomethyl.

The "$C_{1-6}$ alkyl group" portion of the "$C_{1-6}$ alkoxy $C_{1-6}$ alkyl group", the "$C_{1-6}$ alkylthio $C_{1-6}$ alkyl group", the "amino $C_{1-6}$ alkyl group", "amidino $C_{1-6}$ alkyl group", the "imino $C_{1-6}$ alkyl group", the "$C_{1-6}$ alkoxycarbonylamino $C_{1-6}$ alkyl group", the "mercapto $C_{1-6}$ alkyl group", the "hydroxy $C_{1-6}$ alkyl group", and the "carboxy $C_{1-6}$ alkyl group" in $R^1$ means a linear or branched saturated hydrocarbon group containing 1 to 6 carbon atoms, or a saturated hydrocarbon group having a cyclic structure and containing 3 to 6 carbon atoms. Examples of the saturated hydrocarbon group having a cyclic structure include the groups represented by the following.

[Formula 48]

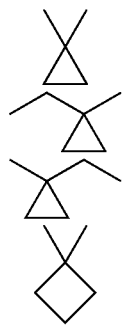

The term "amino $C_{3-10}$ cycloalkyl group" means a "$C_{3-10}$ cycloalkyl" group substituted with an amino group. Examples of the "amino $C_{3-10}$ cycloalkyl group" specifically include aminocyclopropyl, aminocyclobutyl, aminocyclopentyl and aminocyclohexyl.

Examples of a substituent which may be contained in the "optionally substituted $C_{1-6}$ alkyl group" include
(1) a halogen atom,
(2) a cyano group,
(3) a hydroxy group,
(4) a $C_{1-6}$ alkylcarbonyl group which may be optionally substituted with one to three halogen atoms,
(5) a carboxyl group,
(6) an amino group which may be optionally substituted with one or two, same or different groups selected from the group consisting of:
(a) a $C_{1-6}$ alkyl group which may be optionally substituted with
  (a1) one to three halogen atoms,
  (a2) a cyano group,
  (a3) a hydroxyl group,
  (a4) a $C_{1-6}$ alkoxy group,
  (a5) a $C_{3-10}$ cycloalkyl group,
  (a6) a $C_{3-10}$ cycloalkoxy group, or
  (a7) a $C_{1-6}$ alkoxycarbonylamino group,
(b) a $C_{3-10}$ cycloalkyl group which may be optionally substituted with $C_{1-6}$ alkyl or one to three halogen atoms,
(c) a $C_{6-10}$ aryl group which may be optionally substituted with one to four, same or different groups selected from the group consisting of a halogen atom, a cyano group, a $C_{1-6}$ alkyl group which may be optionally substituted with one to three halogen atoms, a $C_{1-6}$ alkoxycarbonylamino group, and a $C_{1-6}$ alkoxy group which may be optionally substituted with one to three halogen atoms,
(d) a 5- to 10-membered heteroaryl group which may be optionally substituted with one to four, same or different groups selected from the group consisting of substituents described in (f3) above, and
(e) a 4- to 10-membered saturated heterocyclic group which may be optionally substituted with one to four, same or different groups selected from the group consisting of substituents described in (f3) above,
(7) a 4- to 10-membered cyclic amino group wherein the ring may be optionally substituted with
  (a) a halogen atom,
  (b) a hydroxy group,
  (c) a $C_{1-6}$ alkyl group which may be optionally substituted with one to three halogen atoms, a hydroxy group, or a $C_{1-6}$ alkoxy group which may be optionally substituted with one to three halogen atoms,
  (d) a $C_{1-6}$ alkoxy group which may be optionally substituted with one to three halogen atoms, a hydroxy group, or a $C_{1-6}$ alkoxy group which may be optionally substituted with one to three halogen atoms, or
  (e) a mono- or di-$C_{1-6}$ alkylamino group, wherein the alkyl may be optionally substituted with one to three halogen atoms,
(8) a $C_{1-6}$ alkoxy group which may be optionally substituted with
  (a) a hydroxy group,
  (b) a $C_{1-6}$ alkoxy group which may be optionally substituted with one to three halogen atoms,
  (c) a $C_{3-10}$ cycloalkyl group which may be optionally substituted with one to three halogen atoms or a $C_{1-6}$ alkyl group, or
  (d) one to three halogen atoms,
(9) a 4- to 10-membered saturated heterocyclic group, wherein the ring may be optionally substituted with (g1) to (g5) above,
(10) a 4- to 10-membered cyclic amino group, wherein the ring may be optionally substituted with (g1) to (g5) above,
(11) a 4- to 10-membered cyclic aminocarbonyl group, wherein the ring may be optionally substituted with (g1) to (g5) above,
(12) a $C_{6-10}$ aryl group which may be optionally substituted with one to four, same or different groups selected from the group consisting of:
  (a) a halogen atom,
  (b) a cyano group,
  (c) a hydroxy group,
  (d) a carboxyl group,
  (e) a $C_{1-6}$ alkyl group which may be optionally substituted with one to three halogen atoms,
  (f) a $C_{1-6}$ alkoxy group which may be optionally substituted with one to three halogen atoms,
  (g) a $C_{1-6}$ alkoxycarbonylamino group,
  (h) a $C_{1-6}$ alkylsulfonylamino group, wherein the alkyl may be optionally substituted with one to three halogen atoms,
  (i) a $C_{3-10}$ cycloalkyl group which may be optionally substituted with one to three halogen atoms, a $C_{1-6}$ alkoxy group or a $C_{1-6}$ alkyl group,
  (j) a $C_{1-6}$ alkylcarbonylamino group, wherein the alkyl may be optionally substituted with one to three halogen atoms,
  (k) an amino group which may be optionally substituted with one or two, same or different groups selected from the group consisting of:
    (k1) a $C_{1-6}$ alkyl group which may be optionally substituted with one to three halogen atoms, a cyano group, a hydroxy group, a $C_{1-6}$ alkoxy group, a $C_{3-10}$ cycloalkyl group or a $C_{1-6}$ alkoxycarbonylamino group,
    (k2) a $C_{3-10}$ cycloalkyl group which may be optionally substituted with one to three halogen atoms or a $C_{1-6}$ alkyl group, and
    (k3) a phenyl group which may be optionally substituted with one to four, same or different groups selected from the group consisting of a halogen atom, a cyano group, a $C_{1-6}$ alkyl group, a $C_{1-6}$ alkoxycarbonylamino group and a $C_{1-6}$ alkoxy group,
  (l) an aminocarbonyl group which may be optionally substituted with one or two, same or different groups selected from the group consisting of (i) to (iii) in (lk) above,
  (m) a 4- to 10-membered cyclic amino group which may be optionally substituted with one to four, same or different groups selected from the group consisting of:
    (m1) a halogen atom,
    (m2) a $C_{1-6}$ alkyl group which may be optionally substituted with $C_{1-6}$ alkoxy, hydroxy, or one to three halogen atoms, (m3) a $C_{1-6}$ alkoxy group which may be optionally substituted with one to three halogen atoms, and
(m4) a $C_{1-6}$ alkoxycarbonylamino group,
(n) a 4- to 10-membered cyclic aminocarbonyl group which may be optionally substituted with one to four, same or different groups selected from the group consisting of (i) to (iv) in (lm) above, and
(o) a $C_{1-6}$ alkoxycarbonyl group,
(13) a 5- to 10-membered heteroaryl group which may be optionally substituted with (la) to (ln) above,
(14) a $C_{3-10}$ cycloalkyl group which may be optionally substituted with a halogen atom or a $C_{1-6}$ alkyl group,
(15) a $C_{3-10}$ cycloalkoxy group which may be optionally substituted with a halogen atom or a $C_{1-6}$ alkyl group,
(16) a $C_{6-10}$ aryloxy group which may be optionally substituted with (la) to (ln) above,
(17) a 5- to 10-membered heteroaryloxy group which may be optionally substituted with (la) to (ln) above,
(18) a 4- to 10-membered saturated heterocyclic oxy group which may be optionally substituted with (la) to (ln) above,
(19) a mono- or di-$C_{1-6}$ alkylaminocarbonyl group wherein the alkyl may be optionally substituted with one to three halogen atoms,
(20) a mono- or di-$C_{1-6}$ alkylaminosulfonyl group wherein the alkyl may be optionally substituted with one to three halogen atoms,
(21) a $C_{1-6}$ alkylsulfonyl group wherein the alkyl may be optionally substituted with one to three halogen atoms,
(22) a $C_{1-6}$ alkylcarbonylamino group wherein the alkyl may be optionally substituted with one to three halogen atoms,
(23) a $C_{1-6}$ alkylsulfonylamino group wherein the alkyl may be optionally substituted with one to three halogen atoms,
(24) a $C_{1-6}$ alkoxycarbonylamino group, and
(25) a $C_{1-6}$ alkoxycarbonyl group wherein the alkoxy may be optionally substituted with
(a) a $C_{1-6}$ alkoxy group,
(b) a $C_{4-7}$ cycloalkoxy group,
(c) a mono- or di-$C_{1-6}$ alkylamino group,
(d) a 4- to 7-membered cyclic amino group,
(e) a mono- or di-$C_{1-6}$ alkylaminocarbonyl group,
(f) a 4- to 7-membered cyclic aminocarbonyl group,
(g) a $C_{1-6}$ alkylcarbonyloxy group which may be optionally substituted with
(g1) one to three fluorine atoms,
(g2) a hydroxy group,
(g3) a $C_{1-4}$ alkoxy group,
(g4) a carboxyl group,
(g5) a 5- or 6-membered saturated heterocyclic group,
(g6) a $C_{3-6}$ cycloalkyl group,
(g7) a $C_{1-4}$ alkoxycarbonyl group,
(g8) a $C_{1-4}$ alkoxycarbonylamino group,
(g9) a mono- or di-$C_{1-6}$ alkylamino group,
(g10) a 5- to 7-membered cyclic amine group,
(g11) one or two nitrooxy groups,
(g12) a mono- or di-$C_{1-6}$ alkylaminocarbonyl group, or
(g13) a 5- to 7-membered cyclic aminocarbonyl group,
(h) a $C_{3-10}$ cycloalkylcarbonyloxy group which may be optionally substituted with a hydroxy group,
(i) a $C_{6-10}$ arylcarbonyloxy group which may be optionally substituted with a $C_{1-4}$ alkyl group, a $C_{1-4}$ alkoxy group, or a $C_{1-4}$ alkylcarbonyloxy group,
(j) a 5- to 10-membered heteroarylcarbonyloxy group,
(k) a 5- or 6-membered saturated heterocyclic carbonyloxy group which may be optionally substituted with a $C_{1-4}$ alkyl group or a $C_{1-4}$ alkoxy group
(l) a $C_{1-6}$ alkoxycarbonyloxy group,
(m) a $C_{3-10}$ cycloalkoxycarbonyloxy group, or
(n) a 2-oxo-1,3-dioxol-4-yl group which may be optionally substituted with
(n1) a $C_{1-4}$ alkyl group which may be optionally substituted with one to three halogen atoms or a $C_{1-4}$ alkoxy group),
(n2) a $C_{3-6}$ cycloalkyl group which may be optionally substituted with a $C_{1-4}$ alkoxy group, or
(n3) a $C_{6-10}$ aryl group which may be optionally substituted with a $C_{1-4}$ alkyl group, one to three halogen atoms, or a $C_{1-4}$ alkoxy group.

Examples of a substituent which may be contained in the "optionally substituted $C_{6-10}$ aryl group" include
(1) a halogen atom,
(2) a cyano group,
(3) a hydroxy group,
(4) a $C_{1-6}$ alkylcarbonyl group, wherein the alkyl may be optionally substituted with one to three halogen atoms,
(5) a carboxyl group,
(6) an amino group which may be optionally substituted with one or two, same or different groups selected from the group consisting of:
(a) a $C_{1-6}$ alkyl group which may be optionally substituted with
(a1) one to three halogen atoms,
(a2) a cyano group,
(a3) a hydroxy group,
(a4) a $C_{1-6}$ alkoxy group,
(a5) a $C_{3-10}$ cycloalkyl group which may be optionally substituted with one to three halogen atoms or a $C_{1-6}$ alkyl group, or
(a6) a $C_{1-6}$ alkoxycarbonylamino group,
(b) a $C_{3-10}$ cycloalkyl group which may be optionally substituted with a $C_{1-6}$ alkyl group or one to three halogen atoms,
(c) a phenyl group which may be optionally substituted with
(c1) a halogen atom,
(c2) a cyano group,
(c3) a $C_{1-6}$ alkyl group which may be optionally substituted with one to three halogen atoms,
(c4) a $C_{1-6}$ alkoxycarbonylamino group, or
(c5) a $C_{1-6}$ alkoxy group which may be optionally substituted with one to three halogen atoms,
(d) a 5- or 6-membered heteroaryl group which may be optionally substituted with (c1) to (c5) above, and
(e) a 5- or 6-membered saturated heterocyclic group,
(7) a 4- to 10-membered cyclic amino group wherein the ring may be optionally substituted with
(a) a halogen atom,
(b) a hydroxy group,
(c) a $C_{1-6}$ alkyl group which may be optionally substituted with one to three halogen atoms, a hydroxy group, or a $C_{1-6}$ alkoxy group which may be optionally substituted with one to three halogen atoms,
(d) a $C_{1-6}$ alkoxy group which may be optionally substituted with one to three halogen atoms, a hydroxy group, or a $C_{1-6}$ alkoxy group which may be optionally substituted with one to three halogen atoms, or
(e) a mono- or di-$C_{1-6}$ alkylamino group wherein the alkyl may be optionally substituted with one to three halogen atoms,
(8) a $C_{1-6}$ alkyl group which may be optionally substituted with
(a) a hydroxy group,
(b) a $C_{1-6}$ alkoxy group which may be optionally substituted with one to three halogen atoms, (c) a $C_{3-10}$ cycloalkyl group which may be optionally substituted with one to three halogen atoms or a $C_{1-6}$ alkyl group, or (d) one to three halogen atoms, (9) a $C_{1-6}$ alkoxy group which may be optionally substituted with any of (a) to (d) in (8) above,

(10) a 4- to 10-membered saturated heterocyclic group which may be optionally substituted with (a) to (e) in (7) above,

(11) an aminocarbonyl group wherein the ring may be optionally substituted with one or two, same or different groups selected from the group consisting of (a) to (e) in (6) above,

(12) a 4- to 10-membered cyclic aminocarbonyl group wherein the ring may be optionally substituted with (a) to (e) in (7) above,

(13) a $C_{6-10}$ aryl group which may be optionally substituted with any of (c1) to (c5) above,

(14) a 5- to 10-membered heteroaryl group which may be optionally substituted with any of (c1) to (c5) above,

(15) a $C_{3-10}$ cycloalkyl group which may be optionally substituted with a halogen atom or a $C_{1-6}$ alkyl group,

(16) a $C_{3-10}$ cycloalkoxy group which may be optionally substituted with a halogen atom or a $C_{1-6}$ alkyl group,

(17) a $C_{6-10}$ aryloxy group which may be optionally substituted with any of (c1) to (c5) above,

(18) a 5- to 10-membered heteroaryloxy group which may be optionally substituted with any of (c1) to (c5) above,

(19) a 4- to 10-membered saturated heterocyclic oxy group which may be optionally substituted with any of (a) to (e) in (7) above,

(20) a mono- or di-$C_{1-6}$ alkylaminocarbonyl group wherein the alkyl may be optionally substituted with one to three halogen atoms,

(21) a mono- or di-$C_{1-6}$ alkylaminosulfonyl group wherein the alkyl may be optionally substituted with one to three halogen atoms,

(22) a $C_{1-6}$ alkylsulfonyl group wherein the alkyl may be optionally substituted with one to three halogen atoms,

(23) a $C_{1-6}$ alkylcarbonylamino group wherein the alkyl may be optionally substituted with one to three halogen atoms,

(24) a $C_{1-6}$ alkylsulfonylamino group wherein the alkyl may be optionally substituted with one to three halogen atoms, and

(25) a $C_{1-6}$ alkoxycarbonylamino group.

Examples of a substituent which may be contained in the "optionally substituted $C_{1-6}$ alkoxy group", "optionally substituted $C_{1-6}$ alkylthio group", "optionally substituted $C_{1-6}$ alkylcarbonyl group", "optionally substituted $C_{1-6}$ alkylcarbonylamino group", "optionally substituted $C_{1-6}$ alkylsulfonyl group", "optionally substituted $C_{1-6}$ alkylsulfonylamino group", "optionally substituted $C_{1-6}$ alkylsulfonylaminocarbonyl group", "optionally substituted $C_{1-6}$ alkoxycarbonylamino group", "optionally substituted $C_{2-6}$ alkenyl group", "optionally substituted $C_{2-6}$ alkenyloxy group" and "optionally substituted $C_{2-6}$ alkynyl group" include groups selected from the substituents mentioned in the "optionally substituted $C_{1-6}$ alkyl group".

Examples of a substituent which may be contained in the "optionally substituted $C_{3-10}$ cycloalkyl group", "optionally substituted $C_{3-10}$ cycloalkoxy group", "optionally substituted $C_{3-10}$ cycloalkylcarbonylamino group", "optionally substituted $C_{3-10}$ cycloalkylsulfonyl group", "optionally substituted $C_{3-10}$ cycloalkylsulfonylamino group", "optionally substituted $C_{3-10}$ cycloalkoxycarbonylamino group", "optionally substituted $C_{3-10}$ cycloalkylsulfonylaminocarbonyl group", "optionally substituted $C_{3-10}$ cycloalkylthio group", "optionally substituted $C_{6-10}$ aryloxy group", "optionally substituted $C_{6-10}$ arylthio group", "optionally substituted $C_{6-10}$ arylcarbonyl group", "optionally substituted $C_{6-10}$ arylcarbonylamino group", "optionally substituted $C_{6-10}$ arylsulfonyl group", "optionally substituted $C_{6-10}$ arylsulfonylamino group", "optionally substituted $C_{6-10}$ arylsulfonylaminocarbonyl group", "optionally substituted $C_{6-10}$ aryloxycarbonylamino group", "optionally substituted 5- to 10-membered heteroaryl group", "optionally substituted 5- to 10-membered heteroaryloxy group", "optionally substituted 5- to 10-membered heteroarylcarbonylamino group", "optionally substituted 5- to 10-membered heteroarylsulfonylamino group", "optionally substituted 5- to 10-membered heteroaryloxycarbonylamino group", "optionally substituted 4- to 10-membered saturated heterocyclic group", "optionally substituted 4- to 10-membered saturated heterocyclic oxy group", "optionally substituted 4- to 10-membered saturated heterocyclic oxycarbonyl group", "optionally substituted 4- to 10-membered saturated heterocyclic carbonylamino group", "optionally substituted 4- to 10-membered saturated heterocyclic sulfonylamino group", "optionally substituted 4- to 10-membered saturated heterocyclic sulfonylaminocarbonyl group", "optionally substituted 4- to 10-membered saturated heterocyclic oxycarbonylamino group", "optionally substituted 4- to 10-membered cyclic amino group", "optionally substituted 4- to 10-membered cyclic aminocarbonyl group" and "optionally substituted 4- to 10-membered cyclic aminosulfonyl group" include groups selected from the substituents mentioned in the "optionally substituted $C_{6-10}$ aryl group".

Examples of a substituent which may be contained in the "optionally substituted amino group", the "optionally substituted aminocarbonyl group", the "optionally substituted aminosulfonyl group", the "optionally substituted amino $C_{1-6}$ alkyl group", the amino portion of the "optionally substituted amino $C_{3-10}$ cycloalkyl group"; the "optionally substituted amidino group", the "optionally substituted amidino $C_{1-6}$ alkyl group", the amidino portion of the "optionally substituted amidino $C_{3-10}$ cycloalkyl group"; the "optionally substituted imino $C_{1-6}$ alkyl group", the imino portion of the "optionally substituted imino $C_{3-10}$ cycloalkyl group" and the guanidino portion of "optionally substituted guanidino group" include one or two, same or different groups selected from the group consisting of:

(1) a $C_{1-6}$ alkyl group which may be optionally substituted with (a) one to three halogen atoms, (b) a cyano group, (c) a hydroxy group, (d) a $C_{1-6}$ alkoxy group which may be optionally substituted with one to three halogen atoms, (e) a $C_{3-10}$ cycloalkyl group which may be optionally substituted with one to three halogen atoms or a $C_{1-6}$ alkyl group, or (f) a $C_{1-6}$ alkoxycarbonylamino group, (2) a $C_{3-10}$ cycloalkyl group which may be optionally substituted with a $C_{1-6}$ alkyl group, a $C_{1-6}$ alkoxy group or one to three halogen atoms, (3) a phenyl group which may be optionally substituted with one to four, same or different groups selected from the group consisting of:

(a) a halogen atom, (b) a cyano group, (c) a $C_{1-6}$ alkyl group which may be optionally substituted with one to three halogen atoms, (d) a $C_{1-6}$ alkoxycarbonylamino group, and (e) a $C_{1-6}$ alkoxy group which may be optionally substituted with one to three halogen atoms,
(4) a 5- or 6-membered heteroaryl group which may be optionally substituted with one to four, same or different groups selected from the group consisting of (a) to (e) in (3) above, and
(5) a 5- or 6-membered saturated heterocyclic group.

Examples of a substituent which may be contained in the alkyl portions of the "optionally substituted amino $C_{1-6}$ alkyl group", the "optionally substituted $C_{1-6}$ alkoxycarbonylamino $C_{1-6}$ alkyl group", the "optionally substituted amidino $C_{1-6}$ alkyl group", "optionally substituted imino $C_{1-6}$ alkyl group", the "optionally substituted $C_{1-6}$ alkoxy $C_{1-6}$ alkyl group", the "optionally substituted $C_{1-6}$ alkylthio $C_{1-6}$ alkyl group", the "mercapto $C_{1-6}$ alkyl group", the "hydroxy $C_{1-6}$ alkyl group" and the "carboxyl $C_{1-6}$ alkyl group" include
(1) one to three halogen atoms,
(2) a cyano group,
(3) a hydroxy group,
(4) a $C_{1-6}$ alkoxy group which may be optionally substituted with one to three halogen atoms,
(5) a $C_{3-10}$ cycloalkyl group which may be optionally substituted with one to three halogen atoms or a $C_{1-6}$ alkyl group,
(6) a phenyl group which may be optionally substituted with one to four, same or different groups selected from the group consisting of:
  (a) a halogen atom,
  (b) a cyano group,
  (c) a $C_{1-6}$ alkyl group which may be optionally substituted with one to three halogen atoms,
  (d) a $C_{1-6}$ alkoxycarbonylamino group, and
  (e) a $C_{1-6}$ alkoxy group which may be optionally substituted with one to three halogen atoms,
(7) a 5- or 6-membered heteroaryl group which may be optionally substituted with one to four, same or different groups selected from the group consisting of (f1) to (f5) above, and
(8) a 4- to 6-membered saturated heterocyclic group.

The substituents preferably include one or two fluorine atoms.

In $R^c$, $R^2$, $R^4$, $R^5$, $R^{21}$, $R^{41}$, $R^{42}$, $R^{51}$ and $R^{52}$, examples of a substituent which may be contained in the "optionally substituted $C_{1-6}$ alkoxycarbonyl group" include groups selected from the substituents mentioned in the "optionally substituted $C_{1-6}$ alkyl group".

In $R^e$, $R^f$, $R^g$, $R^h$, $R^i$, $R^k$, $R^m$ and $R^z$, examples of a substituent which may be contained in the "optionally substituted $C_{1-6}$ alkoxycarbonyl group" include
(1) a $C_{1-6}$ alkoxy group,
(2) a $C_{3-7}$ cycloalkoxy group,
(3) a mono- or di-$C_{1-6}$ alkylamino group wherein the alkyl may be optionally substituted with one to three halogen atoms, a $C_{1-4}$ alkoxy group or a $C_{3-10}$ cycloalkoxy group,
(4) a 4- to 7-membered cyclic amino group which may be optionally substituted with a $C_{1-4}$ alkyl group, one to three halogen atoms, a $C_{1-4}$ alkoxy group, a $C_{3-7}$ cycloalkyl group, a $C_{3-7}$ cycloalkoxy group, a hydroxy group, or a cyano group,
(5) a mono- or di-$C_{1-6}$ alkylaminocarbonyl group wherein the alkyl may be optionally substituted with one to three halogen atoms, a $C_{1-4}$ alkoxy group, or a $C_{3-10}$ cycloalkoxy group,
(6) a 4- to 7-membered cyclic aminocarbonyl group which may be optionally substituted with a $C_{1-4}$ alkyl group, one to three halogen atoms, a $C_{1-4}$ alkoxy group, a $C_{3-7}$ cycloalkyl group, a $C_{3-7}$ cycloalkoxy group, a hydroxy group, or a cyano group,
(7) a $C_{1-6}$ alkylcarbonyloxy group which may be optionally substituted with
  (a) one to three fluorine atoms,
  (b) a hydroxy group,
  (c) a $C_{1-4}$ alkoxy group,
  (d) a carboxyl group,
  (f) a 5- or 6-membered saturated heterocyclic group,
  (g) a $C_{3-6}$ cycloalkyl group,
  (h) a $C_{1-4}$ alkoxycarbonyl group,
  (i) a $C_{1-4}$ alkoxycarbonylamino group,
  (j) a mono- or di-$C_{1-6}$ alkylamino group,
  (k) a 5- to 7-membered cyclic amine group,
  (l) one or two nitrooxy groups,
  (m) a mono- or di-$C_{1-6}$ alkylaminocarbonyl group, or
  (n) a 5- to 7-membered cyclic aminocarbonyl group,
(8) a $C_{3-10}$ cycloalkylcarbonyloxy group which may be optionally substituted with a hydroxy group,
(9) a $C_{6-10}$ arylcarbonyloxy group which may be optionally substituted with one to four, same or different substituents selected from the group consisting of a halogen atom, a $C_{1-4}$ alkyl group, a $C_{1-4}$ alkoxy group, a cyano group and a hydroxy group,
(10) a 5- to 10-membered heteroarylcarbonyloxy group which may be optionally substituted with one to four, same or different substituents selected from the group consisting of a halogen atom, a $C_{1-4}$ alkyl group, a $C_{1-4}$ alkoxy group, a cyano group and a hydroxy group,
(11) a 4- to 7-membered saturated heterocyclic carbonyloxy group which may be optionally substituted with one to four, same or different substituents selected from the group consisting of a halogen atom, a $C_{1-4}$ alkyl group, a $C_{1-4}$ alkoxy group, a cyano group and a hydroxy group,
(12) a $C_{1-6}$ alkoxycarbonyloxy group, wherein the alkoxy may be optionally substituted with one to three halogen atoms,
(13) a $C_{3-10}$ cycloalkoxycarbonyloxy group,
(14) a 2-oxo-1,3-dioxol-4-yl group which may be optionally substituted with
  (a) a $C_{1-4}$ alkyl group which may be optionally substituted with a $C_{1-4}$ alkoxy group,
  (b) a $C_{3-6}$ cycloalkyl group which may be optionally substituted with a $C_{1-4}$ alkoxy group or a $C_{1-4}$ alkyl group, or
  (c) a $C_{6-10}$ aryl group which may be optionally substituted with one to four, same or different substituents selected from the group consisting of a $C_{1-4}$ alkoxy group, a $C_{1-4}$ alkyl group and a cyano group,
(15) a hydroxy group,
(16) a cyano group, and
(17) a carboxyl group.

Preferably included are a $C_{1-6}$ alkoxy group, a $C_{3-7}$ cycloalkoxy group, a mono- or di-$C_{1-6}$ alkylamino group, a 4- to 7-membered cyclic amino group, a $C_{1-6}$ alkylcarbonyloxy group, a $C_{1-6}$ alkoxycarbonyloxy group and a 2-oxo-1,3-dioxol-4-yl group which may be optionally substituted with a $C_{1-4}$ alkyl group.

The compound represented by Formula (1) and a pharmaceutically acceptable salt thereof may be present in the form of a hydrate and/or a solvate. Accordingly, such a hydrate and/or a solvate (e.g., an ethanol solvate, etc.) are also encompassed with the compound of the present invention. Moreover, the compound of the present invention encompasses all types of crystalline forms.

Where the compound represented by Formula (1) has an acidic functional group, a pharmaceutically acceptable salt thereof may include: alkaline metal salts such as sodium salt and potassium salt; alkaline-earth metal salts such as calcium salt and magnesium salt; inorganic metal salts such as zinc salt; and organic base salts such as triethylamine, triethanolamine, trihydroxymethylaminomethane, and amino acid.

Where the compound represented by Formula (1) has a basic functional group, a pharmaceutically acceptable salt thereof may include: inorganic acid salts such as hydrochloride, hydrobromate, sulfate, phosphate, and nitrate; and organic acid salts such as acetate, propionate, succinate, lactate, malate, tartrate, citrate, maleate, fumarate, methanesulfonate, p-toluenesulfonate, benzenesulfonate, and ascorbate.

The compound (1) represented by Formula (1) may be present in the form of a tautomer. Accordingly, the compound of the present invention encompasses a tautomer of the compound represented by Formula (1).

The compound represented by Formula (1) has at least two asymmetric carbon atoms. Accordingly, the compound of the present invention encompasses stereoisomers of the compound and a mixture thereof. The compound of the present invention also encompasses a racemate and an optically active form of the compound represented by Formula (1).

When the compound represented by Formula (1) and the compounds described in reference examples are a racemate, these compounds are illustrated, for example, as follows.

[Formula 49]

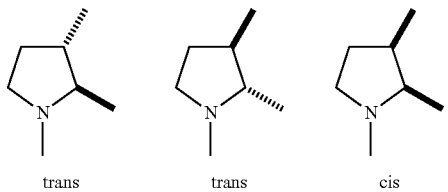

trans    trans    cis

Moreover, the compound represented by Formula (1) and the compounds described in reference examples, if the absolute configuration of asymmetric carbons contained therein is known, can be illustrated, for example, as follows.

[Formula 50]

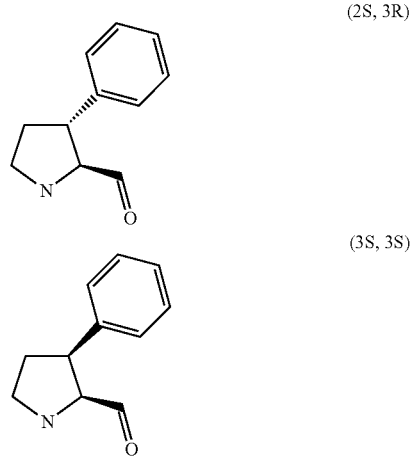

(2S, 3R)

(3S, 3S)

Furthermore, if the steric configuration of each of the compound represented by Formula (1) and the compounds described in reference examples is known, the compounds are illustrated, for example, as follows.

[Formula 51]

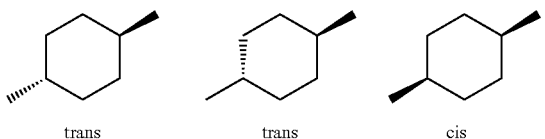

trans    trans    cis

Further, the compound represented by Formula (1) may generate an atropisomer based on axial or planar chirality caused by hindered rotation in molecules. Accordingly, the compound of the present invention also encompasses stereoisomers of the compound and the mixtures thereof.

Hereinafter, a method for producing the compound of the present invention will be described in the following examples. However, these examples are not intended to limit the scope of the present invention. It is to be noted that the following abbreviations may be used to simplify the descriptions in the present description.

Boc group: a tert-butoxycarbonyl group

Cbz group: a benzyloxycarbonyl group

Alloc group: an allyloxycarbonyl group

Fmoc group: a 9-fluorenylmethyloxycarbonyl group

THF: tetrahydrofuran

DMF: N,N-dimethylformamide

Production Method

The compounds according to the present invention can be synthesized by the following synthetic methods and the methods combining known compounds with known synthetic methods.

Compounds used as raw material compounds may be used in the form of a salt. It should be noted that the following reactions are given for illustrative purpose only, and thus that the compound of the present invention can also be produced, as appropriate, by alternative methods based on the knowledge of a person skilled in organic synthesis.

In each of the methods explained below, even in the case that the use of a protecting group is not specifically described, if there is a functional group that requires a protecting group, the functional group may be protected if necessary, and after completion of a reaction or a series of reactions, the functional group may be deprotected so as to obtain a product of interest. As protecting groups, for instance, common ones described in T. W. Greene and P. G. M. Wuts, "Protective Groups in Organic Synthesis", 3rd Ed., John Wiley and Sons, inc., New York (1999) can be used. Examples of a protecting group for an amino group specifically include benzyloxycarbonyl, tert-butoxycarbonyl, acetyl and benzyl; and examples of a protecting group for a hydroxy group specifically include trialkylsilyl, acetyl and benzyl.

Introduction and removal of such a protecting group can be carried out by common methods in organic synthetic chemistry (for example, see the method described in T. W. Greene and P. G. M. Wuts, "Protective Groups in Organic Synthesis", 3rd Ed., John Wiley and Sons, inc., New York (1999)) or a method equivalent thereto.

Production Method 1

The compound represented by Formula (1) is produced, for example, by the following process.

[Formula 52]

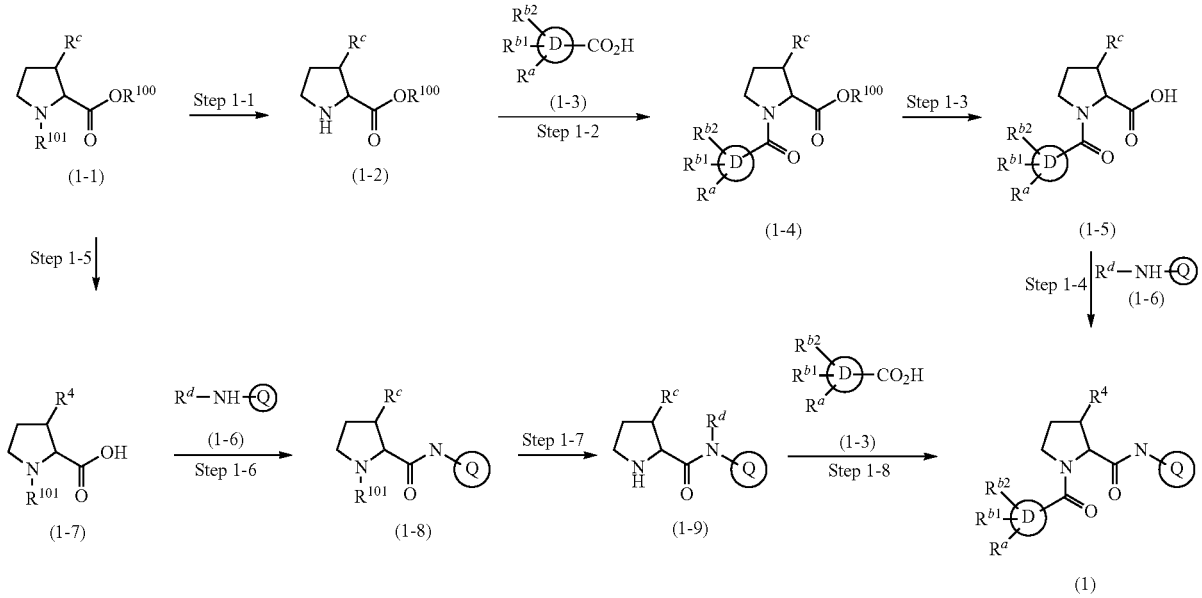

[wherein ring D, L, $R^a$, $R^{b1}$, $R^{b2}$, $R^c$, $R^d$, and ring Q have the same definitions as those described in [1] above, $R^{100}$ represents a $C_{1-4}$ alkyl group or a benzyl group, and $R^{101}$ represents a Cbz group, a Boc group, an Alloc group, a benzyl group or a Fmoc group].

Raw Material Compounds

The compounds represented by Formula (1-1), Formula (1-2) and Formula (1-7) are commercially available or can be produced by known synthetic methods (e.g., Tetrahedron Lett. 2010, 51, 6745, Org. Lett. 2009, 11, 4056, Bioorg. Med. Chem. 2011, 19, 5833).

Compound (1-3) is commercially available or can be produced by known synthetic methods (e.g., WO1993/005021, WO2009/152133, JP55151539).

Compound (1-6) is commercially available or can be produced by known synthetic methods (e.g., Chem. Commun. 2009, 48, 7581, WO2008/012782).

Step 1-1: Step of Producing Compound (1-2)

Compound (1-2) can be produced, for instance, according to the method described in Protective Groups in Organic Synthesis $3^{rd}$ Edition (John Wiley & Sons, Inc.), using Compound (1-1) as a raw material.

Step 1-2: Step of Producing Compound (1-4)

Compound (1-4) can be produced by allowing Compound (1-2) to react with Compound (1-3) in an inert solvent, using a condenser, and if necessary, in the presence of a base. If necessary, a phase-transfer catalyst can be added to the reaction system.

The base is not particularly limited and may be a compound used as a base in a common reaction. Examples of the base include: organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline; and inorganic bases such as sodium hydrogen carbonate, potassium hydrogen carbonate, sodium carbonate, potassium carbonate, sodium hydroxide, and sodium hydride. The base can be used at an equivalent ratio of generally 0.1:1 to 100:1, and preferably 1:1 to 5:1, with respect to Compound (1-3).

Examples of the phase-transfer catalyst include quaternary ammonium salts such as tetrabutylammonium bromide and benzyltriethylammonium bromide, and crown ether such as 18-crown-6-ether. The phase-transfer catalyst can be used at an equivalent ratio of generally 0.01:1 to 100:1, and preferably 0.1:1 to 3:1, with respect to Compound (1-3).

Examples of the condenser include those described in Jikken Kagaku Koza (edited by The Chemical Society of Japan, Maruzen), Vol. 22. Examples of such a condenser include: phosphoric esters such as diethyl cyanophosphate and diphenylphosphoryl azide; carbodiimides such as 1-ethyl-3-(3-dimethylaminopropyl)-carbodiimide hydrochloride (WSC.HCl) and dicyclohexyl carbodiimide (DCC); combinations of disulfides such as 2,2'-dipyridyldisulfide with phosphines such as triphenylphosphine; phosphorus halides such as N,N'-bis(2-oxo-3-oxazolidinyl)phosphinic chloride (BOPCl); combinations of azodicarboxylic diesters such as diethyl azodicarboxylate with phosphines such as triphenylphosphine; 2-halo-1-lower alkyl pyridinium halides such as 2-chloro-1-methyl pyridinium iodide; 1,1'-carbonyldiimidazole (CDI); diphenylphosphorylazide (DPPA); diethylphosphorylcyanide (DEPC); tetrafluoroborates such as 2-(1H-benzotriazol-1-yl)-1,1,3,3-tetramethyluroniumtetrafluoroborate (TBTU), and 2-chloro-1,3-dimethylimidazolidiniumtetrafluoroborate (CIB); and phosphates such as 2-(1H-benzotriazol-1-yl)-1,1,3,3-tetramethyluroniumhexafluorophosphate (HBTU), benzotriazol-1-yloxytris(dimethylamino)phosphoniumhexafluorophosphate (BOP), benzotriazol-1-yloxytris(pyrrolidino)phosphoniumhexafluorophosphate (PYBOP), and 2-(7-aza-1H-benzotriazol-1-yl)-1,1,3,3-tetramethyluroniumhexafluorophosphate (HATU).

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; ketone solvents such as acetone; and aprotic solvents such as acetonitrile, N,N-dimethylformamide, dimethyl sulfoxide, and hexamethylenephosphoramide. A mixed solvent thereof may also be used.

The reaction temperature is not particularly limited, and it is preferably selected from a range between approximately −70° C. and 100° C. and more preferably 0° C. to 40° C.

Moreover, Compound (1-4) can also be produced by converting Compound (1-3) to an acid halide using a halogenating reagent (e.g., 1-chloro-N,N,2-trimethylpropenylamine, phosphorus oxychloride, phosphorus trichloride, thionyl chloride, or phosphorous pentachloride), and then allowing the acid halide to react with Compound (1-2), in an inert solvent, and if necessary in the presence of a base.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; ester solvents such as ethyl acetate and isopropyl acetate; ketone solvents such as methyl ethyl ketone and acetone; and aprotic solvents such as acetonitrile, N,N-dimethylformamide, dimethyl sulfoxide, and hexamethylenephosphoramide. Examples of the base include organic bases such as N-methylmorpholine, triethylamine, diisopropylethylamine, tributylamine, 1,8-diazabicyclo [4.3.0]non-5-ene, 1,4-diazabicyclo[5.4.0]undec-7-ene, pyridine, dimethylaminopyridine, and picoline. The halogenating reagent can be used at an equivalent ratio of 0.1:1 to 100:1, and preferably 0.8:1 to 3:1, with respect to Compound (1-3). The reaction temperature is not particularly limited, and it is preferably selected from a range between approximately −30° C. and 60° C.

Step 1-3: Step of Producing Compound (1-5)

Compound (1-5) can be produced by hydrolyzing Compound (1-4) according to a known method (e.g., see Protective Groups in Organic Synthesis 3$^{rd}$ Edition (John Wiley & Sons, Inc.), Comprehensive Organic transformation, R. C. Larock, et al., VCH publisher Inc., 1989. etc.).

Step 1-4: Step of Producing the Compound Represented by Formula (1)

The compound represented by Formula (1) can be produced from Compound (1-5) and Compound (1-6) according to the manner of Step 1-2.

Step 1-5: Step of Producing Compound (1-7)

Compound (1-7) can be produced from Compound (1-1) according to the manner of Step 1-3.

Step 1-6: Step of Producing Compound (1-8)

Compound (1-8) can be produced from Compound (1-7) and Compound (1-6) according to the manner of Step 1-2.

Step 1-7: Step of Producing Compound (1-9)

Compound (1-9) can be produced from Compound (1-8) according to the manner of Step 1-1.

Step 1-8: Step of Producing the Compound Represented by Formula (1)

The compound represented by Formula (1) can be produced from Compound (1-9) and Compound (1-3) according to the manner of Step 1-2.

Production Method 2

Among the compounds represented by Formula (1-7), 3-substituted pyrrolidine-2-carboxylic acid derivatives (racemate) represented by Formula (2-11) and (2-12) can be produced, for example, by the following process.

[Formula 53]

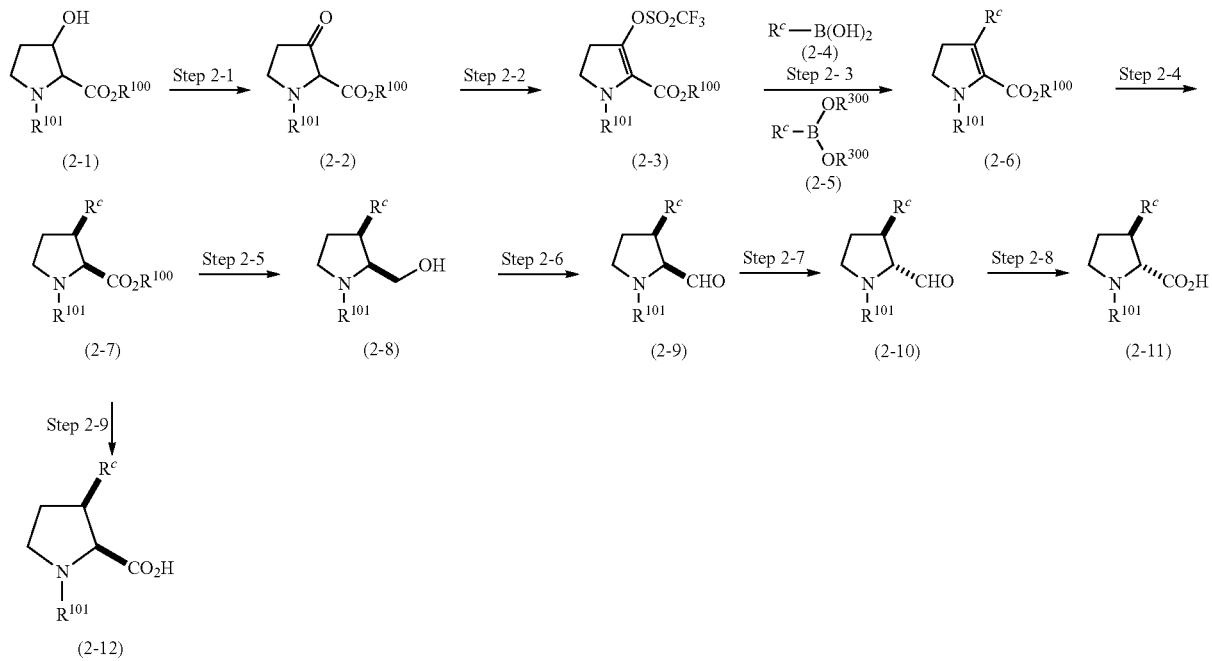

wherein $R^c$ have the same definitions as those described in [1] above; $R^{100}$ represents a $C_{1-4}$ alkyl group or a benzyl group; $R^{300}$ represents a $C_{1-6}$ alkyl group, or they may bind to each other to form a ring structure; and $R^{101}$ represents a Cbz group, a Boc group, an Alloc group, a benzyl group, or a Fmoc group].

Raw Material Compounds

The compound represented by Formula (2-1) can be produced by suitably protecting a functional group(s) of 3-hydroxyproline, which is commercially available, according to a known protection method (e.g., Protective Groups in Organic Synthesis 3$^{rd}$ Edition (John Wiley & Sons, Inc.)).

Moreover, the compound represented by Formula (2-2) can be produced according to a known production method (e.g., Org. Lett. 2007, 9, 4255., Tetrahedron Lett. 1995, 36, 6209).

Step 2-1: Step of Producing Compound (2-2)

Compound (2-2) can be produced by oxidizing Compound (2-1), for instance, according to the known method described in Comprehensive Organic transformation, R. C. Larock, et al., VCH publisher Inc., 1989. etc. Examples of the oxidation method preferably include Dess-Martin oxidation, Swern oxidation, Parikh-Doering oxidation, TPAP oxidation and PCC oxidation.

Step 2-2: Step of Producing Compound (2-3)

Compound (2-3) can be produced by allowing Compound (2-2) to react with trifluoromethanesulfonic anhydride or N,N-ditrifluoromethanesulfonylaminobenzene in an inert solvent and in the presence of a base.

The base is not particularly limited and may be a compound used as a base in a common reaction. Examples of the base include: organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline; and inorganic bases such as sodium methoxide, sodium tert-butoxide, potassium tert-butoxide, lithium diisopropylamide, lithium bis(trimethylsilyl)amide, potassium bis(trimethylsilyl)amide, sodium bis(trimethylsilyl)amide, lithiumamide, n-butyllithium, sodium hydrogen carbonate, potassium hydrogen carbonate, sodium carbonate, potassium carbonate, sodium hydroxide, and sodium hydride. The base can be used at an equivalent ratio of generally 0.1:1 to 100:1, and preferably 0.8:1 to 3:1, with respect to Compound (3-2).

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; and aprotic solvents such as N,N-dimethylformamide, dimethyl sulfoxide, and hexamethylenephosphoramide. A mixed solvent thereof may also be used. The reaction temperature is not particularly limited. It is preferably selected from a range between approximately 0° C. and 40° C.

Step 2-3: Step of Producing Compound (2-6)

Compound (2-6) can be produced by allowing Compound (2-3) to react with Compound (2-4) or Compound (2-5) in a suitable inert solvent, in the presence of a suitable metallic reagent or a suitable ligand, and if necessary, in the presence of a base. The reaction temperature is in a range between approximately −78° C. and the boiling point of the solvent, and it is preferably 25° C. to 120° C. The reaction time is 10 minutes to 5 days.

Examples of the metallic reagent specifically include: copper reagents such as copper iodide; and palladium reagents such as palladium(II) acetate, palladium(II) chloride, tetrakis(triphenylphosphine)palladium, tris(dibenzylideneacetone)dipalladium(0), bis(dibenzylideneacetone)palladium, 1,1'-bis(diphenylphosphino)ferrocenedichloropalladium(II), palladium-carbon, dichlorobis(tri-o-tolylphosphine)palladium(II), bis(tri-tert-butylphosphine)palladium(0), bis(triphenylphosphine)palladium(II) dichloride, bis(triphenylphosphine)palladium(II) diacetate, benzyl bis(triphenylphosphine)palladium(II) chloride, [1,2-bis(diphenylphosphino)ethane]palladium(II) dichloride, [1,3-bis(diphenylphosphino)propane]palladium(II) dichloride, [1,4-bis(diphenylphosphino)butane]palladium(II) dichloride, bis(tricyclohexylphosphine)palladium(II), bis(methyldiphenylphosphine)palladium(II) dichloride, bis(benzonitrile)palladium(II) dichloride, bis(acetonitrile)palladium(II) dichloride, bis(2,4-pentanedionate)palladium(II), dichloro(1,5-cyclooctadiene)palladium(II), aryl palladium(II) chloride dimer, poly[N-isopropylacrylamide-co-4-(diphenylphosphino)styrene]palladium(II) dichloride and 1,1'-bis(diphenylphosphino)ferrocene-palladium(II) dichloride dichloromethane complex. The organic metallic reagent can be used at an equivalent ratio of 0.001:1 to 1:1, and preferably 0.005:1 to 0.2:1, with respect to Compound (2-3).

Examples of the ligand specifically include tri-o-tolylphosphine, tri-tert-butylphosphine, triphenylphosphine, 1,1'-bis(diphenylphosphino)ferrocene, tricyclohexylphosphine, 2,2'-bis(diphenylphosphino)-1,1'-binaphthyl, diethylphenylphosphine, methyldiphenylphosphine, ethyldiphenylphosphine, diphenyl-propylphosphine, dicyclohexylphenylphosphine, methoxydiphenylphosphine, ethoxydiphenylphosphine, tris(2-methylphenyl)phosphine, tris(3-methylphenyl)phosphine, tris(4-methoxyphenyl)phosphine, tris(2,6-dimethoxyphenyl)phosphine, diphenylphosphinobenzene-3-sulfonic acid sodium salts, 4-(dimethylamino)phenyldiphenylphosphine, diphenyl-2-pyridylphosphine, tris(2-furyl)phosphine, tris(2-thienyl)phosphine, bis(diphenylphosphino)methane, 1,2-bis(dimethylphosphino)ethane, 1,2-bis(diphenylphosphino)ethane, 1,3-bis(diphenylphosphino)propane, and 1,4-bis(diphenylphosphino)butane. The ligand can be used at an equivalent ratio of 0.001:1 to 1:1, and preferably 0.005:1 to 0.2:1, with respect to Compound (2-3).

Examples of the base include: organic bases such as triethylamine, N-methylmorpholine, diisopropylethylamine, pyridine, and 4-dimethylaminopyridine; inorganic bases such as potassium carbonate, sodium hydroxide, potassium hydroxide, lithium hydroxide, sodium hydride, potassium hydride, cesium carbonate, sodium carbonate, sodium hydrogen carbonate, and potassium phosphate; and organic metallic reagents such as sodium methoxide, sodium tert-butoxide, potassium tert-butoxide, lithium diisopropylamide, lithium bis(trimethylsilyl)amide, potassium bis(trimethylsilyl)amide, sodium bis(trimethylsilyl)amide, lithium amide, and n-butyl lithium. Examples of the base preferably include potassium carbonate and cesium carbonate. The base can be used at an equivalent ratio of 0.1:1 to 100:1, and preferably 0.5:1 to 5:1, with respect to Compound (2-3).

Examples of the inert solvent specifically include: acetone; acetonitrile; halogenated hydrocarbons such as chloroform and dichloromethane; aromatic hydrocarbons such as benzene and toluene; ether solvents such as diethyl ether, tetrahydrofuran (THF), 1,4-dioxane, dimethoxyethane, tert-butyl methyl ether, and cyclopentyl methyl ether; lower alcohols such as methanol, ethanol, and isopropanol; and aprotic polar solvents such as N,N-dimethylformamide, N-methyl pyrrolidone, and dimethyl sulfoxide. A mixed solvent thereof may also be used. The inert solvent is preferably toluene or N,N-dimethylformamide.

Step 2-4: Step of Producing Compound (2-7)

Compound (2-7) can be obtained in a cis-selective manner by subjecting Compound (2-6) to a hydrogenation reaction, for instance, according to the known method described in Bioorg. Med. Chem. Lett. 2008, 18, 1931. Examples of the metallic catalyst specifically include palladium-carbon, palladium hydroxide, and platinum oxide.

Step 2-5: Step of Producing Compound (2-8)

Compound (2-8) can be produced by reducing Compound (2-7), for instance, according to the known method described in Comprehensive Organic transformation, R. C. Larock, et al., VCH publisher Inc., 1989.

Step 2-6: Step of Producing Compound (2-9)

Compound (2-9) can be produced by oxidizing Compound (2-8), for instance, the known method described in Comprehensive Organic transformation, R. C. Larock, et al., VCH publisher Inc., 1989. Examples of the oxidation method preferably include Dess-Martin oxidation, Swern oxidation, TPAP oxidation, and PCC oxidation.

Alternatively, Compound (2-9) can be directly obtained from Compound (2-7) by reducing the Compound (2-7) with method preferably include Pinnick oxidation and PDC oxidation.

Step 2-9: Step of Producing Compound (2-12)

Compound (2-12) can be produced by a method similar to Step 1-3 using Compound (2-7).

Production Method 3

Among the compounds represented by Formula (1-1), optically active 3-substituted pyrrolidine-2-carboxylic acid esters represented by Formulae (3-10) and (3-13) can be produced, for example, by the following process.

[Formula 54]

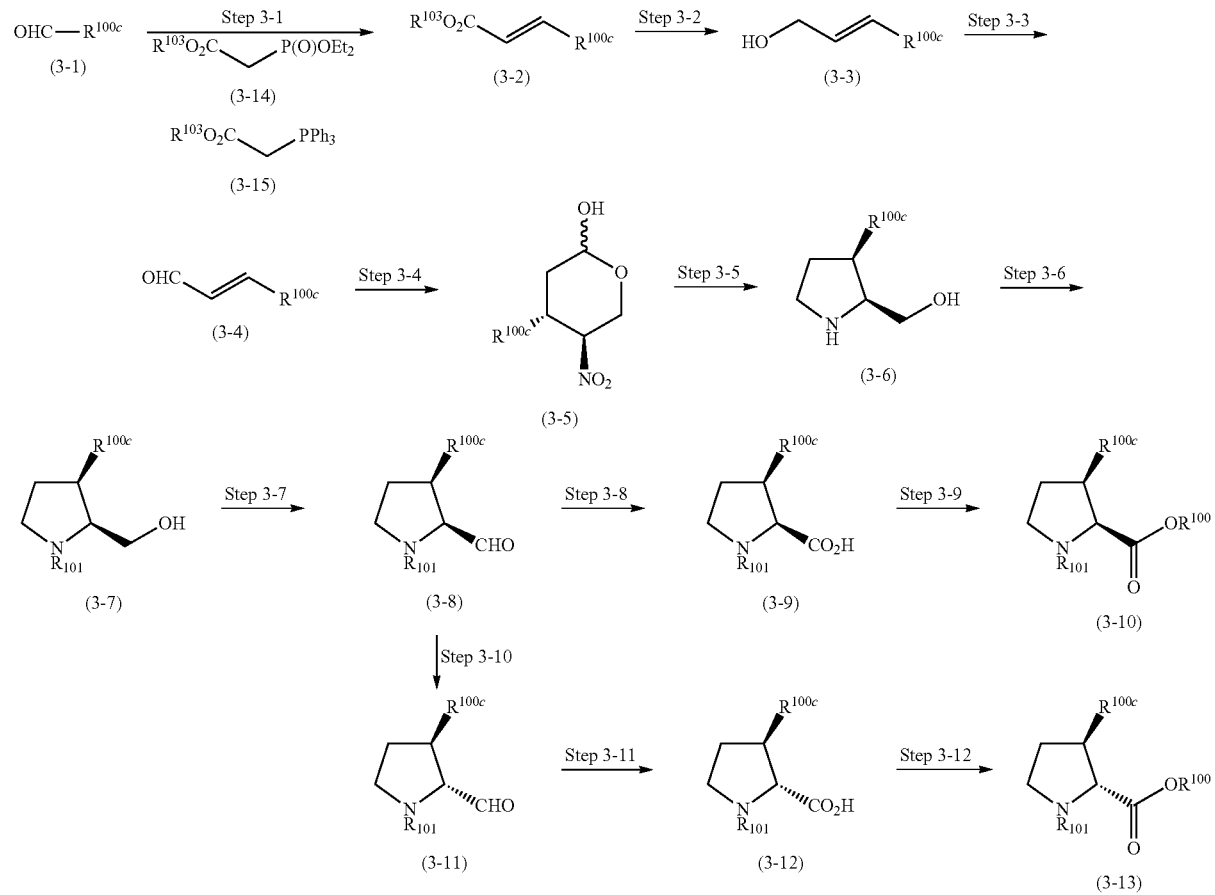

diisobutyl aluminum hydride in an inert solvent. The reaction temperature is selected from a range between −100° C. and 100° C. Examples of the inert solvent specifically include halogenated hydrocarbons such as chloroform and dichloromethane.

Step 2-7: Step of Producing Compound (2-10)

Compound (2-10) can be produced by treating Compound (2-9) with a base such as 1,8-diazabicyclo[5.4.0]undec-7-ene (DBU) according to a method similar to a known method (e.g., Org. Lett. 2009, 11, 4056. etc.), so as to isomerize it. The reaction temperature is not particularly limited, and it is preferably selected from a range between approximately 0° C. and 80° C.

Step 2-8: Step of Producing Compound (2-11)

Compound (2-11) can be produced by oxidizing Compound (2-10) by a method similar to a known method (e.g., Comprehensive Organic transformation, R. C. Larock, et al., VCH publisher Inc., 1989. etc.). Examples of the oxidation

[wherein $R^{100c}$ represents an optionally substituted $C_{6-10}$ aryl group, an optionally substituted 5- to 10-membered heteroaryl group, an optionally substituted $C_{1-6}$ alkyl group, an optionally substituted 4- to 10-membered saturated heterocyclic group, or an optionally substituted $C_{3-10}$ cycloalkyl group; $R^{100}$ represents a hydrogen atom, a $C_{1-4}$ alkyl group, or a benzyl group; $R^{103}$ represents a $C_{1-4}$ alkyl group or a benzyl group; and $R^{101}$ represents a Cbz group, a Boc group, an Alloc group, a benzyl group, or a Fmoc group].

The compounds represented by Formula (3-1), Formula (3-14) and Formula (3-15) are commercially available.

Step 3-1: Step of Producing Compound (3-2)

Compound (3-2) can be produced by allowing Compound (3-1) to react with Compound (3-14) or Compound (3-15) in an inert solvent and in the presence of a base.

The base is not particularly limited and may be a compound used as a base in a common reaction. Examples of the base include: organic bases such as N-methylmorpholine, triethylamine, diisopropylethylamine, tributylamine, 1,8-diazabicyclo[4.3.0]non-5-ene, 1,8-diazabicyclo[5.4.0]undec-7-ene, pyridine, dimethylaminopyridine, and picoline; and inorganic bases such as sodium hydrogen carbonate, potassium hydrogen carbonate, sodium carbonate, potassium carbonate, sodium hydroxide, and sodium hydride. The base can be used at an equivalent ratio of generally 0.1:1 to 100:1, and preferably 0.8:1 to 2:1, with respect to Compound (3-14) or Compound (3-15).

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; and aprotic solvents such as N,N-dimethylformamide, dimethyl sulfoxide, and hexamethylenephosphoamide. A mixed solvent thereof may also be used. The reaction temperature is not particularly limited. It is preferably selected from a range between approximately 0° C. and 60° C.

Step 3-2: Step of Producing Compound (3-3)

Compound (3-3) can be produced by reducing Compound (3-2), for instance, according to the known method described in Comprehensive Organic transformation, R. C. Larock, et al., VCH publisher Inc., 1989. The reducing agent may be preferably lithium aluminum hydride, and the insert solvent may be preferably tetrahydrofuran.

Step 3-3: Step of Producing Compound (3-4)

Compound (3-4) can be produced by oxidizing Compound (3-3), for instance, according to the known method described in Comprehensive Organic transformation, R. C. Larock, et al., VCH publisher Inc., 1989. etc. Examples of the oxidation method preferably include Dess-Martin oxidation, Swern oxidation, TPAP oxidation and PCC oxidation.

Step 3-4: Step of Producing Compound (3-5)

Compound (3-5) can be produced by allowing Compound (3-4) to react with 2-nitroethanol, for instance, according to the known method described in Org. Lett. 2009, 11, 4056 in the presence of optically active diphenyl prolinol trimethylsilyl ether and benzoic acid.

Step 3-5: Step of producing Compound (3-6)

This step can be carried out, for example, by the following production method (i or ii).

i. Compound (3-6) can be produced by allowing Compound (3-5) to react with iron, zinc and tin in an inert solvent. Examples of the inert solvent include: water; acetic acid; alcohol solvents such as methanol, ethanol or 2-propanol; and ether solvents such as tetrahydrofuran, diethyl ether, 1,4-dioxane or 1,2-dimethoxyethane. A mixed solvent thereof may also be used. The reaction temperature is selected from a range between approximately 30° C. and approximately 100° C.

ii. Compound (3-6) can be produced by subjecting Compound (3-5) to a hydrogenation reaction, for instance, according to the known method described in Org. Lett. 2009, 11, 4056. Metal catalysts that can be preferably used herein include palladium hydroxide, palladium-carbon and platinum oxide.

Step 3-6: Step of Producing Compound (3-7)

Compound (3-7) can be produced from Compound (3-6), for instance, according to the known method described in Protective Groups in Organic Synthesis 3$^{rd}$ Edition (John Wiley & Sons, Inc.).

Step 3-7: Step of Producing Compound (3-8)

Compound (3-8) can be produced from Compound (3-7) according to the manner of Step 2-6.

Step 3-8: Step of Producing Compound (3-9)

Compound (3-9) can be produced by oxidizing Compound (3-8) by the known method described in Comprehensive Organic transformation, R. C. Larock, et al., VCH publisher Inc., 1989. Examples of the oxidation method preferably include Pinnick oxidation and PDC oxidation.

Step 3-9: Step of Producing Compound (3-10)

Compound (3-10) can be produced by esterifying Compound (3-9), for instance, the known method described in Comprehensive Organic transformation, R. C. Larock, et al., VCH publisher Inc., 1989.

Step 3-10: Step of Producing Compound (3-11)

Compound (3-11) can be produced by treating Compound (3-8) with a base such as 1,8-diazabicyclo[5.4.0]unde-7-ene (DBU), for instance, according to the known method described in Org. Lett. 2009, 11, 4056, so as to isomerize it. The reaction temperature is not particularly limited, and it is preferably selected from a range between approximately 0° C. and 80° C.

Step 3-11: Step of Producing Compound (3-12)

Compound (3-12) can be produced by oxidizing Compound (3-11), for instance, according to the known method described in Comprehensive Organic transformation, R. C. Larock et al., VCH publisher Inc., 1989. Examples of the oxidation method preferably include Pinnick oxidation and PDC oxidation.

Step 3-12: Step of Producing Compound (3-13)

Compound (3-13) can be produced by esterifying Compound (3-12), for instance, according to the known method described in Comprehensive Organic transformation, R. C. Larock et al., VCH publisher Inc., 1989.

Production Method 4

Among the compounds represented by Formula (1-1), the compound represented by Formula (4-3) or a salt thereof can be produced, for example, by the following process.

[Formula 55]

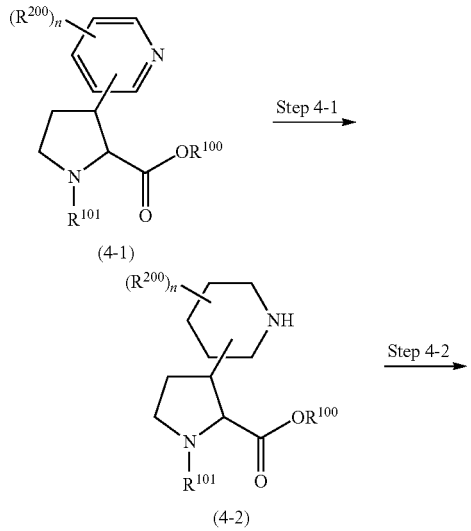

-continued

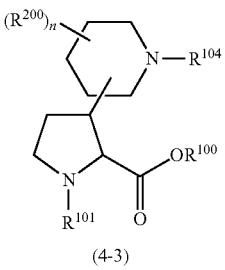

(4-3)

wherein $R^{200}$ represents an optionally substituted $C_{1-6}$ alkyl group, an optionally substituted $C_{1-6}$ alkoxy group or a fluorine atom; n represents 0 to 4; $R^{100}$ represents a hydrogen atom, a $C_{1-4}$ alkyl group or a benzyl group; $R^{101}$ represents a Cbz group, a Boc group, an Alloc group, a benzyl group or a Fmoc group; and $R^{104}$ represents an optionally substituted $C_{1-6}$ alkyl group, an optionally substituted $C_{3-10}$ cycloalkyl group, an optionally substituted $C_{1-6}$ alkylcarbonyl group, an optionally substituted $C_{3-10}$ cycloalkylcarbonyl group, an optionally substituted $C_{6-10}$ arylcarbonyl group, an optionally substituted 5- to 10-membered heteroarylcarbonyl group, an optionally substituted 4- to 10-membered saturated heterocyclic carbonyl group, an optionally substituted $C_{1-6}$ alkylsulfonyl group, an optionally substituted $C_{3-10}$ cycloalkylsulfonyl group, an optionally substituted $C_{6-10}$ arylsulfonyl group, an optionally substituted 5- to 10-membered heteroarylsulfonyl group, an optionally substituted 4- to 10-membered saturated heterocyclic sulfonyl group, an optionally substituted $C_{1-6}$ alkoxycarbonyl group, an optionally substituted $C_{3-10}$ cycloalkoxycarbonyl group, an optionally substituted $C_{6-10}$ aryloxycarbonyl group, an optionally substituted 5- to 10-membered heteroaryloxycarbonyl group or an optionally substituted 4- to 10-membered saturated heterocyclic oxycarbonyl group.

The compound represented by Formula (4-1) can be produced through the above described Production Method 2 or 3, or it is commercially available.

Step 4-1: Step of Producing Compound (4-2)

Compound (4-2) can be produced by reacting Compound (4-1) under hydrogen atmosphere, in an inert solvent, and in the presence of palladium-carbon, palladium hydroxide or platinum oxide. If necessary, an acid can be added to the reaction system.

Examples of the acid include hydrochloric acid water, hydrogen bromide water, sulfuric acid water, acetic acid and trifluoroacetic acid.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; alcohol solvents such as ethanol, methanol, and isopropanol; and acetic acid. A mixed solvent thereof may also be used.

The reaction temperature is not particularly limited, and it is preferably selected from a range between approximately 0° C. and 100° C. and more preferably 25° C. to 80° C.

Step 4-2: Step of Producing Compound (4-3)

Compound (4-3), in which $R^{104}$ represents an optionally substituted $C_{1-6}$ alkyl group or an optionally substituted $C_{3-10}$ cycloalkyl group, can be produced by allowing Compound (4-2) to react with an aldehyde or ketone corresponding thereto in an inert solvent and in the presence of sodium triacetoxyborohydride or sodium cyanoborohydride.

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; alcohol solvents such as ethanol, methanol, and isopropanol; water; and acetic acid. A mixed solvent thereof may also be used. The reaction temperature is not particularly limited, and it is preferably selected from a range between approximately 0° C. and 40° C.

Compound (4-3), in which $R^{104}$ represents an optionally substituted $C_{1-6}$ alkylcarbonyl group, an optionally substituted $C_{3-10}$ cycloalkylcarbonyl group, an optionally substituted $C_{6-10}$ arylcarbonyl group, an optionally substituted 5- to 10-membered heteroarylcarbonyl group, an optionally substituted 4- to 10-membered saturated heterocyclic carbonyl group, an optionally substituted $C_{1-6}$ alkylsulfonyl group, an optionally substituted $C_{3-10}$ cycloalkylsulfonyl group, an optionally substituted $C_{6-10}$ arylsulfonyl group, an optionally substituted 5- to 10-membered heteroarylsulfonyl group, an optionally substituted 4- to 10-membered saturated heterocyclic sulfonyl group, an optionally substituted $C_{1-6}$ alkoxycarbonyl group, an optionally substituted $C_{3-10}$ cycloalkoxycarbonyl group, an optionally substituted $C_{6-10}$ aryloxycarbonyl group, an optionally substituted 5- to 10-membered heteroaryloxycarbonyl group, or an optionally substituted 4- to 10-membered saturated heterocyclic oxycarbonyl group, can be produced by allowing Compound (4-2) to react with the corresponding acid anhydride, acid halide, sulfonyl anhydride, sulfonyl halide, carbonic acid diester, haloformate, or cyanoformate in an inert solvent and in the presence of a base.

The base is not particularly limited and may be a compound used as a base in a common reaction. Examples of the base include: organic bases such as N-methylmorpholine, triethylamine, diisopropylethylamine, tributylamine, 1,8-diazabicyclo[4.3.0]non-5-ene, 1,8-diazabicyclo[5.4.0]undec-7-ene, pyridine, dimethylaminopyridine, and picoline; and inorganic bases such as sodium hydrogen carbonate, potassium hydrogen carbonate, sodium carbonate, potassium carbonate, sodium hydroxide, and sodium hydride. The base can be used at an equivalent ratio of generally 0.1:1 to 100:1, and preferably 0.8:1 to 5:1, with respect to Compound (2-14) or Formula (2-15).

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; and aprotic solvents such as N,N-dimethylformamide, dimethyl sulfoxide, and hexamethylenephosphoamide. A mixture thereof may also be used. The reaction temperature is not particularly limited. It is preferably selected from a range between approximately 0° C. and 40° C.

Production Method 5

Among the compounds represented by Formula (1-1), the compound represented by Formula (5-2) can be produced, for example, by the following process.

[Formula 56]

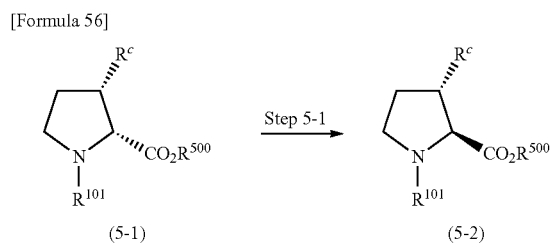

wherein $R^c$ has the same definitions as those described in [1] above; $R^{500}$ represents a $C_{1-4}$ alkyl group, a benzyl group, a 4-methoxybenzyl group or a 2,4-dimethoxybenzyl group; and $R^{101}$ represents a Cbz group, a Boc group, an Alloc group or a Fmoc group.

The compound represented by Formula (5-1) can be produced through the above described Production Method 2, 3 or 4, or it is commercially available.

Step 5-1: Step of Producing Compound (5-2)

Compound (5-2) can be produced by allowing Compound (5-1) to react with a base in an inert solvent. The reaction temperature is not particularly limited, and it is preferably selected from a range between approximately −20° C. and 60° C.

Examples of the base specifically include: organic bases such as triethylamine, N-methylmorpholine, diisopropylethylamine, pyridine, and 4-dimethylaminopyridine; inorganic bases such as potassium carbonate, sodium hydroxide, potassium hydroxide, lithium hydroxide, sodium hydride, potassium hydride, cesium carbonate, sodium carbonate, sodium hydrogen carbonate, and potassium phosphate; and organic metallic reagents such as sodium methoxide, sodium tert-butoxide, potassium tert-butoxide, lithium diisopropylamide, lithium bis(trimethylsilyl)amide, lithium diisopropylamide, potassium bis(trimethylsilyl)amide, sodium bis(trimethylsilyl)amide, lithium amide, and n-butyl lithium. Examples of the base preferably include lithium diisopropylamide and lithium bis(trimethylsilyl)amide. The base can be used at an equivalent ratio of 0.1:1 to 100:1, and preferably 0.5:1 to 5:1, with respect to Compound (3-3).

Examples of the inert solvent specifically include: halogenated hydrocarbons such as chloroform and dichloromethane; aromatic hydrocarbons such as benzene and toluene; ether solvents such as diethyl ether, tetrahydrofuran (THF), 1,4-dioxane, dimethoxyethane, tert-butyl methyl ether, and cyclopentyl methyl ether; aprotic polar solvents such as N,N-dimethylformamide, N-methyl pyrrolidone, and dimethyl sulfoxide; and a mixed solvent thereof. Examples of the solvent preferably include tetrahydrofuran and N,N-dimethylformamide.

Production Method 6

Among the compounds represented by Formula (1-3), the compound represented by Formula (6-8) can be produced, for example, by the following process.

[Formula 57]

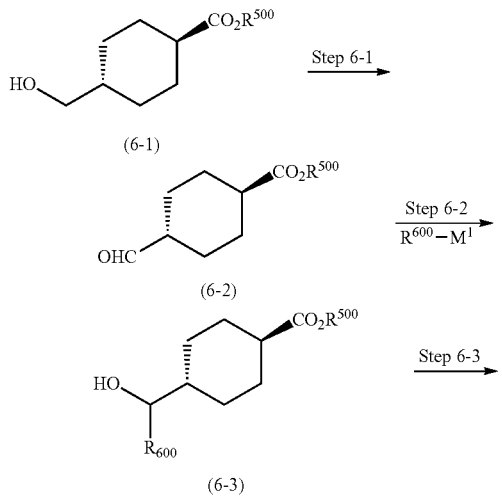

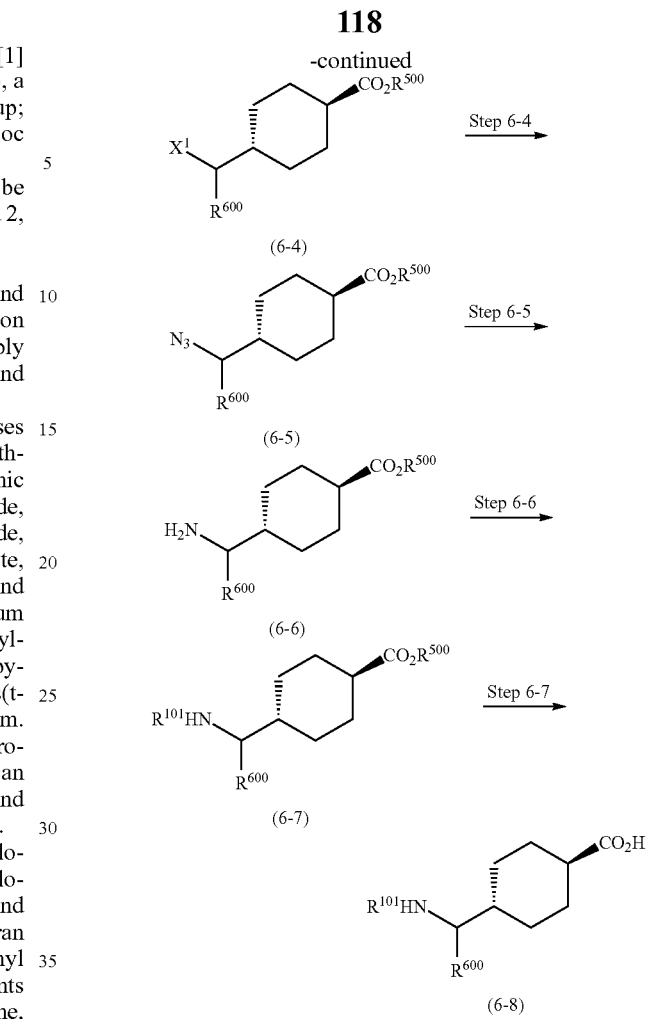

wherein $R^{500}$ represents a $C_{1-4}$ alkyl group, a benzyl group, a 4-methoxybenzyl group or a 2,4-dimethoxybenzyl group; $R^{600}$ represents an optionally substituted $C_{1-6}$ alkyl group or an optionally substituted $C_{3-10}$ cycloalkyl group; $X^1$ represents a leaving group (e.g., a methanesulfonyloxy group, a chloromethanesulfonyloxy group, a trifluoromethanesulfonyloxy group, a benzenesulfonyloxy group, a p-toluenemethanesulfonyloxy group, a chlorine atom, a bromine atom, an iodine atom, etc.); $M^1$ represents a lithium or a magnesium halide; and $R^{101}$ represents a Cbz group, a Boc group, an Alloc group, a benzyl group, or a Fmoc group].

The compound represented by Formula (6-1) can be produced by suitably protecting a functional group(s) of trans-4-(hydroxymethyl)cyclohexanecarboxylic acid, which is commercially available, for instance, according to the known protection method described in Protective Groups in Organic Synthesis $3^{rd}$ Edition (John Wiley & Sons, Inc.), or it is commercially available.

Step 6-1: Step of Producing Compound (6-2)

Compound (6-2) can be produced by oxidizing Compound (6-1), for instance, according to the known method described in Comprehensive Organic transformation, R. C. Larock et al, VCH publisher Inc., 1989. Examples of the oxidation method preferably include Dess-Martin oxidation, Swern oxidation, TPAP oxidation, Parikh-Doering oxidation, PCC oxidation and PDC oxidation.

Step 6-2: Step of Producing Compound (6-3)

Compound (6-3) can be produced by allowing Compound (6-2) to react with alkyl lithium or a Grignard reagent in an inert solvent.

If necessary, Lewis acid can be added to the reaction system.

Examples of the Lewis acid specifically include lithium chloride, lithium bromide, lithium iodide, titanium(IV) tetraisopropoxide, zinc chloride, zinc bromide, aluminum chloride, bismuth(III) chloride, and manganese(II) chloride. The Lewis acid can be used at an equivalent ratio of generally 0.01:1 to 100:1, and preferably 0.1:1 to 3:1, with respect to Compound (6-2).

Examples of the alkyl lithium specifically include methyl lithium, ethyl lithium, n-propyl lithium, n-pentyl lithium, n-hexyl lithium, isopropyl lithium, isobutyl lithium, sec-butyl lithium, tert-butyl lithium, neopentyl lithium, and cyclopentyl lithium.

Examples of the Grignard reagent specifically include methyl magnesium chloride, ethyl magnesium chloride, propyl magnesium chloride, n-butyl magnesium chloride, n-pentyl magnesium chloride, n-hexyl magnesium chloride, isopropyl magnesium chloride, isobutyl magnesium chloride, tert-butyl magnesium chloride, sec-butyl magnesium chloride, cyclopropyl magnesium chloride, cyclobutyl magnesium chloride, cyclopentyl magnesium chloride, cyclohexyl magnesium chloride, cycloheptyl magnesium chloride, 1,1-dimethyl propyl magnesium chloride, 2,2-dimethyl propyl magnesium chloride, 3,3-dimethyl-1-butyl magnesium chloride, 3-methyl butyl magnesium chloride, 2-methyl-2-pentyl magnesium chloride, 2-methyl pentyl magnesium chloride, methyl magnesium bromide, ethyl magnesium bromide, propyl magnesium bromide, n-butyl magnesium bromide, n-pentyl magnesium bromide, n-hexyl magnesium bromide, isopropyl magnesium bromide, isobutyl magnesium bromide, tert-butyl magnesium bromide, sec-butyl magnesium bromide, cyclopropyl magnesium bromide, cyclobutyl magnesium bromide, cyclopentyl magnesium bromide, cyclohexyl magnesium bromide, cycloheptyl magnesium bromide, 1,1-dimethyl propyl magnesium bromide, 2,2-dimethyl propyl magnesium bromide, 3,3-dimethyl-1-butyl magnesium bromide, 3-methyl butyl magnesium bromide, 2-methyl-2-pentyl magnesium bromide, 2-methyl pentyl magnesium bromide, methyl magnesium iodide, ethyl magnesium iodide, n-propyl magnesium iodide, isopropyl magnesium iodide, n-butyl magnesium iodide and isobutyl magnesium iodide.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; and halogenated hydrocarbon solvents such as dichloromethane, chloroform, and 1,2-dichloroethane. A mixed solvent thereof may also be used. The reaction temperature is not particularly limited, and it is preferably selected from a range between approximately −100° C. and 100° C. and more preferably −100° C. to 0° C.

Step 6-3: Step of Producing Compound (6-4)

When $X^1$ represents a methanesulfonyloxy group, a chloromethanesulfonyloxy group, a trifluoromethanesulfonyloxy group, a benzenesulfonyloxy group, or a p-toluenemethanesulfonyloxy group, Compound (6-4) can be produced by allowing Compound (6-3) to react with methanesulfonyl chloride, methanesulfonic acid anhydride, chloromethanesulfonyl chloride, trifluoromethanesulfonyl chloride, trifluoromethanesulfonic acid anhydride, benzenesulfonyl chloride, benzenesulfonic acid anhydride, p-toluenesulfonyl chloride or p-toluenesulfonic acid anhydride, respectively, in an inert solvent and in the presence of a base.

The base is not particularly limited and may be a compound used as a base in a common reaction. Examples of the base include: organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline; and inorganic bases such as sodium methoxide, sodium tert-butoxide, potassium tert-butoxide, lithium diisopropylamide, lithium bis(trimethylsilyl)amide, potassium bis(trimethylsilyl)amide, sodium bis(trimethylsilyl)amide, lithiumamide, n-butyllithium, sodium hydrogen carbonate, potassium hydrogen carbonate, sodium carbonate, potassium carbonate, sodium hydroxide, and sodium hydride. The base can be used at an equivalent ratio of generally 0.1:1 to 100:1, and preferably 0.8:1 to 3:1, with respect to Compound (6-3).

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; and aprotic solvents such as N,N-dimethylformamide, dimethyl sulfoxide, and hexamethylenephosphoamide. A mixed solvent thereof may also be used. The reaction temperature is not particularly limited. It is preferably selected from a range between approximately −20° C. and 40° C.

When $X^1$ represents a chlorine atom, Compound (6-4) can be produced by chlorinating Compound (6-3), for instance, according to the known method described in Comprehensive Organic transformation, R. C. Larock, etc., VCH publisher Inc., 1989. Examples of the chlorinating reagent preferably include oxalyl chloride, thionyl chloride, phosphorus oxychloride, sulfuryl chloride, cyanuric trichloride, carbon tetrachloride or N-chlorosuccinimide.

When $X^1$ represents a bromine atom, Compound (6-4) can be produced by brominating Compound (6-3), for instance, according to the known method described in Comprehensive Organic transformation, R. C. Larock et al., VCH publisher Inc., 1989. Examples of the brominating reagent preferably include phosphorus tribromide, carbon tetrabromide, bromine and N-bromosuccinimide.

When $X^1$ represents an iodine atom, Compound (6-4) can be produced by iodinating Compound (6-3), for instance, according to the known method described in Comprehensive Organic transformation, R. C. Larock, et al., VCH publisher Inc., 1989. Examples of the iodinating reagent preferably include iodine and N-iodosuccinimide.

Step 6-4: Step of Producing Compound (6-5)

Compound (6-5) can be produced by allowing Compound (6-4) to react with sodium azide, potassium azide or lithium azide in an inert solvent.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; and aprotic solvents such as N,N-dimethylformamide, dimethyl sulfoxide, and hexamethylenephosphoamide. A mixed solvent thereof may also be used. The reaction temperature is not particularly limited, and it is preferably selected from a range between approximately 20° C. and 160° C.

Step 6-5: Step of Producing Compound (6-6)

Compound (6-6) can be produced by reducing Compound (6-5), for instance, according to the known method described in *Jikken Kagaku Koza* (edited by The Chemical Society of Japan, Maruzen), Vol. 14.

Step 6-6: Step of Producing Compound (6-7)

Compound (6-7) can be produced from Compound (6-6), for instance, according to the known method described in Protective Groups in Organic Synthesis 3$^{rd}$ Edition (John Wiley & Sons, Inc.).

Step 6-7: Step of Producing Compound (6-8)

Compound (6-8) can be produced by hydrolyzing Compound (6-7), for instance, according to the known method described in Protective Groups in Organic Synthesis 3$^{rd}$ Edition (John Wiley & Sons, Inc.), or Comprehensive Organic transformation, R. C. Larock, et al., VCH publisher Inc., 1989.

Production Method 7

Among the compounds represented by Formula (1-3), the compound represented by Formula (7-5) can be produced, for example, by the following process.

[Formula 58]

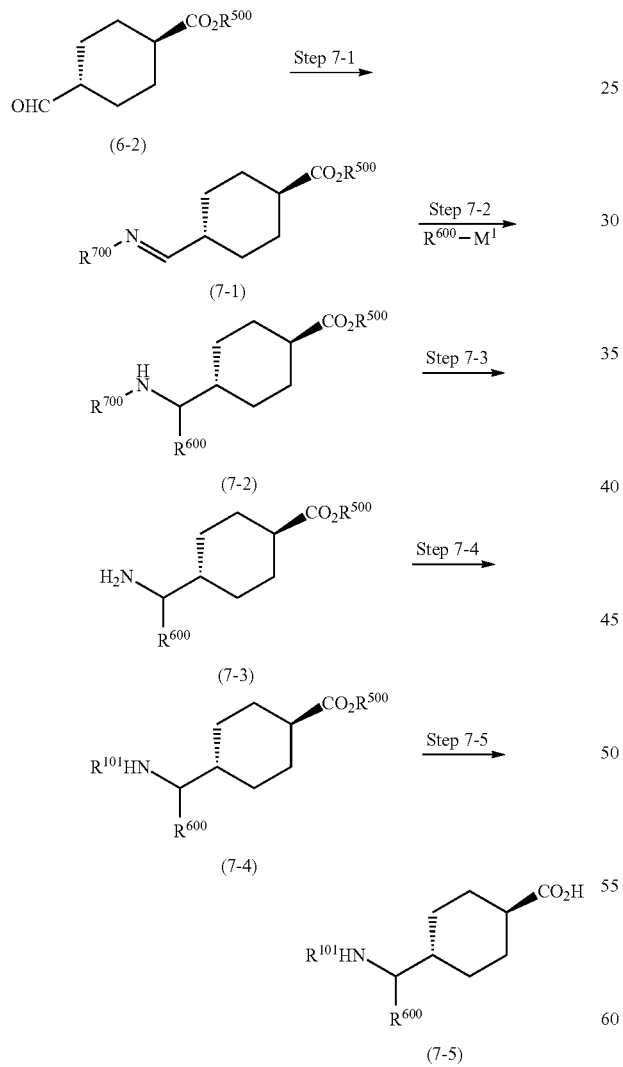

optionally substituted $C_{3-10}$ cycloalkyl group; $M^1$ represents a lithium or a magnesium halide; and $R^{101}$ represents a Cbz group, a Boc group, an Alloc group, a benzyl group or a Fmoc group.

Step 7-1: Step of Producing Compound (7-1)

Compound (7-1) can be produced from Compound (6-2), for instance, according to the known method described in Synlett 1995, 2, 142, Tetrahedron 1999, 53, 4153.

Step 7-2: Step of Producing Compound (7-2)

Compound (7-2) can be produced from Compound (7-1) according to the manner of Step 6-2.

Step 7-3: Step of Producing Compound (7-3)

Compound (7-3) can be produced by reacting Compound (7-2) under hydrogen atmosphere, in an inert solvent, and in the presence of palladium-carbon, palladium hydroxide or platinum oxide. If necessary, an acid can be added to the reaction system.

Examples of the acid include hydrochloric acid water, hydrogen bromide water, sulfuric acid water, acetic acid and trifluoroacetic acid. The acid can be used at an equivalent ratio of generally 0.01:1 to 100:1, and preferably 0.01:1 to 3:1, with respect to Compound (7-2).

Examples of the inert solvent include ether solvents such as tetrahydrofuran, diethyl ether, 1,4-dioxane and 1,2-dimethoxyethane; hydrocarbon solvents such as hexane, heptane, toluene, benzene and xylene; halogenated hydrocarbon solvents such as dichloromethane, chloroform and dichloroethane; alcohol solvents such as ethanol, methanol and isopropanol; and acetic acid. A mixed solvent thereof may also be used. The reaction temperature is not particularly limited, and it is preferably selected from a range between approximately 0° C. and 100° C. and more preferably 25° C. to 80° C.

Step 7-4: Step of Producing Compound (7-4)

Compound (7-4) can be produced from Compound (7-3) according to the manner of Step 6-6.

Step 7-5: Step of Producing Compound (7-5)

Compound (7-5) can be produced from Compound (7-4) according to the manner of Step 6-7.

Production Method 8

Among the compounds represented by Formula (1-3), the compound represented by Formula (8-10) can be produced, for example, by the following process.

[Formula 59]

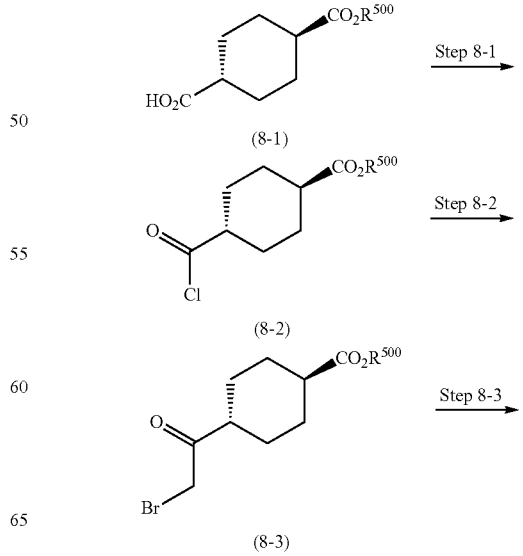

wherein $R^{500}$ represents a $C_{1-4}$ alkyl group, a benzyl group, a 4-methoxybenzyl group or a 2,4-dimethoxybenzyl group; $R^{700}$ represents an optionally substituted benzyl group; $R^{600}$ represents an optionally substituted $C_{1-6}$ alkyl group or an

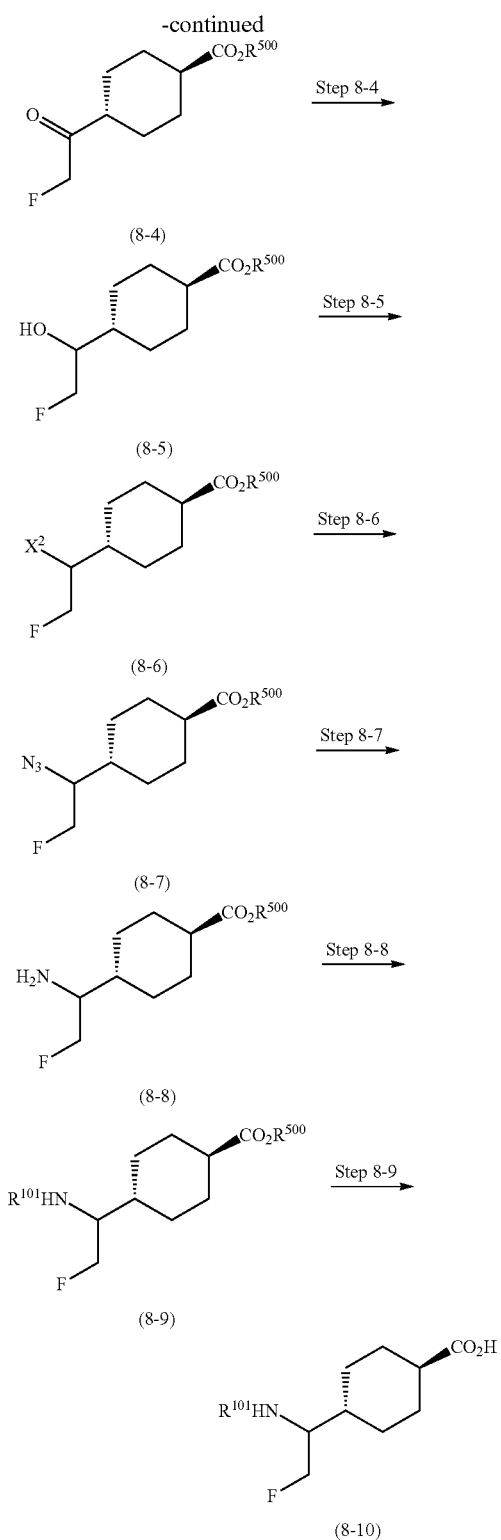

(8-4)
(8-5)
(8-6)
(8-7)
(8-8)
(8-9)
(8-10)

wherein $R^{500}$ represents a $C_{1-4}$ alkyl group, a benzyl group, a 4-methoxybenzyl group or a 2,4-dimethoxybenzyl group; $X^2$ represents a leaving group (e.g., a methanesulfonyloxy group, a chloromethanesulfonyloxy group, a trifluoromethanesulfonyloxy group, a benzenesulfonyloxy group, a p-toluenemethanesulfonyloxy group, a chlorine atom, a bromine atom or an iodine atom); $R^{101}$ represents a Cbz group, a Boc group, an Alloc group, a benzyl group or a Fmoc group; and $X^{800}$ represents a bromine atom or a chlorine atom.

Raw Material Compounds

The compound represented by Formula (8-1) can be produced by suitably protecting a functional group(s) of trans-1,4-cyclohexanedicarboxylic acid, which is commercially available, for instance, according to the known protection method described in Protective Groups in Organic Synthesis 3$^{rd}$ Edition (John Wiley & Sons, Inc.), or trans-1,4-cyclohexanedicarboxylic acid monomethyl ester is commercially available.

Step 8-1: Step of Producing Compound (8-2)

Compound (8-2) can be produced by converting Compound (8-1) to an acid chloride, for instance, according to the known method described in Comprehensive Organic transformation, R. C. Larock et al.

Step 8-2: Step of Producing Compound (8-3)

Compound (8-3) can be produced by allowing Compound (8-2) to react with diazomethane or trimethylsilyldiazomethane in an inert solvent, and then adding hydrobromic acid or hydrochloric acid to the reaction system.

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; and acetonitrile. A mixed solvent thereof may also be used. The reaction temperature is not particularly limited, and it is preferably selected from a range between approximately −40° C. and 40° C.

Step 8-3: Step of Producing Compound (8-4)

Compound (8-4) can be produced by allowing Compound (8-3) to react with lithium fluoride, potassium fluoride, sodium fluoride, cesium fluoride, thallium fluoride, potassium hydrogen fluoride or tetrabutylammonium fluoride in an inert solvent.

If necessary, a crown ether or an acid can be added to the reaction system.

Examples of the crown ether include 18-crown-6, 15-crown-5, dicyclohexyl-18-crown-6, and dibenzo-18-crown-6. The crown ether can be used at an equivalent ratio of generally 0.01:1 to 100:1, and preferably 0.1:1 to 3:1, with respect to Compound (8-3).

Examples of the acid include benzenesulfonic acid, p-toluenesulfonic acid and acetic acid. The acid can be used at an equivalent ratio of generally 0.01:1 to 100:1, and preferably 0.1:1 to 3:1, with respect to Compound (8-3).

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; aprotic solvents such as acetonitrile, N,N-dimethylformamide, dimethyl sulfoxide, hexamethylenephosphoramide, and pyridine; and ethylene glycol. A mixed solvent thereof may also be used. The reaction temperature is not particularly limited, and it is preferably selected from a range between approximately 20° C. and 130° C.

Step 8-4: Step of Producing Compound (8-5)

Compound (8-5) can be produced by reducing Compound (8-4), for instance, according to the known method described in Comprehensive Organic transformation, R. C. Larock et al.

Step 8-5: Step of Producing Compound (8-6)

Compound (8-6) can be produced from Compound (8-5) according to the manner of Step 6-3.

Step 8-6: Step of Producing Compound (8-7)

Compound (8-7) can be produced from Compound (8-6) according to the manner of Step 6-4.

Step 8-7: Step of Producing Compound (8-8)

Compound (8-8) can be produced from Compound (8-7) according to the manner of Step 6-5.

Step 8-8: Step of Producing Compound (8-9)

Compound (8-9) can be produced from Compound (8-8) according to the manner of Step 6-6.

Step 8-9: Step of Producing Compound (8-10)

Compound (8-10) can be produced from Compound (8-9) according to the manner of Step 6-7.

Production Method 9

Among the compounds represented by Formula (1-3), the compound represented by Formula (9-9) can be produced, for example, by the following process.

[Formula 60]

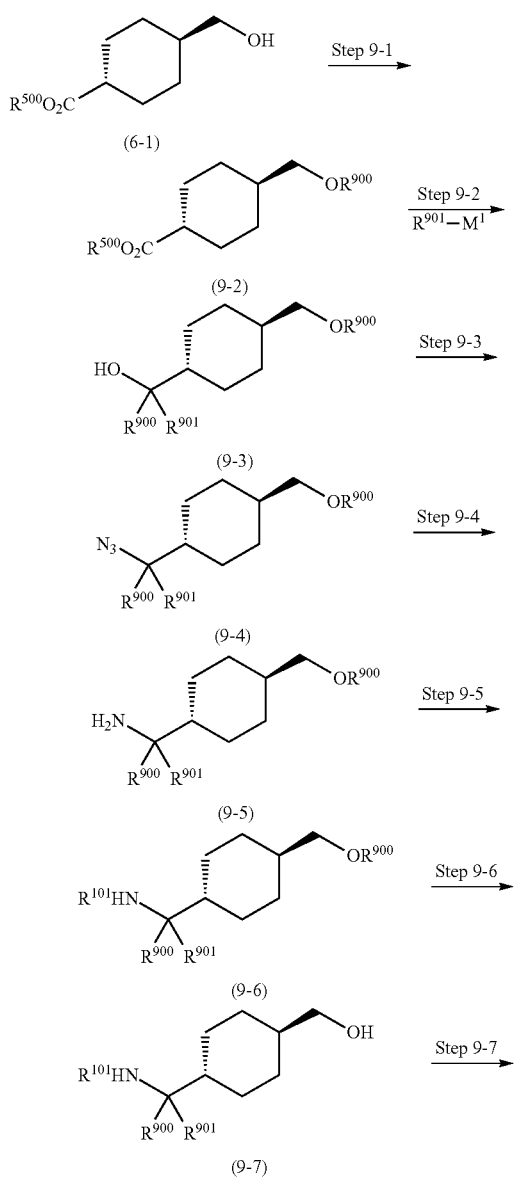

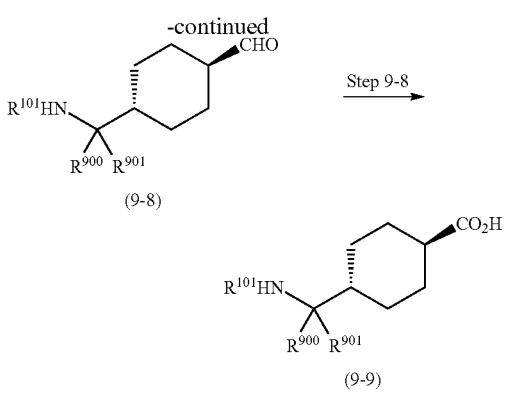

wherein $R^{500}$ represents a $C_{1-4}$ alkyl group, a benzyl group, a 4-methoxybenzyl group or a 2,4-dimethoxybenzyl group; $R^{900}$ represents a trimethylsilyl group, a triethylsilyl group, a tert-butyldimethylsilyl group, a tert-butyldiphenylsilyl group, a triisopropylsilyl group, a diethylisopropylsilyl group or an optionally substituted benzyl group; $R^{901}$ represents an optionally substituted $C_{1-6}$ alkyl group or an optionally substituted $C_{3-10}$ cycloalkyl group; $M^1$ represents a lithium or a magnesium halide; and $R^{101}$ represents a Cbz group, a Boc group, an Alloc group, a benzyl group or a Fmoc group.

Step 9-1: Step of Producing Compound (9-2)

Compound (9-2) can be produced from Compound (6-1), for instance, according to the known method described in Protective Groups in Organic Synthesis $3^{rd}$ Edition (John Wiley & Sons, Inc.).

Step 9-2: Step of Producing Compound (9-3)

Compound (9-3) can be produced by allowing Compound (9-2) to react with alkyl lithium or a Grignard reagent in an inert solvent. If necessary, Lewis acid can also be added to the reaction system.

Specific examples of the Lewis acid include lithium chloride, lithium bromide, lithium iodide, titanium(IV) tetraisopropoxide, zinc chloride, zinc bromide, aluminum chloride, bismuth(III) chloride and manganese(II) chloride. The Lewis acid can be used at an equivalent ratio of generally 0.01:1 to 100:1, and preferably 0.1:1 to 3:1, with respect to Compound (9-2).

Examples of the alkyl lithium specifically include methyl lithium, ethyl lithium, n-propyl lithium, n-pentyl lithium, n-hexyl lithium, isopropyl lithium, isobutyl lithium, sec-butyl lithium, tert-butyl lithium, neopentyl lithium and cyclopentyl lithium.

Examples of the Grignard reagent specifically include methyl magnesium chloride, ethyl magnesium chloride, propyl magnesium chloride, n-butyl magnesium chloride, n-pentyl magnesium chloride, n-hexyl magnesium chloride, isopropyl magnesium chloride, isobutyl magnesium chloride, tert-butyl magnesium chloride, sec-butyl magnesium chloride, cyclopropyl magnesium chloride, cyclobutyl magnesium chloride, cyclopentyl magnesium chloride, cyclohexyl magnesium chloride, cycloheptyl magnesium chloride, 1,1-dimethyl propyl magnesium chloride, 2,2-dimethyl propyl magnesium chloride, 3,3-dimethyl-1-butyl magnesium chloride, 3-methyl butyl magnesium chloride, 2-methyl-2-pentyl magnesium chloride, 2-methyl pentyl magnesium chloride, methyl magnesium bromide, ethyl magnesium bromide, propyl magnesium bromide, n-butyl magnesium bromide, n-pentyl magnesium bromide, n-hexyl magnesium bromide, isopropyl magnesium bromide, isobutyl magnesium bromide, tert-butyl magnesium bromide, sec-butyl magnesium bromide, cyclopropyl magnesium bromide, cyclobutyl magnesium bromide, cyclopentyl magnesium bromide, cyclohexyl magnesium bromide, cycloheptyl magnesium bromide, 1,1-dimethyl propyl magnesium bromide, 2,2-dimethyl propyl magnesium bromide, 3,3-dimethyl-1-butyl magnesium bromide, 3-methyl butyl magnesium bromide, 2-methyl-2-pentyl magnesium bromide, 2-methyl pentyl magnesium bromide, methyl magnesium iodide, ethyl magnesium iodide, n-propyl magnesium iodide, isopropyl magnesium iodide, n-butyl magnesium iodide and isobutyl magnesium iodide.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; and halogenated hydrocarbon solvents such as dichloromethane, chloroform, and dichloroethane. A mixed solvent thereof may also be used. The reaction temperature is not particularly limited, and it is preferably selected from a range between approximately −20° C. and 50° C.

Step 9-3: Step of Producing Compound (9-4)

Compound (9-4) can be produced by allowing Compound (9-3) to react with hydrogen azide, sodium azide or trimethylsilyl azide in an inert solvent and in the presence or absence of an acid. If necessary, an additive can be added to the reaction system.

Examples of the acid specifically include trifluoroacetic acid, sulfuric acid, and hydrochloric acid. The acid can be used at an equivalent ratio of generally 0.01:1 to 100:1, and preferably 0.1:1 to 20:1, with respect to Compound (9-3).

Examples of the additive specifically include a boron trifluoride diethyl ether complex, 15-crown-5, 18-crown-6, and HY-zeolite. The additive can be used at an equivalent ratio of generally 0.01:1 to 100:1, and preferably 0.1:1 to 20:1, with respect to Compound (9-3).

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; and aprotic solvents such as acetonitrile, N,N-dimethylformamide, dimethyl sulfoxide, hexamethylenephosphoramide, and pyridine. A mixed solvent thereof may also be used. The reaction temperature is not particularly limited, and it is preferably selected from a range between approximately −20° C. and 100° C.

Step 9-4: Step of Producing Compound (9-5)

Compound (9-5) can be produced from Compound (9-4) according to the manner of Step 6-5.

Step 9-5: Step of Producing Compound (9-6)

Compound (9-6) can be produced from Compound (9-5) according to the manner of Step 6-6.

Step 9-6: Step of Producing Compound (9-7)

Compound (9-7) can be produced by deprotecting Compound (9-6), for instance, according to the known method described in Protective Groups in Organic Synthesis 3$^{rd}$ Edition (John Wiley & Sons, Inc.), or Comprehensive Organic transformation, R. C. Larock et al., VCH publisher Inc., 1989.

Step 9-7: Step of Producing Compound (9-8)

Compound (9-8) can be produced by oxidizing Compound (9-7) according to the manner of Step 2-6. Examples of the oxidation method preferably include Dess-Martin oxidation, Swern oxidation, Parikh-Doering oxidation, TPAP oxidation and PCC oxidation.

Step 9-8: Step of Producing Compound (9-9)

Compound (9-9) can be produced by oxidizing Compound (9-8) according to the manner of Step 2-8. Examples of the oxidation method preferably include Pinnick oxidation and PDC oxidation.

Production Method 10

Among the compounds represented by Formula (1-3), the compound represented by Formula (10-7) can be produced, for example, by the following process.

[Formula 61]

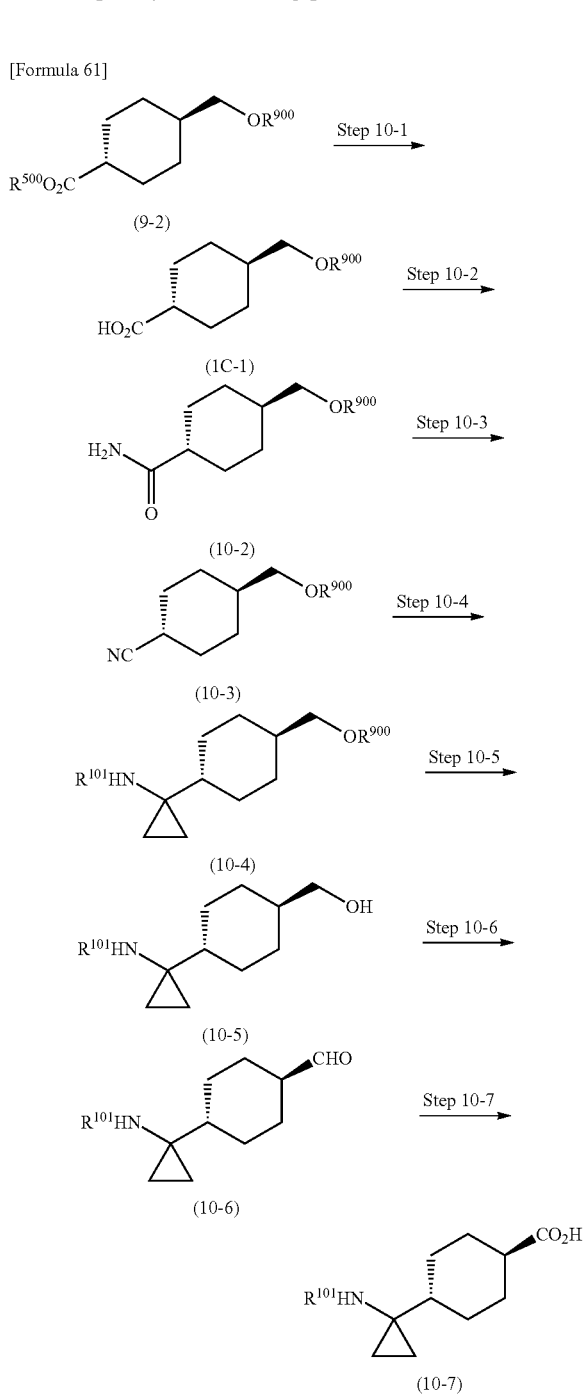

wherein $R^{500}$ represents a $C_{1-4}$ alkyl group, a benzyl group, a 4-methoxybenzyl group or a 2,4-dimethoxybenzyl group; $R^{900}$ represents a trimethylsilyl group, a triethylsilyl group, a tert-butyldimethylsilyl group, a tert-butyldiphenylsilyl group, a triisopropylsilyl group, a diethylisopropylsilyl group or an optionally substituted benzyl group; and $R^{101}$ represents a Cbz group, a Boc group, an Alloc group, a benzyl group or a Fmoc group.

Step 10-1: Step of Producing Compound (10-1)

Compound (10-1) can be produced by hydrolyzing Compound (9-2), for instance, according to the known method described in Protective Groups in Organic Synthesis $3^{rd}$ Edition (John Wiley & Sons, Inc.), Comprehensive Organic transformation, R. C. Larock et al., VCH publisher Inc., 1989.

Step 10-2: Step of Producing Compound (10-2)

Compound (10-2) can be produced by condensing Compound (10-1) using ammonium chloride or ammonia water, for instance, according to the known method described in Comprehensive Organic transformation, R. C. Larock et al., VCH publisher Inc., 1989.

Step 10-3: Step of Producing Compound (10-3)

Compound (10-3) can be produced by dehydrating Compound (10-2), for instance, according to the known method described in Comprehensive Organic transformation, R. C. Larock et al., VCH publisher Inc., 1989.

Step 10-4: Step of Producing Compound (10-4)

Compound (10-4) can be produced by subjecting Compound (10-3) to the following reactions (1) and (2).

(1) Compound (10-3) is allowed to react with ethylmagnesium bromide in an inert solvent and in the presence of titanium(IV) tetraisopropoxide or methyltitanium(IV) triisopropoxide. The titanium(IV) tetraisopropoxide or methyltitanium(IV) triisopropoxide can be used at an equivalent ratio of generally 0.01:1 to 100:1, and preferably 0.1:1 to 3:1, with respect to Compound (10-3).

Examples of the inert solvent include: ether solvents such as tetrahydrofuran, diethyl ether, 1,4-dioxane and 1,2-dimethoxyethane; and hydrocarbon solvents such as hexane, heptane, toluene, benzene and xylene. A mixed solvent thereof may also be used. The reaction temperature is not particularly limited, and it is preferably selected from a range between approximately −20° C. and 60° C.

(2) A boron trifluoride diethyl ether complex was added to the reaction solution obtained in (1) above to react with them. The boron trifluoride diethyl ether complex can be used at an equivalent ratio of generally 0.01:1 to 100:1, and preferably 0.1:1 to 5:1, with respect to Compound (10-3).

Step 10-5: Step of Producing Compound (10-5)

Compound (10-5) can be produced by removing a protecting group from Compound (10-4) according to the manner of Step 9-6.

Step 10-6: Step of Producing Compound (10-6)

Compound (10-6) can be produced from Compound (10-5) according to the manner of Step 2-6. Examples of the oxidation method preferably include Dess-Martin oxidation, Swern oxidation, Parikh-Doering oxidation, TPAP oxidation and PCC oxidation.

Step 10-7: Step of Producing Compound (10-7)

Compound (10-7) can be produced from Compound (10-6) according to the manner of Step 2-8. Examples of the oxidation method preferably include Pinnick oxidation and PDC oxidation.

Production Method 11

Among the compounds represented by Formula (1), those having a group that is hydrolyzed in vivo to regenerate a carboxyl group can be produced by esterifying the corresponding carboxylic acid, for instance, according to the known method described in Comprehensive Organic transformation, R. C. Larock et al., VCH publisher Inc., 1989.

Production Method 12

Among the compounds represented by Formula (1-3), the compound represented by Formula (12-9) can be produced, for example, by the following process.

[Formula 62]

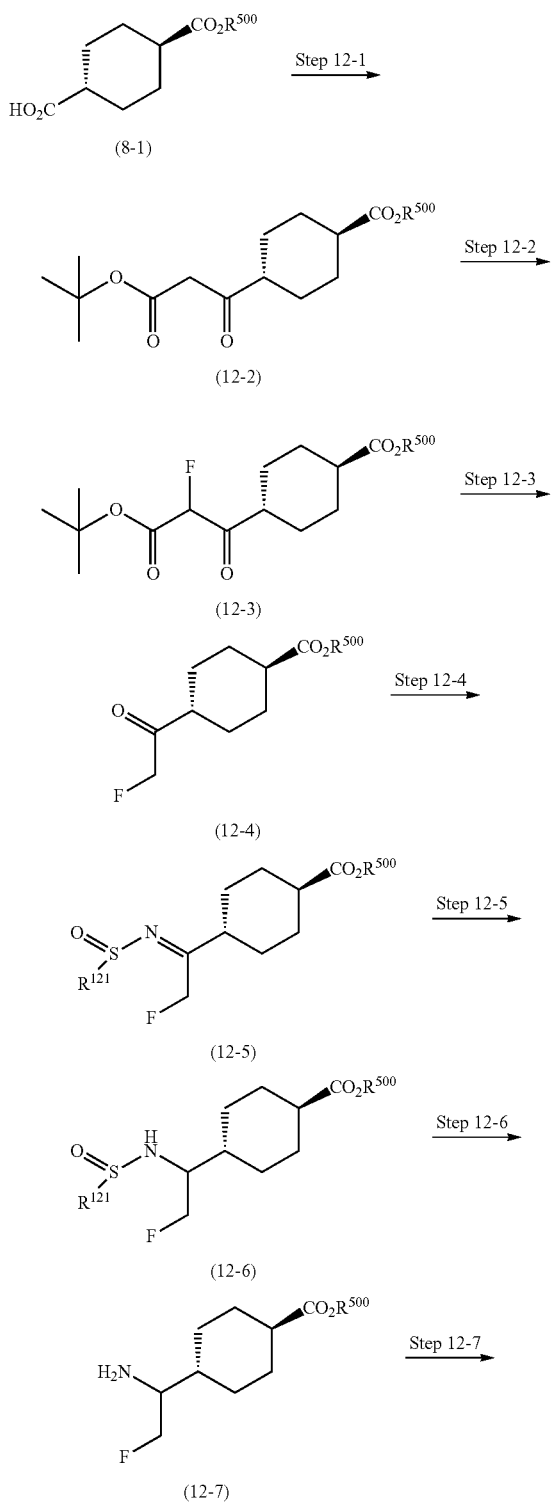

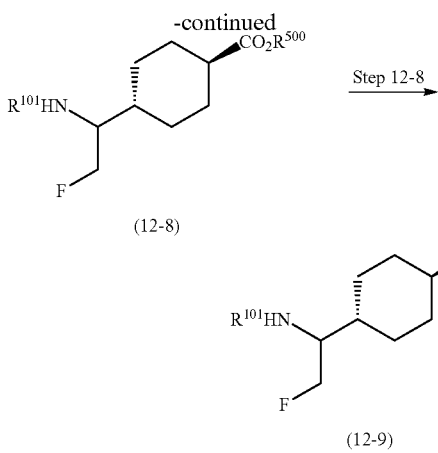

wherein $R^{500}$ represents a $C_{1-4}$ alkyl group, a benzyl group, a 4-methoxybenzyl group or a 2,4-dimethoxybenzyl group; $R^{121}$ represents a 4-methylphenyl group or a tert-butyl group; and $R^{101}$ represents a Cbz group, a Boc group, an Alloc group, a benzyl group or a Fmoc group.

Step 12-1: Step of Producing Compound (12-2)

Compound (12-2) can be produced, for example, by performing the following production method i, ii or iii.

i. Compound (8-1) is allowed to react with N,N'-carbonyl diimidazole, oxalyl chloride, thionyl chloride, ethyl chloroformate, isobutyl chloroformate, propyl chloroformate or isopropyl chloroformate, for instance, according to the known method described in J. Org. Chem., 1997, 62, 2292. The reaction temperature is selected from a range between approximately −10° C. and approximately 50° C. Subsequently, a metal enolate of tert-butyl acetate is added to this reaction mixture to react with them so as to produce Compound (12-2). The reaction temperature is selected from a range between approximately −80° C. and approximately 50° C.

ii. Compound (8-1) is allowed to react with N,N'-carbonyl diimidazole by a method similar to a known method (e.g., Org. Lett., 2011, 13, 6284. etc.). The reaction temperature is selected from a range between approximately −20° C. and approximately 50° C. Subsequently, the reaction product is allowed to react with isopropylmagnesium bromide or isopropylmagnesium chloride, so as to produce Compound (12-2). The reaction temperature is selected from a range between approximately −20° C. and approximately 50° C.

iii. From Compound (8-1), an acid chloride can be prepared, for instance, according to the known method described in Comprehensive Organic transformation, R. C. Larock, et al.

Subsequently, the acid chloride is allowed to react with Meldrum's acid in an inert solvent and if necessary in the presence of a base. Examples of the inert solvent include: halogenated hydrocarbon solvents such as dichloromethane, chloroform or 1,2-dichloroethane; ether solvents such as tetrahydrofuran, diethyl ether, 1,4-dioxane or 1,2-dimethoxyethane; and hydrocarbon solvents such as hexane, heptane, toluene, benzene or xylene. A mixed solvent thereof may also be used. The reaction temperature is not particularly limited, and it is preferably selected from a range between approximately −40° C. and 50° C. The base is not particularly limited and may be a compound used as a base in a common reaction. Examples of the base include: organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine and picoline; and inorganic bases such as sodium hydrogen carbonate, potassium hydrogen carbonate, sodium carbonate, potassium carbonate, sodium hydroxide and sodium hydride. The base can be used at an equivalent ratio of generally 0.1:1 to 100:1, and preferably 1:1 to 5:1, with respect to Compound (8-1). The generated product is then allowed to react with tert-butyl alcohol so as to produce Compound (12-2). The reaction temperature is selected from a range between approximately −20° C. and approximately 120° C.

Step 12-2: Step of Producing Compound (12-3)

Compound (12-3) can be produced by allowing Compound (12-2) to react with Selectfluor, N-fluorobenzenesulfonimide, N-fluoromethanesulfonimide, N-fluorotrifluoromethanesulfonimide, or fluorine in an inert solvent.

Examples of the inert solvent include ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; and acetonitrile. A mixed solvent thereof may also be used. The reaction temperature is not particularly limited, and it is preferably selected from a range between approximately −40° C. and 50° C.

Step 12-3: Step of Producing Compound (12-4)

Compound (12-4) can be produced by decarboxylating Compound (12-3), for instance, according to the known method described in Comprehensive Organic transformation, R. C. Larock et al.

Step 12-4: Step of Producing Compound (12-5)

Compound (12-5) can be produced by allowing Compound (12-4) to react with (R)-2-methyl-2-propanesulfinamide, (S)-2-methyl-2-propanesulfinamide, (R)-4-methylbenzene-1-sulfinamide or (S)-4-methylbenzene-1-sulfinamide in an inert solvent and in the presence of titanium tetrabutoxide, titanium tetraethoxide or titanium tetraisopropoxide.

Examples of the inert solvent include: ether solvents such as tetrahydrofuran, diethyl ether, 1,4-dioxane and 1,2-dimethoxyethane; halogenated hydrocarbon solvents such as dichloromethane, chloroform and dichloroethane; and hydrocarbon solvents such as hexane, heptane, toluene, benzene and xylene. A mixed solvent thereof may also be used. The reaction temperature is not particularly limited, and it is preferably selected from a range between approximately −20° C. and 100° C.

Step 12-5: Step of Producing Compound (12-6)

Compound (12-6) can be produced, for example, by performing the following production method i or ii.

i. Compound (12-6) can be produced by reducing Compound (12-5) with borane, sodium borohydride, sodium triacetoxyborohydride, sodium cyanoborohydride, L-selectride, K-selectride, diisobutyl aluminum hydride, lithium borohydride, lithium aluminum hydride, lithium triethylborohydride, boron zinc hydride, sodium bis(2-methoxyethoxy)aluminum hydride or 9-BBN in an inert solvent. Examples of the inert solvent include ether solvents such as tetrahydrofuran, diethyl ether, 1,4-dioxane and 1,2-dimethoxyethane; halogenated hydrocarbon solvents such as dichloromethane, chloroform and dichloroethane; hydrocarbon solvents such as hexane, heptane, toluene, benzene and xylene; and aprotic solvents such as acetonitrile, N,N-dimethylformamide, dimethyl sulfoxide, hexamethylenephosphoramide and pyridine. A mixed solvent thereof may also be used. The reaction temperature is not particularly limited, and it is preferably selected from a range between approximately −100° C. and 100° C.

ii. Compound (12-6) can be produced by allowing Compound (12-5) to react with a dichloro(cymene)ruthenium dimer and a ligand in an isopropanol solvent, and if necessary in the presence of a base and Molecular Sieves 4 Å. Examples of the ligand include 2-amino-2-methyl-1-propanol, 2-aminoethanol, (1R,2S)-2-amino-1,2-diphenylethanol, (1S,2R)-2-amino-1,2-diphenylethanol, (1S,2R)-cis-1-amino-2-indanol, (1R,2S)-cis-1-amino-2-indanol, L-prolinol, R-prolinol, (S)-diphenyl(pyrrolidin-2-yl)methanol, and (R)-diphenyl(pyrrolidin-2-yl)methanol. The ligand can be used at an equivalent ratio of generally 0.01:1 to 2:1, and preferably 0.01:1 to 0.2:1, with respect to Compound (12-5). Examples of the base include tert-butoxy potassium and potassium hydroxide. The base can be used at an equivalent ratio of generally 0.01:1 to 2:1, and preferably 0.01:1 to 1.0:1, with respect to Compound (12-5).

The reaction temperature is not particularly limited, and it is preferably selected from a range between approximately −100° C. and 100° C.

Step 12-6: Step of Producing Compound (12-7)

Compound (12-7) can be produced by allowing Compound (12-6) to react with an acid in an inert solvent.

Examples of the acid include hydrochloric acid, hydrobromic acid, sulfuric acid, trifluoroacetic acid, benzenesulfonic acid, p-toluenesulfonic acid and acetic acid.

Examples of the inert solvent include ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; alcohol solvents such as ethanol, methanol, and isopropanol; and aprotic solvents such as acetonitrile, N,N-dimethylformamide, dimethyl sulfoxide, hexamethylenephosphoramide, and pyridine. A mixed solvent thereof may also be used. The reaction temperature is not particularly limited, and it is preferably selected from a range between approximately −100° C. and 100° C.

Step 12-7: Step of Producing Compound (12-8)

Compound (12-8) can be produced from Compound (12-7) according to the manner of Step 6-6.

Step 12-8: Step of Producing Compound (12-9)

Compound (12-9) can be produced from Compound (12-8) according to the manner of Step 6-7.

The intermediates and final products obtained in the above described processes can be converted to other compounds included in the present invention by appropriately converting the functional groups thereof to other groups. In particular, they can be converted to other compounds included in the present invention by extending various side chains on the basis of an amino group, an amidino group, a hydroxy group, a carbonyl group, a halogen group, etc.; by converting a nitro group, a carboxyl group, a halogen group, a hydroxy group, etc. to amino groups; or by converting a carboxyl group, etc. to ester or amido groups, and as appropriate by performing appropriate protection and deprotection. Such conversion of functional groups and extension of side chains are carried out according to common general methods (e.g., Comprehensive Organic transformation, R. C. Larock et al.).

The intermediates and final products obtained in the above described processes can be isolated and purified by subjecting them to common purification methods in organic synthetic chemistry, such as neutralization, filtration, extraction, washing, drying, concentration, recrystallization, and various types of chromatography. The intermediates may also be subjected to the subsequent reaction without being particularly purified.

Optical isomers or atropisomers of the compound of the present invention may be obtained as racemates, or when optically active starting raw materials or intermediates are used, they may be obtained as optically active substances. If necessary, a racemate as a raw material, an intermediate or a final product can be physically or chemically divided into the corresponding optical enantiomers, at a suitable stage in each of the above described processes, according to known separation methods such as a method of using an optically active column or a fractional crystallization method. For instance, in a diastereomer method, two types of diastereomers or diastereomeric salts are formed from a racemate using an optically active resolution agent. Since these different diastereomers generally have different physical properties, they can be divided according to known methods such as fractional crystallization.

A pharmaceutically acceptable salt of the compound of the present invention, which is represented by Formula (1), can be produced by mixing the compound represented by Formula (1) having sufficient basicity or acidity for the formation of a salt with a pharmaceutically acceptable acid or base in a solvent such as water, methanol, ethanol, or acetone.

The compound of the present invention is considered to be applicable to the treatment of various diseases because of FXIa-inhibitory activity and blood coagulation-suppressive activity. The compound described in the present description is useful as a preventive agent or a therapeutic agent for thromboembolism (e.g., vein thrombosis, myocardial infarction, pulmonary embolism, cerebral embolism, slowly progressing cerebral thrombosis). The present compound is expected to be effective for arterial thrombosis, vein thrombosis, septicemia and thrombosis caused by exposing blood to an artificial surface such as of an artificial valve, an indwelling catheter, a stent, a heart and lung apparatus, or a blood dialysis device. Moreover, the present compound is expected to be effective for inflammatory diseases such as articular rheumatism or ulcerative colitis. In addition, the present compound is effective for the improvement of therapeutic effects on these diseases.

The compound of the present invention can be orally or parenterally administered. In the case of oral administration, it can be administered in a commonly used dosage form. In the case of parenteral administration, it can be administered in the form of a local administration agent, an injection, a transdermal agent, a transnasal agent, or the like. An oral agent and a rectal administration agent may be in the form of a capsule, a tablet, a pill, powder, a cachet, a suppository, and liquid. An injection may be in the form of an aseptic solution or suspension. A local administration agent may be in the form of a cream, an ointment, lotion, or a transdermal agent such as an ordinary patch agent, and matrix agent.

These dosage forms can be prepared with pharmaceutically acceptable excipients and additives according to ordinary methods. Examples of the pharmaceutically acceptable excipients and additives include a carrier, a binder, a perfume, a buffer, a thickener, a coloring agent, a stabilizer, an emulsifier, a disperser, a suspending agent, and an antiseptic.

Examples of the pharmaceutically acceptable carrier include magnesium carbonate, magnesium stearate, talc, sugar, lactose, pectin, dextrin, starch, gelatin, Tragacanth, methyl cellulose, sodium carboxymethyl cellulose, low melting wax, and cacao butter. A capsule can be formulated by putting the compound of the present invention and a pharmaceutically acceptable carrier thereinto. The compound of the present invention may be mixed with a pharmaceutically acceptable excipient, or without being mixed with the excipient, it may be putted into a capsule. A cachet can be produced in the same manner.

Examples of a liquid formulation used for injection include a solution, a suspension, and an emulsion. The liquid formulation includes, for example, an aqueous solution or a water-propylene glycol solution. The liquid formulation can be also produced in the form of a solution of polyethylene glycol or/and propylene glycol, which may contain water. A liquid formulation suitable for oral administration can be produced by adding the compound of the present invention to water, and if necessary, adding a coloring agent, a perfume, a stabilizer, a sweetener, a solubilizer, a thickener, and the like to the solution. Alternatively, such a liquid formulation suitable for oral administration can also be produced by adding the compound of the present invention and a disperser to water to thicken the mixed solution. Examples of the thickener include pharmaceutically acceptable natural or synthetic rubber, resin, methyl cellulose, sodium carboxymethyl cellulose, and known suspending agents.

The applied dose varies depending on the type of each compound, or depending on the disease, age, body weight, sex and symptom of a patient, an administration route, and the like. In general, the compound of the present invention is administered to an adult (body weight: 50 kg) at a dose of 0.1 to 1000 mg/day, and preferably of 1 to 300 mg/day, once or divided over two or three administrations per day. Alternatively, the present compound can also be administered once for several days or several weeks.

The compound of the present invention can be used in combination with another drug such as a different anticoagulant agent or antiplatelet agent (hereinafter abbreviated as a "combined drug") for the purpose of enhancing the effects thereof. The administration periods of the compound of the present invention and a combined drug are not limited. They may be administered to a subject, simultaneously or with a certain time lag. Moreover, the compound of the present invention and a combined drug may also be combined as a mixture. The dose of a combined drug can be determined, as appropriate, based on a clinically applied dose as a standard. Furthermore, the mixing ratio between the compound of the present invention and a combined drug can be determined, as appropriate, depending on a subject, an administration route, a disease, symptoms, a combination, etc. For instance, when a subject is a human, 0.01 to 100 parts by weight of a combined drug may be used with respect to 1 part by weight of the compound of the present invention.

Examples of the other anticoagulant agents include thrombin inhibitors (e.g., dabigatran, AZD-0837, MPC-0920, Org-27306 and NU-172), other FXIa factor inhibitors (e.g., ISIS-FXIRx), other plasma kallikrein inhibitors, FVIIa factor inhibitors (e.g., PCI-27483,), FIXa factor inhibitors (e.g., TTP-889, REGI and REG2), and FXa factor inhibitors (e.g., rivaroxaban, apixaban, edoxaban, YM-150, TAK-442, betrixaban, erivaxaban, LY-517717, AVE-3247, GW-813893, R-1663 and DB-772d). Examples of the antiplatelet agent include GPIIb/IIIa blockers (e.g., Abciximab, Epifibatide and Tirofiban), P2Y1 and P2Y12 antagonists (e.g., clopidogrel, prasugrel, Ticagrelor and Elinogrel), thromboxane receptor antagonists, and aspirin.

The combined drug is preferably an antiplatelet agent or the like. The aforementioned combined drugs may also be used by combining two or more types of the drugs at an appropriate ratio.

When the compound of the present invention is used in combination with a combined drug, the doses of these agents can be reduced to a safe range in view of the side effects thereof. Accordingly, side effects, which would be caused by these agents, can be safely prevented.

EXAMPLES

Hereinafter, the present invention will be described more specifically with reference to Reference Examples, Examples, and Test Examples. However, the present invention is not intended to be limited to these Examples. In this context, not all compound names shown in Reference Examples and Examples below follow the IUPAC nomenclature. In addition, abbreviations may be used for easier understanding of the descriptions, and these abbreviations have the same meaning as those described above.

The following abbreviations may be used herein.

In NMR data of Reference Examples and Examples, the following abbreviations will be used.
Me: Methyl group
Et: Ethyl group
Bu: Butyl group
Bn: Benzyl group
Bz: Benzoyl group
tert-: tertiary
Boc: tert-Butoxycarbonyl group
Tf: Trifluoromethane sulfonyl group
THF: Tetrahydrofuran
DMF: N,N-Dimethylformamide
TFA: Trifluoroacetic acid
DBU: 1,8-Diazabicyclo[5.4.0]undeca-7-ene
WSC.HCl: 1-Ethyl-3-(3-dimethylaminopropyl)carbodiimide hydrochloride
s: Singlet
brs: Broad singlet
d: Doublet
t: Triplet
m: Multiplet
br: Broad
J: Coupling constant
Hz: Hertz
CDCl$_3$: Deuterated chloroform
DMSO-d$_6$: Deuterated dimethylsulfoxide Reference Example 1 tert-Butyl 4-{cis-1-[trans-4-(tert-butoxycarbonylaminomethyl)cyclohexanecarbonyl]-3-phenylpyrrolidine-2-carboxamide}benzoate

[Formula 63]

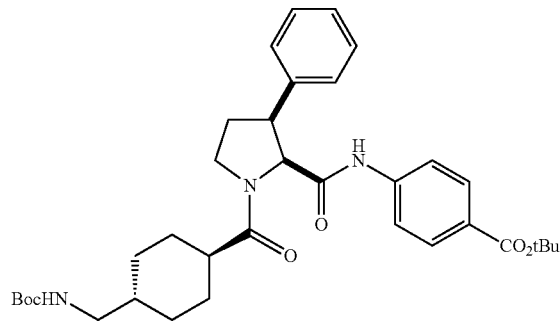

To a solution of commercially available trans-4-(tert-butoxycarbonylaminomethyl)cyclohexanecarboxylic acid (187 mg, 0.727 mmol) in DMF (3 mL), 1-hydroxybenzotriazole (140 mg, 0.914 mmol), WSC.HCl (175 mg, 0.913 mmol), triethylamine (213 μL, 1.53 mmol), and the compound of Reference Example 1-2 (244.5 mg, 0.61 mmol) were added, and the mixture was stirred at room temperature for 2 hours. A saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution once, then dried over sodium sulfate, and filtered, and the filtrate was concentrated under reduced pressure. The obtained residue was purified by silica gel column chromatography to obtain the title compound (90.6 mg, 23%).

MS (ESI+) 606 (M+1, 31%)

Reference Example 1-1 tert-Butyl 4-(cis-1-tert-butoxycarbonyl-3-phenylpyrrolidine-2-carboxamide)benzoate

[Formula 64]

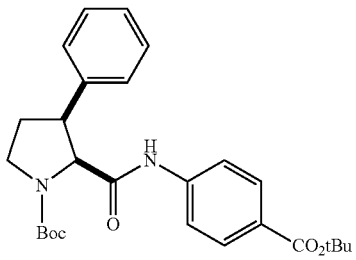

tert-Butyl 4-aminobenzoate (815 mg, 4.22 mmol) known from literature (e.g., J. Med. Chem. 2008, 51, 7751.) and commercially available cis-1-tert-butoxycarbonyl-3-phenylpyrrolidine-2-carboxylic acid (1.29 g, 4.43 mmol) were dissolved in pyridine (13 mL), then phosphorus oxychloride (551 μL, 5.91 mmol) was added thereto dropwise in an ice bath. After 3 hours, a saturated aqueous solution of sodium bicarbonate was added to the reaction solution, followed by extraction with ethyl acetate. The organic layer was washed with 1 mol/L hydrochloric acid twice and with a saturated aqueous solution of sodium bicarbonate and a saturated saline solution once, then dried over sodium sulfate, and filtered, and the filtrate was concentrated under reduced pressure. The obtained residue was purified by silica gel column chromatography to obtain the title compound (1.23 g, 63%).

MS (ESI+) 467 (M+1, 58%)

Reference Example 1-2 tert-Butyl 4-(cis-3-phenylpyrrolidine-2-carboxamide)benzoate hydrochloride

[Formula 65]

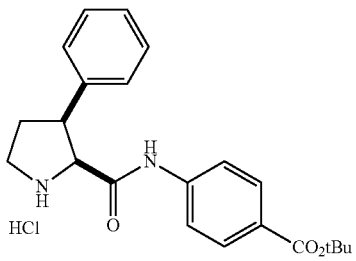

To a solution of the compound of Reference Example 1-1 (1.23 g, 2.64 mmol) in 1,4-dioxane (26 mL), a solution of 4 mol/L hydrochloric acid-1,4-dioxane (13 mL) was added, and the mixture was stirred at room temperature. After 2 hours, toluene was added to the reaction solution, and the mixture was concentrated under reduced pressure to obtain the title compound (661.4 mg, 62%).

MS (ESI+) 367 (M+1, 100%)

Reference Example 2 tert-Butyl 5-{cis-1-[trans-4-(tert-butoxycarbonylaminomethyl)cyclohexanecarbonyl]-3-phenylpyrrolidine-2-carboxamide}-1H-indole-2-carboxylate

[Formula 66]

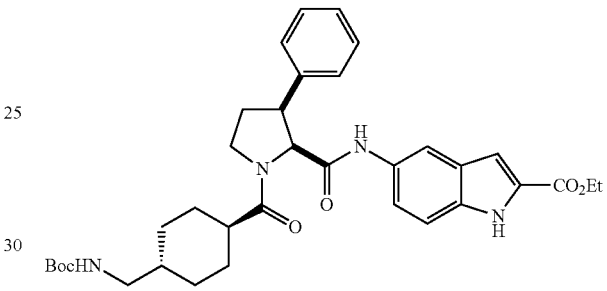

The same procedure as described in Reference Example 1 was carried out to obtain the title compound (342.3 mg, 46%) from the compound of Reference Example 2-3 (419.2 mg, 1.22 mmol).

MS (ESI+) 617 (M+1, 53%)

Reference Example 2-1

Ethyl 5-amino-1H-indole-2-carboxylate

[Formula 67]

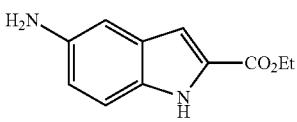

To a solution of ethyl 5-nitro-1H-indole-2-carboxylate (1.00 g, 4.27 mmol) in methanol (20 mL), palladium-carbon (907 mg) was added, and the mixture was stirred for 3 hours under hydrogen atmosphere. The reaction solution was filtered through Celite and the filtrate was concentrated under reduced pressure to obtain the title compound (876 mg, 100%).

$^1$H NMR (CDCl$_3$, 400 MHz) δ 8.70 (br, 1H), 7.24 (d, J=8.6 Hz, 1H), 7.04 (m, 1H), 6.94 (m, 1H), 6.82 (m, 1H), 4.40 (q, J=7.1 Hz, 2H), 3.57 (br, 2H), 1.41 (t, J=7.1 Hz, 3H).

Reference Example 2-2

Ethyl 5-(cis-1-tert-butoxycarbonyl-3-phenylpyrrolidine-2-carboxamide)-1H-indole-2-carboxylate

[Formula 68]

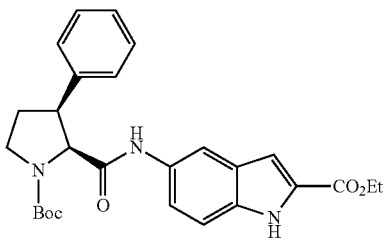

The same procedure as described in Reference Example 1 was carried out to obtain the title compound (582.0 mg, 77%) from the compound of Reference Example 2-1 (323.2 mg, 1.58 mmol).
MS (ESI+) 617 (M+1, 52%)

Reference Example 2-3

Ethyl 5-(cis-3-phenylpyrrolidine-2-carboxamide)-1H-indole-2-carboxylate hydrochloride

[Formula 69]

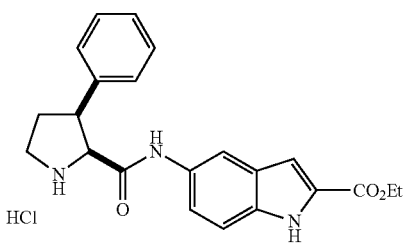

The same procedure as described in Reference Example 1-2 was carried out to obtain the title compound (419.2 mg, 83%) from the compound of Reference Example 2-2 (582.0 mg, 1.22 mmol).
MS (ESI+) 378 (M+1, 100%)

Reference Example 3

5-{cis-1-[trans-4-(tert-Butoxycarbonylaminomethyl)cyclohexanecarbonyl]-3-phenylpyrrolidine-2-carboxamide}-1H-indole-2-carboxylic acid

[Formula 70]

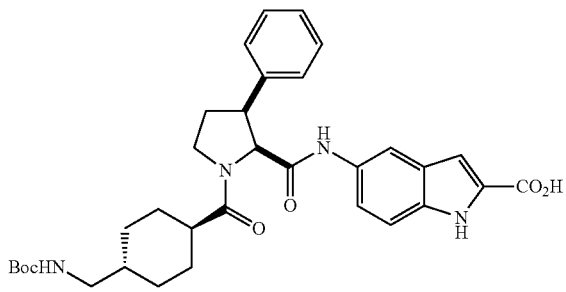

The compound of Reference Example 2 (278 mg, 0.451 mmol) was dissolved in ethanol (2 mL) and THF (2 mL), a 1 mol/L aqueous solution of sodium hydroxide (2 mL) was added thereto, and the mixture was stirred at room temperature for 19 hours. A 5% aqueous solution of potassium hydrogensulfate was added to the reaction solution, followed by extraction with chloroform twice. The organic layer was washed with a saturated saline solution, dried over anhydrous sodium sulfate, filtered, and then the organic layer was concentrated under reduced pressure to obtain the title compound (256.8 mg, 97%).
MS (ESI+) 589 (M+1, 50%)

Reference Example 4

5-{cis-1-[trans-4-(tert-Butoxycarbonylaminomethyl)cyclohexanecarbonyl]-3-phenylpyrrolidine-2-carboxamide}-1H-indole-2-carboxamide

[Formula 71]

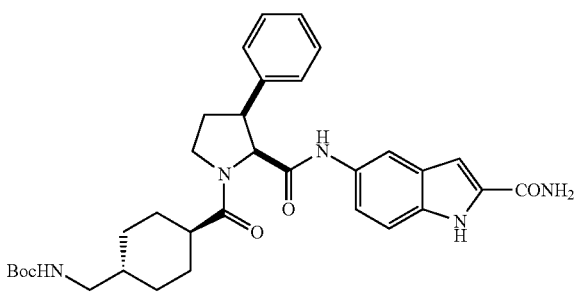

A mixture of the compound of Reference Example 3 (66.8 mg, 0.114 mmol), ammonium chloride (12.1 mg, 0.226 mmol), 1-hydroxybenzotriazole (26.1 mg, 0.170 mmol), WSC.HCl (32.6 mg, 0.170 mmol), triethylamine (47.4 µl, 0.34 mmol), and DMF (2 mL) was stirred at room temperature. After 3 hours, a saturated aqueous solution of ammonium chloride was added thereto, followed by extraction with ethyl acetate. The organic layer was washed with a saturated aqueous solution of ammonium chloride twice and with a saturated aqueous solution of sodium bicarbonate and a saturated saline solution once, dried over sodium sulfate, filtered, and then the organic layer was concentrated under reduced pressure to obtain the title compound (68.7 mg, 100%).
MS (ESI+) 588 (M+1, 53%)

Reference Example 5

5-{cis-1-[trans-4-(tert-Butoxycarbonylaminomethyl)cyclohexanecarbonyl]-N-methyl-3-phenylpyrrolidine-2-carboxamide}-1H-indole-2-carboxylic acid

[Formula 72]

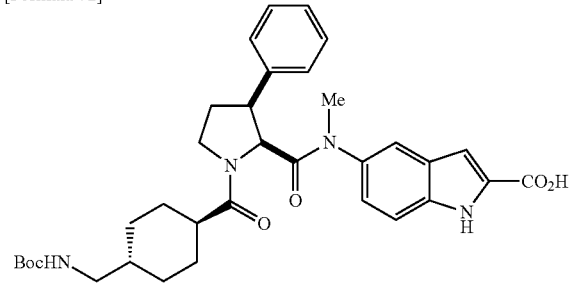

The same procedure as described in Reference Example 3 was carried out to obtain the title compound (22.8 mg, 95%) from the compound of Reference Example 5-1 (25.1 mg, 0.0398 mmol).
MS (ESI+) 603 (M+1, 40%)

Reference Example 5-1

Ethyl 5-{cis-1-[trans-4-(tert-butoxycarbonylaminomethyl)cyclohexanecarbonyl]-N-methyl-3-phenylpyrrolidine-2-carboxamide}-1H-indole-2-carboxylate

[Formula 73]

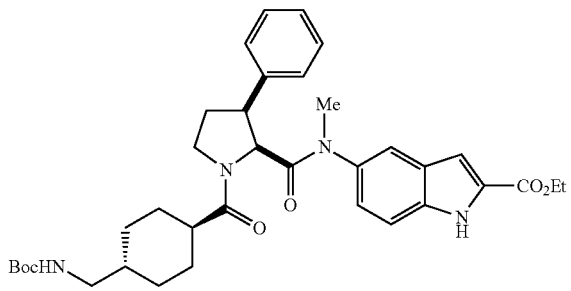

To a solution of the compound of Reference Example 2 (32.0 mg, 0.0592 mmol) in DMF (2 mL), potassium carbonate (12.3 mg, 0.0890 mmol) and methyl iodide (4.1 μl, 0.0659 mmol) were added, and the mixture was stirred at room temperature for 10 hours. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate, filtered, and the filtrate was concentrated under reduced pressure. The obtained residue was purified by silica gel column chromatography to obtain the title compound (25.1 mg, 67%).

MS (ESI+) 631 (M+1, 44%)

Reference Example 6 tert-Butyl 4-{(2S,3S)-1-[trans-4-(tert-butoxycarbonylaminomethyl)cyclohexanecarbonyl]-3-phenylpyrrolidine-2-carboxamide}benzoate

[Formula 74]

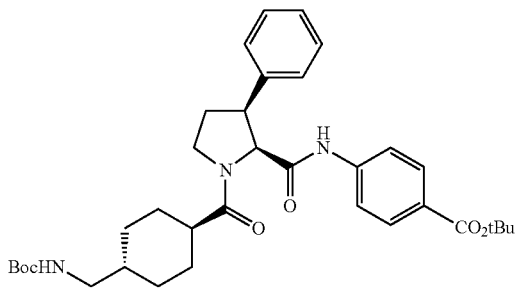

The same procedure as described in Reference Example 1 was carried out to obtain the title compound (62.0 mg, 53%) from the compound of Reference Example 6-2 (78.4 mg, 0.195 mmol).

MS (ESI+) 606 (M+1, 31%)

Reference Example 6-1 tert-Butyl 4-[(2S,3S)-1-tert-butoxycarbonyl-3-phenylpyrrolidine-2-carboxamide]benzoate

[Formula 75]

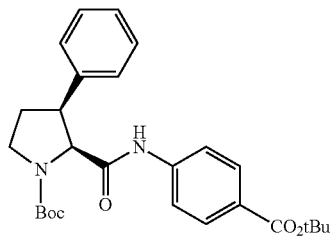

The same procedure as described in Reference Example 1-1 was carried out to obtain the title compound (302.4 mg, 36%) from (2S,3S)-1-tert-butoxycarbonyl-3-phenylpyrrolidine-2-carboxylic acid (520.5 mg, 1.79 mmol) known from literature (e.g., Org. Lett, 2009, 11, 18, 4056.).

MS (ESI+) 467 (M+1, 58%)

Reference Example 6-2 tert-Butyl 4-[(2S,3S)-3-phenylpyrrolidine-2-carboxamide]benzoate hydrochloride

[Formula 76]

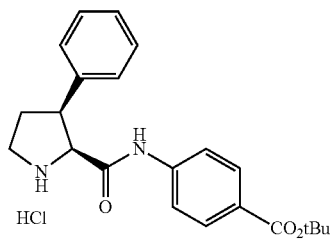

The same procedure as described in Reference Example 1-2 was carried out to obtain the title compound (206.3 mg, 79%) from the compound of Reference Example 6-1 (302.4 mg, 0.648 mmol).

MS (ESI+) 367 (M+1, 100%)

Reference Example 7

Methyl 4-[(2S,3S)-1-{trans-4-[1-(tert-butoxycarbonylamino)ethyl]cyclohexanecarbonyl}-3-phenylpyrrolidine-2-carboxamide]-2-fluorobenzoate

[Formula 77]

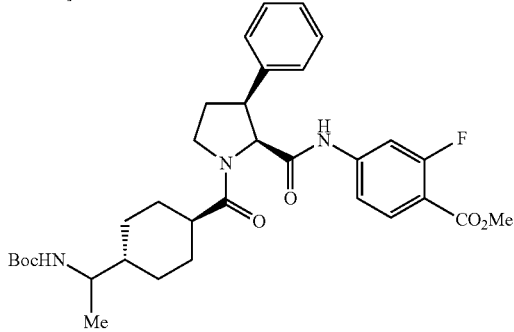

The same procedure as described in Reference Example 1 was carried out to obtain the title compound (257 mg, 72%) from the compound of Reference Example 7-2 (267 mg, 0.780 mmol) and the compound of Reference Example 7-9 (163 mg, 0.60 mmol).

MS (ESI+) 596 (M+1, 31%)

Reference Example 7-1

Methyl 4-[(2S,3S)-1-tert-butoxycarbonyl-3-phenylpyrrolidine-2-carboxamide]-2-fluorobenzoate

[Formula 78]

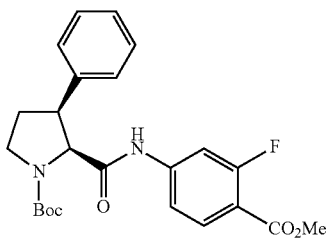

The same procedure as described in Reference Example 1-1 was carried out to obtain the title compound (345.0 mg, 32%) from (2S,3S)-1-tert-butoxycarbonyl-3-phenylpyrrolidine-2-carboxylic acid (520.5 mg, 1.79 mmol) and methyl 4-amino-2-fluorobenzoate (489 mg, 2.89 mmol).

MS (ESI+) 443 (M+1, 10%)

Reference Example 7-2

Methyl 4-[(2S,3S)-3-phenylpyrrolidine-2-carboxamide]-2-fluorobenzoate

[Formula 79]

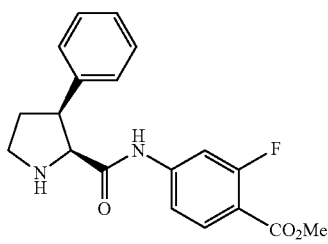

To a solution of the compound of Reference Example 7-1 (345 mg, 0.780 mmol) in chloroform (4 mL), trifluoroacetic acid (2 mL) was added, and the mixture was stirred for 2 hours. The solvent was concentrated under reduced pressure, then a saturated aqueous solution of sodium bicarbonate was added to the residue, followed by extraction with chloroform. The organic layer was washed with a saturated saline solution, then dried over sodium sulfate, and filtered, and the filtrate was concentrated under reduced pressure. The obtained residue was purified by silica gel column chromatography to obtain the title compound (267 mg, 100%).

MS (ESI+) 343 (M+1, 80%)

Reference Example 7-3

Benzyl trans-4-(hydroxymethyl)cyclohexanecarboxylate

[Formula 80]

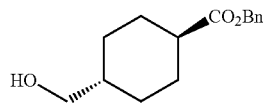

To a solution of trans-4-(hydroxymethyl)cyclohexanecarboxylic acid (9.18 g, 58.03 mmol) in DMF (70 mL), sodium bicarbonate (9.75 g, 116 mmol), sodium iodide (870 mg, 5.80 mmol), and benzyl chloride (8.82 g, 69.7 mmol) were added at room temperature, and the mixture was stirred at 60° C. for 6 hours. The reaction solution was allowed to cool, a saturated aqueous solution of ammonium chloride was added thereto, followed by extraction with ethyl acetate. The organic layer was washed with a saturated aqueous solution of ammonium chloride twice and with a saturated saline solution once, then dried over sodium sulfate, and filtered, and the filtrate was concentrated under reduced pressure. The obtained residue was purified by silica gel column chromatography to obtain the title compound (11.59 g, 80%).

$^1$H NMR (CDCl$_3$, 300 MHz) δ 7.39-7.26 (m, 5H), 5.11 (s, 2H), 3.46 (d, J=6.2 Hz, 2H), 2.35-2.27 (m, 1H), 2.09-2.03 (m, 2H), 1.90-1.85 (m, 2H), 1.61-1.34 (m, 4H), 1.06-0.96 (m, 2H).

Reference Example 7-4

Benzyl trans-4-formylcyclohexanecarboxylate

[Formula 81]

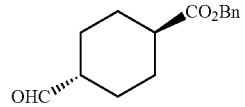

Molecular sieves 4 Å (4.30 g) was added to a solution of the compound of Reference Example 7-3 (4.31 g, 17.36 mmol) in acetonitrile (30 mL). 4-Methylmorpholine N-oxide (3.05 g, 26.03 mmol) and tetrapropylammonium perruthenate (610 mg, 1.74 mmol) were added thereto in an ice bath, and the mixture was stirred at room temperature. After 3 hours, the reaction solution was filtered through Celite and the filtrate was concentrated under reduced pressure. The obtained residue was purified by silica gel column chromatography to obtain the title compound (2.73 g, 64%).

$^1$H NMR (CDCl$_3$, 300 MHz) δ 9.63 (d, J=1.3 Hz, 1H), 7.40-7.32 (m, 5H), 5.12 (s, 2H), 2.37-2.05 (m, 5H), 1.80-1.45 (m, 3H), 1.37-1.24 (m, 2H).

Reference Example 7-5

Benzyl trans-4-(1-hydroxyethyl)cyclohexanecarboxylate

[Formula 82]

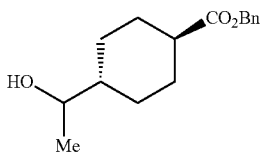

To a solution of the compound of Reference Example 7-4 (880 mg, 3.57 mmol) in THF (12 mL), a solution of methyl magnesium bromide in THF (0.93 mol/L) was added dropwise at −78° C. After the mixture was stirred at −78° C. for 5 hours, a saturated aqueous solution of ammonium chloride was added, followed by extraction with ethyl acetate. The organic layer was washed with a saturated saline solution, then dried over sodium sulfate, and filtered, and the filtrate was concentrated under reduced pressure. The obtained residue was purified by silica gel column chromatography to obtain the title compound (486.7 mg, 52%).

$^1$H NMR (CDCl$_3$, 300 MHz) δ 7.37-7.31 (m, 5H), 5.11 (s, 2H), 3.56 (m, 1H), 2.33-2.25 (m, 1H), 2.09-1.95 (m, 3H), 1.79-1.75 (m, 1H), 1.54-1.39 (m, 2H), 1.34-1.24 (m, 2H), 1.16 (d, J=6.2 Hz, 3H), 1.15-1.04 (m, 2H).

Reference Example 7-6

Benzyl trans-4-[1-(methanesulfonyloxy)ethyl]cyclohexanecarboxylate

[Formula 83]

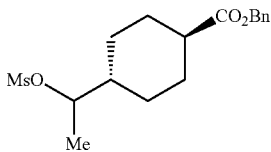

To a solution of the compound of Reference Example 7-5 (454.6 mg, 1.73 mmol) in THF (5 mL), trimethylamine (482 μl, 3.46 mmol) and methanesulfonyl chloride (201 μl, 2.60 mmol) were added in an ice bath. The mixture was stirred at room temperature for 2 hours, then a saturated aqueous solution of ammonium chloride was added thereto, followed by extraction with ethyl acetate. The organic layer was washed with a saturated saline solution, then dried over sodium sulfate, and filtered, and the filtrate was concentrated under reduced pressure. The obtained residue was purified by silica gel column chromatography to obtain the title compound (528.2 mg, 90%).

$^1$H NMR (CDCl$_3$, 300 MHz) δ 7.39-7.32 (m, 5H), 5.11 (s, 2H), 4.66-4.57 (m, 1H), 3.00 (s, 3H), 2.34-2.25 (m, 1H), 2.11-2.07 (m, 2H), 1.97-1.93 (m, 1H), 1.83-1.79 (m, 1H), 1.57-1.34 (m, 6H), 1.17-1.06 (m, 2H).

Reference Example 7-7

Benzyl trans-4-(1-azidoethyl)cyclohexanecarboxylate

[Formula 84]

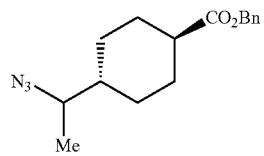

To a solution of the compound of Reference Example 7-6 (276.9 mg, 0.813 mmol) in DMF (2 mL), sodium azide (79.3 mg, 1.22 mmol) was added. The mixture was stirred at 60° C. for 6 hours, then allowed to cool, and then a saturated aqueous solution of ammonium chloride was added thereto, followed by extraction with ethyl acetate. The organic layer was washed with a saturated aqueous solution of ammonium chloride twice and with a saturated saline solution once, then dried over sodium sulfate, and filtered, and the filtrate was concentrated under reduced pressure. The obtained residue was purified by silica gel column chromatography to obtain the title compound (154.9 mg, 66%).

$^1$H NMR (CDCl$_3$, 300 MHz) δ 7.39-7.32 (m, 5H), 5.11 (s, 2H), 3.33-3.24 (m, 1H), 2.30-2.24 (m, 1H), 2.09-2.04 (m, 2H), 1.97-1.91 (m, 1H), 1.80-1.74 (m, 1H), 1.54-1.30 (m, 3H), 1.24 (d, J=6.8 Hz, 3H), 1.18-1.02 (m, 2H).

Reference Example 7-8

Benzyl trans-4-[1-(tert-butoxycarbonylamino)ethyl]cyclohexanecarboxylate

[Formula 85]

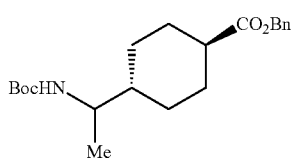

The compound of Reference Example 7-7 (1.33 g, 4.63 mmol) was dissolved in THF (20 mL) and water (2 mL), triphenylphosphine (2.43 g, 9.26 mmol) was added thereto, and the reaction solution was heated to reflux. After 2 hours, the reaction solution was allowed to cool, a saturated aqueous solution of sodium bicarbonate (20 mL) and di-tert-butyl dicarbonate (2.02 g, 9.26 mmol) were added thereto, and the mixture was stirred for 14 hours. A saturated aqueous solution of ammonium chloride was added to the reaction solution, followed by extraction with ethyl acetate. The organic layer was washed with a saturated saline solution, then dried over sodium sulfate, and filtered, and the filtrate was concentrated under reduced pressure. The obtained residue was purified by silica gel column chromatography to obtain the title compound (1.56 g, 93%).

$^1$H NMR (CDCl$_3$, 300 MHz) δ 7.39-7.31 (m, 5H), 5.10 (s, 2H), 4.32 (m, 1H), 3.51 (m, 1H), 2.32-2.23 (m, 1H), 2.07-2.03 (m, 2H), 1.88-1.76 (m, 2H), 1.58-1.26 (m, 12H), 1.11-0.99 (m, 5H).

Reference Example 7-9 trans-4-[1-(tert-Butoxycarbonylamino)ethyl]cyclohexanecarboxylic acid

[Formula 86]

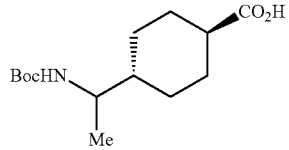

To a solution of the compound of Reference Example 7-8 (1.28 g, 3.55 mmol) in methanol (7 mL), palladium-carbon (1.30 g) was added, and the mixture was stirred for 4 hours under hydrogen atmosphere. The reaction solution was filtered through Celite and the filtrate was concentrated under reduced pressure to obtain the title compound (960 mg, 100%).

MS (ESI+) 272 (M+1, 11%)

Reference Example 8

4-[(2S,3S)-1-{trans-4-[1-(tert-Butoxycarbonylamino)ethyl]cyclohexanecarbonyl}-3-phenylpyrrolidine-2-carboxamide]-2-fluorobenzoic acid

[Formula 87]

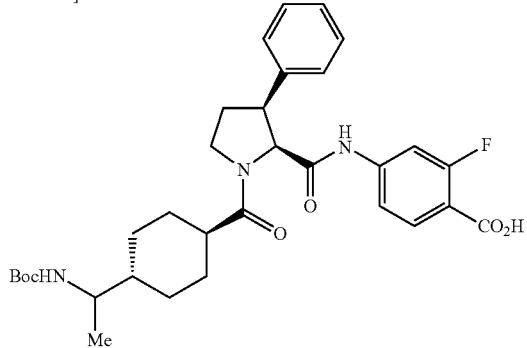

The same procedure as described in Reference Example 3 was carried out to obtain the title compound (107.6 mg, 68%) from the compound of Reference Example 7 (161.8 mg, 0.272 mmol).

MS (ESI+) 582 (M+1, 8%)

Reference Example 9

Methyl 4-[(2S,3S)-1-{trans-4-[1-(tert-butoxycarbonylamino)ethyl]cyclohexanecarbonyl}-3-phenylpyrrolidine-2-carboxamide]-3-methylbenzoate

[Formula 88]

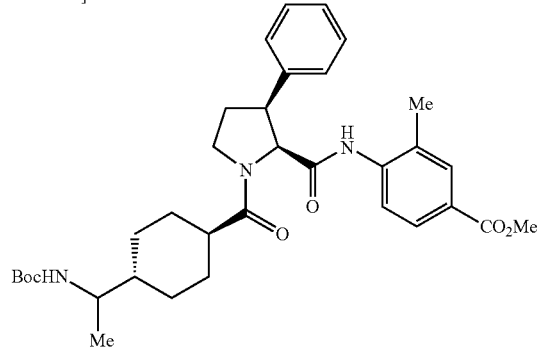

The same procedure as described in Reference Example 1 was carried out to obtain the title compound (136.1 mg, 66%) from the compound of Reference Example 9-2 (154 mg, 0.346 mmol) and the compound of Reference Example 7-9 (93.9 mg, 0.346 mmol).

MS (ESI+) 592 (M+1, 33%)

Reference Example 9-1

Methyl 4-[(2S,3S)-1-(tert-butoxycarbonyl)-3-phenylpyrrolidine-2-carboxamide]-3-methylbenzoate

[Formula 89]

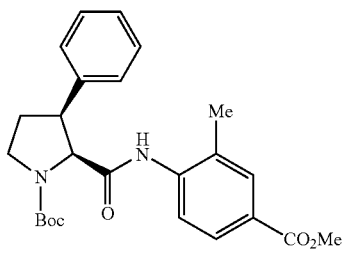

The same procedure as described in Reference Example 1-1 was carried out to obtain the title compound (151.7 mg, 43%) from (2S,3S)-1-tert-butoxycarbonyl-3-phenylpyrrolidine-2-carboxylic acid (232 mg, 0.796 mmol) and methyl 4-amino-3-methylbenzoate (145 mg, 0.876 mmol).

MS (ESI+) 439 (M+1, 10%)

Reference Example 9-2

Methyl 4-[(2S,3S)-3-phenylpyrrolidine-2-carboxamide]-3-methylbenzoate trifluoroacetate

[Formula 90]

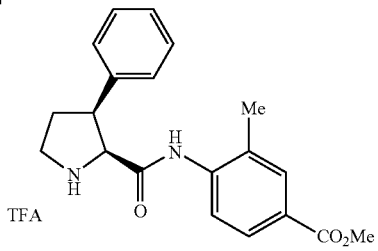

To a solution of the compound of Reference Example 9-1 (151.7 mg, 0.346 mmol) in chloroform (2 mL), trifluoroacetic acid (1 mL) was added, and the mixture was stirred for 2 hours. After the mixture was concentrated under reduced pressure, toluene (2 mL) was added to the residue, followed by concentration under reduced pressure again. Chloroform (3 mL) and hexane (3 mL) were further added, and concentration under reduced pressure was carried out twice to obtain the title compound (154 mg, 100%).

MS (ESI+) 339 (M+1, 61%)

Reference Example 10

4-[(2S,3S)-1-{trans-4-[1-(tert-Butoxycarbonylamino)ethyl]cyclohexanecarbonyl}-3-phenylpyrrolidine-2-carboxamide]-3-methylbenzoic acid

[Formula 91]

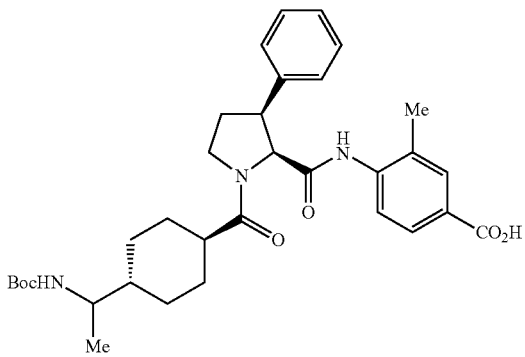

The same procedure as described in Reference Example 3 was carried out to obtain the title compound (71.7 mg, 82%) from the compound of Reference Example 9 (89.9 mg, 0.152 mmol).

MS (ESI+) 578 (M+1, 24%)

Reference Example 11 tert-Butyl 1-{trans-4-[(2S,3S)-3-cyclohexyl-2-(quinolin-6-ylcarbonyl)pyrrolidine-1-carbonyl]cyclohexyl}ethylcarbamate

[Formula 92]

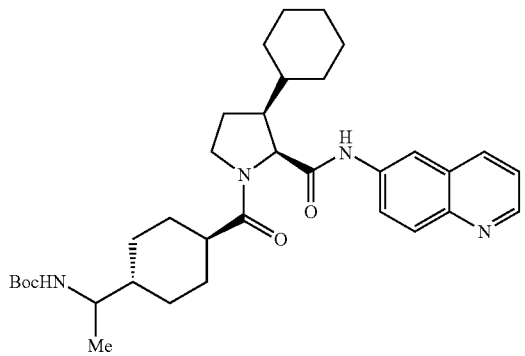

The same procedure as described in Reference Example 1 was carried out to obtain the title compound (40.5 mg, 54%) from the compound of Reference Example 11-3 (41.6 mg, 0.130 mmol) and the compound of Reference Example 7-9 (40.8 mg, 0.143 mmol).

MS (ESI+) 577 (M+1, 81%)

Reference Example 11-1

(2S,3S)-1-tert-Butoxycarbonyl-3-cyclohexylpyrrolidine-2-carboxylic acid

[Formula 93]

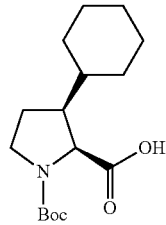

To a solution of (2S,3S)-1-tert-butoxycarbonyl-3-phenylpyrrolidine-2-carboxylic acid (632 mg, 2.17 mmol) known from literature (e.g. Org. Lett, 2009, 11, 18, 4056.) in acetic acid (10 mL), platinum oxide (274 mg) was added, and the mixture was stirred for 3.5 hours under a pressure of 0.4 Mpa and under hydrogen atmosphere. The reaction solution was filtered through Celite, and the filtrate was concentrated under reduced pressure to obtain the title compound (627.8 mg, 97%).

MS (ESI+) 298 (M+1, 15%)

Reference Example 11-2 tert-Butyl (2S,3S)-3-cyclohexyl-2-(quinolin-6-ylcarbamoyl)pyrrolidine-1-carboxylate

[Formula 94]

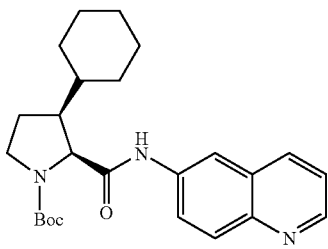

The same procedure as described in Reference Example 1 was carried out to obtain the title compound (55.0 mg, 12%) from the compound of Reference Example 11-1 (326.6 mg, 1.10 mmol) and 6-aminoquinoline (190 mg, 1.32 mmol).

MS (ESI+) 424 (M+1, 100%)

Reference Example 11-3

(2S,3S)-3-Cyclohexyl-N-(quinolin-6-yl)pyrrolidine-2-carboxamide bis(trifluoroacetate)

[Formula 95]

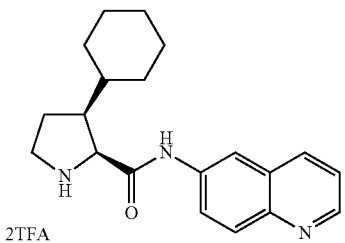

The same procedure as described in Reference Example 9-2 was carried out to obtain the title compound (41.6 mg, 100%) from the compound of Reference Example 11-2 (55.0 mg, 0.130 mmol).

MS (ESI+) 324 (M+1, 100%)

Reference Example 12 tert-Butyl trans-4-[cis-2-(4-cyanophenylcarbamoyl)-3-phenylpyrrolidine-1-carbonyl]cyclohexylmethylcarbamate

[Formula 96]

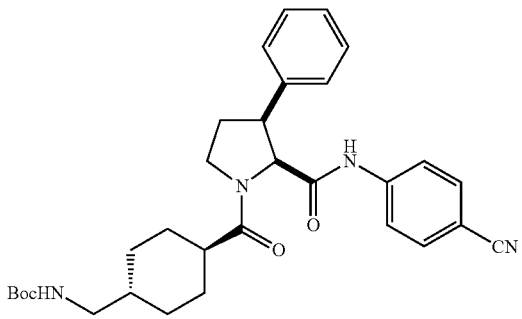

The same procedure as described in Reference Example 1-1 was carried out to obtain the title compound (65 mg, 52%) from the compound of Reference Example 19-3 (100 mg, 0.23 mmol) and 4-aminobenzonitrile (30 mg, 0.25 mmol).

MS (ESI+) 531 (M+1, 17%)

Reference Example 13 tert-Butyl trans-4-{cis-2-[4-(5-oxo-2,5-dihydro-1,2,4-oxazol-3-yl)phenylcarbamoyl]-3-phenylpyrrolidine-1-carbonyl}cyclohexylmethylcarbamate

[Formula 97]

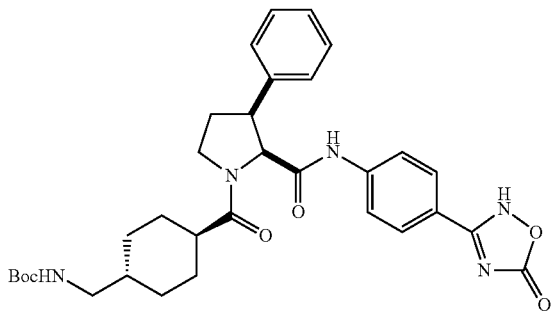

A solution of the compound of Reference Example 12 (46 mg, 0.086 mmol), hydroxylamine hydrochloride (30 mg, 0.43 mmol), and triethylamine (0.12 mL, 0.86 mmol) in ethanol (1 mL) was stirred at 80° C. After 1 hour, the mixture was allowed to cool, an aqueous solution of ammonium chloride was added, followed by extraction with chloroform. The organic layer was washed with a saturated saline solution, dried over sodium sulfate and filtered, and then the filtrate was concentrated under reduced pressure. The obtained residue was diluted in THF (1 mL), 1,1'-carbonyldiimidazole (15 mg, 0.086 mmol) and triethylamine (36.0 µl, 0.26 mmol) were added, and the mixture was stirred at room temperature overnight. The solvent was removed under reduced pressure, and the obtained residue was purified by silica gel column chromatography to obtain the title compound (25 mg, 49%).

MS (ESI+) 590 (M+1, 9%)

Reference Example 14 tert-Butyl trans-4-{cis-2-[3-fluoro-4-(5-oxo-2,5-dihydro-1,2,4-oxazol-3-yl)phenylcarbamoyl]-3-phenylpyrrolidine-1-carbonyl}cyclohexylmethylcarbamate

[Formula 98]

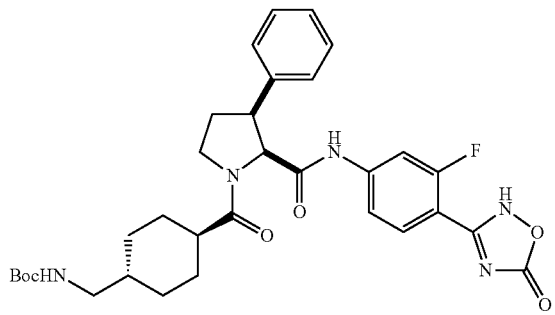

The same procedure as described in Reference Example 13 was carried out to obtain the title compound (17 mg, 32%) from the compound of Reference Example 14-1 (48 mg, 0.087 mmol).

MS (ESI+) 608 (M+1, 16%)

Reference Example 14-1 tert-Butyl trans-4-[cis-2-(4-cyano-3-fluorophenylcarbamoyl)-3-phenylpyrrolidine-1-carbonyl]cyclohexylmethylcarbamate

[Formula 99]

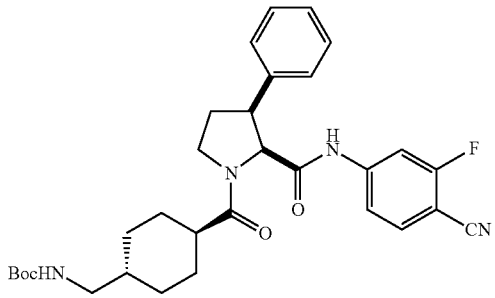

The same procedure as described in Reference Example 1-1 was carried out to obtain the title compound (49 mg, 45%) from the compound of Reference Example 19-3 (86 mg, 0.20 mmol) and 4-amino-2-fluorobenzonitrile (29 mg, 0.24 mmol).

MS (ESI+) 549 (M+1, 15%)

Reference Example 15

4-{(2R,3S)-1-[trans-4-(tert-Butoxycarbonylaminomethyl)cyclohexanecarbonyl]-3-phenylpyrrolidine-2-carboxamide}benzoic acid

[Formula 100]

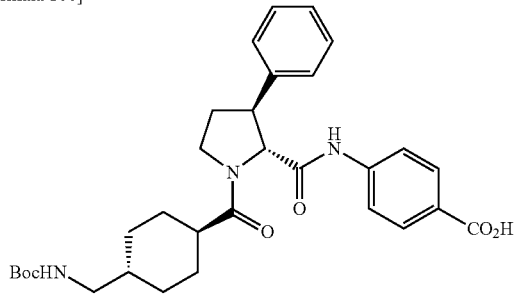

The same procedure as described in Reference Example 19 was carried out to obtain the title compound (47 mg, 98%) from the compound of Reference Example 15-3 (49 mg, 0.087 mmol).
MS (ESI+) 550 (M+1, 14%)

Reference Example 15-1

Methyl 4-[(2R,3S)-1-tert-butoxycarbonyl-3-phenylpyrrolidine-2-carboxamide]benzoate

[Formula 101]

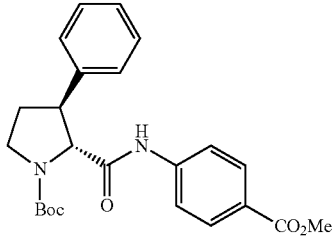

The same procedure as described in Reference Example 1-1 was carried out to obtain the title compound (250 mg, 62%) from (2R,3S)-1-tert-butoxycarbonyl-3-phenylpyrrolidine-2-carboxylic acid (290 mg, 0.95 mmol) known from literature (e.g., Org. Lett. 2009, 11, 4056.s).
MS (ESI+) 425 (M+1, 76%)

Reference Example 15-2

Methyl 4-[(2R,3S)-3-phenylpyrrolidine-2-carboxamide]benzoate hydrochloride

[Formula 102]

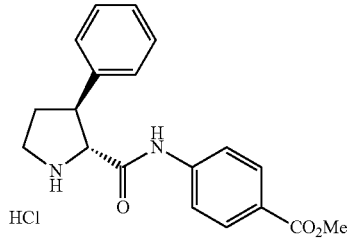

The same procedure as described in Reference Example 1-2 was carried out to obtain the title compound (255 mg, 100%) from the compound of Reference Example 15-1 (300 mg, 0.71 mmol).
MS (ESI+) 325 (M+1, 100%)

Reference Example 15-3

Methyl 4-{(2R,3S)-1-[trans-4-(tert-butoxycarbonylaminomethyl)cyclohexanecarbonyl]-3-phenylpyrrolidine-2-carboxamide}benzoate

[Formula 103]

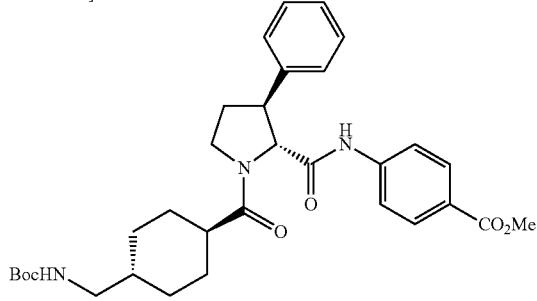

The same procedure as described in Reference Example 1 was carried out to obtain the title compound (49 mg, 67%) from the compound of Reference Example 15-2 (33 mg, 0.13 mmol).
MS (ESI+) 564 (M+1, 18%)

Reference Example 16 tert-Butyl 4-{trans-1-[trans-4-(tert-butoxycarbonylaminomethyl)cyclohexanecarbonyl]-3-phenylpyrrolidine-2-carboxamide}benzoate

[Formula 104]

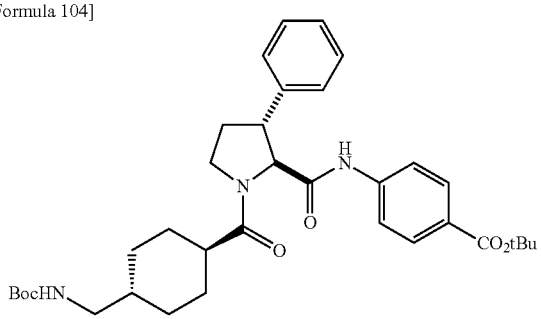

The same procedure as described in Reference Example 1 was carried out to obtain the title compound (44 mg, 67%) from the compound of Reference Example 16-2 (40 mg, 0.11 mmol).
MS (ESI+) 606 (M+1, 24%)

Reference Example 16-1 tert-Butyl 4-(trans-1-tert-butoxycarbonyl-3-phenylpyrrolidine-2-carboxamide)benzoate

[Formula 105]

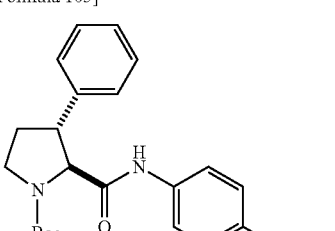

The same procedure as described in Reference Example 1-1 was carried out to obtain the title compound (335 mg, 55%) from tert-butyl 4-aminobenzoate (304 mg, 1.57 mmol) known from literature (e.g., J. Med. Chem. 2008, 51, 7751.) and commercially available trans-1-tert-butoxycarbonyl-3-phenylpyrrolidine-2-carboxylic acid (400 mg, 1.31 mmol).

MS (ESI+) 467 (M+I, 12%)

Reference Example 16-2 tert-Butyl 4-(trans-3-phenylpyrrolidine-2-carboxamide)benzoate

[Formula 106]

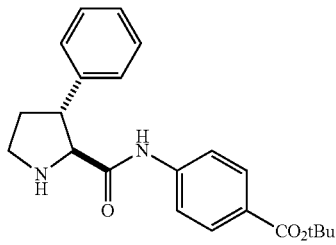

The same procedure as described in Reference Example 7-2 was carried out to obtain the title compound (220 mg, 85%) from the compound of Reference Example 16-1 (330 mg, 0.71 mmol).

MS (ESI+) 367 (M+I, 100%)

Reference Example 17 tert-Butyl 4-{cis-1-[trans-4-(tert-butoxycarbonylaminomethyl)cyclohexanecarbonyl]-3-cyclohexylpyrrolidine-2-carboxamide}benzoate

[Formula 107]

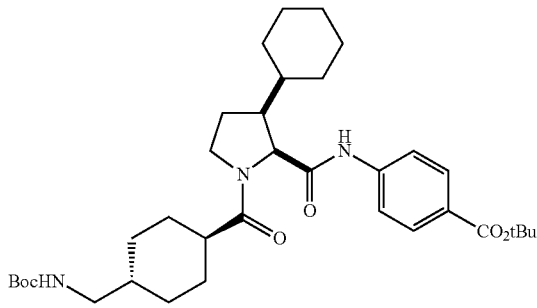

The same procedure as described in Reference Example 1 was carried out to obtain the title compound (22 mg, 69%) from the compound of Reference Example 17-2 (22 mg, 0.053 mmol).

MS (ESI+) 612 (M+1, 21%)

Reference Example 17-1 tert-Butyl 4-(cis-1-tert-butoxycarbonyl-3-cyclohexylpyrrolidine-2-carboxamide)benzoate

[Formula 108]

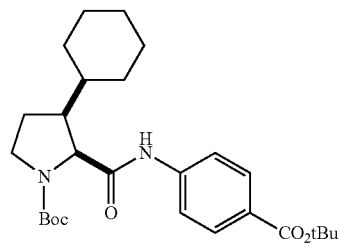

To a solution of commercially available cis-1-tert-butoxycarbonyl-3-phenylpyrrolidine-2-carboxylic acid (120 mg, 0.41 mmol) in methanol (3 mL)/acetic acid (1 mL), platinum oxide (40 mg) was added, and the mixture was stirred for 3.5 hours under a pressure of 0.4 MPa and under hydrogen atmosphere. The reaction solution was filtered through Celite and the filtrate was concentrated under reduced pressure to obtain cis-1-tert-butoxycarbonyl-3-cyclohexylpyrrolidine-2-carboxylic acid (120 mg, 98%).

Subsequently, the same procedure as described in Reference Example 1-1 was carried out to obtain the title compound (130 mg, 37%) from cis-1-tert-butoxycarbonyl-3-cyclohexylpyrrolidine-2-carboxylic acid (220 mg, 0.74 mmol) and tert-butyl 4-aminobenzoate (186 mg, 0.96 mmol).

MS (ESI+) 473 (M+1, 9%)

Reference Example 17-2 tert-Butyl 4-(cis-3-cyclohexylpyrrolidine-2-carboxamide)benzoate hydrochloride

[Formula 109]

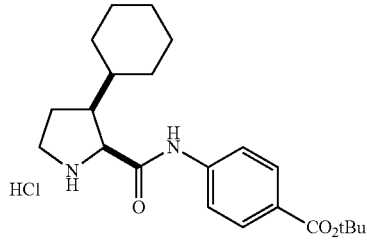

The same procedure as described in Reference Example 1-2 was carried out to obtain the title compound (110 mg, 98%) from the compound of Reference Example 17-1 (130 mg, 0.11 mmol).

MS (ESI+) 373 (M+1, 100%)

Reference Example 18 tert-Butyl 4-{(2S,3S)-1-[trans-4-(tert-butoxycarbonylaminomethyl)cyclohexanecarbonyl]-3-cyclohexylpyrrolidine-2-carboxamide}-2-fluorobenzoate

[Formula 110]

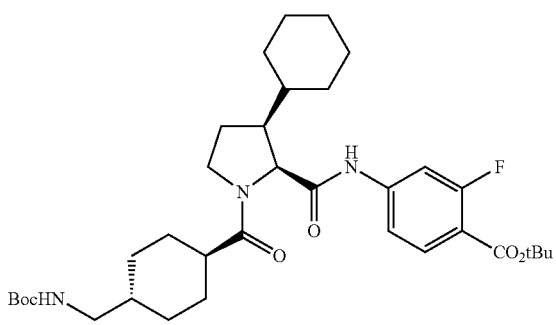

The same procedure as described in Reference Example 1 was carried out to obtain the title compound (44 mg, 67%) from the compound of Reference Example 18-2 (40 mg, 0.11 mmol).
MS (ESI+) 606 (M+1, 15%)

Reference Example 18-1 tert-Butyl 4-[(2S,3S)-1-tert-butoxycarbonyl-3-cyclohexylpyrrolidine-2-carboxamide]-2-fluorobenzoate

[Formula 111]

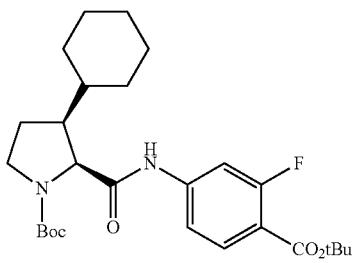

The same procedure as described in Reference Example 1-1 was carried out to obtain the title compound (50 mg, 20%) from the compound of Reference Example 11-1 (150 mg, 0.51 mmol) and tert-butyl 4-amino-2-fluorobenzoate (137 mg, 0.65 mmol).
MS (ESI+) 491 (M+1, 13%)

Reference Example 18-2 tert-Butyl 4-[(2S,3S)-3-cyclohexylpyrrolidine-2-carboxamide]-2-fluorobenzoate hydrochloride

[Formula 112]

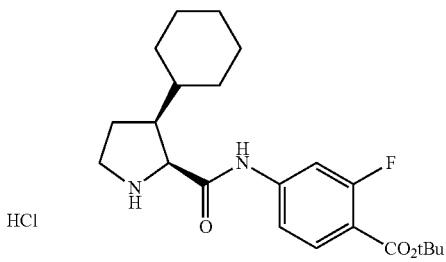

The same procedure as described in Reference Example 1-2 was carried out to obtain the title compound (42 mg, 99%) from the compound of Reference Example 18-1 (50 mg, 0.10 mmol).
MS (ESI+) 391 (M+1, 100%)

Reference Example 19

4-{cis-1-[trans-4-(tert-Butoxycarbonylaminomethyl)cyclohexanecarbonyl]-3-phenylpyrrolidine-2-carboxamide}-2-methoxybenzoic acid

[Formula 113]

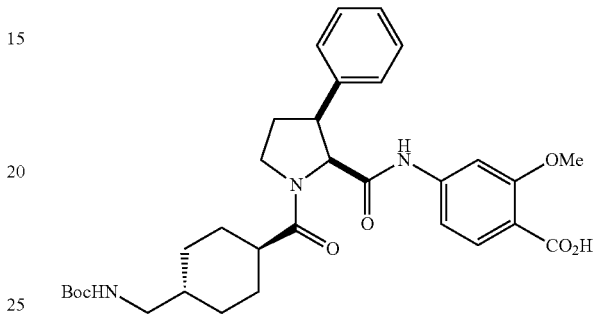

To a solution of the compound of Reference Example 19-4 (30 mg, 0.051 mmol) in methanol (2 mL), a 1 mol/L aqueous solution of sodium hydroxide (1 mL) was added, and the mixture was stirred at 60° C. After 1 hour, the mixture was allowed to cool, and a 5% aqueous solution of potassium hydrogensulfate was added thereto, followed by extraction with chloroform. The organic layer was washed with a saturated saline solution, dried over sodium sulfate and filtered, and then the solvent was removed under reduced pressure to obtain the title compound (29 mg, 98%).
MS (ESI+) 580 (M+I, 26%)

Reference Example 19-1

1-tert-Butyl 2-methyl cis-3-phenylpyrrolidine-1,2-dicarboxylate

[Formula 114]

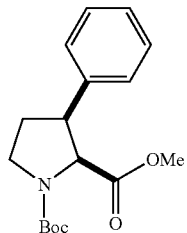

A solution of commercially available cis-1-tert-butoxycarbonyl-3-phenylpyrrolidine-2-carboxylic acid (580 mg, 2.00 mmol), 1-hydroxybenzotriazole (351 mg, 2.60 mmol), WSC.HCl (498 mg, 2.60 mmol), and triethylamine (0.56 mL, 4.00 mmol) in methanol (10 mL) was stirred at room temperature. After 14 hours, the reaction solution was heated to reflux. After 2 hours, the reaction solution was allowed to cool, water was added thereto, followed by extraction with ethyl acetate. The organic layer was washed with a saturated saline solution, dried over anhydrous sodium sulfate and filtered, and then the organic layer was concentrated under reduced pressure. The obtained residue was purified by silica gel column chromatography to obtain the title compound (605 mg, 99%).
MS (ESI+) 306 (M+1, 17%)

Reference Example 19-2

Methyl 4-{cis-1-[trans-4-(tert-butoxycarbonylaminomethyl)cyclohexanecarbonyl]-3-phenylpyrrolidine-2-carboxylate

[Formula 115]

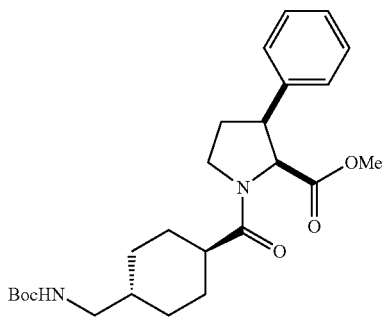

To a solution of the compound of Reference Example 19-1 (605 mg, 1.98 mmol) in chloroform (2 mL), a 4 mol/L hydrochloric acid-dioxane solution (2 mL) was added, and the mixture was stirred at room temperature. After 1 hour, the solvent was removed under reduced pressure. To the obtained residue, trans-4-(tert-butoxycarbonylaminomethyl)cyclohexanecarboxylic acid (489 mg, 1.90 mmol), 1-hydroxybenzotriazole (385 mg, 2.97 mmol), WSC.HCl (546 mg, 2.97 mmol), triethylamine (0.83 mL, 5.94 mmol), and DMF (10 mL) were added, and the mixture was stirred at room temperature. After 14 hours, a saturated aqueous solution of ammonium chloride was added, followed by extraction with ethyl acetate. The organic layer was washed with a saturated saline solution, dried over anhydrous sodium sulfate and filtered, and then the solvent was removed under reduced pressure. The obtained residue was purified by silica gel column chromatography to obtain the title compound (789 mg, 90%).

MS (ESI+) 445 (M+1, 58%)

Reference Example 19-3

4-{cis-1-[trans-4-(tert-Butoxycarbonylaminomethyl)cyclohexanecarbonyl]-3-phenylpyrrolidine-2-carboxylic acid

[Formula 116]

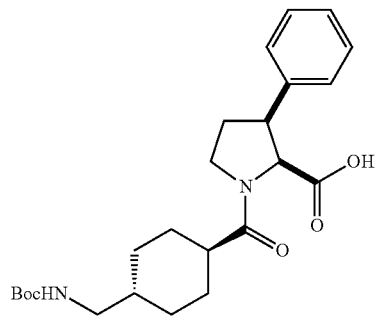

To a solution of the compound of Reference Example 19-2 (789 mg, 1.77 mmol) in methanol (5 mL), a 1 mol/L aqueous solution of sodium hydroxide (5 mL) was added, and the mixture was heated to reflux. After 8 hours, the reaction solution was allowed to cool, and a 5% aqueous solution of potassium hydrogensulfate was added thereto, followed by extraction with chloroform. The organic layer was washed with a saturated saline solution, dried over sodium sulfate and filtered, and then the solvent was removed under reduced pressure to obtain the title compound (640 mg, 84%).

MS (ESI+) 431 (M+1, 7%)

Reference Example 19-4

Methyl 4-{cis-1-[trans-4-(tert-butoxycarbonylaminomethyl)cyclohexanecarbonyl]-3-phenylpyrrolidine-2-carboxamide}-2-methoxy benzoate

[Formula 117]

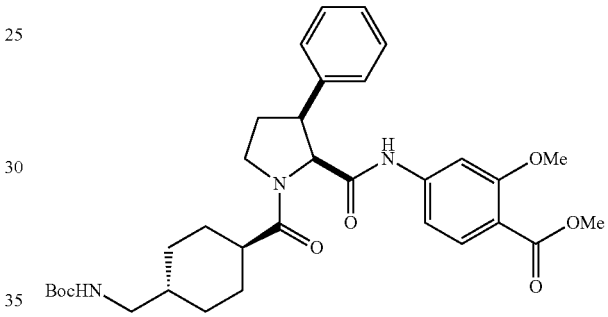

The same procedure as described in Reference Example 1-1 was carried out to obtain the title compound (30 mg, 51%) from the compound of Reference Example 19-3 (43 mg, 0.10 mmol) and methyl 4-amino-2-methoxy benzoate (20 mg, 0.11 mmol).

MS (ESI+) 594 (M+1, 10%)

Reference Example 20

4-{cis-1-[trans-4-(tert-Butoxycarbonylaminomethyl)cyclohexanecarbonyl]-3-phenylpyrrolidine-2-carboxamide}-2-chlorobenzoic acid

[Formula 118]

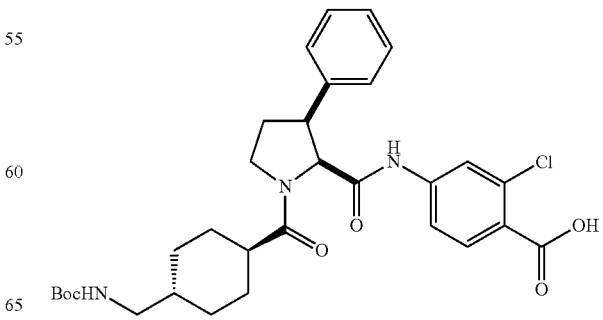

The same procedure as described in Reference Example 19 was carried out to obtain the title compound (20 mg, 96%) from the compound of Reference Example 20-1 (26 mg, 0.043 mmol).

MS (ESI+) 585 (M+1, 14%)

Reference Example 20-1

Methyl 4-{cis-1-[trans-4-(tert-butoxycarbonylaminomethyl)cyclohexanecarbonyl]-3-phenylpyrrolidine-2-carboxamide}-2-chlorobenzoate

[Formula 119]

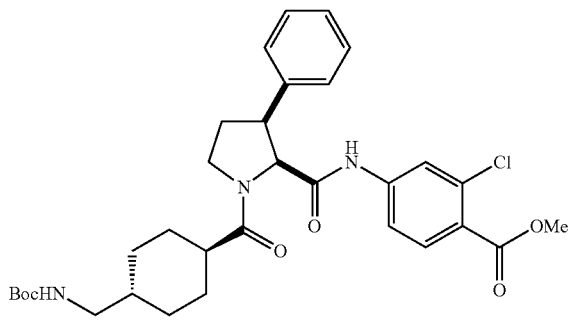

The same procedure as described in Reference Example 1-1 was carried out to obtain the title compound (28 mg, 47%) from the compound of Reference Example 19-3 (43 mg, 0.10 mmol) and methyl 4-amino-2-chlorobenzoate (22 mg, 0.12 mmol).

MS (ESI+) 598 (M+1, 10%)

Reference Example 21 tert-Butyl trans-4-[cis-3-phenyl-2-(quinolin-6-ylcarbonyl)pyrrolidine-1-carbonyl]cyclohexylmethylcarbamate

[Formula 120]

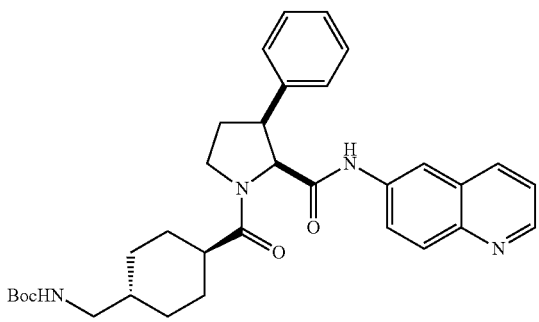

The same procedure as described in Reference Example 1-1 was carried out to obtain the title compound (17 mg, 47%) from the compound of Reference Example 19-3 (22 mg, 0.05 mmol) and 6-aminoquinoline (9 mg, 0.06 mmol).

MS (ESI+) 557 (M+1, 62%)

Reference Example 22

4-{cis-1-[trans-4-(tert-Butoxycarbonylaminomethyl)cyclohexanecarbonyl]-3-phenylpyrrolidine-2-carboxamide}-2-fluorobenzamide

[Formula 121]

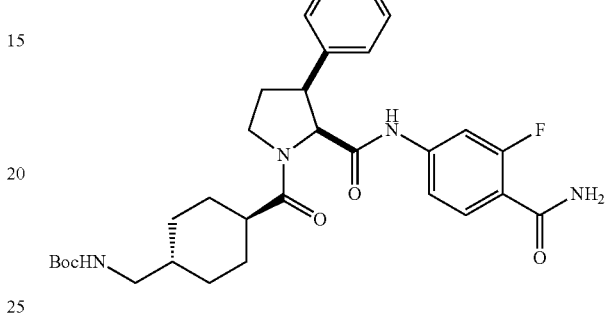

The title compound (12 mg, 24%) was obtained as a byproduct of the process in Reference Example 14.

MS (ESI+) 567 (M+1, 3%)

Reference Example 23

5-{(2S,3S)-1-[trans-4-(tert-Butoxycarbonylaminomethyl)cyclohexanecarbonyl]-3-phenylpyrrolidine-2-carboxamide}-1H-indole-2-carboxylic acid

[Formula 122]

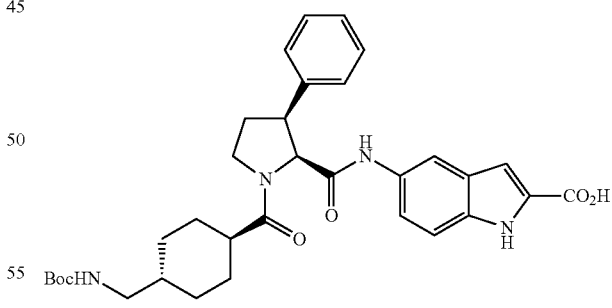

By using (2S,3S)-1-tert-butoxycarbonyl-3-phenylpyrrolidine-2-carboxylic acid as the starting material, the same procedures as described in Reference Example 1, Reference Example 1-2, Reference Example 1, and Reference Example 3 were carried out in order to obtain the title compound.

MS (ESI+) 589 (M+1, 54%)

Reference Example 24

5-{(2S,3S)-1-[trans-4-(tert-Butoxycarbonylaminomethyl)cyclohexanecarbonyl]-3-phenylpyrrolidine-2-carboxamide}-1H-indole-2-carboxamide

[Formula 123]

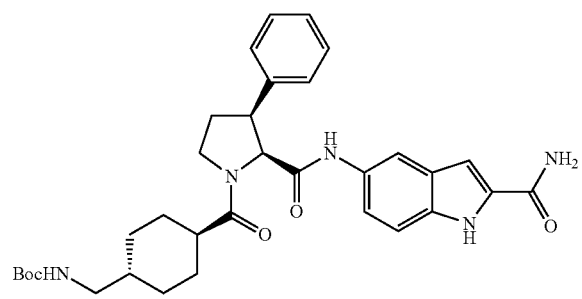

The same procedure as described in Reference Example 4 was carried out to obtain the title compound (160 mg, 85%) from the compound of Reference Example 23 (190 mg, 0.32 mmol).

MS (ESI+) 588 (M+1, 57%)

Reference Example 25

Methyl 4-{cis-1-[trans-4-(hydroxymethyl)cyclohexanecarbonyl]-3-phenylpyrrolidine-2-carboxamide}benzoate

[Formula 124]

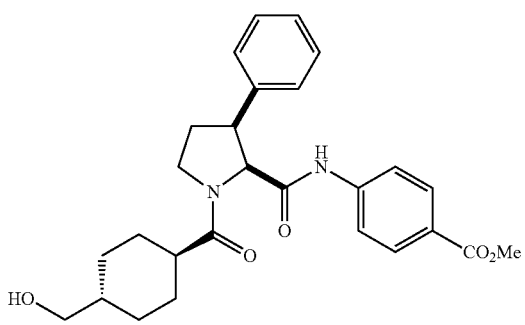

The same procedure as described in Reference Example 1 was carried out to obtain the title compound (31 mg, 52%) from 4-hydroxymethyl-1-cyclohexanecarboxylic acid (21 mg, 0.13 mmol) and the compound of Reference Example 25-2 (51 mg, 0.14 mmol).

MS (ESI+) 465 (M+1, 82%)

Reference Example 25-1

Methyl 4-(cis-1-tert-butoxycarbonyl-3-phenylpyrrolidine-2-carboxamide)benzoate

[Formula 125]

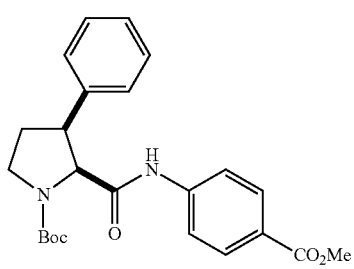

The same procedure as described in Reference Example 1-1 was carried out to obtain the title compound (683 mg, 54%) from commercially available cis-1-tert-butoxycarbonyl-3-phenylpyrrolidine-2-carboxylic acid (916 mg, 3.14 mmol) and methyl 4-aminobenzoate (544 mg, 3.60 mmol).

MS (ESI+) 425 (M+1, 18%)

Reference Example 25-2

Methyl 4-(cis-3-phenylpyrrolidine-2-carboxamide)benzoate hydrochloride

[Formula 126]

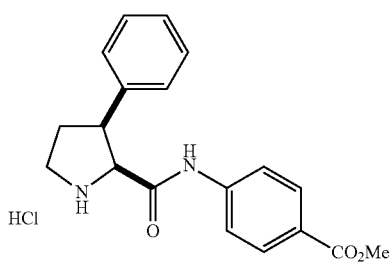

The same procedure as described in Reference Example 1-2 was carried out to obtain the title compound (576 mg, 100%) from the compound of Reference Example 25-1 (680 mg, 1.60 mmol).

MS (ESI+) 325 (M+1, 100%)

Reference Example 26 tert-Butyl 1-{trans-4-[(2S,3S)-3-cyclohexyl-2-(quinolin-6-ylcarbonyl)pyrrolidine-1-carbonyl]cyclohexyl}propylcarbamate

[Formula 127]

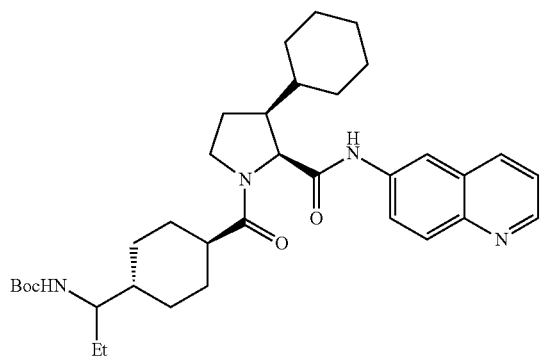

The same procedure as described in Reference Example 1 was carried out to obtain the title compound (60.0 mg, 66%) from the compound of Reference Example 11-3 (50.0 mg, 0.154 mmol) and the compound of Reference Example 26-5 (50.0 mg, 0.169 mmol).

MS (ESI+) 591 (M+1, 100%)

Reference Example 26-1

Benzyl trans-4-(1-hydroxypropyl)cyclohexanecarboxylate

[Formula 128]

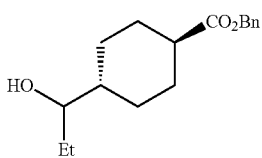

To a solution of the compound of Reference Example 7-4 (1.44 g, 5.85 mmol) in THF (20 mL), a solution of ethyl magnesium bromide in THF (0.9 mol/L) was added dropwise at −78° C. After the mixture was stirred at −78° C. for 5 hours, a saturated aqueous solution of ammonium chloride was added, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (677.0 mg, 42%).

MS (ESI+) 277 (M+1, 100%)

Reference Example 26-2

Benzyl trans-4-[1-(methanesulfonyloxy)propyl]cyclohexanecarboxylate

[Formula 129]

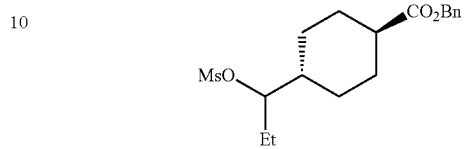

The same procedure as described in Reference Example 7-6 was carried out to obtain the title compound (380.0 mg, 98%) from the compound of Reference Example 26-1 (300 mg, 1.09 mmol).

MS (ESI+) 354 (M+1, 100%)

Reference Example 26-3

Benzyl trans-4-(1-azide propyl)cyclohexanecarboxylate

[Formula 130]

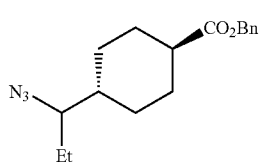

The same procedure as described in Reference Example 7-7 was carried out to obtain the title compound (293.0 mg, 91%) from the compound of Reference Example 26-2 (380.0 mg, 1.07 mmol).

$^1$H NMR (DMSO-$d_6$, 300 MHz) δ 7.40-7.30 (5H, m), 5.07 (2H, s), 3.19-3.19 (1H, m), 2.32-2.25 (2H, m), 1.94 (2H, d, J=11.0 Hz), 1.79-1.02 (8H, m), 0.92 (3H, t, J=7.3 Hz).

Reference Example 26-4

Benzyl trans-4-[1-(tert-butoxycarbonylamino)propyl]cyclohexanecarboxylate

[Formula 131]

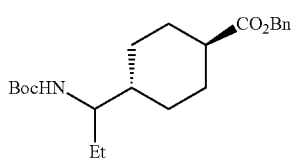

The same procedure as described in Reference Example 7-8 was carried out to obtain the title compound (305.0 mg, 84%) from the compound of Reference Example 26-3 (293.0 mg, 0.972 mmol).

¹H NMR (DMSO-d₆, 300 MHz) δ 7.39-7.27 (5H, m), 6.50 (1H, d, J=9.4 Hz), 5.06 (2H, s), 3.14-3.04 (1H, m), 2.28-2.20 (1H, m), 1.91 (2H, d, J=11.0 Hz), 1.68 (2H, d, J=12.7 Hz), 1.48-1.16 (14H, m), 1.01-0.90 (2H, m), 0.77 (3H, t, J=7.3 Hz).

Reference Example 26-5 trans-4-[1-(tert-Butoxycarbonylamino)propyl]cyclohexanecarboxylic acid

[Formula 132]

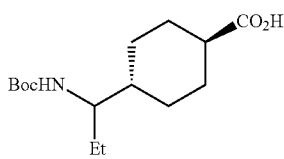

The same procedure as described in Reference Example 7-9 was carried out to obtain the title compound (222.0 mg, 97%) from the compound of Reference Example 26-4 (300.0 mg, 0.80 mmol).

¹H NMR (DMSO-d₆, 300 MHz) δ 6.49 (1H, d, J=9.5 Hz), 3.14-3.04 (1H, m), 2.08-1.99 (1H, m), 1.88-1.64 (5H, m), 1.36-1.17 (14H, m), 0.98-0.85 (2H, m), 0.77 (3H, t, J=7.3 Hz).

Reference Example 27

4-[(2S,3S)-1-{trans-4-[1-(tert-Butoxycarbonylamino)ethyl]cyclohexanecarbonyl}-3-cyclohexylpyrrolidine-2-carboxamide]-2-fluorobenzoic acid

[Formula 133]

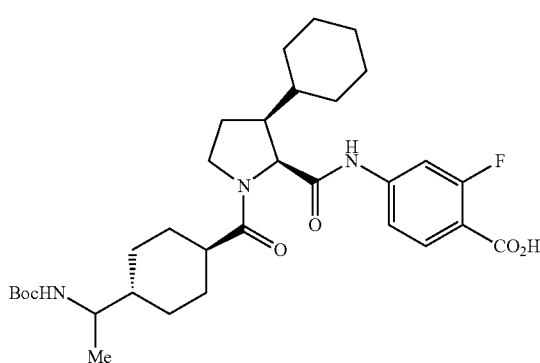

The same procedure as described in Reference Example 3 was carried out to obtain the title compound (69.0 mg, 82%) from the compound of Reference Example 27-3 (85.9 mg, 0.143 mmol).

MS (ESI+) 588 (M+1, 15%)

Reference Example 27-1

Methyl 4-[(2S,3S)-1-tert-butoxycarbonyl-3-cyclohexylpyrrolidine-2-carboxamide]-2-fluorobenzoate

[Formula 134]

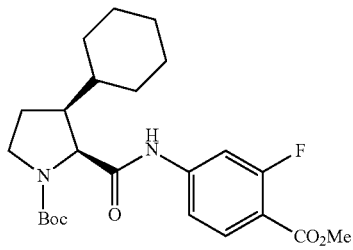

To a solution of the compound of Reference Example 11-1 (358 mg, 1.20 mmol) in dichloromethane (4 mL), oxalyl chloride (113 μL, 1.32 mmol) and DMF (5 μL) were added at 0° C., and the mixture was stirred for 20 minutes. To the reaction solution, a solution of methyl 4-amino-2-fluorobenzoate (105.4 mg, 0.623 mmol) and diisopropylethylamine (310 μL, 1.80 mmol) in dichloromethane (2 mL) was added at 0° C., and the mixture was stirred for 2 hours. A saturated aqueous solution of ammonium chloride was added to the reaction mixture, followed by extraction with ethyl acetate. The organic layer was washed with a saturated saline solution, then dried over magnesium sulfate and filtered, and the filtrate was concentrated under reduced pressure. The obtained residue was purified by silica gel column chromatography to obtain the title compound (83.2 mg, 30%).

MS (ESI+) 449 (M+1, 84%)

Reference Example 27-2

Methyl 4-[(2S,3S)-3-cyclohexylpyrrolidine-2-carboxamide]-2-fluorobenzoate hydrochloride

[Formula 135]

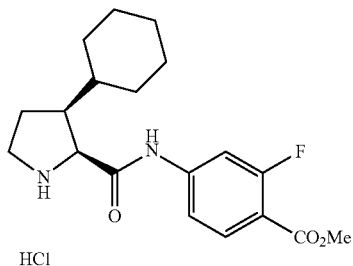

The same procedure as described in Reference Example 1-2 was carried out to obtain the title compound (71 mg, 100%) from the compound of Reference Example 27-1 (83.2 mg, 0.186 mmol).

MS (ESI+) 349 (M+1, 84%)

Reference Example 27-3

Methyl 4-[(2S,3S)-1-{trans-4-[1-(tert-butoxycarbonylamino)ethyl]cyclohexanecarbonyl}-3-cyclohexylpyrrolidine-2-carboxamide]-2-fluorobenzoate

[Formula 136]

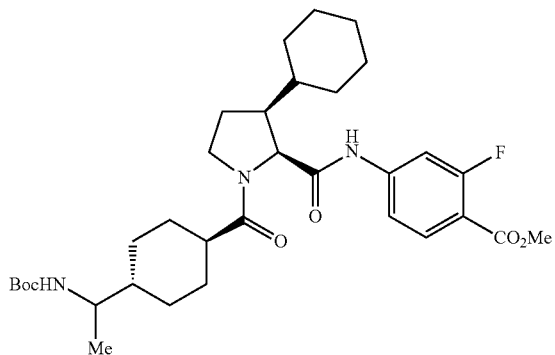

The same procedure as described in Reference Example 1 was carried out to obtain the title compound (85.9 mg, 77%) from the compound of Reference Example 27-2 (71 mg, 0.185 mmol).

MS (ESI+) 602 (M+1, 11%)

Reference Example 28

4-[(2S,3R)-1-{trans-4-[1-(tert-Butoxycarbonylamino)propyl]cyclohexanecarbonyl}-3-phenylpyrrolidine-2-carboxamide]-3-fluorobenzoic acid

[Formula 137]

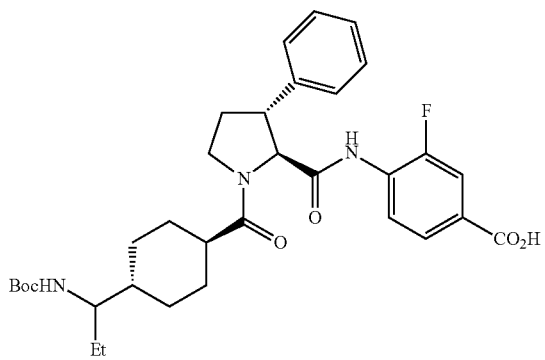

To a solution of the compound of Reference Example 28-3 (32 mg, 0.05 mmol) in methanol (5 mL), a 1 mol/L aqueous solution of sodium hydroxide (2 mL) was added, and the mixture was stirred at 50° C. for 2 hours. A 5% aqueous solution of potassium hydrogensulfate was added to the reaction solution, followed by extraction with chloroform twice. The organic layer was washed with a saturated saline solution, dried over anhydrous sodium sulfate and filtered, and then the organic layer was concentrated under reduced pressure to obtain the title compound (30 mg, 100%).

MS (ESI+) 596 (M+1, 14%)

Reference Example 28-1

Methyl 4-[(2S,3R)-1-tert-butoxycarbonyl-3-phenylpyrrolidine-2-carboxamide]-3-fluorobenzoate

[Formula 138]

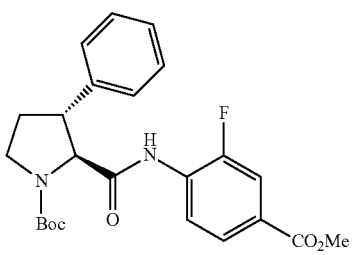

The same procedure as described in Reference Example 1-1 was carried out to obtain the title compound (437 mg, 78%) from the compound of Reference Example 31-4 (400 mg, 1.37 mmol) and methyl 4-amino-3-fluorobenzoate (256 mg, 1.51 mmol).

MS (ESI+) 443 (M+1, 7%)

Reference Example 28-2

Methyl 4-[(2S,3R)-3-phenylpyrrolidine-2-carboxamide]-3-fluorobenzoate trifluoroacetate

[Formula 139]

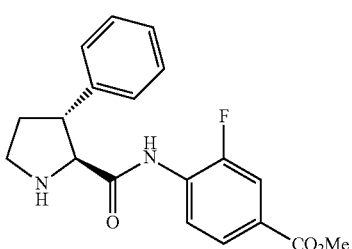

The same procedure as described in Reference Example 9-2 was carried out to obtain the title compound (40 mg, 100%) from the compound of Reference Example 28-1 (40 mg, 0.09 mmol).

MS (ESI+) 343 (M+1, 100%)

Reference Example 28-3

Methyl 4-[(2S,3R)-1-{trans-4-[1-(tert-butoxycarbo-nylamino)propyl]cyclohexanecarbonyl}-3-[phe-nylpyrrolidine]-2-carboxamide]-3-fluorobenzoate

[Formula 140]

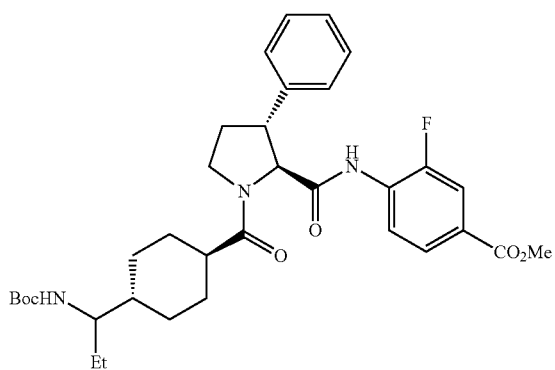

The same procedure as described in Reference Example 1 was carried out to obtain the title compound (32 mg, 60%) from the compound of Reference Example 28-2 (40 mg, 0.09 mmol) and the compound of Reference Example 26-5 (29 mg, 0.10 mmol).

MS (ESI+) 610 (M+1, 21%)

Reference Example 29

5-[(2S,3S)-1-{trans-4-[1-(tert-Butoxycarbonyl)amino-2-fluoroethyl]cyclohexanecarbonyl}-3-cyclohexylpyrrolidine-2-carboxamide]-1-methyl-1H-indole-2-carboxylic acid

[Formula 141]

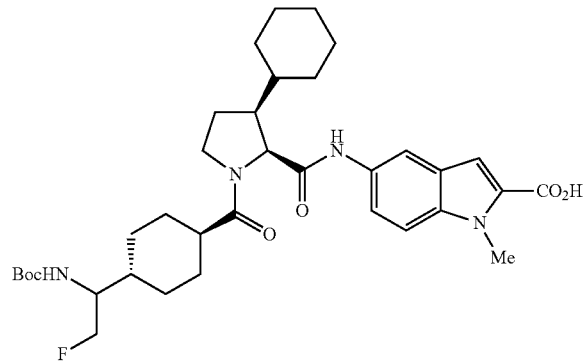

The same procedure as described in Reference Example 28 was carried out to obtain the title compound (44 mg, 92%) from the compound of Reference Example 29-3 (50 mg, 0.08 mmol).

MS (ESI+) 641 (M+1, 100%)

Reference Example 29-1

Ethyl 5-[(2S,3S)-1-tert-butoxycarbonyl-3-cyclohexylpyrrolidine-2-carboxamide]-1-methyl-1H-indole-2-carboxylate

[Formula 142]

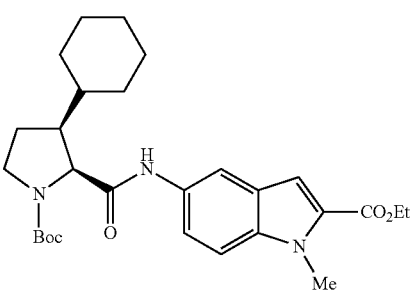

The same procedure as described in Reference Example 1 was carried out to obtain the title compound (120 mg, 57%) from the compound of Reference Example 11-1 (125 mg, 0.42 mmol) and the compound of Reference Example 47-2 (110 mg, 0.50 mmol).

MS (ESI+) 498 (M+1, 100%)

Reference Example 29-2

Ethyl 5-[(2S,3S)-3-cyclohexylpyrrolidine-2-carboxamide]-1-methyl-1H-indole-2-carboxylate trifluoroacetate

[Formula 143]

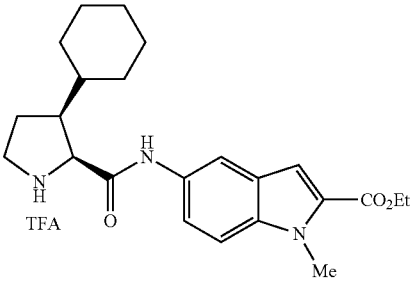

The same procedure as described in Reference Example 9-2 was carried out to obtain the title compound (120 mg, 100%) from the compound of Reference Example 29-1 (120 mg, 0.24 mmol).

MS (ESI+) 398 (M+1, 100%)

Reference Example 29-3

Ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-methyl-1H-indole-2-carboxylate

[Formula 144]

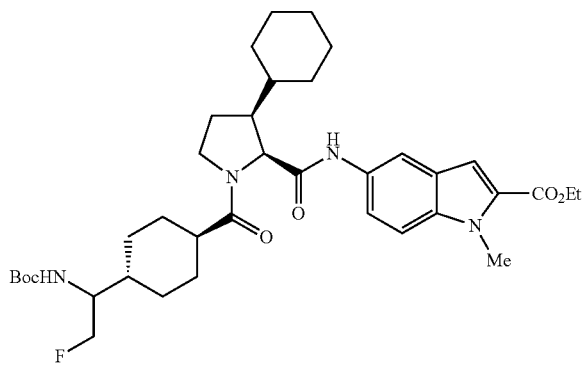

The same procedure as described in Reference Example 1 was carried out to obtain the title compound (151 mg, 94%) from the compound of Reference Example 29-2 (120 mg, 0.24 mmol) and the compound of Reference Example 31-11 (77 mg, 0.27 mmol).

MS (ESI+) 669 (M+1, 21%)

Reference Example 30

5-[(2S,3S)-1-{trans-4-[1-(tert-Butoxycarbonyl)amino-2-fluoroethyl]cyclohexanecarbonyl}-3-phenylpyrrolidine-2-carboxamide]-1-methyl-1H-indole-2-carboxylic acid

[Formula 145]

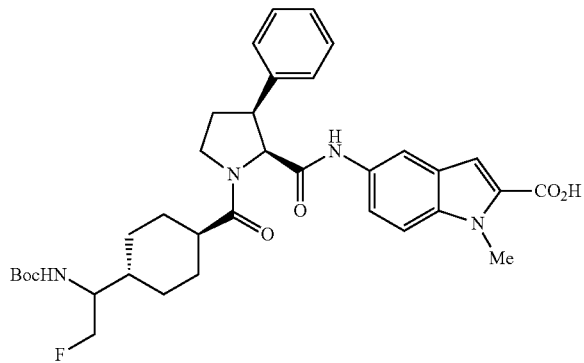

The same procedure as described in Reference Example 28 was carried out to obtain the title compound (40 mg, 100%) from the compound of Reference Example 30-3 (43 mg, 0.06 mmol).

MS (ESI+) 635 (M+1, 100%)

Reference Example 30-1

Ethyl 5-[(2S,3S)-1-tert-butoxycarbonyl-3-phenylpyrrolidine-2-carboxamide]-1-methyl-1H-indole-2-carboxylate

[Formula 146]


To a solution of (2S,3S)-1-tert-butoxycarbonyl-3-phenylpyrrolidine-2-carboxylic acid (112 mg, 0.382 mmol) known from literature (e.g., Org. Lett, 2009, 11, 18, 4056.) in DMF (5 mL), 1-hydroxybenzotriazole (117 mg, 0.764 mmol), WSC.HCl (146 mg, 0.764 mmol), triethylamine (0.16 mL, 1.15 mmol), and the compound of Reference Example 47-2 (100 mg, 0.458 mmol) were added, and the mixture was stirred at 65° C. for 5 hours. After the reaction solution was allowed to cool, a saturated aqueous solution of ammonium chloride was added to the reaction mixture, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (105 mg, 56%).

MS (ESI+) 492 (M+1, 100%)

Reference Example 30-2

Ethyl 5-[(2S,3S)-3-phenylpyrrolidine-2-carboxamide]-1-methyl-1H-indole-2-carboxylate trifluoroacetate

[Formula 147]

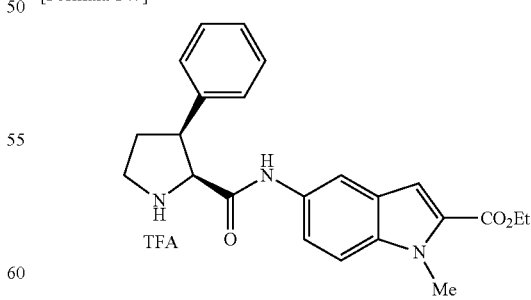

The same procedure as described in Reference Example 9-2 was carried out to obtain the title compound (104 mg, 100%) from the compound of Reference Example 30-1 (105 mg, 0.21 mmol).

MS (ESI+) 392 (M+1, 100%)

Reference Example 30-3

Ethyl 5-[(2S,3S)-1-{trans-4-[1-(tert-butoxycarbonyl)amino-2-fluoroethyl]cyclohexanecarbonyl}-3-phenylpyrrolidine-2-carboxamide]-1-methyl-1H-indole-2-carboxylate

[Formula 148]

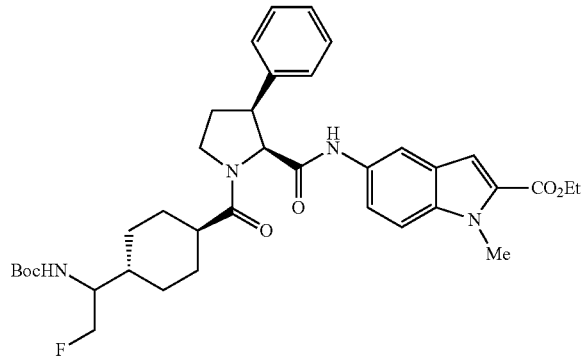

The same procedure as described in Reference Example 1 was carried out to obtain the title compound (118 mg, 83%) from the compound of Reference Example 30-2 (104 mg, 0.21 mmol) and the compound of Reference Example 31-11 (68 mg, 0.24 mmol).

MS (ESI+) 663 (M+1, 100%)

Reference Example 31 tert-Butyl 4-[(2S,3R)-1-{trans-4-[1-(tert-butoxycarbonyl)amino-2-fluoroethyl]cyclohexanecarbonyl}-3-phenylpyrrolidine-2-carboxamide]benzoate

[Formula 149]

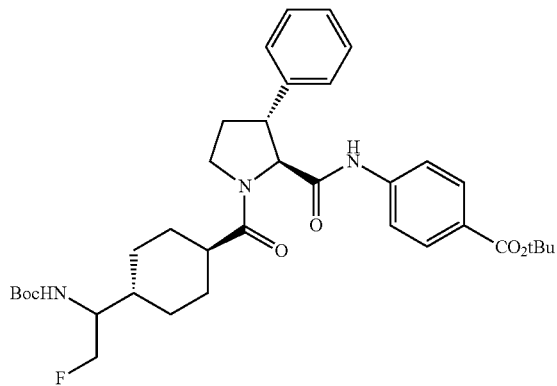

The same procedure as described in Reference Example 1 was carried out to obtain the title compound (188.9 mg, 83%) from the compound of Reference Example 31-11 (104 mg, 0.359 mmol) and the compound of Reference Example 31-6 (203 mg, 0.503 mmol).

MS (ESI+) 638 (M+1, 100%)

Reference Example 31-1 tert-Butyl (2R,3R)-2-(hydroxymethyl)-3-phenylpyrrolidine-1-carboxylate

[Formula 150]

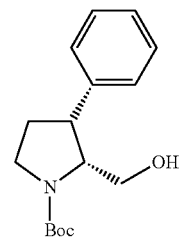

To a solution of trans-cinnamaldehyde (134.2 g, 1.015 mol) in methanol (2 L), (2R)-2-[diphenyl[(trimethylsilyl)oxy]methyl]pyrrolidine (16.5 g, 50.6 mmol), nitroethanol (138.8 g, 1.524 mol), and benzoic acid (12.4 g, 101.5 mmol) were added, and the mixture was stirred at room temperature for 3 days under nitrogen atmosphere. Sodium bicarbonate (424.2 g, 5.05 mol) was added thereto, and the mixture was further stirred for 12 hours. The reaction solution was concentrated under reduced pressure, distilled water was added thereto, followed by extraction with ethyl acetate. The obtained organic layer was dried over sodium sulfate and filtered, and then the filtrate was concentrated under reduced pressure. After the residue was dissolved in a mixed solvent of ethyl acetate and hexane (1:1) under heating at 80° C., the reaction solution was stirred and gradually cooled to room temperature. After 3 hours, the precipitated solid was filtered out to obtain (4R,5R)-4-phenyl-5-nitrotetrahydro-2H-pyran-2-ol (128.68 g, 0.576 mol, >99% ee).

To a solution of (4R,5R)-4-phenyl-5-nitrotetrahydro-2H-pyran-2-ol (15.0 g, 67.0 mmol) in methanol (1.5 L), palladium hydroxide (15.0 g) was added, and the mixture was stirred under hydrogen atmosphere overnight. The reaction solution was filtered through Celite, and the filtrate was concentrated under reduced pressure. The residue was dissolved in acetonitrile (225 mL), di-tert-butyl dicarbonate (21.9 g, 101 mmol) was added, and the mixture was stirred overnight. The reaction solution was concentrated under reduced pressure and then purified by silica gel column chromatography to obtain the title compound (10.2 g, 55%).

MS (ESI+) 278 (M+1, 2.8%)

Reference Example 31-2 tert-Butyl (2R,3R)-2-formyl-3-phenylpyrrolidine-1-carboxylate

[Formula 151]

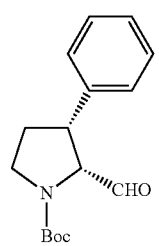

To a solution of the compound of Reference Example 31-1 (20.9 g, 75 mmol) in dichloromethane (200 mL), N-methylmorpholine N-oxide (13.2 g, 113 mmol) and molecular sieves 4 Å (10.5 g) were added, and the mixture was stirred for 10 minutes. Subsequently, tetrapropylammonium perruthenate (1.32 g, 3.75 mmol) was added thereto, and the mixture was stirred overnight. The reaction solution was filtered through silica gel, and the filtrate was concentrated under reduced pressure. The obtained residue was purified by silica gel column chromatography to obtain the title compound (13.7 g, 66%).

MS (ESI+) 276 (M+I, 3.7%)

Reference Example 31-3 tert-Butyl (2S,3R)-2-formyl-3-phenylpyrrolidine-1-carboxylate

[Formula 152]

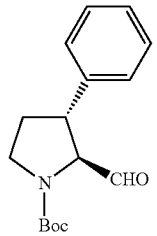

To a solution of the compound of Reference Example 31-2 (13.7 g, 50 mmol) in dichloromethane (170 mL), DBU (7.56 g, 50 mmol) was added, and the mixture was stirred at room temperature overnight. A pH 7 phosphate buffer was added to the reaction mixture, followed by extraction with ethyl acetate. The organic layer was washed with a saturated saline solution, then dried over sodium sulfate and filtered, and the filtrate was concentrated under reduced pressure to obtain the title compound (13.7 g, 100%).

MS (ESI+) 276 (M+I, 5%)

Reference Example 31-4

(2S,3R)-1-tert-Butoxycarbonyl-3-phenylpyrrolidine-2-carboxylic acid

[Formula 153]

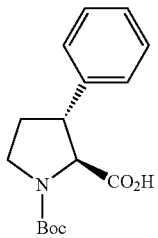

The compound of Reference Example 31-3 (12.45 g, 45.1 mmol) was dissolved in a mixed solvent of tert-butanol and distilled water (3:1, 240 mL), then sodium dihydrogenphosphate dihydrate (21.1 g, 135 mmol), 2-methyl-2-butene (15.8 g, 226 mmol), and sodium chlorite (11.7 g, 90 mmol) were added, and the mixture was stirred for 1 hour. A pH 7 phosphate buffer was added to the reaction solution, followed by extraction with ethyl acetate. The organic layer was dried over sodium sulfate and filtered, and then the filtrate was concentrated under reduced pressure. The obtained residue was recrystallized by using a mixed solution of chloroform/hexane to obtain the title compound (5.3 g, 40%).

MS (ESI+) 292 (M+1, 17%)

Reference Example 31-5 tert-Butyl 4-[(2S,3R)-1-tert-butoxycarbonyl-3-phenylpyrrolidine-2-carboxamide]benzoate

[Formula 154]

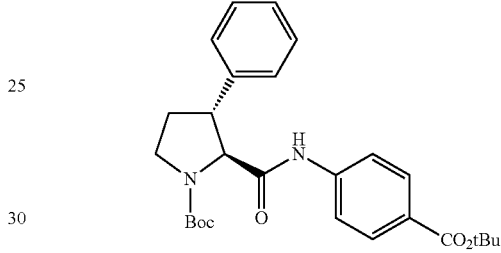

The same procedure as described in Reference Example 1-1 was carried out to obtain the title compound (234.9 mg, 69%) from tert-butyl 4-aminobenzoate (128 mg, 0.662 mmol) and the compound of Reference Example 31-4 (212.2 mg, 0.728 mmol).

MS (ESI+) 467 (M+1, 78%)

Reference Example 31-6 tert-Butyl 4-[(2S,3R)-3-phenylpyrrolidine-2-carboxamide]benzoate hydrochloride

[Formula 155]

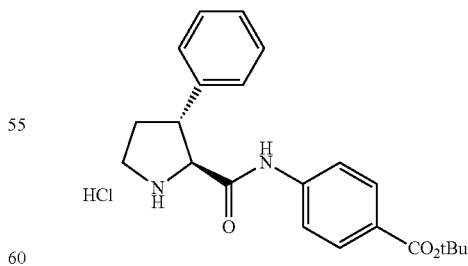

The same procedure as described in Reference Example 1-2 was carried out to obtain the title compound (204 mg, 100%) from the compound of Reference Example 31-5 (234.9 mg, 0.503 mmol).

MS (ESI+) 367 (M+1, 100%)

Reference Example 31-7

Methyl trans-4-(bromoacetyl)cyclohexanecarboxylate

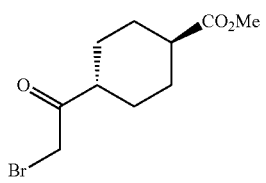

[Formula 156]

To a solution of trans-1,4-cyclohexanedicarboxylic acid monomethyl ester (9.98 g, 53.60 mmol) in dichloromethane (60 mL), oxalyl chloride (10.20 mL, 119 mmol) and DMF (50 µL) were added at room temperature. The reaction solution was heated to reflux for 1 hour, then was allowed to cool to room temperature, and then was concentrated under reduced pressure. Toluene was added to the residue and concentrated under reduced pressure, then THF (30 mL) and acetonitrile (30 mL) were added thereto, and then (trimethylsilyl)diazomethane (32.2 mL, 64.32 mmol) was added dropwise in an ice bath. The reaction mixture was stirred for 1 hour in an ice bath and then further stirred for 1 hour at room temperature. The reaction solution was cooled in an ice bath, then an aqueous solution of 48% hydrobromic acid (11.75 g, 69.7 mmol) was added dropwise, and the mixture was stirred for 15 minutes. A saturated aqueous solution of sodium bicarbonate was added to the reaction mixture, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (7.89 g, 56%).

$^1$H NMR (CDCl$_3$, 300 MHz) δ 3.96 (s, 2H), 3.67 (s, 3H), 2.77-2.69 (m, 1H), 2.32-2.25 (m, 1H), 2.11-1.98 (m, 4H), 1.58-1.40 (m, 4H).

Reference Example 31-8

Methyl trans-4-(fluoroacetyl)cyclohexanecarboxylate

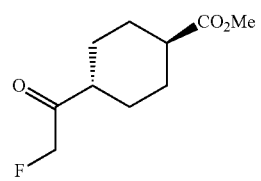

[Formula 157]

To a solution of the compound of Reference Example 31-7 (7.89 g, 30.0 mmol) in acetonitrile (50 mL), potassium fluoride (8.71 g, 150 mmol) and 18-crown-6 (3.96 g, 14.98 mmol) were added. The mixture was heated to reflux for 5 hours, then was allowed to cool, and then a saturated aqueous solution of ammonium chloride was added to the reaction mixture, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (5.29 g, 87%).

$^1$H NMR (CDCl$_3$, 300 MHz) δ 4.96 (s, 1H), 4.80 (s, 1H), 3.67 (s, 3H), 2.69-2.61 (m, 1H), 2.33-2.24 (m, 1H), 2.11-2.07 (m, 2H), 1.99-1.95 (m, 2H), 1.58-1.34 (m, 4H).

Reference Example 31-9

Methyl trans-4-(2-fluoro-1-hydroxyethyl)cyclohexanecarboxylate

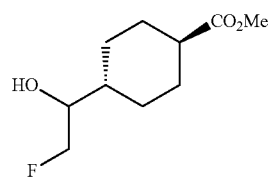

[Formula 158]

To a solution of the compound of Reference Example 31-8 (5.29 g, 26.16 mmol) in methanol (50 mL), sodium borohydride (693 mg, 18.32 mmol) was added in an ice bath, and the mixture was stirred for 45 minutes. A 0.5 mol/L aqueous solution of hydrochloric acid was added to the reaction mixture in an ice bath, followed by extraction with ethyl acetate. The organic layer was washed with a saturated aqueous solution of sodium bicarbonate and a saturated saline solution, then dried over sodium sulfate and filtered, and the filtrate was concentrated under reduced pressure. The obtained residue was purified by silica gel column chromatography to obtain the title compound (4.76 g, 89%).

$^1$H NMR (CDCl$_3$, 400 MHz) δ 4.58-4.55 (m, 0.5H), 4.48-4.23 (m, 1H), 4.36-4.32 (m, 0.5H), 3.66 (s, 3H), 3.65-3.59 (m, 1H), 2.28-2.21 (m, 1H), 2.07-1.96 (m, 3H), 1.78-1.73 (m, 1H), 1.54-1.38 (m, 3H), 1.22-1.12 (m, 2H).

Reference Example 31-10

Methyl trans-4-[1-(tert-butoxycarbonyl)amino-2-fluoroethyl]cyclohexanecarboxylate

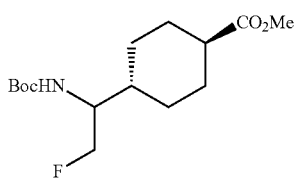

[Formula 159]

To a solution of the compound of Reference Example 31-9 (4.76 g, 23.31 mmol) in THF (50 mL), trimethylamine (4.72 g, 46.65 mmol) and methanesulfonyl chloride (4.00 g, 34.90 mmol) were added in an ice bath. The reaction mixture was stirred for 2 hours at room temperature, then a saturated aqueous solution of ammonium chloride was added, followed by extraction with ethyl acetate. The organic layer was washed with a saturated sodium bicarbonate and a saturated saline solution, then dried over sodium sulfate and filtered, and the filtrate was concentrated under reduced pressure.

The obtained residue was dissolved in DMF (40 mL), then sodium azide (2.27 g, 34.90 mmol) was added. The mixture was stirred for 4 hours at 90° C. and then was allowed to cool, then a saturated aqueous solution of ammonium chloride was added, followed by extraction with ethyl acetate. The organic layer was washed with a saturated aqueous solution of ammonium chloride twice and with a saturated saline solution, then dried over sodium sulfate and filtered, and the filtrate was concentrated under reduced pressure.

The obtained residue was dissolved in THF (40 mL) and water (4 mL), then triphenylphosphine (9.17 g, 34.96 mmol) was added, and then the mixture was heated to reflux. After 3 hours, the reaction solution was allowed to cool, then a saturated aqueous solution of sodium bicarbonate (40 mL) and di-tert-butyl dicarbonate (7.63 g, 34.96 mmol) were added thereto, and the mixture was stirred for 2 hours. Water was added to the reaction solution, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (6.04 g, 85%).

$^1$H NMR (CDCl$_3$, 400 MHz) δ 4.72-4.70 (m, 1H), 4.62-4.59 (m, 0.5H), 4.50-4.47 (m, 1H), 4.38-4.35 (m, 0.5H), 3.66 (s, 3H), 3.65-3.48 (m, 1H), 2.28-2.20 (m, 1H), 2.05-2.02 (m, 2H), 1.94-1.86 (m, 2H), 1.55-1.48 (m, 1H), 1.45-1.42 (m, 10H), 1.40-1.36 (m, 1H), 1.17-1.03 (m, 2H).

Reference Example 31-11 trans-4-[1-(tert-Butoxycarbonyl)amino-2-fluoro-ethyl]cyclohexanecarboxylic acid

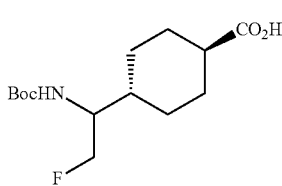

[Formula 160]

The compound of Reference Example 31-10 (11.94 g, 39.36 mmol) was dissolved in methanol (115 mL) and THF (115 mL), then a 1 mol/L aqueous solution of sodium hydroxide (115 mL) was added thereto, and the mixture was stirred at room temperature for 6 hours. A 5% aqueous solution of potassium hydrogensulfate was added to the reaction solution, followed by extraction with chloroform. The organic layer was dried over anhydrous sodium sulfate and filtered, and then the organic layer was concentrated under reduced pressure to obtain the title compound (11.21 g, 98%).

$^1$H NMR (DMSO-d$_6$, 300 MHz) δ 6.87 (m, 1H), 4.48-4.37 (m, 1H), 4.32-4.21 (m, 1H), 3.45-3.34 (m, 1H), 2.11-2.03 (m, 1H), 1.89-1.86 (m, 2H), 1.71-1.67 (m, 2H), 1.37-1.30 (m, 10H), 1.23-1.17 (m, 2H), 1.13-0.95 (m, 2H).

Reference Example 32

5-[(2S,3S)-1-{trans-4-[1-(tert-Butoxycarbonyl)amino-2-fluoroethyl]cyclohexanecarbonyl}-3-(4-methoxycyclohexyl)pyrrolidine-2-carboxamide]-1-methyl-1H-indole-2-carboxylic acid

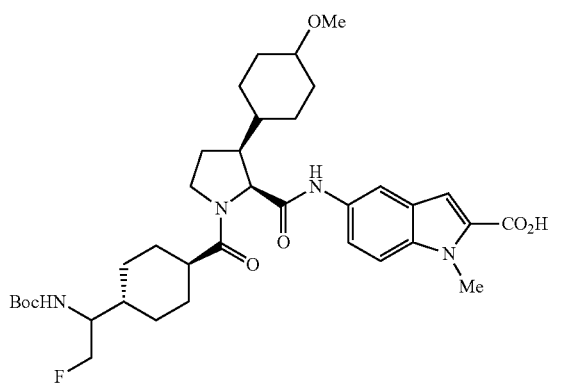

[Formula 161]

The same procedure as described in Reference Example 28 was carried out to obtain the title compound (15 mg, 52%) from the compound of Reference Example 32-6 (30 mg, 0.04 mmol).

MS (ESI+) 671 (M+1, 100%)

Reference Example 32-1 tert-Butyl (2S,3S)-2-(hydroxymethyl)-3-(4-methoxyphenyl)pyrrolidine-1-carboxylate

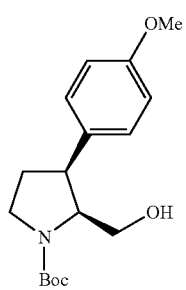

[Formula 162]

By using (2S)-2-[diphenyl[(trimethylsilyl)oxy]methyl]pyrrolidine (488 mg, 2.12 mmol) as the catalyst, the same procedure as described in Reference Example 31-1 was carried out to obtain the title compound (3.9 g, 60%) from trans-p-methoxycinnamaldehyde (3.43 g, 21.15 mol).

MS (ESI+) 308 (M+1, 100%)

Reference Example 32-2 tert-Butyl (2S,3S)-2-formyl-3-(4-methoxyphenyl)pyrrolidine-1-carboxylate

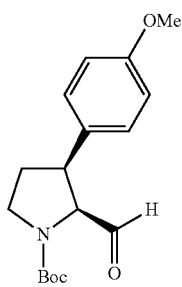

[Formula 163]

To a solution of the compound of Reference Example 32-1 (600 mg, 1.95 mmol) in acetonitrile (10 mL), N-methylmorpholine N-oxide (343 mg, 2.93 mmol) and molecular sieves 4 Å (300 mg) were added, and the mixture was stirred for 10 minutes. Subsequently, tetrapropylammonium perruthenate (206 mg, 0.58 mmol) was added, and the mixture was stirred at room temperature for 2 hours. The reaction solution was filtered through Celite, and the filtrate was concentrated under reduced pressure. The obtained residue was purified by silica gel column chromatography to obtain the title compound (570 mg, 96%).

MS (ESI+) 306 (M+1, 7%)

Reference Example 32-3

(2S,3S)-1-tert-Butoxycarbonyl-3-(4-methoxyphenyl)pyrrolidine-2-carboxylic acid

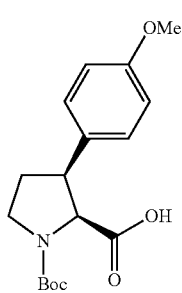

[Formula 164]

The compound of Reference Example 32-2 (570 mg, 1.87 mmol) was dissolved in a mixed solvent of tert-butanol and distilled water (3:1, 8.5 mL), then sodium dihydrogenphosphate dihydrate (875 mg, 5.61 mmol), 2-methyl-2-butene (1 mL, 9.35 mmol), and sodium chlorite (428 mg, 3.74 mmol) were added thereto, and the mixture was stirred at room temperature for 4 hours. A 1 mol/L aqueous solution of sodium hydroxide (5 mL) was added to the reaction solution, and the mixture was stirred for several minutes, before washing with ethyl acetate. A 5% aqueous solution of potassium hydrogensulfate was added to the aqueous layer, followed by extraction with chloroform twice. The organic layer was washed with a saturated saline solution, then dried over sodium sulfate and filtered, and the filtrate was concentrated under reduced pressure to obtain the title compound (540 mg, 90%).

MS (ESI+) 322 (M+1, 7%)

Reference Example 32-4

Ethyl 5-[(2S,3S)-1-tert-butoxycarbonyl-3-(4-methoxyphenyl)pyrrolidine-2-carboxamide]-1-methyl-1H-indole-2-carboxylate

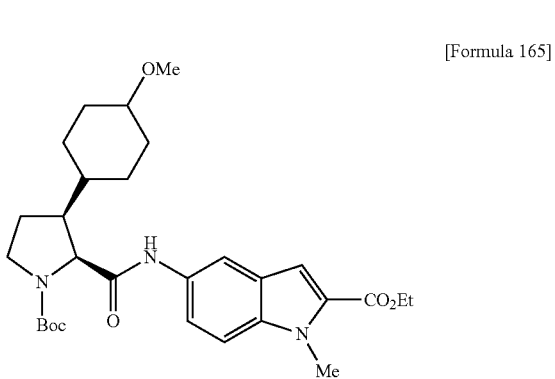 [SMILES: CCOC(=O)c1cc2cc(NC(=O)[C@@H]3[C@H](C4CCC(OC)CC4)CCN3C(=O)OC(C)(C)C)ccc2n1C]

[Formula 165]

The same procedure as described in Reference Example 11-1 was carried out to obtain a crude product (128 mg) from the compound of Reference Example 32-3 (138 mg, 0.391 mmol). The same procedure as described in Reference Example 30-1 was carried out to obtain the title compound (45 mg, 43%) from the obtained crude product and the compound of Reference Example 47-2 (59 mg, 0.25 mmol).

MS (ESI+) 528 (M+1, 100%)

Reference Example 32-5

Ethyl 5-[(2S,3S)-1-tert-butoxycarbonyl-3-(4-methoxyphenyl)pyrrolidine-2-carboxamide]-1-methyl-1H-indole-2-carboxylate trifluoroacetate

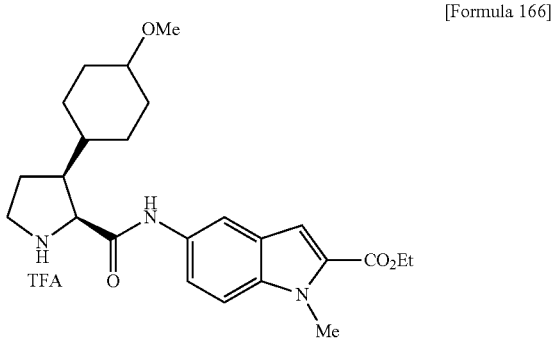 [SMILES: CCOC(=O)c1cc2cc(NC(=O)[C@H]3NCC[C@H]3C3CCC(OC)CC3)ccc2n1C]

[Formula 166]

The same procedure as described in Reference Example 9-2 was carried out to obtain the title compound (45 mg, 100%) from the compound of Reference Example 32-4 (45 mg, 0.09 mmol).

MS (ESI+) 428 (M+1, 100%)

Reference Example 32-6

Ethyl 5-[(2S,3S)-1-{trans-4-[1-(tert-butoxycarbonyl)amino-2-fluoroethyl]cyclohexanecarbonyl}-3-(4-methoxycyclohexyl)pyrrolidine-2-carboxamide]-1-methyl-1H-indole-2-carboxylate

[Formula 167]

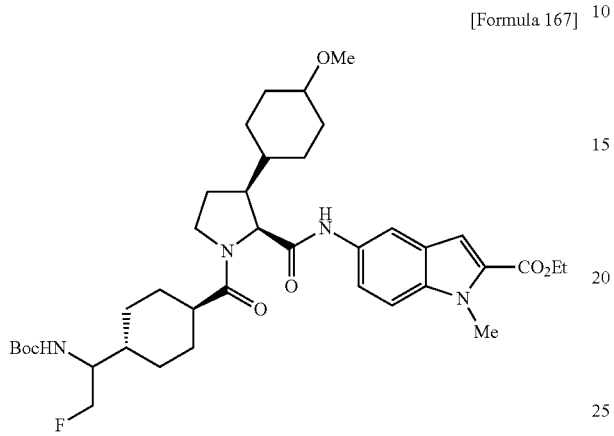

The same procedure as described in Reference Example 1 was carried out to obtain the title compound (42 mg, 71%) from the compound of Reference Example 32-5 (45 mg, 0.09 mmol) and the compound of Reference Example 31-11 (32 mg, 0.11 mmol).

MS (ESI+) 699 (M+1, 100%)

Reference Example 33

5-[(2S,3S)-1-{trans-4-[1-(tert-Butoxycarbonyl)amino-2-fluoroethyl]cyclohexanecarbonyl}-3-(4-methoxycyclohexyl)pyrrolidine-2-carboxamide]-1-benzofuran-2-carboxylic acid

[Formula 168]

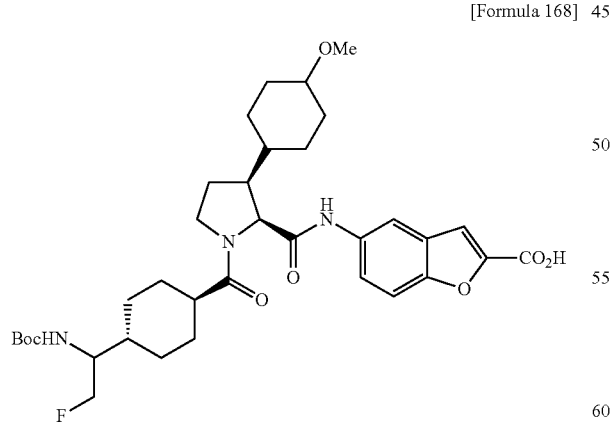

The same procedure as described in Reference Example 28 was carried out to obtain the title compound (30 mg, 97%) from the compound of Reference Example 33-3 (32 mg, 0.06 mmol).

MS (ESI+) 658 (M+1, 100%)

Reference Example 33-1

Ethyl 5-[(2S,3S)-1-tert-butoxycarbonyl-3-(4-methoxyphenyl)pyrrolidine-2-carboxamide]-1-benzofuran-2-carboxylate

[Formula 169]

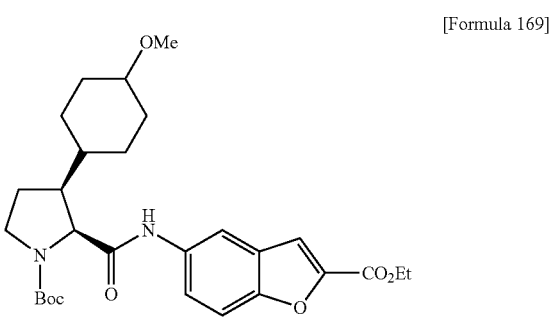 [SMILES: CCOC(=O)c1cc2cc(NC(=O)[C@@H]3[C@H](C4CCC(OC)CC4)CCN3C(=O)OC(C)(C)C)ccc2o1]

The same procedure as described in Reference Example 30-1 was carried out to obtain the title compound (32 mg, 11%) from ethyl 5-amino-1-benzofuran-2-carboxylate (141 mg, 0.69 mmol).

MS (ESI+) 515 (M+1, 100%)

Reference Example 33-2

Ethyl 5-[(2S,3S)-3-(4-methoxyphenyl)pyrrolidine-2-carboxamide]-1-benzofuran-2-carboxylate trifluoroacetate

[Formula 170]

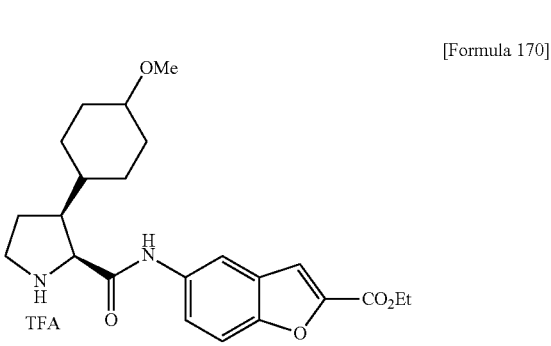 [SMILES: CCOC(=O)c1cc2cc(NC(=O)[C@H]3NCC[C@H]3C3CCC(OC)CC3)ccc2o1]

The same procedure as described in Reference Example 9-2 was carried out to obtain the title compound (32 mg, 100%) from the compound of Reference Example 33-1 (32 mg, 0.06 mmol).

MS (ESI+) 415 (M+1, 100%)

Reference Example 33-3

Ethyl 5-[(2S,3S)-1-{trans-4-[1-(tert-butoxycarbonyl)amino-2-fluoroethyl]cyclohexanecarbonyl}-3-(4-methoxycyclohexyl)pyrrolidine-2-carboxamide]-1-benzofuran-2-carboxylate

[Formula 171]

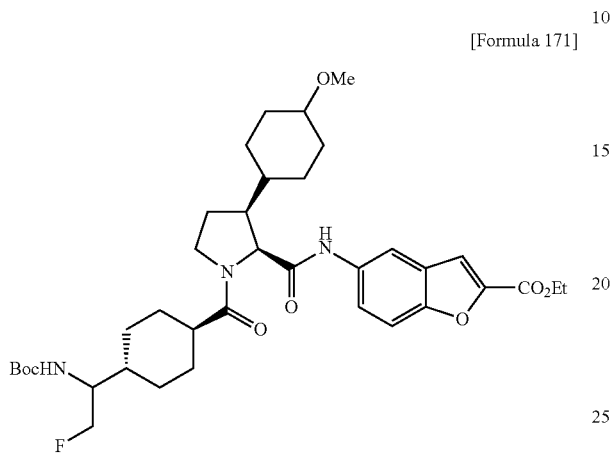

The same procedure as described in Reference Example 1 was carried out to obtain the title compound (32 mg, 78%) from the compound of Reference Example 33-2 (32 mg, 0.06 mmol) and the compound of Reference Example 31-11 (22 mg, 0.08 mmol).

MS (ESI+) 686 (M+1, 100%)

Reference Example 34

5-[(2S,3S)-1-{trans-4-[1-(tert-Butoxycarbonyl)amino-2-fluoroethyl]cyclohexanecarbonyl}-3-cyclohexylpyrrolidine-2-carboxamide]-3-chloro-1H-indole-2-carboxylic acid

[Formula 172]

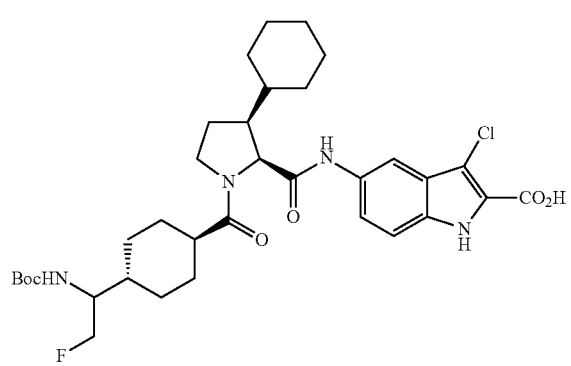

The same procedure as described in Reference Example 28 was carried out to obtain the title compound (26 mg, 97%) from the compound of Reference Example 34-4 (30 mg, 0.04 mmol).

MS (ESI+) 661 (M+1, 100%)

Reference Example 34-1

Ethyl 5-[(2S,3S)-1-tert-butoxycarbonyl-3-cyclohexylpyrrolidine-2-carboxamide]-1H-indole-2-carboxylate

[Formula 173]

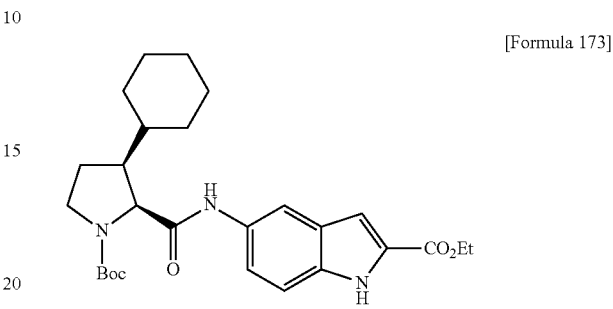

The same procedure as described in Reference Example 1 was carried out to obtain the title compound (300 mg, 70%) from the compound of Reference Example 11-1 (265 mg, 0.89 mmol) and the compound of Reference Example 2-1 (200 mg, 0.98 mmol).

MS (ESI+) 484 (M+1, 100%)

Reference Example 34-2

Ethyl 5-[(2S,3S)-1-tert-butoxycarbonyl-3-cyclohexylpyrrolidine-2-carboxamide]-3-chloro-1H-indole-2-carboxylate

[Formula 174]

[Formula 174]

To a solution of the compound of Reference Example 34-1 (100 mg, 0.207 mmol) in DMF (3 mL), N-chlorosuccinimide (28 mg, 0.209 mmol) was added, and the mixture was stirred at 60° C. for 24 hours. The reaction solution was allowed to cool, then water was added thereto, followed by extraction with ethyl acetate. The organic layer was washed with a saturated saline solution, then dried over sodium sulfate and filtered, and the filtrate was concentrated under reduced pressure to obtain the title compound (108 mg, 100%).

MS (ESI+) 518 (M+1, 100%)

Reference Example 34-3

Ethyl 5-[(2S,3S)-3-cyclohexylpyrrolidine-2-carboxamide]-3-chloro-1H-indole-2-carboxylate trifluoroacetate

[Formula 175]

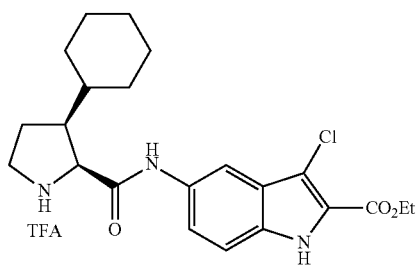

The same procedure as described in Reference Example 9-2 was carried out to obtain the title compound (69 mg, 100%) from the compound of Reference Example 34-2 (70 mg, 0.135 mmol).

MS (ESI+) 418 (M+1, 100%)

Reference Example 34-4

Ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-3-chloro-1H-indole-2-carboxylate

[Formula 176]

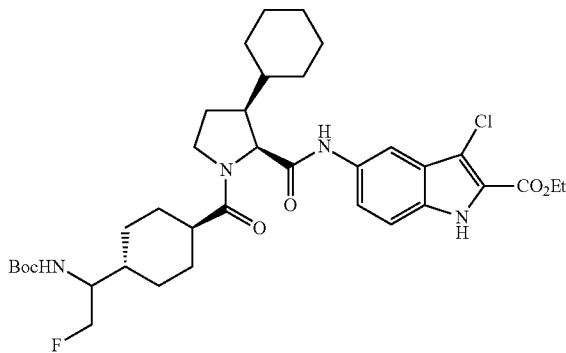

The same procedure as described in Reference Example 1 was carried out to obtain the title compound (72 mg, 78%) from the compound of Reference Example 34-3 (69 mg, 0.134 mmol) and the compound of Reference Example 31-11 (47 mg, 0.16 mmol).

MS (ESI+) 686 (M+1, 100%)

Reference Example 35

5-[(2S,3S)-1-{trans-4-[1-(tert-Butoxycarbonyl)amino-2-fluoroethyl]cyclohexanecarbonyl}-3-cyclohexylpyrrolidine-2-carboxamide]-1H-indole-2-carboxylic acid

[Formula 177]

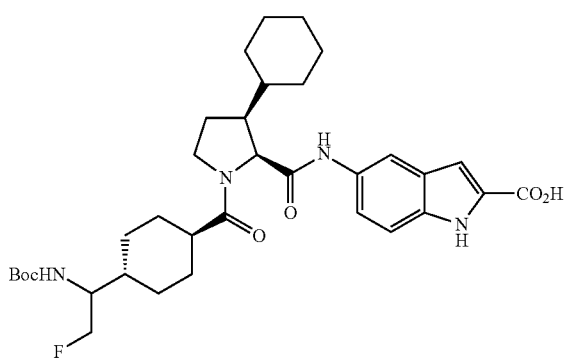

The same procedure as described in Reference Example 28 was carried out to obtain the title compound (60 mg, 98%) from the compound of Reference Example 35-2 (64 mg, 0.098 mmol).

MS (ESI+) 627 (M+1, 100%)

Reference Example 35-1

Ethyl 5-[(2S,3S)-3-cyclohexylpyrrolidine-2-carboxamide]-1H-indole-2-carboxylate trifluoroacetate

[Formula 178]

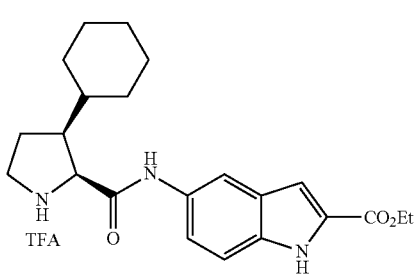

The same procedure as described in Reference Example 9-2 was carried out to obtain the title compound (128 mg, 100%) from the compound of Reference Example 34-1 (130 mg, 0.27 mmol).

MS (ESI+) 384 (M+1, 100%)

Reference Example 35-2

Ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1H-indole-2-carboxylate

[Formula 179]

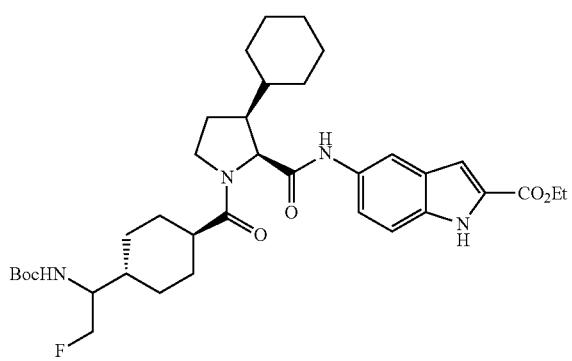

The same procedure as described in Reference Example 1 was carried out to obtain the title compound (128 mg, 72%) from the compound of Reference Example 35-1 (128 mg, 0.27 mmol) and the compound of Reference Example 31-11 (93 mg, 0.32 mmol).

MS (ESI+) 655 (M+1, 100%)

Reference Example 36 tert-Butyl 5-[(2S,3S)-1-{trans-4-[1-(tert-butoxycarbonyl)amino-2-fluoroethyl]cyclohexanecarbonyl}-3-(4-methoxyphenyl)pyrrolidine-2-carboxamide]-1-benzofuran-2-carboxylate

[Formula 180]

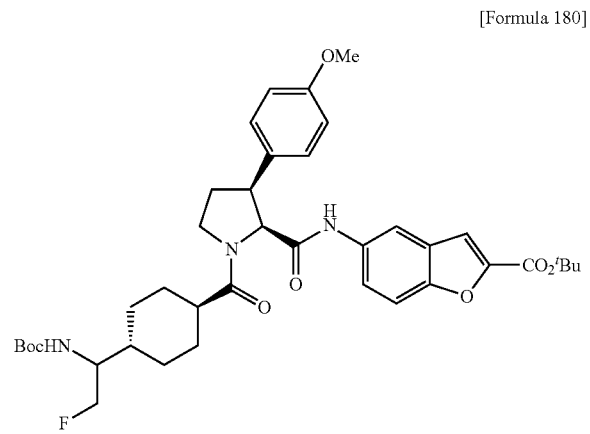 [SMILES: COc1ccc([C@@H]2CCN(C(=O)[C@H]3CC[C@H](C(CF)NC(=O)OC(C)(C)C)CC3)[C@@H]2C(=O)Nc2ccc3oc(C(=O)OC(C)(C)C)cc3c2)cc1]

The same procedure as described in Reference Example 1 was carried out to obtain the title compound (43 mg, 65%) from the compound of Reference Example 36-4 (50 mg, 0.093 mmol) and the compound of Reference Example 31-11 (33 mg, 0.112 mmol).

MS (ESI+) 708 (M+1, 100%)

Reference Example 36-1 tert-Butyl 5-nitro-1-benzofuran-2-carboxylate

[Formula 181]

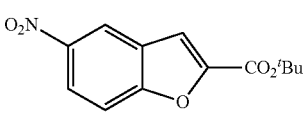

Ethyl 5-nitro-1-benzofuran-2-carboxylate (2.0 g, 8.54 mmol) was suspended in a mixed solvent of methanol (3.2 mL) and THF (3.2 mL), then a 4 mol/L aqueous solution of sodium hydroxide (3.2 mL) was added thereto, and the mixture was stirred at 70° C. for 1 hour. A 1 mol/L aqueous solution of hydrochloric acid was added to the reaction solution, followed by extraction with ethyl acetate twice. The organic layer was washed with a saturated saline solution, dried over anhydrous sodium sulfate and filtered, and then the solvent was concentrated under reduced pressure to obtain a crude product. The obtained crude product was dissolved in DMF (20 mL), then 1,1-di-tert-butoxy-N,N-dimethylmethaneamide (13.9 g, 68.32 mmol) was added, and the mixture was stirred at 80° C. for 11 hours. Water was added to the reaction solution, followed by extraction with ethyl acetate. The organic layer was washed with a saturated saline solution, dried over anhydrous sodium sulfate and filtered, and then the organic layer was concentrated under reduced pressure to obtain a crude product. Chloroform (10 mL) was added to the obtained crude product, and the crystal was filtered out to obtain the title compound (1.76 g, 78%).

$^1$H NMR (CDCl$_3$, 300 MHz) δ 12.43 (s, 1H), 8.13-8.11 (m, 1H), 7.61-7.59 (m, 1H), 7.34 (s, 1H), 2.11-1.98 (m, 4H), 1.64-1.59 (m, 9H).

Reference Example 36-2 tert-Butyl 5-amino-1-benzofuran-2-carboxylate

[Formula 182]

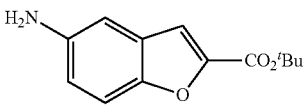

To a solution of the compound of Reference Example 36-1 (1.76 g, 6.69 mmol) in methanol (15 mL), palladium-carbon (500 mg) was added, and the mixture was stirred for 5.5 hours under hydrogen atmosphere. The reaction solution was filtered through Celite, and the filtrate was concentrated under reduced pressure to obtain the title compound (1.45 g, 93%).

MS (ESI+) 234 (M+1, 100%)

Reference Example 36-3 tert-Butyl 5-[(2S,3S)-1-tert-butoxycarbonyl-3-(4-methoxyphenyl)pyrrolidine-2-carboxamide]-1-benzofuran-2-carboxylate

[Formula 183]

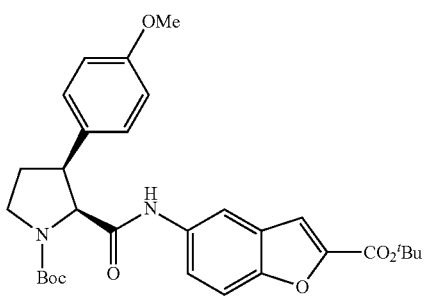

The same procedure as described in Reference Example 30-1 was carried out to obtain the title compound (54 mg, 28%) from the compound of Reference Example 32-3 (115 mg, 0.357 mmol) and the compound of Reference Example 36-2 (100 mg, 0.429 mmol).
MS (ESI+) 537 (M+1, 100%)

Reference Example 36-4 tert-Butyl 5-[(2S,3S)-3-(4-methoxyphenyl)pyrrolidine-2-carboxamide]-1-benzofuran-2-carboxylate hydrochloride

[Formula 184]

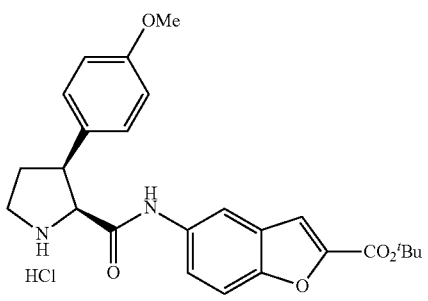

The same procedure as described in Reference Example 1-2 was carried out to obtain the title compound (47 mg, 100%) from the compound of Reference Example 36-3 (54 mg, 0.10 mmol).
MS (ESI+) 437 (M+1, 100%)

Reference Example 37

5-[(2S,3S)-1-{trans-4-[1-(tert-Butoxycarbonyl)amino-2-fluoroethyl]cyclohexanecarbonyl}-3-(4-fluorophenyl)pyrrolidine-2-carboxamide]-1-benzofuran-2-carboxylic acid

[Formula 185]

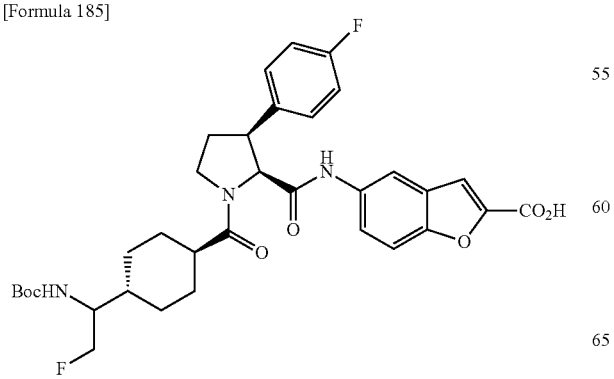

The same procedure as described in Reference Example 28 was carried out to obtain the title compound (45 mg, 47%) from the compound of Reference Example 37-6 (100 mg, 0.150 mmol).
MS (ESI+) 640 (M+1, 100%)

Reference Example 37-1 tert-Butyl (2S,3S)-3-(4-fluorophenyl)-2-(hydroxymethyl)pyrrolidine-1-carboxylate

[Formula 186]

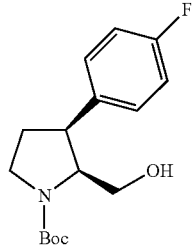

By using (2S)-2-[diphenyl[(trimethylsilyl)oxy]methyl]pyrrolidine (774 mg, 3.33 mmol) as the catalyst, the same procedure as described in Reference Example 31-1 was carried out to obtain the title compound (4.0 g, 41%) from trans-p-fluorocinnamaldehyde (5.0 g, 33.3 mmol).
MS (ESI+) 296 (M+1, 100%)

Reference Example 37-2 tert-Butyl (2S,3S)-3-(4-fluorophenyl)-2-formylpyrrolidine-1-carboxylate

[Formula 187]

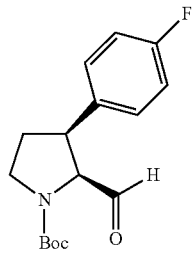

The same procedure as described in Reference Example 31-2 was carried out to obtain the title compound (2.7 g, 71%) from the compound of Reference Example 37-1 (3.82 g, 12.9 mmol).
MS (ESI+) 294 (M+1, 7%)

Reference Example 37-3

(2S,3S)-1-tert-Butoxycarbonyl-3-(4-fluorophenyl)pyrrolidine-2-carboxylic acid

[Formula 188]

The same procedure as described in Reference Example 31-4 was carried out to obtain the title compound (2.6 g, 91%) from the compound of Reference Example 37-2 (2.7 g, 9.2 mmol).

MS (ESI+) 310 (M+1, 5%)

Reference Example 37-4

Ethyl 5-[(2S,3S)-1-tert-butoxycarbonyl-3-(4-fluorophenyl)pyrrolidine-2-carboxamide]-1-benzofuran-2-carboxylate

[Formula 189]

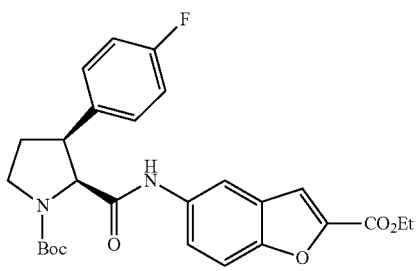

The same procedure as described in Reference Example 1-1 was carried out to obtain the title compound (210 mg, 44%) from the compound of Reference Example 37-3 (300 mg, 0.97 mmol) and ethyl 5-amino-1-benzofuran-2-carboxylate (219 mg, 1.07 mmol).

MS (ESI+) 497 (M+1, 100%)

Reference Example 37-5

Ethyl 5-[(2S,3S)-3-(4-fluorophenyl)pyrrolidine-2-carboxamide]-1-benzofuran-2-carboxylate trifluoroacetate

[Formula 190]

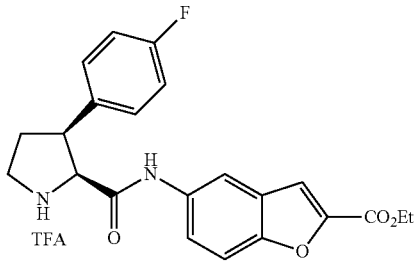

The same procedure as described in Reference Example 9-2 was carried out to obtain the title compound (209 mg, 100%) from the compound of Reference Example 37-4 (210 mg, 0.423 mmol).

MS (ESI+) 397 (M+1, 100%)

Reference Example 37-6

Ethyl 5-[(2S,3S)-1-{trans-4-[1-(tert-butoxycarbonyl)amino-2-fluoroethyl]cyclohexanecarbonyl}-3-(4-fluorophenyl)pyrrolidine-2-carboxamide]-1-benzofuran-2-carboxylate

[Formula 191]

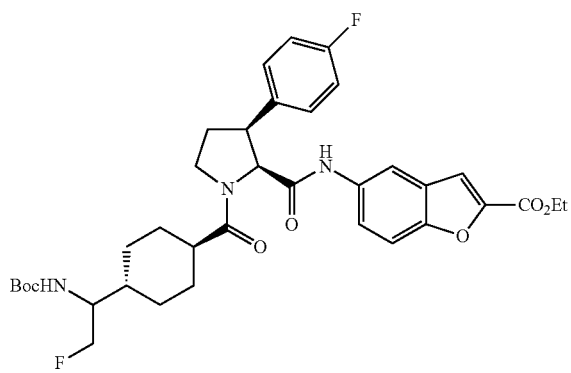

The same procedure as described in Reference Example 1 was carried out to obtain the title compound (205 mg, 73%) from the compound of Reference Example 37-5 (209 mg, 0.423 mmol) and the compound of Reference Example 31-11 (147 mg, 0.508 mmol).

MS (ESI+) 668 (M+1, 100%)

Reference Example 38

5-[(2S,3S)-1-{trans-4-[1-(tert-Butoxycarbonyl)amino-2-fluoroethyl]cyclohexanecarbonyl}-3-(4-fluorophenyl)pyrrolidine-2-carboxamide]-1H-indole-2-carboxylic acid

[Formula 192]

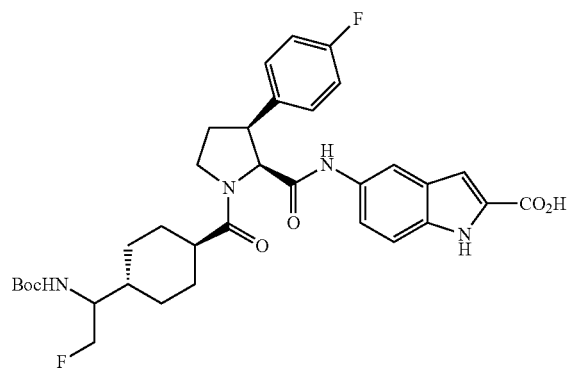

The same procedure as described in Reference Example 28 was carried out to obtain the title compound (41 mg, 86%) from the compound of Reference Example 38-3 (50 mg, 0.075 mmol).

MS (ESI+) 639 (M+1, 100%)

Reference Example 38-1

Ethyl 5-[(2S,3S)-1-tert-butoxycarbonyl-3-(4-fluorophenyl)pyrrolidine-2-carboxamide]-1H-indole-2-carboxylate

[Formula 193]

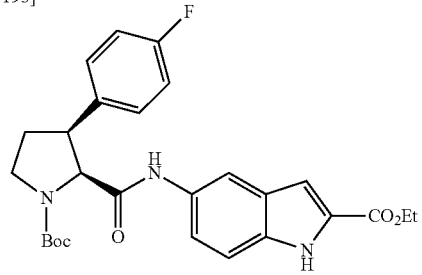

The same procedure as described in Reference Example 1 was carried out to obtain the title compound (308 mg, 64%) from the compound of Reference Example 37-3 (300 mg, 0.97 mmol) and the compound of Reference Example 2-1 (238 mg, 0.98 mmol).
MS (ESI+) 496 (M+1, 100%)

Reference Example 38-2

Ethyl 5-[(2S,3S)-3-(4-fluorophenyl)pyrrolidine-2-carboxamide]-1H-indole-2-carboxylate trifluoroacetate

[Formula 194]

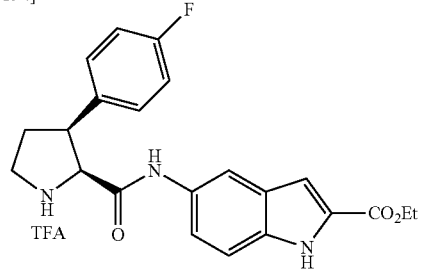

The same procedure as described in Reference Example 9-2 was carried out to obtain the title compound (199 mg, 100%) from the compound of Reference Example 38-1 (200 mg, 0.404 mmol).
MS (ESI+) 396 (M+1, 100%)

Reference Example 38-3

Ethyl 5-[(2S,3S)-1-{trans-4-[1-(tert-butoxycarbonyl)amino-2-fluoroethyl]cyclohexanecarbonyl}-3-(4-fluorophenyl)pyrrolidine-2-carboxamide]-1H-indole-2-carboxylate

[Formula 195]

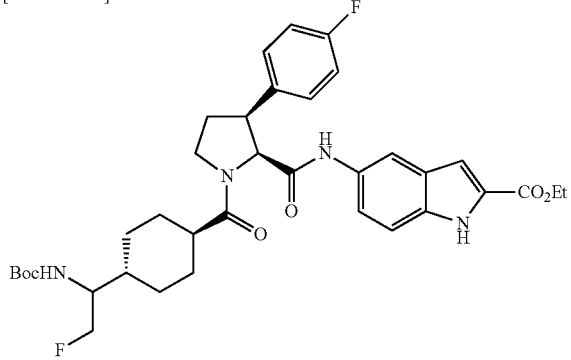

The same procedure as described in Reference Example 1 was carried out to obtain the title compound (153 mg, 57%) from the compound of Reference Example 38-2 (199 mg, 0.404 mmol) and the compound of Reference Example 31-11 (140 mg, 0.484 mmol).
MS (ESI+) 667 (M+1, 100%)

Reference Example 39

5-[(2S,3S)-1-{trans-4-[1-(tert-Butoxycarbonyl)amino-2-fluoroethyl]cyclohexanecarbonyl}-3-cyclohexylpyrrolidine-2-carboxamide]-3-methyl-1H-indole-2-carboxylic acid

[Formula 196]

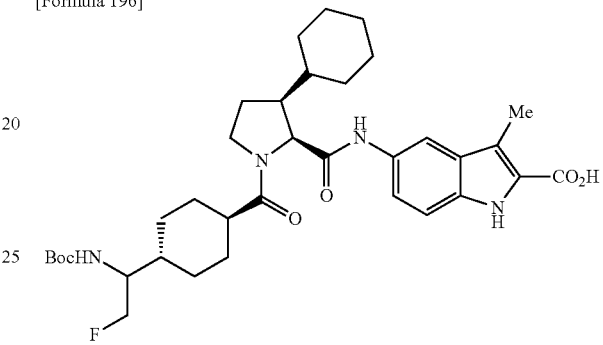

The same procedure as described in Reference Example 28 was carried out to obtain the title compound (44 mg, 92%) from the compound of Reference Example 39-5 (50 mg, 0.075 mmol).
MS (ESI+) 641 (M+1, 100%)

Reference Example 39-1

Ethyl 3-methyl-5-nitro-1H-indole-2-carboxylate

[Formula 197]

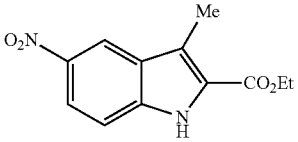

To a solution of 3-methyl-5-nitro-1H-indole-2-carboxylic acid (400 mg, 1.82 mmol) in DMF (5 mL), potassium carbonate (755 mg, 5.46 mmol) and ethyl iodide (284 mg, 2.20 mmol) were added, and the mixture was stirred at room temperature for 6 hours. Water was added to the reaction solution, followed by extraction with ethyl acetate twice. The organic layer was washed with a saturated saline solution, dried over anhydrous sodium sulfate and filtered, and then the organic layer was concentrated under reduced pressure to obtain the title compound (440 mg, 100%).
MS (ESI−) 247 (M−1, 97%)

Reference Example 39-2

Ethyl 5-amino-3-methyl-1H-indole-2-carboxylate

[Formula 198]

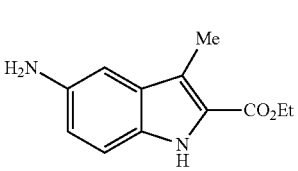

The same procedure as described in Reference Example 36-2 was carried out to obtain the title compound (355 mg, 92%) from the compound of Reference Example 39-1 (440 mg, 1.77 mmol).

MS (ESI+) 219 (M+1, 100%)

Reference Example 39-3

Ethyl 5-[(2S,3S)-1-tert-butoxycarbonyl-3-cyclohexylpyrrolidine-2-carboxamide]-3-methyl-1H-indole-2-carboxylate

[Formula 199]

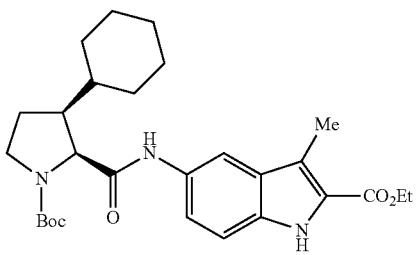

The same procedure as described in Reference Example 1 was carried out to obtain the title compound (305 mg, 80%) from the compound of Reference Example 11-1 (227 mg, 0.764 mmol) and the compound of Reference Example 39-2 (200 mg, 0.916 mmol).

MS (ESI+) 498 (M+1, 100%)

Reference Example 39-4

Ethyl 5-[(2S,3S)-3-cyclohexylpyrrolidine-2-carboxamide]-3-methyl-1H-indole-2-carboxylate trifluoroacetate

[Formula 200]

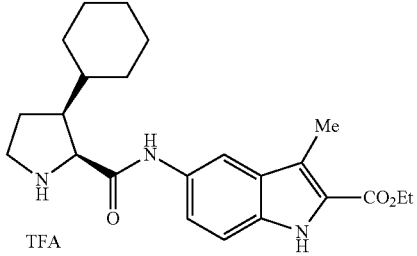

The same procedure as described in Reference Example 9-2 was carried out to obtain the title compound (119 mg, 100%) from the compound of Reference Example 39-3 (200 mg, 0.241 mmol).

MS (ESI+) 398 (M+1, 100%)

Reference Example 39-5

Ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-3-methyl-1H-indole-2-carboxylate

[Formula 201]

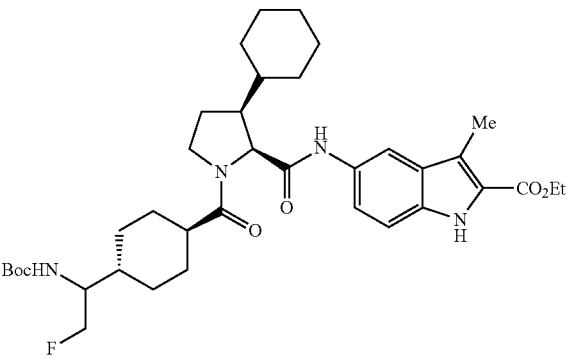

The same procedure as described in Reference Example 1 was carried out to obtain the title compound (98 mg, 61%) from the compound of Reference Example 39-4 (119 mg, 0.241 mmol) and the compound of Reference Example 31-11 (84 mg, 0.289 mmol).

MS (ESI+) 669 (M+1, 100%)

Reference Example 40

5-[(2S,3S)-1-{trans-4-[1-(tert-Butoxycarbonyl)amino-2-fluoroethyl]cyclohexanecarbonyl}-3-cyclohexylpyrrolidine-2-carboxamide]-3-fluoro-1H-indole-2-carboxylic acid

[Formula 202]

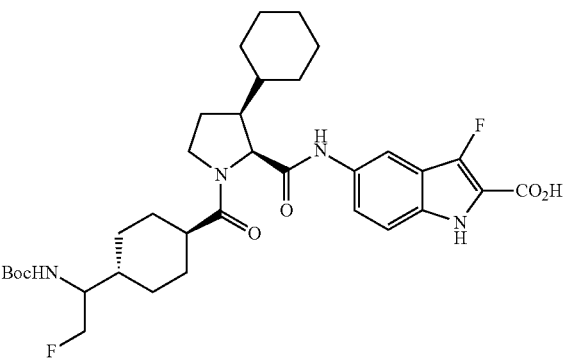

The same procedure as described in Reference Example 28 was carried out to obtain the title compound (7.0 mg, 68%) from the compound of Reference Example 40-3 (8 mg, 0.016 mmol).

MS (ESI+) 645 (M+1, 100%)

Reference Example 40-1

Ethyl 5-[(2S,3S)-1-tert-butoxycarbonyl-3-cyclohexylpyrrolidine-2-carboxamide]-3-fluoro-1H-indole-2-carboxylate

[Formula 203]

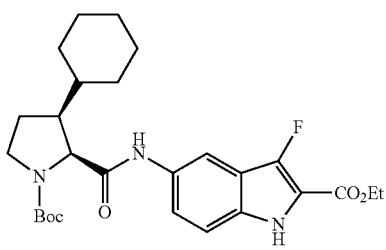

To a solution of the compound of Reference Example 34-1 (100 mg, 0.207 mmol) in dichloroethane (2 mL), 1-fluoro-2,4,6-trimethylpyridinium trifluoromethanesulfonate (191 mg, 0.662 mmol) was added, and the mixture was stirred at 90° C. for 8 hours. The reaction solution was allowed to cool, then water was added thereto, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (8.0 mg, 8%).

MS (ESI+) 502 (M+1, 100%)

Reference Example 40-2

Ethyl 5-[(2S,3S)-3-cyclohexylpyrrolidine-2-carboxamide]-3-fluoro-1H-indole-2-carboxylate trifluoroacetate

[Formula 204]

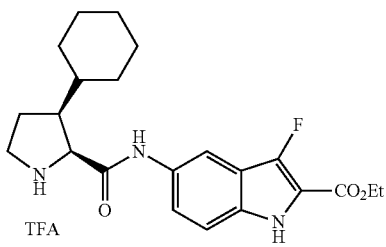

The same procedure as described in Reference Example 9-2 was carried out to obtain the title compound (8.0 mg, 100%) from the compound of Reference Example 40-1 (8.0 mg, 0.016 mmol).

MS (ESI+) 402 (M+1, 100%)

Reference Example 40-3

Ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-3-fluoro-1H-indole-2-carboxylate

[Formula 205]

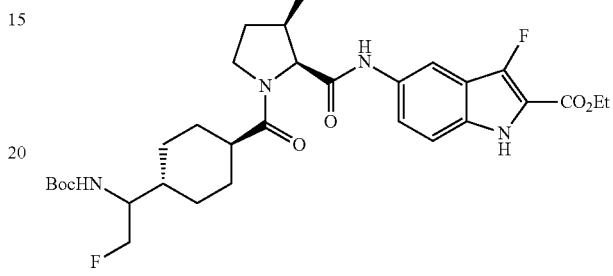

The same procedure as described in Reference Example 1 was carried out to obtain the title compound (8.0 mg, 74%) from the compound of Reference Example 40-2 (8.0 mg, 0.016 mmol) and the compound of Reference Example 31-11 (6.0 mg, 0.289 mmol).

MS (ESI+) 673 (M+1, 100%)

Reference Example 41

4-[(2S,3R)-1-{trans-4-[1-(tert-Butoxycarbonylamino)ethyl]cyclohexanecarbonyl}-3-cyclohexylpyrrolidine-2-carboxamide]-3-fluorobenzoic acid

[Formula 206]

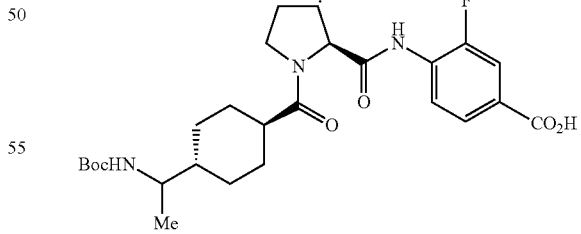

The same procedure as described in Reference Example 3 was carried out to obtain the title compound (26.8 mg, 64%) from the compound of Reference Example 41-4 (42.8 mg, 0.0711 mmol).

MS (ESI+) 588 (M+1, 67%)

Reference Example 41-1

(2S,3R)-1-tert-Butoxycarbonyl-3-cyclohexylpyrrolidine-2-carboxylic acid

[Formula 207]

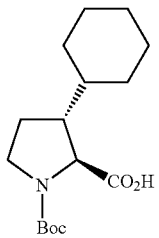

The same procedure as described in Reference Example 11-1 was carried out to obtain the title compound (4.13 g, 100%) from the compound of Reference Example 31-4 (4.05 g, 13.90 mmol).
MS (ESI+) 298 (M+1, 29%)

Reference Example 41-2

Methyl 4-[(2S,3R)-1-tert-butoxycarbonyl-3-cyclohexylpyrrolidine-2-carboxamide]-3-fluorobenzoate

[Formula 208]

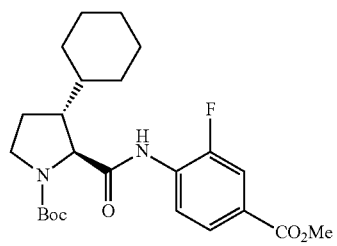

The same procedure as described in Reference Example 1-1 was carried out to obtain the title compound (64.8 mg, 16%) from the compound of Reference Example 41-1 (276.2 mg, 0.929 mmol) and methyl 4-amino-3-fluorobenzoate (173 mg, 1.02 mmol).
MS (ESI+) 449 (M+1, 19%)

Reference Example 41-3

Methyl 4-[(2S,3R)-3-cyclohexylpyrrolidine-2-carboxamide]-3-fluorobenzoate trifluoroacetate

[Formula 209]

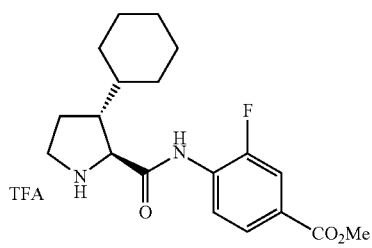

The same procedure as described in Reference Example 9-2 was carried out to obtain the title compound (64.3 mg, 100%) from the compound of Reference Example 41-2 (64.8 mg, 0.125 mmol).
MS (ESI+) 349 (M+1, 100%)

Reference Example 41-4

Methyl 4-[(2S,3R)-1-{trans-4-[1-(tert-butoxycarbonylamino)ethyl]cyclohexanecarbonyl}-3-cyclohexylpyrrolidine-2-carboxamide]-3-fluorobenzoate

[Formula 210]

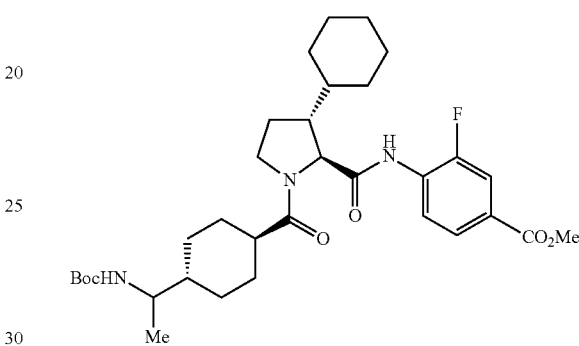

The same procedure as described in Reference Example 1 was carried out to obtain the title compound (62.0 mg, 71%) from the compound of Reference Example 7-9 (49.5 mg, 0.173 mmol) and the compound of Reference Example 41-3 (64.3 mg, 0.145 mmol).
MS (ESI+) 602 (M+1, 46%)

Reference Example 42

4-{(2S,3R)-1-[trans-4-(tert-Butoxycarbonylaminomethyl)cyclohexanecarbonyl]-3-phenylpyrrolidine-2-carboxamide}-2,5-difluoro benzoic acid

[Formula 211]

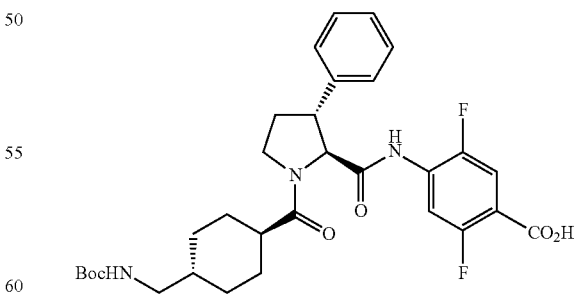

The same procedure as described in Reference Example 3 was carried out to obtain the title compound (212.3 mg, 87%) from the compound of Reference Example 42-4 (249.3 mg, 0.416 mmol).
MS (ESI+) 586 (M+1, 17%)

Reference Example 42-1

Methyl 4-amino-2,5-difluoro benzoate

[Formula 212]

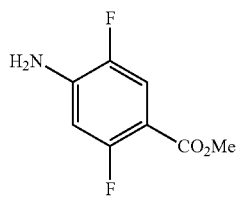

The same procedure as described in Reference Example 2-1 was carried out to obtain the title compound (409.7 mg, 97%) from methyl 2,5-difluoro-4-nitrobenzoate (488 mg, 2.25 mmol).
$^1$H NMR (CDCl$_3$, 300 MHz) δ 7.60-7.54 (m, 1H), 6.48-6.42 (m, 1H), 3.87 (s, 3H).

Reference Example 42-2

Methyl 4-[(2S,3R)-1-tert-butoxycarbonyl-3-phenylpyrrolidine-2-carboxamide]-2,5-difluorobenzoate

[Formula 213]

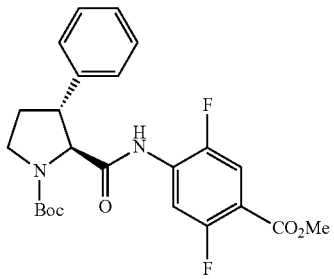

The same procedure as described in Reference Example 1-1 was carried out to obtain the title compound (320.7 mg, 75%) from the compound of Reference Example 31-4 (298 mg, 1.02 mmol) and the compound of Reference Example 42-1 (173.9 mg, 0.929 mmol).
MS (ESI+) 461 (M+1, 44%)

Reference Example 42-3

Methyl 4-[(2S,3R)-3-phenylpyrrolidine-2-carboxamide]-2,5-difluorobenzoate

[Formula 214]

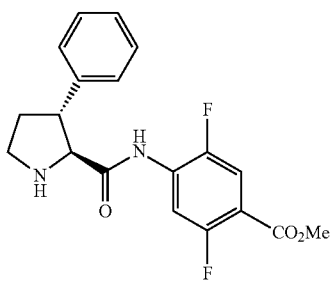

The same procedure as described in Reference Example 7-2 was carried out to obtain the title compound (255.8 mg, 100%) from the compound of Reference Example 42-2 (320.7 mg, 0.696 mmol).
MS (ESI+) 361 (M+1, 100%)

Reference Example 42-4

Methyl 4-{(2S,3R)-1-[trans-4-(tert-butoxycarbonylaminomethyl)cyclohexanecarbonyl]-3-phenylpyrrolidine-2-carboxamide}-2,5-difluoro benzoate

[Formula 215]

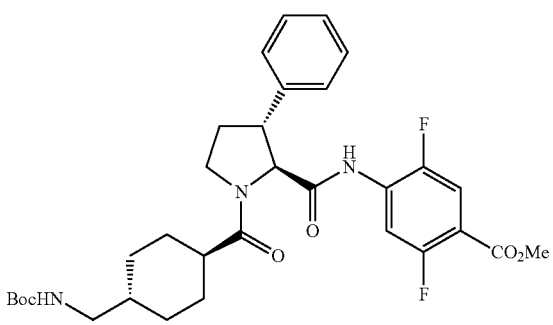

The same procedure as described in Reference Example 1 was carried out to obtain the title compound (348.9 mg, 84%) from the compound of Reference Example 42-3 (255.8 mg, 0.696 mmol).
MS (ESI+) 600 (M+1, 22%)

Reference Example 43 tert-Butyl trans-4-{[(2S,3R)-2-(2,5-difluoro-4-methylcarbamoyl)phenylcarbamoyl)-3-phenylpyrrolidine-1-carbonyl]cyclohexyl}methylcarbamate

[Formula 216]

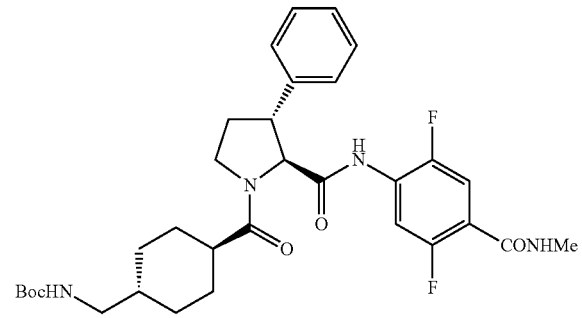

The same procedure as described in Reference Example 4 was carried out to obtain the title compound (43.0 mg, 60%) from the compound of Reference Example 42 (70.2 mg, 0.120 mmol) and methylamine hydrochloride (12.1 mg, 0.179 mmol).
MS (ESI+) 599 (M+1, 27%)

Reference Example 44

4-{(2S,3S)-1-[trans-4-(tert-Butoxycarbonylaminomethyl)cyclohexanecarbonyl]-3-cyclohexylpyrrolidine-2-carboxamide}-3-fluorobenzoic acid

[Formula 217]

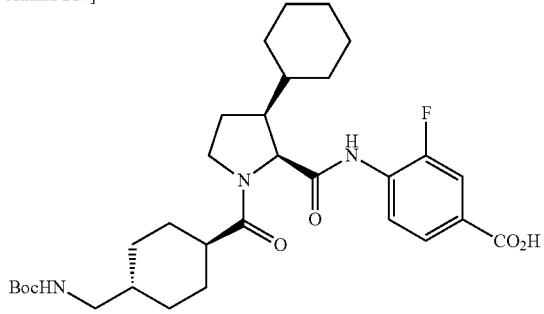

The same procedure as described in Reference Example 3 was carried out to obtain the title compound (29.7 mg, 91%) from the compound of Reference Example 44-3 (33.6 mg, 0.0572 mmol).
MS (ESI+) 574 (M+1, 32%)

Reference Example 44-1

Methyl 4-[(2S,3S)-1-tert-butoxycarbonyl-3-cyclohexylpyrrolidine-2-carboxamide]-3-fluorobenzoate

[Formula 218]

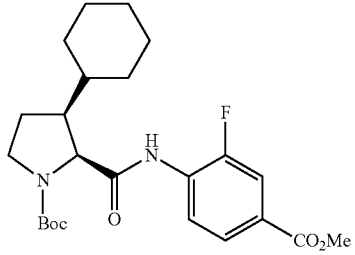

The same procedure as described in Reference Example 1-1 was carried out to obtain the title compound (95.7 mg, 26%) from the compound of Reference Example 11-1 (240.5 mg, 0.809 mmol) and methyl 4-amino-3-fluorobenzoate (150.5 mg, 0.890 mmol).
MS (ESI+) 449 (M+1, 24%)

Reference Example 44-2

Methyl 4-[(2S,3S)-3-cyclohexylpyrrolidine-2-carboxamide]-3-fluorobenzoate hydrochloride

[Formula 219]

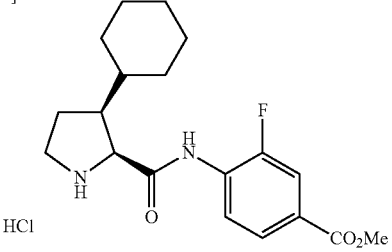

The same procedure as described in Reference Example 1-2 was carried out to obtain the title compound (82.0 mg, 100%) from the compound of Reference Example 44-1 (95.7 mg, 0.213 mmol).
MS (ESI+) 349 (M+1, 100%)

Reference Example 44-3

Methyl 4-{(2S,3S)-1-[trans-4-(tert-butoxycarbonylaminomethyl)cyclohexanecarbonyl]-3-cyclohexylpyrrolidine-2-carboxamide}-3-fluorobenzoate

[Formula 220]

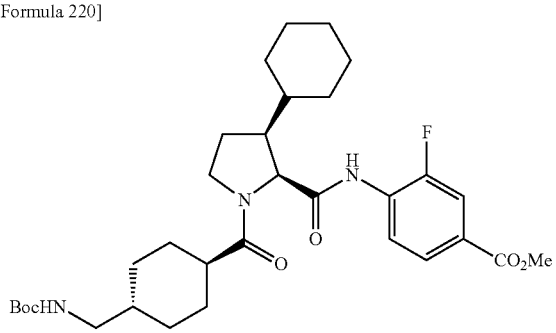

The same procedure as described in Reference Example 1 was carried out to obtain the title compound (79.4 mg, 63%) from the compound of Reference Example 44-2 (82.0 mg, 0.213 mmol).
MS (ESI+) 588 (M+1, 36%)

Reference Example 45

5-[(2S,3R)-1-{trans-4-[1-(tert-Butoxycarbonyl)amino-2-fluoroethyl]cyclohexanecarbonyl}-3-phenylpyrrolidine-2-carboxamide]-1-benzofuran-2-carboxylic acid

[Formula 221]

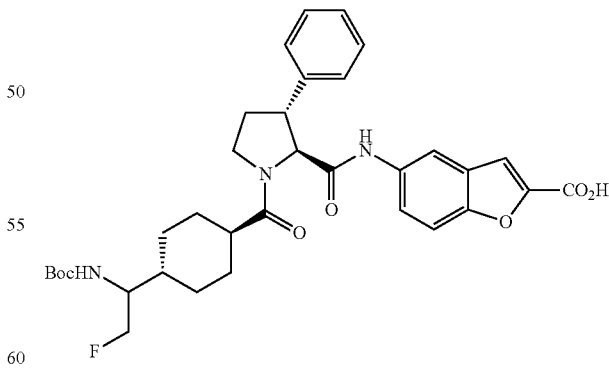

The same procedure as described in Reference Example 3 was carried out to obtain the title compound (59.5 mg, 97%) from the compound of Reference Example 45-3 (64.4 mg, 0.099 mmol).
MS (ESI+) 622 (M+1, 100%)

Reference Example 45-1

Ethyl 5-[(2S,3R)-1-tert-butoxycarbonyl-3-phenylpyrrolidine-2-carboxamide]-1-benzofuran-2-carboxylate

[Formula 222]

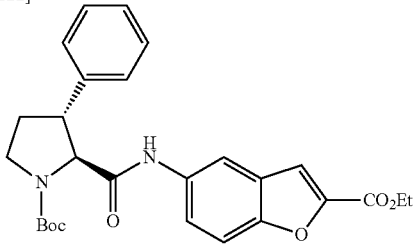

The same procedure as described in Reference Example 1 was carried out to obtain the title compound (986 mg, 100%) from the compound of Reference Example 31-4 (600 mg, 2.06 mmol) and ethyl 5-amino-1-benzofuran-2-carboxylate (423 mg, 2.06 mmol).
MS (ESI+) 479 (M+1, 53%)

Reference Example 45-2

Ethyl 5-[(2S,3R)-3-phenylpyrrolidine-2-carboxamide]-1-benzofuran-2-carboxylate hydrochloride

[Formula 223]

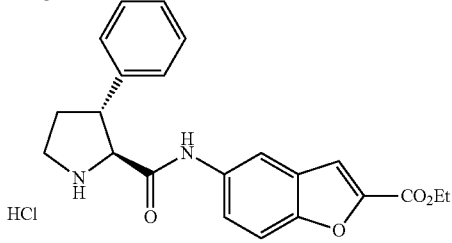

The same procedure as described in Reference Example 1-2 was carried out to obtain the title compound (794.2 mg, 93%) from the compound of Reference Example 45-1 (986 mg, 2.06 mmol).
MS (ESI+) 379 (M+1, 100%)

Reference Example 45-3

Ethyl 5-[(2S,3R)-1-{trans-4-[1-(tert-butoxycarbonyl)amino-2-fluoroethyl]cyclohexanecarbonyl}-3-phenylpyrrolidine-2-carboxamide]-1-benzofuran-2-carboxylate

[Formula 224]

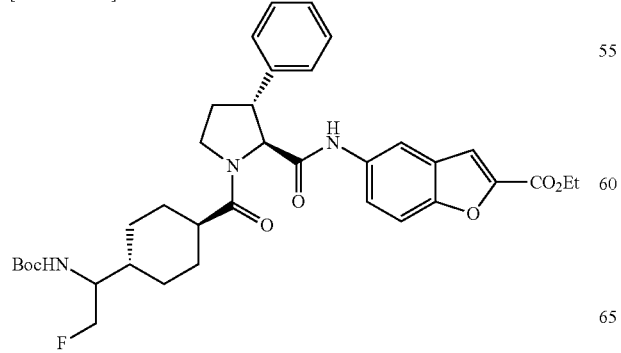

The same procedure as described in Reference Example 1 was carried out to obtain the title compound (159 mg, 99%) from the compound of Reference Example 45-2 (113 mg, 0.273 mmol) and the compound of Reference Example 31-11 (71.7 mg, 0.248 mmol).
MS (ESI+) 650 (M+1, 100%)

Reference Example 46

5-[(2S,3R)-1-{trans-4-[1-(tert-Butoxycarbonylamino)ethyl]cyclohexanecarbonyl}-3-phenylpyrrolidine-2-carboxamide]-1-benzofuran-2-carboxylic acid

[Formula 225]

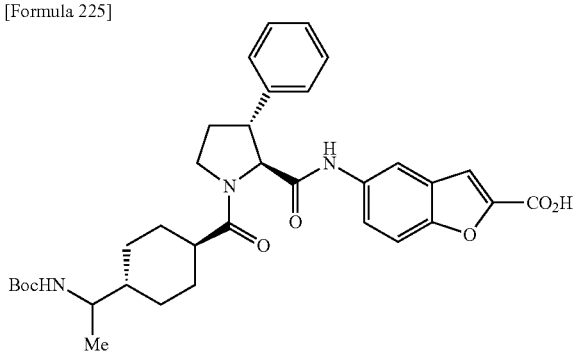

The same procedure as described in Reference Example 3 was carried out to obtain the title compound (21.8 mg, 100%) from the compound of Reference Example 46-1 (22.8 mg, 0.0361 mmol).
MS (ESI+) 604 (M+1, 48%)

Reference Example 46-1

Ethyl 5-[(2S,3R)-1-{trans-4-[1-(tert-butoxycarbonylamino)ethyl]cyclohexanecarbonyl}-3-phenylpyrrolidine-2-carboxamide]-1-benzofuran-2-carboxylate

[Formula 226]

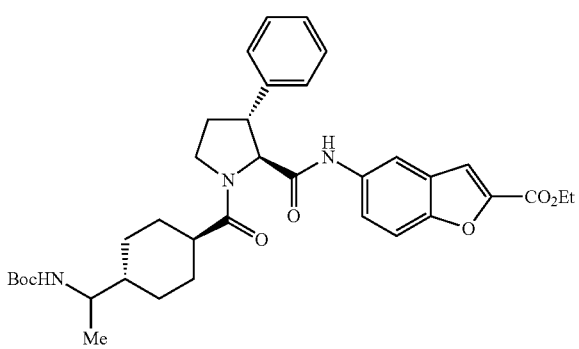

The same procedure as described in Reference Example 1 was carried out to obtain the title compound (69.4 mg, 74%) from the compound of Reference Example 45-2 (61.9 mg, 0.149 mmol) and the compound of Reference Example 7-9 (42.6 mg, 0.149 mmol).
MS (ESI+) 632 (M+1, 39%)

Reference Example 47

5-[(2S,3R)-1-{trans-4-[1-(tert-Butoxycarbonyl)amino-2-fluoroethyl]cyclohexanecarbonyl}-3-phenylpyrrolidine-2-carboxamide]-1-methyl-1H-indole-2-carboxylic acid

[Formula 227]

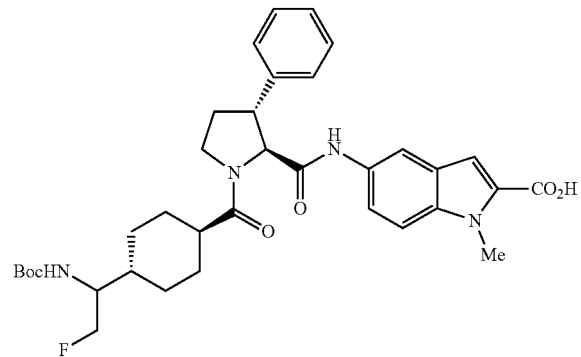

The same procedure as described in Reference Example 3 was carried out to obtain the title compound (64.1 mg, 100%) from the compound of Reference Example 47-5 (67.1 mg, 0.101 mmol).

MS (ESI+) 635 (M+1, 19%)

Reference Example 47-1

Ethyl 1-methyl-5-nitro-1H-indole-2-carboxylate

[Formula 228]

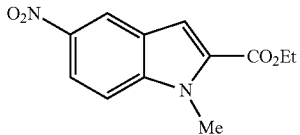

To a solution of ethyl 5-nitro-1H-indole-2-carboxylate (1.12 g, 4.78 mmol) in DMF (10 mL), potassium carbonate (1.32 g, 9.55 mmol) and methyl iodide (446 μL, 7.17 mmol) were added, and the mixture was stirred for 2.5 hours at 60° C. The reaction solution was allowed to cool, then a saturated aqueous solution of ammonium chloride was added, followed by extraction with ethyl acetate. The organic layer was washed with a saturated aqueous solution of ammonium chloride twice and with a saturated saline solution once, then dried over anhydrous sodium sulfate and filtered, and the filtrate was concentrated under reduced pressure to obtain the title compound (1.18 g, 100%).

$^{1}$H NMR (CDCl$_3$, 300 MHz) δ 8.65 (d, J=2.2 Hz, 1H), 8.25 (dd, J=2.2, 11.3 Hz, 1H), 7.45 (s, 1H), 7.43 (d, J=11.3 Hz, 1H), 4.40 (q, J=7.1 Hz, 2H), 4.13 (s, 3H), 1.42 (t, J=7.1 Hz, 3H).

Reference Example 47-2

Ethyl 5-amino-1-methyl-1H-indole-2-carboxylate

[Formula 229]

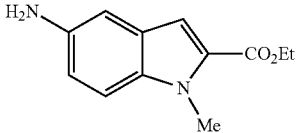

The same procedure as described in Reference Example 2-1 was carried out to obtain the title compound (783 mg, 75%) from the compound of Reference Example 47-1 (1.18 g, 4.78 mmol).

MS (ESI+) 219 (M+1, 100%)

Reference Example 47-3

Ethyl 5-[(2S,3R)-1-tert-butoxycarbonyl-3-phenylpyrrolidine-2-carboxamide]-1-methyl-1H-indole-2-carboxylate

[Formula 230]

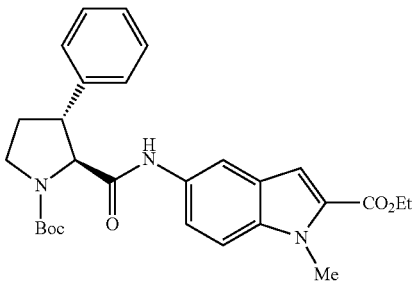

The same procedure as described in Reference Example 1 was carried out to obtain the title compound (988.2 mg, 99%) from the compound of Reference Example 31-4 (622 mg, 2.14 mmol) and the compound of Reference Example 47-2 (443.5 mg, 2.03 mmol).

MS (ESI+) 492 (M+1, 30%)

Reference Example 47-4

Ethyl 1-methyl-5-[(2S,3R)-3-phenylpyrrolidine-2-carboxamide]-1H-indole-2-carboxylate hydrochloride

[Formula 231]

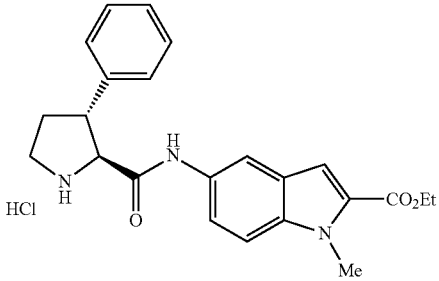

The same procedure as described in Reference Example 1-2 was carried out to obtain the title compound (414 mg, 100%) from the compound of Reference Example 47-3 (475.5 mg, 0.967 mmol).

MS (ESI+) 392 (M+1, 100%)

Reference Example 47-5

Ethyl 5-[(2S,3R)-1-{trans-4-[1-(tert-butoxycarbonyl)amino-2-fluoroethyl]cyclohexanecarbonyl}-3-phenylpyrrolidine-2-carboxamide]-1-methyl-1H-indole-2-carboxylate

[Formula 232]

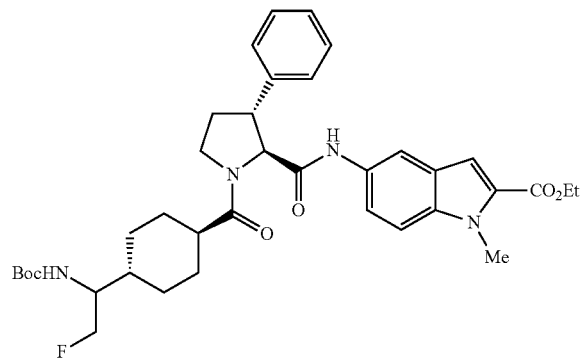

The same procedure as described in Reference Example 1 was carried out to obtain the title compound (237.6 mg, 71%) from the compound of Reference Example 47-4 (238 mg, 0.556 mmol) and the compound of Reference Example 31-11 (146 mg, 0.505 mmol).

MS (ESI+) 663 (M+1, 17%)

Reference Example 48

5-[(2S,3S)-1-{trans-4-[1-(tert-Butoxycarbonyl)amino-2-fluoroethyl]cyclohexanecarbonyl}-3-phenylpyrrolidine-2-carboxamide]-1-benzofuran-2-carboxylic acid

[Formula 233]

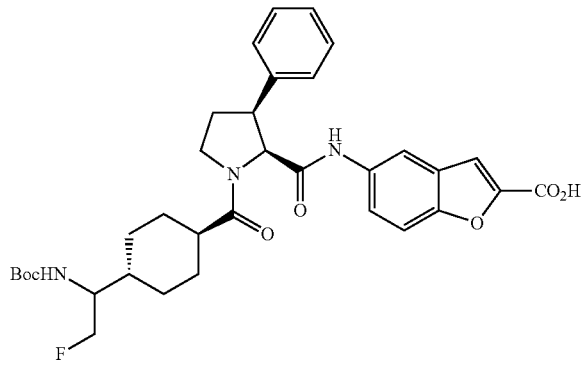

The same procedure as described in Reference Example 3 was carried out to obtain the title compound (67.7 mg, 87%) from the compound of Reference Example 48-2 (81.3 mg, 0.125 mmol).

MS (ESI+) 622 (M+1, 100%)

Reference Example 48-1

Ethyl 5-[(2S,3S)-3-phenylpyrrolidine-2-carboxamide]-1-benzofuran-2-carboxylate

[Formula 234]

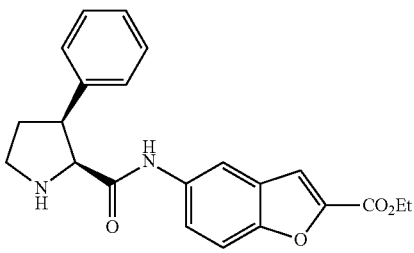

To a solution of (2S,3S)-1-tert-butoxycarbonyl-3-phenylpyrrolidine-2-carboxylic acid (1.33 g, 4.57 mmol) in DMF (10 mL), 1-hydroxybenzotriazole (1.05 g, 6.86 mmol), WSC.HCl (1.31 g, 6.83 mmol), triethylamine (1.27 mL, 9.11 mmol), and ethyl 5-amino-1-benzofuran-2-carboxylate (937 mg, 4.57 mmol) were added, and the mixture was stirred at 75° C. for 4 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution once, respectively, then dried over sodium sulfate and filtered, and the filtrate was concentrated under reduced pressure. The obtained residue was purified by silica gel column chromatography to obtain a crude product (1.85 g).

To a solution of the obtained crude product (1.85 g) in chloroform (10 mL), trifluoroacetic acid (10 mL) was added, and the mixture was stirred for 1.5 hour. After the mixture was concentrated under reduced pressure, a saturated aqueous solution of sodium bicarbonate was added to the residue, followed by extraction with chloroform. The organic layer was washed with a saturated saline solution, then dried over sodium sulfate and filtered, and the filtrate was concentrated under reduced pressure. The obtained residue was purified by silica gel column chromatography to obtain the title compound (693.3 mg, 43%).

MS (ESI+) 379 (M+1, 100%)

Reference Example 48-2

Ethyl 5-[(2S,3S)-1-{trans-4-[1-(tert-butoxycarbonyl)amino-2-fluoroethyl]cyclohexanecarbonyl}-3-phenylpyrrolidine-2-carboxamide]-1-benzofuran-2-carboxylate

[Formula 235]

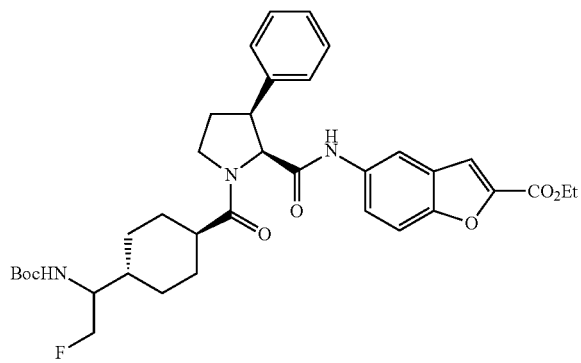

The same procedure as described in Reference Example 1 was carried out to obtain the title compound (187 mg, 100%) from the compound of Reference Example 48-1 (131.4 mg, 0.317 mmol) and the compound of Reference Example 31-11 (83.3 mg, 0.288 mmol).
MS (ESI+) 650 (M+1, 42%)

Reference Example 49

5-[(2S,3R)-1-{trans-4-[1-(tert-Butoxycarbonyl)amino-2-fluoroethyl]cyclohexanecarbonyl}-3-phenylpyrrolidine-2-carboxamide]-3-chloro-1-methyl-1H-indole-2-carboxylic acid

[Formula 236]

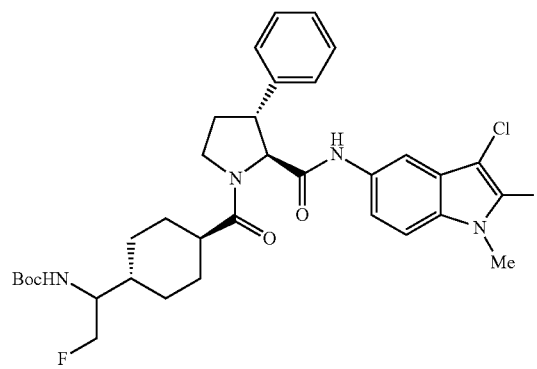

The same procedure as described in Reference Example 3 was carried out to obtain the title compound (22.0 mg, 100%) from the compound of Reference Example 49-1 (23.0 mg, 0.0330 mmol).
MS (ESI+) 669 (M+1, 100%)

Reference Example 49-1

Ethyl 5-[(2S,3R)-1-{trans-4-[1-(tert-butoxycarbonyl)amino-2-fluoroethyl]cyclohexanecarbonyl}-3-phenylpyrrolidine-2-carboxamide]-3-chloro-1-methyl-1H-indole-2-carboxylate

[Formula 237]

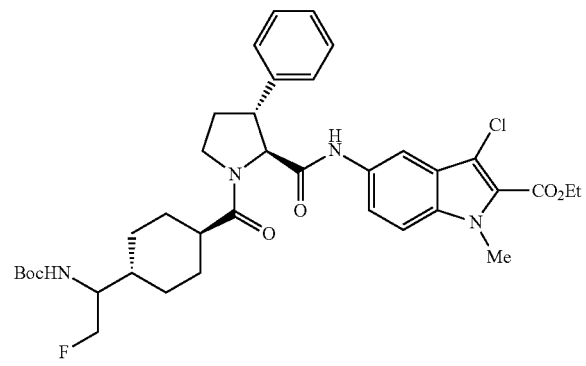

To a solution of the compound of Reference Example 47-5 (43.8 mg, 0.0661 mmol) in DMF (2 mL), N-chlorosuccinimide (11.5 mg, 0.0861 mmol) was added, and the mixture was stirred at 50° C. for 3 hours. After the reaction solution was allowed to cool, a saturated aqueous solution of ammonium chloride was added, followed by extraction with ethyl acetate. The organic layer was washed with a saturated aqueous solution of ammonium chloride twice and with a saturated aqueous solution of sodium bicarbonate and a saturated saline solution once, respectively, then dried over anhydrous sodium sulfate and filtered, and the filtrate was concentrated under reduced pressure. The obtained residue was purified by silica gel column chromatography to obtain the title compound (23.0 mg, 50%).
MS (ESI+) 697 (M+1, 100%)

Reference Example 50

5-[(2S,3S)-1-{trans-4-[1-(tert-Butoxycarbonyl)amino-2-fluoroethyl]cyclohexanecarbonyl}-3-cyclohexylpyrrolidine-2-carboxamide]-1-benzofuran-2-carboxylic acid

[Formula 238]

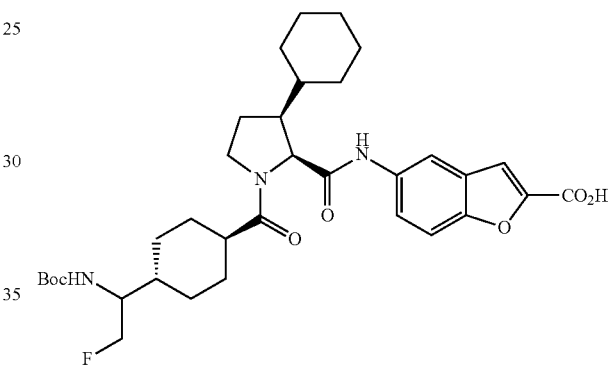

The same procedure as described in Reference Example 3 was carried out to obtain the title compound (67.4 mg, 91%) from the compound of Reference Example 49-1 (77.7 mg, 0.118 mmol).
MS (ESI+) 628 (M+1, 100%)

Reference Example 50-1

Ethyl 5-[(2S,3S)-1-tert-butoxycarbonyl-3-cyclohexylpyrrolidine-2-carboxamide]-1-benzofuran-2-carboxylate

[Formula 239]

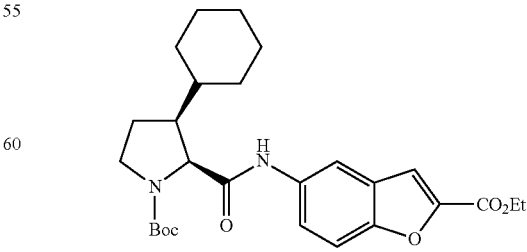

The same procedure as described in Reference Example 1-1 was carried out to obtain the title compound (177 mg, 25%) from the compound of Reference Example 11-1 (480 mg, 1.614 mmol) and ethyl 5-amino-1-benzofuran-2-carboxylate (301 mg, 1.47 mmol).

MS (ESI+) 485 (M+1, 45%)

Reference Example 50-2

Ethyl 5-[(2S,3S)-3-cyclohexylpyrrolidine-2-carboxamide]-1-benzofuran-2-carboxylate hydrochloride

[Formula 240]

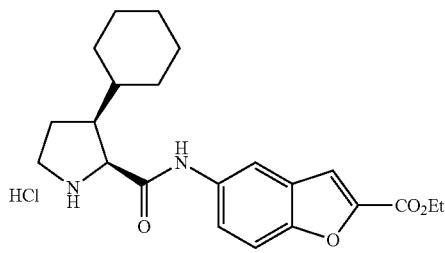

The same procedure as described in Reference Example 1-2 was carried out to obtain the title compound (153 mg, 100%) from the compound of Reference Example 50-1 (177 mg, 0.365 mmol).

MS (ESI+) 385 (M+1, 100%)

Reference Example 50-3

Ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate

[Formula 241]

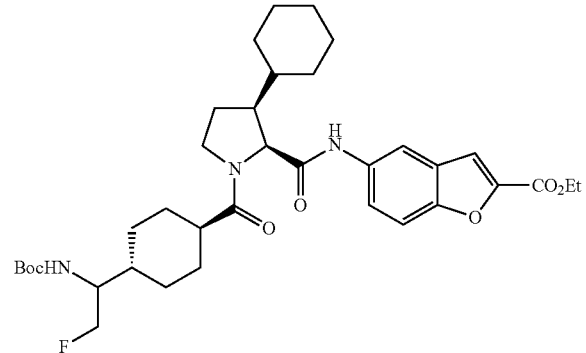

The same procedure as described in Reference Example 1 was carried out to obtain the title compound (162.4 mg, 80%) from the compound of Reference Example 50-2 (153 mg, 0.365 mmol) and the compound of Reference Example 31-11 (116.3 mg, 0.402 mmol).

MS (ESI+) 656 (M+1, 100%)

Reference Example 51 tert-Butyl [1-(trans-4-{[(2S,3S)-3-cyclohexyl-2-{[2-(morpholin-4-ylcarbonyl)-1-benzofuran-5-yl]carbamoyl}pyrrolidin-1-yl]carbonyl}cyclohexyl)-2-fluoroethyl]carbamate

[Formula 242]

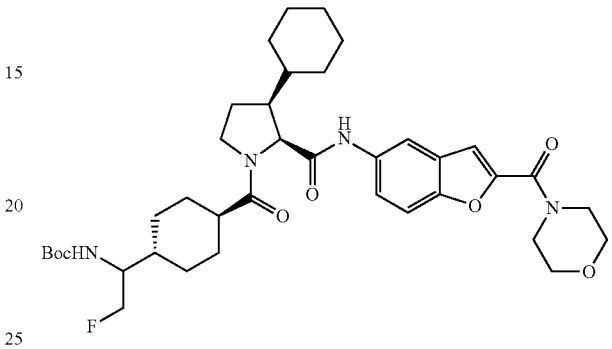

The same procedure as described in Reference Example 4 was carried out to obtain the title compound (12.3 mg, 51%) from the compound of Reference Example 50 (21.9 mg, 0.0349 mmol) and morpholine (6.1 μL, 0.0693 mmol).

MS (ESI+) 697 (M+1, 100%)

Reference Example 52

6-[(2S,3R)-1-{trans-4-[1-(tert-Butoxycarbonyl)amino-2-fluoroethyl]cyclohexanecarbonyl}-3-phenylpyrrolidine-2-carboxamide]pyridine-3-carboxylic acid

[Formula 243]

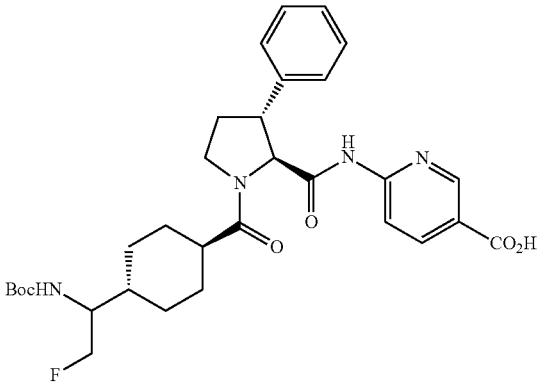

The same procedure as described in Reference Example 3 was carried out to obtain the title compound (81.2 mg, 90%) from the compound of Reference Example 52-3 (92.1 mg, 0.154 mmol).

MS (ESI+) 583 (M+1, 100%)

Reference Example 52-1

Methyl 6-[(2S,3R)-1-tert-butoxycarbonyl-3-phenylpyrrolidine-2-carboxamide]pyridine-3-carboxylate

[Formula 244]

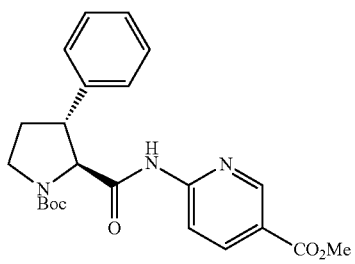

The same procedure as described in Reference Example 1-1 was carried out to obtain the title compound (234.4 mg, 66%) from the compound of Reference Example 31-4 (127.5 mg, 0.838 mmol) and methyl 6-aminonicotinate (244.2 mg, 0.838 mmol).
MS (ESI+) 426 (M+1, 48%)

Reference Example 52-2

Methyl 6-[(2S,3R)-3-phenylpyrrolidine-2-carboxamide]pyridine-3-carboxylate hydrochloride

[Formula 245]

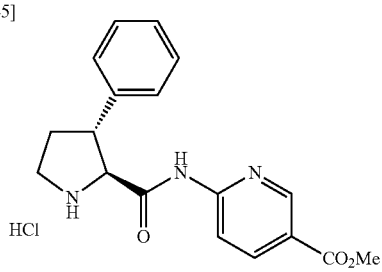

The same procedure as described in Reference Example 1-2 was carried out to obtain the title compound (218 mg, 100%) from the compound of Reference Example 52-1 (234.4 mg, 0.551 mmol).
MS (ESI+) 326 (M+1, 100%)

Reference Example 52-3

Methyl 6-[(2S,3R)-1-{trans-4-[1-(tert-butoxycarbonyl)amino-2-fluoroethyl]cyclohexanecarbonyl}-3-phenylpyrrolidine-2-carboxamide]pyridine-3-carboxylate

[Formula 246]

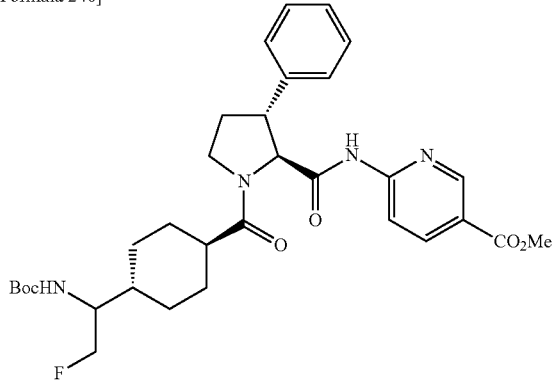

The same procedure as described in Reference Example 1 was carried out to obtain the title compound (143.8 mg, 74%) from the compound of Reference Example 52-2 (130.2 mg, 0.327 mmol) and the compound of Reference Example 31-11 (104 mg, 0.359 mmol).
MS (ESI+) 597 (M+1, 100%)

Reference Example 53

5-[(2S,3S)-1-{trans-4-[(1S)-1-(tert-Butoxycarbonyl)amino-2-fluoroethyl]cyclohexanecarbonyl}-3-cyclohexylpyrrolidine-2-carboxamide]-1-benzofuran-2-carboxylic acid

[Formula 247]

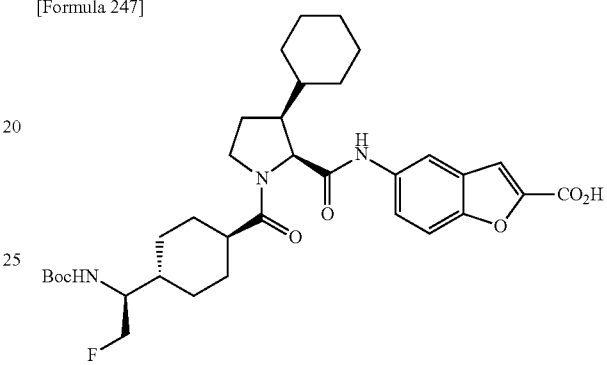

The same procedure as described in Reference Example 3 was carried out to obtain the title compound (515.1 mg, 91%) from the compound of Reference Example 53-4 (592.4 mg, 0.903 mmol).
MS (ESI+) 628 (M+I, 100%)

Reference Example 53-1

Benzyl trans-4-[1-(tert-butoxycarbonyl)amino-2-fluoroethyl]cyclohexanecarboxylate

[Formula 248]

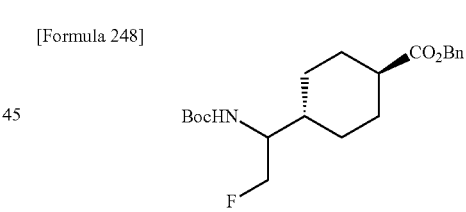

To a solution of the compound of Reference Example 31-11 (4.14 g, 14.31 mmol) in DMF (30 mL), potassium carbonate (3.96 g, 28.65 mmol) and benzyl bromide (2.57 g, 15.02 mmol) were added, and the mixture was stirred at room temperature for 4 hours. A saturated aqueous solution of ammonium chloride was added to the reaction solution, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (5.14 g, 95%).
$^1$H NMR (CDCl$_3$, 400 MHz) δ 7.35-7.34 (m, 5H), 5.11 (s, 2H), 4.72-4.70 (m, 1H), 4.61-4.35 (m, 2H), 3.59-3.51 (m, 1H), 2.32-2.26 (m, 1H), 2.09-2.05 (m, 2H), 1.94-1.86 (m, 2H), 1.59-1.44 (m, 11H), 1.16-1.06 (m, 2H).

Reference Example 53-2

Benzyl trans-4-[(1S)-1-(tert-butoxycarbonyl)amino-2-fluoroethyl]cyclohexanecarboxylate

[Formula 249]

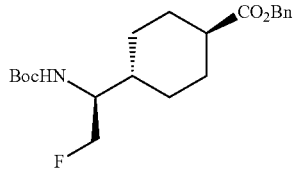

The compound of Reference Example 53-1 as a racemate was separated by HPLC under the following conditions to obtain the title compound.
CHIRALCEL (registered trademark) OD-H (0.46 cmI.D.×25 cmL), Mobile phase: n-hexane/2-propanol (5/1), Flow rate: 0.5 mL/min, Wavelength: 254 nm, RT 12.078 min

Reference Example 53-3 trans-4-[(1S)-1-(tert-Butoxycarbonyl)amino-2-fluoroethyl]cyclohexanecarboxylic acid

[Formula 250]

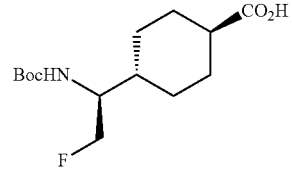

To a solution of the compound of Reference Example 53-2 (540 mg, 1.423 mmol) in methanol (20 mL), palladium-carbon (760 mg) was added, and the mixture was stirred for 3 hours under hydrogen atmosphere. The reaction solution was filtered through Celite, and the filtrate was concentrated under reduced pressure to obtain the title compound (411 mg, 100%).
$^1$H NMR (DMSO-$d_6$, 300 MHz) δ 6.87 (m, 1H), 4.48-4.37 (m, 1H), 4.32-4.21 (m, 1H), 3.45-3.34 (m, 1H), 2.11-2.03 (m, 1H), 1.89-1.86 (m, 2H), 1.71-1.67 (m, 2H), 1.37-1.30 (m, 10H), 1.23-1.17 (m, 2H), 1.13-0.95 (m, 2H).

Reference Example 53-4

Ethyl 5-[(2S,3S)-1-{trans-4-[(1S)-1-(tert-butoxycarbonyl)amino-2-fluoroethyl]cyclohexanecarbonyl}-3-cyclohexylpyrrolidine-2-carboxamide]-1-benzofuran-2-carboxylate

[Formula 251]

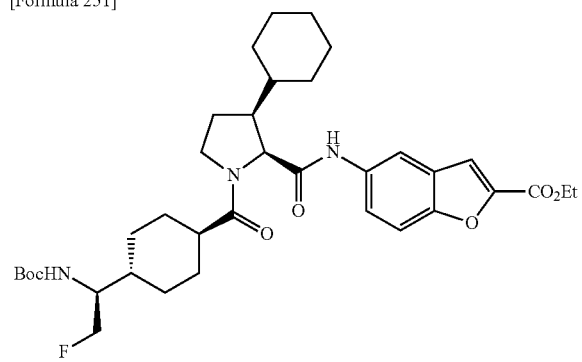

The same procedure as described in Reference Example 1 was carried out to obtain the title compound (443.8 mg, 72%) from the compound of Reference Example 50-2 (397.8 mg, 0.945 mmol) and the compound of Reference Example 53-3 (273.4 mg, 0.945 mmol).
MS (ESI+) 656 (M+1, 100%)

Reference Example 54

5-[(2S,3S)-1-{trans-4-[(1R)-1-(tert-Butoxycarbonyl)amino-2-fluoroethyl]cyclohexanecarbonyl}-3-cyclohexylpyrrolidine-2-carboxamide]-1-benzofuran-2-carboxylic acid

[Formula 252]

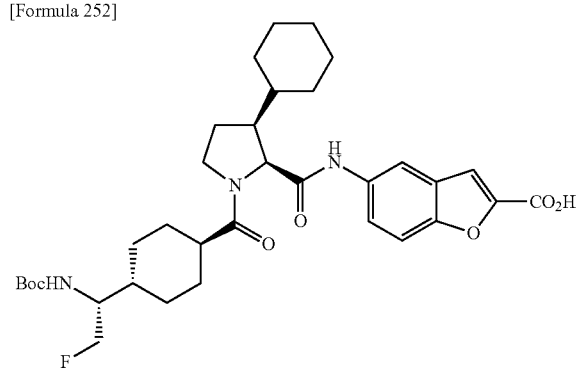

The same procedure as described in Reference Example 3 was carried out to obtain the title compound (57.0 mg, 100%) from the compound of Reference Example 54-3 (45.0 mg, 0.0686 mmol).
MS (ESI+) 628 (M+1, 100%)

Reference Example 54-1

Benzyl trans-4-[(1R)-1-(tert-butoxycarbonyl)amino-2-fluoroethyl]cyclohexanecarboxylate

[Formula 253]

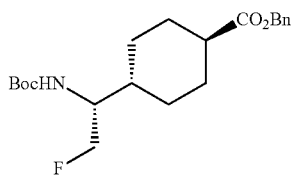

The compound of Reference Example 53-1 as a racemate was separated by HPLC under the following conditions to obtain the title compound.
CHIRALCEL (registered trademark) OD-H (0.46 cmI.D.×25 cmL), Mobile phase: n-hexane/2-propanol (5/1), Flow rate: 0.5 mL/min, Wavelength: 254 nm, RT 15.783 min

Reference Example 54-2 trans-4-[(1R)-1-(tert-Butoxycarbonyl)amino-2-fluoroethyl]cyclohexanecarboxylic acid

[Formula 254]

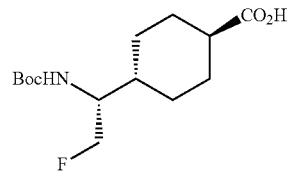

The same procedure as described in Reference Example 53-3 was carried out to obtain the title compound (35.0 mg, 72%) from the compound of Reference Example 54-1 (49.0 mg, 0.169 mmol).

¹H NMR (DMSO-d₆, 300 MHz) δ 6.87 (m, 1H), 4.48-4.37 (m, 1H), 4.32-4.21 (m, 1H), 3.45-3.34 (m, 1H), 2.11-2.03 (m, 1H), 1.89-1.86 (m, 2H), 1.71-1.67 (m, 2H), 1.37-1.30 (m, 10H), 1.23-1.17 (m, 2H), 1.13-0.95 (m, 2H).

Reference Example 54-3

Ethyl 5-[(2S,3S)-1-{trans-4-[(1R)-1-(tert-butoxycarbonyl)amino-2-fluoroethyl]cyclohexanecarbonyl}-3-cyclohexylpyrrolidine-2-carboxamide]-1-benzofuran-2-carboxylate

[Formula 255]

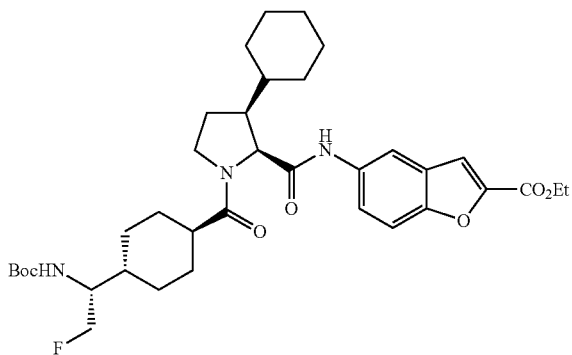

The same procedure as described in Reference Example 1 was carried out to obtain the title compound (45.4 mg, 57%) from the compound of Reference Example 50-2 (47.0 mg, 0.122 mmol) and the compound of Reference Example 54-2 (35.0 mg, 0.121 mmol).

MS (ESI+) 656 (M+1, 100%)

Reference Example 55

5-[(2S,3S)-1-{trans-4-[(1S)-1-(tert-Butoxycarbonyl)amino-2-fluoroethyl]cyclohexanecarbonyl}-3-cyclohexylpyrrolidine-2-carboxamide]-3-methyl-1-benzofuran-2-carboxylic acid

[Formula 256]

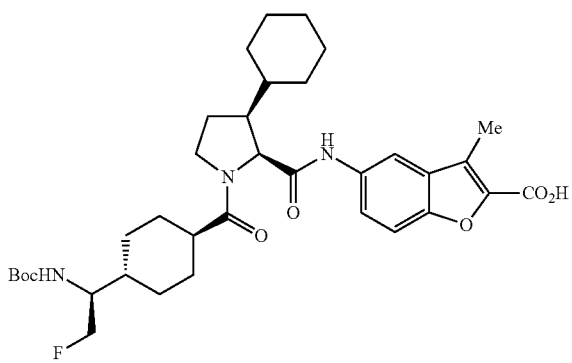

The same procedure as described in Reference Example 3 was carried out to obtain the title compound (103.0 mg, 94%) from the compound of Reference Example 55-4 (114.9 mg, 0.172 mmol).

MS (ESI+) 642 (M+1, 100%)

Reference Example 55-1

Ethyl 5-amino-3-methyl-1-benzofuran-2-carboxylate

[Formula 257]

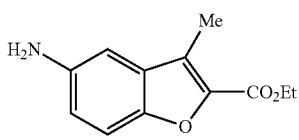

To a solution of ethyl 3-methylbenzofuran-2-carboxylate (1.88 g, 9.20 mmol) in chloroform (15 mL), fuming nitric acid (90%, 3.40 g, 48.5 mmol) was added dropwise in an ice bath, and the mixture was stirred at room temperature for 2 days. The reaction solution was cooled in an ice bath, a saturated aqueous solution of sodium bicarbonate was added thereto, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain a crude product (1.36 g).

To a solution of the crude product (1.36 g) in methanol (30 mL), palladium-carbon (2.0 g) was added, and the mixture was stirred for 3 hours under hydrogen atmosphere. The reaction solution was filtered through Celite, and the filtrate was concentrated under reduced pressure. The obtained residue was purified by silica gel column chromatography to obtain the title compound (450.0 mg, 22%).

¹H NMR (DMSO-d₆, 300 MHz) δ 7.31 (d, J=8.6 Hz, 1H), 6.80 (dd, J=2.2, 8.6 Hz, 1H), 6.73 (d, J=2.2 Hz, 1H), 5.05 (s, 2H), 4.30 (q, J=7.1 Hz, 2H), 2.42 (s, 3H), 1.31 (t, J=7.1 Hz, 3H).

Reference Example 55-2

Ethyl 5-[(2S,3S)-1-tert-butoxycarbonyl-3-cyclohexylpyrrolidine-2-carboxamide]-3-methyl-1-benzofuran-2-carboxylate

[Formula 258]

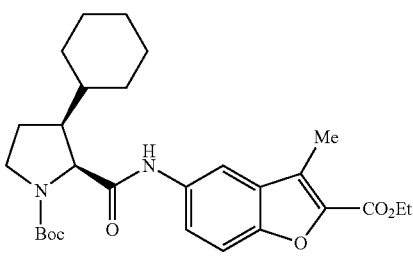

The same procedure as described in Reference Example 1-1 was carried out to obtain the title compound (99.0 mg, 32%) from the compound of Reference Example 11-1 (191.7 mg, 0.645 mmol) and the compound of Reference Example 55-1 (134.6 mg, 0.614 mmol).

MS (ESI+) 499 (M+1, 38%)

Reference Example 55-3

Ethyl 5-[(2S,3S)-3-cyclohexylpyrrolidine-2-carboxamide]-3-methyl-1-benzofuran-2-carboxylate hydrochloride

[Formula 259]

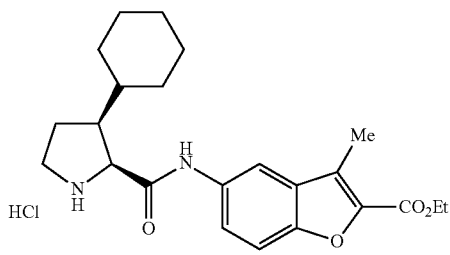

The same procedure as described in Reference Example 1-2 was carried out to obtain the title compound (86.2 mg, 100%) from the compound of Reference Example 55-2 (99.0 mg, 0.1986 mmol).

MS (ESI+) 399 (M+1, 100%)

Reference Example 55-4

Ethyl 5-[(2S,3S)-1-{trans-4-[(1S)-1-(tert-butoxycarbonyl)amino-2-fluoroethyl]cyclohexanecarbonyl}-3-cyclohexylpyrrolidine-2-carboxamide]-3-methyl-1-benzofuran-2-carboxylate

[Formula 260]

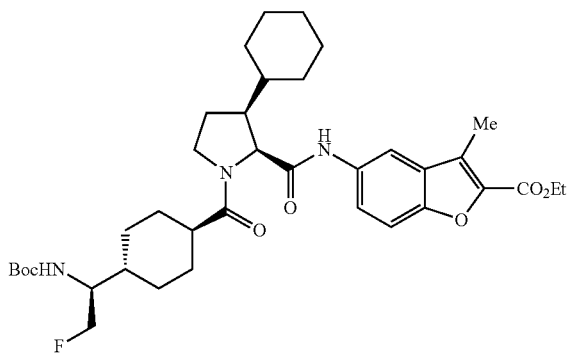

The same procedure as described in Reference Example 1 was carried out to obtain the title compound (141.9 mg, 86%) from the compound of Reference Example 55-3 (86.2 mg, 0.1986 mmol) and the compound of Reference Example 53-3 (70.0 mg, 0.2419 mmol).

MS (ESI+) 670 (M+1, 100%)

Reference Example 56

5-[(2S,3S)-1-{trans-4-[(1S)-1-(tert-Butoxycarbonyl)amino-2-fluoroethyl]cyclohexanecarbonyl}-3-phenylpyrrolidine-2-carboxamide]-1-benzofuran-2-carboxylic acid

[Formula 261]

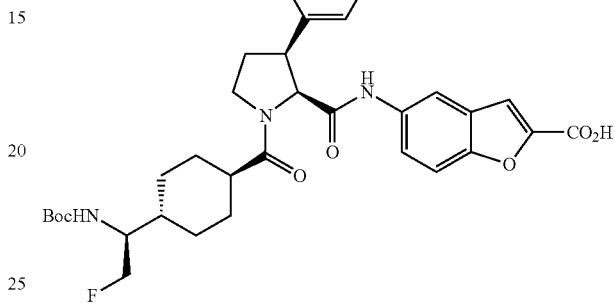

The same procedure as described in Reference Example 3 was carried out to obtain the title compound (206.3 mg, 82%) from the compound of Reference Example 56-1 (263.6 mg, 0.406 mmol).

MS (ESI+) 622 (M+1, 100%)

Reference Example 56-1

Ethyl 5-[(2S,3S)-1-{trans-4-[(1S)-1-(tert-butoxycarbonyl)amino-2-fluoroethyl]cyclohexanecarbonyl}-3-phenylpyrrolidine-2-carboxamide]-1-benzofuran-2-carboxylate

[Formula 262]

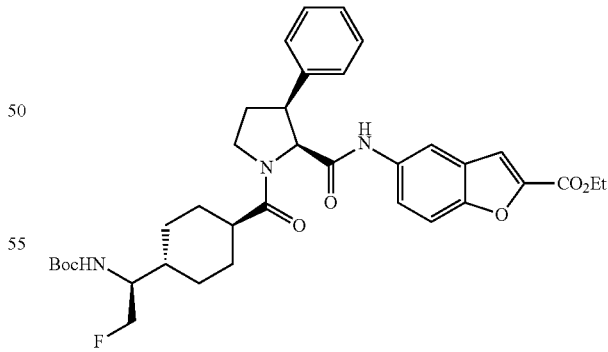

The same procedure as described in Reference Example 1 was carried out to obtain the title compound (263.6 mg, 90%) from the compound of Reference Example 48-1 (188.0 mg, 0.453 mmol) and the compound of Reference Example 53-3 (131 mg, 0.453 mmol).

MS (ESI+) 650 (M+1, 42%)

Reference Example 57

5-[(2S,3R)-1-{trans-4-[(1S)-1-(tert-Butoxycarbonyl)amino-2-fluoroethyl]cyclohexanecarbonyl}-3-phenylpyrrolidine-2-carboxamide]-1-benzofuran-2-carboxylic acid

[Formula 263]

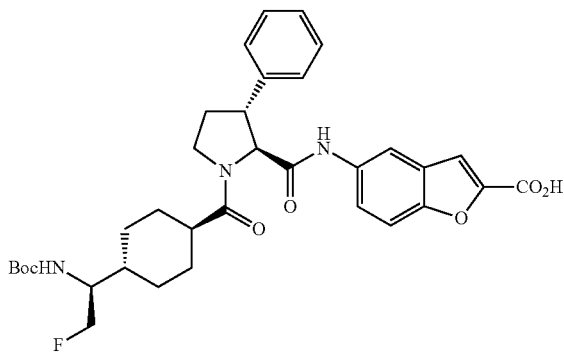

The same procedure as described in Reference Example 3 was carried out to obtain the title compound (219 mg, 97%) from the compound of Reference Example 57-1 (235.3 mg, 0.362 mmol).

MS (ESI+) 622 (M+1, 100%)

Reference Example 57-1

Ethyl 5-[(2S,3R)-1-{trans-4-[(1S)-1-(tert-butoxycarbonyl)amino-2-fluoroethyl]cyclohexanecarbonyl}-3-phenylpyrrolidine-2-carboxamide]-1-benzofuran-2-carboxylate

[Formula 264]

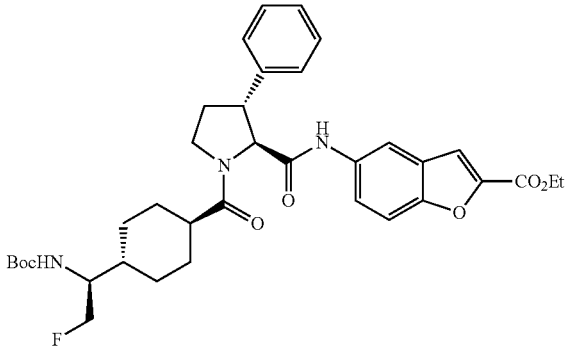

The same procedure as described in Reference Example 1 was carried out to obtain the title compound (235.3 mg, 79%) from the compound of Reference Example 45-2 (173.5 mg, 0.458 mmol) and the compound of Reference Example 53-3 (133 mg, 0.458 mmol).

MS (ESI+) 650 (M+1, 100%)

Reference Example 58 tert-Butyl [1-(trans-4-{[(2S,3R)-3-cyclohexyl-2-(quinolin-6-ylcarbamoyl)pyrrolidin-1-yl]carbonyl}cyclohexyl)ethyl]carbamate

[Formula 265]

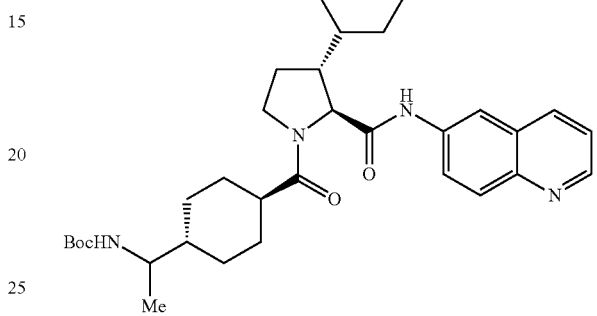

The same procedure as described in Reference Example 1 was carried out to obtain the title compound (12.4 mg, 46%) from the compound of Reference Example 58-2 (14.9 mg, 0.0463 mmol) and the compound of Reference Example 7-9 (15.8 mg, 0.0554 mmol).

MS (ESI+) 577 (M+1, 100%)

Reference Example 58-1 tert-Butyl (2S,3R)-3-cyclohexyl-2-(quinolin-6-ylcarbamoyl)pyrrolidine-1-carboxylate

[Formula 266]

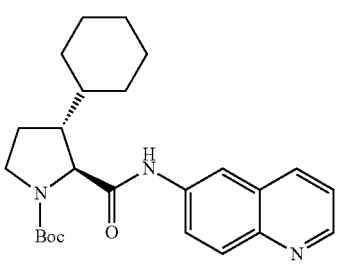

The same procedure as described in Reference Example 1-1 was carried out to obtain the title compound (19.6 mg, 6.5%) from the compound of Reference Example 41-1 (213.0 mg, 0.716 mmol) and 6-aminoquinoline (124.0 mg, 0.86 mmol).

MS (ESI+) 424 (M+1, 100%)

Reference Example 58-2

(2S,3R)-3-Cyclohexyl-N-(quinolin-6-yl)pyrrolidine-2-carboxamide

[Formula 267]

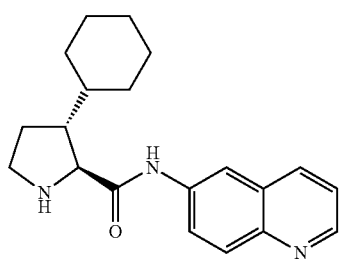

The same procedure as described in Reference Example 7-2 was carried out to obtain the title compound (14.9 mg, 100%) from the compound of Reference Example 58-1 (19.6 mg, 0.0463 mmol).

MS (ESI+) 324 (M+1, 100%)

Reference Example 59 tert-Butyl [1-(trans-4-{[(2S,3S)-3-cyclohexyl-2-(2-hydroxymethyl-1-benzofuran-5-ylcarbamoyl)pyrrolidin-1-yl]carbonyl}cyclohexyl)-2-fluoroethyl]carbamate

[Formula 268]

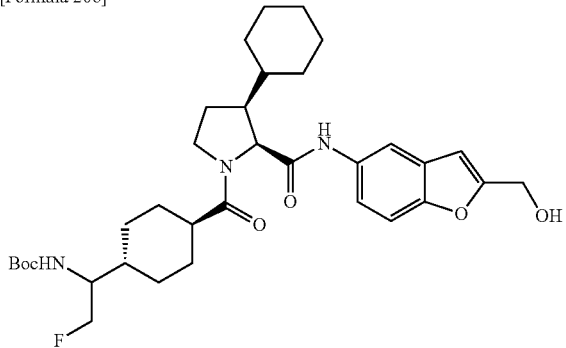

To a solution of the compound of Reference Example 50 (92.0 mg, 0.1466 mmol) in THF (2.0 mL), triethylamine (40.9 µL, 0.294 mmol) and chloroethyl formate (40.9 µL, 0.22 mmol) were added in an ice bath, and the mixture was stirred for 1 hour. An aqueous solution (1.0 mL) of sodium borohydride (11.1 mg, 0.293 mmol) was added dropwise to the reaction solution in an ice bath, and the mixture was stirred for 2 hours. A saturated aqueous solution of ammonium chloride was added to the reaction solution, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (29.2 mg, 32%).

MS (ESI+) 614 (M+1, 100%)

Reference Example 60

[(2,2-Dimethylpropanoyl)oxy]methyl 4-[(2S,3S)-1-{trans-4-[1-(tert-butoxycarbonylamino)ethyl]cyclohexanecarbonyl}-3-phenylpyrrolidine-2-carboxamide]-2-fluorobenzoate

[Formula 269]

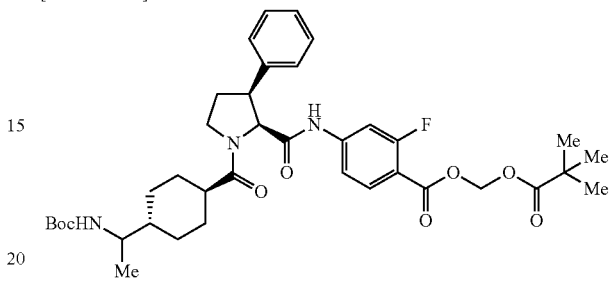

To a solution of the compound of Reference Example 8 (63.0 mg, 0.108 mmol) in DMF (2 mL), potassium bicarbonate (11.9 mg, 0.119 mmol) and chloromethyl pivalate (31.6 µL, 0.216 mmol) were added, and the mixture was stirred at room temperature for 5 hours. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (53.4 mg, 71%).

MS (ESI+) 696 (M+1, 20%)

Reference Example 61

[(2,2-Dimethylpropanoyl)oxy]methyl 4-[(2S,3S)-1-{trans-4-[1-(tert-butoxycarbonylamino)ethyl]cyclohexanecarbonyl}-3-cyclohexylpyrrolidine-2-carboxamide]-2-fluorobenzoate

[Formula 270]

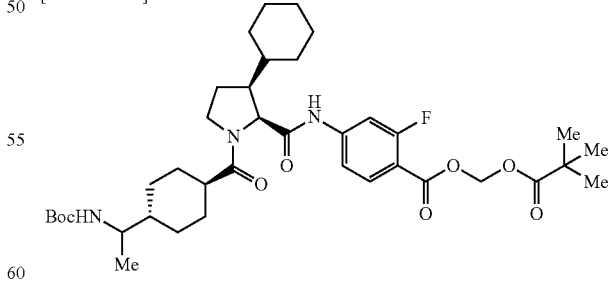

The same procedure as described in Reference Example 60 was carried out to obtain the title compound (51.4 mg, 87%) from the compound of Reference Example 27 (49.3 mg, 0.0839 mmol).

MS (ESI+) 702 (M+1, 18%)

Reference Example 62

[(2,2-Dimethylpropanoyl)oxy]methyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate

[Formula 271]

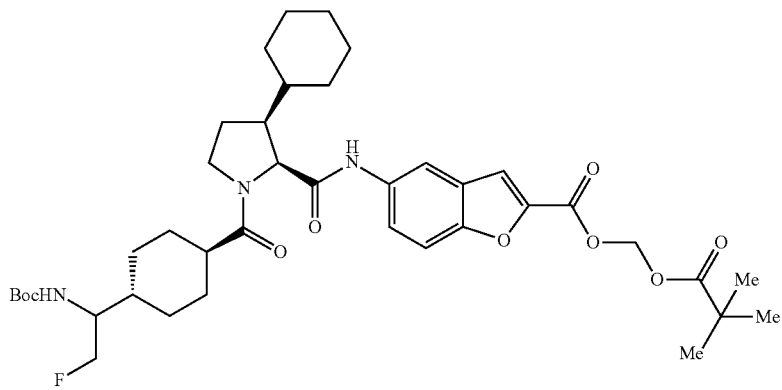

To a solution of the compound of Reference Example 50 (102.6 mg, 0.163 mmol) in DMF (2 mL), potassium carbonate (22.6 mg, 0.164 mmol) and iodine methyl pivalate (59.3 mg, 0.245 mmol) were added, and the mixture was stirred at room temperature for 18 hours. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (128.9 mg, >99%).

MS (ESI+) 742 (M+1, 18%)

Reference Example 63

3-(Morpholin-4-yl)propyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate

[Formula 272]

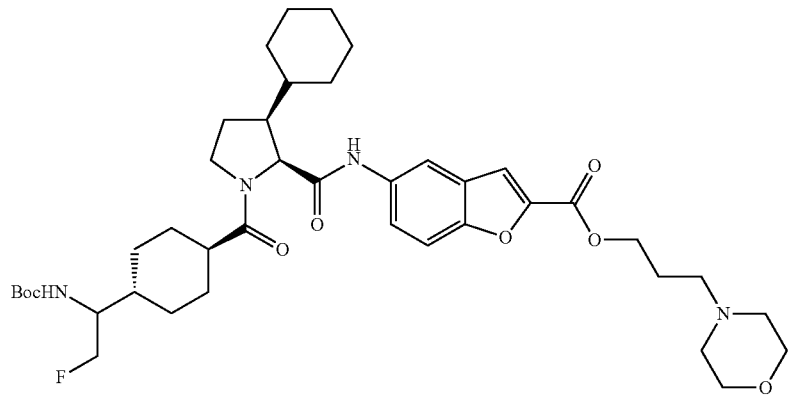

To a solution of the compound of Reference Example 50 (336.8 mg, 0.537 mmol) in DMF (3 mL), 1-hydroxybenzotriazole (164 mg, 1.08 mmol), WSC.HCl (206 mg, 1.08 mmol), triethylamine (224 μL, 1.61 mmol), and 3-morpholino propanol (117 mg, 0.806 mmol) were added, and the mixture was stirred at room temperature for 2 hours. A saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution, then dried over sodium sulfate and filtered, and the filtrate was concentrated under reduced pressure. The obtained residue was purified by silica gel column chromatography to obtain the title compound (300.6 mg, 74%).

MS (ESI+) 755 (M+1, 100%)

Reference Example 64

2-(Morpholin-4-yl)ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate the mixture was stirred at 80° C. for 3 hours. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (79.7 mg, 83%).

MS (ESI+) 741 (M+1, 100%)

Reference Example 65

1-{[(Propan-2-yloxy)carbonyl]oxy}ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate

[Formula 273]

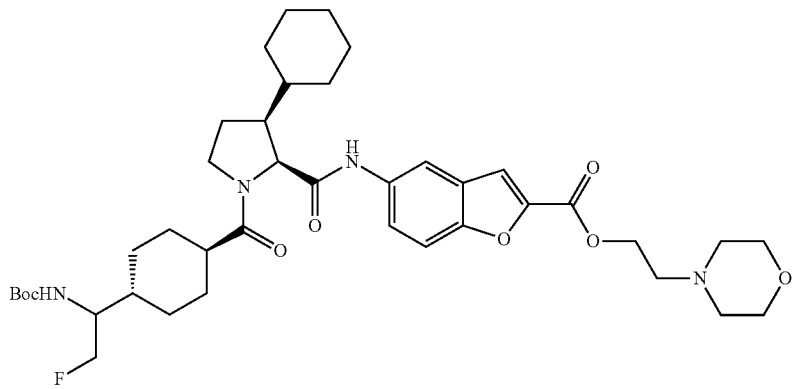

To a solution of the compound of Reference Example 50 (81.7 mg, 0.130 mmol) in DMF (2 mL), potassium carbonate (43.1 mg, 0.312 mmol) and N-(2-chloroethyl)morpholine hydrochloride (29.1 mg, 0.156 mmol) were added, and

[Formula 274]

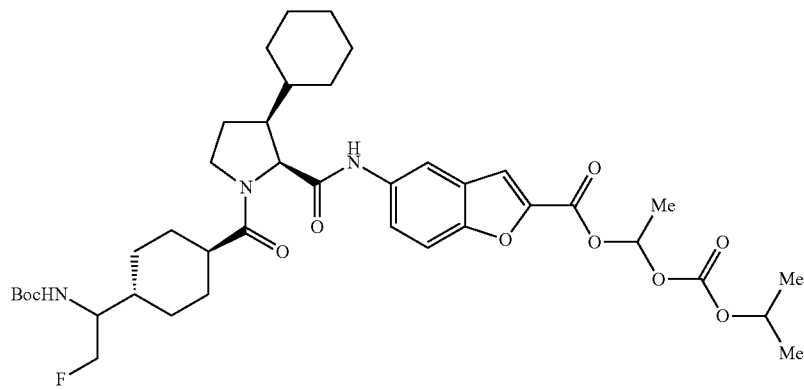

To a solution of the compound of Reference Example 50 (100.9 mg, 0.161 mmol) in DMF (2 mL), potassium carbonate (44.4 mg, 0.321 mmol) and 1-chloroethyl isopropylcarbamate (40.2 mg, 0.241 mmol) were added, and the mixture was stirred for 1.5 hours at 60° C. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (41.6 mg, 34%).

MS (ESI+) 758 (M+1, 20%)

Reference Example 66

Butanoyloxymethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate Reference Example 67

3-Methoxypropyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate

[Formula 276]

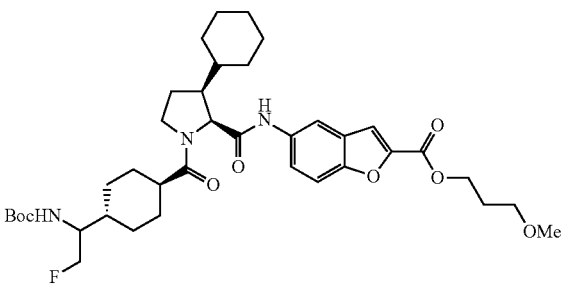

[Formula 275]

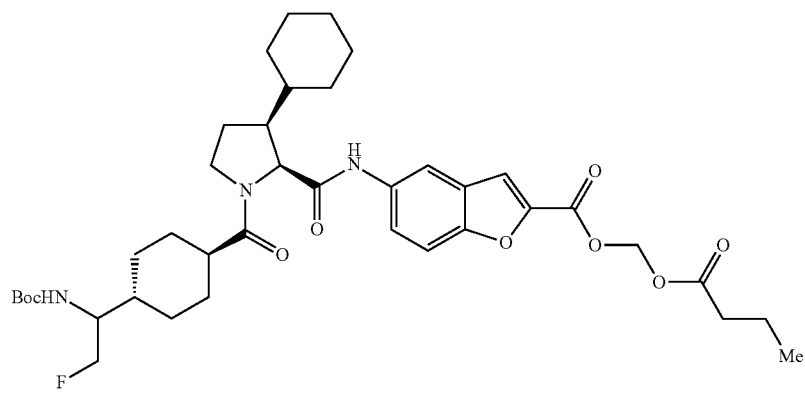

The same procedure as described in Reference Example 65 was carried out to obtain the title compound (12.1 mg, 17%) from the compound of Reference Example 50 (58.9 mg, 0.0938 mmol).

MS (ESI+) 728 (M+1, 33%)

To a solution of the compound of Reference Example 50 (114.3 mg, 0.182 mmol) in DMF (2 mL), potassium carbonate (50.3 mg, 0.364 mmol) and 1-bromo-3-methoxypropane (41.8 mg, 0.273 mmol) were added, and the mixture was stirred at 50° C. for 1 hour. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (121.2 mg, 95%).

MS (ESI+) 700 (M+1, 68%)

Reference Example 68

{[(Propan-2-yloxy)carbonyl]oxy}methyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate

[Formula 277]

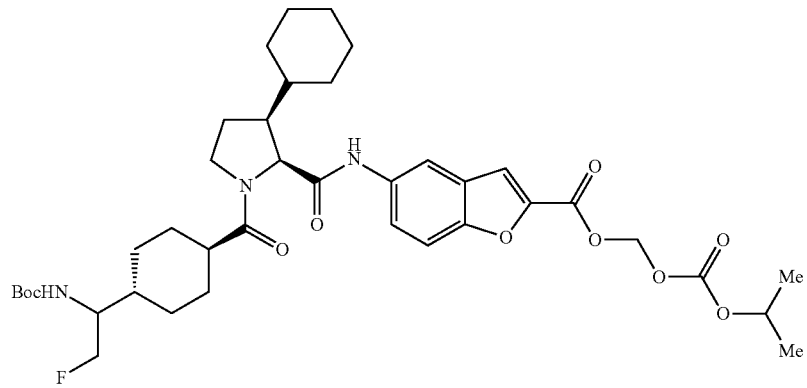

The same procedure as described in Reference Example 67 was carried out to obtain the title compound (42.8 mg, 43%) from the compound of Reference Example 50 (83.4 mg, 0.133 mmol).

MS (ESI+) 744 (M+1, 60%)

Reference Example 69

3-Methoxypropyl 5-[(2S,3S)-1-{trans-4-[(1S)-1-(tert-butoxycarbonyl)amino-2-fluoroethyl]cyclohexanecarbonyl}-3-cyclohexylpyrrolidine-2-carboxamide]-3-methyl-1-benzofuran-2-carboxylate

[Formula 278]

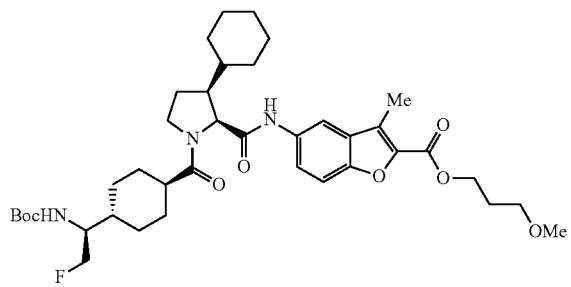

The same procedure as described in Reference Example 67 was carried out to obtain the title compound (60.7 mg, 87%) from the compound of Reference Example 55 (62.5 mg, 0.0974 mmol).

MS (ESI+) 714 (M+1, 48%)

Reference Example 70

Tetrahydrofuran-2-ylmethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-1-benzofuran-2-carboxylate

[Formula 279]

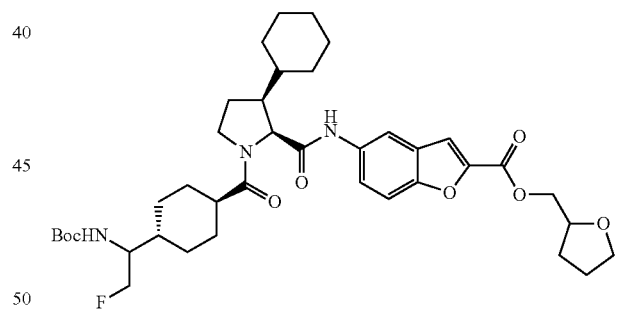

To a solution of the compound of Reference Example 50 (31.2 mg, 0.0497 mmol) in DMF (2 mL), potassium carbonate (13.7 mg, 0.0991 mmol) and tetrahydrofurfuryl bromide (12.3 mg, 0.0745 mmol) were added, and the mixture was stirred at 90° C. for 5 hours. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (25.8 mg, 73%).

MS (ESI+) 712 (M+1, 50%)

Reference Example 71

3-Methoxypropyl 5-[(2S,3S)-1-{trans-4-[(1S)-1-(tert-butoxycarbonyl)amino-2-fluoroethyl]cyclohexanecarbonyl}-3-phenylpyrrolidine-2-carboxamide]-1-benzofuran-2-carboxylate

[Formula 280]

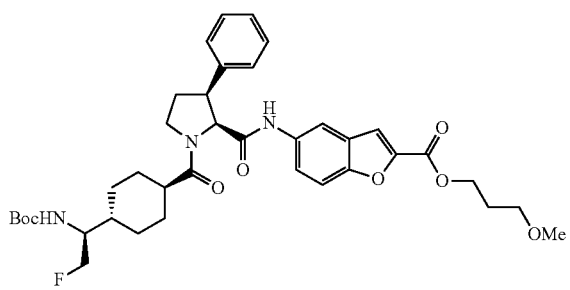

The same procedure as described in Reference Example 67 was carried out to obtain the title compound (121.0 mg, 77%) from the compound of Reference Example 56 (141.4 mg, 0.227 mmol).
MS (ESI+) 694 (M+1, 100%)

Reference Example 72

3-Methoxypropyl 5-[(2S,3R)-1-{trans-4-[(1S)-1-(tert-butoxycarbonyl)amino-2-fluoroethyl]cyclohexanecarbonyl}-3-phenylpyrrolidine-2-carboxamide]-1-benzofuran-2-carboxylate

[Formula 281]

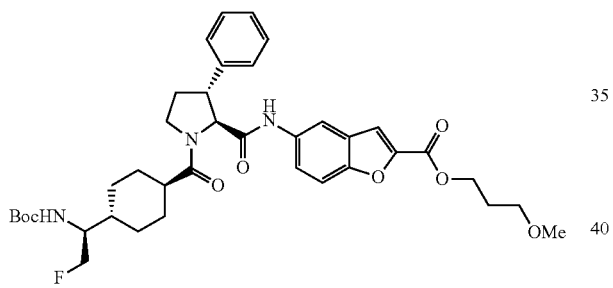

The same procedure as described in Reference Example 67 was carried out to obtain the title compound (114.0 mg, 83%) from the compound of Reference Example 57 (123.8 mg, 0.199 mmol).
MS (ESI+) 694 (M+1, 100%)

Reference Example 73

3-Methoxypropyl 5-[(2S,3S)-1-{trans-4-[(1S)-1-(tert-butoxycarbonyl)amino-2-fluoroethyl]cyclohexanecarbonyl}-3-cyclohexylpyrrolidine-2-carboxamide]-1-benzofuran-2-carboxylate

[Formula 282]

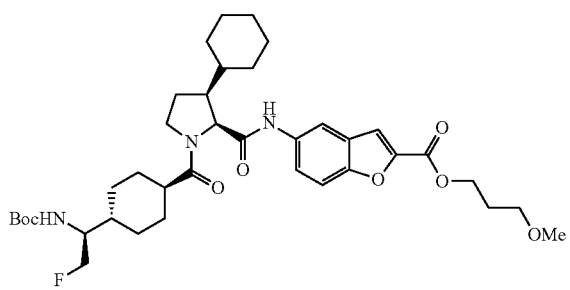

The same procedure as described in Reference Example 67 was carried out to obtain the title compound (142.4 mg, 88%) from the compound of Reference Example 53 (144.5 mg, 0.230 mmol).
MS (ESI+) 700 (M+1, 68%)

Reference Example 74

Ethyl 4-[(2S,3S)-1-{trans-4-[1-(tert-butoxycarbonylamino)propyl]cyclohexanecarbonyl}-3-cyclohexylpyrrolidine-2-carboxamide]benzoate

[Formula 283]

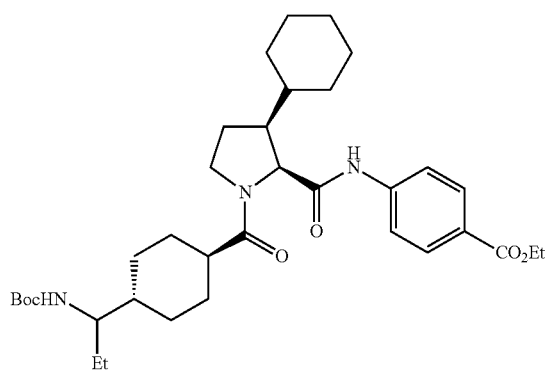

The same procedure as described in Reference Example 1 was carried out to obtain the title compound (90.0 mg, 92%) from the compound of Reference Example 74-2 (55.0 mg, 0.16 mmol) and the compound of Reference Example 26-5 (50.0 mg, 0.18 mmol).

MS (ESI+) 612 (M+1, 21%)

Reference Example 74-1

Ethyl 4-[(2S,3S)-1-tert-butoxycarbonyl-3-cyclohexylpyrrolidine-2-carboxamide]benzoate

[Formula 284]

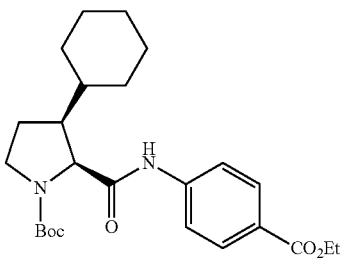

The same procedure as described in Reference Example 27-1 was carried out to obtain the title compound (54.0 mg, 45%) from the compound of Reference Example 11-1 (80.0 mg, 0.27 mmol) and ethyl 4-aminobenzoate (53.0 mg, 0.32 mmol).

MS (ESI+) 445 (M+1, 20%)

Reference Example 74-2

Ethyl 4-[(2S,3S)-3-cyclohexylpyrrolidine-2-carboxamide]benzoate trifluoroacetate

[Formula 285]

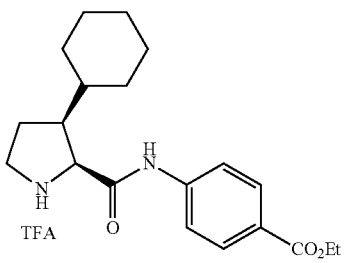

The same procedure as described in Reference Example 9-2 was carried out to obtain the title compound (55.0 mg, 100%) from the compound of Reference Example 74-1 (54.0 mg, 0.12 mmol).

MS (ESI+) 345 (M+1, 100%)

Reference Example 75

Methyl 4-[(2S,3R)-1-{trans-4-[1-(tert-butoxycarbonyl)amino-2-fluoroethyl]cyclohexanecarbonyl}-3-phenylpyrrolidine-2-carboxamide]-3-fluorobenzoate

[Formula 286]

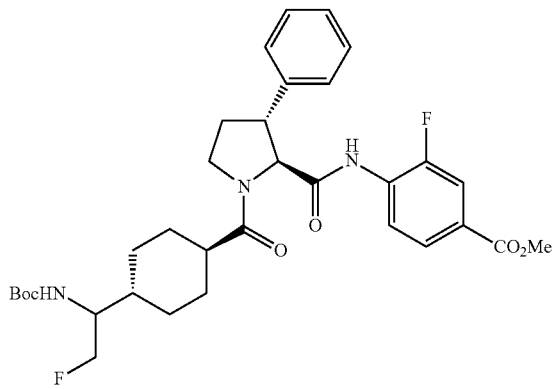

The same procedure as described in Reference Example 1 was carried out to obtain the title compound (33.0 mg, 60%) from the compound of Reference Example 28-2 (40.0 mg, 0.09 mmol) and the compound of Reference Example 31-11 (29.0 mg, 0.1 mmol).

MS (ESI+) 614 (M+1, 27%)

Reference Example 76

3-Methoxypropyl 5-[(2S,3S)-1-{trans-4-[1-(tert-butoxycarbonyl)amino-2-fluoroethyl]cyclohexanecarbonyl}-3-phenylpyrrolidine-2-carboxamide]-1H-indole-2-carboxylate

[Formula 287]

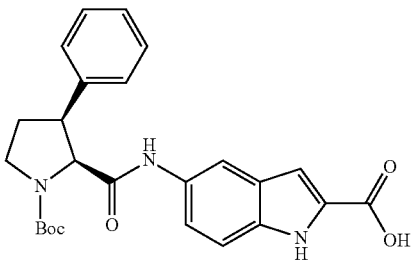

The same procedure as described in Reference Example 1 was carried out to obtain the title compound (92.0 mg, 66%) from the compound of Reference Example 76-3 (104.0 mg, 0.20 mmol) and the compound of Reference Example 31-11 (70.0 mg, 0.24 mmol).

MS (ESI+) 693 (M+1, 100%)

Reference Example 76-1

5-[(2S,3S)-1-tert-Butoxycarbonyl-3-phenylpyrrolidine-2-carboxamide]-1H-indole-2-carboxylic acid

[Formula 288]

The compound of Reference Example 2-2 (100.0 mg, 0.21 mmol) was dissolved in methanol (10 mL), a 1 mol/L aqueous solution of sodium hydroxide (5 mL) was added, and the mixture was stirred at 60° C. for 3 hours. A 5% aqueous solution of potassium hydrogensulfate was added to the reaction solution, followed by extraction with chloroform twice. The organic layer was washed with a saturated saline solution, dried over anhydrous sodium sulfate and filtered, and then the organic layer was concentrated under reduced pressure to obtain the title compound (94.0 mg, 100%).

MS (ESI+) 450 (M+1, 100%)

Reference Example 76-2

3-Methoxypropyl 5-[(2S,3S)-1-tert-butoxycarbonyl-3-phenylpyrrolidine-2-carboxamide]-1H-indole-2-carboxylate

[Formula 289]

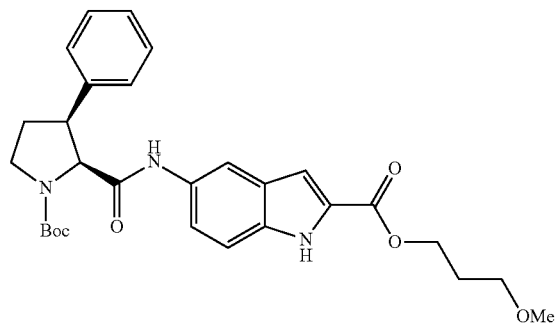

To a solution of the compound of Reference Example 76-1 (94.0 mg, 0.21 mmol) in DMF (5 mL), potassium carbonate (87.0 mg, 0.63 mmol) and 1-bromo-3-methoxypropane (48.0 mg, 0.31 mmol) were added, and the mixture was stirred at room temperature overnight. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (105.0 mg, 96%).

MS (ESI+) 522 (M+1, 100%)

Reference Example 76-3

3-Methoxypropyl 5-[(2S,3S)-3-phenylpyrrolidine-2-carboxamide]-1H-indole-2-carboxylate trifluoroacetate

[Formula 290]

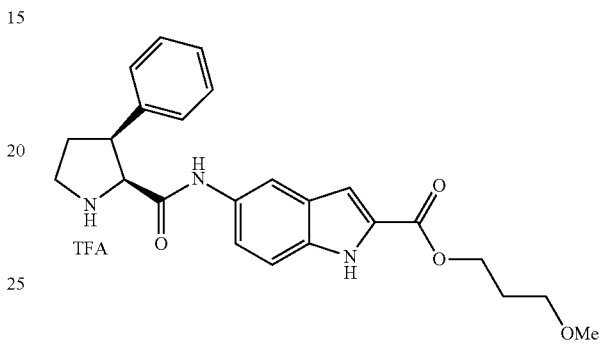

The same procedure as described in Reference Example 9-2 was carried out to obtain the title compound (104.0 mg, 100%) from the compound of Reference Example 76-2 (105.0 mg, 0.20 mmol).

MS (ESI+) 422 (M+1, 100%)

Reference Example 77

3-Methoxypropyl 5-[(2S,3R)-1-{trans-4-[1-(tert-butoxycarbonyl)amino-2-fluoroethyl]cyclohexanecarbonyl}-3-phenylpyrrolidine-2-carboxamide]-1H-indole-2-carboxylate

[Formula 291]

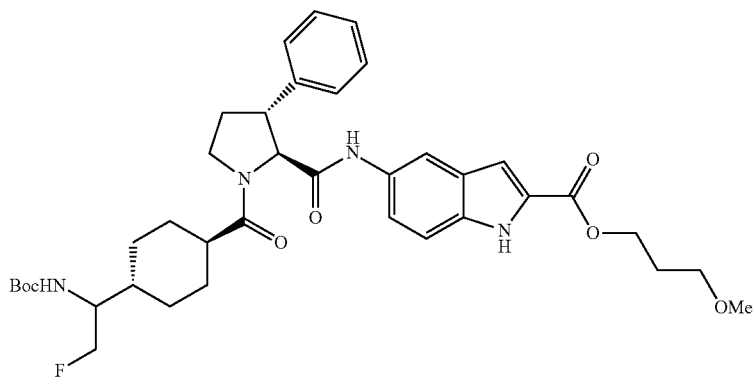

The same procedure as described in Reference Example 1 was carried out to obtain the title compound (96.0 mg, 66%) from the compound of Reference Example 77-4 (109.0 mg, 0.21 mmol) and the compound of Reference Example 31-11 (73.0 mg, 0.25 mmol).

MS (ESI+) 693 (M+1, 100%)

Reference Example 77-1

Ethyl 5-[(2S,3R)-1-tert-butoxycarbonyl-3-phenylpyrrolidine-2-carboxamide]-1H-indole-2-carboxylate

[Formula 292]

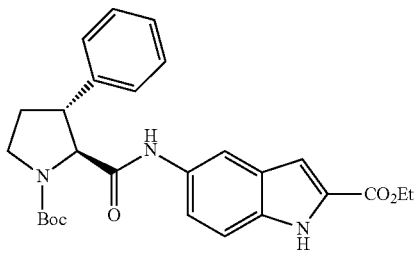

The same procedure as described in Reference Example 1 was carried out to obtain the title compound (308.0 mg, 94%) from the compound of Reference Example 31-4 (200.0 mg, 0.69 mmol) and the compound of Reference Example 2-1 (168.0 mg, 0.82 mmol).

MS (ESI+) 478 (M+1, 100%)

Reference Example 77-2

5-[(2S,3R)-1-tert-Butoxycarbonyl-3-phenylpyrrolidine-2-carboxamide]-1H-indole-2-carboxylic acid

[Formula 293]

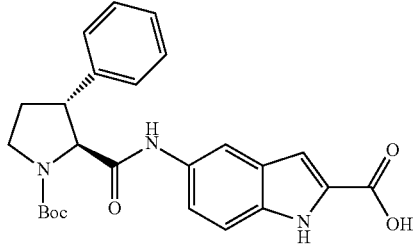

The same procedure as described in Reference Example 76-1 was carried out to obtain the title compound (94.0 mg, 100%) from the compound of Reference Example 77-1 (100.0 mg, 0.21 mmol).

MS (ESI+) 450 (M+1, 100%)

Reference Example 77-3

3-Methoxypropyl 5-[(2S,3R)-1-tert-butoxycarbonyl-3-phenylpyrrolidine-2-carboxamide]-1H-indole-2-carboxylate

[Formula 294]

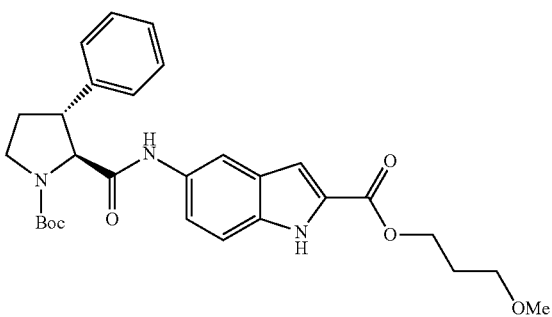

The same procedure as described in Reference Example 76-2 was carried out to obtain the title compound (110.0 mg, 100%) from the compound of Reference Example 77-2 (94.0 mg, 0.21 mmol).

MS (ESI+) 522 (M+1, 100%)

Reference Example 77-4

3-Methoxypropyl 5-[(2S,3R)-3-phenylpyrrolidine-2-carboxamide]-1H-indole-2-carboxylate trifluoroacetate

[Formula 295]

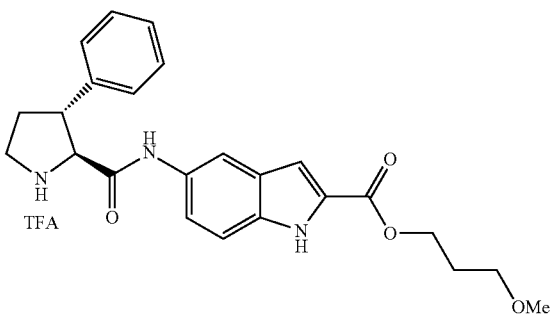

The same procedure as described in Reference Example 9-2 was carried out to obtain the title compound (109.0 mg, 100%) from the compound of Reference Example 77-3 (110.0 mg, 0.21 mmol).

MS (ESI+) 422 (M+1, 100%).

Reference Example 78

4-({(3S)-1-[(trans-4-{(1S)-1-[(tert-Butoxycarbonyl)amino]-2-fluoroethyl}cyclohexyl)carbonyl]-3-cyclohexyl-L-prolyl}amino)benzoic acid

[Formula 296]

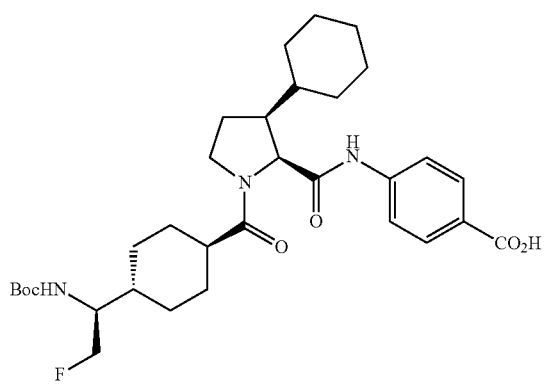

The same procedure as described in Reference Example 19 was carried out to obtain the title compound (60.0 mg, 79%) from the compound of Reference Example 78-1 (80.0 mg, 0.13 mmol).

MS (ESI+) 588 (M+1, 100%)

Reference Example 78-1

Ethyl 4-({(3S)-1-[(trans-4-{(1S)-1-[(tert-butoxycarbonyl)amino]-2-fluoroethyl}cyclohexyl)carbonyl]-3-cyclohexyl-L-prolyl}amino)benzoate

[Formula 297]

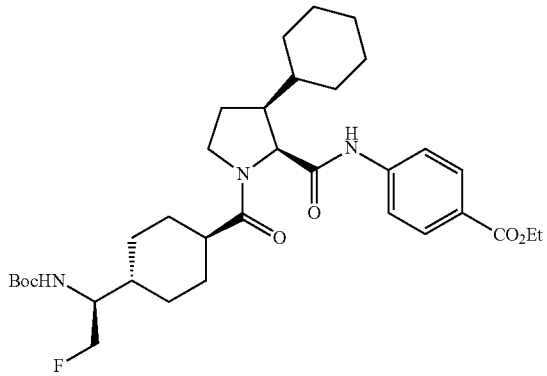

The same procedure as described in Reference Example 1 was carried out to obtain the title compound (280.0 mg, 92%) from the compound of Reference Example 74-2 (218.0 mg, 0.494 mmol) and the compound of Reference Example 53-3 (150.0 mg, 0.518 mmol).

MS (ESI+) 616 (M+1, 100%)

Reference Example 79

5-{[(3S)-1-[(trans-4-{(1S)-1-[(tert-Butoxycarbonyl)amino]-2-fluoroethyl}cyclohexyl)carbonyl]-3-(4-methoxycyclohexyl)-L-prolyl]amino}-1-benzofuran-2-carboxylic acid

[Formula 298]

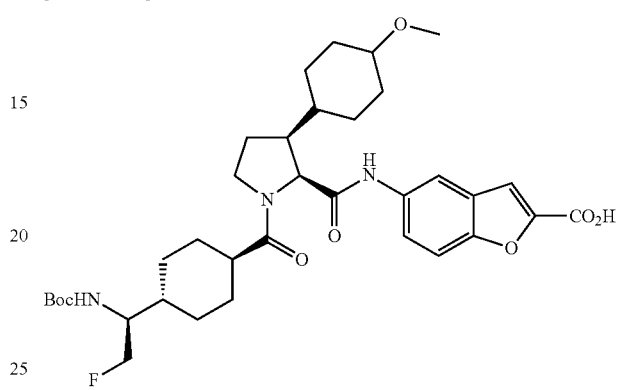

The same procedure as described in Reference Example 19 was carried out to obtain the title compound (3.2 mg, 33%) from the compound of Reference Example 79-1 (10.0 mg, 0.015 mmol).

MS (ESI+) 658 (M+1, 100%)

Reference Example 79-1

Ethyl 5-{[(3S)-1-[(trans-4-{(1S)-1-[(tert-butoxycarbonyl)amino]-2-fluoroethyl}cyclohexyl)carbonyl]-3-(4-methoxycyclohexyl)-L-prolyl]amino}-1-benzofuran-2-carboxylate

[Formula 299]

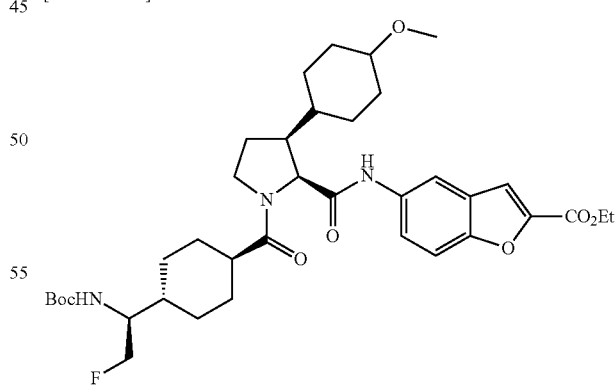

The same procedure as described in Reference Example 1 was carried out to obtain the title compound (43.0 mg, 43%) from the compound of Reference Example 33-2 (75.0 mg, 0.146 mmol) and the compound of Reference Example 53-3 (51.0 mg, 0.175 mmol).

MS (ESI+) 686 (M+1, 100%)

Reference Example 80

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-ethyl-1H-indole-2-carboxylic acid

[Formula 300]

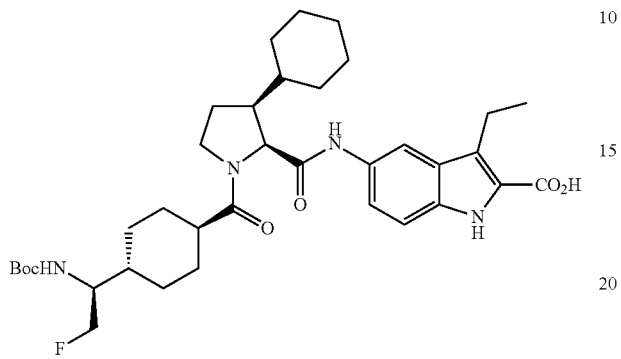

The same procedure as described in Reference Example 19 was carried out to obtain the title compound (7.0 mg, 68%) from the compound of Reference Example 80-7 (11.0 mg, 0.016 mmol).

MS (ESI+) 655 (M+1, 100%)

Reference Example 80-1

Ethyl 5-[(tert-butoxycarbonyl)amino]-1H-indole-2-carboxylate

[Formula 301]

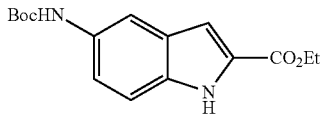

Commercially available ethyl 5-aminoindole-2-carboxylate (250 mg, 1.22 mmol) was dissolved in dichloromethane (15 mL), then triethylamine (0.51 ml, 3.66 mmol) and di-tert-butyl dicarbonate (666 mg, 3.05 mmol) were added, and the mixture was stirred at room temperature for 14 hours. A saturated aqueous solution of ammonium chloride was added to the reaction solution, followed by extraction with ethyl acetate. The organic layer was washed with a saturated saline solution, then dried over sodium sulfate and filtered, and the filtrate was concentrated under reduced pressure to obtain the title compound (247 mg, 67%).

MS (ESI+) 609 (2M+1, 100%)

Reference Example 80-2

Ethyl 3-bromo-5-[(tert-butoxycarbonyl)amino]-1H-indole-2-carboxylate

[Formula 302]

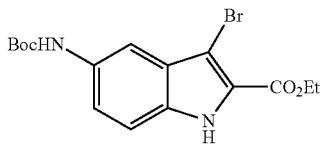

The compound of Reference Example 80-1 (247 mg, 0.812 mmol) was dissolved in dichloromethane (10 mL), then N-bromo succinimide (145 mg, 0.815 mmol) was added, and the mixture was stirred at room temperature for 14 hours. The reaction solution was concentrated, then water was added to the obtained residue, followed by extraction with ethyl acetate. The organic layer was washed with a saturated saline solution, then dried over sodium sulfate and filtered, and the filtrate was concentrated under reduced pressure to obtain the title compound (318 mg, 100%).

MS (ESI+) 327 (M+1)-$^t$Bu, 100%)

Reference Example 80-3

Ethyl 5-[(tert-butoxycarbonyl)amino]-3-ethyl-1H-indole-2-carboxylate

[Formula 303]

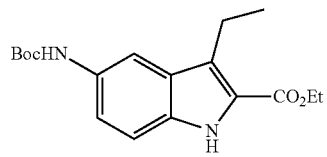

A commercially available solution of diethylzinc hexane (3.3 ml, 3.28 mmol) was added dropwise to a commercially available solution of zinc chloride in THF (13.2 ml, 6.56 mmol), and the mixture was stirred for 1.5 hours at 70° C. The obtained solution was added to a solution of the compound of Reference Example 80-2 (318 mg, 0.82 mmol) and bis(tris-tert-butylphosphine)palladium(0) (84.0 mg, 0.164 mmol) in THF (26 ml), and the mixture was stirred for 1.5 hours at room temperature. Water was added to the reaction solution, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (238.0 mg, 87%).

MS (ESI+) 277 (M+1)-$^t$Bu, 100%)

Reference Example 80-4

Ethyl 5-amino-3-ethyl-1H-indole-2-carboxylate hydrochloride

[Formula 304]

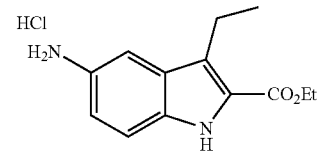

The same procedure as described in Reference Example 1-2 was carried out to obtain the title compound (62.3 mg, 100%) from the compound of Reference Example 80-3 (77.0 mg, 0.232 mmol).

MS (ESI+) 233 (M+I, 100%)

Reference Example 80-5

Ethyl 5-{[(3S)-1-(tert-butoxycarbonyl)-3-cyclohexyl-L-prolyl]amino}-3-ethyl-1H-indole-2-carboxylate

[Formula 305]

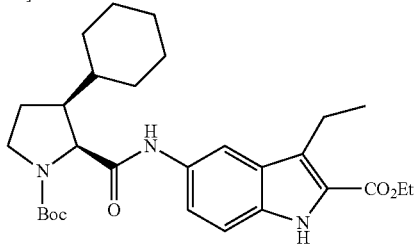

The same procedure as described in Reference Example 1 was carried out to obtain the title compound (20.0 mg, 17%) from the compound of Reference Example 11-1 (62.0 mg, 0.208 mmol) and the compound of Reference Example 80-4 (62.3 mg, 0.232 mmol).
MS (ESI+) 512 (M+1, 100%)

Reference Example 80-6

Ethyl 5-{[(3S)-3-cyclohexyl-L-prolyl]amino}-3-ethyl-1H-indole-2-carboxylate trifluoroacetate

[Formula 306]

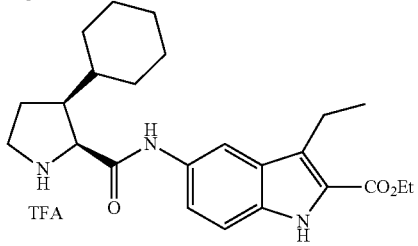

The same procedure as described in Reference Example 9-2 was carried out to obtain the title compound (20.0 mg, 100%) from the compound of Reference Example 80-5 (20.0 mg, 0.039 mmol).
MS (ESI+) 412 (M+1, 100%)

Reference Example 80-7

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-3-ethyl-1H-indole-2-carboxylate

[Formula 307]

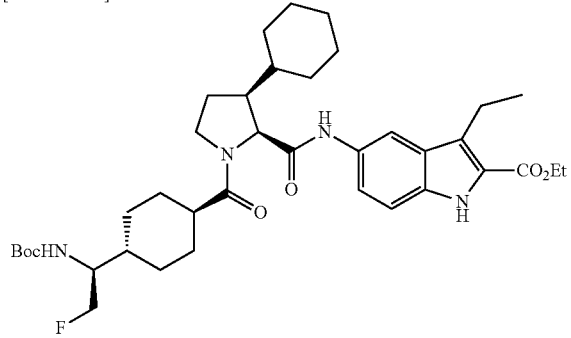

The same procedure as described in Reference Example 1 was carried out to obtain the title compound (11.0 mg, 41%) from the compound of Reference Example 80-6 (20.0 mg, 0.039 mmol) and the compound of Reference Example 53-3 (14.0 mg, 0.047 mmol).
MS (ESI+) 683 (M+1, 100%)

Reference Example 81

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-1H-indole-2-carboxylic acid

[Formula 308]

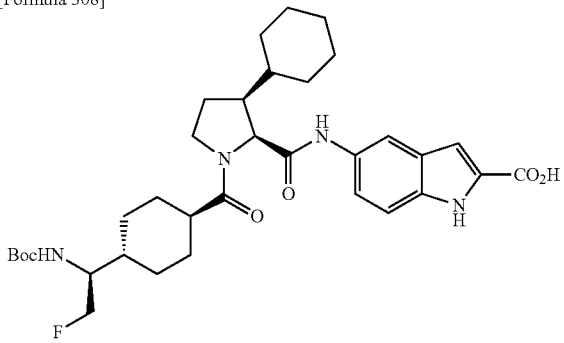

The same procedure as described in Reference Example 19 was carried out to obtain the title compound (18.0 mg, 100%) from the compound of Reference Example 81-1 (19.0 mg, 0.029 mmol).
MS (ESI+) 627 (M+1, 100%)

Reference Example 81-1

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-indole-2-carboxylate

[Formula 309]

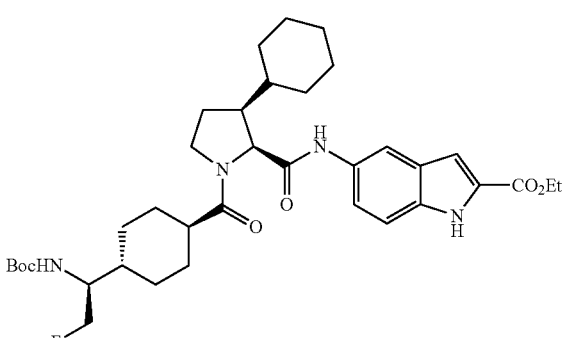

The same procedure as described in Reference Example 1 was carried out to obtain the title compound (40.0 mg, 61%) from the compound of Reference Example 35-1 (48.0 mg, 0.10 mmol) and the compound of Reference Example 53-3 (33.0 mg, 0.11 mmol).
MS (ESI+) 655 (M+1, 100%)

Reference Example 82

3-Methoxypropyl 4-({(3S)-1-[(trans-4-{(1S)-1-[(tert-butoxycarbonyl)amino]-2-fluoroethyl}cyclohexyl)carbonyl]-3-cyclohexyl-L-prolyl}amino)benzoate

[Formula 310]

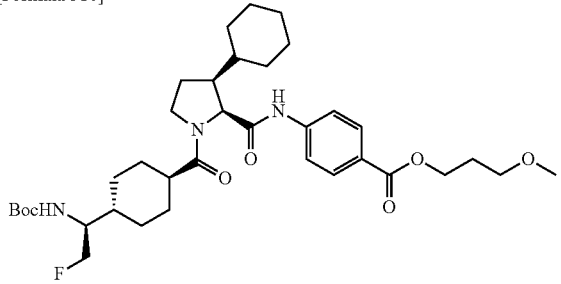

The same procedure as described in Reference Example 1 was carried out to obtain the title compound (23.0 mg, 54%) from the compound of Reference Example 82-3 (31.5 mg, 0.065 mmol) and the compound of Reference Example 53-3 (23.0 mg, 0.079 mmol).
MS (ESI+) 660 (M+1, 100%)

Reference Example 82-1

4-{[(3S)-1-(tert-Butoxycarbonyl)-3-cyclohexyl-L-prolyl]amino}benzoic acid

[Formula 311]

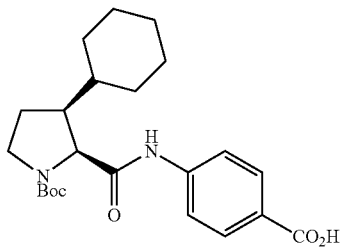

The same procedure as described in Reference Example 19 was carried out to obtain the title compound (41.0 mg, 98%) from the compound of Reference Example 74-1 (45.0 mg, 0.10 mmol).
MS (ESI+) 417 (M+1, 100%)

Reference Example 82-2 tert-Butyl (2S,3S)-3-cyclohexyl-2-({4-[(3-methoxypropoxy)carbonyl]phenyl}carbamoyl)pyrrolidine-1-carboxylate

[Formula 312]

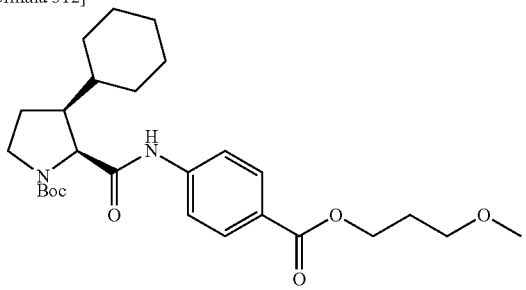

The same procedure as described in Reference Example 67 was carried out to obtain the title compound (32.0 mg, 67%) from the compound of Reference Example 82-1 (41.0 mg, 0.098 mmol).
MS (ESI+) 489 (M+1, 100%)

Reference Example 82-3

3-Methoxypropyl 4-{[(3S)-3-cyclohexyl-L-prolyl]amino}benzoate trifluoroacetate

[Formula 313]

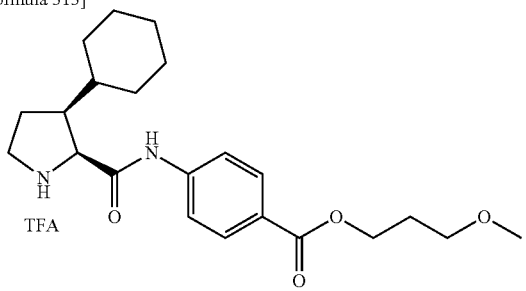

The same procedure as described in Reference Example 9-2 was carried out to obtain the title compound (31.5 mg, 100%) from the compound of Reference Example 82-2 (32.0 mg, 0.065 mmol).
MS (ESI+) 389 (M+1, 100%)

Reference Example 83

3-Methoxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-indole-2-carboxylate

[Formula 314]

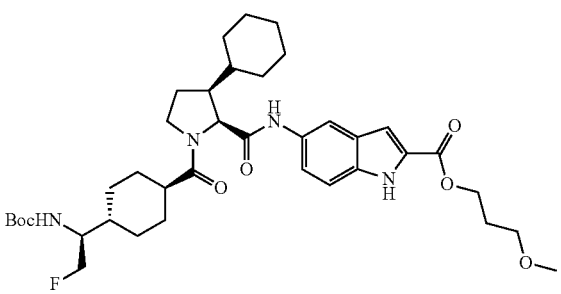

The same procedure as described in Reference Example 1 was carried out to obtain the title compound (48.0 mg, 69%) from the compound of Reference Example 83-3 (54.0 mg, 0.10 mmol) and the compound of Reference Example 53-3 (32.0 mg, 0.11 mmol).
MS (ESI+) 699 (M+1, 100%)

Reference Example 83-1

5-{[(3S)-1-(tert-Butoxycarbonyl)-3-cyclohexyl-L-prolyl]amino}-1H-indole-2-carboxylic acid

[Formula 315]

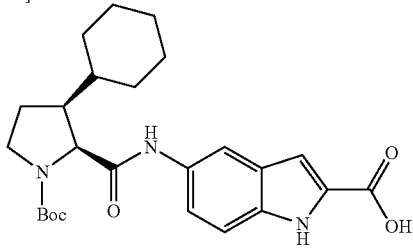

The same procedure as described in Reference Example 19 was carried out to obtain the title compound (141.0 mg, 100%) from the compound of Reference Example 34-1 (150.0 mg, 0.31 mmol).
MS (ESI+) 456 (M+1, 100%)

Reference Example 83-2

3-Methoxypropyl 5-{[(3S)-1-(tert-butoxycarbonyl)-3-cyclohexyl-L-prolyl]amino}-1H-indole-2-carboxylate

[Formula 316]

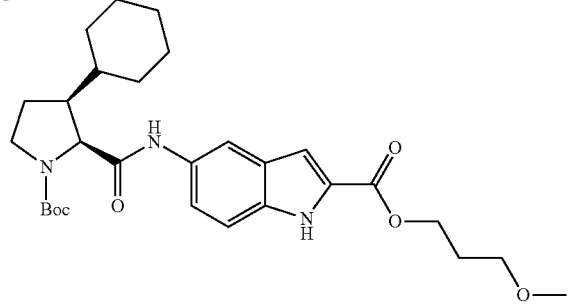

The same procedure as described in Reference Example 67 was carried out to obtain the title compound (144.0 mg, 88%) from the compound of Reference Example 83-1 (141.0 mg, 0.31 mmol).
MS (ESI+) 528 (M+1, 100%)

Reference Example 83-3

3-Methoxypropyl 5-{[(3S)-3-cyclohexyl-L-prolyl]amino}-1H-indole-2-carboxylate trifluoroacetate

[Formula 317]

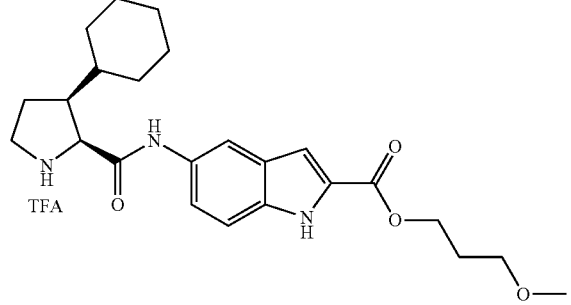

The same procedure as described in Reference Example 9-2 was carried out to obtain the title compound (54 mg, 100%) from the compound of Reference Example 82-2 (54.0 mg, 0.1 mmol).
MS (ESI+) 428 (M+1, 100%)

Reference Example 84

5-{[(3S)-1-[(trans-4-{(1S)-1-[(tert-Butoxycarbonyl)amino]-2-fluoroethyl}cyclohexyl)carbonyl]-3-(cis-4-methoxycyclohexyl)-L-prolyl]amino}-1-benzofuran-2-carboxylic acid

[Formula 318]

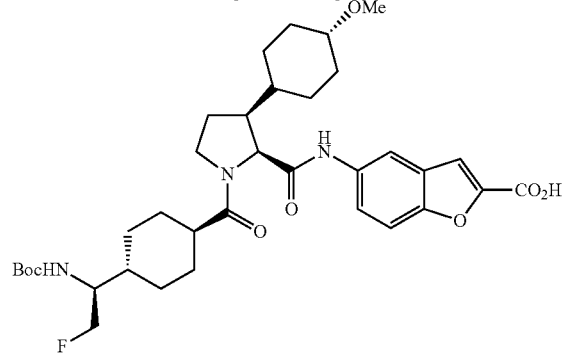

The same procedure as described in Reference Example 19 was carried out to obtain the title compound (5.0 mg, 63%) from the compound of Reference Example 84-1 (8.0 mg, 0.012 mmol).
MS (ESI+) 658 (M+1, 100%)

Reference Example 84-1

Ethyl 5-{[(3S)-1-[(trans-4-{(1S)-1-[(tert-butoxycarbonyl)amino]-2-fluoroethyl}cyclohexyl)carbonyl]-3-(cis-4-methoxycyclohexyl)-L-prolyl]amino}-1-benzofuran-2-carboxylate

[Formula 319]

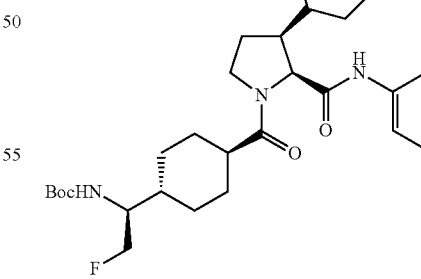

The compound of Reference Example 33-3 as a racemate was separated by HPLC under the following conditions to obtain the title compound.
CHIRALCEL (registered trademark) OD-H (0.46 cmI.D.×25 cmL), Mobile phase: n-hexane/2-propanol (2/1), Flow rate: 1 mL/min, Wavelength: 254 nm, RT 7.475 min

Reference Example 85

5-{[(3S)-1-[(trans-4-{(1S)-1-[(tert-Butoxycarbonyl)amino]-2-fluoroethyl}cyclohexyl)carbonyl]-3-(trans-4-methoxycyclohexyl)-L-prolyl]amino}-1-benzofuran-2-carboxylic acid

[Formula 320]

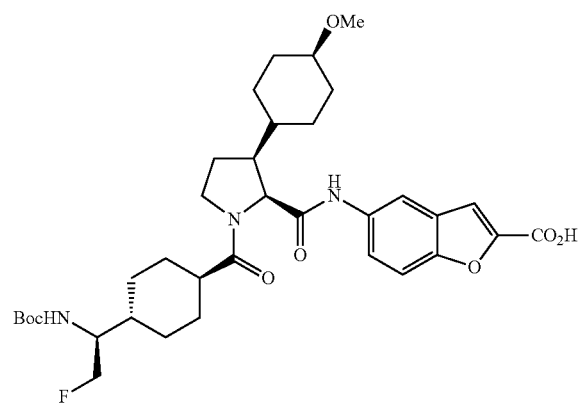

The same procedure as described in Reference Example 19 was carried out to obtain the title compound (20.0 mg, 89%) from the compound of Reference Example 85-1 (23.0 mg, 0.034 mmol).

MS (ESI+) 658 (M+1, 100%)

Reference Example 85-1

Ethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 321]

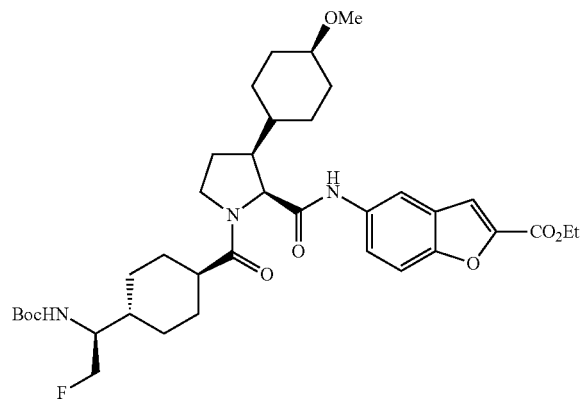

The compound of Reference Example 33-3 as a racemate was separated by HPLC under the following conditions to obtain the title compound.

CHIRALCEL (registered trademark) OD-H (0.46 cmI.D.×25 cmL), Mobile phase: n-hexane/2-propanol (2/1), Flow rate: 1 mL/min, Wavelength: 254 nm, RT 16.613 min

Reference Example 86

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-chloro-1H-indole-2-carboxylic acid

[Formula 322]

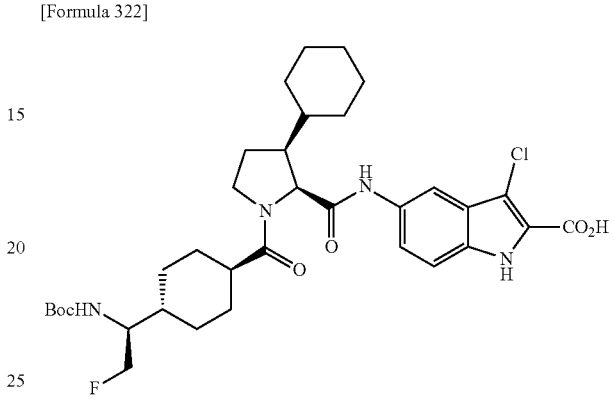

The same procedure as described in Reference Example 19 was carried out to obtain the title compound (20 mg, 87%) from the compound of Reference Example 86-1 (24.3 mg, 0.035 mmol).

MS (ESI+) 661 (M+1, 100%)

Reference Example 86-1

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-3-chloro-1H-indole-2-carboxylate

[Formula 323]

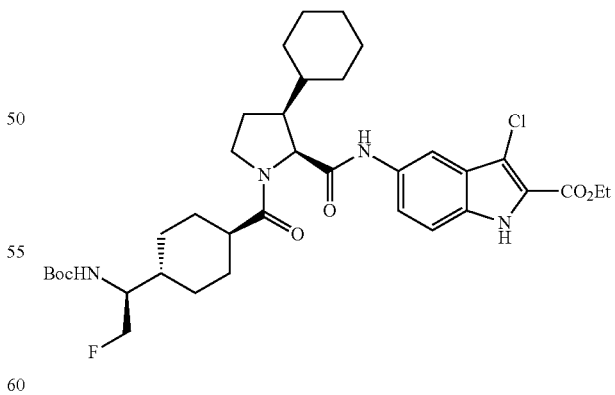

The same procedure as described in Reference Example 1 was carried out to obtain the title compound (24.3 mg, 90%) from the compound of Reference Example 34-3 (20.0 mg, 0.039 mmol) and the compound of Reference Example 53-3 (12.0 mg, 0.041 mmol).

MS (ESI+) 689 (M+1, 100%)

Reference Example 87

(3S)-1-[(trans-4-{(1S)-1-[(tert-Butoxycarbonyl)amino]-2-fluoroethyl}cyclohexyl)carbonyl]-3-cyclohexyl-N-[4-(1H-tetrazol-5-yl)phenyl]-L-prolinamide

[Formula 324]

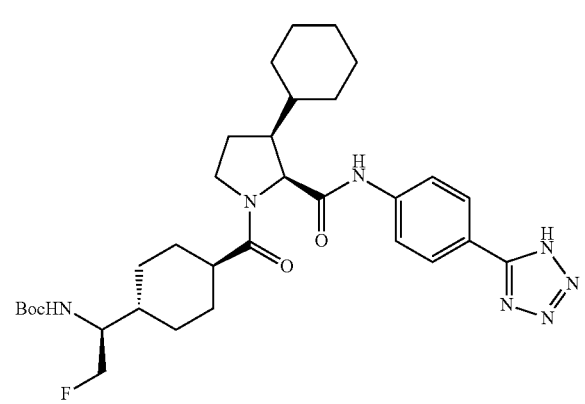

The same procedure as described in Reference Example 1 was carried out to obtain the title compound (36 mg, 14%) from the compound of Reference Example 87-2 (160 mg, 0.424 mmol) and the compound of Reference Example 53-3 (123 mg, 0.425 mmol).

MS (ESI+) 612 (M+1, 100%)

Reference Example 87-1 tert-Butyl (2S,3S)-3-cyclohexyl-2-{[4-(1H-tetrazol-5-yl)phenyl]carbamoyl}pyrrolidine-1-carboxylate

[Formula 325]

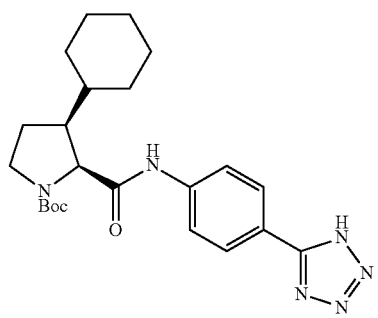

The same procedure as described in Reference Example 138-2 was carried out to obtain the title compound (670 mg, 91%) from the compound of Reference Example 11-1 (500 mg, 1.68 mmol) and commercially available 4-(1H-tetrazol-5-yl)-phenylamine (298 mg, 1.85 mmol).

MS (ESI+) 441 (M+1, 22%)

Reference Example 87-2

(3S)-3-Cyclohexyl-N-[4-(1H-tetrazol-5-yl)phenyl]-L-prolinamide hydrochloride

[Formula 326]

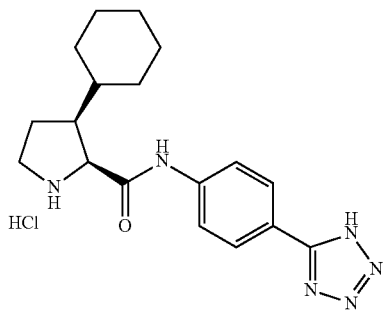

To a solution of the compound of Reference Example 87-1 (668 mg, 1.52 mmol) in chloroform (3 mL), 4 mol/L hydrochloric acid-1,4-dioxane (2.6 ml) was added, and the mixture was stirred for 2 hours. The mixture was concentrated under reduced pressure to obtain the title compound (625 mg, 100%).

MS (ESI+) 341 (M+1, 100%)

Reference Example 88

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-1-(2-fluoroethyl)-1H-indole-2-carboxylic acid

[Formula 327]

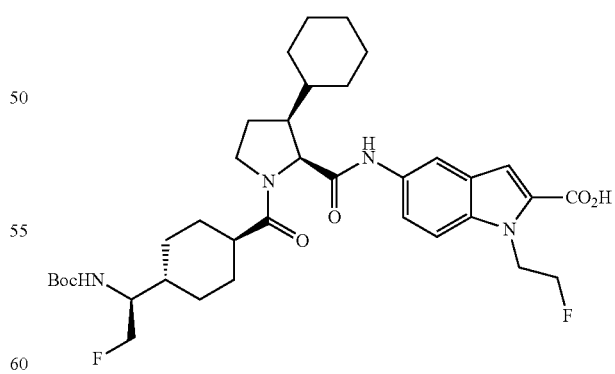

The same procedure as described in Reference Example 19 was carried out to obtain the title compound (22.2 mg, 26%) from the compound of Reference Example 88-5 (81.0 mg, 0.116 mmol).

MS (ESI+) 673 (M+1, 100%)

Reference Example 88-1

Ethyl 1-(2-fluoroethyl)-5-nitro-1H-indole-2-carboxylate

[Formula 328]

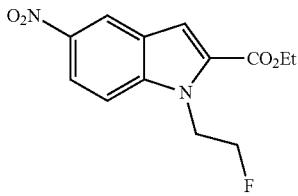

To a solution of commercially available ethyl 5-nitroindole-2-carboxylate (500.0 mg, 2.13 mmol) in DMF (5 mL), potassium carbonate (588.0 mg, 4.26 mmol) and commercially available 1-fluoro-2-ethyl iodide (556.0 mg, 3.20 mmol) were added, and the mixture was stirred at 60° C. for 4 hours. A saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (540.0 mg, 90%).

MS (ESI+) 281 (M+1, 100%)

Reference Example 88-2

Ethyl 5-amino-1-(2-fluoroethyl)-1H-indole-2-carboxylate

[Formula 329]

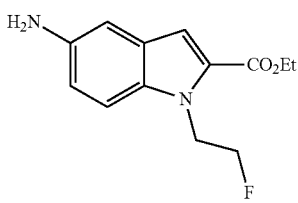

The compound of Reference Example 88-1 (540.0 mg, 1.93 mmol) was dissolved in a mixed solvent of ethanol (10 mL) and water (5 mL), then reduced iron (598.0 mg, 9.63 mmol) and ammonium chloride (124.0 mg, 2.32 mmol) were added, and the mixture was stirred at 95° C. for 5 hours. The reaction mixture was filtered through Celite, followed by extraction of the filtrate with ethyl acetate. The organic layer was washed with a saturated aqueous solution of sodium bicarbonate once and with a saturated saline solution once, then dried over sodium sulfate and filtered, and the filtrate was concentrated under reduced pressure to obtain the title compound (484.0 mg, 100%).

MS (ESI+) 251 (M+1, 100%)

Reference Example 88-3

Ethyl 5-{[(3S)-1-(tert-butoxycarbonyl)-3-cyclohexyl-L-prolyl]amino}-1-(2-fluoroethyl)-1H-indole-2-carboxylate

[Formula 330]

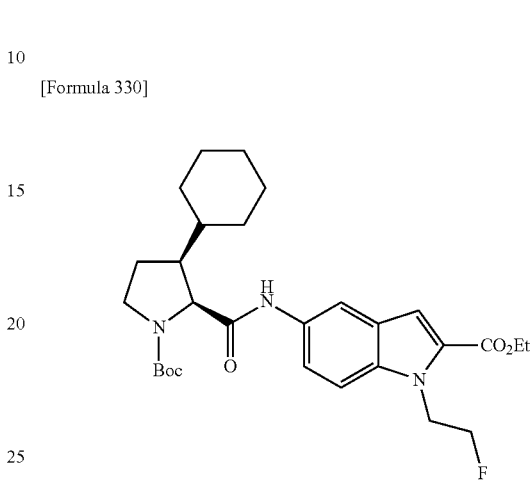

The same procedure as described in Reference Example 1 was carried out to obtain the title compound (253.0 mg, 95%) from the compound of Reference Example 11-1 (150.0 mg, 0.504 mmol) and the compound of Reference Example 88-3 (250.0 mg, 0.55 mmol).

MS (ESI+) 530 (M+1, 100%)

Reference Example 88-4

Ethyl 5-{[(3S)-3-cyclohexyl-L-prolyl]amino}-1-(2-fluoroethyl)-1H-indole-2-carboxylate trifluoroacetate

[Formula 331]

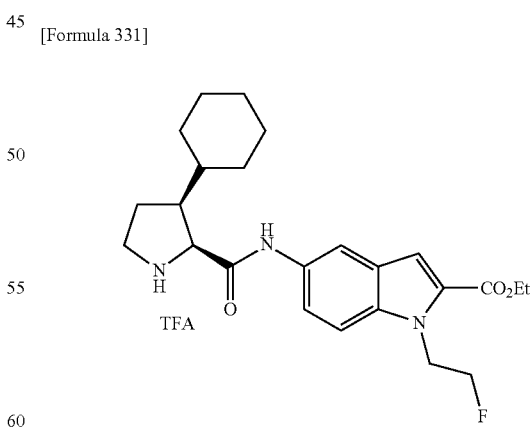

The same procedure as described in Reference Example 9-2 was carried out to obtain the title compound (100.0 mg, 100%) from the compound of Reference Example 88-3 (100.0 mg, 0.19 mmol).

MS (ESI+) 430 (M+1, 100%)

Reference Example 88-5

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-(2-fluoroethyl)-1H-indole-2-carboxylate

[Formula 332]

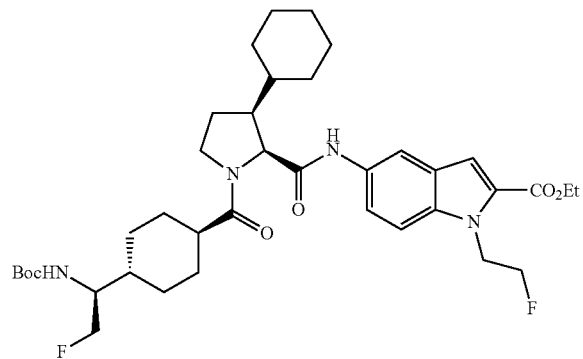

The same procedure as described in Reference Example 1 was carried out to obtain the title compound (81.0 mg, 61%) from the compound of Reference Example 88-4 (100.0 mg, 0.19 mmol) and the compound of Reference Example 53-3 (60.0 mg, 0.208 mmol).

MS (ESI+) 701 (M+1, 100%)

Reference Example 89

(3S)-1-[(trans-4-{(1S)-1-[(tert-Butoxycarbonyl)amino]-2-fluoroethyl}cyclohexyl)carbonyl]-3-cyclohexyl-N-{4-[(dimethylsulfamoyl)carbamoyl]phenyl}-L-prolinamide

[Formula 333]

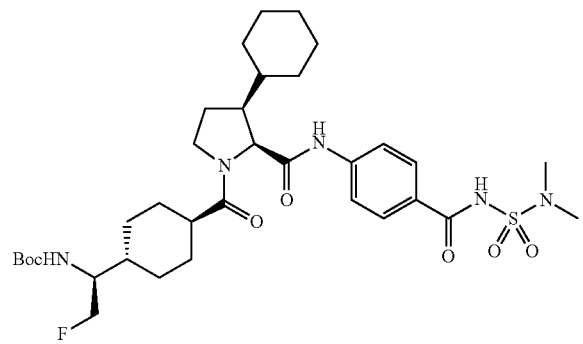

The same procedure as described in Reference Example 1 was carried out to obtain the title compound (9.5 mg, 69%) from the compound of Reference Example 89-2 (9.6 mg, 0.02 mmol) and the compound of Reference Example 53-3 (6.1 mg, 0.021 mmol).

MS (ESI+) 694 (M+1, 3%)

Reference Example 89-1 tert-Butyl (2S,3S)-3-cyclohexyl-2-({4-[(dimethylsulfamoyl)carbamoyl]phenyl}carbamoyl)pyrrolidine-1-carboxylate

[Formula 334]

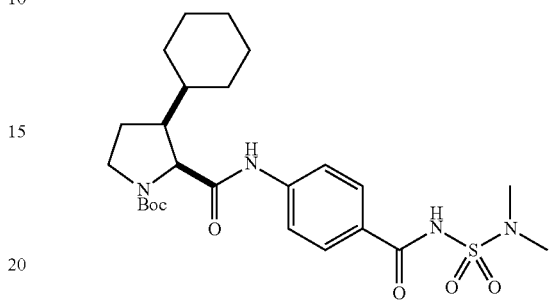

To a solution of the compound of Reference Example 82-1 (21.6 mg, 0.052 mmol) in dichloromethane (2 mL), WSC.HCl (19.9 mg, 0.104 mmol), N,N-dimethyl-4-aminopyridine (7.0 mg, 0.057 mmol) and N,N-dimethylsulfamide (9 mg, 0.073 mmol) were added, and the mixture was stirred at room temperature overnight. A saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution once, then dried over sodium sulfate and filtered, and the filtrate was concentrated under reduced pressure. The obtained residue was purified by silica gel column chromatography to obtain the title compound (10.4 mg, 38%).

MS (ESI+) 523 (M+1, 7%)

Reference Example 89-2

(3S)-3-Cyclohexyl-N-{4-[(dimethylsulfamoyl)carbamoyl]phenyl}-L-prolinamide hydrochloride

[Formula 335]

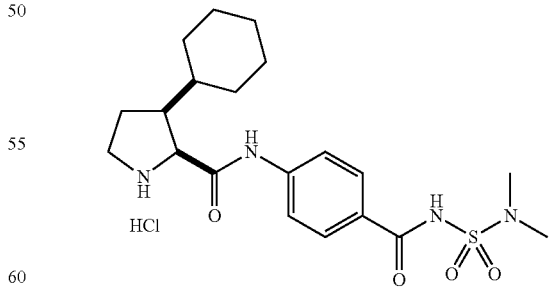

The same procedure as described in Reference Example 1-2 was carried out to obtain the title compound (9.6 mg, 100%) from the compound of Reference Example 89-1 (10.4 mg, 0.02 mmol).

MS (ESI+) 423 (M+1, 100%)

Reference Example 90

(2S)-Tetrahydrofuran-2-ylmethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-methyl-1H-indole-2-carboxylate

[Formula 336]

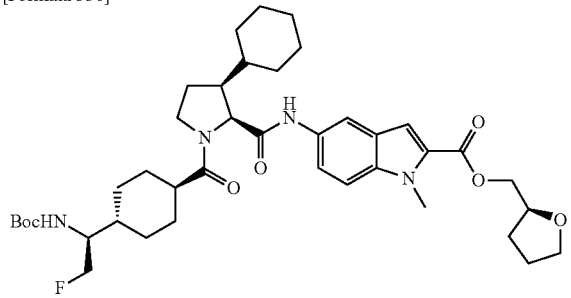

The same procedure as described in Reference Example 1 was carried out to obtain the title compound (49.0 mg, 58%) from the compound of Reference Example 90-2 (64.0 mg, 0.117 mmol) and the compound of Reference Example 53-3 (38.0 mg, 0.13 mmol).
MS (ESI+) 725 (M+1, 100%)

Reference Example 90-1

(2S)-Tetrahydrofuran-2-ylmethyl 5-{[(3S)-1-(tert-butoxycarbonyl)-3-cyclohexyl-L-prolyl]amino}-1-methyl-1H-indole-2-carboxylate

[Formula 337]

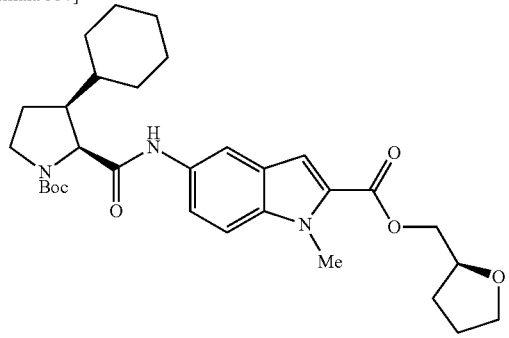

The same procedure as described in Reference Example 145-2 was carried out to obtain the title compound (65.0 mg, 41%) from the compound of Reference Example 145-1 (135 mg, 0.287 mmol) and (R)-(−)-tetrahydrofurfuryl alcohol (88 mg, 0.862 mmol).
MS (ESI+) 554 (M+1, 25%)

Reference Example 90-2

(2S)-Tetrahydrofuran-2-ylmethyl 5-{[(3S)-3-cyclohexyl-L-prolyl]amino}-1-methyl-1H-indole-2-carboxylate trifluoroacetate

[Formula 338]

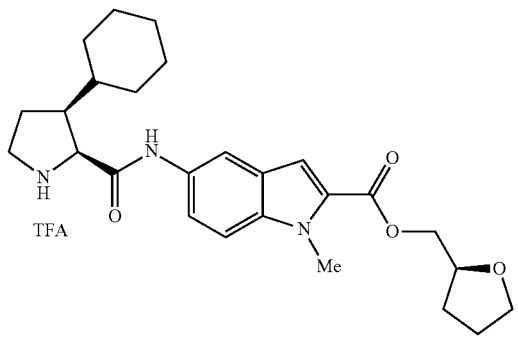

The same procedure as described in Reference Example 9-2 was carried out to obtain the title compound (64 mg, 100%) from the compound of Reference Example 90-1 (65.0 mg, 0.117 mmol).
MS (ESI+) 454 (M+1, 100%)

Reference Example 91

3-(2-Methoxyethoxy)propyl 5-({(3S)-1-[(trans-4-{(1S)-1-[(tert-butoxycarbonyl)amino]-2-fluoroethyl}cyclohexyl)carbonyl-3-cyclohexyl)carbonyl]-3-cyclohexyl-L-prolyl}amino)-1-methyl-1H-indole-2-carboxylate

[Formula 339]

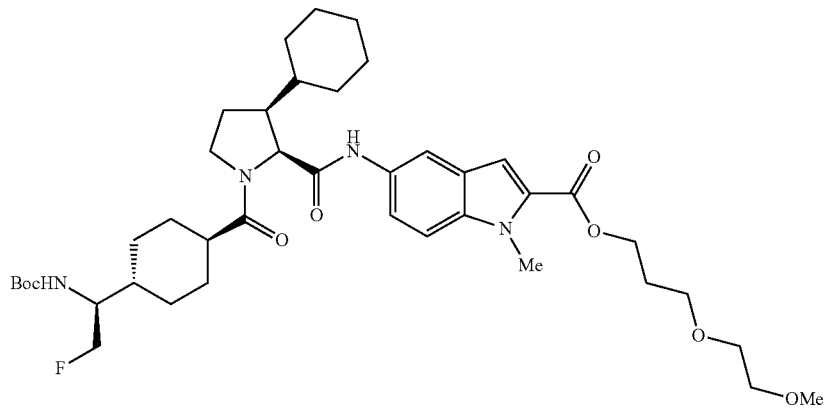

267

The same procedure as described in Reference Example 1 was carried out to obtain the title compound (205.0 mg, 67%) from the compound of Reference Example 91-2 (234.0 mg, 0.402 mmol) and the compound of Reference Example 53-3 (129.0 mg, 0.447 mmol).

MS (ESI+) 757 (M+1, 100%)

Reference Example 91-1

3-(2-Methoxyethoxyl)propyl 5-{[(3S)-1-(tert-butoxycarbonyl)-3-cyclohexyl-L-prolyl]amino}-1-methyl-1H-indole-2-carboxylate

[Formula 340]

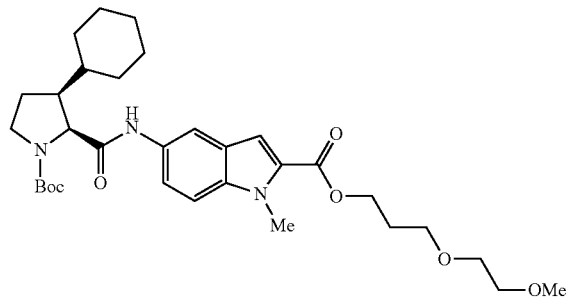

The same procedure as described in Reference Example 67 was carried out to obtain the title compound (236.0 mg, 100%) from the compound of Reference Example 145-1 (188.8 mg, 0.402 mmol).

MS (ESI+) 586 (M+1, 100%)

268

Reference Example 91-2

3-(2-Methoxyethoxyl)propyl 5-{[(3S)-3-cyclohexyl-L-prolyl]amino}-1-methyl-1H-indole-2-carboxylate trifluoroacetate

[Formula 341]

The same procedure as described in Reference Example 9-2 was carried out to obtain the title compound (234 mg, 100%) from the compound of Reference Example 91-1 (236 mg, 0.402 mmol).

MS (ESI+) 486 (M+1, 100%)

Reference Example 92

3-(Morpholin-4-yl)propyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 342]

The same procedure as described in Reference Example 141 was carried out to obtain the title compound (54.2 mg, 45%) from the compound of Reference Example 140 (99.7 mg, 0.161 mmol) and 4-(3-hydroxypropyl)-morpholine (66.7 mg, 0.483 mmol).

MS (ESI+) 748 (M+1, 100%)

Reference Example 93

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-methyl-1H-indole-2-carboxylic acid

[Formula 343]

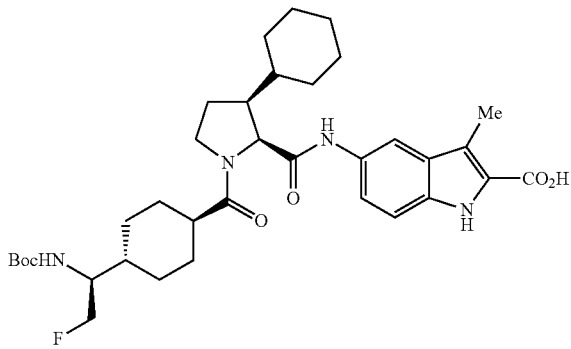

The same procedure as described in Reference Example 19 was carried out to obtain the title compound (60.6 mg, 90%) from the compound of Reference Example 93-1 (50.0 mg, 0.075 mmol).

MS (ESI+) 641 (M+1, 100%)

Reference Example 93-1

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-3-methyl-1H-indole-2-carboxylate

[Formula 344]

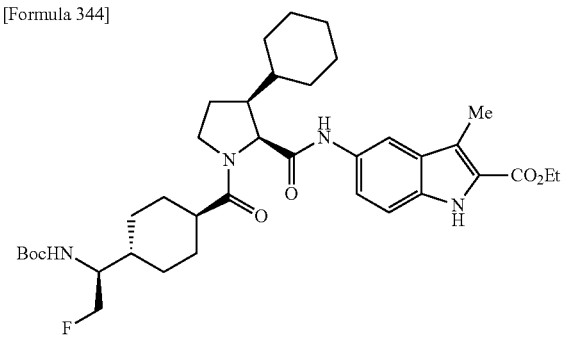

The same procedure as described in Reference Example 1 was carried out to obtain the title compound (98.0 mg, 61%) from the compound of Reference Example 39-4 (119.0 mg, 0.241 mmol) and the compound of Reference Example 53-3 (84.0 mg, 0.289 mmol).

MS (ESI+) 669 (M+1, 100%)

Reference Example 94 tert-Butyl [(1S)-1-(trans-4-{[(2S,3S)-3-cyclohexyl-2-({2-[(methylsulfonyl)carbamoyl]-1H-indol-5-yl}carbamoyl)pyrrolidin-1-yl]carbonyl}cyclohexyl)-2-fluoroethyl]carbamate

[Formula 345]

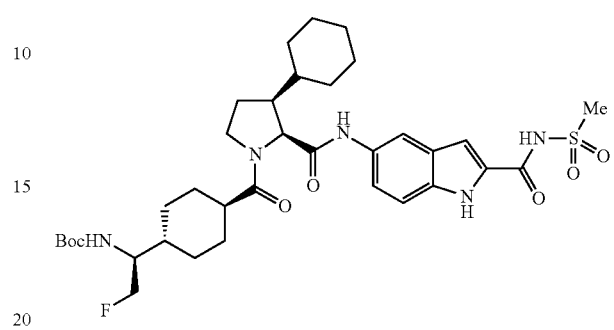

The same procedure as described in Reference Example 1 was carried out to obtain the title compound (80.0 mg, 55%) from the compound of Reference Example 94-2 (96.9 mg, 0.207 mmol) and the compound of Reference Example 53-3 (66.0 mg, 0.227 mmol).

MS (ESI+) 704 (M+1, 100%)

Reference Example 94-1 tert-Butyl (2S,3S)-3-cyclohexyl-2-({2-[(methylsulfonyl)carbamoyl]-1H-indol-5-yl}carbamoyl)pyrrolidine-1-carboxylate

[Formula 346]

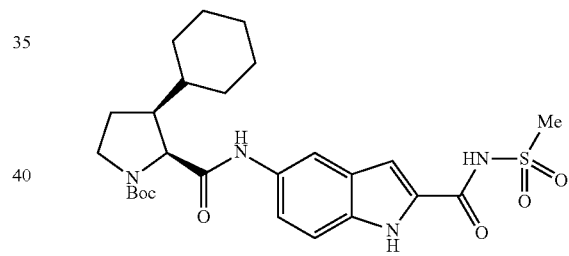

The same procedure as described in Reference Example 89-1 was carried out to obtain the title compound (110.0 mg, 100%) from the compound of Reference Example 83-1 (94.3 mg, 0.207 mmol) and methane sulfonamide (27.6 mg, 0.29 mmol).

MS (ESI+) 533 (M+1, 25%)

Reference Example 94-2

5-{[(3S)-3-Cyclohexyl-L-prolyl]amino}-N-(methylsulfonyl)-1H-indole-2-carboxamide hydrochloride

[Formula 347]

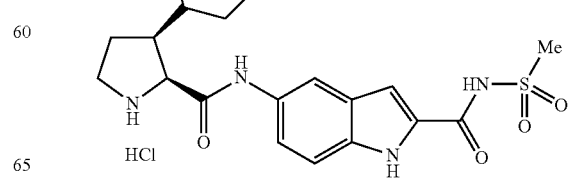

The same procedure as described in Reference Example 1-2 was carried out to obtain the title compound (96.9 mg, 100%) from the compound of Reference Example 94-1 (110.0 mg, 0.207 mmol).
MS (ESI+) 433 (M+1, 100%)

Reference Example 95

(3S)-1-[(trans-4-{(1S)-1-[(tert-Butoxycarbonyl) amino]-2-fluoroethyl}cyclohexyl)carbonyl]-3-cyclohexyl-N-[4-(3-methyl-1,2,4-oxadiazol-5-yl)phenyl]-L-prolinamide

[Formula 348]

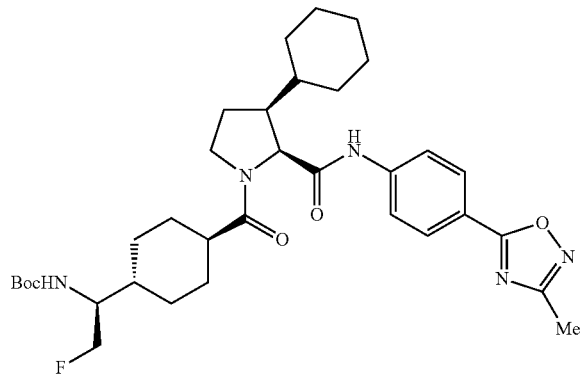

The same procedure as described in Reference Example 1 was carried out to obtain the title compound (75.0 mg, 54%) from the compound of Reference Example 95-5 (99.0 mg, 0.22 mmol) and the compound of Reference Example 53-3 (70.0 mg, 0.24 mmol).
MS (ESI+) 626 (M+1, 100%)

Reference Example 95-1

(1E)-N'-[(4-Nitrobenzoyl)oxy]ethanimidamide

[Formula 349]

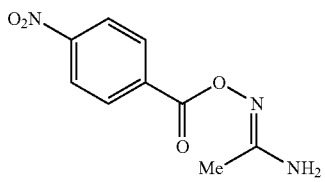

A 50% aqueous solution of hydroxylamine (5 ml, 76.0 mmol) and acetonitrile (4 ml, 76.0 mmol) were added to ethanol (100 mL), and the mixture was stirred at 90° C. for 1 hour. The reaction solution was concentrated, and the obtained residue was dried. The residue was dissolved in dichloromethane (30 ml), then diisopropylethylamine (10 ml, 60 mmol) was added thereto, then the mixture was stirred at 0° C. for 5 minutes, then a solution of 4-nitrobenzoyl chloride (7.24 g, 39.0 mmol) in dichloromethane (20 ml) was added, and the mixture was stirred at 0° C. for 1 hour and then stirred at room temperature overnight. Water was added to the reaction mixture, followed by extraction with ethyl acetate. The organic layer was washed with a saturated saline solution once, then dried over sodium sulfate and filtered, and the filtrate was concentrated under reduced pressure. Ethyl acetate (80 ml) was added to the obtained residue, then the mixture was stirred at room temperature for 1 hour, and then the obtained solid was filtered out to obtain the title compound (3.29 g, 19%).
$^1$H NMR (CDCl$_3$, 300 MHz) δ 8.36-8.28 (m, 4H), 6.67 (brs, 2H), 1.82 (s, 3)

Reference Example 95-2

3-Methyl 5-(4-nitrophenyl)-1,2,4-oxadiazole

[Formula 350]

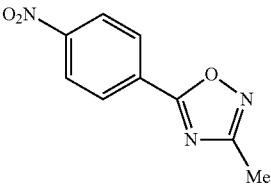

The compound of Reference Example 95-1 (3.29 g, 14.7 mmol) was dissolved in THF (50 ml), a 1 mol/L solution of tetra-n-butylammonium fluoride in THF (1.47 ml, 1.47 mmol) was added thereto, and the mixture was stirred at room temperature overnight. Water was added to the reaction solution, followed by extraction with ethyl acetate. The organic layer was washed with a saturated saline solution once, then dried over sodium sulfate and filtered, and the filtrate was concentrated under reduced pressure. The obtained residue was recrystallized by using ethyl acetate to obtain the title compound (2.08 g, 69%).
$^1$H NMR (CDCl$_3$, 300 MHz) δ 8.45-8.40 (m, 2H), 8.36-8.31 (m, 2H), 2.46 (s, 3H).

Reference Example 95-3

4-(3-Methyl-1,2,4-oxadiazol-5-yl)aniline

[Formula 351]

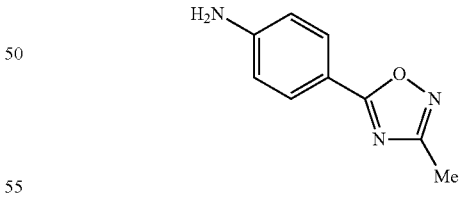

The compound of Reference Example 95-2 (300.0 mg, 1.46 mmol) was dissolved in acetic acid (25 mL), then reduced iron (815.0 mg, 13.1 mmol) was added thereto, and the mixture was stirred at room temperature for 5 hours. Insoluble matter was removed by using a magnet, then the mixture was concentrated under reduced pressure, and then toluene (5 mL) was added to the residue for concentrated under reduced pressure. Toluene (5 mL) was added to the residue again for concentration under reduced pressure, then the residue was dissolved in a mixed solution of chloroform/hexane (10/1), then amine silica gel was added thereto, and the mixture was stirred at room temperature for 1 hour. The mixture was filtered through Celite and the filtrate was concentrated. The obtained residue was purified by silica gel column chromatography to obtain the title compound (175.0 mg, 68%).

MS (ESI+) 176 (M+1, 100%)

Reference Example 95-4 tert-Butyl (2S,3S)-3-cyclohexyl-2-{[4-(3-methyl-1,2,4-oxadiazol-5-yl)phenyl]carbamoyl}pyrrolidine-1-carboxylate

[Formula 352]

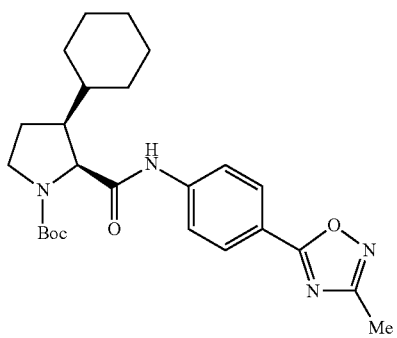

The same procedure as described in Reference Example 1-1 was carried out to obtain the title compound (100.0 mg, 24%) from the compound of Reference Example 95-3 (175.0 mg, 1.0 mmol) and the compound of Reference Example 11-1 (275.0 mg, 0.92 mmol).

MS (ESI+) 455 (M+1, 100%)

Reference Example 95-5

(3S)-3-Cyclohexyl-N-[4-(3-methyl-1,2,4-oxadiazol-5-yl)phenyl]-L-prolinamide trifluoroacetate

[Formula 353]

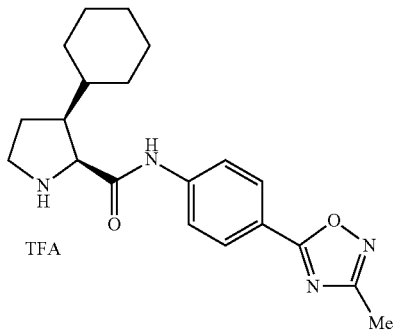

The same procedure as described in Reference Example 9-2 was carried out to obtain the title compound (99.0 mg, 100%) from the compound of Reference Example 95-4 (100.0 mg, 0.22 mmol).

MS (ESI+) 355 (M+1, 100%)

Reference Example 96

(3S)-1-[(trans-4-{(1S)-1-[(tert-Butoxycarbonyl)amino]-2-fluoroethyl}cyclohexyl)carbonyl]-3-cyclohexyl-N-[4-(5-oxo-2,5-dihydro-1,2,4-oxadiazol-3-yl)phenyl]-L-prolinamide

[Formula 354]

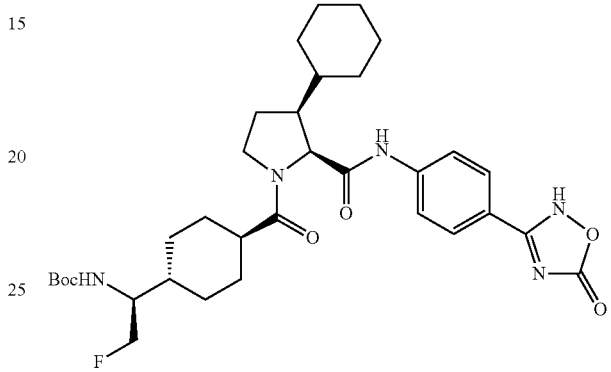

The same procedure as described in Reference Example 1 was carried out to obtain the title compound (108 mg, 70%) from the compound of Reference Example 96-4 (106.5 mg, 0.248 mmol) and the compound of Reference Example 53-3 (72 mg, 0.248 mmol).

MS (ESI+) 628 (M+1, 100%)

Reference Example 96-1 tert-Butyl (2S,3S)-2-[(4-cyanophenyl)carbamoyl]-3-cyclohexylpyrrolidine-1-carboxylate

[Formula 355]

The same procedure as described in Reference Example 1-1 was carried out to obtain the title compound (150 mg, 22%) from the compound of Reference Example 11-1 (500 mg, 1.68 mmol) and 4-aminobenzonitrile (259 mg, 2.1 mmol).

MS (ESI+) 398 (M+1, 7.3%)

Reference Example 96-2 tert-Butyl (2S,3S)-3-cyclohexyl-2-{[4-(N-hydroxy-carbamimidoyl)phenyl]carbamoyl}pyrrolidine-1-carboxylate

[Formula 356]

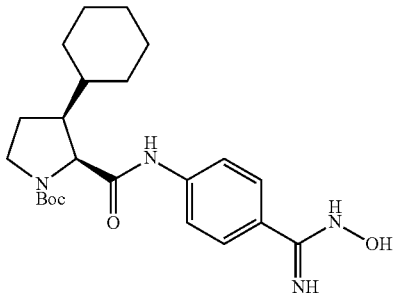

A solution of the compound of Reference Example 96-1 (150 mg, 0.377 mmol), hydroxyamine hydrochloride (79 mg, 1.13 mmol), and triethylamine (210 μL, 1.51 mmol) in ethanol (1.7 mL) was stirred at 90° C. for 6 hours. The reaction solution was allowed to cool, then a 10% aqueous solution of ammonium chloride was added thereto, followed by extraction with ethyl acetate. The organic layer was washed with a saturated saline solution, then dried over sodium sulfate and filtered, and the filtrate was concentrated under reduced pressure to obtain the title compound (174 mg, 100%).

MS (ESI+) 431 (M+1, 100%)

Reference Example 96-3 tert-Butyl (2S,3S)-3-cyclohexyl-2-{[4-(5-oxo-2,5-dihydro-1,2,4-oxadiazol-3-yl)phenyl]carbamoyl}pyrrolidine-1-carboxylate

[Formula 357]

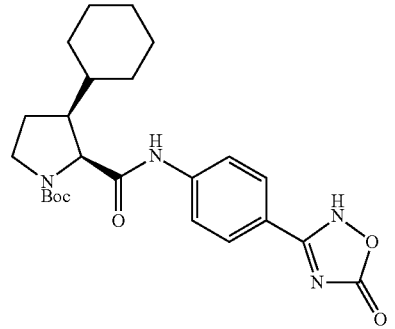

DBU (113 mL, 0.754 mmol) and CDI (92 mg, 0.566 mmol) were added to a solution of the compound of Reference Example 96-2 (150 mg, 0.377 mmol) in tetrahydrofuran (2 mL), and the mixture was stirred at room temperature overnight. Water was added to the reaction solution, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (113 mg, 66%).

MS (ESI+) 457 (M+1, 2.0%)

Reference Example 96-4

(3S)-3-Cyclohexyl-N-[4-(5-oxo-2,5-dihydro-1,2,4-oxadiazol-3-yl)phenyl]-L-prolinamide hydrochloride

[Formula 358]

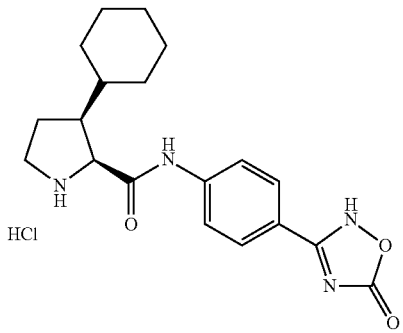

The same procedure as described in Reference Example 1-2 was carried out to obtain the title compound (97.2 mg, 100%) from the compound of Reference Example 96-3 (113 mg, 0.248 mmol).

MS (ESI+) 357 (M+1, 100%)

Reference Example 97

A Diastereo Mixture of A and B

A: tert-Butyl [(1S)-2-fluoro-1-(trans-4-{[(2S,3R)-2-{[4-(5-oxo-2,5-dihydro-1,2,4-oxadiazol-3-yl)phenyl]carbamoyl}-3-(piperidin-1-yl)pyrrolidin-1-yl]carbonyl}cyclohexyl)ethyl]carbamate B: tert-Butyl [(1S)-2-fluoro-1-(trans-4-{[(2R,3S)-2-{[4-(5-oxo-2,5-dihydro-1,2,4-oxadiazol-3-yl)phenyl]carbamoyl}-3-(piperidin-1-yl)pyrrolidin-1-yl]carbonyl}cyclohexyl)ethyl]carbamate

[Formula 359]

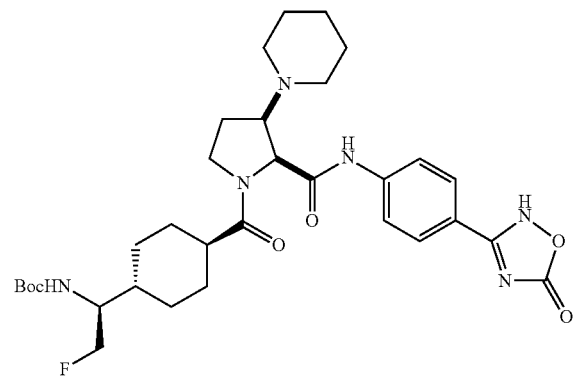

The same procedure as described in Reference Example 1 was carried out to obtain the title compound (40.0 mg, 100%) from the compound of Reference Example 97-4

(27.2 mg, 0.0633 mmol) and the compound of Reference Example 53-3 (19 mg, 0.0657 mmol).

MS (ESI+) 628 (M+1, 34%)

Reference Example 97-1

(rac.)-tert-Butyl (2S,3R)-2-[(4-cyanophenyl)carbamoyl]-3-(piperidin-1-yl)pyrrolidine-1-carboxylate

[Formula 360]

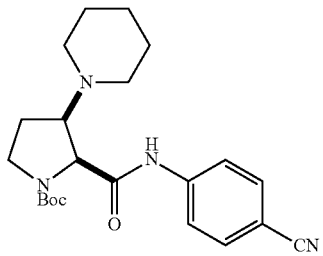

The same procedure as described in Reference Example 1-1 was carried out to obtain the title compound (74 mg, 59%) from the compound of Reference Example 147-2 (94.0 mg, 0.315 mmol) and 4-aminobenzonitrile (49 mg, 0.415 mmol).

MS (ESI+) 399 (M+1, 100%)

Reference Example 97-2 tert-Butyl (2S,3R)-2-{[4-(N-hydroxycarbamimidoyl)phenyl]carbamoyl}-3-(piperidin-1-yl)pyrrolidine-1-carboxylate

[Formula 361]

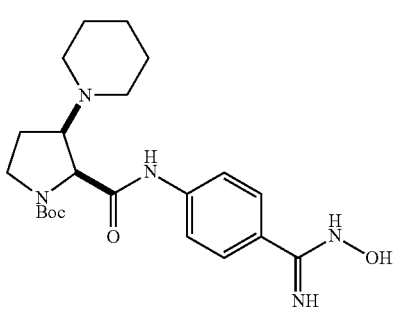

The same procedure as described in Reference Example 96-2 was carried out to obtain the title compound (73 mg, 91%) from the compound of Reference Example 97-1 (74 mg, 0.186 mmol) and hydroxyamine hydrochloride (39 mg, 0.561 mmol).

MS (ESI+) 432 (M+1, 100%)

Reference Example 97-3

(rac.)-tert-Butyl (2S,3R)-2-{[4-(5-oxo-2,5-dihydro-1,2,4-oxadiazol-3-yl)phenyl]carbamoyl}-3-(piperidin-1-yl)pyrrolidine-1-carboxylate

[Formula 362]

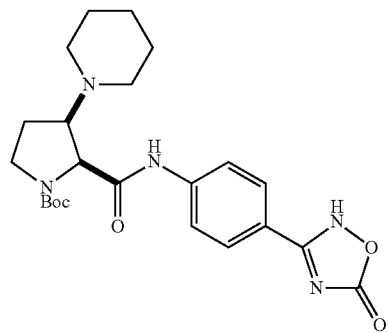

The same procedure as described in Reference Example 96-3 was carried out to obtain the title compound (29 mg, 38%) from the compound of Reference Example 97-2 (74 mg, 0.169 mmol).

MS (ESI+) 458 (M+1, 100%)

Reference Example 97-4

(rac.)-(3R)—N-[4-(5-Oxo-2,5-dihydro-1,2,4-oxadiazol-3-yl)phenyl]-3-piperidin-1-yl-L-prolinamide hydrochloride

[Formula 363]

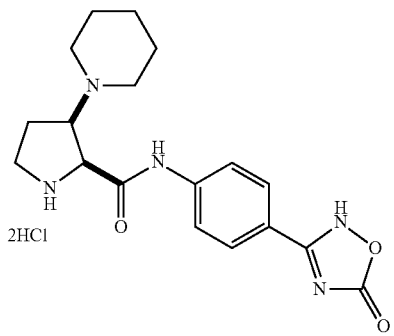

The same procedure as described in Reference Example 1-2 was carried out to obtain the title compound (27.2 mg, 100%) from the compound of Reference Example 97-3 (29 mg, 0.0634 mmol).

MS (ESI+) 358 (M+1, 100%)

Reference Example 98

(3S)-1-[(trans-4-{(1S)-1-[(tert-Butoxycarbonyl)amino]-2-fluoroethyl}cyclohexyl)carbonyl]-3-cyclohexyl-N-{4-[(phenylsulfonyl)carbamoyl]phenyl}-L-prolinamide

[Formula 364]

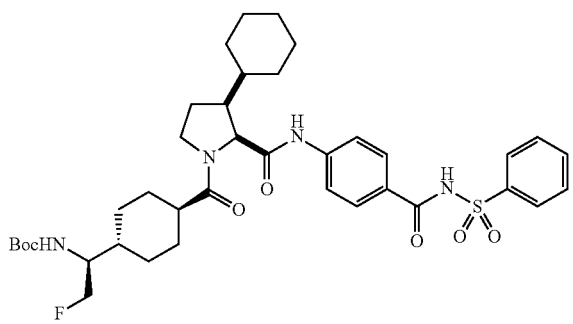

The same procedure as described in Reference Example 1 was carried out to obtain the title compound (33.0 mg, 59%) from the compound of Reference Example 98-2 (43.0 mg, 0.077 mmol) and the compound of Reference Example 53-3 (25.0 mg, 0.085 mmol).

MS (ESI+) 727 (M+1, 100%)

Reference Example 98-1 tert-Butyl (2S,3S)-3-cyclohexyl-2-({4-[(phenylsulfonyl)carbamoyl]phenyl}carbamoyl)pyrrolidine-1-carboxylate

[Formula 365]

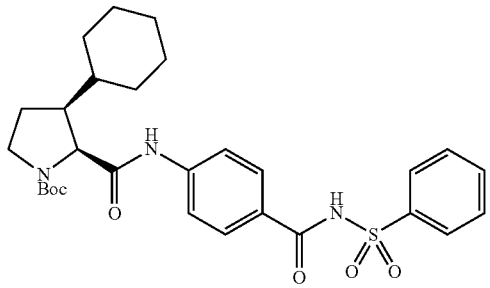

The same procedure as described in Reference Example 89-1 was carried out to obtain the title compound (43.0 mg, 22%) from the compound of Reference Example 82-1 (145.0 mg, 0.348 mmol) and commercially available benzenesulfonamide (77.0 mg, 0.49 mmol).

MS (ESI+) 556 (M+1, 69%)

Reference Example 98-2

(3S)-3-Cyclohexyl-N-{4-[(phenylsulfonyl)carbamoyl]phenyl}-L-prolinamide trifluoroacetate

[Formula 366]

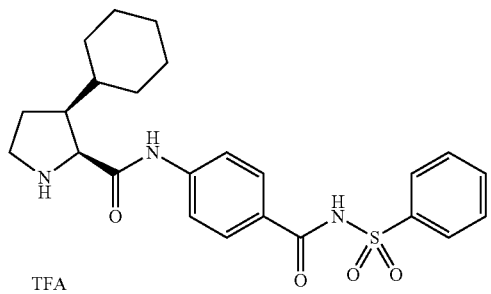

The same procedure as described in Reference Example 9-2 was carried out to obtain the title compound (43 mg, 100%) from the compound of Reference Example 94-1 (43.0 mg, 0.077 mmol).

MS (ESI+) 456 (M+1, 100%)

Reference Example 99

(3S)-1-[(trans-4-{(1S)-1-[(tert-Butoxycarbonyl)amino]-2-fluoroethyl}cyclohexyl)carbonyl]-3-cyclohexyl-N-{4-[(4,5-dimethyl-1,3-oxazol-2-yl)sulfamoyl]phenyl}-L-prolinamide

[Formula 367]

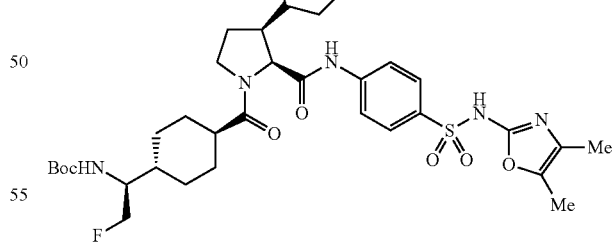

The same procedure as described in Reference Example 1 was carried out to obtain the title compound (13.0 mg, 21%) from the compound of Reference Example 98-2 (55.0 mg, 0.101 mmol) and the compound of Reference Example 53-3 (32.0 mg, 0.111 mmol).

MS (ESI+) 718 (M+1, 100%)

281

Reference Example 99-1 tert-Butyl (2S,3S)-3-cyclohexyl-2-({4-[(4,5-dimethyl-1,3-oxazol-2-yl)sulfamoyl]phenyl}carbamoyl)pyrrolidine-1-carboxylate

[Formula 368]

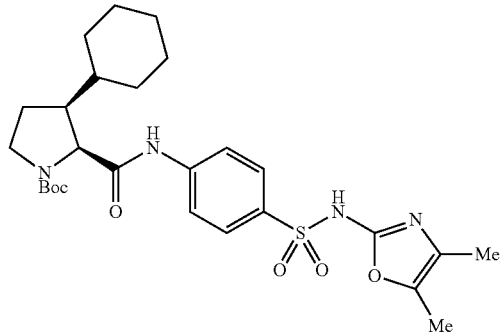

The same procedure as described in Reference Example 1-1 was carried out to obtain the title compound (55.0 mg, 22%) from the compound of Reference Example 11-1 (150.0 mg, 0.504 mmol) and commercially available 4-amino-N-(4,5-dimethyl-2-oxazolyl)benzenesulfonamide (162.0 mg, 0.61 mmol).

MS (ESI+) 547 (M+1, 100%)

282

Reference Example 99-2

(3S)-3-Cyclohexyl-N-{4-[(4,5-dimethyl-1,3-oxazol-2-yl)sulfamoyl]phenyl}-L-prolinamide trifluoroacetate

[Formula 369]

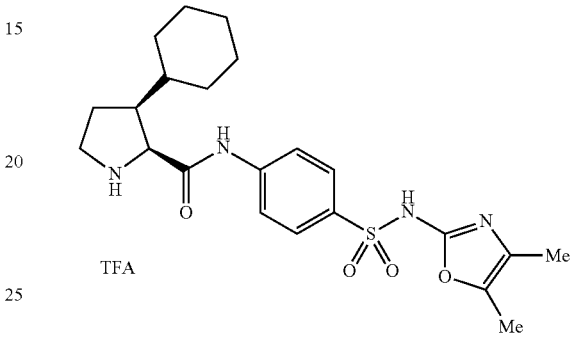

The same procedure as described in Reference Example 9-2 was carried out to obtain the title compound (55 mg, 100%) from the compound of Reference Example 99-1 (55.0 mg, 0.101 mmol).

MS (ESI+) 447 (M+1, 100%)

Reference Example 100

1-{[(Cyclohexyloxy)carbonyl]oxy}ethyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 370]

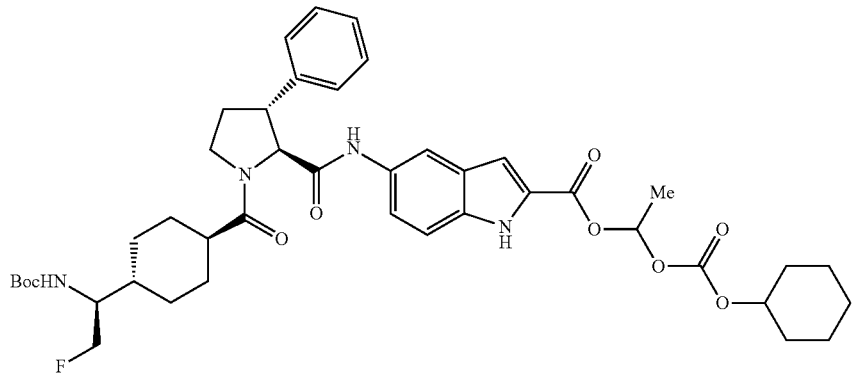

The same procedure as described in Reference Example 150 was carried out to obtain the title compound (65.1 mg, 46%) from the compound of Reference Example 140 (110.4 mg, 0.178 mmol) and 1-chloroethyl cyclohexyl carbonate (55.1 mg, 0.267 mmol).

MS (ESI+) 791 (M+1, 100%)

Reference Example 101

(3S)-1-[(trans-4-{(1S)-1-[(tert-Butoxycarbonyl) amino]-2-fluoroethyl}cyclohexyl)carbonyl]-3-cyclohexyl-N-{2-[(phenylsulfonyl)carbamoyl]-1-benzofuran-5-yl}-L-prolinamide

[Formula 371]

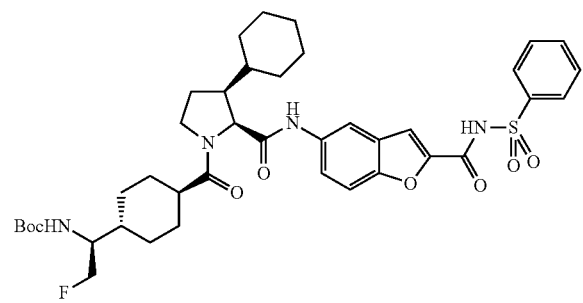

The same procedure as described in Reference Example 1 was carried out to obtain the title compound (53.0 mg, 69%) from the compound of Reference Example 101-2 (59.0 mg, 0.10 mmol) and the compound of Reference Example 53-3 (32.0 mg, 0.11 mmol).

MS (ESI+) 767 (M+1, 100%)

Reference Example 101-1 tert-Butyl (2S,3S)-3-cyclohexyl-2-({2-[(phenylsulfonyl)carbamoyl]-1-benzofuran-5-yl}carbamoyl)pyrrolidine-1-carboxylate

[Formula 372]

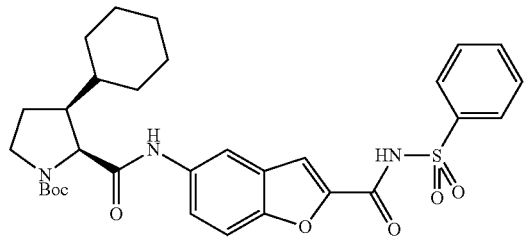

The same procedure as described in Reference Example 89-1 was carried out to obtain the title compound (59.0 mg, 23%) from the compound of Reference Example 119-1 (200.0 mg, 0.438 mmol) and commercially available benzenesulfonamide (96.0 mg, 0.613 mmol).

MS (ESI+) 596 (M+1, 100%)

Reference Example 101-2

(3S)-3-Cyclohexyl-N-{2-[(phenylsulfonyl)carbamoyl]-1-benzofuran-5-yl}-L-prolinamide trifluoroacetate

[Formula 373]

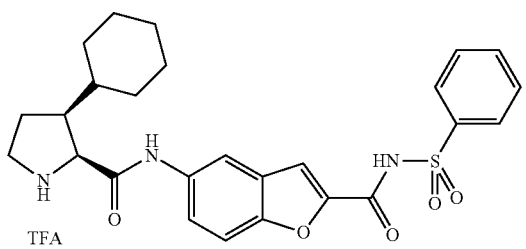

The same procedure as described in Reference Example 9-2 was carried out to obtain the title compound (59 mg, 100%) from the compound of Reference Example 101-1 (59.0 mg, 0.10 mmol).

MS (ESI+) 496 (M+1, 100%)

Reference Example 102 tert-Butyl [(1S)-2-fluoro-1-(trans-4-{[(2S,3R)-2-({2-[(morpholin-4-ylsulfonyl)carbamoyl]-1H-indol-5-yl}carbamoyl)-3-phenylpyrrolidin-1-yl]carbonyl}cyclohexyl)ethyl]carbamate

[Formula 374]

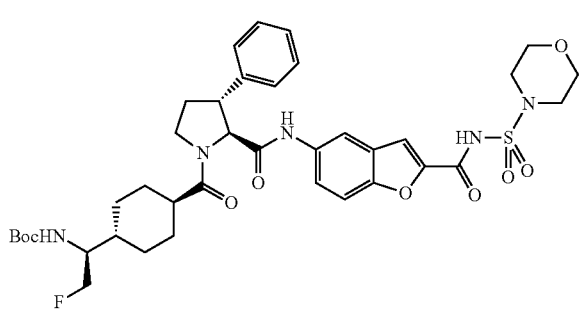

The same procedure as described in Reference Example 89-1 was carried out to obtain the title compound (34.2 mg, 27%) from the compound of Reference Example 140 (101.9 mg, 0.164 mmol) and the compound of Reference Example 102-2 (40.9 mg, 0.246 mmol).

MS (ESI+) 769 (M+1, 29%)

Reference Example 102-1

Benzyl(morpholin-4-ylsulfonyl)carbamate

[Formula 375]

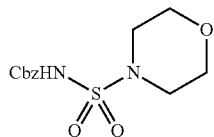

Commercially available chlorosulfonyl isocyanate (2.0 g, 14.13 mmol) was dissolved in dichloromethane (20 ml), then a solution of benzyl alcohol (1.53 g, 14.13 mmol) in dichloromethane (6 ml) was added thereto, and the mixture was stirred at 0° C. for 1.5 hours. A solution of morpholine (1.23 g, 14.13 mmol) in dichloromethane (10 ml) and triethylamine (5.9 ml, 42.4 mmol) were added to the reaction solution, then the mixture was stirred at 0° C. for 1 hour and then stirred at room temperature for 1 hour. The reaction solution was concentrated under reduced pressure, a 1 mol/L hydrochloride water was added to the obtained residue, followed by extraction with ethyl acetate. The organic layer was washed with a 1 mol/L hydrochloride water once and with a saturated saline solution once, then dried over sodium sulfate and filtered, and the filtrate was concentrated under reduced pressure. The obtained residue was purified by silica gel column chromatography to obtain the title compound (1.7 g, 40%).

MS (ESI+) 301 (M+1, 29%).

Reference Example 102-2

Morpholine-4-sulfonamide

[Formula 376]

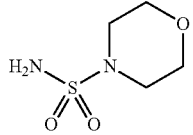

The same procedure as described in Reference Example 53-3 was carried out to obtain the title compound (103 mg, 97%) from the compound of Reference Example 102-1 (192.0 mg, 0.639 mmol).

MS (ESI+) 167 (M+1, 100%)

Reference Example 103

(3S)-1-[(trans-4-{(1S)-1-[(tert-Butoxycarbonyl)amino]-2-fluoroethyl}cyclohexyl)carbonyl]-3-cyclohexyl-N-{2-[(2,2-difluoroethyl)carbamoyl]-1-benzofuran-5-yl}-L-prolinamide

[Formula 377]

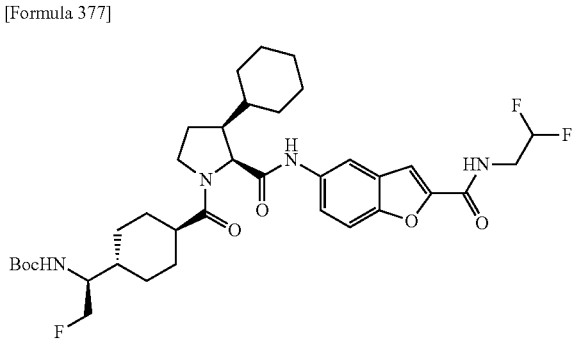 [SMILES: CC(C)(C)OC(=O)N[C@H](CF)[C@H]1CC[C@H](C(=O)N2CC[C@@H](C3CCCCC3)[C@H]2C(=O)Nc2ccc3oc(C(=O)NCC(F)F)cc3c2)CC1]

The same procedure as described in Reference Example 1 was carried out to obtain the title compound (83.0 mg, 39%) from the compound of Reference Example 103-2 (165.0 mg, 0.318 mmol) and the compound of Reference Example 53-3 (98.3 mg, 0.34 mmol).

MS (ESI+) 691 (M+1, 100%)

Reference Example 103-1 tert-Butyl (2S,3S)-3-cyclohexyl-2-({2-[(2,2-difluoroethyl)carbamoyl]-1-benzofuran-5-yl}carbamoyl)pyrrolidine-1-carboxylate

[Formula 378]

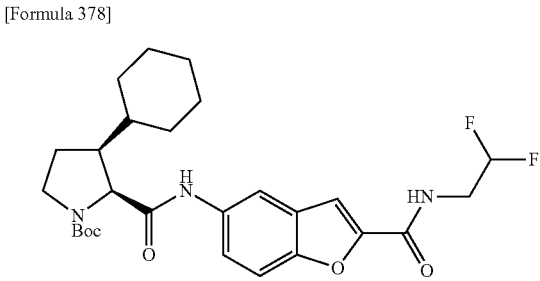 [SMILES: CC(C)(C)OC(=O)N1CC[C@@H](C2CCCCC2)[C@H]1C(=O)Nc1ccc2oc(C(=O)NCC(F)F)cc2c1]

The same procedure as described in Reference Example 89-1 was carried out to obtain the title compound (165.0 mg, 71%) from the compound of Reference Example 119-1 (200.0 mg, 0.438 mmol) and commercially available 1-amino-2,2-difluoroethane (70.0 mg, 0.613 mmol).

MS (ESI+) 520 (M+1, 69%)

Reference Example 103-2

(3S)-3-Cyclohexyl-N-{2-[(2,2-difluoroethyl)carbamoyl]-1-benzofuran-5-yl}-L-prolinamide trifluoroacetate

[Formula 379]

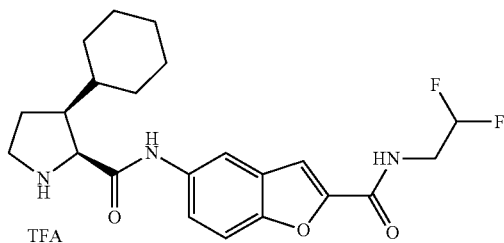

The same procedure as described in Reference Example 9-2 was carried out to obtain the title compound (165 mg, 100%) from the compound of Reference Example 103-1 (165.0 mg, 0.318 mmol).
MS (ESI+) 420 (M+1, 100%)

Reference Example 104

Tetrahydrofuran-2-ylmethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-indole-2-carboxylate The same procedures as described in Reference Example 9-2 and Reference Example 1 were carried out in this order to obtain the title compound (43.8 mg, 90%) from the compound of Reference Example 104-1 (36.8 mg, 0.068 mmol).
MS (ESI+) 711 (M+1, 100%)

Reference Example 104-1

Tetrahydrofuran-2-ylmethyl 5-({(3S)-1-(tert-butoxycarbonyl)-3-cyclohexyl-L-prolyl}amino)-1H-indole-2-carboxylate

[Formula 381]

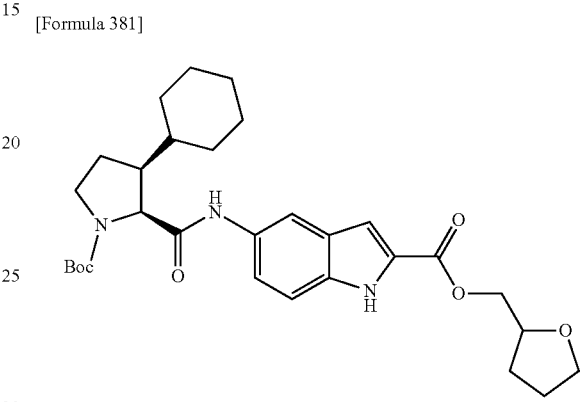

The same procedures as described in Reference Example 3 and Reference Example 63 were carried out in this order to obtain the title compound (36.8 mg, 56%) from the compound of Reference Example 34-1 (55.8 mg, 0.122 mmol) and tetrahydrofuran-2-ylmethanol (35.6 μL, 0.367 mmol).
MS (ESI+) 540 (M+1, 46%)

[Formula 380]

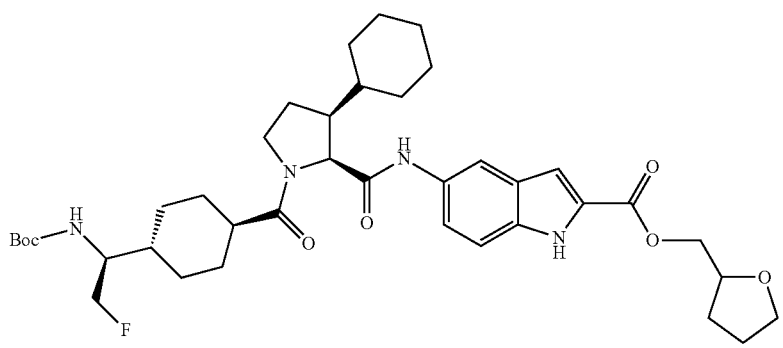

Reference Example 105

2-Methyl-1-(propanoyloxy)propyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 382]

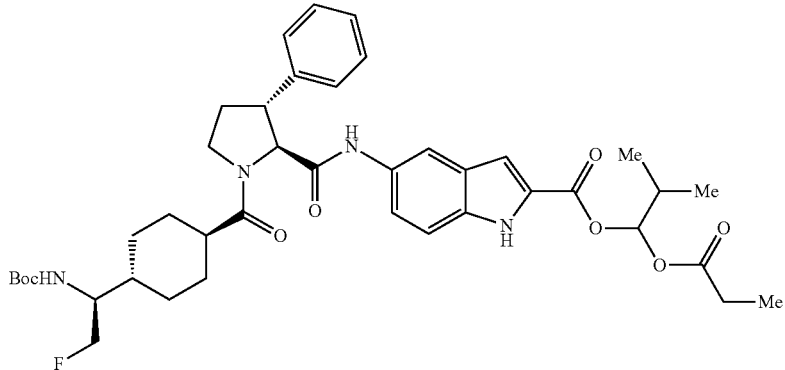

The same procedure as described in Reference Example 150 was carried out to obtain the title compound (21.3 mg, 14%) from the compound of Reference Example 140 (122.1 mg, 0.197 mmol) and 1-chloroisobutyl propionate (64.9 mg, 0.394 mmol).

MS (ESI+) 749 (M+1, 100%)

The same procedure as described in Reference Example 63 was carried out to obtain the title compound (50.9 mg, 23%) from the compound of Reference Example 81 (189 mg, 0.301 mmol) and tetrahydro-2H-pyran-4-ylmethanol (105 mg, 0.904 mmol).

MS (ESI+) 725 (M+1, 100%)

Reference Example 106

Tetrahydro-2H-pyran-4-ylmethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-indole-2-carboxylate

[Formula 383]

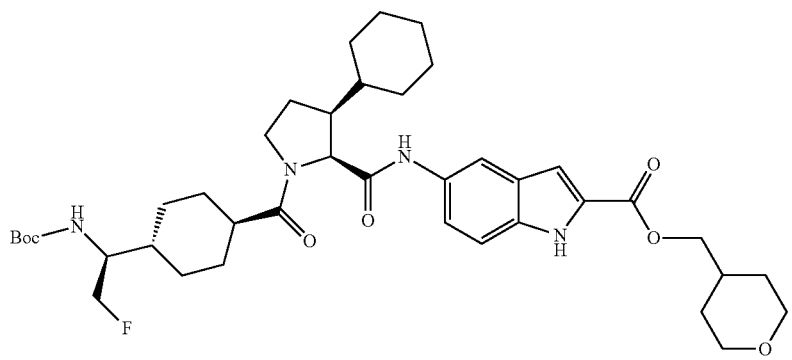

Reference Example 107

(2S)-2-Methoxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-indole-2-carboxylate

[Formula 384]

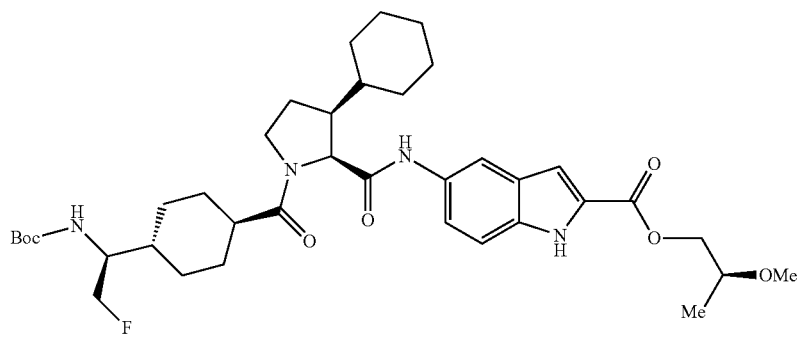

The same procedure as described in Reference Example 63 was carried out to obtain the title compound (40.6 mg, 20%) from the compound of Reference Example 81 (182 mg, 0.290 mmol) and Reference Example 146-2 (78.5 mg, 0.871 mmol).

MS (ESI+) 699 (M+1, 100%)

The same procedure as described in Reference Example 65 was carried out to obtain the title compound (31.3 mg, 26%) from the compound of Reference Example 81 (100 mg, 0.160 mmol) and 1-[(chlorocarbonyl)oxy]ethyl propan-2-yl carbonate (39.9 mg, 0.239 mmol).

MS (ESI+) 757 (M+1, 100%)

Reference Example 108

1-{[(Propan-2-yloxy)carbonyl]oxy}ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-indole-2-carboxylate

[Formula 385]

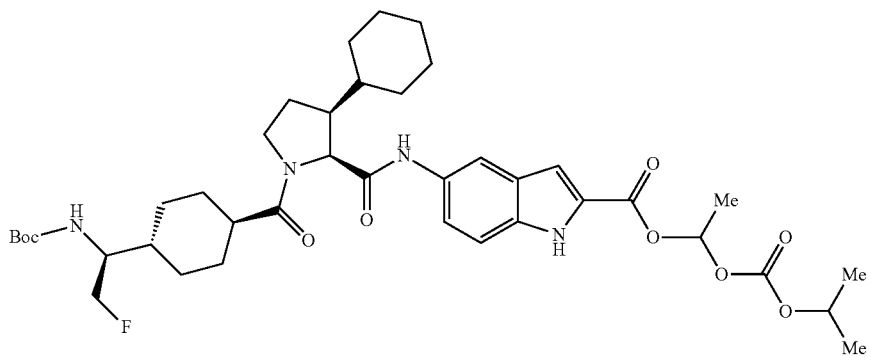

Reference Example 109

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)furo[2,3-b]pyridine-2-carboxylic acid

[Formula 386]

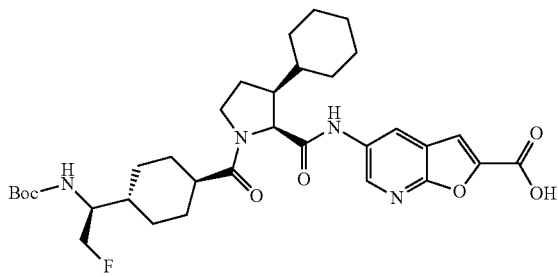

The same procedure as described in Reference Example 3 was carried out to obtain the title compound from the compound of Reference Example 109-4 (17.1 mg, 0.027 mmol).

MS (ESI+) 629 (M+1, 74%)

Reference Example 109-1

Methyl 5-nitrofuro[2,3-b]pyridine-2-carboxylate

[Formula 387]

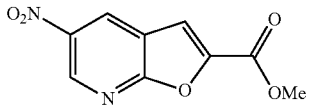

An aqueous solution (4.4 mL) of sodic nitro malonaldehyde monohydrate (490 mg, 3.12 mmol) was added dropwise to a solution of methyl 5-amino-2-furoate (440 mg, 3.12 mmol) in methanol (4.4 mL). Methanol and water were added to the obtained suspension until it became a solution. Concentrated hydrochloric acid was added slowly to the obtained solution in an ice bath, and the precipitated solid was filtered out. The obtained filtrate was suspended in DMF (4.4 mL) and water (4.4 mL), then the suspension was heated with stirring at 80° C., a solution was thus obtained, then the obtained solution was gradually allowed to cool and then placed in an ice bath. The obtained precipitate was filtered out and dried to obtain the title compound (171 mg, 25%).

$^{1}$H-NMR (CDCl$_{3}$): δ 9.41 (d, 1H, J=2.2 Hz), 8.92 (d, 1H, J=2.2 Hz), 7.67 (s, 1H), 4.04 (s, 3H).

Reference Example 109-2

Methyl 5-aminofuro[2,3-b]pyridine-2-carboxylate

[Formula 388]

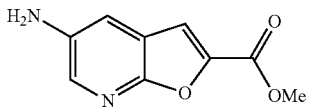

To a mixed solvent of reduced iron (226 mg, 3.65 mmol) in methanol/water (4.86 mL/2.43 mL), the compound of Reference Example 109-1 (162 mg, 0.729 mmol) and ammonium chloride (46.8 mg, 0.875 mmol) were added, and the mixture was heated with stirring at 75° C. for 2 hours. After having been allowed to cool, insoluble matter was filtered off from the reaction mixture, followed by dilution with ethyl acetate, then the resultant was washed serially with water and a saturated saline solution, then dried over sodium sulfate, and then the mixture was concentrated to obtain the title compound (110 mg, 79%).

$^{1}$H-NMR (d-DMSO): δ 7.88 (d, 1H, J=2.9 Hz), 7.58 (s, 1H), 7.27 (d, 1H, J=2.9 Hz), 5.36 (s, 2H), 3.87 (s, 3H),

Reference Example 109-3

Methyl 5-({(3S)-1-(tert-butoxycarbonyl)-3-cyclohexyl-L-prolyl}amino)furo[2,3-b]pyridine-2-carboxylate

[Formula 389]

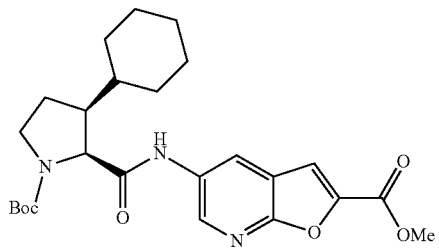

The same procedure as described in Reference Example 1 was carried out to obtain the title compound (38.6 mg, 28%) from the compound of Reference Example 109-2 (56.1 mg, 0.292 mmol).

MS (ESI+) 472 (M+1, 100%)

Reference Example 109-4

Methyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)furo[2,3-b]pyridine-2-carboxylate

[Formula 390]

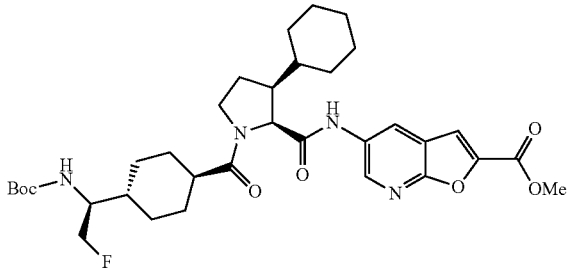

The same procedures as described in Reference Example 9-2 and Reference Example 1 were carried out in this order to obtain the title compound (17.4 mg, 33%) from the compound of Reference Example 109-3 (38.6 mg, 0.082 mmol).

MS (ESI+) 643 (M+1, 100%)

Reference Example 110

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-1-benzothiophene-2-carboxylic acid

[Formula 391]

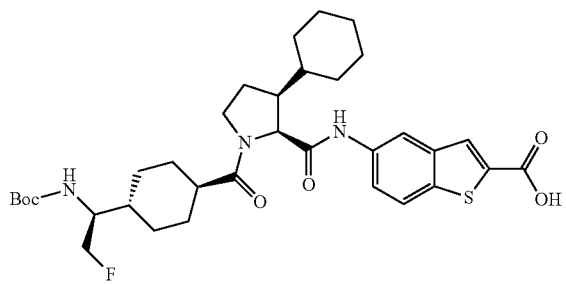

The same procedure as described in Reference Example 3 was carried out to obtain the title compound from the compound of Reference Example 110-4 (358 mg, 0.54 mmol).
MS (ESI+) 644 (M+1, 36%)

Reference Example 110-1

Methyl 5-nitro-1-benzothiophene-2-carboxylate

[Formula 392]

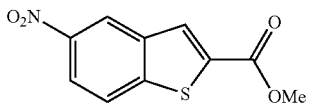

Potassium carbonate (1.73 g, 12.5 mmol) was added to a solution of 2-chloro-5-nitrobenzaldehyde (1.94 g, 10.5 mmol) and methyl 2-mercapto acetate (1.11 g, 10.5 mmol) in DMF (21 mL), and the mixture was stirred at room temperature overnight. Water (100 mL) was added thereto, then the reaction solution was stirred at room temperature for 1 hour, and then the obtained precipitate was filtered out and dried to obtain the title compound (2.35 g, 94%).
¹H-NMR (d-DMSO): δ 9.00 (s, 1H), 8.47-8.42 (m, 1H), 8.40-8.28 (m, 2H), 3.92 (s, 3H).

Reference Example 110-2

Methyl 5-amino-1-benzothiophene-2-carboxylate

[Formula 393]

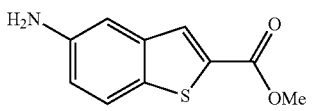

The same procedure as described in Reference Example 109-2 was carried out to obtain the title compound (193 mg, 94%) from the compound of Reference Example 110-1 (237 mg, 0.99 mmol).

¹H-NMR (d-DMSO): δ 7.93 (s, 1H), 7.65 (d, 1H, J=8.8 Hz), 7.05 (d, 1H. J=2.2 Hz), 6.88 (dd, 1H, J=2.2, 8.8 Hz), 5.30 (s, 2H), 3.85 (s, 3H).

Reference Example 110-3 tert-Butyl (2S,3S)-3-cyclohexyl-2-{[2-(methoxycarbonyl)-1-benzothiophen-5-yl]carbamoyl}pyrrolidine-1-carboxylate

[Formula 394]

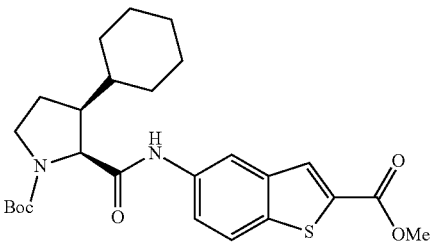

The same procedure as described in Reference Example 1 was carried out to obtain the title compound (351 mg, 77%) from the compound of Reference Example 110-2 (193 mg, 0.93 mmol).
MS (ESI+) 487 (M+1, 30%)

Reference Example 110-4

Methyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzothiophene-2-carboxylate

[Formula 395]

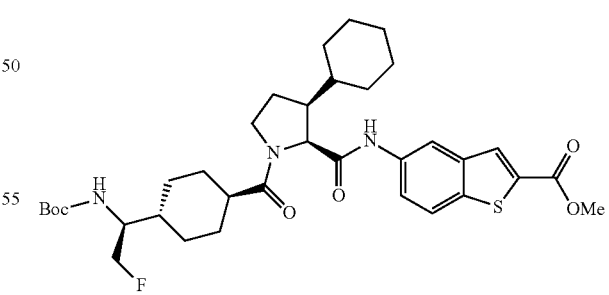

The same procedures as described in Reference Example 9-2 and Reference Example 1 were carried out in this order to obtain the title compound (361 mg, 76%) from the compound of Reference Example 110-3 (351 mg, 0.72 mmol).
MS (ESI+) 658 (M+1, 100%)

Reference Example 111

(2R)-2-Methoxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-indole-2-carboxylate

[Formula 396]

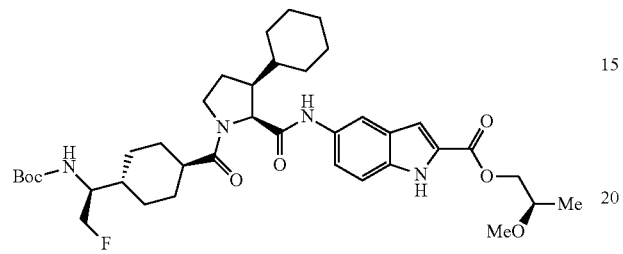

The same procedure as described in Reference Example 63 was carried out to obtain the title compound (132 mg, 38%) from the compound of Reference Example 81 (308 mg, 0.492 mmol) and the compound of Reference Example 170-1 (133 mg, 1.48 mmol).

MS (ESI+) 699 (M+1, 100%)

Reference Example 112

(3S)-1-[(trans-4-{(1S)-1-[(tert-Butoxycarbonyl)amino]-2-fluoroethyl}cyclohexyl)carbonyl]-3-cyclohexyl-N-{3-fluoro-4-[(phenylsulfonyl)carbamoyl]phenyl}-L-prolinamide

[Formula 397]

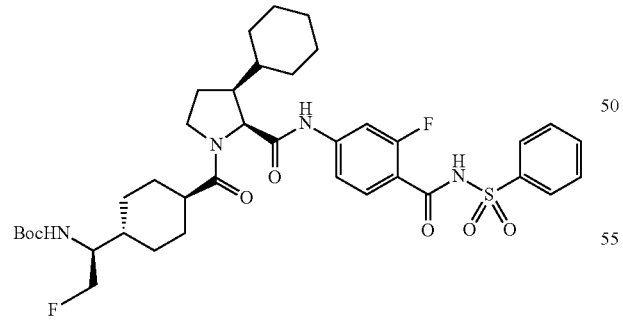

The same procedure as described in Reference Example 1 was carried out to obtain the title compound (45.0 mg, 65%) from the compound of Reference Example 112-2 (53.0 mg, 0.093 mmol) and the compound of Reference Example 53-3 (29.0 mg, 0.102 mmol).

MS (ESI+) 745 (M+1, 56%)

Reference Example 112-1 tert-Butyl (2S,3S)-3-cyclohexyl-2-({3-fluoro-4-[(phenylsulfonyl)carbamoyl]phenyl}carbamoyl)pyrrolidine-1-carboxylate

[Formula 398]

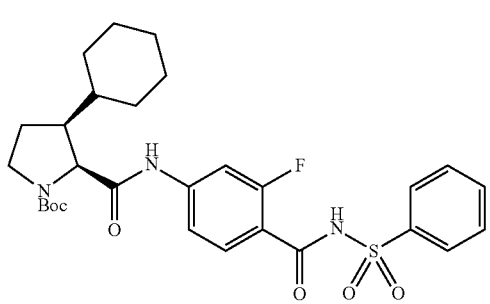

The same procedure as described in Reference Example 89-1 was carried out to obtain the title compound (53.0 mg, 30%) from the compound of Reference Example 143-1 (135.0 mg, 0.31 mmol) and commercially available benzenesulfonamide (68.0 mg, 0.43 mmol).

MS (ESI+) 574 (M+1, 100%)

Reference Example 112-2

(3S)-3-Cyclohexyl-N-{3-fluoro-4-[(phenylsulfonyl)carbamoyl]phenyl}-L-prolinamide trifluoroacetate

[Formula 399]

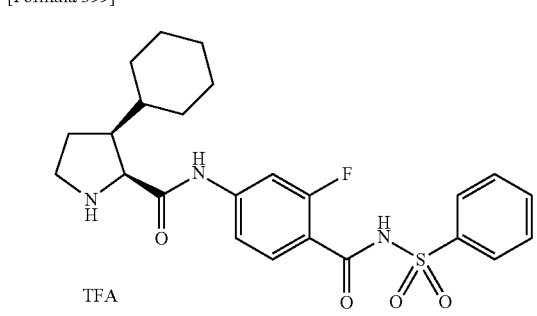

The same procedure as described in Reference Example 9-2 was carried out to obtain the title compound (53 mg, 100%) from the compound of Reference Example 112-1 (53.0 mg, 0.093 mmol).

MS (ESI+) 474 (M+1, 100%)

Reference Example 113 tert-Butyl [(1S)-1-(trans-4-{[(2S,3S)-3-cyclohexyl-2-({4-[(pyridin-2-ylsulfonyl)carbamoyl]phenyl}carbamoyl)pyrrolidin-1-yl]carbonyl}cyclohexyl)-2-fluoroethyl]carbamate

[Formula 400]

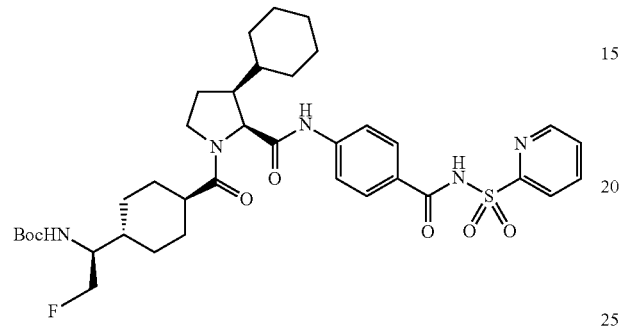

The same procedure as described in Reference Example 1 was carried out to obtain the title compound (83.0 mg, 68%) from the compound of Reference Example 113-2 (94.0 mg, 0.169 mmol) and the compound of Reference Example 53-3 (54.0 mg, 0.186 mmol).

MS (ESI+) 728 (M+1, 100%)

Reference Example 113-1 tert-Butyl (2S,3S)-3-cyclohexyl-2-({4-[(pyridin-2-ylsulfonyl)carbamoyl]phenyl}carbamoyl)pyrrolidine-1-carboxylate

[Formula 401]

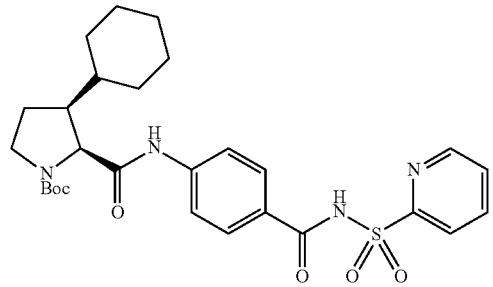

The same procedure as described in Reference Example 89-1 was carried out to obtain the title compound (94.0 mg, 43%) from the compound of Reference Example 82-1 (164.0 mg, 0.394 mmol) and commercially available pyridine-2-sulfonamide (176.0 mg, 0.552 mmol).

MS (ESI+) 557 (M+1, 69%)

Reference Example 113-2

(3S)-3-Cyclohexyl-N-{4-[(pyridin-2-ylsulfonyl)carbamoyl]phenyl}-L-prolinamide trifluoroacetate

[Formula 402]

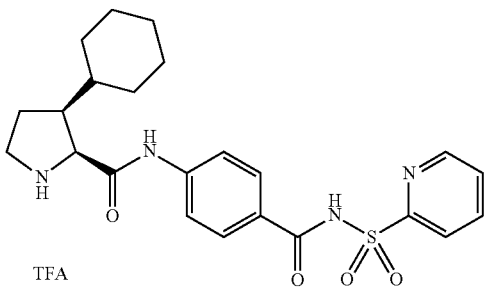

The same procedure as described in Reference Example 9-2 was carried out to obtain the title compound (94 mg, 100%) from the compound of Reference Example 113-1 (94.0 mg, 0.169 mmol).

MS (ESI+) 457 (M+1, 100%)

Reference Example 114 tert-Butyl [(1S)-2-fluoro-1-(trans-4-{[(2S,3R)-3-(piperidin-1-yl)-2-{[4-(1H-tetrazol-5-yl)phenyl]carbamoyl}pyrrolidin-1-yl]carbonyl}cyclohexyl)ethyl]carbamate

[Formula 403]

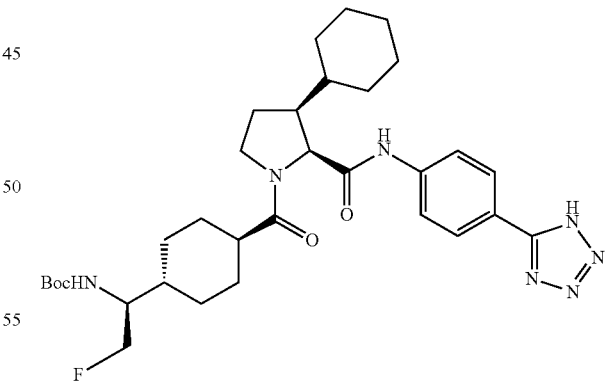

The same procedure as described in Reference Example 1 was carried out to obtain the title compound (10 mg, 23%) from the compound of Reference Example 114-5 (24 mg, 0.0703 mmol) and the compound of Reference Example 53-3 (21 mg, 0.070 mmol).

MS (ESI+) 613 (M+1, 100%)

Reference Example 114-1

(rac.)-1-Benzyl 2-methyl (2S,3R)-3-(piperidin-1-yl)pyrrolidine-1,2-dicarboxylate

[Formula 404]

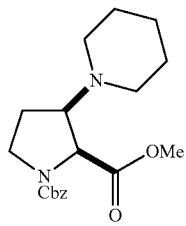

The same procedure as described in Reference Example 147-1 was carried out to obtain the title compound (105 mg, 30%) from 1-benzyl 2-methyl-3-oxopyrrolidine-1,2-dicarboxylate (283 mg, 1.02 mmol) known from literature (e.g., J. Org. Chem. 1985, 50, 25, 5223.).

MS (ESI+) 347 (M+1, 100%)

Reference Example 114-2

1-Benzyl 2-methyl (2S,3R)-3-(piperidin-1-yl)pyrrolidine-1,2-dicarboxylate

[Formula 405]

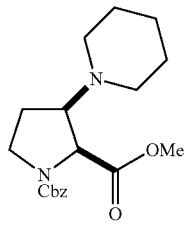

The compound of Reference Example 114-1 as a racemate was separated by HPLC under the following conditions to obtain the title compound.
CHIRALCEL OD-H (0.46 cmI.D.×25 cmL), Mobile phase: n-hexane/isopropanol (4/1), Flow rate: 1.0 mL/min, Wavelength: 220 nm, RT 5.830 min

Reference Example 114-3

(3R)-1-[(Benzyloxy)carbonyl]-3-piperidin-1-yl-L-proline

[Formula 406]

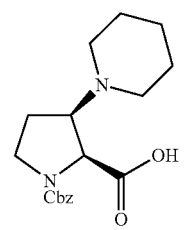

The same procedure as described in Reference Example 147-2 was carried out to obtain the title compound (42 mg, 100%) from the compound of Reference Example 114-2 (43 mg, 0.124 mmol).

MS (ESI+) 333 (M+1, 100%)

Reference Example 114-4

Benzyl(2S,3R)-3-(piperidin-1-yl)-2-{[4-(1H-tetrazol-5-yl)phenyl]carbamoyl}pyrrolidine-1-carboxylate

[Formula 407]

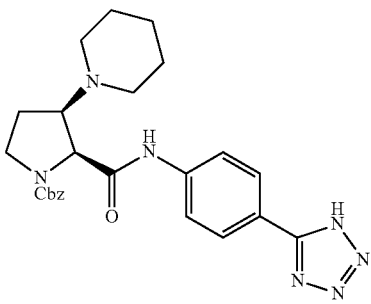

The same procedure as described in Reference Example 138-2 was carried out to obtain the title compound (34 mg, 58%) from the compound of Reference Example 114-4 (42 mg, 0.124 mmol) and commercially available 4-(1H-tetrazol-5-yl)-phenylamine (22 mg, 0.136 mmol).

MS (ESI+) 476 (M+1, 100%)

Reference Example 114-5

Benzyl(2S,3R)-3-(piperidin-1-yl)-2-{[4-(1H-tetrazol-5-yl)phenyl]carbamoyl}pyrrolidine-1-carboxylate

[Formula 408]

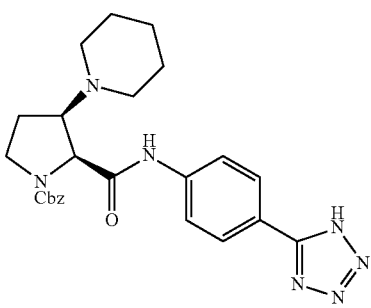

The diastereo mixture of Reference Example 114-4 was separated by HPLC under the following conditions to obtain the title compound.

Reference Example 114-6

(3R)-3-Piperidin-1-yl-N-[4-(1H-tetrazol-5-yl)phenyl]-L-prolinamide

[Formula 409]

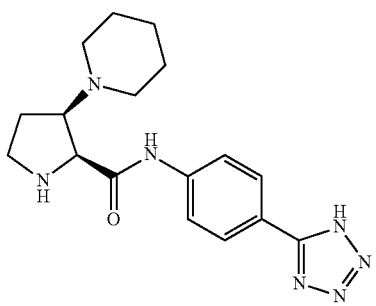

To a solution of the compound of Reference Example 114-5 (34 mg, 0.0715 mmol) in ethanol (1 mL), palladium-carbon (17 mg) was added, and the mixture was stirred for 3 hours under hydrogen atmosphere. The reaction solution was filtered through Celite, and the filtrate was concentrated under reduced pressure to obtain the title compound (24 mg, 98%).

MS (ESI+) 342 (M+1, 3.9%)

Reference Example 115

(3S)-1-[(trans-4-{(1S)-1-[(tert-Butoxycarbonyl)amino]-2-fluoroethyl}cyclohexyl)carbonyl]-3-cyclohexyl-N-(4-{[(2-fluorophenyl)sulfonyl]carbamoyl}phenyl)-L-prolinamide

[Formula 410]

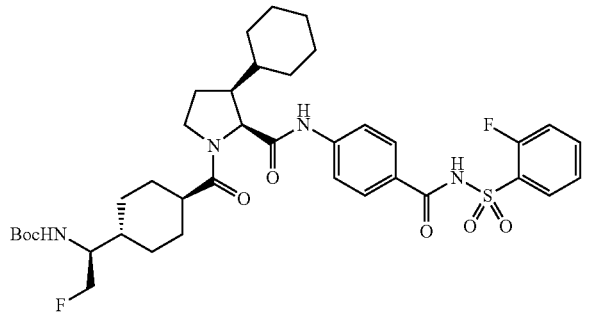

The same procedure as described in Reference Example 1 was carried out to obtain the title compound (25.0 mg, 71%) from the compound of Reference Example 115-2 (27.0 mg, 0.047 mmol) and the compound of Reference Example 53-3 (15.0 mg, 0.052 mmol).

MS (ESI+) 745 (M+1, 100%)

Reference Example 115-1 tert-Butyl (2S,3S)-3-cyclohexyl-2-[(4-{[(2-fluorophenyl)sulfonyl]carbamoyl}phenyl)carbamoyl]pyrrolidine-1-carboxylate

[Formula 411]

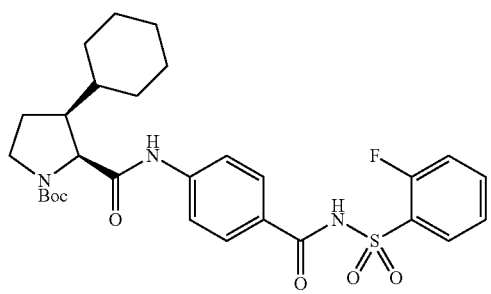

The same procedure as described in Reference Example 89-1 was carried out to obtain the title compound (27.0 mg, 24%) from the compound of Reference Example 82-1 (82.0 mg, 0.197 mmol) and commercially available 2-fluorobenzenesulfonamide (48.0 mg, 0.276 mmol).

MS (ESI+) 574 (M+1, 100%)

Reference Example 115-2

(3S)-3-Cyclohexyl-N-(4-{[(2-fluorophenyl)sulfonyl]carbamoyl}phenyl)-L-prolinamide trifluoroacetate

[Formula 412]

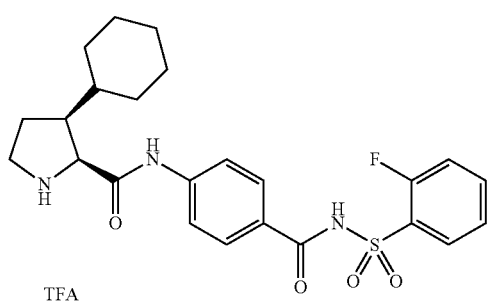

The same procedure as described in Reference Example 9-2 was carried out to obtain the title compound (27 mg, 100%) from the compound of Reference Example 115-1 (27.0 mg, 0.047 mmol).

MS (ESI+) 474 (M+1, 100%)

Reference Example 116 tert-Butyl [(1S)-1-(trans-4-{[(2S,3S)-3-cyclohexyl-2-({4-[(pyridin-2-ylmethyl)carbamoyl]phenyl}carbamoyl)pyrrolidin-1-yl]carbonyl}cyclohexyl)-2-fluoroethyl]carbamate

[Formula 413]

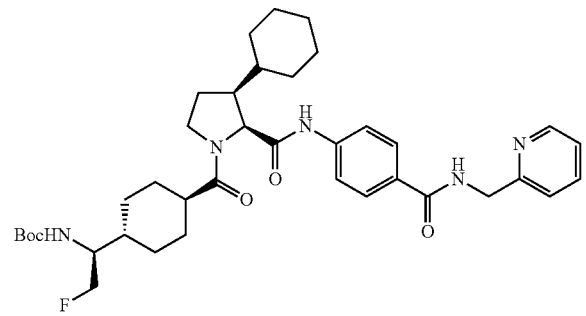

The same procedure as described in Reference Example 1 was carried out to obtain the title compound (38.0 mg, 86%) from the compound of Reference Example 116-2 (33.0 mg, 0.065 mmol) and the compound of Reference Example 53-3 (21.0 mg, 0.072 mmol).

MS (ESI+) 678 (M+1, 100%)

Reference Example 116-1 tert-Butyl (2S,3S)-3-cyclohexyl-2-({4-[(pyridin-2-ylmethyl)carbamoyl]phenyl}carbamoyl)pyrrolidine-1-carboxylate

[Formula 414]

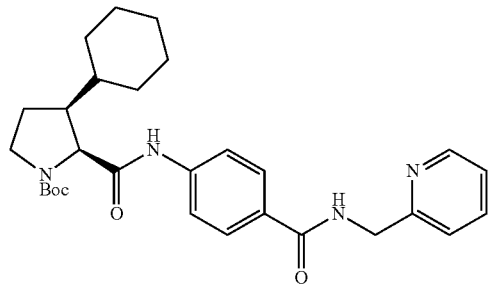

The same procedure as described in Reference Example 89-1 was carried out to obtain the title compound (33.0 mg, 33%) from the compound of Reference Example 82-1 (82.0 mg, 0.197 mmol) and commercially available 1-(pyridin-2-yl)methanamine (30.0 mg, 0.276 mmol).

MS (ESI+) 507 (M+1, 100%)

Reference Example 116-2

(3S)-3-Cyclohexyl-N-{4-[(pyridin-2-ylmethyl)carbamoyl]phenyl}-L-prolinamide trifluoroacetate

[Formula 415]

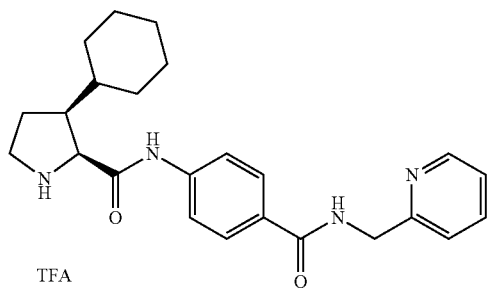

The same procedure as described in Reference Example 9-2 was carried out to obtain the title compound (33 mg, 100%) from the compound of Reference Example 116-1 (33.0 mg, 0.065 mmol).

MS (ESI+) 474 (M+1, 4%)

Reference Example 117

6-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-chloroimidazo[1,2-a]pyridine-2-carboxylic acid

[Formula 416]

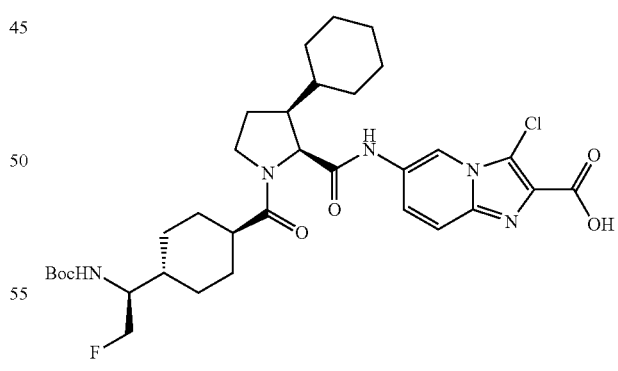

The same procedure as described in Reference Example 3 was carried out to obtain the title compound (8.2 mg, 97%) from the compound of Reference Example 117-4 (8.8 mg, 0.01274 mmol).

MS (ESI+) 662 (M+1, 100%)

Reference Example 117-1

Ethyl 6-{[(3S)-1-(tert-butoxycarbonyl)-3-cyclo-hexyl-L-prolyl]amino}imidazo[1,2-a]pyridine-2-carboxylate

[Formula 417]

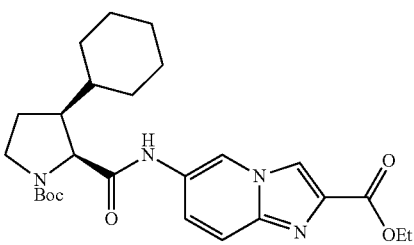

The same procedure as described in Reference Example 138-2 was carried out to obtain the title compound (303 mg, 35%) from the compound of Reference Example 11-1 (539 mg, 1.81 mmol) and commercially available ethyl 6-aminoimidazo[1,2-A]pyridine-2-carboxylate (446 mg, 2.17 mmol).

MS (ESI+) 485 (M+1, 100%)

Reference Example 117-2

Ethyl 6-{[(3S)-1-(tert-butoxycarbonyl)-3-cyclo-hexyl-L-prolyl]amino}-3-chloroimidazo[1,2-a]pyridine-2-carboxylate

[Formula 418]

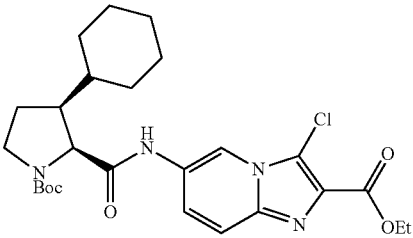

The same procedure as described in Reference Example 34-2 was carried out to obtain the title compound (109.5 mg, 51%) from the compound of Reference Example 117-1 (199.1 mg, 0.411 mmol).

MS (ESI+) 519 (M+1, 100%)

Reference Example 117-3

Ethyl 3-chloro-6-{[(3S)-3-cyclohexyl-L-prolyl]amino}imidazo[1,2-a]pyridine-2-carboxylate bis(trifluoroacetate)

[Formula 419]

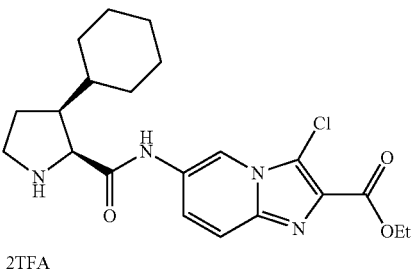

2TFA

The same procedure as described in Reference Example 9-2 was carried out to obtain the title compound (26.2 mg, 100%) from the compound of Reference Example 117-2 (21 mg, 0.04046 mmol).

MS (ESI+) 419 (M+1, 100%)

Reference Example 117-4

Ethyl 6-({(3S)-1-[(trans-4-{(1S)-1-[(tert-butoxycarbonyl)amino]-2-fluoroethyl}cyclohexyl)carbonyl]-3-cyclohexyl-L-prolyl}amino)-3-chloroimidazo[1,2-a]pyridine-2-carboxylate

[Formula 420]

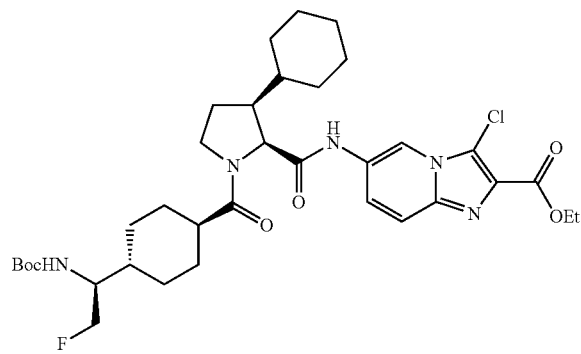

The same procedure as described in Reference Example 1 was carried out to obtain the title compound (8.8 mg, 32%) from the compound of Reference Example 117-3 (26.2 mg, 0.04046 mmol) and the compound of Reference Example 53-3 (14 mg, 0.0484 mmol).

MS (ESI+) 690 (M+1, 100%)

Reference Example 118

5-{[(3R)-1-[(trans-4-{(1S)-1-[(tert-Butoxycarbonyl)amino]-2-fluoroethyl}cyclohexyl)carbonyl]-3-(4-oxocyclohexyl)-D-prolyl]amino}-1-benzofuran-2-carboxylic acid

[Formula 421]

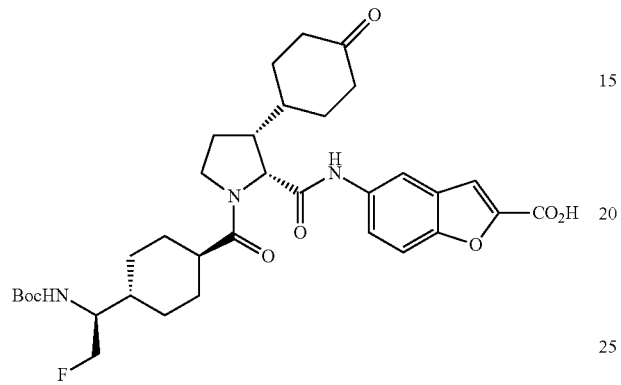

The same procedure as described in Reference Example 3 was carried out to obtain the title compound (12.8 mg, 92%) from the compound of Reference Example 118-3 (14.5 mg, 0.0216 mmol).

MS (ESI+) 642 (M+1, 100%)

Reference Example 118-1 tert-Butyl (2R,3R)-2-{[2-(ethoxycarbonyl)-1-benzofuran-5-yl]carbamoyl}-3-(4-oxocyclohexyl)pyrrolidine-1-carboxylate

[Formula 422]

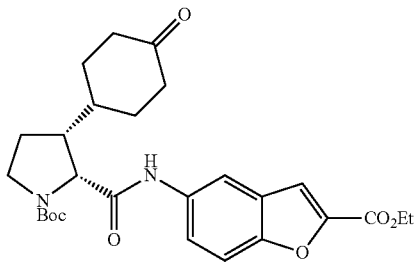

The same procedure as described in Reference Example 161-3 was carried out to obtain the title compound (50.9 mg, 54%) from the compound of Reference Example 166-4 (59.0 mg, 0.189 mmol) and ethyl 5-amino-1-benzofuran-2-carboxylate (38.9 mg, 0.189 mmol).

MS (ESI+) 499 (M+1, 26%)

Reference Example 118-2

Ethyl 5-{[(3R)-3-(4-oxocyclohexyl)-D-prolyl]amino}-1-benzofuran-2-carboxylate hydrochloride

[Formula 423]

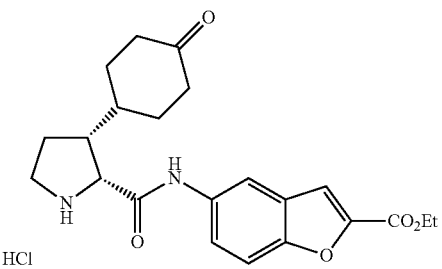

The same procedure as described in Reference Example 1-2 was carried out to obtain the title compound (44.3 mg, 100%) from the compound of Reference Example 118-1 (50.9 mg, 0.102 mmol).

MS (ESI+) 399 (M+1, 100%)

Reference Example 118-3

Ethyl 5-{[(3R)-1-[(trans-4-{(1S)-1-[(tert-butoxycarbonyl)amino]-2-fluoroethyl}cyclohexyl)carbonyl]-3-(4-oxocyclohexyl)-D-prolyl]amino}-1-benzofuran-2-carboxylate

[Formula 424]

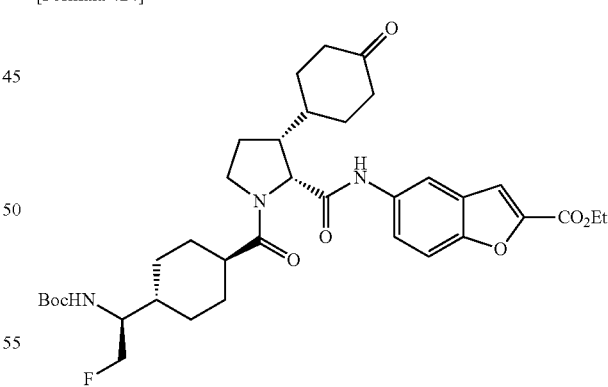

The same procedure as described in Reference Example 1 was carried out to obtain the title compound (14.5 mg, 21%) from the compound of Reference Example 118-2 (44.3 mg, 0.102 mmol) and the compound of Reference Example 53-3 (32.5 mg, 0.112 mmol).

MS (ESI+) 670 (M+1, 44%)

Reference Example 119

3-Ethoxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 425]

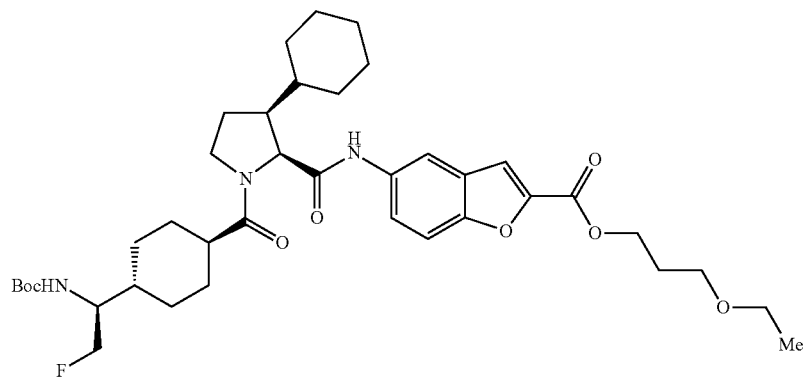

The same procedure as described in Reference Example 1 was carried out to obtain the title compound (146 mg, 96%) from the compound of Reference Example 119-3 (93 mg, 0.21 mmol) and the compound of Reference Example 53-3 (68 mg, 0.23 mmol).

MS (ESI+) 714 (M+1, 85%)

Reference Example 119-1

5-{[(3S)-1-(tert-Butoxycarbonyl)-3-cyclohexyl-L-prolyl]amino}-1-benzofuran-2-carboxylic acid

[Formula 426]

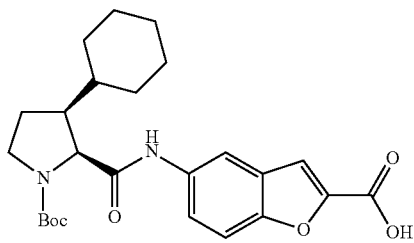

The compound of Reference Example 50-1 (964.0 mg, 1.99 mmol) was dissolved in methanol (30.0 mL) and tetrahydrofuran (30.0 mL), then a 1 mol/L aqueous solution of sodium hydroxide (15.0 mL) was added thereto, and the mixture was stirred at 50° C. for 2 hours. A 5% aqueous solution of potassium hydrogensulfate was added to the reaction solution, followed by extraction with chloroform twice. The organic layer was washed with a saturated saline solution, dried over anhydrous sodium sulfate and filtered, and then the organic layer was concentrated under reduced pressure (908 mg, 1.99 mmol).

MS (ESI+) 457 (M+1, 20%)

Reference Example 119-2 tert-Butyl (2S,3S)-3-cyclohexyl-2-({2-[(3-ethoxy-propoxy)carbonyl]-1-benzofuran-5-yl}carbamoyl)pyrrolidine-1-carboxylate

[Formula 427]

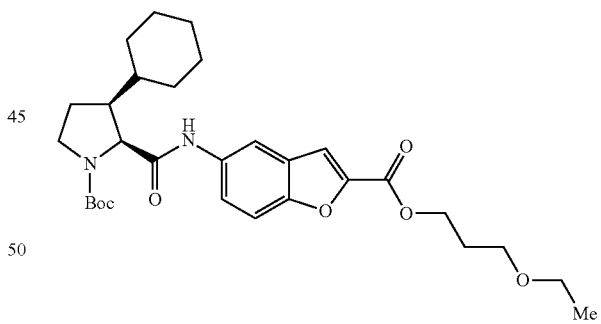

To a solution of the compound obtained in Reference Example 119-1 (159.0 mg, 0.35 mmol) in DMF (4.0 mL), 1-hydroxybenzotriazole (61.0 mg, 0.46 mmol), 1-ethyl-3-(3-dimethylaminopropyl)carbodiimide hydrochloride (87 mg, 0.46 mmol), triethylamine (195 μL, 1.4 mmol), and 3-ethoxy-1-propanol (240 μL, 2.1 mmol) were added, and the mixture was stirred at 50° C. for 8 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution once, respectively, then dried over sodium sulfate and filtered, and the filtrate was concentrated under reduced pressure. The obtained residue was purified by silica gel column chromatography to obtain the title compound (115.8 mg, 61%).

MS (ESI+) 543 (M+1, 34%)

Reference Example 119-3

3-Ethoxypropyl 5-{[(3S)-3-cyclohexyl-L-prolyl]amino}-1-benzofuran-2-carboxylate hydrochloride

[Formula 428]

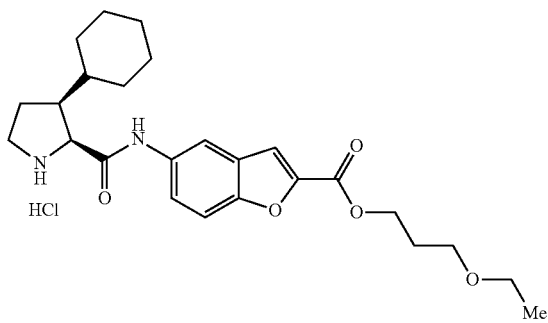

The same procedure as described in Reference Example 1-2 was carried out to obtain the title compound (93 mg, 100%) from the compound of Reference Example 119-2 (115 mg, 0.21 mmol).

MS (ESI+) 443 (M+1, 100%)

Reference Example 120

Tetrahydro-2H-pyran-4-ylmethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 429]

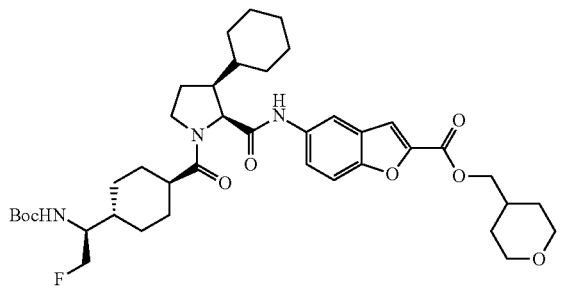

The same procedure as described in Reference Example 1 was carried out to obtain the title compound (103 mg, 89%) from the compound of Reference Example 120-2 (73 mg, 0.16 mmol) and the compound of Reference Example 53-3 (51 mg, 0.18 mmol).

MS (ESI+) 726 (M+1, 83%)

Reference Example 120-1 tert-Butyl (2S,3S)-3-cyclohexyl-2-({2-[(tetrahydro-2H-pyran-4-ylmethoxy)carbonyl]-1-benzofuran-5-yl}carbamoyl)pyrrolidine-1-carboxylate

[Formula 430]

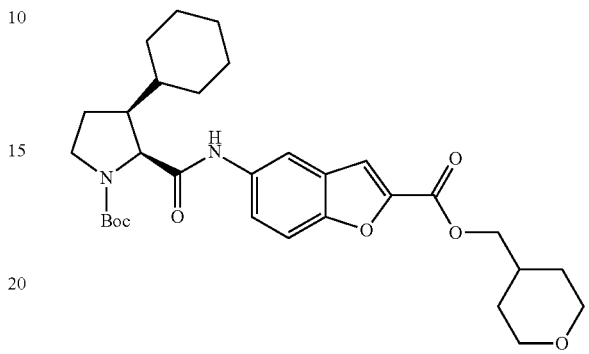

To a solution of the compound obtained in Reference Example 119-1 (132.0 mg, 0.29 mmol) in DMF (4.0 mL), 1-hydroxybenzotriazole (51.0 mg, 0.38 mmol), 1-ethyl-3-(3-dimethylaminopropyl)carbodiimide hydrochloride (73.0 mg, 0.38 mmol), triethylamine (162 μL, 1.2 mmol), and tetrahydropyran-4-methanol (101 mg, 0.87 mmol) were added, and the mixture was stirred at 50° C. for 7 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution once, respectively, then dried over sodium sulfate and filtered, and the filtrate was concentrated under reduced pressure. The obtained residue was purified by silica gel column chromatography to obtain the title compound (89.6 mg, 56%).

MS (ESI+) 555 (M+1, 41%)

Reference Example 120-2

Tetrahydro-2H-pyran-4-ylmethyl 5-{[(3S)-3-cyclohexyl-L-prolyl]amino}-1-benzofuran-2-carboxylate hydrochloride

[Formula 431]

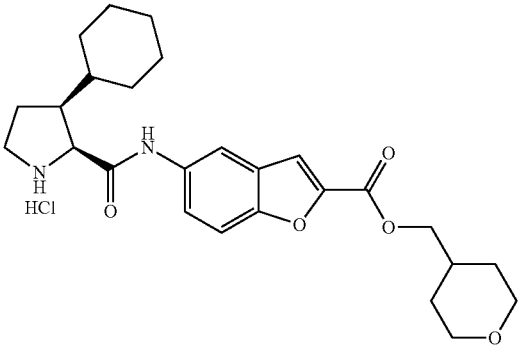

315

The same procedure as described in Reference Example 1-2 was carried out to obtain the title compound (73 mg, 100%) from the compound of Reference Example 120-1 (89 mg, 0.16 mmol).

MS (ESI+) 455 (M+1, 100%)

Reference Example 121

(2S)-Tetrahydrofuran-2-ylmethyl 5-({(3S)-1-[(trans-4-{(1S)-1-[(tert-butoxycarbonyl)amino]-2-fluoroethyl}cyclohexyl)carbonyl-3-cyclohexyl)carbonyl]-3-cyclohexyl-L-prolyl}amino)-1-benzofuran-2-carboxylate

[Formula 432]

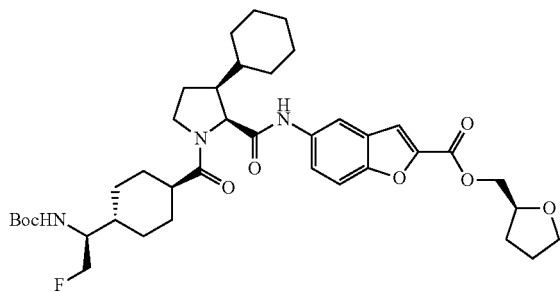

The same procedure as described in Reference Example 1 was carried out to obtain the title compound (18.3 mg, 51%) from the compound of Reference Example 121-3 (23.8 mg, 0.05 mmol) and the compound of Reference Example 53-3 (14.4 mg, 0.050 mmol).

MS (ESI+) 712 (M+1, 55%)

Reference Example 121-1 tert-Butyl (2S,3S)-3-cyclohexyl-2-({2-[(tetrahydrofuran-2-methoxy)carbonyl]-1-benzofuran-5-yl}carbamoyl)pyrrolidine-1-carboxylate

[Formula 433]

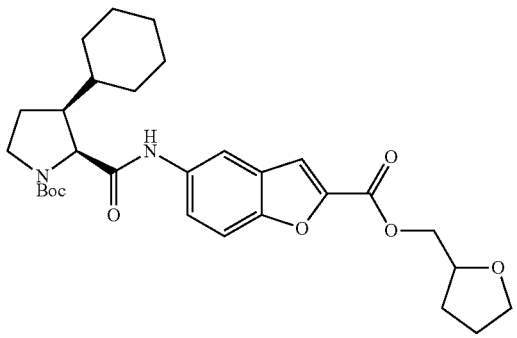

The same procedure as described in Reference Example 76-2 was carried out to obtain the title compound (129.3 mg, 73%) from the compound of Reference Example 119-1 (150 mg, 0.328 mmol) and tetrahydrofurfuryl bromide (81 mg, 0.492 mmol).

MS (ESI+) 541 (M+1, 25%)

Reference Example 121-2 tert-Butyl (2S,3S)-3-cyclohexyl-2-[(2-{[(2S)-tetrahydrofuran-2-ylmethoxy]carbonyl}-1-benzofuran-5-yl)carbamoyl]pyrrolidine-1-carboxylate

[Formula 434]

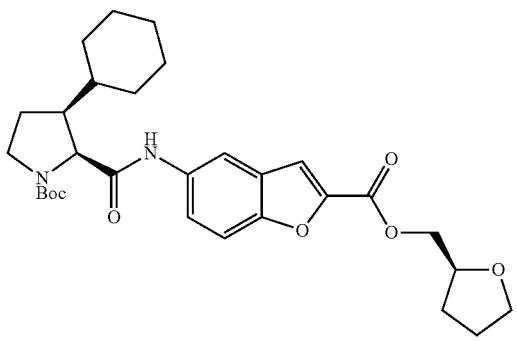

The diastereo mixture of Reference Example 121-1 was separated by HPLC under the following conditions to obtain the title compound.

CHIRALPAK IC (0.46 cmI.D.×25 cmL), Mobile phase: n-hexane/ethanol (4/1), Flow rate: 1.0 mL/min, Wavelength: 254 nm, RT 20.029 min

Reference Example 121-3

(2S)-Tetrahydrofuran-2-ylmethyl 5-{[(3S)-3-cyclohexyl-L-prolyl]amino}-1-benzofuran-2-carboxylate hydrochloride

[Formula 435]

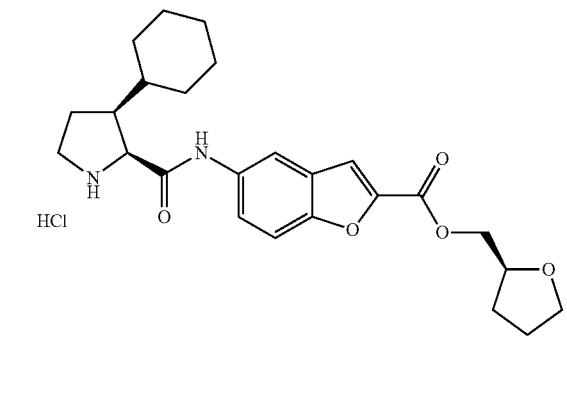

The same procedure as described in Reference Example 1-2 was carried out to obtain the title compound (23.8 mg, 100%) from the compound of Reference Example 121-2 (27.1 mg, 0.05 mmol).

MS (ESI+) 441 (M+1, 100%)

Reference Example 122

(2R)-Tetrahydrofuran-2-ylmethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 436]

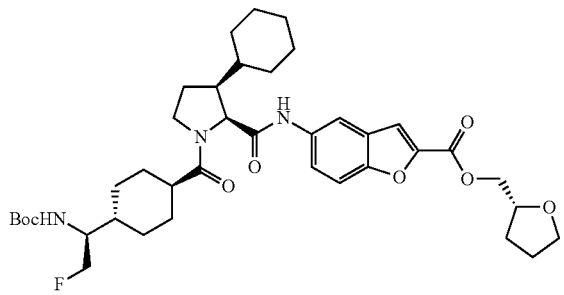

The same procedure as described in Reference Example 1 was carried out to obtain the title compound (13.6 mg, 40%) from the compound of Reference Example 122-2 (22.6 mg, 0.0474 mmol) and the compound of Reference Example 53-3 (13.7 mg, 0.0474 mmol).

MS (ESI+) 712 (M+1, 55%)

Reference Example 122-1 tert-Butyl (2S,3S)-3-cyclohexyl-2-[(2-{[(2R)-tetrahydrofuran-2-ylmethoxy]carbonyl}-1-benzofuran-5-yl)carbamoyl]pyrrolidine-1-carboxylate

[Formula 437]

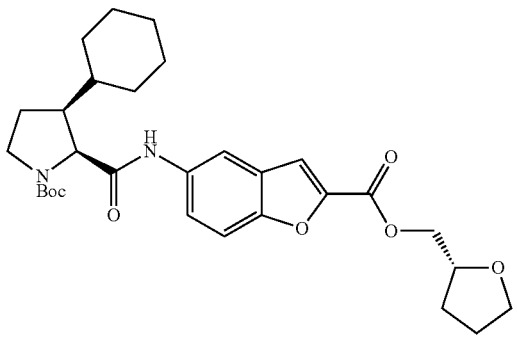

The diastereo mixture of Reference Example 121-1 was separated by HPLC under the following conditions to obtain the title compound.

CHIRALPAK IC (0.46 cmI.D.×25 cmL), Mobile phase: n-hexane/ethanol (4/1), Flow rate: 1.0 mL/min, Wavelength: 254 nm, RT 17.233 min

Reference Example 122-2

(2R)-Tetrahydrofuran-2-ylmethyl 5-{[(3S)-3-cyclohexyl-L-prolyl]amino}-1-benzofuran-2-carboxylate hydrochloride

[Formula 438]

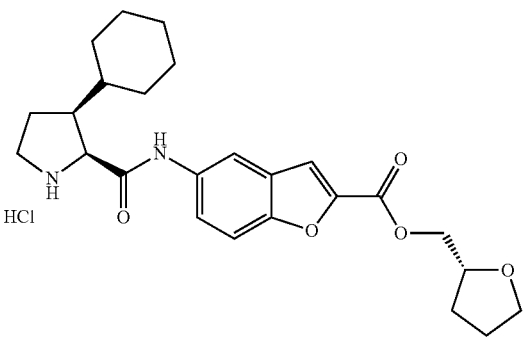

The same procedure as described in Reference Example 1-2 was carried out to obtain the title compound (333 mg, 100%) from the compound of Reference Example 122-1 (380 mg, 0.70 mmol).

MS (ESI+) 441 (M+1, 100%)

Reference Example 123

1,3-Diethoxypropan-2-yl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 439]

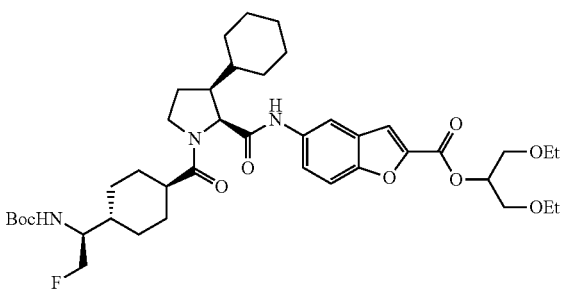

The same procedure as described in Reference Example 1 was carried out to obtain the title compound (80.2 mg, 60%) from the compound of Reference Example 123-4 (92.5 mg, 0.177 mmol) and the compound of Reference Example 53-3 (51.2 mg, 0.177 mmol).

MS (ESI+) 702 (M−55, 100%)

Reference Example 123-1

1,3-Diethoxypropan-2-yl 5-nitro-1-benzofuran-2-carboxylate

[Formula 440]

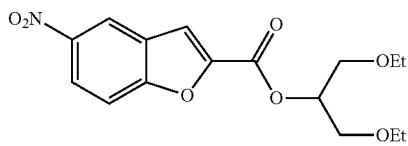

To a solution of commercially available 5-nitrobenzofuran-2-carboxylic acid (100 mg, 0.482 mmol) in DMF (3.5 mL), 1-hydroxybenzotriazole (85 mg, 0.627 mmol), WSC.HCl (120 mg, 0.627 mmol), triethylamine (270 μL, 1.93 mmol), and 1,3-diethoxy-2-propanol (456 μL, 2.92 mmol) were added, and the mixture was stirred at 50° C. for 14 hours. A saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution once, then dried over sodium sulfate and filtered, and the filtrate was concentrated under reduced pressure. The obtained residue was purified by silica gel column chromatography to obtain the title compound (106.1 mg, 65%).

MS (ESI+) 338 (M+1, 100%)

Reference Example 123-2

1,3-Diethoxypropan-2-yl 5-amino-1-benzofuran-2-carboxylate

[Formula 441]

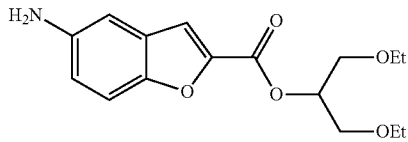

The same procedure as described in Reference Example 2-1 was carried out to obtain the title compound (94.3 mg, 97%) from the compound of Reference Example 123-1 (106 mg, 0.315 mmol).

MS (ESI+) 308 (M+1, 100%)

Reference Example 123-3 tert-Butyl (2S,3S)-3-cyclohexyl-2-[(2-{[(1,3-diethoxypropan-2-yl)oxy]carbonyl}-1-benzofuran-5-yl)carbamoyl]pyrrolidine-1-carboxylate

[Formula 442]

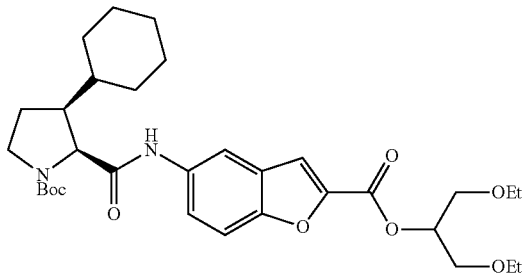

The same procedure as described in Reference Example 138-2 was carried out to obtain the title compound (103.8 mg, 64%) from the compound of Reference Example 11-1 (82.7 mg, 0.278 mmol) and the compound of Reference Example 123-2 (94.0 mg, 0.306 mmol).

MS (ESI+) 587 (M+1, 100%)

Reference Example 123-4

1,3-Diethoxypropan-2-yl 5-{[(3S)-3-cyclohexyl-L-prolyl]amino}-1-benzofuran-2-carboxylate hydrochloride

[Formula 443]

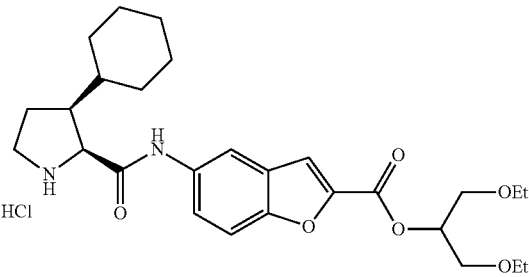

The same procedure as described in Reference Example 1-2 was carried out to obtain the title compound (92.5 mg, 100%) from the compound of Reference Example 123-3 (103.8 mg, 0.177 mmol).

MS (ESI+) 487 (M+1, 100%)

Reference Example 124

3-Methoxypropyl 5-({(3S)-1-[(trans-4-{(1S)-1-[(tert-butoxycarbonyl)amino]-2,2-difluoroethyl}cyclohexyl)carbonyl]-3-cyclohexyl-L-prolyl}amino)-1-benzofuran-2-carboxylate

[Formula 444]

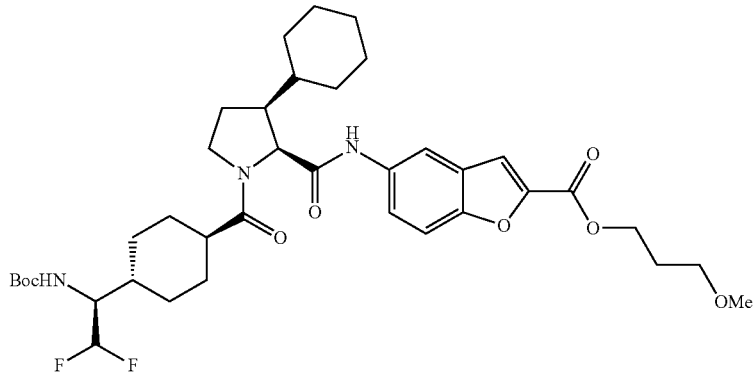

The same procedure as described in Reference Example 1 was carried out to obtain the title compound (196.6 mg, 85%) from the compound of Reference Example 124-4 (109.1 mg, 0.355 mmol) and the compound of Reference Example 124-7 (150.0 mg, 0.323 mmol).
MS (ESI+) 718 (M+1, 42%)

Reference Example 124-1

Methyl trans-4-(3-tert-butoxy-3-oxopropanoyl)cyclohexanecarboxylate

[Formula 445]

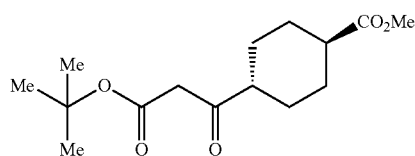

To a solution of trans-1,4-cyclohexanedicarboxylic acid monomethyl ester (30.00 g, 161.1 mmol) in tetrahydrofuran (180 ml), carbonyldiimidazole (28.7 g, 177 mmol, 1.1 eq) was added in an ice bath, and the mixture was stirred at room temperature for 1 hour. Separately, tert-butyl acetate (19.65 g, 169.2 mmol, 1.05 eq) was added dropwise to LHMDS (1.0 mol/L in THF, 338 ml, 338 mmol, 2.1 eq) at −78° C., and the mixture was stirred for 1 hour. Subsequently, a reaction solution of trans-1,4-cyclohexanedicarboxylic acid monomethyl ester and carbonyldiimidazole was added dropwise at −78° C., and the mixture was stirred for 3 hours. A saturated aqueous solution of ammonium chloride was added to the reaction solution, and the reaction solvent was concentrated under reduced pressure. The residue was extracted with diethyl ether, the organic layer was washed with a 0.1 mol/L aqueous solution of sodium hydroxide and a saturated saline solution, then dried over sodium sulfate and filtered, and the filtrate was concentrated under reduced pressure to obtain AF-2727 (34.25 g, 75%).
$^1$H NMR (CDCl$_3$, 300 MHz) δ 3.66 (s, 3H), 3.38 (s, 2H), 2.46 (m, 1H), 2.27-2.23 (m, 1H), 2.09-1.98 (m, 5H), 1.52-1.31 (m, 12H).

Reference Example 124-2

Propan-2-yl trans-4-{(1Z)—N—[(S)-tert-butylsulfinyl]-2,2-difluoroethanimidoyl}cyclohexanecarboxylate

[Formula 446]

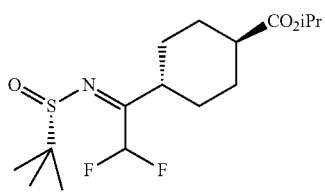

To a solution of the compound of Reference Example 124-1 (203.2 g, 0.715 mmol) in acetonitrile (1.5 L), selectfluor (379.8 g, 1.07 mol, 1.5 eq) was added at room temperature, and the mixture was stirred at 40° C. for 28 hours. A saturated aqueous solution of sodium bicarbonate was added to the reaction solution for concentration of the solution under reduced pressure. Water was added to the residue, followed by extraction with ethyl acetate. The organic layer was washed with a saturated aqueous solution of ammonium chloride and a saturated saline solution, then dried over sodium sulfate and filtered, and the filtrate was concentrated under reduced pressure to obtain a crude product (211.11 g).

To a solution of the obtained crude product (211.11 g) in chloroform (800 ml), trifluoroacetic acid (330 g, 4.28 mol) was added at room temperature, and the mixture was stirred at 40° C. for 4 hours. The reaction solution was concentrated under reduced pressure, toluene was added to the residue for concentration under reduced pressure. A saturated aqueous solution of sodium bicarbonate was added to the residue, followed by extraction with chloroform. The organic layer was dried over sodium sulfate and filtered, and the filtrate was concentrated under reduced pressure to obtain a crude product (80.99 g).

To a solution of the obtained crude product (80.89 g) in tetrahydrofuran (340 ml), titanium tetraisopropoxide (212.59 g) and (S)-(−)-2-methyl-2-propane sulfine amide (45.39 g) were added, and the mixture was heated to reflux for 8 hours. The reaction solution was allowed to cool, then a saturated aqueous solution of sodium bicarbonate and ethyl acetate were added, and the mixture was stirred at room temperature for 15 minutes before filtration through Celite. The mixed solution was separated, then the organic layer was washed with a saturated aqueous solution of sodium bicarbonate and a saturated saline solution, then dried over sodium sulfate and filtered, and the filtrate was concentrated under reduced pressure. The obtained residue was purified by silica gel column chromatography to obtain the title compound (16.31 g, 6.4%).

MS (ESI+) 352 (M+1, 100%)

Reference Example 124-3

Propan-2-yl trans-4-[(1S)-1-{[(S)-tert-butylsulfinyl]amino}-2,2-difluoroethyl]cyclohexanecarboxylate

[Formula 447]

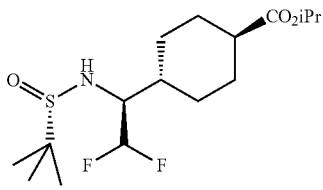

To a solution of the compound of Reference Example 124-2 (2.01 g, 5.72 mmol) in tetrahydrofuran (8 ml), K-selectride (1.0 mol/L in THF, 7.4 ml, 7.4 mmol) was added dropwise at −78° C., and the mixture was stirred for 1 hour. A saturated aqueous solution of ammonium chloride was added to the reaction solution, then the reaction mixture was allowed to cool to room temperature, followed by extraction with ethyl acetate. The organic layer was washed with a saturated aqueous solution of sodium bicarbonate and a saturated saline solution, then dried over sodium sulfate and filtered, and the filtrate was concentrated under reduced pressure. The obtained residue was purified by silica gel column chromatography to obtain the title compound (1.31 g, 65%).

MS (ESI+) 354 (M+1, 100%)

Reference Example 124-4 trans-4-{(1S)-1-[(tert-Butoxycarbonyl)amino]-2,2-difluoroethyl}cyclohexanecarboxylic acid

[Formula 448]

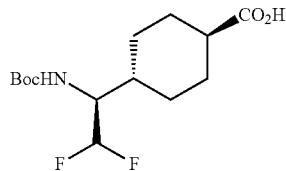

To a solution of the compound of Reference Example 124-2 (1.31 g, 3.71 mmol) in methanol (10 ml), 4 N hydrochloric acid-dioxane (10 ml) was added dropwise in an ice bath, and the mixture was stirred for 4 hours. The reaction solution was concentrated under reduced pressure, and toluene was added thereto for concentration under reduced pressure twice. To a solution of the obtained residue in tetrahydrofuran (10 ml) and a saturated aqueous solution of sodium bicarbonate (10 ml), tert-butyl dicarbonate (972 mg, 4.45 mmol) was added, and the mixture was stirred at room temperature for 12 hours. A saturated aqueous solution of ammonium chloride was added to the reaction solution, followed by extraction with ethyl acetate. The organic layer was washed with a saturated saline solution, then dried over sodium sulfate and filtered, and the filtrate was concentrated under reduced pressure. The obtained residue was dissolved in tetrahydrofuran (11 ml) and ethanol (11 ml), then a 10% aqueous solution of sodium hydroxide (11 ml) was added thereto, and the mixture was heated to reflux. After 12 hours, the reaction mixture was allowed to cool to room temperature and the reaction solution was concentrated under reduced pressure. Diethyl ether was added to the obtained residue for separation, then a 5% aqueous solution of potassium hydrogensulfate was added to the aqueous layer, followed by extraction with chloroform three times. The organic layer was washed with a saturated saline solution, then dried over sodium sulfate and filtered, and the filtrate was concentrated under reduced pressure to obtain the title compound (1.04 g, 91% for 3 steps).

Reference Example 124-5

3-Methoxypropyl 5-amino-1-benzofuran-2-carboxylate

[Formula 449]

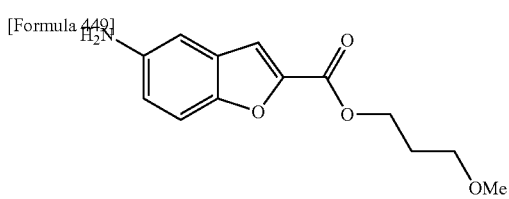

To a solution of 5-nitrobenzofuran-2-carboxylic acid (4.50 g, 21.7 mmol) in DMF (65 mL), potassium carbonate (4.50 g, 32.6 mmol) and 1-bromo-3-methoxypropane (2.67 ml, 23.9 mmol) were added, and the mixture was stirred at 100° C. for 3 hours. Water was added to the reaction mixture, followed by extraction with ethyl acetate twice. The organic layers were combined, washed with water and a saturated saline solution, then dried over sodium sulfate and filtered, and the filtrate was concentrated under reduced pressure to obtain a crude product (6.40 g).

To a solution of the obtained crude product in ethyl acetate (51 mL), palladium-carbon (640 mg) was added, and the mixture was stirred for 15 hours under hydrogen atmosphere. The reaction solution was filtered through Celite, and the filtrate was concentrated under reduced pressure. The obtained residue was purified by silica gel column chromatography to obtain the title compound (5.29 g, 98%).

MS (ESI+) 250 (M+1, 100%)

Reference Example 124-6 tert-Butyl (2S,3S)-3-cyclohexyl-2-({2-[(3-methoxy-propoxy)carbonyl]-1-benzofuran-5-yl}carbamoyl)pyrrolidine-1-carboxylate

[Formula 450]

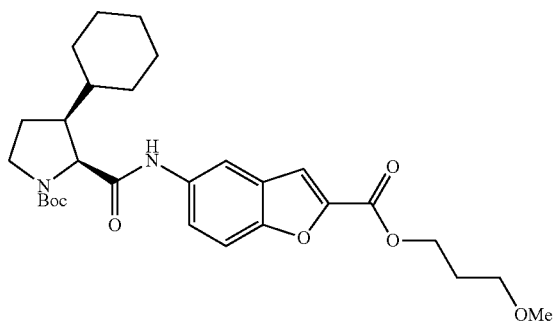

The same procedure as described in Reference Example 138-2 was carried out to obtain the title compound (6.26 g, 88%) from the compound of Reference Example 11-1 (4.00 g, 13.45 mmol) and the compound of Reference Example 124-5 (3.69 g, 14.80 mmol).

MS (ESI+) 529 (M+1, 100%)

Reference Example 124-7

3-Methoxypropyl 5-{[(3S)-3-cyclohexyl-L-prolyl]amino}-1-benzofuran-2-carboxylate hydrochloride

[Formula 451]

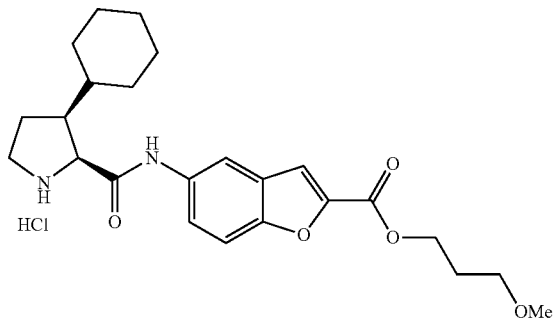

The same procedure as described in Reference Example 1-2 was carried out to obtain the title compound (2.78 g, 100%) from the compound of Reference Example 124-6 (3.00 g, 5.75 mmol).

MS (ESI+) 429 (M+1, 100%)

Reference Example 125

5-({(3S)-1-[(trans-4-{(1S)-1-[(tert-Butoxycarbonyl)amino]-2,2-difluoroethyl}cyclohexyl)carbonyl]-3-cyclohexyl-L-prolyl}amino)-1-benzofuran-2-carboxylic acid

[Formula 452]

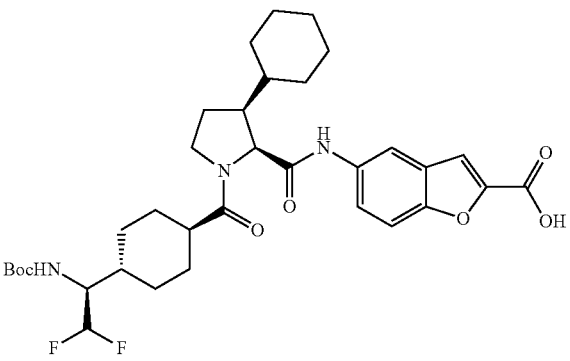

The same procedure as described in Reference Example 3 was carried out to obtain the title compound (82.3 mg, 96%) from the compound of Reference Example 124 (95.1 mg, 0.133 mmol).

MS (ESI+) 718 (M+1, 42%)

Reference Example 126

(3S)-1-[(trans-4-{(1S)-1-[(tert-Butoxycarbonyl)amino]-2-fluoroethyl}cyclohexyl)carbonyl]-3-cyclohexyl-N-{4-[(methylsulfonyl)carbamoyl]phenyl}-L-prolinamide

[Formula 453]

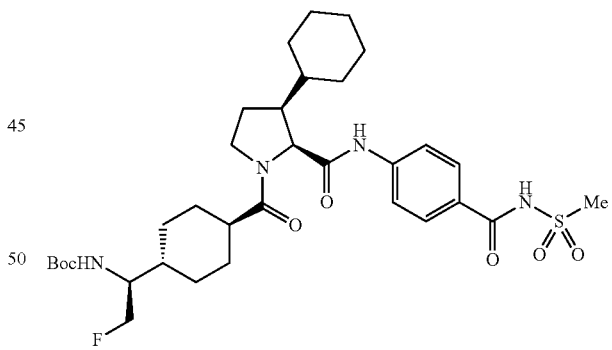

To a solution of the compound of Reference Example 78 (67.3 mg, 0.1145 mmol) in dichloromethane (2 ml), 4-dimethylaminopyridine (14.0 mg, 0.115 mmol), WSC.HCl (43.9 mg, 0.229 mmol), and methane sulfonamide (15.2 mg, 0.160 mmol) were added, and the mixture was stirred at room temperature overnight. A saturated aqueous solution of ammonium chloride was added to the reaction mixture, followed by extraction with chloroform/methanol (10:1). The organic layer was washed with a saturated saline solution, then dried over sodium sulfate and filtered, and the filtrate was concentrated under reduced pressure. The obtained residue was purified by silica gel column chromatography to obtain the title compound (15.5 mg, 20%).

MS (ESI+) 665 (M+1, 10%)

Reference Example 127

Methyl {6-[({(2S,3S)-1-[(trans-4-{(1S)-1-[(tert-butoxycarbonyl)amino]-2-fluoroethyl}cyclohexyl)carbonyl]-3-cyclohexylpyrrolidin-2-yl}carbonyl)amino]-1,3-benzothiazol-2-yl}carbamate

[Formula 454]

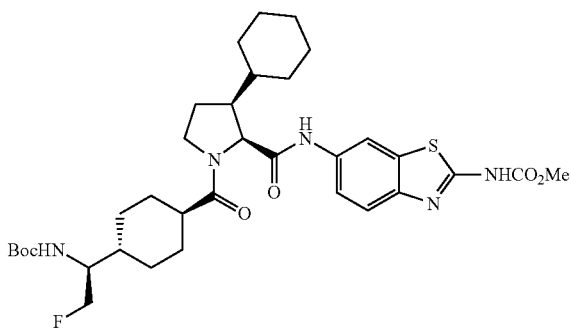

The same procedure as described in Reference Example 1 was carried out to obtain the title compound (3.0 mg, 68%) from the compound of Reference Example 127-4 (2.87 mg, 0.0657 mmol) and the compound of Reference Example 53-3 (2.3 mg, 0.0795 mmol).
MS (ESI+) 674 (M+1, 100%)

Reference Example 127-1

Methyl (6-nitro-1,3-benzothiazol-2-yl)carbamate

[Formula 455]

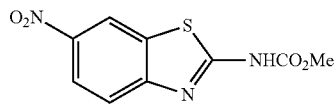

To a solution of 2-amino-6-nitrobenzothiazole (526.7 mg, 2.70 mmol) in pyridine (5 ml), methyl chloroformate (313 μL, 4.05 mmol) was added dropwise in an ice bath, and the mixture was stirred at 60° C. for 5 hours. The reaction solution was allowed to cool, then water was added thereto in an ice bath. The precipitated solid was filtered out, and the filtrate was washed with water, tetrahydrofuran, and hexane in this order to obtain the title compound (308.3 mg, 45%).
MS (ESI+) 254 (M+1, 100%)

Reference Example 127-2

Methyl (6-amino-1,3-benzofuran thiazol-2-yl)carbamate

[Formula 456]

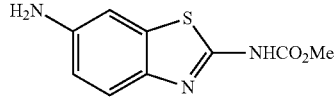

To a solution of the compound of Reference Example 127-1 (308.3 mg, 1.22 mmol) in methanol (10 mL), palladium-carbon (150 mg) and ammonium formate (767 mg, 12.2 mmol) were added, and the mixture was heated to reflux for 3 hours. The reaction solution was allowed to cool, then was filtered through Celite, and the filtrate was concentrated under reduced pressure. A saturated aqueous solution of sodium bicarbonate was added to the obtained residue, followed by extraction with chloroform. The organic layer was washed with a saturated aqueous solution of ammonium chloride and a saturated saline solution, then dried over sodium sulfate and filtered, and the filtrate was concentrated under reduced pressure. The obtained residue was purified by silica gel column chromatography to obtain the title compound (17.7 mg, 6.5%).
MS (ESI+) 224 (M+1, 100%)

Reference Example 127-3 tert-Butyl (2S,3S)-3-cyclohexyl-2-({2-[(methoxycarbonyl)amino]-1,3-benzothiazol-6-yl}carbamoyl)pyrrolidine-1-carboxylate

[Formula 457]

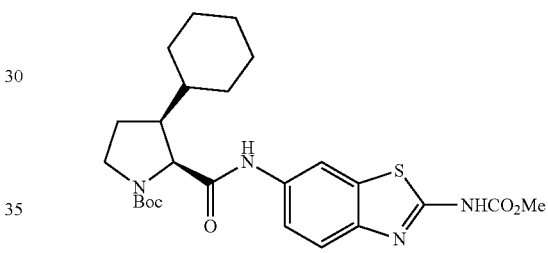

The same procedure as described in Reference Example 1-1 was carried out to obtain the title compound (3.3 mg, 8.2%) from the compound of Reference Example 127-2 (17.8 mg, 0.0797 mmol) and the compound of Reference Example 53-3 (26.1 mg, 0.0877 mmol).
MS (ESI+) 503 (M+1, 100%)

Reference Example 127-4

Methyl (6-{[(3S)-3-cyclohexyl-L-prolyl]amino}-1,3-benzothiazol-2-yl)carbamate hydrochloride

[Formula 458]

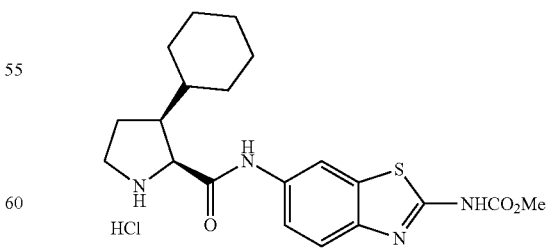

The same procedure as described in Reference Example 1-2 was carried out to obtain the title compound (2.87 mg, 100%) from the compound of Reference Example 127-3 (3.3 mg, 0.00657 mmol).
MS (ESI+) 403 (M+1, 100%)

Reference Example 128

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-2,3-dihydro-1-benzofuran-2-carboxylic acid

[Formula 459]

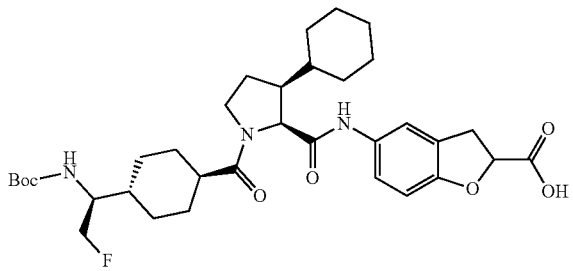

The same procedure as described in Reference Example 3 was carried out to obtain the title compound (22.2 mg, 100%) from the compound of Reference Example 128-1 (24.1 mg, 0.034 mmol).

MS (ESI+) 630 (M+1, 87%)

Reference Example 128-1 tert-Butyl (2S,3S)-3-cyclohexyl-2-({2-[(3-methoxypropyl)carbonyl]-2,3-dihydro-1-benzofuran-5-yl}carbamoyl)pyrrolidine-1-carboxylate

[Formula 460]

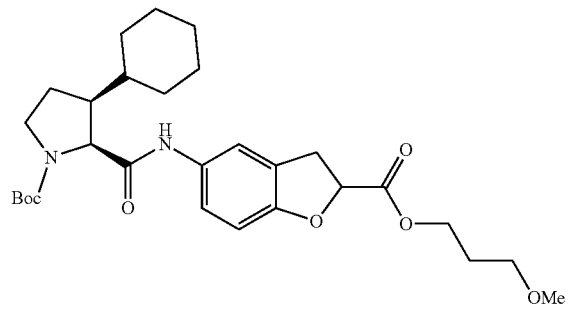

The compound of Reference Example 124-5 (16.8 g, 60.2 mmol) was dissolved in ethyl acetate, then 10% palladium-carbon (1.68 g) was added, and the mixture was stirred at room temperature for 7 hours. The reaction solution was filtered through Celite, and the filtrate was concentrated under reduced pressure (15.3 g, 100%). 9.34 g (37.5 mmol) of the obtained residue was added to a solution of the compound of Reference Example 11-1 (10.1 g, 34.1 mmol), HATU (13.6 g, 35.8 mmol), and diisopropylethylamine (11.9 mL, 68.1 mmol) in DMF (253 mL), and the mixture was stirred at room temperature for 1 hour and then at 65° C. for 8.5 hours. A mixed solution of toluene/ethyl acetate (150 mL/50 mL) was added to the reaction solution, then water (200 mL) was added thereto, and the mixture was stirred at room temperature for 15 minutes. The obtained aqueous layer was extracted with a mixed solvent of toluene/ethyl acetate (75 mL/25 mL), then combined with the obtained organic layer and washed with water (100 mL), and the organic layer was concentrated. The obtained residue was purified by silica gel chromatography to obtain the title compound (58.4 mg, 0.3%).

MS (ESI+) 252 (M+1, 100%)

Reference Example 128-2

3-Methoxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-2,3-dihydro-1-benzofuran-2-carboxylate

[Formula 461]

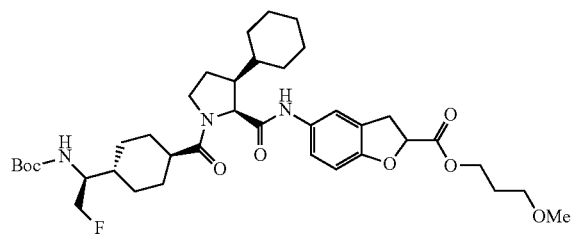

The same procedure as described in Reference Example 1 was carried out to obtain the title compound (25.7 mg, 33%) from the compound of Reference Example 128-1 (58.4 mg, 0.110 mmol).

MS (ESI+) 702 (M+1, 40%)

Reference Example 129

1,3-Dimethoxypropan-2-yl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 462]

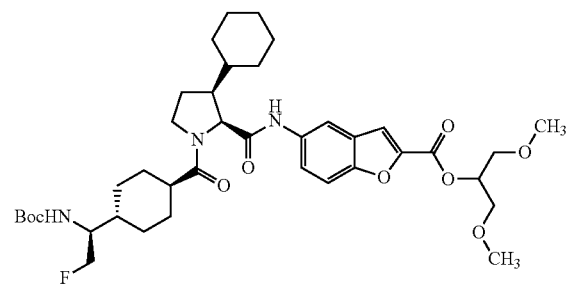

The same procedure as described in Reference Example 1 was carried out to obtain the title compound (173 mg, 83%) from the compound of Reference Example 129-2 (131 mg, 0.28 mmol) and the compound of Reference Example 53-3 (83 mg, 0.28 mmol).

MS (ESI+) 730 (M+1, 37%)

Reference Example 129-1 tert-Butyl (2S,3S)-3-cyclohexyl-2-[(2-{[(1,3-dimethoxypropan-2-yl)oxy]carbonyl}-1-benzofuran-5-yl)carbamoyl]pyrrolidine-1-carboxylate

[Formula 463]

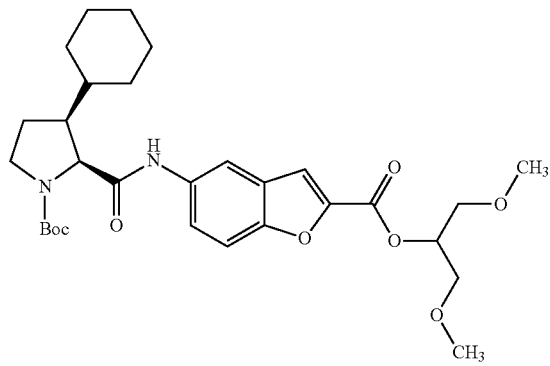

To a solution of the compound obtained in Reference Example 119-1 (200 mg, 0.438 mmol) in DMF (3.2 mL), 1-hydroxybenzotriazole (77.0 mg, 0.57 mmol), 1-ethyl-3-(3-dimethylaminopropyl)carbodiimide hydrochloride (109 mg, 0.57 mmol), triethylamine (244 μL, 1.75 mmol), and 1,3-dimethoxy-2-propanol (320 μl, 2.63 mmol) were added, and the mixture was stirred at 50° C. for 6 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution once, respectively, then dried over sodium sulfate and filtered, and the filtrate was concentrated under reduced pressure. The obtained residue was purified by silica gel column chromatography to obtain the title compound (160 mg, 15%).

MS (ESI+) 559 (M+1, 27%)

Reference Example 129-2

1,3-Dimethoxypropan-2-yl 5-{[(3S)-3-cyclohexyl-L-prolyl]amino}-1-benzofuran-2-carboxylate

[Formula 464]

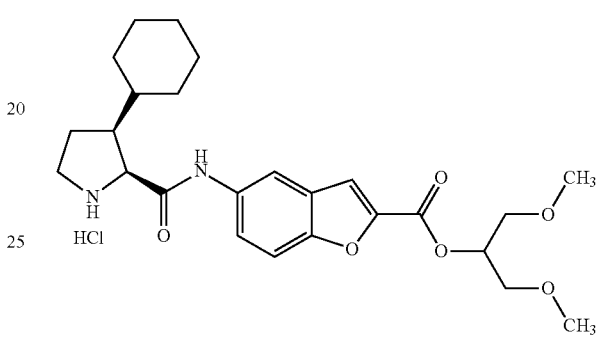

The same procedure as described in Reference Example 1-2 was carried out to obtain the title compound (131 mg, 100%) from the compound of Reference Example 129-1 (160 mg, 0.29 mmol).

MS (ESI+) 459 (M+1, 100%)

Reference Example 130

4-Methoxybutyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 465]

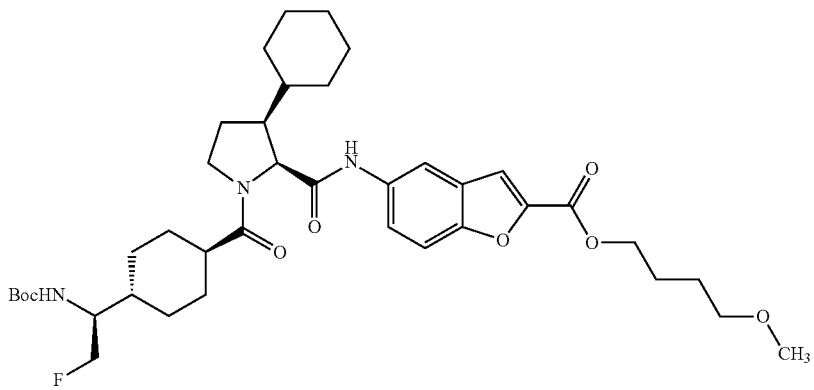

The same procedure as described in Reference Example 1 was carried out to obtain the title compound (155 mg, 87%) from the compound of Reference Example 130-2 (111 mg, 0.25 mmol) and the compound of Reference Example 53-3 (73 mg, 0.25 mmol).

MS (ESI+) 714 (M+1, 56%)

Reference Example 130-1 tert-Butyl (2S,3S)-3-cyclohexyl-2-({2-[(4-methoxybutoxy)carbonyl]-1-benzofuran-5-yl}carbamoyl)pyrrolidine-1-carboxylate

[Formula 466]

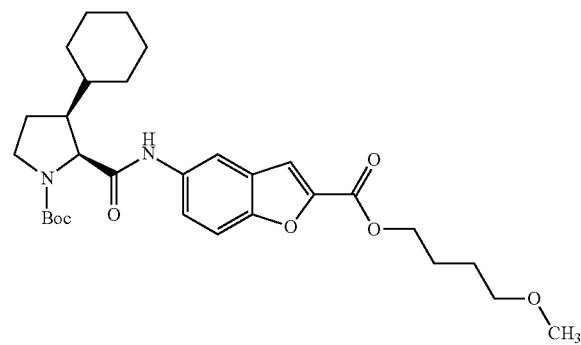

To a solution of the compound obtained in Reference Example 119-1 (150 mg, 0.33 mmol) in DMF (3.0 mL), potassium carbonate (138 mg, 0.99 mmol) and 1-chloro-4-methoxybutane (61.0 mg, 0.50 mmol) were added, and the mixture was stirred at 80° C. for 8 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (136 mg, 76%).

MS (ESI+) 543 (M+1, 32%)

Reference Example 130-2

4-Methoxybutyl 5-{[(3S)-3-cyclohexyl-L-prolyl]amino}-1-benzofuran-2-carboxylate hydrochloride

[Formula 467]

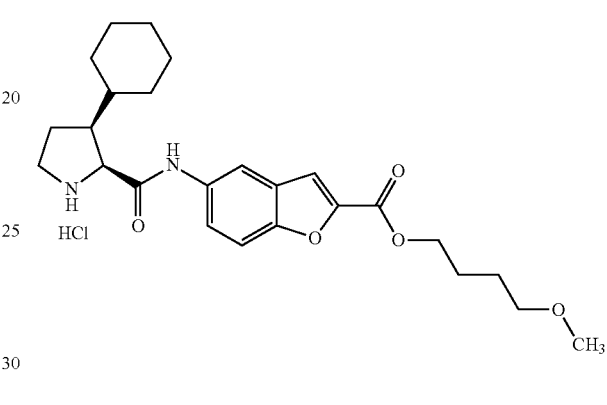

The same procedure as described in Reference Example 1-2 was carried out to obtain the title compound (111 mg, 100%) from the compound of Reference Example 130-1 (135 mg, 0.25 mmol).

MS (ESI+) 443 (M+1, 100%)

Reference Example 131

3-(2-Methoxyethoxyl)propyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 468]

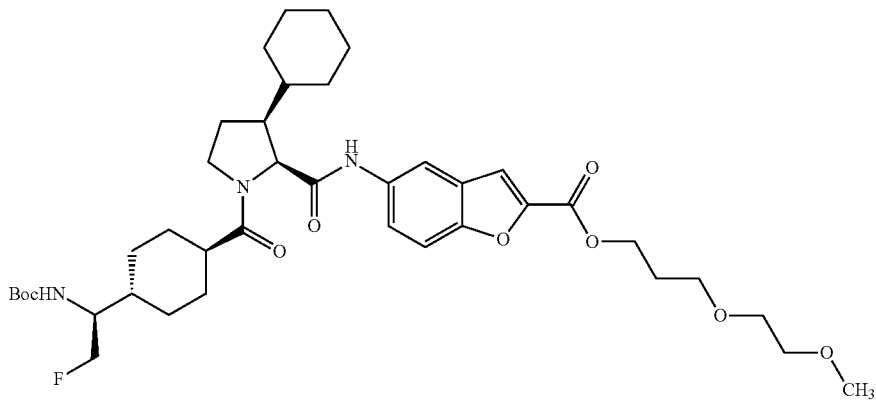

The same procedure as described in Reference Example 1 was carried out to obtain the title compound (153 mg, 89%) from the compound of Reference Example 131-2 (126 mg, 0.27 mmol) and the compound of Reference Example 53-3 (78 mg, 0.27 mmol).

MS (ESI+) 744 (M+1, 27%)

Reference Example 131-1 tert-Butyl (2S,3S)-3-cyclohexyl-2-[(2-{[3-(2-methoxyethoxy)propoxy]carbonyl}-1-benzofuran-5-yl)carbamoyl]pyrrolidine-1-carboxylate

[Formula 469]

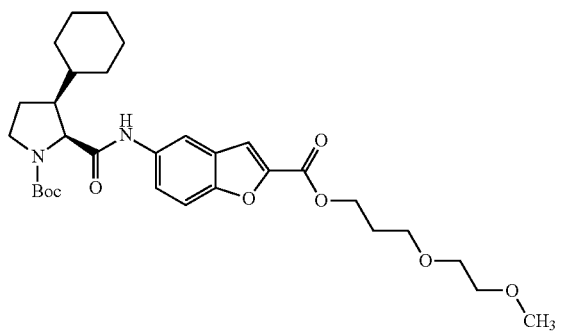

To a solution of the compound obtained in Reference Example 119-1 (150 mg, 0.33 mmol) in DMF (3.0 mL), potassium carbonate (138 mg, 0.99 mmol) and 3-(2-methoxyethoxy)propyl bromide (98.0 mg, 0.50 mmol) were added, and the mixture was stirred at 80° C. for 3 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (153 mg, 81%).

MS (ESI+) 573 (M+1, 20%)

Reference Example 131-2

3-(2-Methoxyethoxy)propyl 5-{[(3S)-3-cyclohexyl-L-prolyl]amino}-1-benzofuran-2-carboxylate hydrochloride

[Formula 470]

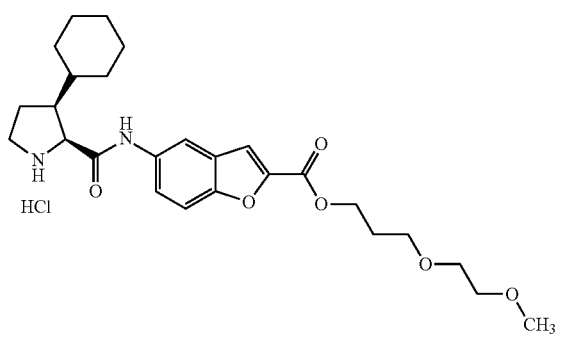

The same procedure as described in Reference Example 1-2 was carried out to obtain the title compound (126 mg, 100%) from the compound of Reference Example 131-1 (153 mg, 0.27 mmol).

MS (ESI+) 473 (M+1, 100%)

Reference Example 132

5-({(3S)-3-(Benzyloxy)-1-[(trans-4-{(1S)-1-[(tert-butoxycarbonyl)amino]-2-fluoroethyl}cyclohexyl)carbonyl]-L-prolyl}amino)-1-benzofuran-2-carboxylic acid

[Formula 471]

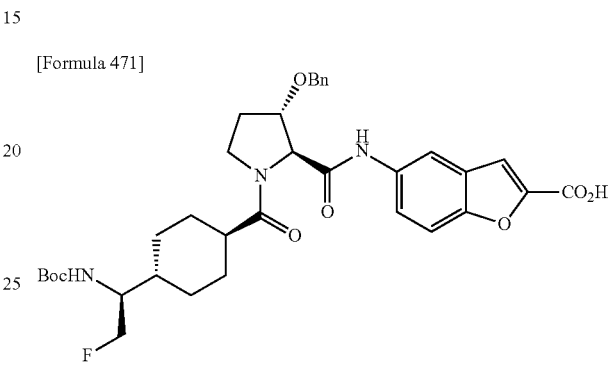

The same procedure as described in Reference Example 3 was carried out to obtain the title compound (108 mg, 99%) from the compound of Reference Example 132-4 (114 mg, 0.168 mmol).

MS (ESI+) 652 (M+1, 100%)

Reference Example 132-1

1-tert-Butyl 2-methyl (2S,3S)-3-(benzyloxy)pyrrolidine-1,2-dicarboxylate

[Formula 472]

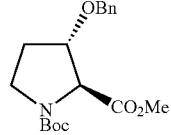

To a solution of commercially available (2S,3S)-1-(tert-butoxycarbonyl)-3-hydroxypyrrolidine-2-carboxylic acid methyl ester (300 mg, 1.22 mmol) and benzyl bromide (177 µl, 1.46 mmol) in N,N-dimethylformamide (5 ml), sodium hydride (60% in oil, 59 mg, 1.35 mmol) was added in an ice bath, and the mixture was stirred at room temperature for 3 hours. A saturated aqueous solution of ammonium chloride was added to the reaction mixture in an ice bath, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (272 mg, 66%).

MS (ESI+) 336 (M+1, 1.4%)

Reference Example 132-2

(3S)-3-(Benzyloxy)-1-(tert-butoxycarbonyl)-L-proline

[Formula 473]

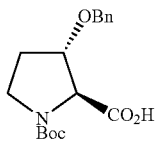

The same procedure as described in Reference Example 3 was carried out to obtain the title compound (170 mg, 67%) from the compound of Reference Example 132-1 (266 mg, 0.793 mmol).
MS (ESI+) 322 (M+1, 0.8%)

Reference Example 132-3 tert-Butyl (2S,3S)-3-(benzyloxy)-2-{[2-(ethoxycarbonyl)-1-benzofuran-5-yl]carbamoyl}pyrrolidine-1-carboxylate

[Formula 474]

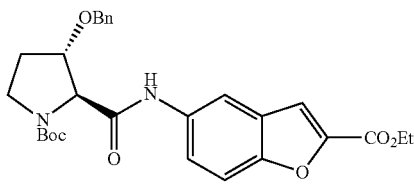

The same procedure as described in Reference Example 138-2 was carried out to obtain the title compound (101.7 mg, 80%) from the compound of Reference Example 132-2 (80 mg, 0.249 mmol) and 5-amino-1-benzofuran-2-carboxylate (66 mg, 0.324 mmol).
MS (ESI+) 509 (M+1, 100%)

Reference Example 132-4

Ethyl 5-{[(3S)-3-(benzyloxy)-L-prolyl]amino}-1-benzofuran-2-carboxylate hydrochloride

[Formula 475]

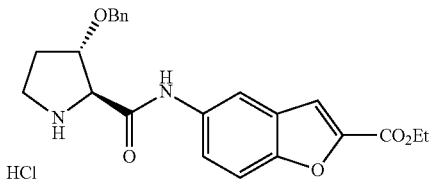

The same procedure as described in Reference Example 1-2 was carried out to obtain the title compound (85 mg, 97%) from the compound of Reference Example 132-3 (101 mg, 0.199 mmol).
MS (ESI+) 409 (M+1, 100%)

Reference Example 132-5

Ethyl 5-({(3S)-3-(benzyloxy)-1-[(trans-4-{(1S)-1-[(tert-butoxycarbonyl)amino]-2-fluoroethyl}cyclohexyl)carbonyl]-L-prolyl}amino)-1-benzofuran-2-carboxylate

[Formula 476]

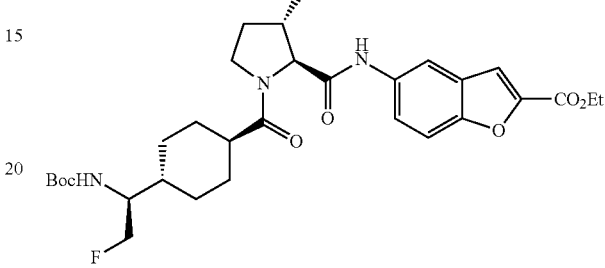

The same procedure as described in Reference Example 1 was carried out to obtain the title compound (114 mg, 87%) from the compound of Reference Example 132-3 (85 mg, 0.192 mmol) and the compound of Reference Example 53-3 (59 mg, 0.201 mmol).
MS (ESI+) 680 (M+1, 100%)

Reference Example 133 tert-Butyl [(1S)-1-(trans-4-{[(2S,3S)-3-cyclohexyl-2-{[2-(2-oxo-1,3-oxazolidin-3-yl)-1,3-benzothiazol-6-yl]carbamoyl}pyrrolidin-1-yl]carbonyl}cyclohexyl)-2-fluoroethyl]carbamate

[Formula 477]

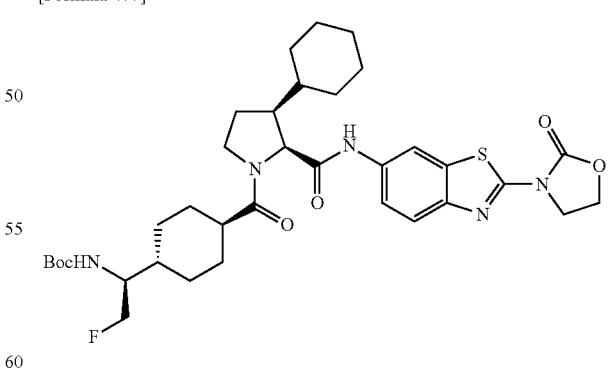

The same procedure as described in Reference Example 1 was carried out to obtain the title compound (5.0 mg, 13%) from the compound of Reference Example 133-3 (30.8 mg, 0.0583 mmol) and the compound of Reference Example 53-3 (20.2 mg, 0.0699 mmol).
MS (ESI+) 686 (M+1, 100%)

339

Reference Example 133-1

3-(6-Amino-1,3-benzothiazol-2-yl)-1,3-oxazolidin-2-one

[Formula 478]

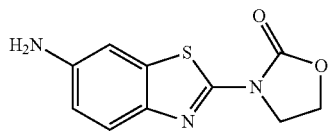

To a solution of 2-amino-6-nitrobenzothiazole (343.5 mg, 1.76 mmol) in acetonitrile (17 ml), potassium carbonate (608 mg, 4.4 mmol) and 2-bromoethyl chloroformate (252 μL, 2.11 mmol) were added. The reaction solution was heated to reflux for 4 hours, then was allowed to cool to room temperature, then water and ethyl acetate were added, and then the mixture was filtered through Celite. The solution was separated, then the organic layer was washed with a saturated aqueous solution of ammonium chloride and a saturated saline solution, then dried over sodium sulfate and filtered, and the filtrate was concentrated under reduced pressure to obtain a crude product. To a solution of the obtained crude product in tetrahydrofuran (6 ml), methanol (4 ml), and water (2 ml), reduced iron (385 mg, 6.90 mmol) and ammonium chloride (111 mg, 2.07 mmol) were added, and the mixture was heated to reflux for 1 hour. The reaction solution was allowed to cool, then filtered through Celite, and the filtrate was concentrated under reduced pressure. A saturated aqueous solution of ammonium chloride was added to the obtained residue, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (39.1 mg, 9.4%).

MS (ESI+) 236 (M+1, 88%)

340

Reference Example 133-2 tert-Butyl (2S,3S)-3-cyclohexyl-2-{[2-(2-oxo-1,3-oxazolidin-3-yl)-1,3-benzothiazol-6-yl]carbamoyl}pyrrolidine-1-carboxylate

[Formula 479]

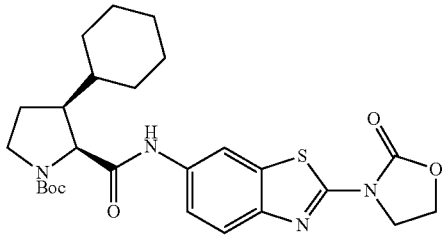

The same procedure as described in Reference Example 138-2 was carried out to obtain the title compound (32.0 mg, 51%) from the compound of Reference Example 133-1 (31.3 mg, 0.133 mmol) and the compound of Reference Example 53-3 (36.0 mg, 0.121 mmol).

MS (ESI+) 515 (M+1, 100%)

Reference Example 133-3

(3S)-3-Cyclohexyl-N-[2-(2-oxo-1,3-oxazolidin-3-yl)-1,3-benzothiazol-6-yl]-L-prolinamide

[Formula 480]

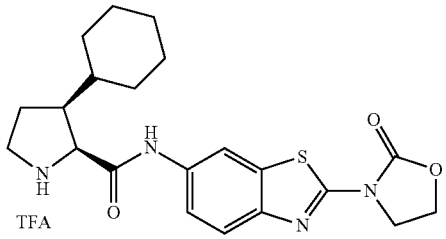

The same procedure as described in Reference Example 9-2 was carried out to obtain the title compound (30.8 mg, 100%) from the compound of Reference Example 133-2 (30.0 mg, 0.0583 mmol).

MS (ESI+) 415 (M+1, 100%)

Reference Example 134

4-Ethoxybutyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 481]

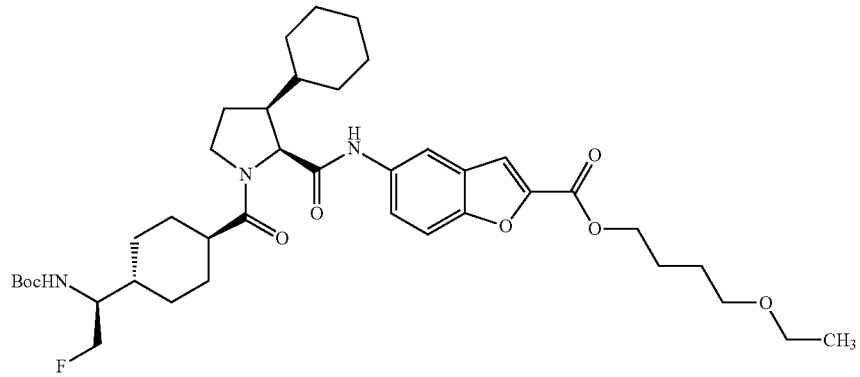

The same procedure as described in Reference Example 1 was carried out to obtain the title compound (21.9 mg, 56%) from the compound of Reference Example 134-2 (25.0 mg, 0.054 mmol) and the compound of Reference Example 53-3 (16.0 mg, 0.054 mmol).
MS (ESI+) 728 (M+1, 100%)

Reference Example 134-1 tert-Butyl (2S,3S)-3-cyclohexyl-2-({2-[(4-ethoxybutoxy)carbonyl]-1-benzofuran-5-yl}carbamoyl)pyrrolidine-1-carboxylate

[Formula 482]

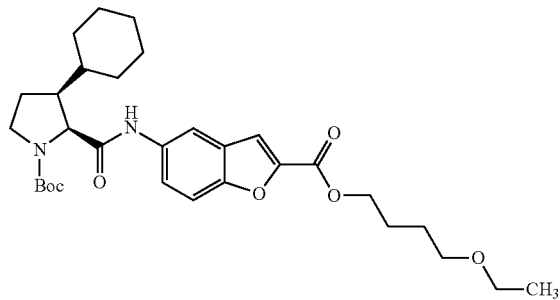

To a solution of the compound obtained in Reference Example 119-1 (44.0 mg, 0.096 mmol) in DMF (1.0 mL), 1-hydroxybenzotriazole (17.0 mg, 0.125 mmol), 1-ethyl-3-(3-dimethylaminopropyl)carbodiimide hydrochloride (24 mg, 0.125 mmol), triethylamine (54.0 μL, 0.38 mmol), 4-ethoxybutan-1-ol (680 mg, 0.58 mmol) were added, and the mixture was stirred at 50° C. for 8 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (30.0 mg, 56%).
MS (ESI+) 557 (M+1, 27%)

Reference Example 134-2

4-Ethoxybutyl 5-{[(3S)-3-cyclohexyl-L-prolyl]amino}-1-benzofuran-2-carboxylate hydrochloride

[Formula 483]

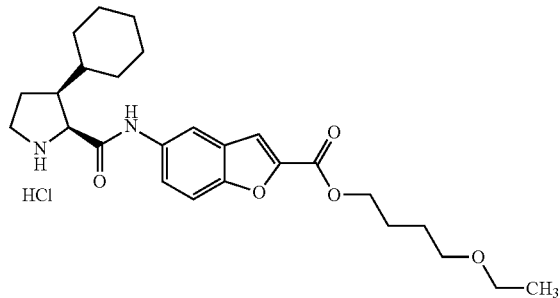

The same procedure as described in Reference Example 1-2 was carried out to obtain the title compound (25.0 mg, 100%) from the compound of Reference Example 134-1 (30.0 mg, 0.054 mmol).
MS (ESI+) 457 (M+1, 100%)

Reference Example 135

5-({(3S)-1-[(trans-4-{(1S)-1-[(tert-Butoxycarbonyl)amino]-2-fluoroethyl}cyclohexyl)carbonyl]-3-phenyl-L-prolyl}amino)-1H-indole-2-carboxylic acid

[Formula 484]

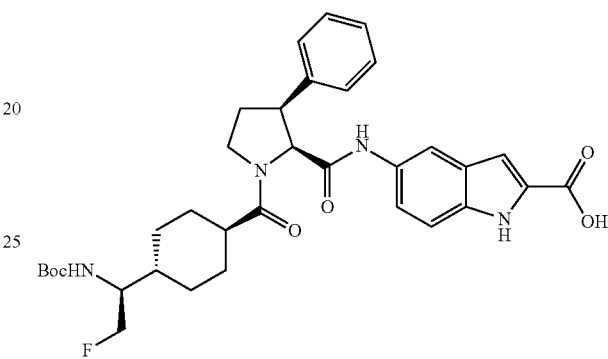

The compound of Reference Example 135-2 (87.3 mg, 0.14 mmol) was dissolved in ethanol (1.5 mL) and tetrahydrofuran (1.5 mL), a 1 mol/L aqueous solution of sodium hydroxide (1.0 mL) was added thereto, and the mixture was stirred at 50° C. for 1 hour. A 5% aqueous solution of potassium hydrogensulfate was added to the reaction solution, followed by extraction with chloroform twice. The organic layer was washed with a saturated saline solution, dried over anhydrous sodium sulfate and filtered, and then the organic layer was concentrated under reduced pressure to obtain the title compound (87.0 mg, 100%).
MS (ESI+) 621 (M+1, 100%)

Reference Example 135-1

Ethyl 5-{[(3S)-3-phenyl-L-prolyl]amino}-1H-indole-2-carboxylate hydrochloride

[Formula 485]

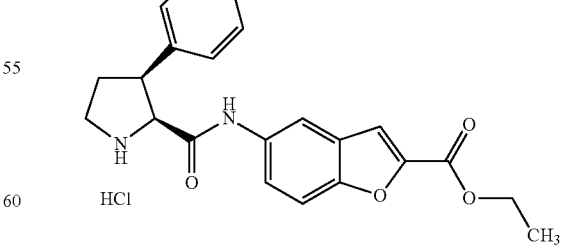

The same procedure as described in Reference Example 1-2 was carried out to obtain the title compound (63.5 mg, 100%) from the compound of Reference Example 136-1 (80 mg, 0.17 mmol).
MS (ESI+) 378 (M+1, 100%)

Reference Example 135-2

Ethyl 5-({(3S)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 486]

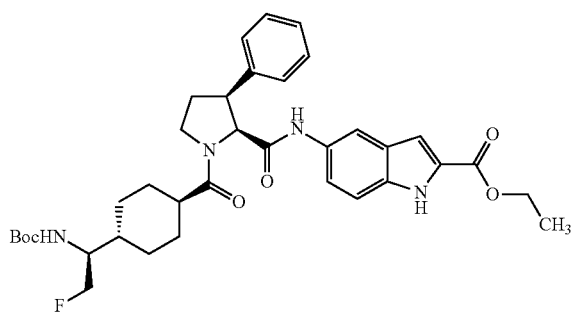

The same procedure as described in Reference Example 1 was carried out to obtain the title compound (87.3 mg, 80%) from the compound of Reference Example 135-1 (63.5 mg, 0.168 mmol) and the compound of Reference Example 53-3 (48.6 mg, 0.168 mmol).
MS (ESI+) 649 (M+1, 100%)

Reference Example 136

3-Ethoxypropyl 5-({(3S)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 487]

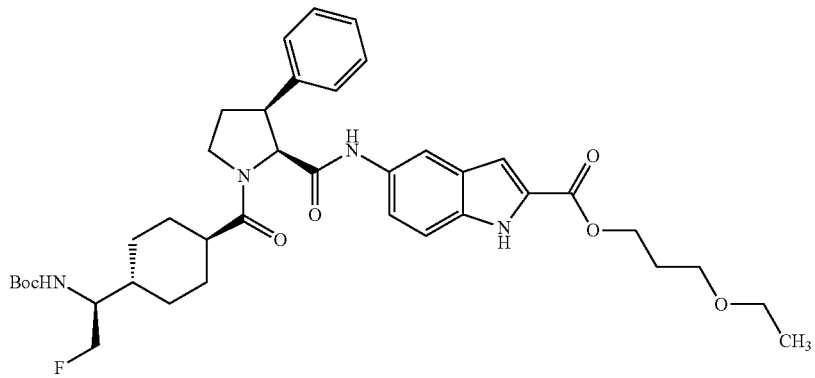

The same procedure as described in Reference Example 1 was carried out to obtain the title compound (62.5 mg, 37%) from the compound of Reference Example 136-3 (104 mg, 0.24 mmol) and the compound of Reference Example 53-3 (69.4 mg, 0.24 mmol).
MS (ESI+) 707 (M+1, 100%)

Reference Example 136-1

Ethyl 5-{[(3S)-1-(tert-butoxycarbonyl)-3-phenyl-L-prolyl]amino}-1H-indole-2-carboxylate

[Formula 488]

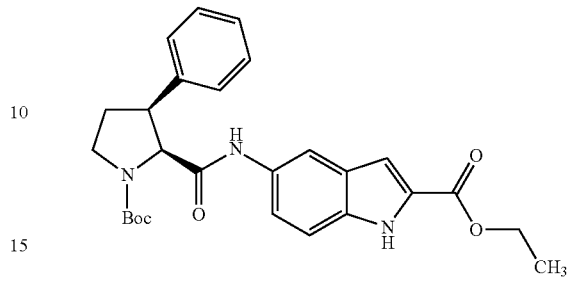

By using (2S,3S)-1-tert-butoxycarbonyl-3-phenylpyrrolidine-2-carboxylic acid as the starting material, The same procedure as described in Reference Example 1-1 was carried out to obtain the title compound (700 mg, 99%) from the compound of Reference Example 2-1 (300 mg, 1.47 mmol).
MS (ESI+) 478 (M+1, 100%)

Reference Example 136-2

3-Ethoxypropyl 5-{[(3S)-1-(tert-butoxycarbonyl)-3-phenyl-L-prolyl]amino}-1H-indole-2-carboxylate

[Formula 489]

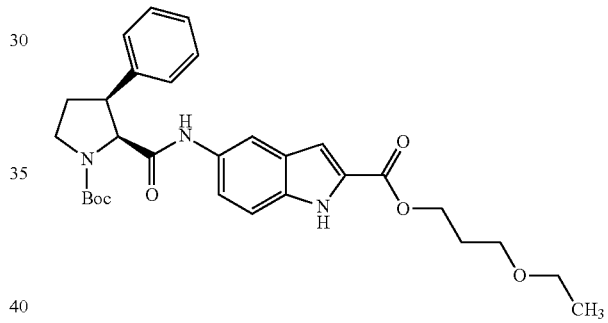

The compound of Reference Example 136-1 (840 mg, 1.75 mmol) was dissolved in ethanol (12.0 mL) and tetrahydrofuran (12.0 mL), a 1 mol/L aqueous solution of sodium hydroxide (8.0 mL) was added thereto, and the mixture was stirred at 50° C. for 2 hours. A 5% aqueous solution of potassium hydrogensulfate was added to the reaction solution, followed by extraction with chloroform twice. The organic layer was washed with a saturated saline solution, dried over anhydrous sodium sulfate and filtered, and then the organic layer was concentrated under reduced pressure (660 mg, 1.47 mmol). To a solution of the obtained compound (200 mg, 0.445 mmol) in DMF (5.0 mL), 1-hydroxybenzotriazole (78.0 mg, 0.579 mmol), 1-ethyl-3-(3-dimethylaminopropyl)carbodiimide hydrochloride (111 mg, 0.579 mmol), triethylamine (248 µL, 1.78 mmol), 3-ethoxy-1-propanol (308 µl, 2.67 mmol), and N,N-dimethyl-4-aminopyridine (163 mg, 1.34 mmol) were added, and the mixture was stirred at 50° C. for 6 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (129 mg, 54%).

MS (ESI+) 536 (M+1, 100%)

Reference Example 136-3

3-Ethoxypropyl 5-{[(3S)-3-phenyl-L-prolyl]amino}-1H-indole-2-carboxylate hydrochloride

[Formula 490]

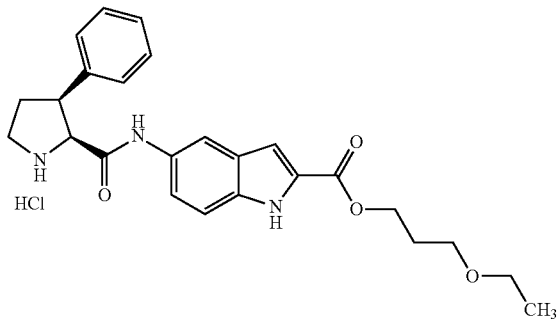

The same procedure as described in Reference Example 1-2 was carried out to obtain the title compound (104 mg, 100%) using the compound from Reference Example 136-2 (129 mg, 0.24 mmol).

MS (ESI+) 436 (M+1, 100%)

Reference Example 137

5-({(3R)-3-(Benzyloxy)-1-[(trans-4-{(1S)-1-[(tert-butoxycarbonyl)amino]-2-fluoroethyl}cyclohexyl)carbonyl]-L-prolyl}amino)-1-benzofuran-2-carboxylic acid

[Formula 491]

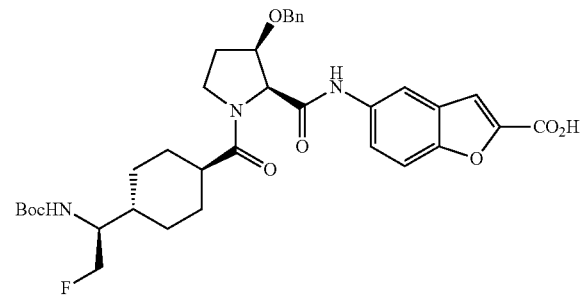

The same procedure as described in Reference Example 3 was carried out to obtain the title compound (43 mg, 100%) from the compound of Reference Example 137-7 (45.0 mg, 0.06620 mmol).

MS (ESI+) 652 (M+1, 100%)

Reference Example 137-1

1-tert-Butyl 2-methyl (2S,3R)-3-(benzoyloxy)pyrrolidine-1,2-dicarboxylate

[Formula 492]

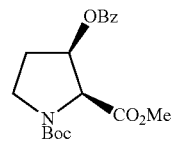

Diethyl azodicarboxylate (a 2.2 mol/L toluene solution, 4.34 mL, 9.54 mmol) was added to a solution of commercially available (2S,3S)-1-(tert-butoxycarbonyl)-3-hydroxypyrrolidine-2-carboxylic acid methyl ester (2.00 g, 8.15 mmol), triphenylphosphine (2.57 g, 9.79 mmol), and benzoic acid (1.2 g, 9.79 mmol) in tetrahydrofuran (40 mL), and the mixture was stirred at room temperature overnight. A saturated aqueous solution of sodium bicarbonate was added to the reaction solution, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (2.30 g, 81%).

MS (ESI+) 350 (M+I, 0.2%)

Reference Example 137-2

(2S,3R)-1-(tert-Butoxycarbonyl)-3-hydroxypyrrolidine-2-carboxylic acid methyl ester

[Formula 493]

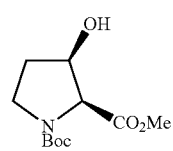

The compound of Reference Example 137-1 (2.3 g, 6.58 mmol) was dissolved in methanol (20 mL), a 1 mol/L aqueous solution of potassium hydroxide (7.3 mL) was added thereto in an ice bath, and the mixture was stirred at 0° C. for 1 hour. A 5% aqueous solution of potassium hydrogensulfate was added to the reaction solution, followed by extraction with ethyl acetate. The organic layer was washed with a saturated saline solution, dried over anhydrous sodium sulfate and filtered, and the filtrate was concentrated under reduced pressure. The obtained residue was purified by silica gel column chromatography to obtain the title compound (1.55 g, 78%).

MS (ESI+) 246 (M+I, 0.5%)

Reference Example 137-3

1-tert-Butyl 2-methyl (2S,3R)-3-(benzyloxy)pyrrolidine-1,2-dicarboxylate

[Formula 494]

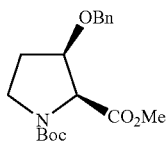

The same procedure as described in Reference Example 132-1 was carried out to obtain the title compound (372 mg, 91%) from the compound of Reference Example 137-2 (300 mg, 1.22 mmol).
MS (ESI+) 336 (M+1, 1%)

Reference Example 137-4

(3R)-3-(Benzyloxy)-1-(tert-butoxycarbonyl)-L-proline

[Formula 495]

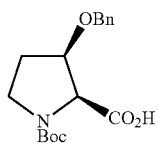

The same procedure as described in Reference Example 3 was carried out to obtain the title compound (268 mg, 75%) from the compound of Reference Example 137-3 (372 mg, 1.11 mmol).
MS (ESI+) 322 (M+1, 0.2%)

Reference Example 137-5 tert-Butyl (2S,3R)-3-(benzyloxy)-2-{[2-(ethoxycarbonyl)-1-benzofuran-5-yl]carbamoyl}pyrrolidine-1-carboxylate

[Formula 496]

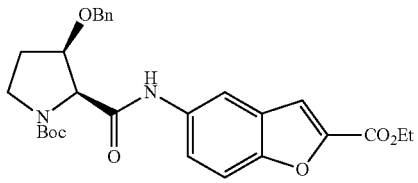

The same procedure as described in Reference Example 138-2 was carried out to obtain the title compound (46.5 mg, 63%) from the compound of Reference Example 137-4 (47 mg, 0.146 mmol) and 5-amino-1-benzofuran-2-carboxylate (61 mg, 0.292 mmol).
MS (ESI+) 509 (M+1, 100%)

Reference Example 137-6

Ethyl 5-{[(3R)-3-(benzyloxy)-L-prolyl]amino}-1-benzofuran-2-carboxylate hydrochloride

[Formula 497]

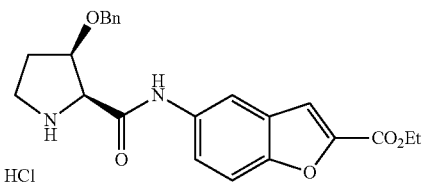

The same procedure as described in Reference Example 1-2 was carried out to obtain the title compound (40 mg, 99%) from the compound of Reference Example 132-5 (46 mg, 0.0905 mmol).
MS (ESI+) 409 (M+1, 100%)

Reference Example 137-7

Ethyl 5-({(3R)-3-(benzyloxy)-1-[(trans-4-{(1S)-1-[(tert-butoxycarbonyl)amino]-2-fluoroethyl}cyclohexyl)carbonyl]-L-prolyl}amino)-1-benzofuran-2-carboxylate

[Formula 498]

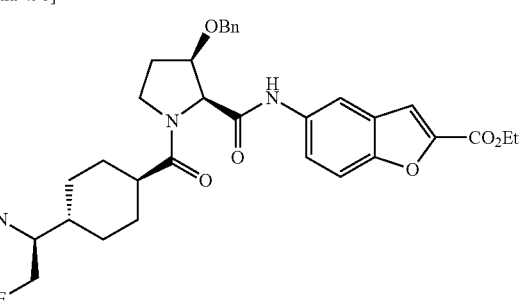

The same procedure as described in Reference Example 1 was carried out to obtain the title compound (45.7 mg, 68%) from the compound of Reference Example 137-6 (40 mg, 0.0899 mmol) and the compound of Reference Example 53-3 (29 mg, 0.0988 mmol).
MS (ESI+) 680 (M+1, 100%)

Reference Example 138

5-{[(3S)-1-[(trans-4-{(1S)-1-[(tert-Butoxycarbonyl)amino]-2-fluoroethyl}cyclohexyl)carbonyl]-3-(2-methylphenyl)-L-propyl]amino}-1-benzofuran-2-carboxylic acid

[Formula 499]

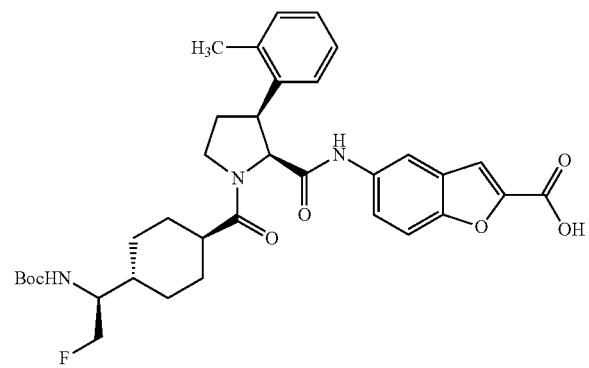

The same procedure as described in Reference Example 119-1 was carried out to obtain the title compound (127.0 mg, 97%) from the compound of Reference Example 138-4 (138 mg, 0.207 mmol).

MS (ESI+) 636 (M+1, 100%)

Reference Example 138-1

(2S,3S)-1-(tert-Butoxycarbonyl)-3-(2-methylphenyl)pyrrolidine-2-carboxylic acid

[Formula 500]

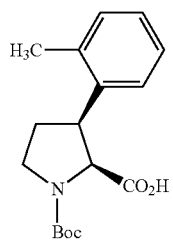

The same procedures as described in Reference Examples 32-1, 32-2, and 32-3 were carried out to obtain the title compound (961 mg, 32%) from trans-o-methyl cinnamaldehyde (1.46 g, 10.0 mmol).

MS (ESI+) 306 (M+1, 67%)

Reference Example 138-2 tert-Butyl (2S,3S)-2-{[2-(ethoxycarbonyl)-1-benzofuran-5-yl]carbamoyl}-3-(2-methylphenyl)pyrrolidine-1-carboxylate

[Formula 501]

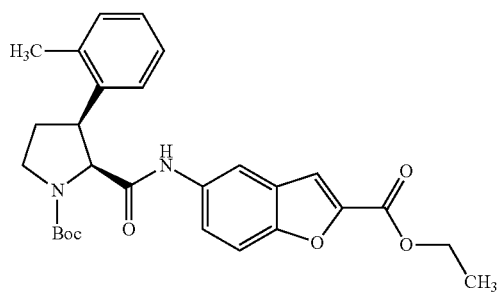

To a solution of the compound obtained in Reference Example 138-1 (297 mg, 0.97 mmol) in DMF (7.0 mL), N,N-diisopropylethylamine (340 µl, 1.95 mmol) and N,N,N',N'-tetramethyl-o-(7-azabenzotriazol-1-yl)uronium hexafluorophosphate (388 mg, 1.02 mmol) were added, and the mixture was stirred at room temperature for approximately 15 minutes. Next, ethyl 5-amino-1-benzofuran-2-carboxylate (219 mg, 1.07 mmol) was added, and the mixture was stirred at room temperature for approximately 1 hour and then stirred at 70° C. for 5 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (478 mg, 99%).

Rf value 0.20 (hexane/ethyl acetate=3/1)

Reference Example 138-3

Ethyl 5-{[(3S)-3-(2-methylphenyl)-L-prolyl]amino}-1-benzofuran-2-carboxylate hydrochloride

[Formula 502]

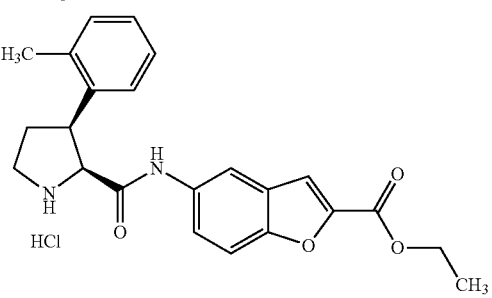

By using the compound of Reference Example 138-2 (100 mg, 0.203 mmol), The same procedure as described in Reference Example 1-2 was carried out to obtain the title compound (79.7 mg, 99%).

MS (ESI+) 393 (M+I, 100%)

Reference Example 138-4

Ethyl 5-{[(3S)-1-[(trans-4-{(1S)-1-[(tert-butoxycarbonyl)amino]-2-fluoroethyl}cyclohexyl)carbonyl]-3-(2-methylphenyl)-L-prolyl]amino}-1-benzofuran-2-carboxylate

[Formula 503]

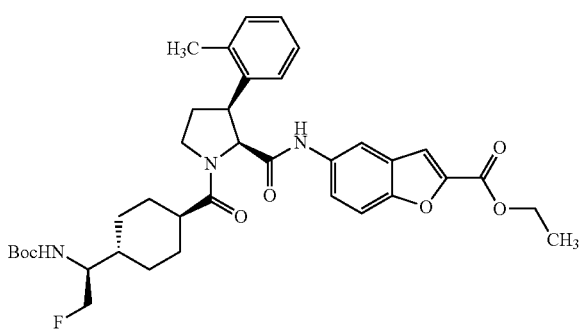

The same procedure as described in Reference Example 1 was carried out to obtain the title compound (134 mg, 99%) from the compound of Reference Example 138-3 (79.7 mg, 0.20 mmol) and the compound of Reference Example 53-3 (58.7 mg, 0.20 mmol).

MS (ESI+) 664 (M+1, 100%)

Reference Example 139

5-({(3S)-1-[(trans-4-{(1S)-1-[(tert-Butoxycarbonyl)amino]-2-fluoroethyl}cyclohexyl)carbonyl]-3-phenyl-L-prolyl}amino)-1-methyl-1H-indole-2-carboxylic acid

[Formula 504]

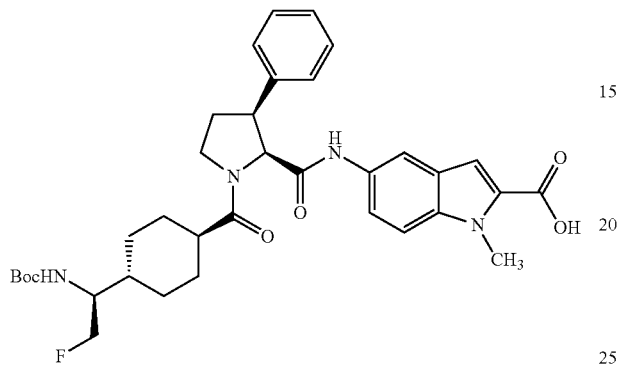

The same procedure as described in Reference Example 119-1 was carried out to obtain the title compound (76.6 mg, 77%) from the compound of Reference Example 139-3 (124 mg, 0.187 mmol).

MS (ESI+) 635 (M+1, 100%)

Reference Example 139-1

Ethyl 5-{[(3S)-1-(tert-butoxycarbonyl)-3-phenyl-L-prolyl]amino}-1-methyl-1H-indole-2-carboxylate

[Formula 505]

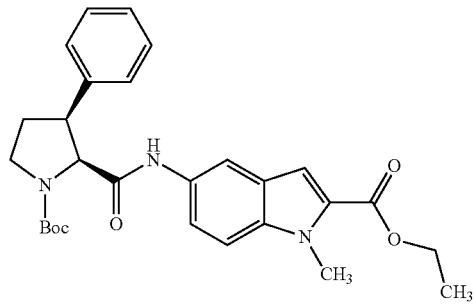

The same procedure as described in Reference Example 138-2 was carried out to obtain the title compound (615 mg, 99%) from (2S,3S)-1-tert-butoxycarbonyl-3-phenylpyrrolidine-2-carboxylic acid (364 mg, 1.25 mmol) and the compound of Reference Example 47-2 (300 mg, 1.38 mmol).

MS (ESI+) 492 (M+1, 100%)

Reference Example 139-2

Ethyl 1-methyl-5-{[(3S)-3-phenyl-L-prolyl]amino}-1H-indole-2-carboxylate hydrochloride

[Formula 506]

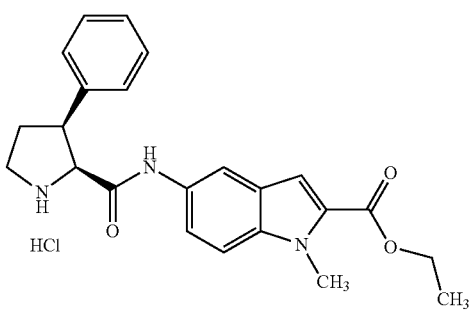

The same procedure as described in Reference Example 1-2 was carried out to obtain the title compound (78.2 mg, 99%) using the compound from Reference Example 139-1 (100 mg, 0.203 mmol).

MS (ESI+) 392 (M+1, 100%)

Reference Example 139-3

Ethyl 5-({(3S)-1-[(trans-4-{(1S)-1-[(tert-butoxycarbonyl)amino]-2-fluoroethyl}cyclohexyl)carbonyl]-3-phenyl-L-prolyl}amino)-1-methyl-1H-indole-2-carboxylate

[Formula 507]

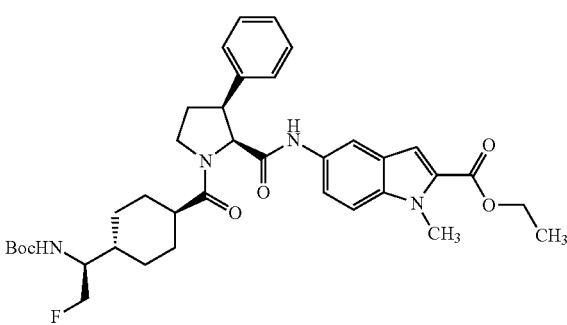

The same procedure as described in Reference Example 1 was carried out to obtain the title compound (124 mg, 93%) from the compound of Reference Example 139-2 (78.2 mg, 0.20 mmol) and the compound of Reference Example 53-3 (58.7 mg, 0.20 mmol).

MS (ESI+) 663 (M+1, 100%)

Reference Example 140

5-({(3R)-1-[(trans-4-{(1S)-1-[(tert-Butoxycarbonyl)amino]-2-fluoroethyl}cyclohexyl)carbonyl]-3-phenyl-L-prolyl}amino)-1H-indole-2-carboxylic acid

[Formula 508]

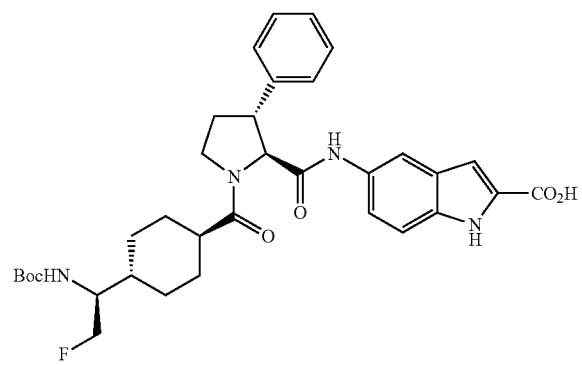

The same procedure as described in Reference Example 3 was carried out to obtain the title compound (610 mg, 97%) from the compound of Reference Example 140-3 (652.5 mg, 1.01 mmol).

MS (ESI+) 621 (M+1, 100%)

Reference Example 140-1

Ethyl 5-{[(3R)-1-(tert-butoxycarbonyl)-3-phenyl-L-prolyl]amino}-1H-indole-2-carboxylate

[Formula 509]

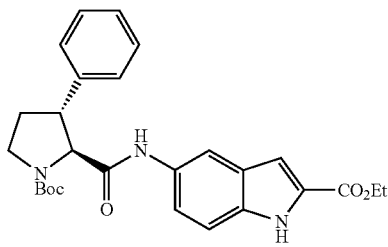

The same procedure as described in Reference Example 1 was carried out to obtain the title compound (560.6 mg, 90%) from the compound of Reference Example 31-4 (378.0 mg, 1.30 mmol) and the compound of Reference Example 2-1 (265 mg, 0.130 mmol).

MS (ESI+) 478 (M+1, 100%)

Reference Example 140-2

Ethyl 5-{[(3R)-3-phenyl-L-prolyl]amino}-1H-indole-2-carboxylate hydrochloride

[Formula 510]

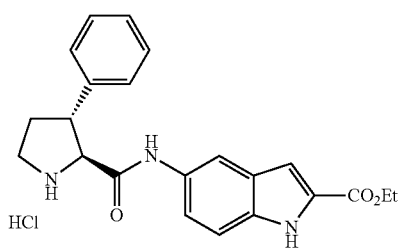

The same procedure as described in Reference Example 1-2 was carried out to obtain the title compound (484 mg, 100%) from the compound of Reference Example 140-1 (560.6 mg, 1.17 mmol).

MS (ESI+) 378 (M+1, 100%)

Reference Example 140-3

Ethyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 511]

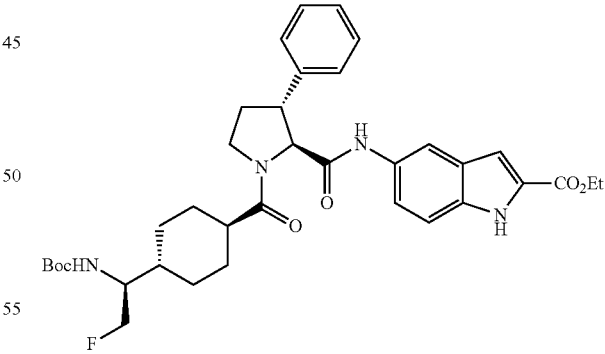

The same procedure as described in Reference Example 1 was carried out to obtain the title compound (652.5 mg, 86%) from the compound of Reference Example 140-2 (484 mg, 1.17 mmol) and the compound of Reference Example 53-3 (372 mg, 1.29 mmol).

MS (ESI+) 649 (M+1, 100%)

Reference Example 141

3-Ethoxypropyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 512]

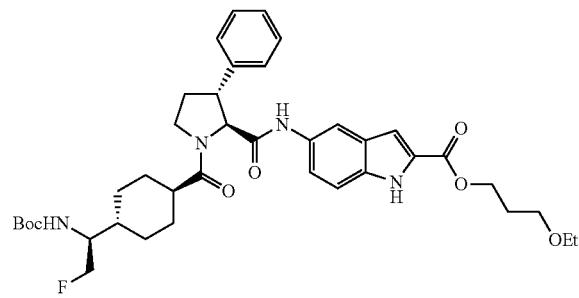

To a solution of the compound of Reference Example 140 (167.5 mg, 0.270 mmol) in DMF (3 mL), 4-dimethylaminopyridine (62.1 mg, 0.41 mmol), WSC.HCl (77.7 mg, 0.41 mmol), triethylamine (113 μL, 0.81 mmol), and 3-ethoxy-1-propanol (169 mg, 1.62 mmol) were added, and the mixture was stirred at room temperature for 2 hours. A saturated aqueous solution of ammonium chloride was added to the reaction mixture, followed by extraction with ethyl acetate. The organic layer was washed with a saturated aqueous solution of ammonium chloride twice and with a saturated aqueous solution of sodium bicarbonate and a saturated saline solution, then dried over sodium sulfate and filtered, and the filtrate was concentrated under reduced pressure. The obtained residue was purified by silica gel column chromatography to obtain the title compound (75.0 mg, 39%).
MS (ESI+) 707 (M+1, 15%)

Reference Example 142

3-Ethoxypropyl 5-({(3S)-1-[(trans-4-{(1S)-1-[(tert-butoxycarbonyl)amino]-2-fluoroethyl}cyclohexyl)carbonyl]-3-phenyl-L-prolyl}amino)-1-methyl-1H-indole-2-carboxylate

[Formula 513]

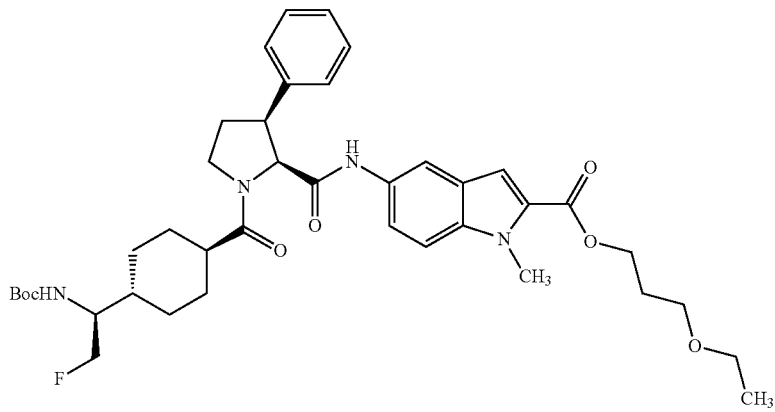

The same procedure as described in Reference Example 1 was carried out to obtain the title compound (134 mg, 68%) from the compound of Reference Example 142-2 (122 mg, 0.272 mmol) and the compound of Reference Example 53-3 (78.7 mg, 0.272 mmol).
MS (ESI+) 721 (M+1, 100%)

Reference Example 142-1

3-Ethoxypropyl 5-{[(3S)-1-(tert-butoxycarbonyl)-3-phenyl-L-prolyl]amino}-1-methyl-1H-indole-2-carboxylate

[Formula 514]

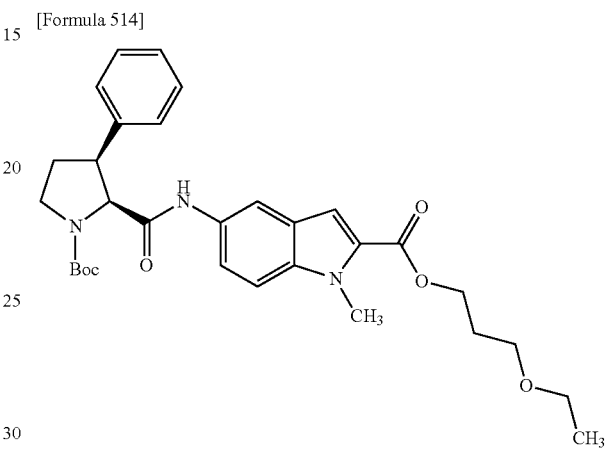

The compound obtained in Reference Example 139-1 (654 mg, 1.33 mmol) was dissolved in ethanol (5.0 mL) and tetrahydrofuran (5.0 mL), then a 1 mol/L aqueous solution of sodium hydroxide (9.0 mL) was added thereto, and the mixture was stirred at 50° C. for 2 hours. A 5% aqueous solution of potassium hydrogensulfate was added to the reaction solution, followed by extraction with chloroform twice. The organic layer was washed with a saturated saline solution, dried over anhydrous sodium sulfate and filtered, and then the organic layer was concentrated under reduced pressure (559 mg, 1.20 mmol). To a solution of the obtained compound (150 mg, 0.323 mmol) in DMF (4.0 mL), 1-hydroxybenzotriazole (57.0 mg, 0.42 mmol), 1-ethyl-3-(3-dimethylaminopropyl)carbodiimide hydrochloride (80.5 mg, 0.42 mmol), triethylamine (180 μL, 1.29 mmol), 3-ethoxy-1-propanol (224 μl, 1.94 mmol), and N,N-dimethyl-4-aminopyridine (118 mg, 0.97 mmol) were added, and the mixture was stirred at 50° C. for 6 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (150 mg, 85%).

MS (ESI+) 550 (M+1, 100%)

Reference Example 142-2

3-Ethoxypropyl 1-methyl-5-{[(3S)-3-phenyl-L-prolyl]amino}-1H-indole-2-carboxylate hydrochloride

[Formula 515]

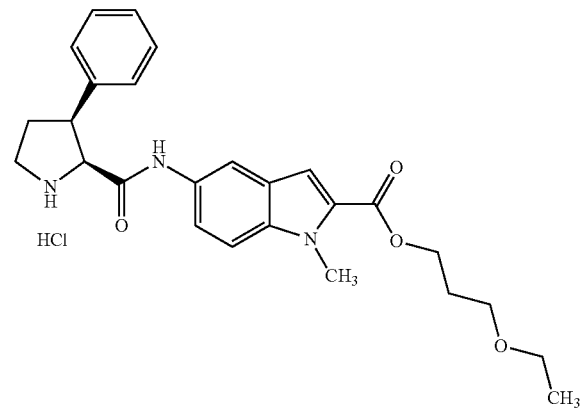

By using the compound of Reference Example 142-1 (150 mg, 0.272 mmol), The same procedure as described in Reference Example 1-2 was carried out to obtain the title compound (122 mg, 99%).

MS (ESI+) 450 (M+1, 100%)

Reference Example 143

3-Ethoxypropyl 4-({(3S)-1-[(trans-4-{1-[(tert-butoxycarbonyl)amino]ethyl}cyclohexyl)carbonyl]-3-cyclohexyl-L-prolyl}amino)-2-fluorobenzoate

[Formula 516]

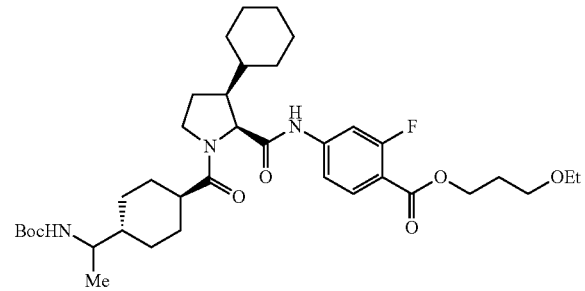

The same procedure as described in Reference Example 1 was carried out to obtain the title compound (31.2 mg, 20%) from the compound of Reference Example 7-9 (69.7 mg, 0.257 mmol) and the compound of Reference Example 143-3 (107 mg, 0.234 mmol).

MS (ESI+) 674 (M+1, 17%)

Reference Example 143-1

4-{[(3S)-1-(tert-Butoxycarbonyl)-3-cyclohexyl-L-prolyl]amino}-2-fluorobenzoic acid

[Formula 517]

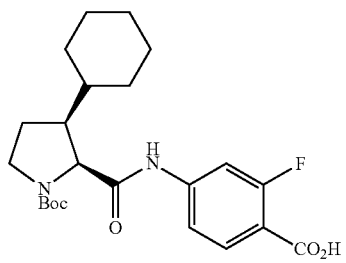

The same procedure as described in Reference Example 3 was carried out to obtain the title compound (166.1 mg, 71%) from the compound of Reference Example 27-1 (240.1 mg, 0.535 mmol).

MS (ESI+) 435 (M+1, 2.6%)

Reference Example 143-2 tert-Butyl (2S,3S)-3-cyclohexyl-2-({4-[(3-ethoxypropoxy)carbonyl]-3-fluorophenyl}carbamoyl)pyrrolidine-1-carboxylate

[Formula 518]

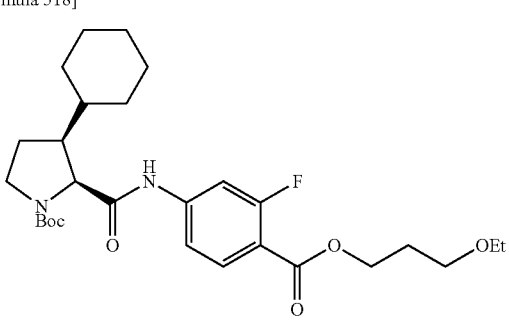

The same procedure as described in Reference Example 141 was carried out to obtain the title compound (121.6 mg, 61%) from the compound of Reference Example 143-1 (166.1 mg, 0.382 mmol).

MS (ESI+) 435 (M+1, 17%)

Reference Example 143-3

3-Ethoxypropyl 4-{[(3S)-3-cyclohexyl-L-prolyl]amino}-2-fluorobenzoate hydrochloride

[Formula 519]

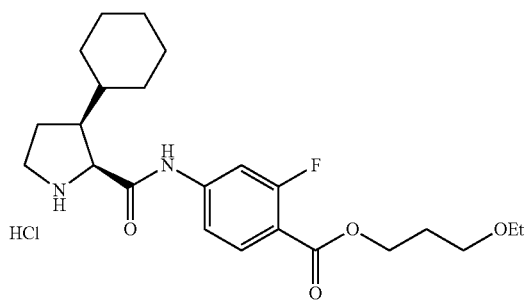

The same procedure as described in Reference Example 1-2 was carried out to obtain the title compound (107 mg, 100%) from the compound of Reference Example 143-2 (121.6 mg, 0.234 mmol).

MS (ESI+) 421 (M+1, 100%)

Reference Example 144

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-1-methyl-1H-indole-2-carboxylic acid

[Formula 520]

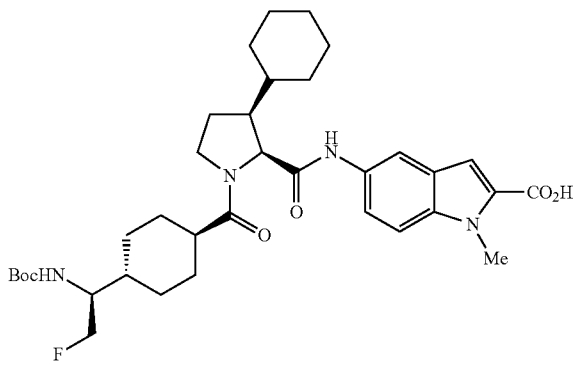

The same procedure as described in Reference Example 19 was carried out to obtain the title compound (52.0 mg, 84%) from the compound of Reference Example 144-1 (65.0 mg, 0.097 mmol).

MS (ESI+) 641 (M+1, 100%)

Reference Example 144-1

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-methyl-1H-indole-2-carboxylate

[Formula 521]

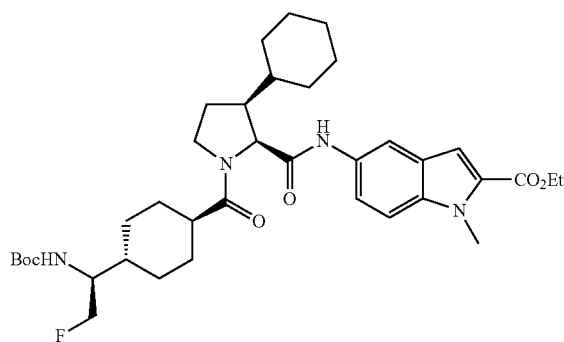

The same procedure as described in Reference Example 1 was carried out to obtain the title compound (24.3 mg, 90%) from the compound of Reference Example 29-2 (54.4 mg, 0.11 mmol) and the compound of Reference Example 53-3 (33.4 mg, 0.116 mmol).

MS (ESI+) 689 (M+1, 100%)

Reference Example 145

3-Ethoxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-methyl-1H-indole-2-carboxylate

[Formula 522]

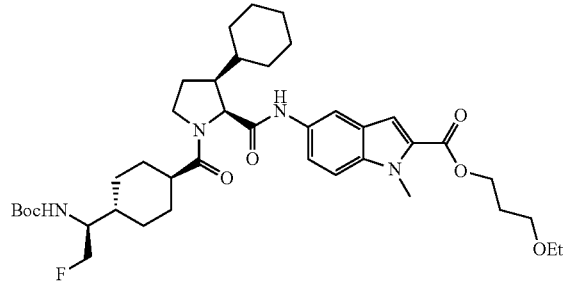

The same procedure as described in Reference Example 1 was carried out to obtain the title compound (117.0 mg, 76%) from the compound of Reference Example 145-3 (104.0 mg, 0.211 mmol) and the compound of Reference Example 53-3 (67.0 mg, 0.232 mmol).

MS (ESI+) 727 (M+1, 100%)

Reference Example 145-1

5-{[(3S)-1-(tert-Butoxycarbonyl)-3-cyclohexyl-L-prolyl]amino}-1-methyl-1H-indole-2-carboxylic acid

[Formula 523]

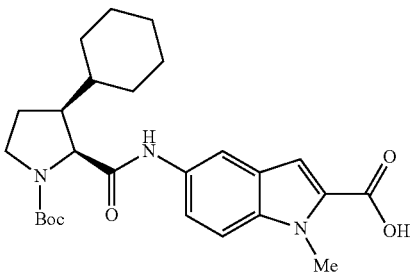

The same procedure as described in Reference Example 19 was carried out to obtain the title compound (270.0 mg, 100%) from the compound of Reference Example 29-1 (280.0 mg, 0.57 mmol).

MS (ESI+) 470 (M+1, 100%)

Reference Example 145-2

3-Ethoxypropyl 5-{[(3S)-1-(tert-butoxycarbonyl)-3-cyclohexyl-L-prolyl]amino}-1-methyl-1H-indole-2-carboxylate

[Formula 524]

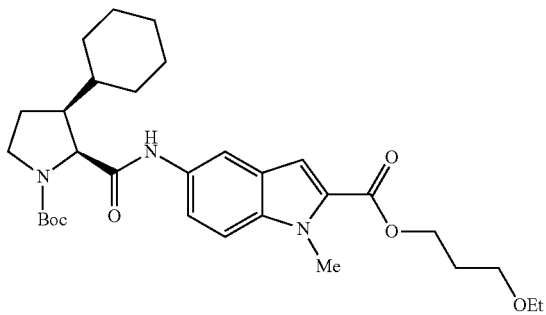

To a solution of the compound of Reference Example 145-1 (135.0 mg, 0.287 mmol) in DMF (5 mL), 1-hydroxybenzotriazole (57.0 mg, 0.373 mmol), WSC.HCl (72.0 mg, 0.373 mmol), triethylamine (160 µL, 1.15 mmol), N,N-dimethyl-4-aminopyridine (105.0 mg, 0.86 mmol), and 3-ethoxy-1-propanol (90.0 mg, 0.862 mmol) were added, and the mixture was stirred at 50° C. for 8 hours. Water was added to the reaction mixture, followed by extraction with ethyl acetate. The organic layer was washed with a saturated saline solution once, then dried over sodium sulfate and filtered, and the filtrate was concentrated under reduced pressure. The obtained residue was purified by silica gel column chromatography to obtain the title compound (117.0 mg, 73%).

MS (ESI+) 556 (M+1, 100%)

Reference Example 145-3

3-Ethoxypropyl 5-{[(3S)-3-cyclohexyl-L-prolyl]amino}-1-methyl-1H-indole-2-carboxylate hydrochloride

[Formula 525]

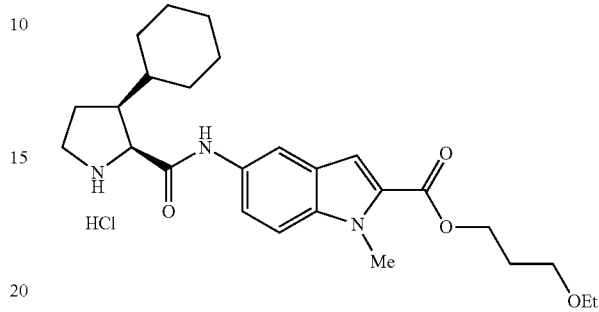

The same procedure as described in Reference Example 1-2 was carried out to obtain the title compound (104 mg, 100%) from the compound of Reference Example 145-2 (117 mg, 0.211 mmol).

MS (ESI+) 456 (M+1, 100%)

Reference Example 146

(2S)-2-Methoxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 526]

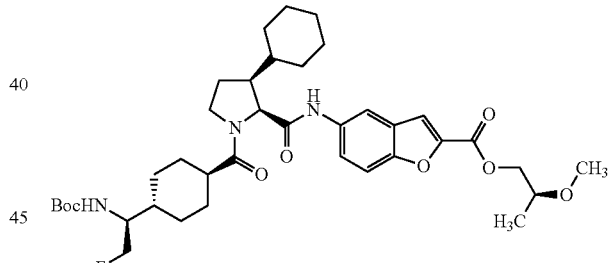

The same procedure as described in Reference Example 1 was carried out to obtain the title compound (188 mg, 77%) from the compound of Reference Example 146-4 (149 mg, 0.35 mmol) and the compound of Reference Example 53-3 (100 mg, 0.35 mmol).

MS (ESI+) 700 (M+1, 63%)

Reference Example 146-1

{[(2S)-2-Methoxypropoxy]methyl}benzene

[Formula 527]

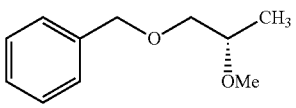

(S)-(+)-1-Benzyloxy-2-propanol (500 mg, 3.00 mmol) was dissolved in tetrahydrofuran (12.0 mL), then sodium hydride (144 mg, 3.3 mmol) was added, and the mixture was stirred for 15 minutes in an ice bath. Further, methyl iodide (224 μl, 3.6 mmol) was slowly added dropwise, and the mixture was stirred for 6 hours. A saturated aqueous solution of ammonium chloride was added to the reaction solution, followed by extraction with ethyl acetate. The organic layer was washed with a saturated saline solution, dried over anhydrous sodium sulfate and filtered, and then the organic layer was concentrated under reduced pressure. The obtained residue was purified by silica gel column chromatography to obtain the title compound (316 mg, 59%).

MS (ESI+) 181 (M+1, 61%)

Reference Example 146-2

(2S)-2-Methoxypropan-1-ol

[Formula 528]

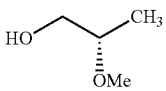

10% Palladium-carbon (540 mg) was added to a solution of the compound obtained in Reference Example 146-1 (340 mg, 1.89 mmol) in tetrahydrofuran (15.0 mL), and the mixture was stirred under hydrogen atmosphere for 6 hours. The reaction solution was filtered through Celite, and the solution was concentrated under reduced pressure to obtain the title compound (158 mg, 100%).

$^1$H NMR (CDCl$_3$, 300 MHz) δ 3.52 (m, 1H), 3.39 (m, 2H), 3.32 (s, 3H), 1.05 (d, J=6.0 Hz, 3H).

Reference Example 146-3 tert-Butyl (2S,3S)-3-cyclohexyl-2-[(2-{[(2S)-2-methoxypropoxy]carbonyl}-1-benzofuran-5-yl)carbamoyl]pyrrolidine-1-carboxylate

[Formula 529]

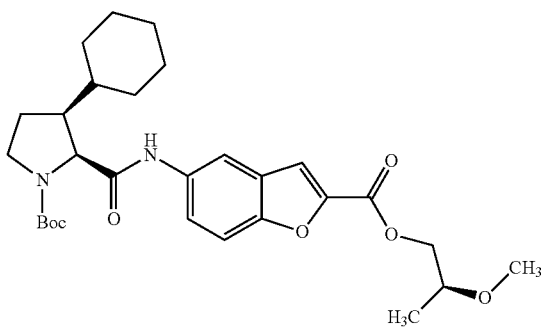

To a solution of the compound obtained in Reference Example 119-1 (200 mg, 0.44 mmol) in DMF (5.0 mL), 1-hydroxybenzotriazole (77.0 mg, 0.572 mmol), 1-ethyl-3-(3-dimethylaminopropyl)carbodiimide hydrochloride (110 mg, 0.572 mmol), triethylamine (245 μL, 1.76 mmol), the compound obtained in Reference Example 146-2 (119 mg, 1.32 mmol), and N,N-dimethyl-4-aminopyridine (161 mg, 1.32 mmol) were added, and the mixture was stirred at 50° C. for 6 hours. After the reaction solution was allowed to cool, a saturated aqueous solution of ammonium chloride was added to the reaction mixture, followed by extraction with ethyl acetate. The organic layer was washed with a saturated aqueous solution of ammonium chloride twice and with a saturated saline solution once, then dried over sodium sulfate and filtered, and the filtrate was concentrated under reduced pressure. The obtained residue was purified by silica gel column chromatography to obtain the title compound (184 mg, 79%).

MS (ESI+) 529 (M+1, 59%)

Reference Example 146-4

(2S)-2-Methoxypropyl 5-{[(3S)-3-cyclohexyl-L-prolyl]amino}-1-benzofuran-2-carboxylate hydrochloride

[Formula 530]

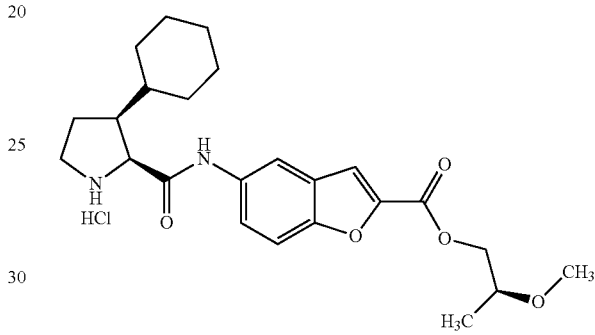

By using the compound of Reference Example 146-3 (183 mg, 0.347 mmol), The same procedure as described in Reference Example 1-2 was carried out to obtain the title compound (149 mg, 99%).

MS (ESI+) 429 (M+1, 100%)

Reference Example 147

A Diastereo Mixture of A and B

A: 5-{[(3R)-1-[(trans-4-{(1S)-1-[(tert-Butoxycarbonyl)amino]-2-fluoroethyl}cyclohexyl)carbonyl]-3-(piperidin-1-yl)-L-prolyl]amino}-1-benzofuran-2-carboxylic acid
B: 5-{[(3S)-1-[(trans-4-{(1S)-1-[(tert-Butoxycarbonyl)amino]-2-fluoroethyl}cyclohexyl)carbonyl]-3-(piperidin-1-yl)-D-prolyl]amino}-1-benzofuran-2-carboxylic acid

[Formula 531]

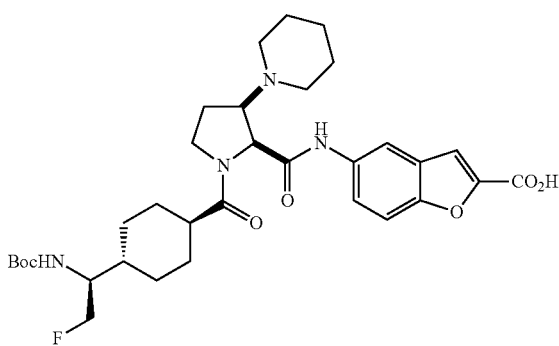

The same procedure as described in Reference Example 3 was carried out to obtain the title compound (90.2 mg, 100%) from the compound of Reference Example 147-5 (54.0 mg, 0.0822 mmol).

MS (ESI+) 629 (M+1, 100%)

Reference Example 147-1

(rac.)-1-tert-Butyl 2-ethyl (2S,3R)-3-(piperidin-1-yl)pyrrolidine-1,2-dicarboxylate

[Formula 532]

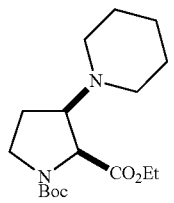

To a solution of 1-tert butyl 2-ethyl (2S)-3-oxopyrrolidine-1,2-dicarboxylate (1.1 g, 4.27 mmol) known from literature (e.g., J. Org. Chem. 1985, 50, 25, 5223.) and piperidine (845 µl, 8.55 mmol) in dichloromethane (17 ml), acetic acid (2 ml) and then hydrogenation triacetoxy boron sodium (2.72 g, 12.8 mmol) were added in an ice bath, and the mixture was stirred at room temperature for 15 hours. A saturated aqueous solution of sodium bicarbonate was added to the reaction mixture, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (600 mg, 43%).

MS (ESI+) 327 (M+1, 100%)

Reference Example 147-2

(rac.)-(3R)-1-(tert-Butoxycarbonyl)-3-piperidin-1-yl-L-proline

[Formula 533]

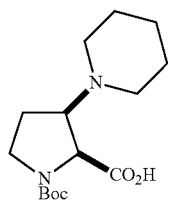

The compound of Reference Example 147-1 (606 mg, 1.86 mmol) was dissolved in ethanol (2 mL) and THF (2 mL), then a 2 mol/L aqueous solution of sodium hydroxide (2.78 ml, 5.57 mmol) was added thereto, and the mixture was stirred at 90° C. for 4 hours. The reaction solution was allowed to cool to room temperature for concentration under reduced pressure. Water was added to the residue, and the aqueous layer was washed with diethyl ether. 2 N Hydrochloric acid was added to the aqueous layer for neutralization and concentration under reduced pressure. THF was added to the residue, then insoluble matter was filtered off, and the obtained filtrate was concentrated under reduced pressure to obtain the title compound (536 mg, 97%).

MS (ESI+) 299 (M+1, 100%)

Reference Example 147-3

(rac)-tert-Butyl (2S,3R)-2-{[2-(ethoxycarbonyl)-1-benzofuran-5-yl]carbamoyl}-3-(piperidin-1-yl)pyrrolidine-1-carboxylate

[Formula 534]

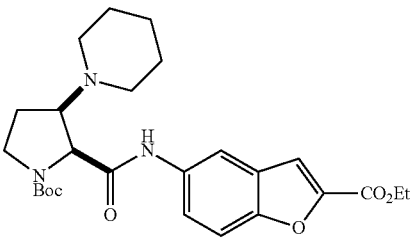

The same procedure as described in Reference Example 138-2 was carried out to obtain the title compound (101 mg, 78%) from the compound of Reference Example 147-2 (80 mg, 0.268 mmol) and 5-amino-1-benzofuran-2-carboxylate (61 mg, 0.295 mmol).

MS (ESI+) 486 (M+1, 100%)

Reference Example 147-4

(rac.)-Ethyl 5-{[(3R)-3-(piperidin-1-yl)-L-prolyl]amino}-1-benzofuran-2-carboxylate dihydrochloride

[Formula 535]

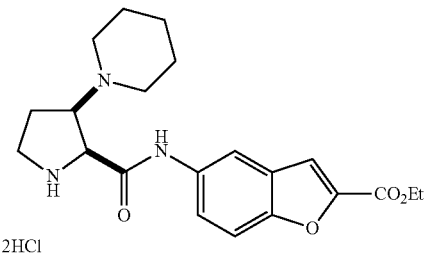

The same procedure as described in Reference Example 1-2 was carried out to obtain the title compound (98.9 mg, 100%) from the compound of Reference Example 147-3 (99 mg, 0.204 mmol).

MS (ESI+) 386 (M+1, 100%)

Reference Example 147-5

A Diastereo Mixture of A and B

A: Ethyl 5-{[(3R)-1-[(trans-4-{(1S)-1-[(tert-butoxycarbonyl)amino]-2-fluoroethyl}cyclohexyl)carbonyl]-3-(piperidin-1-yl)-L-prolyl]amino}-1-benzofuran-2-carboxylate B: Ethyl 5-{[(3S)-1-[(trans-4-{(1S)-1-[(tert-butoxycarbonyl)amino]-2-fluoroethyl}cyclohexyl)carbonyl]-3-(piperidin-1-yl)-D-prolyl]amino}-1-benzofuran-2-carboxylate

[Formula 536]

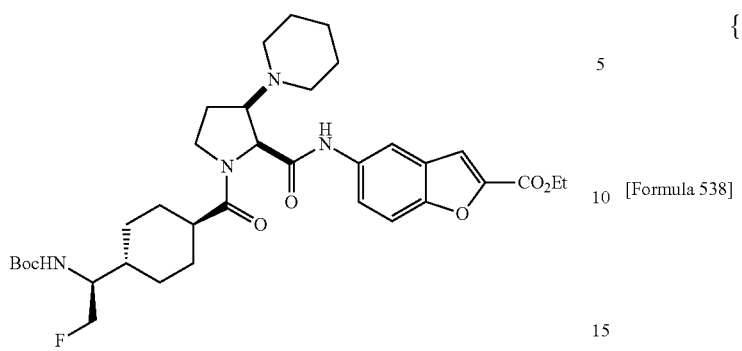

The same procedure as described in Reference Example 1 was carried out to obtain the title compound (54 mg, 40%) from the compound of Reference Example 147-5 (98 mg, 0.2039 mmol) and the compound of Reference Example 53-3 (60 mg, 0.207 mmol).

MS (ESI+) 657 (M+1, 100%)

Reference Example 148

(2R)-2-(2-Methoxyethoxyl)propyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 537]

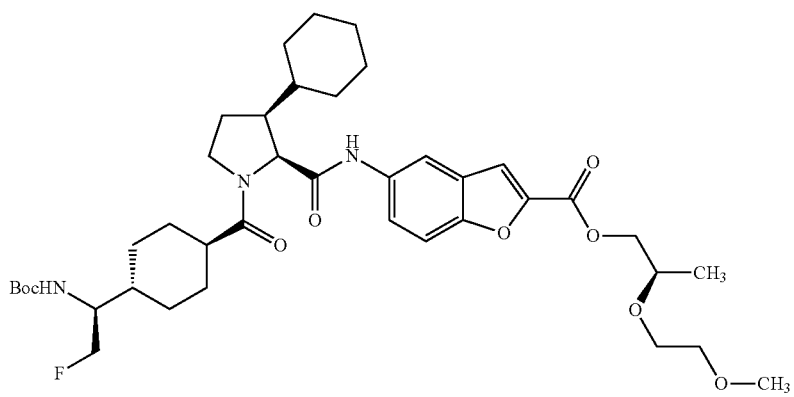

To a solution of the compound obtained in Reference Example 54 (365 mg, 0.58 mmol) in DMF (6 mL), 1-hydroxybenzotriazole (93.0 mg, 0.69 mmol), 1-ethyl-3-(3-dimethylaminopropyl)carbodiimide hydrochloride (132 mg, 0.69 mmol), triethylamine (294 μL, 2.11 mmol), and the compound obtained in Reference Example 148-2 (70.8 mg, 0.53 mmol) were added, and the mixture was stirred at 50° C. for 7 hours. A saturated aqueous solution of ammonium chloride was added to the reaction mixture, followed by extraction with ethyl acetate. The organic layer was washed with a saturated aqueous solution of sodium bicarbonate twice and with a saturated saline solution once, then dried over sodium sulfate and filtered, and the filtrate was concentrated under reduced pressure. The obtained residue was purified by silica gel column chromatography to obtain the title compound (90.5 mg, 23%).

MS (ESI+) 744 (M+1, 45%)

Reference Example 148-1

{[(2R)-2-(2-Methoxyethoxy)propoxy]methyl}benzene

[Formula 538]

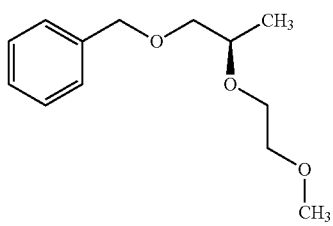

By using (R)-(−)-1-benzyloxy-2-propanol (400 mg, 2.41 mmol) and 2-chloroethyl methyl ether (264 μl, 2.89 mmol), The same procedure as described in Reference Example 146-1 was carried out to obtain the title compound (119 mg, 22%).

Rf value 0.39 (hexane/ethyl acetate=4/1)

Reference Example 148-2

(2R)-2-(2-Methoxyethoxyl)propan-1-ol

[Formula 539]

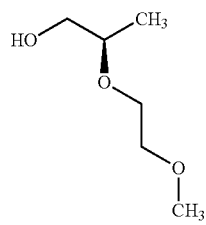

By using the compound obtained in Reference Example 148-1 (118 mg, 0.53 mmol), The same procedure as described in Reference Example 146-2 was carried out to obtain the title compound (70.8 mg, 100%).

MS (ESI+) 135 (M+1, 100%)

Reference Example 149

5-{[(3R)-1-[(trans-4-{(1S)-1-[(tert-Butoxycarbonyl)amino]-2-fluoroethyl}cyclohexyl)carbonyl]-3-(4-methoxyphenyl)-L-prolyl]amino}-1H-indole-2-carboxylic acid

[Formula 540]

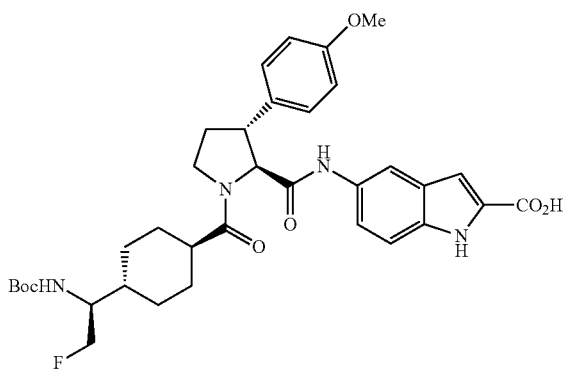

The same procedure as described in Reference Example 3 was carried out to obtain the title compound (290.0 mg, 86%) from the compound of Reference Example 149-4 (352.6 mg, 0.519 mmol).

MS (ESI+) 651 (M+1, 100%)

Reference Example 149-1

(2S,3R)-1-(tert-Butoxycarbonyl)-3-(4-methoxyphenyl)pyrrolidine-2-carboxylic acid

[Formula 541]

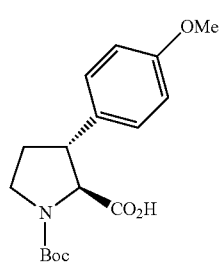

According to the procedure described in the literature (Org. Lett. 2009, 11, 4056-4059.), (4R,5R)-4-(2-methoxyphenyl)-5-nitrotetrahydro-2H-pyran-2-ol (4.45 g, 83%, >99% ee) was obtained from 4-methoxy cinnamaldehyde (3.43 g, 21.1 mmol) by using (2R)-2-[diphenyl[(trimethylsilyl)oxy]methyl]pyrrolidine as a catalyst.

To a solution of the obtained (4R,5R)-4-(2-methoxyphenyl)-5-nitrotetrahydro-2H-pyran-2-ol (4.45 g, 17.6 mmol) in methanol (150 ml), palladium hydroxide (2.50 g) was added, and the mixture was stirred overnight under the pressure of 0.4 MPa and under hydrogen atmosphere. The reaction solution was filtered through Celite, and the filtrate was concentrated under reduced pressure. The residue was dissolved in acetonitrile (200 mL), then di-tert-butyl dicarbonate (7.70 g, 35.2 mmol) was added thereto, and the mixture was stirred overnight. The reaction solution was concentrated under reduced pressure and then purified by silica gel column chromatography to obtain tert-butyl (4R,5R)-3-(4-methoxyphenyl)-2-(hydroxymethyl)pyrrolidine-1-carboxylate (3.65 g, 67%).

To a solution of the obtained (4R,5R)-3-(4-methoxyphenyl)-2-(hydroxymethyl)pyrrolidine-1-carboxylate (1.1 g, 3.58 mmol) in acetonitrile (20 mL), N-methylmorpholine N-oxide (629 mg, 5.37 mmol) and molecular sieves (600 mg) were added, and the mixture was stirred for 10 minutes. Then tetrapropylammonium perruthenate (377 mg, 1.07 mmol) was added, and the mixture was stirred for 4.5 hours. The reaction solution was filtered through Celite and silica gel, and the obtained filtrate was concentrated under reduced pressure to obtain tert-butyl (2R,3R)-3-(4-methoxyphenyl)-2-formylpyrrolidine-1-carboxylate (830 mg, 2.72 g).

To a solution of the obtained tert-butyl (2R,3R)-3-(4-methoxyphenyl)-2-formylpyrrolidine-1-carboxylate (830 mg, 2.72 mmol) in dichloromethane (10 mL), DBU (0.43 mL, 2.86 mmol) was added, and the mixture was stirred at room temperature overnight. A pH 7 phosphate buffer was added to the reaction mixture, followed by extraction with ethyl acetate. The organic layer was washed with a saturated saline solution, then dried over sodium sulfate and filtered, and the filtrate was concentrated under reduced pressure to obtain tert-butyl (2S,3R)-2-formyl-3-(4-methoxyphenyl)-pyrrolidine-1-carboxylate (845 mg, 100%).

tert-Butyl (2S,3R)-2-formyl-3-(4-methoxyphenyl)-pyrrolidine-1-carboxylate (845 mg, 2.72 mmol) was dissolved in a mixed solvent of tert-butanol and distilled water (3:1, 20 mL), then sodium dihydrogenphosphate dihydrate (1.27 mg, 8.16 mmol), 2-methyl-2-butene (1.45 mL, 13.6 mmol), and sodium chlorite (703 mg, 5.44 mmol) were added thereto, and the mixture was stirred for 1 hour. Ethyl acetate and a 1 mol/L aqueous solution of sodium hydroxide were added to the reaction solution for adjustment of pH to 8-9 and separation, and the aqueous layer was separated. Ethyl acetate and 1 mol/L hydrochloric acid were added to the aqueous layer for adjustment of pH to 6 and extraction of the organic layer, then the resultant was concentrated under reduced pressure to obtain the title compound (760 mg, 87%).

MS (ESI+) 322 (M+1, 17%)

Reference Example 149-2

Ethyl 5-{[(3R)-1-(tert-butoxycarbonyl)-3-(4-methoxyphenyl)-L-prolyl]amino}-1H-indole-2-carboxylate

[Formula 542]

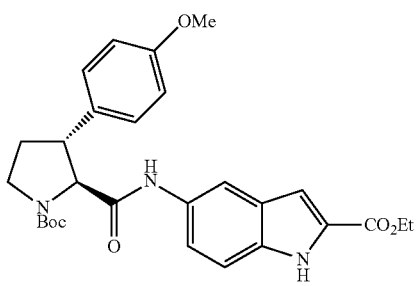

The same procedure as described in Reference Example 1 was carried out to obtain the title compound (345.0 mg, 81%) from the compound of Reference Example 149-1 (270.4 mg, 0.841 mmol) and the compound of Reference Example 2-1 (171.7 mg, 0.841 mmol).

MS (ESI+) 508 (M+1, 100%)

Reference Example 149-3

Ethyl 5-{[(3R)-3-(4-methoxyphenyl)-L-prolyl]amino}-1H-indole-2-carboxylate trifluoroacetate

[Formula 543]

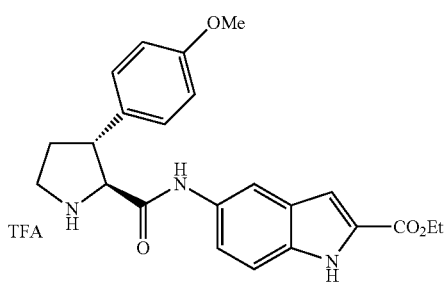

The same procedure as described in Reference Example 9-2 was carried out to obtain the title compound (357 mg, 100%) from the compound of Reference Example 149-2 (345.0 mg, 0.68 mmol).

MS (ESI+) 408 (M+1, 100%)

Reference Example 149-4

Ethyl 5-{[(3R)-1-[(trans-4-{(1S)-1-[(tert-butoxycarbonyl)amino]-2-fluoroethyl}cyclohexyl)carbonyl]-3-(4-methoxyphenyl)-L-prolyl]amino}-1H-indole-2-carboxylate

[Formula 544]

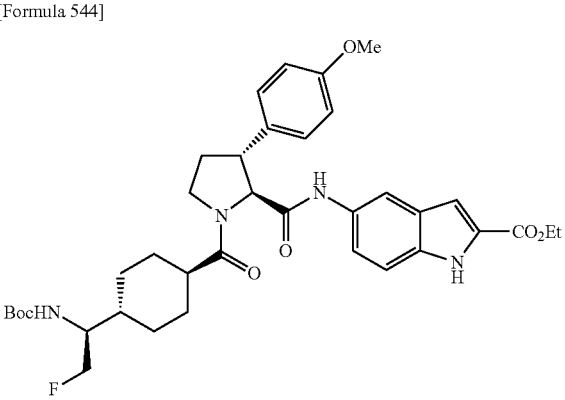

The same procedure as described in Reference Example 1 was carried out to obtain the title compound (352.6 mg, 76%) from the compound of Reference Example 149-3 (357 mg, 0.68 mmol) and the compound of Reference Example 53-3 (216 mg, 0.748 mmol).

MS (ESI+) 679 (M+1, 100%)

Reference Example 150

(5-Methyl-2-oxo-1,3-disoxol-4-yl)methyl 5-({(3R)-1-[(trans-4-{(1S)-1-[(tert-butoxycarbonyl)amino]-2-fluoroethyl}cyclohexyl)carbonyl-3-phenyl-L-prolyl}amino)-1H-indole-2-carboxylate

[Formula 545]

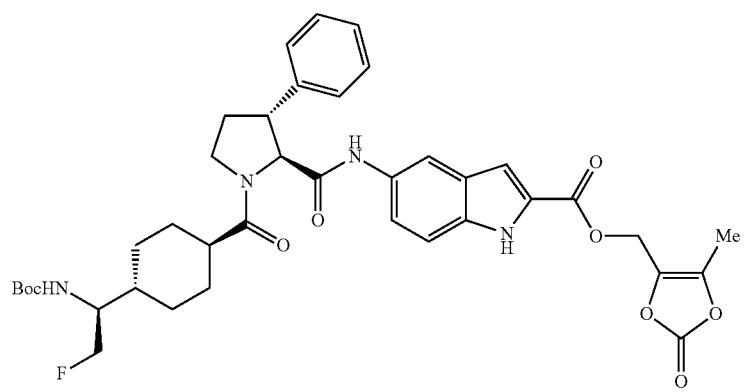

To a solution of the compound of Reference Example 140 (60.0 mg, 0.0967 mmol) in DMF (1 mL), potassium carbonate (26.7 mg, 0.193 mmol) and 4-chloromethyl-5-methyl-1,3-dioxol-2-one (14.6 μL, 0.126 mmol) were added, and the mixture was stirred at room temperature overnight. A saturated aqueous solution of ammonium chloride was added to the reaction mixture, followed by extraction with ethyl acetate. The organic layer was washed with a saturated aqueous solution of ammonium chloride twice and with a saturated saline solution, then dried over sodium sulfate, filtered, and the filtrate was concentrated under reduced pressure. The obtained residue was purified by silica gel column chromatography to obtain the title compound (59.4 mg, 84%).

MS (ESI+) 733 (M+I, 49%)

Reference Example 151

2-(Morpholin-4-yl)ethyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 546]

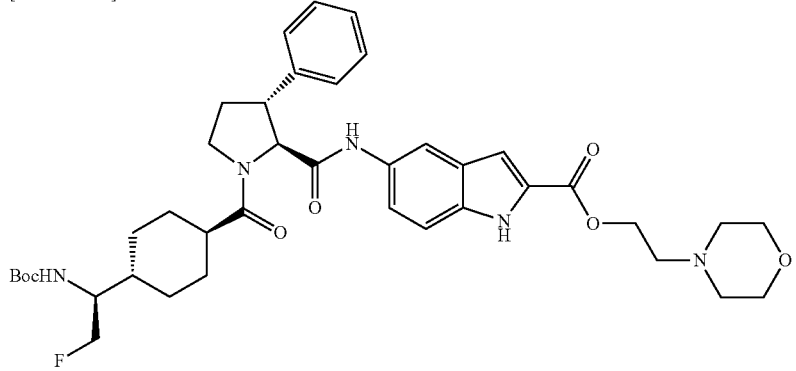

The same procedure as described in Reference Example 150 was carried out to obtain the title compound (73.5 mg, 99%) from the compound of Reference Example 140 (62.8 mg, 0.101 mmol) and N-(2-chloroethyl)morpholine hydrochloride (36.7 mg, 0.202 mmol).

MS (ESI+) 734 (M+1, 100%)

Reference Example 152

3-(Benzyloxy)propyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 547]

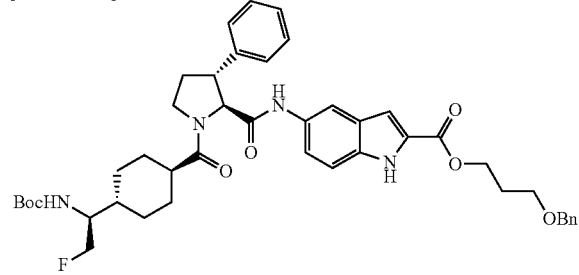

The same procedure as described in Reference Example 150 was carried out to obtain the title compound (196.2 mg, 84%) from the compound of Reference Example 140 (187.2 mg, 0.302 mmol) and benzyl 3-bromopropyl ether (80.0 μL, 0.453 mmol).

MS (ESI+) 769 (M+1, 100%)

Reference Example 153

(2S)-2-Methoxypropyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 548]

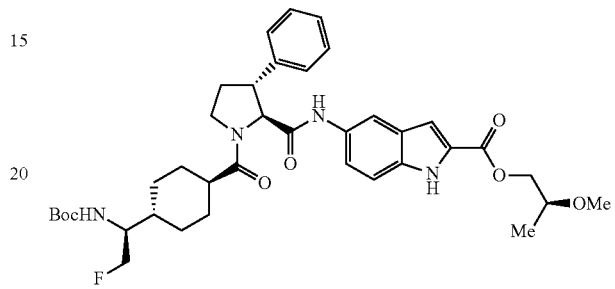

The same procedure as described in Reference Example 141 was carried out to obtain the title compound (10.1 mg, 4.1%) from the compound of Reference Example 140 (221.4 mg, 0.357 mmol) and Reference Example 146-2 (96.7 mg, 1.07 mmol).

MS (ESI+) 693 (M+1, 100%)

Reference Example 154

2-Methoxyethyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 549]

The same procedure as described in Reference Example 150 was carried out to obtain the title compound (111.5 mg, 74%) from the compound of Reference Example 140 (137.5 mg, 0.222 mmol) and 2-bromoethyl methyl ether (46.3 mg, 0.333 mmol).

MS (ESI+) 679 (M+1, 100%)

Reference Example 155

4-Methoxybutyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 550]

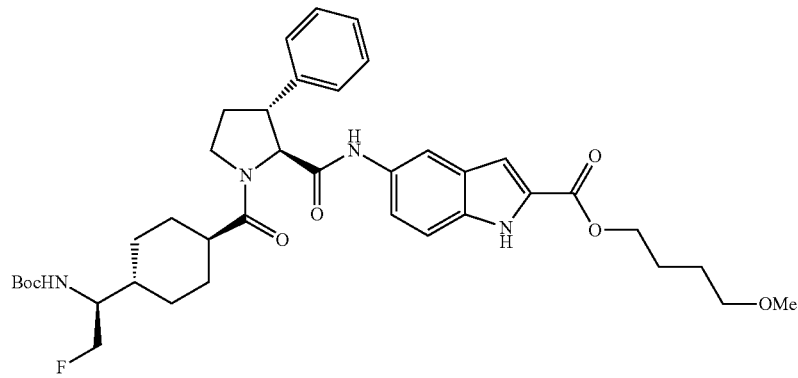

The same procedure as described in Reference Example 150 was carried out to obtain the title compound (85.4 mg, 55%) from the compound of Reference Example 140 (136.0 mg, 0.219 mmol) and 1-chloro-4-methoxybutane (40.3 mg, 0.329 mmol).

MS (ESI+) 707 (M+1, 100%)

Reference Example 156

3-(2-Methoxyethoxy)propyl 5-({(3R)-1-[(trans-4-{(1S)-1-[(tert-butoxycarbonyl)amino]-2-fluoroethyl}cyclohexyl)carbonyl]-3-phenyl-L-prolyl}amino)-1H-indole-2-carboxylate

[Formula 551]

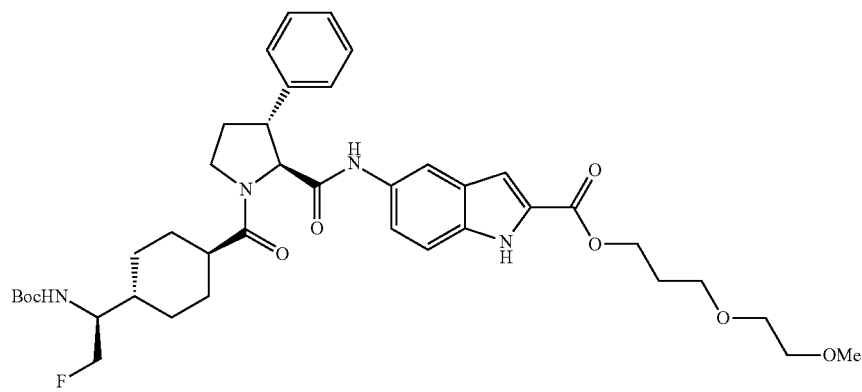

The same procedure as described in Reference Example 150 was carried out to obtain the title compound (162.9 mg, 78%) from the compound of Reference Example 140 (175.2 mg, 0.282 mmol) and 3-(2-methoxyethoxy)propyl bromide (66.7 μL, 0.338 mmol).

MS (ESI+) 737 (M+1, 100%)

Reference Example 157

5-{[(3R)-1-[(trans-4-{(1S)-1-[(tert-Butoxycarbonyl)amino]-2-fluoroethyl}cyclohexyl)carbonyl]-3-(4-fluorophenyl)-L-prolyl]amino}-1H-indole-2-carboxylic acid

[Formula 552]

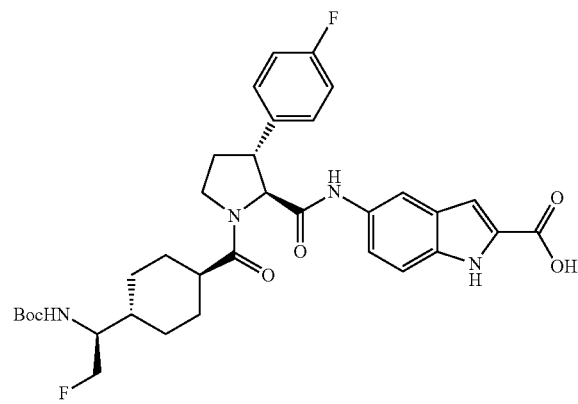

The same procedure as described in Reference Example 3 was carried out to obtain the title compound (35.0 mg, 100%) from the compound of Reference Example 157-4 (65.2 mg, 0.0978 mmol).

MS (ESI+) 639 (M+1, 100%)

Reference Example 157-1

(3R)-1-(tert-Butoxycarbonyl)-3-(4-fluorophenyl)-L-proline

[Formula 553]

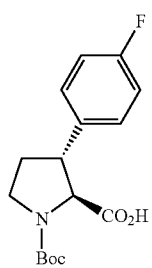

The same procedure as described in Reference Example 149-1 was carried out to obtain the title compound (49.6 mg, 0.39%) from 4-fluorocinnamaldehyde (6.26 g, 40.86 mmol).

MS (ESI+) 310 (M+1, 1.2%)

Reference Example 157-2

Ethyl 5-{[(3R)-1-(tert-butoxycarbonyl)-3-(4-fluorophenyl)-L-prolyl]amino-}1H-indole-2-carboxylate

[Formula 554]

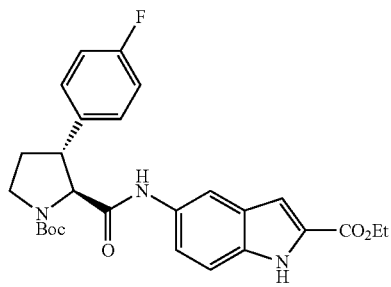

The same procedure as described in Reference Example 1 was carried out to obtain the title compound (72.3 mg, 91%) from the compound of Reference Example 157-1 (49.6 mg, 0.16 mmol) and the compound of Reference Example 2-1 (32.7 mg, 0.16 mmol).

MS (ESI+) 496 (M+1, 100%)

Reference Example 157-3

Ethyl 5-{[(3R)-3-(4-fluorophenyl)-L-prolyl]amino}-1H-indole-2-carboxylate

[Formula 555]

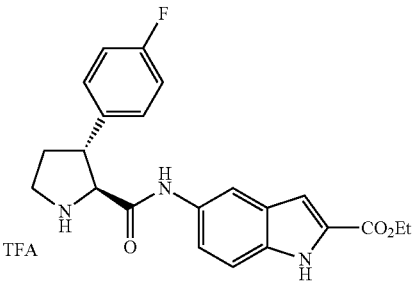

The same procedure as described in Reference Example 9-2 was carried out to obtain the title compound (75.0 mg, 100%) from the compound of Reference Example 157-2 (72.3 mg, 0.146 mmol).

MS (ESI+) 396 (M+1, 100%)

Reference Example 157-4

Ethyl 5-{[(3R)-1-[(trans-4-{(1S)-1-[(tert-butoxycarbonyl)amino]-2-fluoroethyl}cyclohexyl)carbonyl]-3-(4-fluorophenyl)-L-prolyl]amino}-1H-indole-2-carboxylate

[Formula 556]

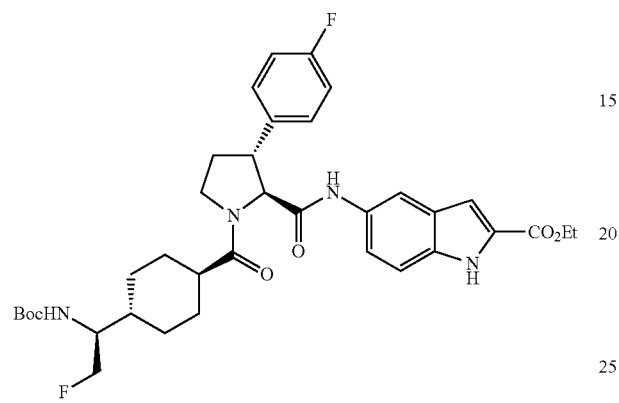

The same procedure as described in Reference Example 1 was carried out to obtain the title compound (65.2 mg, 67%) from the compound of Reference Example 157-3 (75.0 mg, 0.146 mmol) and the compound of Reference Example 53-3 (50.7 mg, 0.175 mmol).

MS (ESI+) 668 (M+1, 100%)

Reference Example 158

Methyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1,3-benzoxazole-2-carboxylate

[Formula 557]

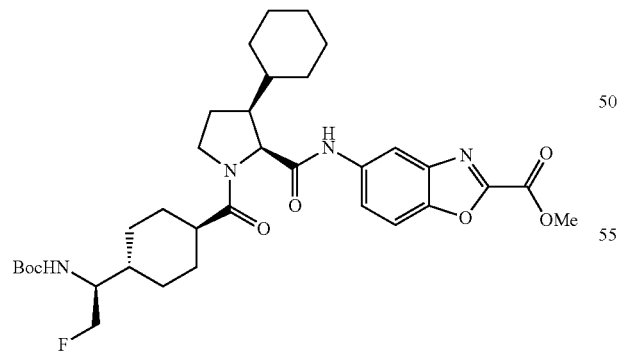

The same procedure as described in Reference Example 1 was carried out to obtain the title compound (228.7 mg, 64%) from the compound of Reference Example 158-2 (263.4 mg, 0.559 mmol) and the compound of Reference Example 53-3 (178.0 mg, 0.615 mmol).

MS (ESI+) 643 (M+1, 67%)

Reference Example 158-1

Methyl 5-{[(3S)-1-(tert-butoxycarbonyl)-3-cyclohexyl-L-prolyl]amino}-1,3-benzoxazole-2-carboxylate

[Formula 558]

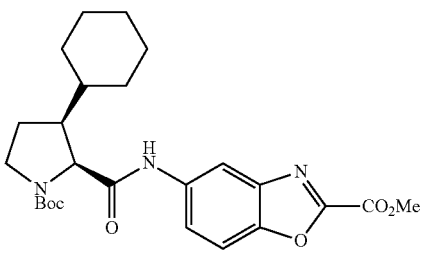

The same procedure as described in Reference Example 1 was carried out to obtain the title compound (263.4 mg, 80%) from the compound of Reference Example 11-1 (208.8 mg, 0.702 mmol) and methyl 5-aminobenzo[d]oxazole-2-carboxylate (148.4 mg, 0.772 mmol).

MS (ESI+) 472 (M+1, 61%)

Reference Example 158-2

Methyl 5-{[(3S)-3-cyclohexyl-L-prolyl]amino}-1,3-benzoxazole-2-carboxylate hydrochloride

[Formula 559]

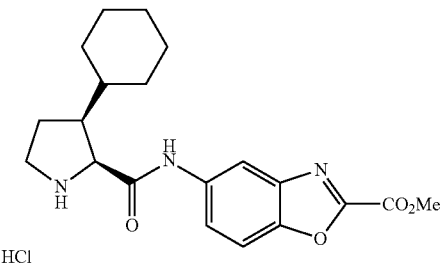

The same procedure as described in Reference Example 1-2 was carried out to obtain the title compound (229 mg, 100%) from the compound of Reference Example 157-1 (263.4 mg, 0.559 mmol).

MS (ESI+) 372 (M+1, 100%)

Reference Example 159

3-(2-Methoxyethoxy)propyl 5-({(3S)-1-[(trans-4-{[(tert-butoxycarbonyl)amino]methyl}cyclohexyl)carbonyl]-3-cyclohexyl-L-prolyl}amino)-1-benzofuran-2-carboxylate

[Formula 560]

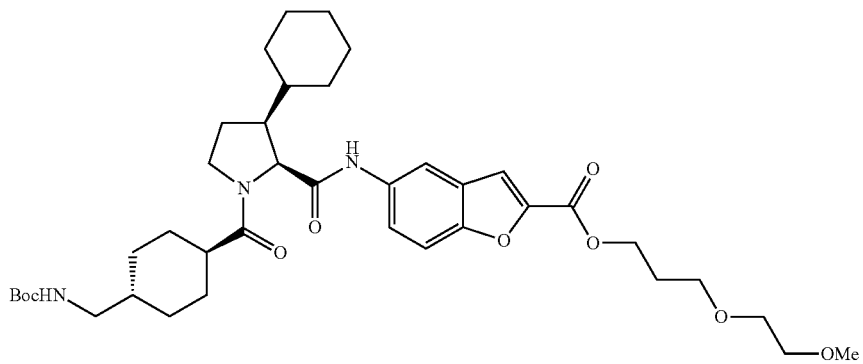

The same procedure as described in Reference Example 1 was carried out to obtain the title compound (142.2 mg, 61%) from the compound of Reference Example 159-2 (170 mg, 0.328 mmol) and BOC-tranexamic acid (92.8 mg, 0.361 mmol).

MS (ESI+) 712 (M+1, 24%)

Reference Example 159-1 tert-Butyl (2S,3S)-3-cyclohexyl-2-[(2-{[3-(2-methoxyethoxy)propoxy]carbonyl}-1-benzofuran-5-yl)carbamoyl]pyrrolidine-1-carboxylate

[Formula 561]

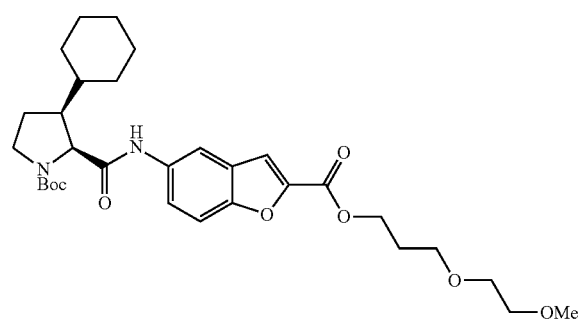

The same procedure as described in Reference Example 150 was carried out to obtain the title compound (187.7 mg, 59%) from the compound of Reference Example 119-1 (253 mg, 0.554 mmol) and 3-(2-methoxyethoxy)propyl bromide (163.8 mg, 0.831 mmol).

MS (ESI+) 573 (M+1, 20%)

Reference Example 159-2

3-(2-Methoxyethoxy)propyl 5-{[(3S)-3-cyclohexyl-L-prolyl]amino}-1-benzofuran-2-carboxylate hydrochloride

[Formula 562]

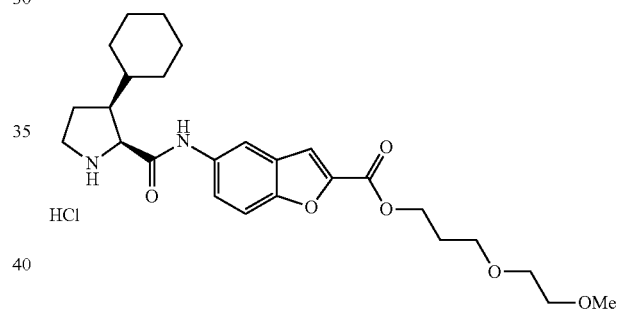

The same procedure as described in Reference Example 1-2 was carried out to obtain the title compound (170 mg, 100%) from the compound of Reference Example 159-1 (187.7 mg, 0.328 mmol).

MS (ESI+) 473 (M+1, 100%)

Reference Example 160

5-({(3S)-1-[(trans-4-{[(tert-Butoxycarbonyl)amino]methyl}cyclohexyl)carbonyl]-3-cyclohexyl-L-prolyl}amino)-1-benzofuran-2-carboxylic acid

[Formula 563]

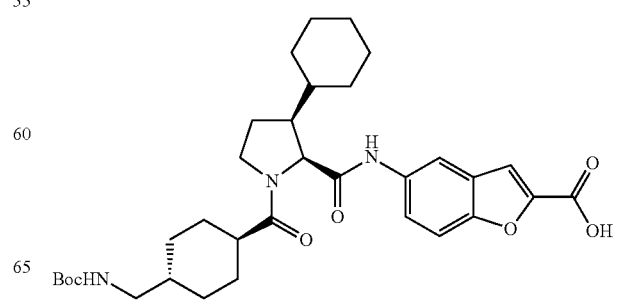

The same procedure as described in Reference Example 3 was carried out to obtain the title compound (48.7 mg, 100%) from the compound of Reference Example 159 (58.3 mg, 0.0819 mmol).

MS (ESI+) 596 (M+1, 100%)

Reference Example 161

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-1H-pyrrolo[3,2-b]pyridine-2-carboxylic acid

[Formula 564]

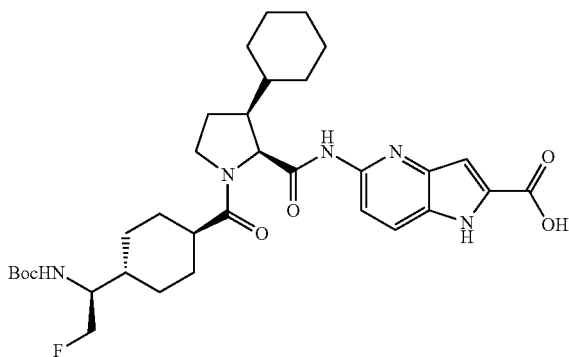

The same procedure as described in Reference Example 3 was carried out to obtain the title compound (40.8 mg, 63%) from the compound of Reference Example 161-5 (67.8 mg, 0.103 mmol).

MS (ESI+) 628 (M+1, 100%)

Reference Example 161-1 di-tert-Butyl (6-methyl-5-nitropyridin-2-yl)imidodicarbonate

[Formula 565]

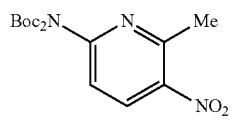

To a solution of 2-amino-6-methyl-5-nitropyridine (3.02 g, 19.72 mmol) in dichloromethane (25 ml), N,N-dimethylaminopyridine (43.4 mg, 0.355 mmol) and di-tert-butyl dicarbonate (8.61 g, 39.44 mmol) were added, and the mixture was stirred at room temperature for 16 hours. Water was added to the reaction solution, followed by extraction with dichloromethane. The organic layer was washed with water twice and with a saturated saline solution, then dried over sodium sulfate and filtered, and the filtrate was concentrated under reduced pressure to obtain the title compound (7.93 g, 100%).

$^1$H-NMR (DMSO-$d_6$, 300 MHz) δ 8.51 (d, J=9.0 Hz, 1H), 8.31 (s, 1H), 7.63 (d, J=9.0 Hz, 1H), 2.69 (s, 3H), 1.45 (s, 18H).

Reference Example 161-2

Ethyl 3-{6-[(tert-butoxycarbonyl)amino]-3-nitropyridin-2-yl}-2-oxopropanoate

[Formula 566]

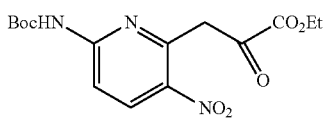

To a solution of the compound of Reference Example 161-1 (6.97 g, 19.72 mmol) in ethanol (20 ml), sodium ethoxide (a 20% solution in ethanol, 14.09 g, 41.4 mmol) was added, and the mixture was stirred at room temperature for 4 days. Water was added to the reaction solution in an ice bath, followed by extraction with ethyl acetate. The organic layer was washed with water and a saturated saline solution, then dried over sodium sulfate and filtered, and the filtrate was concentrated under reduced pressure. The obtained residue was purified by silica gel column chromatography to obtain the title compound (3.18 g, 46%).

MS (ESI+) 354 (M+I, 100%)

Reference Example 161-3

Ethyl 5-amino-1H-pyrrolo[3,2-b]pyridine-2-carboxylate

[Formula 567]

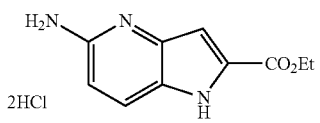

Reduced iron (288 mg, 5.16 mmol) was added to acetic acid (4 ml), and the mixture was stirred at 80° C. for 20 minutes. To this solution, a solution of the compound of Reference Example 161-2 (227.9 mg, 0.645 mmol) in acetic acid (2 ml) and ethanol (5 ml) was added dropwise, and the mixture was stirred at 80° C. for 1 hour. The reaction solution was allowed to cool, then filtered through Celite, and then the filtrate was concentrated under reduced pressure. A saturated aqueous solution of sodium bicarbonate was added to the obtained residue, followed by extraction with ethyl acetate. The organic layer was washed with a saturated aqueous solution of sodium bicarbonate and a saturated saline solution, then dried over sodium sulfate and filtered, and the filtrate was concentrated under reduced pressure. A solution of 4 mol/L hydrochloric acid-1,4-dioxane (5 mL) was added to the obtained residue, and the mixture was stirred at room temperature for 1 hour. Toluene was added to the reaction solution for concentration under reduced pressure to obtain the title compound (104.5 mg, 58%).

MS (ESI+) 306 (M+I, 100%)

Reference Example 161-4

Ethyl 5-{[(3S)-1-(tert-butoxycarbonyl)-3-cyclohexyl-L-prolyl]amino}-1H-pyrrolo[3,2-b]pyridine-2-carboxylate

[Formula 568]

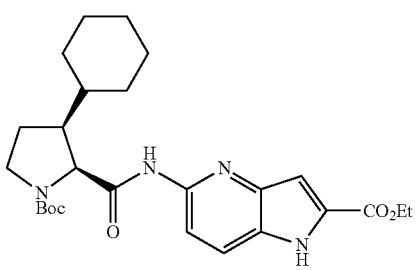

To a solution of the compound of Reference Example 11-1 (100.2 mg, 0.337 mmol) and the compound of Reference Example 161-3 (103.1 mg, 0.371 mmol) in dichloromethane (3 ml), triethylamine (259 µL, 1.69 mmol) and CIP (141 mg, 0.51 mmol) were added, and the mixture was stirred at room temperature for 1 hour. A saturated aqueous solution of ammonium chloride was added to the reaction mixture, followed by extraction with ethyl acetate. The organic layer was washed with a saturated saline solution, then dried over sodium sulfate and filtered, and the filtrate was concentrated under reduced pressure. The obtained residue was purified by silica gel column chromatography to obtain the title compound (86.1 mg, 53%).

MS (ESI+) 485 (M+1, 100%)

Reference Example 161-5

Ethyl 5-{[(3S)-3-cyclohexyl-L-prolyl]amino}-1H-pyrrolo[3,2-b]pyridine-2-carboxylate dihydrochloride

[Formula 569]

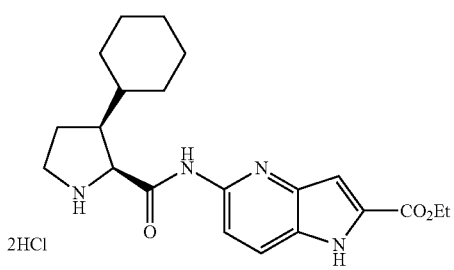

The same procedure as described in Reference Example 1-2 was carried out to obtain the title compound (82.0 mg, 100%) from the compound of Reference Example 161-4 (86.1 mg, 0.178 mmol).

MS (ESI+) 385 (M+1, 100%)

Reference Example 161-6

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-pyrrolo[3,2-b]pyridine-2-carboxylate

[Formula 570]

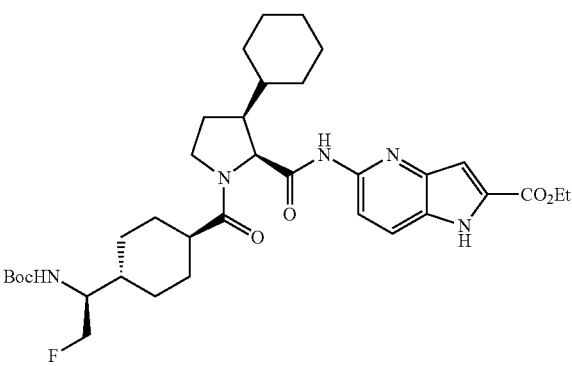

The same procedure as described in Reference Example 1 was carried out to obtain the title compound (67.8 mg, 58%) from the compound of Reference Example 161-5 (82.0 mg, 0.178 mmol) and the compound of Reference Example 53-3 (56.5 mg, 0.195 mmol).

MS (ESI+) 656 (M+1, 100%)

Reference Example 162

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-1H-pyrrolo[2,3-c]pyridine-2-carboxylic acid

[Formula 571]

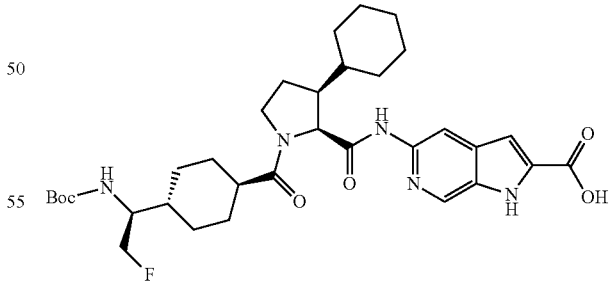

The same procedure as described in Reference Example 3 was carried out to obtain the title compound (80.0 mg, quant.) from the compound of Reference Example 162-5 (83.2 mg, 0.127 mmol).

MS (ESI+) 628 (M+1, 100%)

Reference Example 162-1

4-Methyl-5-nitro-2-(N,N'-di-tert-butyloxycarbonylamino)pyridine

[Formula 572]

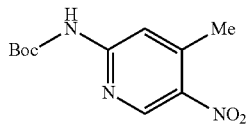

To a solution of 2-amino-4-methyl-5-nitropyridine (345 mg, 2.25 mmol) in dichloromethane (6.9 mL), a solution of DMAP (5.2 mg, 0.04 mmol) and Boc2O (983 mg, 4.51 mmol) in dichloromethane (3.5 mL) was added, and the mixture was stirred at room temperature for 3 hours. The reaction solution was washed with water three times and dried, and the solution was concentrated to obtain the title compound (892 mg). The title compound was used in the next reaction without purification.

$^1$H-NMR (CDCl$_3$): δ 9.03 (s, 1H), 7.55 (s, 1H), 2.68 (s, 3H), 1.52 (s, 9H).

Reference Example 162-2

Ethyl 3-(6-tert-butoxycarbonylamino-3-nitropyridin-4-yl)-2-oxopropionate

[Formula 573]

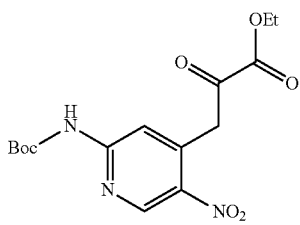

The same procedure as described in Reference Example 161-2 was carried out to obtain the title compound (209 mg, 26%) from the compound of Reference Example 162-2 (892 mg)

$^1$H-NMR (CDCl$_3$): δ 9.13 (s, 1H), 8.03 (s, 1H), 4.60 (s, 2H), 4.42 (q, 2H, J=7.2 Hz), 2.68 (s, 3H), 1.41 (t, 3H, J=7.2 Hz).

Reference Example 162-3

Ethyl 5-tert-butoxycarbonylamino-1H-pyrrolo[2,3-c]pyridine-2-carboxylate

[Formula 574]

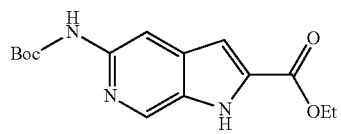

The same procedure as described in Reference Example 161-3 was carried out to obtain the title compound (184 mg, quant.) from the compound of Reference Example 162-2 (205 mg, 0.58 mmol).

MS (ESI+) 306 (M+1, 100%)

Reference Example 162-4

Methyl 5-{[(3S)-1-(tert-butoxycarbonyl)-3-cyclohexyl-L-prolyl]amino}-1H-pyrrolo[2,3-c]pyridine-2-carboxylate

[Formula 575]

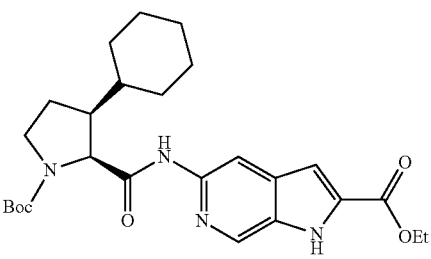

The same procedures as described in Reference Example 1-2 and Reference Example 161-4 were carried out in this order to obtain the title compound (124 mg, 44%) from the compound of Reference Example 162-3 (184 mg, 0.60 mmol).

MS (ESI+) 486 (M+2, 100%)

Reference Example 162-5

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1H-pyrrolo[2,3-c]pyridine-2-carboxylate

[Formula 576]

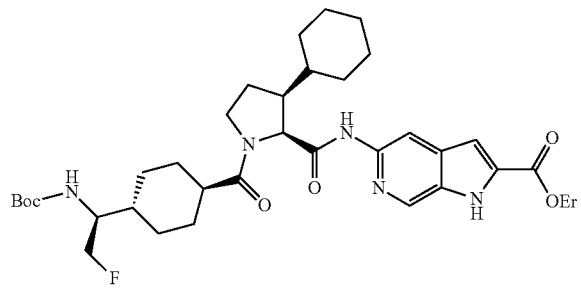

The same procedures as described in Reference Example 161-5 and Reference Example 161-6 were carried out in this order to obtain the title compound (83.2 mg, 50%) from the compound of Reference Example 162-4 (122 mg, 0.252 mmol).

MS (ESI+) 656 (M+1, 100%)

Reference Example 163

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-chloro-1H-indole-2-carboxylic acid

[Formula 577]

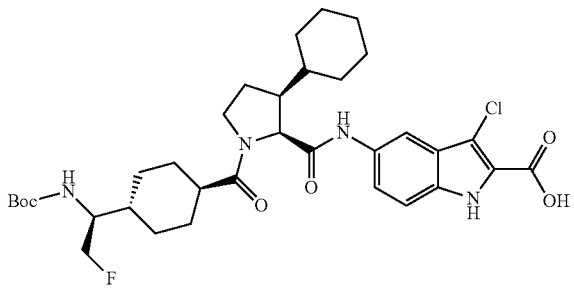

NCS (61.4 mg, 0.460 mmol) was added to a solution of the compound of Reference Example 81-1 (298 mg, 0.455 mmol) in DMF (9 mL), and the mixture was heated with stirring at 60° C. for 7 days. Water was added thereto, followed by extraction with ethyl acetate, and then the extract was washed with water and a saturated saline solution. The reaction solution was dried over sodium sulfate and then purified by silica gel chromatography (ethyl acetate/hexane-based chromatography). The same procedure as described in Reference Example 3 was carried out to provide the title compound (246 mg, 82%) from the obtained solid.

MS (ESI+) 661 (M+1, 100%)

Reference Example 164

Methyl 6-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1,3-benzoxazole-2-carboxylate

[Formula 578]

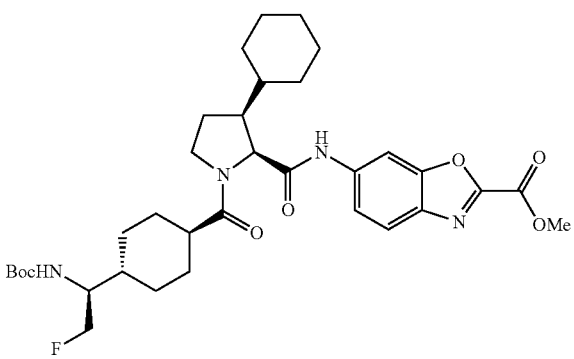

The same procedure as described in Reference Example 1 was carried out to obtain the title compound (76.7 mg, 98%) from the compound of Reference Example 164-2 (49.8 mg, 0.122 mmol) and the compound of Reference Example 53-3 (38.9 mg, 0.134 mmol).

MS (ESI+) 643 (M+1, 48%)

Reference Example 164-1

Methyl 6-{[(3S)-1-(tert-butoxycarbonyl)-3-cyclohexyl-L-prolyl]amino}-1,3-benzoxazole-2-carboxylate

[Formula 579]

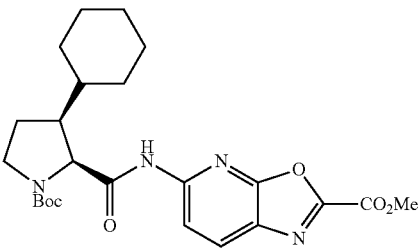

The same procedure as described in Reference Example 161-3 was carried out to obtain the title compound (57.6 mg, 28%) from the compound of Reference Example 11-1 (131.6 mg, 0.443 mmol) and commercially available 6-aminobenzoxazole-2-carboxylic acid ethyl ester (85.0 mg, 0.443 mmol).

MS (ESI+) 472 (M+1, 100%)

Reference Example 164-2

Methyl 6-{[(3S)-3-cyclohexyl-L-prolyl]amino}-1,3-benzoxazole-2-carboxylate hydrochloride

[Formula 580]

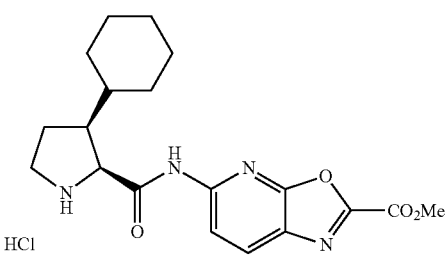

The same procedure as described in Reference Example 1-2 was carried out to obtain the title compound (49.8 mg, 100%) from the compound of Reference Example 164-1 (57.6 mg, 0.122 mmol).

MS (ESI+) 372 (M+1, 100%)

Reference Example 165

5-({(3R)-1-[(trans-4-{(1S)-1-[(tert-Butoxycarbonyl)amino]-2-fluoroethyl}cyclohexyl)carbonyl]-3-phenyl-L-prolyl}amino)-3-chloro-1H-indole-2-carboxylic acid

[Formula 581]

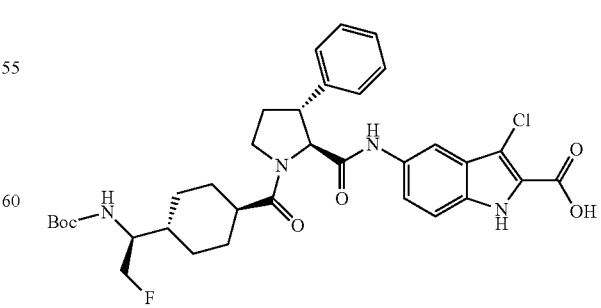

To a solution of the compound of Reference Example 140 (3.05 g, 4.91 mmol) in DMF (24.6 mL), potassium carbonate (849 mg, 6.14 mmol) and methyl iodide (321 μL, 5.16 mmol) were added, and the mixture was stirred at room temperature overnight. Water was added, followed by extraction with ethyl acetate, then the extract was washed with water and a saturated saline solution. The resultant was dried over sodium sulfate and purified by silica gel chromatography (ethyl acetate/hexane). The same procedure as described in Reference Example 163 was carried out to provide the title compound (644 mg, 20%) from the obtained solid.

MS (ESI+) 655 (M+1, 100%)

Reference Example 166

5-{[(3R)-1-[(trans-4-{(1S)-1-[(tert-Butoxycarbonyl)amino]-2-fluoroethyl}cyclohexyl)carbonyl]-3-(cis-4-methoxycyclohexyl)-D-prolyl]amino}-1-benzofuran-2-carboxylic acid

[Formula 582]

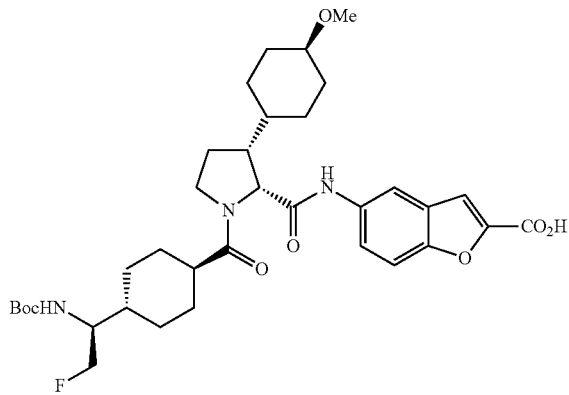

The same procedure as described in Reference Example 3 was carried out to obtain the title compound (125.2 mg, 86%) from the compound of Reference Example 166-11 (151.8 mg, 0.221 mmol).

MS (ESI+) 658 (M+1, 86%)

Reference Example 166-1 tert-Butyl (2R,3R)-2-(hydroxymethyl)-3-(4-methoxyphenyl)pyrrolidine-1-carboxylate

[Formula 583]

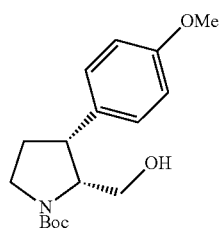

To a solution of trans-4-methoxy cinnamaldehyde (16.19 g, 99.82 mmol) in methanol (85 mL), (2R)-2-[diphenyl[(trimethylsilyl)oxy]methyl]pyrrolidine (1.61 g, 4.99 mmol), nitroethanol (13.63 g, 149.7 mol), and benzoic acid (1.21 g, 9.98 mmol) were added, and the mixture was stirred at 40° C. for 10 hours under nitrogen atmosphere. The reaction solution was allowed to cool to room temperature, and the precipitated solid was filtered out and washed with ethyl acetate and hexane to obtain (4R,5R)-4-(2-methoxyphenyl)-5-nitrotetrahydro-2H-pyran-2-ol (12.86 g, 51%).

To a solution of obtained (4R,5R)-4-(2-methoxyphenyl)-5-nitrotetrahydro-2H-pyran-2-ol (12.86 g, 50.78 mmol) in ethanol (200 ml) and water (100 ml), zinc (66.41 g, 1.02 mol) and ammonium chloride (54.32 g, 1.02 mol) were added, and the mixture was stirred at 50° C. for 1 hour. The reaction solution was allowed to cool, a saturated aqueous solution of sodium bicarbonate was added, and the mixture was stirred for 10 minutes, and then filtered through Celite. Ethyl acetate was added to the filtrate for separation, then di-tert-butyl dicarbonate (16.62 g, 76.17 mmol) was added to the aqueous layer, and the mixture was stirred at room temperature overnight. Ethyl acetate was added to the reaction solution for separation, then the obtained organic layer was washed with a saturated saline solution, dried over sodium sulfate and filtered, and then the filtrate was concentrated under reduced pressure. Hexane was added to the obtained residue, and the precipitated solid was filtered out to obtain the title compound (8.68 g, 56%).

MS (ESI+) 308 (M+1, 28%)

Reference Example 166-2 tert-Butyl (2R,3R)-2-(hydroxymethyl)-3-(4-hydroxyphenyl)pyrrolidine-1-carboxylate

[Formula 584]

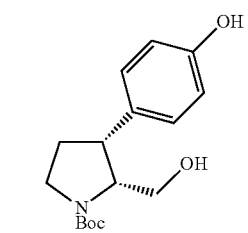

To a solution of the compound of Reference Example 166-1 (1.80 g, 5.86 mmol) in dichloromethane (10 mL), boron tribromide (a 1.0 mol/L solution in dichloromethane, 29.3 mL) was added at 0° C., and the mixture was stirred at room temperature overnight. A saturated aqueous solution of sodium bicarbonate was added dropwise to the reaction solution at 0° C., and ethyl acetate was added for separation. di-tert-Butyl dicarbonate (1.92 g, 8.79 mmol) was added to the aqueous layer, and the mixture was stirred at room temperature for 4 hours. The reaction solution was extracted with chloroform three times, the organic layer was dried over sodium sulfate and filtered, and then the filtrate was concentrated under reduced pressure. The obtained residue was purified by silica gel column chromatography to obtain the title compound (1.23 g, 72%).

MS (ESI+) 294 (M+1, 24%)

Reference Example 166-3

A Diastereo Mixture of A and B

A: tert-Butyl (2R,3R)-3-(cis-4-hydroxycyclohexyl)-2-(hydroxymethyl)pyrrolidine-1-carboxylate B: tert-Butyl (2R,3R)-3-(trans-4-hydroxycyclohexyl)-2-(hydroxymethyl)pyrrolidine-1-carboxylate

[Formula 585]

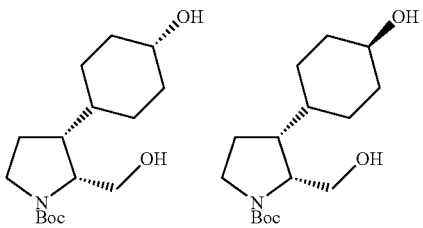

To a solution of the compound of Reference Example 166-2 (1.23 g, 4.20 mmol) in acetic acid (30 mL), platinum oxide (250 mg) was added, and the mixture was stirred for 4 hours under a pressure of 0.4 Mpa and under hydrogen atmosphere. The reaction solution was filtered through Celite, then toluene was added, and the mixture was concentrated under reduced pressure. The obtained residue was purified by silica gel column chromatography to obtain the title compound (614.4 mg, 49%).

MS (ESI+) 300 (M+1, 28%)

Reference Example 166-4

(3R)-1-(tert-Butoxycarbonyl)-3-(4-oxocyclohexyl)-D-proline

[Formula 586]

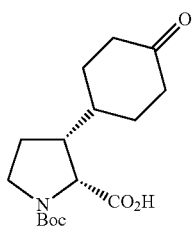

To a solution of the compound of Reference Example 166-3 (614.6 mg, 2.05 mmol) in dimethylsulfoxide (8 ml), triethylamine (4.1 mL, 14.4 mmol) and a pyridine-sulfur trioxide complex (48.8%, 2.61 g, 8.00 mmol) were added, and the mixture was stirred at room temperature for 1 hour. Water was added to the reaction solution, followed by extraction with ethyl acetate. The organic layer was washed with a saturated aqueous solution of ammonium chloride three times and with a saturated saline solution, then dried over sodium sulfate and filtered, and the filtrate was concentrated under reduced pressure.

The obtained residue was dissolved in a mixed solvent of tert-butanol and distilled water (3:1, 8 mL), then sodium dihydrogenphosphate dihydrate (959 mg, 6.15 mmol), 2-methyl-2-butene (1.14 mL, 10.3 mmol), and sodium chlorite (469 mg, 4.10 mmol) were added, and the mixture was stirred for 1 hour. The reaction solution was cooled in an ice bath then a saturated aqueous solution of sodium thiosulfate and a 5% aqueous solution of potassium hydrogensulfate were added, followed by extraction with chloroform three times. The organic layers were combined, then a 1 mol/L aqueous solution of sodium hydroxide was added for separation. A 5% aqueous solution of potassium hydrogensulfate was added to the aqueous layer for adjustment of pH<4, followed by extraction with chloroform three times. The combined organic layer was washed with a saturated saline solution, then dried over sodium sulfate and filtered, and the filtrate was concentrated under reduced pressure to obtain the title compound (550.1 mg, 86%).

MS (ESI+) 312 (M+1, 0.95%)

Reference Example 166-5

1-tert-Butyl 2-methyl (2R,3R)-3-(4-oxocyclohexyl)pyrrolidine-1,2-dicarboxylate

[Formula 587]

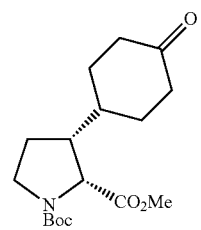

To a solution of the compound of Reference Example 166-4 (550.1 mg, 1.77 mmol) in N,N-dimethylformamide (5 mL), potassium carbonate (488 mg, 3.53 mmol) and methyl iodide (165 µL, 2.65 mmol) were added, and the mixture was stirred at room temperature for 1 hour. The reaction solution was cooled in an ice bath, then a saturated aqueous solution of ammonium chloride was added, followed by extraction with ethyl acetate. The organic layer was washed with a saturated aqueous solution of ammonium chloride twice and with a saturated saline solution, then dried over sodium sulfate and filtered, and the filtrate was concentrated under reduced pressure. The obtained residue was purified by silica gel column chromatography to obtain the title compound (408.8 mg, 71%).

MS (ESI+) 325 (M+1, 0.89%)

Reference Example 166-6

1-tert-Butyl 2-methyl (2R,3R)-3-(trans-4-hydroxycyclohexyl)pyrrolidine-1,2-dicarboxylate

[Formula 588]

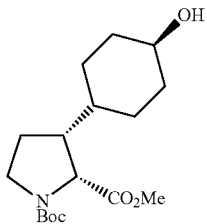

To a solution of the compound of Reference Example 166-5 (408.8 mg, 1.25 mmol) in tetrahydrofuran (5 mL), sodium borohydride (142 mg, 3.75 mmol) was added in an ice bath, and the mixture was stirred at room temperature overnight. The reaction solution was cooled in an ice bath, then a saturated aqueous solution of ammonium chloride was added, followed by extraction with ethyl acetate three times. The combined organic layer was washed with a saturated saline solution, then dried over sodium sulfate and filtered, and the filtrate was concentrated under reduced pressure. The obtained residue was purified by silica gel column chromatography to obtain the title compound (284.9 mg, 70%).

MS (ESI+) 328 (M+1, 1.5%)

Reference Example 166-7

1-tert-Butyl 2-methyl (2R,3R)-3-(trans-4-methoxy-cyclohexyl)pyrrolidine-1,2-dicarboxylate

[Formula 589]

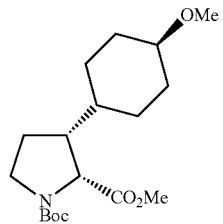

To a solution of the compound of Reference Example 166-6 (284.9 mg, 0.87 mmol) in N,N-dimethylformamide (4 mL), sodium hydride (60% in oil, 87 mg, 2.18 mmol) was added in an ice bath, and the mixture was stirred for 10 minutes. Methyl iodide (542 μL, 8.70 mmol) was added to the reaction solution at 0° C., and the mixture was stirred at room temperature for 2 hours. The reaction solution was cooled in an ice bath, then a saturated aqueous solution of ammonium chloride was added, followed by extraction with ethyl acetate. The organic layer was washed with a saturated aqueous solution of ammonium chloride and a saturated saline solution, then dried over sodium sulfate and filtered, and the filtrate was concentrated under reduced pressure. The obtained residue was purified by silica gel column chromatography to obtain the title compound (222 mg, 75%).

MS (ESI+) 342 (M+1, 0.8%)

Reference Example 166-8

(3R)-1-(tert-Butoxycarbonyl)-3-(trans-4-methoxycyclohexyl)-D-proline

[Formula 590]

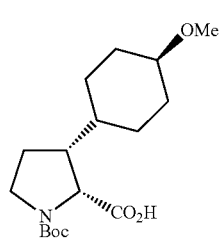

To a solution of the compound of Reference Example 166-7 (222 mg, 0.65 mmol) in tetrahydrofuran (1.5 mL) and methanol (1.5 mL), 1 N sodium hydroxide (3 mL) was added, and the mixture was stirred at 100° C. for 10 hours. After the reaction solution was allowed to cool, a 5% aqueous solution of potassium hydrogensulfate was added, followed by extraction with chloroform three times. The combined organic layer was dried over sodium sulfate and filtered, and the filtrate was concentrated under reduced pressure to obtain the title compound (213 mg, 95%).

MS (ESI+) 328 (M+1, 0.75%)

Reference Example 166-9 tert-Butyl (2R,3R)-2-{[2-(ethoxycarbonyl)-1-benzofuran-5-yl]carbamoyl}-3-(trans-4-methoxycyclohexyl)pyrrolidine-1-carboxylate

[Formula 591]

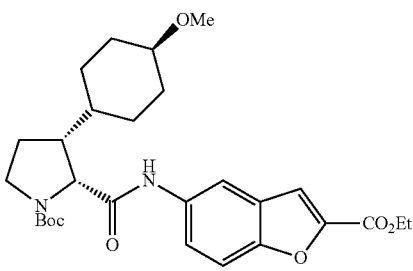

The same procedure as described in Reference Example 161-3 was carried out to obtain the title compound (216.4 mg, 68%) from the compound of Reference Example 166-8 (203 mg, 0.62 mmol) and ethyl 5-amino-1-benzofuran-2-carboxylate (127.2 mg, 0.62 mmol).

MS (ESI+) 515 (M+1, 41%)

Reference Example 166-10

Ethyl 5-{[(3R)-3-(trans-4-methoxycyclohexyl)-D-prolyl]amino}-1-benzofuran-2-carboxylate hydrochloride

[Formula 592]

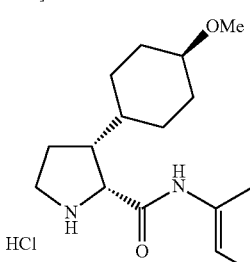

The same procedure as described in Reference Example 1-2 was carried out to obtain the title compound (190.0 mg 100%) from the compound of Reference Example 166-9 (216.4 mg, 0.421 mmol).

MS (ESI+) 415 (M+1, 100%)

Reference Example 166-11

Ethyl 5-{[(3R)-1-[(trans-4-{(1S)-1-[(tert-butoxycarbonyl)amino]-2-fluoroethyl}cyclohexyl)carbonyl]-3-(trans-4-methoxycyclohexyl)-D-prolyl]amino}-1-benzofuran-2-carboxylate

[Formula 593]

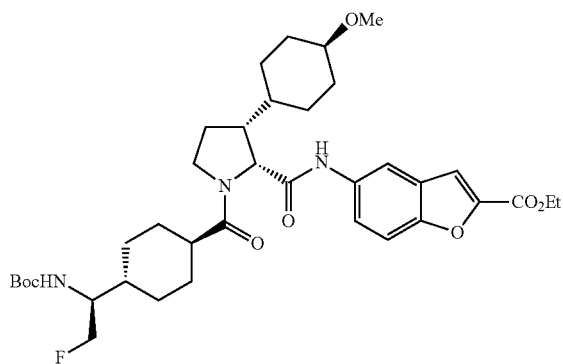

The same procedure as described in Reference Example 1 was carried out to obtain the title compound (151.8 mg, 53%) from the compound of Reference Example 166-10 (190 mg, 0.421 mmol) and the compound of Reference Example 53-3 (134 mg, 0.463 mmol).

MS (ESI+) 686 (M+1, 100%)

Reference Example 167

3-Methoxypropyl 5-{[(3R)-1-[(trans-4-{(1S)-1-[(tert-butoxycarbonyl)amino]-2-fluoroethyl}cyclohexyl)carbonyl]-3-(trans-4-methoxycyclohexyl)-D-prolyl]amino}-1-benzofuran-2-carboxylate

[Formula 594]

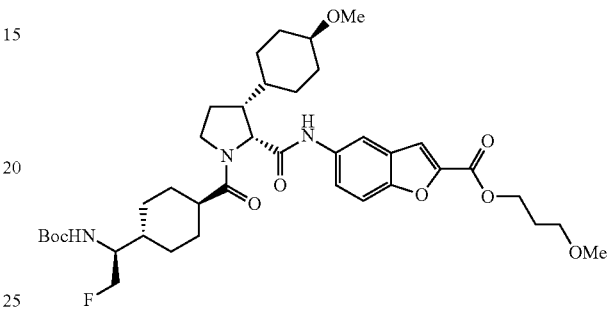

The same procedure as described in Reference Example 150 was carried out to obtain the title compound (101.7 mg, 100%) from the compound of Reference Example 166 (74.2 mg, 0.113 mmol) and 1-bromo-3-methoxypropane (13.9 μL, 0.124 mmol).

MS (ESI+) 730 (M+1, 55%)

Reference Example 168

3-(2-Methoxyethoxyl)propyl 5-{[(3R)-1-[(trans-4-{(1S)-1-[(tert-butoxycarbonyl)amino]-2-fluoroethyl}cyclohexyl)carbonyl]-3-(trans-4-methoxycyclohexyl)-D-prolyl]amino}-1-benzofuran-2-carboxylate

[Formula 595]

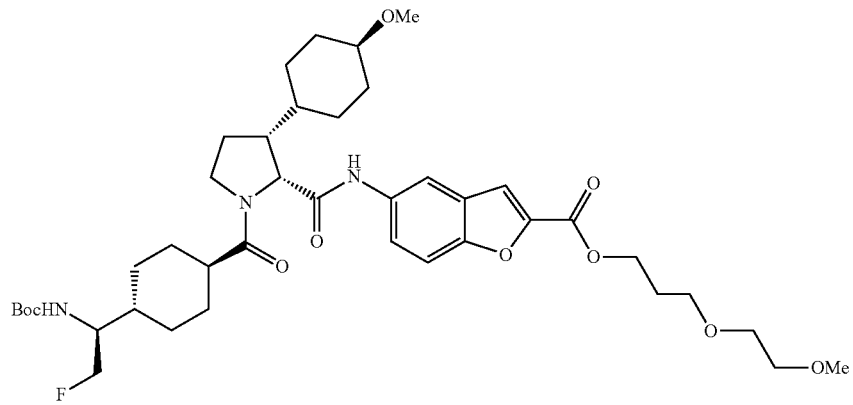

The same procedure as described in Reference Example 150 was carried out to obtain the title compound (59.6 mg, 68%) from the compound of Reference Example 166 (74.1 mg, 0.113 mmol) and 3-(2-methoxyethoxyl)propyl bromide (28.9 mg, 0.147 mmol).

MS (ESI+) 774 (M+1, 12%)

Reference Example 169

Ethyl 5-{[(3R)-1-[(trans-4-{(1S)-1-[(tert-butoxycarbonyl)amino]-2-fluoroethyl}cyclohexyl)carbonyl]-3-(trans-4-methoxycyclohexyl)-D-prolyl]amino}-1-benzofuran-2-carboxylate

[Formula 596]

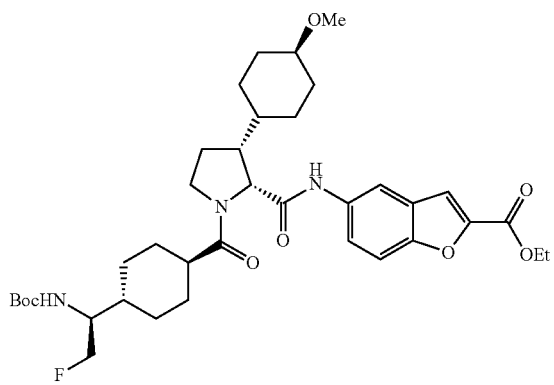

The same procedure as described in Reference Example 150 was carried out to obtain the title compound (70.9 mg, 96%) from the compound of Reference Example 166 (71.3 mg, 0.108 mmol) and ethyl iodide (11.1 μL, 0.162 mmol).

MS (ESI+) 658 (M+1, 100%)

Reference Example 170

(2R)-2-Methoxypropyl 5-{[(3R)-1-[(trans-4-{(1S)-1-[(tert-butoxycarbonyl)amino]-2-fluoroethyl}cyclohexyl)carbonyl]-3-(trans-methoxycyclohexyl)-D-prolyl]amino}-1-benzofuran-2-carboxylate The same procedure as described in Reference Example 148 was carried out to obtain the title compound (82.8 mg, 98%) from the compound of Reference Example 170-1 (149 mg, 0.35 mmol) and the compound of Reference Example 166 (76.0 mg, 0.115 mmol).

MS (ESI+) 730 (M+1, 39%)

Reference Example 170-1

(2R)-2-Methoxypropan-1-ol

[Formula 598]

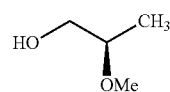

By using (R)-(−)-1-benzyloxy-2-propanol (500 mg, 3.00 mmol), the same procedures as described in Reference Examples 146-1 and 167-2 were carried out to obtain the title compound (169 mg, 63%).

$^1$H NMR (CDCl$_3$, 300 MHz) δ 3.52 (m, 1H), 3.39 (m, 2H), 3.32 (s, 3H), 1.05 (d, J=6.0 Hz, 3H).

[Formula 597]

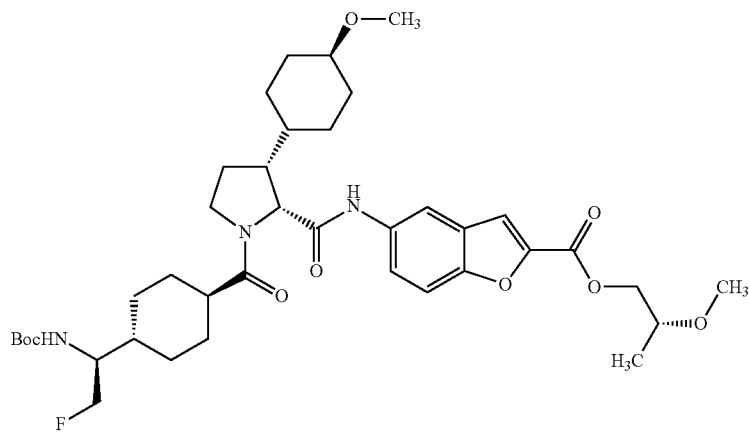

Reference Example 171

(2S)-2-Methoxypropyl 5-{[(3R)-1-[(trans-4-{(1S)-1-[(tert-butoxycarbonyl)amino]-2-fluoroethyl}cyclohexyl)carbonyl]-3-(trans-methoxy-cyclohexyl)-D-prolyl]amino}-1-benzofuran-2-carboxylate

[Formula 599]

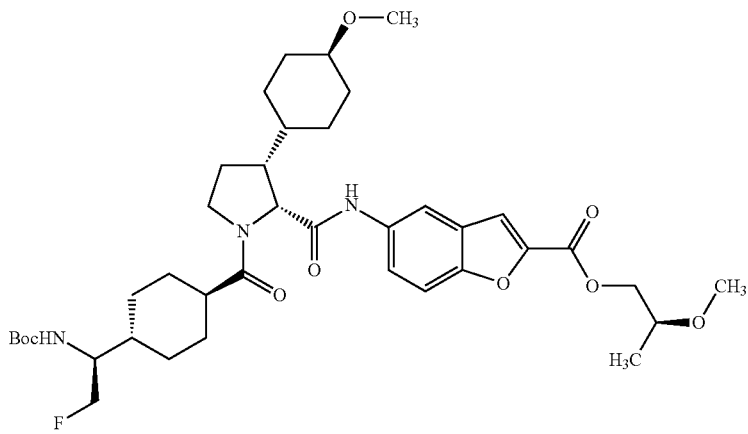

The same procedure as described in Reference Example 148 was carried out to obtain the title compound (47.6 mg, 57%) from the compound of Reference Example 170-1 (75.1 mg, 0.1145 mmol) and the compound of Reference Example 146-1 (103 mg, 1.14 mmol).

MS (ESI+) 730 (M+1, 35%)

Reference Example 172

5-{[(3R)-1-[(trans-4-{(1S)-1-[(tert-Butoxycarbonyl)amino]-2-fluoroethyl}cyclohexyl)carbonyl]-3-(4-methoxycyclohexyl)-D-prolyl]amino}-1H-indole-2-carboxylic acid

[Formula 600]

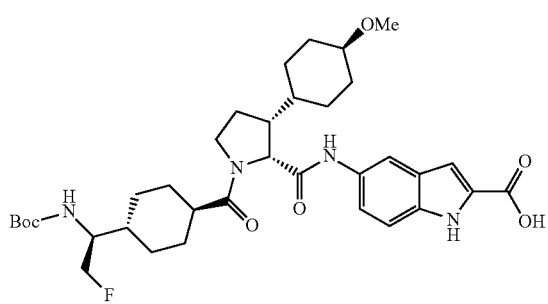

The same procedure as described in Reference Example 3 was carried out to obtain the title compound from the compound of Reference Example 172-2 (14.3 mg, 0.021 mmol).

MS (ESI+) 657 (M+1, 100%)

Reference Example 172-1

Ethyl 5-{[(3R)-1-(tert-butoxycarbonyl)-3-(4-methoxycyclohexyl)-D-prolyl]amino}-1H-indole-2-carboxylate

[Formula 601]

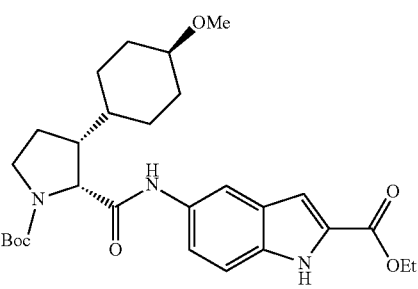

The same procedure as described in Reference Example 1 was carried out to obtain the title compound (29.7 mg, 73%) from the compound of Reference Example 2-1 (16.2 mg, 0.079 mmol) and the compound of Reference Example 166-8 (26 mg, 0.079 mmol).

MS (ESI+) 514 (M+1, 60%)

Reference Example 172-2

Ethyl 5-{[(3R)-1-[(trans-4-{(1S)-1-[(tert-butoxycarbonyl)amino]-2-fluoroethyl}cyclohexyl)carbonyl]-3-(4-methoxycyclohexyl)-D-prolyl]amino}-1H-indole-2-carboxylate

[Formula 602]

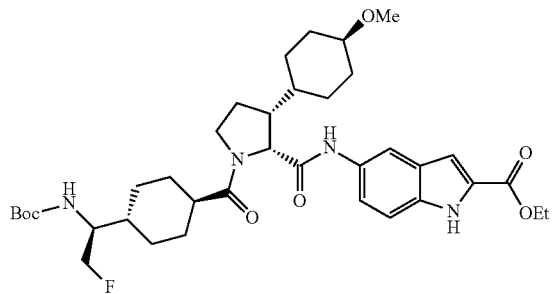

The same procedures as described in Reference Example 1-2 and Reference Example 1 were carried out in this order to obtain the title compound (14.3 mg, 36%) from the compound of Reference Example 172-1 (29.6 mg, 0.058 mmol).

MS (ESI+) 685 (M+1, 100%)

Reference Example 173

Ethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 603]

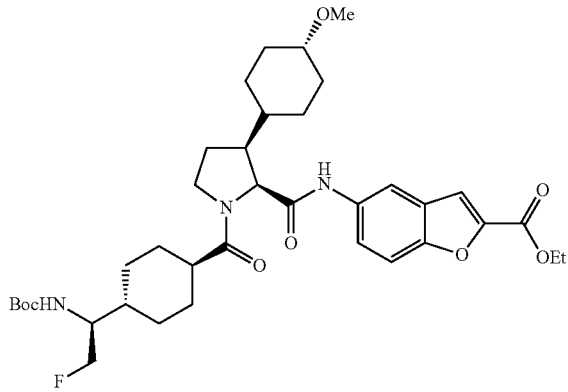

The same procedure as described in Reference Example 1 was carried out to obtain the title compound (440.9 mg, 79%) from the compound of k2 (366 mg, 0.812 mmol) and the compound of Reference Example 173-3 (282 mg, 0.974 mmol).

MS (ESI+) 686 (M+1, 100%)

Reference Example 173-1

Methyl trans-4-(fluoroacetyl)cyclohexanecarboxylate

[Formula 604]

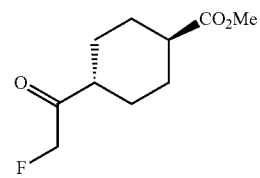

To a solution of the compound of Reference Example 124-1 (7.00 g, 24.62 mmol) in acetonitrile (50 mL), selectfluor (13.08 g, 36.92 mmol) was added at room temperature, and the mixture was stirred at 40° C. for 4 hours and then at room temperature for 13 hours. A saturated aqueous solution of sodium thiosulfate was added to the reaction solution, followed by extraction with ethyl acetate. The organic layer was washed with a saturated aqueous solution of sodium bicarbonate, a saturated aqueous solution of ammonium chloride, and a saturated saline solution, then dried over sodium sulfate and filtered, and the filtrate was concentrated under reduced pressure to obtain a crude product (6.78 g).

To a solution of the obtained crude product (6.64 g, 21.96 mmol) in chloroform (30 mL), trifluoroacetic acid (15.02 g, 131.7 mmol) was added at room temperature, and the mixture was stirred at 40° C. for 4 hours. The reaction solution was concentrated under reduced pressure, then a saturated aqueous solution of sodium bicarbonate was added to the residue, followed by extraction with chloroform. The organic layer was dried over sodium sulfate and filtered, and then the filtrate was concentrated under reduced pressure. The obtained residue was purified by silica gel column chromatography to obtain the title compound (2.92 g, 59%).

$^1$H NMR (CDCl$_3$, 300 MHz) δ 4.96 (s, 1H), 4.80 (s, 1H), 3.67 (s, 3H), 2.69-2.61 (m, 1H), 2.33-2.24 (m, 1H), 2.11-2.07 (m, 2H), 1.99-1.95 (m, 2H), 1.58-1.34 (m, 4H).

Reference Example 173-2 trans-4-{(1S)-1-[(tert-Butoxycarbonyl)amino]-2-fluoroethyl}cyclohexane carboxylic acid

[Formula 605]

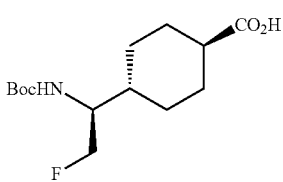

To a solution of the compound of Reference Example 173-1 (599.1 mg, 2.96 mmol) in tetrahydrofuran (5 mL), titanium tetraisopropoxide (2.53 g, 8.90 mmol) and (S)-(−)-2-methyl-2-propane sulfine amide (467 mg, 3.85 mmol) were added, and the mixture was heated to reflux for 8 hours. The reaction solution was allowed to cool, then a saturated aqueous solution of sodium bicarbonate and ethyl acetate were added, then the mixture was stirred at room temperature for 15 minutes, followed by filtration through Celite. After the mixed solution was separated, the organic layer was washed with a saturated aqueous solution of sodium bicarbonate and a saturated saline solution, then dried over sodium sulfate and filtered, and the filtrate was concentrated under reduced pressure to obtain a crude product.

To a solution of the obtained crude product in tetrahydrofuran (3 mL), K-selectride (1.0 mol/L in THF, 3.84 ml, 3.84 mmol) was added dropwise at −78° C., and the mixture was stirred for 1 hour. A saturated aqueous solution of ammonium chloride was added to the reaction solution, then the reaction solution was allowed to cool to room temperature, followed by extraction with ethyl acetate. The organic layer was washed with a saturated aqueous solution of sodium bicarbonate and a saturated saline solution, then dried over sodium sulfate and filtered, and the filtrate was concentrated under reduced pressure.

To a solution of the obtained crude product in methanol (10 ml), 4 mol/L hydrochloric acid-dioxane (10 ml) was added dropwise in an ice bath, and the mixture was stirred for 30 minutes. The reaction solution was concentrated under reduced pressure, then toluene was added, and the mixture was concentrated under reduced pressure twice. Diethyl ether was added to the obtained solid, then the mixture was filtered, the filtrate was washed with diethyl ether and hexane in this order and dried to obtain a crude product.

To a solution of the obtained crude product in tetrahydrofuran (3 ml) and a saturated aqueous solution of sodium bicarbonate (3 ml), di-tert-butyl dicarbonate (434.8 mg, 1.99 mmol) was added, and the mixture was stirred at room temperature for 12 hours. Water was added to the reaction solution, followed by extraction with ethyl acetate. The organic layer was washed with a saturated aqueous solution of ammonium chloride and a saturated saline solution, then dried over sodium sulfate and filtered, and the filtrate was concentrated under reduced pressure. The obtained residue was dissolved in tetrahydrofuran (2 ml) and ethanol (2 ml), and a 10% aqueous solution of sodium hydroxide (2 ml) was added, and the mixture was heated to reflux. After 12 hours, the reaction solution was allowed to cool to room temperature for concentration under reduced pressure. Diethyl ether was added to the residue for separation, then a 5% aqueous solution of potassium hydrogensulfate was added to the aqueous layer for adjustment of pH<5. After extraction with chloroform, the extract was dried over sodium sulfate and filtered, and the filtrate was concentrated under reduced pressure to obtain the title compound (348.0 mg, 41% for 5 steps, 90% ee).

Reference Example 173-3 trans-4-{(1S)-1-[(tert-Butoxycarbonyl)amino]-2-fluoroethyl}cyclohexane carboxylic acid

[Formula 606]

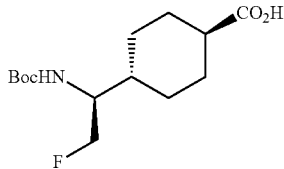

To a solution of the compound of Reference Example 173-2 (25.50 g, 88.13 mmol, 89% ee) in isopropyl acetate (230 g), (R)-(+)-phenylethylamine (10.68 g, 88.13 mmol) was added at 80° C., and the mixture was stirred for 1 hour. The reaction solution was cooled for 1.5 hours to room temperature before undergoing filtration, then the filtrate was washed with hexane/ethyl acetate. After drying, a 5% aqueous solution of potassium hydrogensulfate was added to the obtained solid for adjustment of pH<5, followed by extraction with chloroform. The organic layer was washed with a saturated saline solution, then dried over sodium sulfate and filtered, and the filtrate was concentrated under reduced pressure to obtain the title compound (20.32 g, 80%, 97.3% ee).

Reference Example 173-4 tert-Butyl (2S,3S)-2-(hydroxymethyl)-3-(4-hydroxyphenyl)pyrrolidine-1-carboxylate

[Formula 607]

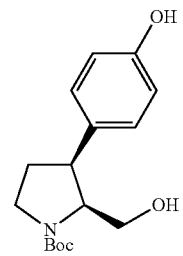

The same procedure as described in Reference Example 166-2 was carried out to obtain the title compound (11.88 g, 82%) from the compound of Reference Example 173-3 (15.16 g, 49.33 mmol).

MS (ESI+) 294 (M+1, 24%)

Reference Example 173-5

A Diastereo Mixture of A and B

A: tert-Butyl (2S,3S)-3-(cis-4-hydroxycyclohexyl)-2-(hydroxymethyl)pyrrolidine-1-carboxylate
B: tert-Butyl (2S,3S)-3-(trans-4-hydroxycyclohexyl)-2-(hydroxymethyl)pyrrolidine-1-carboxylate

[Formula 608]

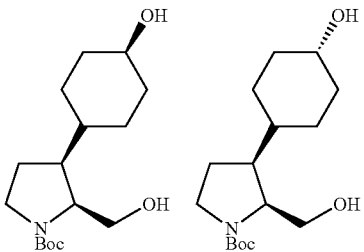

The same procedure as described in Reference Example 166-3 was carried out to obtain the title compound (3.12 g, 26%) from the compound of Reference Example 173-4 (11.88 g, 40.50 mmol).

MS (ESI+) 300 (M+1, 28%)

Reference Example 173-6

(3S)-1-(tert-Butoxycarbonyl)-3-(4-oxocyclohexyl)-L-proline

[Formula 609]

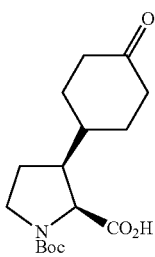

The same procedure as described in Reference Example 166-4 was carried out to obtain the title compound (1.26 g, 37%) from the compound of Reference Example 173-5 (3.12 g, 10.42 mmol).
MS (ESI+) 312 (M+1, 0.95%)

Reference Example 173-7

1-tert-Butyl 2-methyl (2S,3S)-3-(4-oxocyclohexyl)pyrrolidine-1,2-dicarboxylate

[Formula 610]

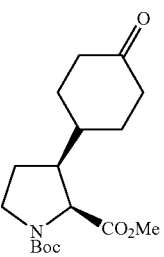

The same procedure as described in Reference Example 166-5 was carried out to obtain the title compound (836.5 mg, 63%) from the compound of Reference Example 173-6 (1.26 g, 4.05 mmol).
MS (ESI+) 325 (M+1, 0.89%)

Reference Example 173-8

1-tert-Butyl 2-methyl (2S,3S)-3-(trans-4-hydroxycyclohexyl)pyrrolidine-1,2-dicarboxylate

[Formula 611]

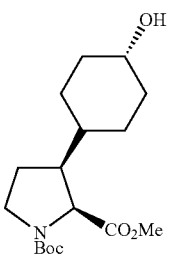

The same procedure as described in Reference Example 166-6 was carried out to obtain the title compound (540.3 mg, 64%) from the compound of Reference Example 173-7 (836.5 mg, 2.57 mmol).
MS (ESI+) 328 (M+1, 1.5%)

Reference Example 173-9

1-tert-Butyl 2-methyl (2S,3S)-3-(cis-4-methoxycyclohexyl)pyrrolidine-1,2-dicarboxylate

[Formula 612]

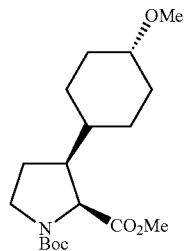

The same procedure as described in Reference Example 166-7 was carried out to obtain the title compound (522.5 mg, 93%) from the compound of Reference Example 173-8 (540.3 mg, 1.65 mmol).
MS (ESI+) 342 (M+1, 0.8%)

Reference Example 173-10

(3S)-1-(tert-Butoxycarbonyl)-3-(trans-4-methoxycyclohexyl)-L-proline

[Formula 613]

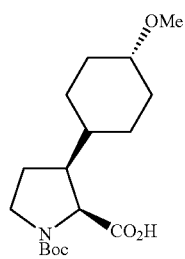

The same procedure as described in Reference Example 166-8 was carried out to obtain the title compound (407 mg, 81%) from the compound of Reference Example 173-9 (522.5 mg, 1.53 mmol).
MS (ESI+) 328 (M+1, 0.75%)

Reference Example 173-11 tert-Butyl (2S,3S)-2-{[2-(ethoxycarbonyl)-1-benzofuran-5-yl]carbamoyl}-3-(trans-4-methoxycyclohexyl)pyrrolidine-1-carboxylate

[Formula 614]

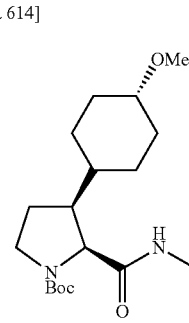

The same procedure as described in Reference Example 161-3 was carried out to obtain the title compound (417.8 mg, 66%) from the compound of Reference Example 173-10 (402.1 mg, 1.23 mmol) and ethyl 5-amino-1-benzofuran-2-carboxylate (278 mg, 1.35 mmol).

MS (ESI+) 515 (M+1, 41%)

Reference Example 173-12

Ethyl 5-{[(3S)-3-(trans-4-methoxycyclohexyl)-L-prolyl]amino}-1-benzofuran-2-carboxylate hydrochloride

[Formula 615]

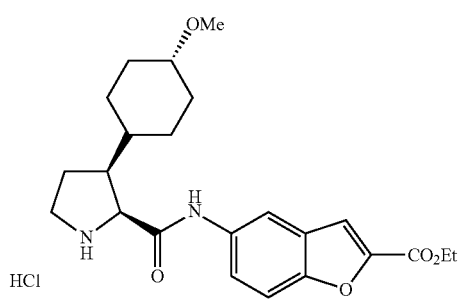

The same procedure as described in Reference Example 1-2 was carried out to obtain the title compound (366 mg. 100%) from the compound of Reference Example 173-11 (417.8 mg, 0.812 mmol).

MS (ESI+) 415 (M+1, 100%)

Reference Example 174

3-Methoxypropyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 616]

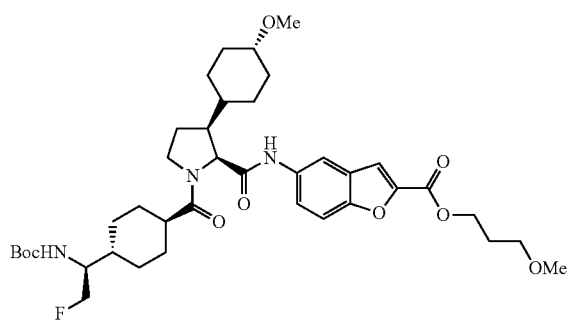

The same procedure as described in Reference Example 150 was carried out to obtain the title compound (55.9 mg, 85%) from the compound of Reference Example 174-1 (59.3 mg, 0.0902 mmol) and the compound of 1-bromo-3-methoxypropane (17.9 mg, 0.108 mmol).

MS (ESI+) 730 (M+1, 95%)

Reference Example 174-1

5-{[(3S)-1-[(trans-4-{(1S)-1-[(tert-Butoxycarbonyl)amino]-2-fluoroethyl}cyclohexyl)carbonyl]-3-(trans-4-methoxycyclohexyl)-L-prolyl]amino}-1-benzofuran-2-carboxylic acid

[Formula 617]

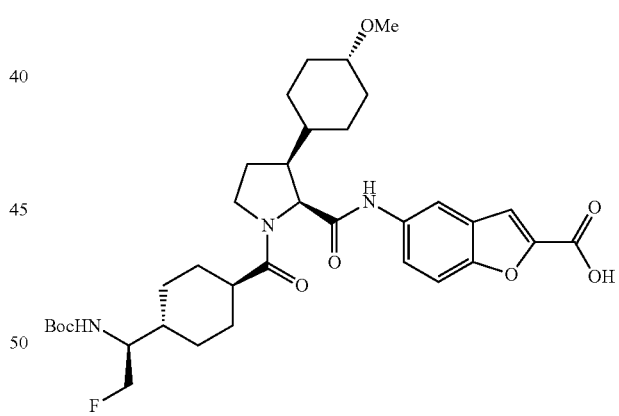

The same procedure as described in Reference Example 3 was carried out to obtain the title compound (330.3 mg, 90%) from the compound of Reference Example 173 (381.3 mg, 0.556 mmol).

MS (ESI+) 658 (M+1, 100%)

Reference Example 175

3-(2-Methoxyethoxy)propyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 618]

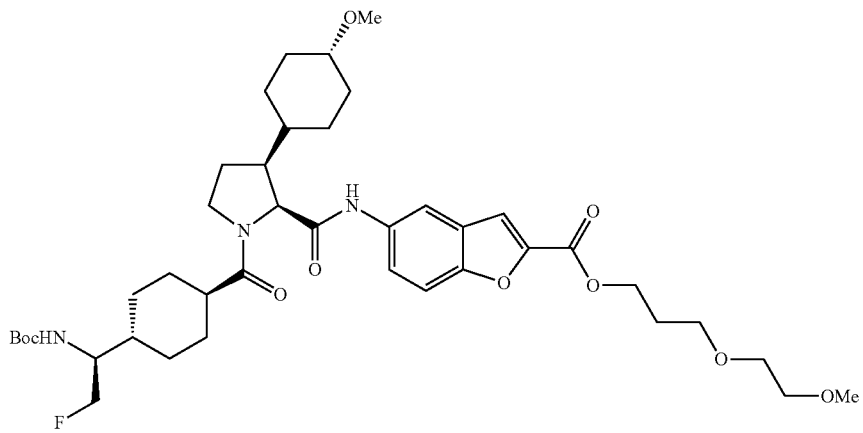

The same procedure as described in Reference Example 150 was carried out to obtain the title compound (63.4 mg, 89%) from the compound of Reference Example 174-1 (60.4 mg, 0.0918 mmol) and 3-(2-methoxyethoxy)propyl bromide (23.4 mg, 0.119 mmol).
MS (ESI+) 774 (M+1, 45%)

Reference Example 176

(2R)-2-Methoxypropyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 619]

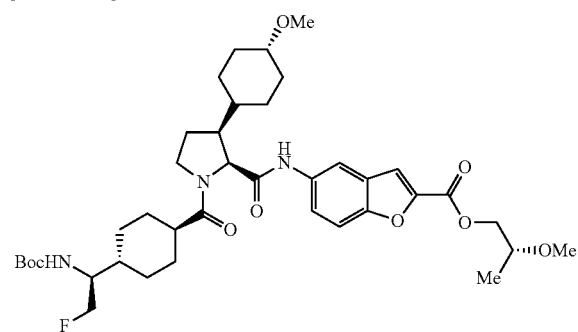

The same procedure as described in Reference Example 148 was carried out to obtain the title compound (42.8 mg, 51%) from the compound of Reference Example 170-1 (149 mg, 0.35 mmol) and the compound of Reference Example 174-1 (76.0 mg, 0.115 mmol).
MS (ESI+) 730 (M+1, 70%)

Reference Example 177

(2S)-2-Methoxypropyl 5-{[(3S)-1-[(trans-4-{(1S)-1-[(tert-butoxycarbonyl)amino]-2-fluoroethyl}cyclohexyl)carbonyl]-3-(4-methoxycyclohexyl)-L-prolyl]amino}-1-benzofuran-2-carboxylate

[Formula 620]

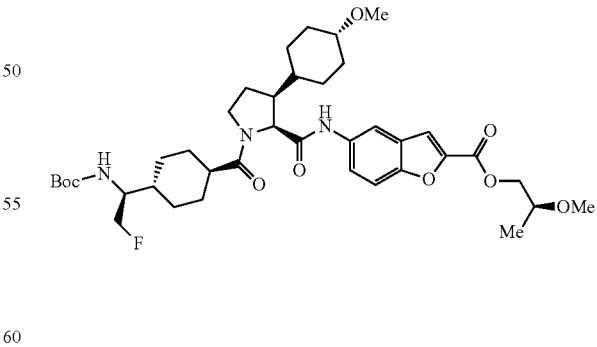

The same procedure as described in Reference Example 63 was carried out to obtain the title compound (53.9 mg, 74%) from the compound of Reference Example 174-1 (66.0 mg, 0.100 mmol).
MS (ESI+) 730 (M+1, 70%)

Reference Example 178

Cyclopentylmethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 621]

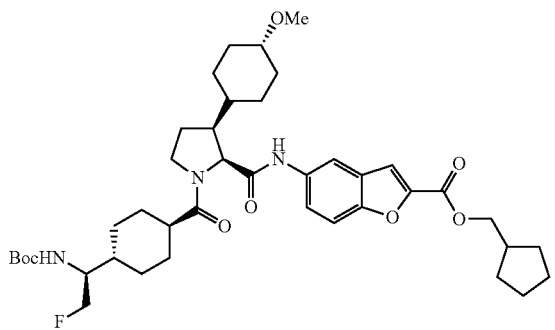

The same procedure as described in Reference Example 150 was carried out to obtain the title compound (48.8 mg, 53%) from the compound of Reference Example 174-1 (82.2 mg, 0.125 mmol) and iodine methyl cyclopentane (39.4 mg, 0.188 mmol).

MS (ESI+) 740 (M+1, 98%)

Reference Example 179

Cyclohexylmethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 622]

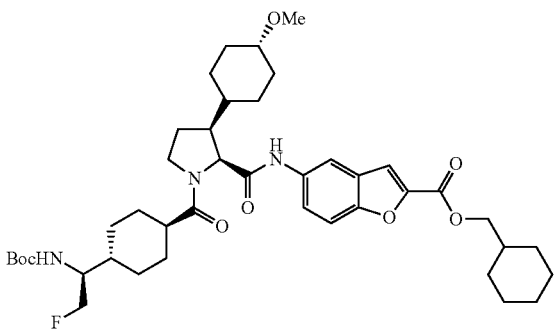

The same procedure as described in Reference Example 150 was carried out to obtain the title compound (93.8 mg, 100%) from the compound of Reference Example 174-1 (80.7 mg, 0.123 mmol) and a cyclohexylmethyl bromide (32.7 mg, 0.185 mmol).

MS (ESI+) 754 (M+1, 100%)

Reference Example 180

2-Methylpropyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 623]

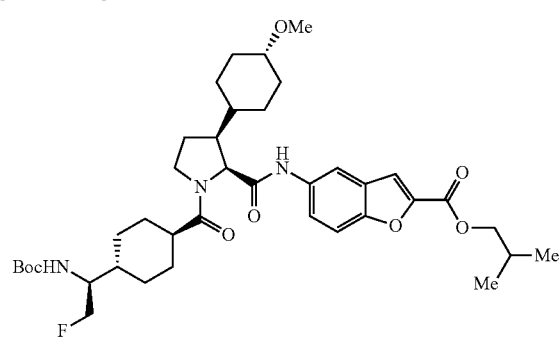

The same procedure as described in Reference Example 150 was carried out to obtain the title compound (79.8 mg, 91%) from the compound of Reference Example 174-1 (81.0 mg, 0.123 mmol) and 1-iodo-2-methylpropane (34.0 mg, 0.185 mmol).

MS (ESI+) 714 (M+1, 100%)

Reference Example 181

3-Ethoxypropyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 624]

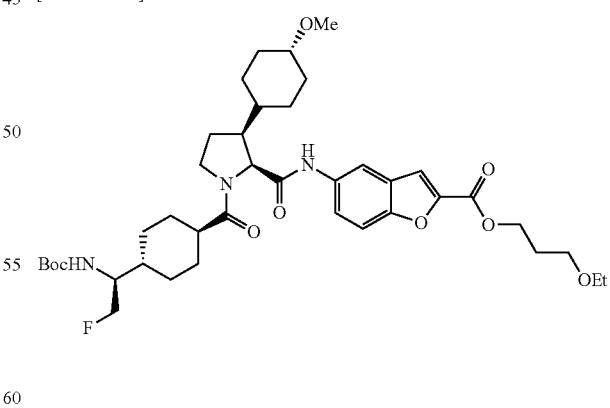

The same procedure as described in Reference Example 141 was carried out to obtain the title compound (34.8 mg, 62%) from the compound of Reference Example 174-1 (49.8 mg, 0.0757 mmol).

MS (ESI+) 744 (M+1, 63%)

Reference Example 182

3-(2-Methoxypropoxyl)propyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 625]

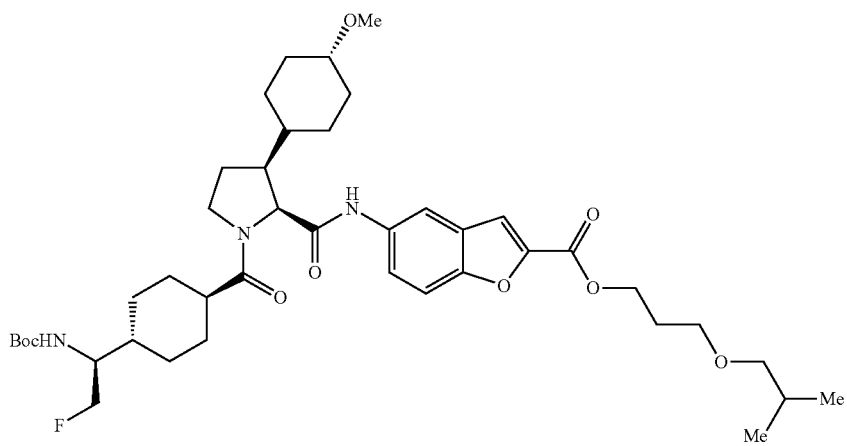

The same procedure as described in Reference Example 141 was carried out to obtain the title compound (22.7 mg, 54%) from the compound of Reference Example 174-1 (36.0 mg, 0.0547 mmol) and isobutoxy propanol (36.1 mg, 0.273 mmol).

MS (ESI+) 772 (M+1, 88%)

Reference Example 183

3-Hydroxypropyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-1-benzofuran-2-carboxylate

[Formula 626]

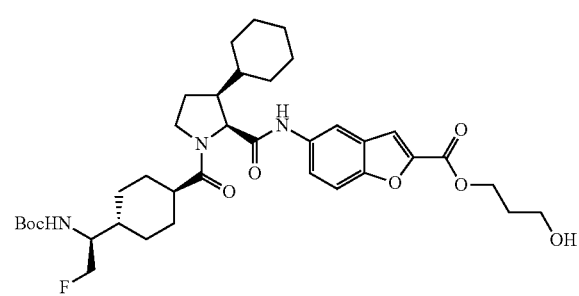

The same procedure as described in Reference Example 76-2 was carried out to obtain the title compound (33.7 mg, 23%) from Reference Example 53 (132.7 mg, 0.211 mmol) and 3-bromo-1-propanol (58.8 mg, 0.423 mmol).

MS (ESI+) 686 (M+1, 100%)

Reference Example 184 tert-Butyl [(1S)-1-(trans-4-{[(2S,3S)-3-cyclohexyl-2-({2-[(dimethylsulfamoyl)carbamoyl]-1H-indol-5-yl}carbamoyl)pyrrolidin-1-yl]carbonyl}cyclohexyl)-2-fluoroethyl]carbamate

[Formula 627]

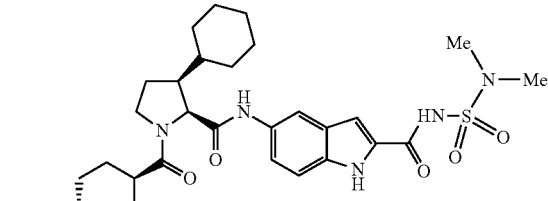

The same procedure as described in Reference Example 89-1 was carried out to obtain the title compound (30.0 mg, 26%) from the compound of Reference Example 81 (100.0 mg, 0.16 mmol) and commercially available N,N-dimethylsulfamide (28.0 mg, 0.225 mmol).

MS (ESI+) 733 (M+1, 58%)

Reference Example 185 tert-Butyl [(1S)-1-(trans-4-{[(2S,3R)-2-({2-[(dimethylsulfamoyl)carbamoyl]-1H-indol-5-yl}carbamoyl)-3-phenylpyrrolidin-1-yl]carbonyl}cyclohexyl)-2-fluoroethyl]carbamate

[Formula 628]

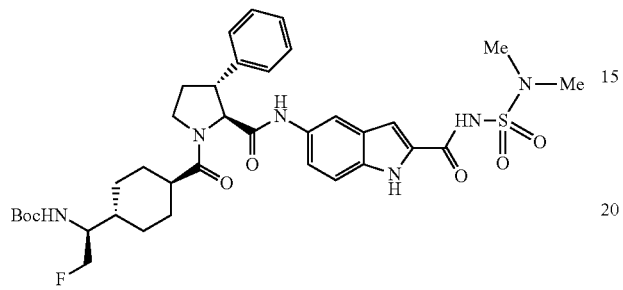

The same procedure as described in Reference Example 89-1 was carried out to obtain the title compound (21.0 mg, 18%) from the compound of Reference Example 140 (100.0 mg, 0.161 mmol) and commercially available N,N-dimethylsulfamide (28.0 mg, 0.225 mmol).

MS (ESI+) 727 (M+1, 100%)

Reference Example 186 tert-Butyl [(1S)-1-(trans-4-{[(2S,3S)-3-cyclohexyl-2-({2-[(morpholin-4-ylsulfonyl)carbamoyl]-1H-indol-5-yl}carbamoyl)pyrrolidin-1-yl]carbonyl}cyclohexyl)-2-fluoroethyl]carbamate

[Formula 629]

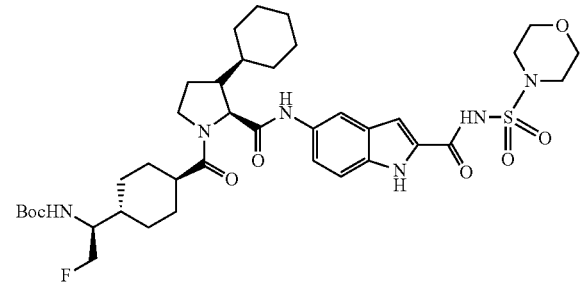

The same procedure as described in Reference Example 89-1 was carried out to obtain the title compound (25.0 mg, 16%) from the compound of Reference Example 81 (129.3 mg, 0.206 mmol) and the compound of Reference Example 102-2 (48.0 mg, 0.289 mmol).

MS (ESI+) 775 (M+1, 100%)

Reference Example 187

(3S)-1-[(trans-4-{(1S)-1-[(tert-Butoxycarbonyl)amino]-2-fluoroethyl}cyclohexyl)carbonyl]-3-cyclohexyl-N-{2-[(dimethylsulfamoyl)carbamoyl]-1-benzofuran-5-yl}-L-prolinamide

[Formula 630]

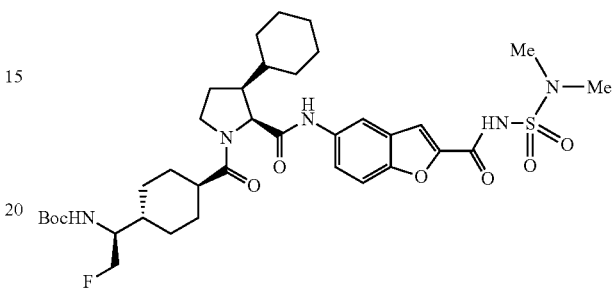

The same procedure as described in Reference Example 89-1 was carried out to obtain the title compound (103.0 mg, 44%) from the compound of Reference Example 53 (200.0 mg, 0.319 mmol) and commercially available N,N-dimethylsulfamide (55.0 mg, 0.447 mmol).

MS (ESI+) 734 (M+1, 50%)

Reference Example 188 tert-Butyl [(1S)-1-(trans-4-{[(2S,3S)-3-cyclohexyl-2-({2-[(morpholin-4-ylsulfonyl)carbamoyl]-1-benzofuran-5-yl}carbamoyl)pyrrolidin-1-yl]carbonyl}cyclohexyl)-2-fluoroethyl]carbamate

[Formula 631]

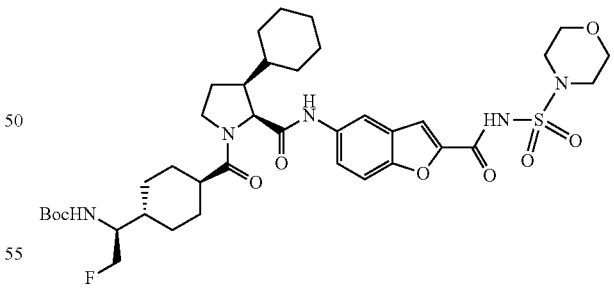

The same procedure as described in Reference Example 89-1 was carried out to obtain the title compound (136.0 mg, 55%) from the compound of Reference Example 53 (200.0 mg, 0.319 mmol) and the compound of Reference Example 102-2 (75.0 mg, 0.447 mmol).

MS (ESI+) 776 (M+1, 100%)

Reference Example 189 tert-Butyl [(1S)-1-(trans-4-{[(2S,3S)-3-cyclohexyl-2-({2-[(piperidin-1-ylsulfonyl)carbamoyl]-1H-indol-5-yl}carbamoyl)pyrrolidin-1-yl]carbonyl}cyclohexyl)-2-fluoroethyl]carbamate

[Formula 632]

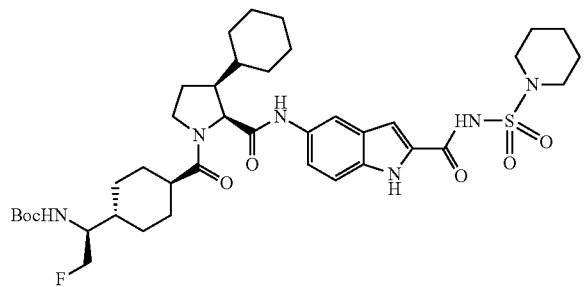

The same procedure as described in Reference Example 89-1 was carried out to obtain the title compound (23 mg, 18%) from the compound of Reference Example 81 (100.0 mg, 0.16 mmol) and the compound of Reference Example 189-2 (37 mg, 0.23 mmol).

MS (ESI+) 773 (M+1, 95%)

Reference Example 189-1

Benzyl(piperidin-1-ylsulfonyl)carbamate

[Formula 633]

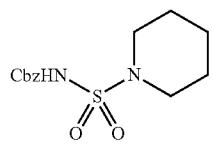

The same procedure as described in Reference Example 102-1 was carried out to obtain the title compound (320 mg, 8%) from commercially available piperidine (1.2 g, 14.13 mmol).

MS (ESI+) 299 (M+1, 100%)

Reference Example 189-2

Piperidine-1-sulfonamide

[Formula 634]

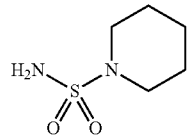

The same procedure as described in Reference Example 53-3 was carried out to obtain the title compound (160 mg, 90%) from the compound of Reference Example 189-1 (320.0 mg, 1.073 mmol).

MS (ESI+) 165 (M+1, 100%)

Reference Example 190 tert-Butyl [(1S)-1-(trans-4-{[(2S,3S)-3-cyclohexyl-2-({2-[(piperidin-1-ylsulfonyl)carbamoyl]-1-benzofuran-5-yl}carbamoyl)pyrrolidin-1-yl]carbonyl}cyclohexyl)-2-fluoroethyl]carbamate

[Formula 635]

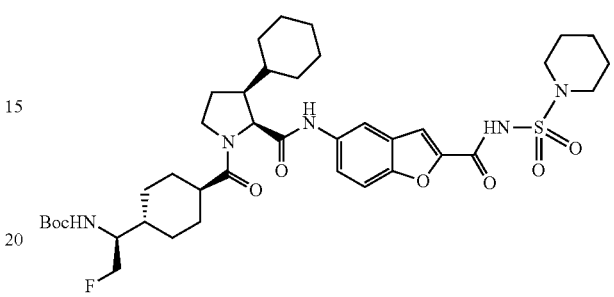

The same procedure as described in Reference Example 89-1 was carried out to obtain the title compound (70.0 mg, 28%) from the compound of Reference Example 53 (200.0 mg, 0.319 mmol) and the compound of Reference Example 189-2 (73.0 mg, 0.447 mmol).

MS (ESI+) 774 (M+1, 52%)

Reference Example 191

(3S)-1-[(trans-4-{(1S)-1-[(tert-Butoxycarbonyl)amino]-2-fluoroethyl}cyclohexyl)carbonyl]-3-cyclohexyl-N-{4-[(dimethylsulfamoyl)carbamoyl]phenyl}-L-prolinamide

[Formula 636]

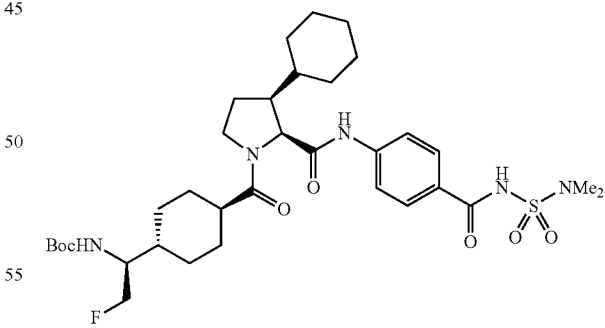

The same procedure as described in Reference Example 1 was carried out to obtain the title compound (9.5 mg, 69%) from the compound of Reference Example 89-2 (9.6 mg, 0.02 mmol) and the compound of Reference Example 53-3 (6.1 mg, 0.021 mmol).

MS (ESI+) 694 (M+1, 3%)

Reference Example 192 tert-Butyl[(1S)-1-(trans-4-{[(2S,3S)-3-cyclohexyl-2-({2-[(pyrrolidin-1-ylsulfonyl)carbamoyl]-1H-indol-5-yl}carbamoyl)pyrrolidin-1-yl]carbonyl}cyclohexyl)-2-fluoroethyl]carbamate

[Formula 637]

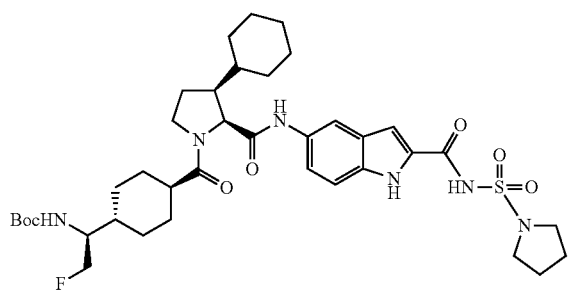

The same procedure as described in Reference Example 89-1 was carried out to obtain the title compound (28.5 mg, 16%) from the compound of Reference Example 81 (150.0 mg, 0.239 mmol) and the compound of Reference Example 192-2 (53.9 mg, 0.359 mmol).
MS (ESI+) 759 (M+1, 55%)

Reference Example 192-1

Benzyl(pyrrolidin-1-ylsulfonyl)carbamate

[Formula 638]

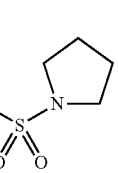

The same procedure as described in Reference Example 102-1 was carried out to obtain the title compound (3.63 g, 91%) from commercially available pyrrolidine (1.0 g, 14.05 mmol).
MS (ESI+) 285 (M+1, 14%)

Reference Example 192-2

Pyrrolidine-1-sulfonamide

[Formula 639]

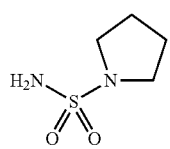

The same procedure as described in Reference Example 53-3 was carried out to obtain the title compound (1.92 g, 100%) from the compound of Reference Example 192-1 (3.63 g, 12.76 mmol).
MS (ESI+) 151 (M+1, 100%)

Reference Example 193

(3S)-1-[(trans-4-{(1S)-1-[(tert-Butoxycarbonyl)amino]-2-fluoroethyl}cyclohexyl)carbonyl]-3-cyclohexyl-N-{2-[(pyrrolidin-1-ylsulfonyl)carbamoyl]-1-benzofuran-5-yl}-L-prolinamide

[Formula 640]

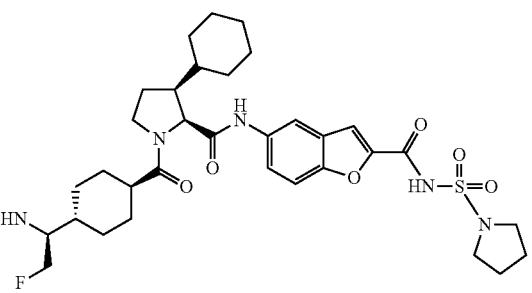

The same procedure as described in Reference Example 89-1 was carried out to obtain the title compound (69.0 mg, 38%) from the compound of Reference Example 53 (150.0 mg, 0.239 mmol) and the compound of Reference Example 192-2 (53.8 mg, 0.358 mmol).
RT 5.875 min (Kinetex 1.7 µC18 100 A, 0.1% trifluoroacetic acid in water/acetonitrile, acetonitrile 1-99% 7.0 min, 0.9 mL/min).

Reference Example 194 tert-Butyl [(1S)-1-(trans-4-{[(2S,3S)-3-cyclohexyl-2-({1-methyl-2-[(pyrrolidin-1-ylsulfonyl)carbamoyl]-1H-indol-5-yl}carbamoyl)pyrrolidin-1-yl]carbonyl}cyclohexyl)-2-fluoroethyl]carbamate

[Formula 641]

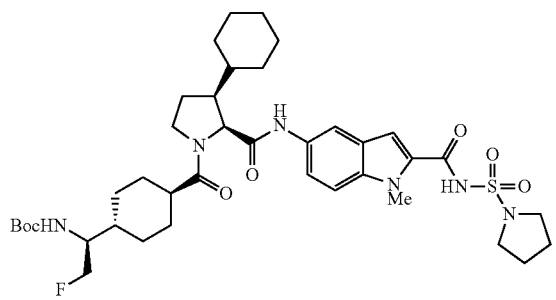

The same procedure as described in Reference Example 89-1 was carried out to obtain the title compound (113.7 mg, 100%) from the compound of Reference Example 144 (91.6 mg, 0.143 mmol) and the compound of Reference Example 192-2 (43.0 mg, 0.286 mmol).
MS (ESI+) 773 (M+1, 100%)

Reference Example 195 tert-Butyl [(1S)-1-(trans-4-{[(2S,3S)-3-cyclohexyl-2-({3-methyl-2-[(piperidin-1-ylsulfonyl)carbamoyl]-1H-indol-5-yl}carbamoyl)pyrrolidin-1-yl]carbonyl}cyclohexyl)-2-fluoroethyl]carbamate

[Formula 642]

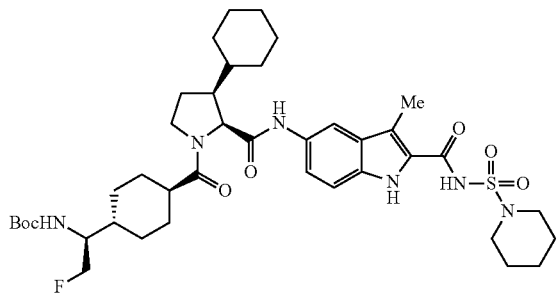

The same procedure as described in Reference Example 89-1 was carried out to obtain the title compound (14.2 mg, 27%) from the compound of Reference Example 93 (43.0 mg, 0.067 mmol) and the compound of Reference Example 189-2 (15.6 mg, 0.094 mmol).
MS (ESI+) 787 (M+1, 71%)

Reference Example 196 tert-Butyl {(1S)-1-[trans-4-({(2S,3S)-3-cyclohexyl-2-[(2-{[di(propan-2-yl)sulfamoyl]carbamoyl}-1H-indol-5-yl)carbamoyl]pyrrolidin-1-yl}carbonyl)cyclohexyl]-2-fluoroethyl}carbamate

[Formula 643]

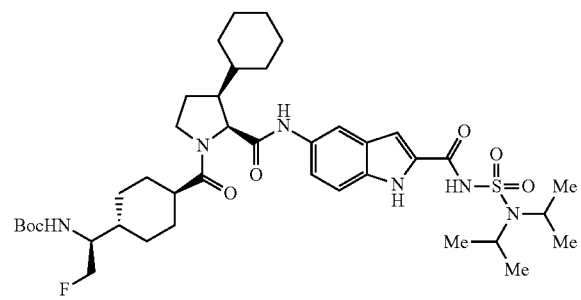

The same procedure as described in Reference Example 89-1 was carried out to obtain the title compound (4.6 mg, 3.6%) from the compound of Reference Example 81 (100.0 mg, 0.160 mmol) and the compound of Reference Example 196-2 (58.0 mg, 0.319 mmol).
MS (ESI+) 789 (M+1, 100%)

Reference Example 196-1

Benzyl [di(propan-2-yl) sulfamoyl)carbamate

[Formula 644]

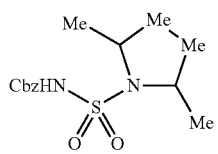

The same procedure as described in Reference Example 102-1 was carried out to obtain the title compound (1.86 g, 84%) from commercially available diisopropylamine (715 mg, 7.07 mmol).
MS (ESI+) 315 (M+1, 100%)

Reference Example 196-2

N,N-Dipropan-2-ylsulfuric diamide

[Formula 645]

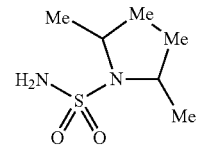

The same procedure as described in Reference Example 53-3 was carried out to obtain the title compound (1.02 g, 96%) from the compound of Reference Example 192-1 (1.86 g, 5.92 mmol).
MS (ESI+) 181 (M+1, 100%)

Reference Example 197

(3S)-1-[(trans-4-{(1S)-1-[(tert-Butoxycarbonyl)amino]-2-fluoroethyl}cyclohexyl)carbonyl]-3-cyclohexyl-N-(2-{[ethyl(propan-2-yl)sulfamoyl]carbonyl}-1-benzofuran-5-yl)-L-prolinamide

[Formula 646]

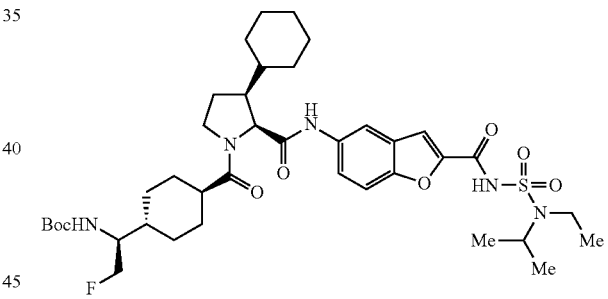

The same procedure as described in Reference Example 89-1 was carried out to obtain the title compound (61.2 mg, 49%) from the compound of Reference Example 53 (100.0 mg, 0.160 mmol) and the compound of Reference Example 197-2 (53.0 mg, 0.319 mmol).
MS (ESI+) 776 (M+1, 100%)

Reference Example 197-1

Benzyl [ethyl(propan-2-yl)sulfamoyl)carbamate

[Formula 647]

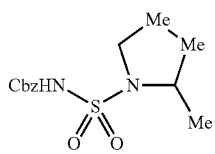

The same procedure as described in Reference Example 102-1 was carried out to obtain the title compound (2.0 g, 94%) from commercially available N-ethyl isopropylamine (615.9 mg, 7.07 mmol).

MS (ESI+) 301 (M+1, 100%)

Reference Example 197-2

N-Ethyl-N-propan-2-ylsulfuric diamide

[Formula 648]

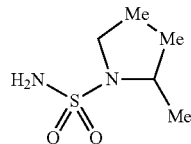

The same procedure as described in Reference Example 53-3 was carried out to obtain the title compound (1.11 g, 100%) from the compound of Reference Example 197-1 (2.0 g, 6.66 mmol).

MS (ESI+) 167 (M+1, 100%)

Reference Example 198

(3S)-1-[(trans-4-{(1S)-1-[(tert-Butoxycarbonyl)amino]-2-fluoroethyl}cyclohexyl)carbonyl]-3-cyclohexyl-N-(2-{[di(propan-2-yl)sulfamoyl]carbamoyl}-1-benzofuran-5-yl)-L-prolinamide

[Formula 649]

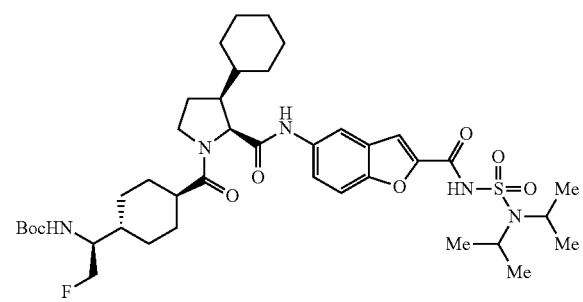

The same procedure as described in Reference Example 89-1 was carried out to obtain the title compound (18.4 mg, 15%) from the compound of Reference Example 53 (100.0 mg, 0.160 mmol) and the compound of Reference Example 196-2 (58.0 mg, 0.319 mmol).

MS (ESI+) 790 (M+1, 100%)

Reference Example 199

3-Methylbutyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 650]

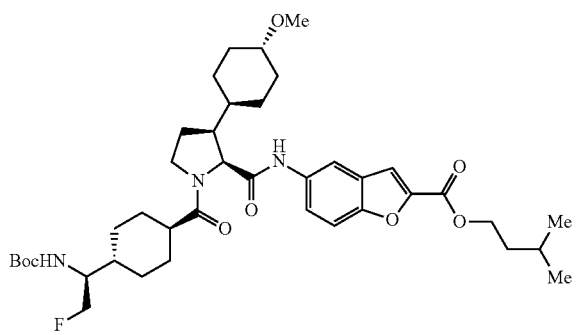

The same procedure as described in Reference Example 150 was carried out to obtain the title compound (17.9 mg, 79%) from the compound of Reference Example 174-1 (20.4 mg, 0.0310 mmol).

MS (ESI+) 728 (M+1, 100%)

Reference Example 200

Tetrahydrofuran-2-ylmethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 651]

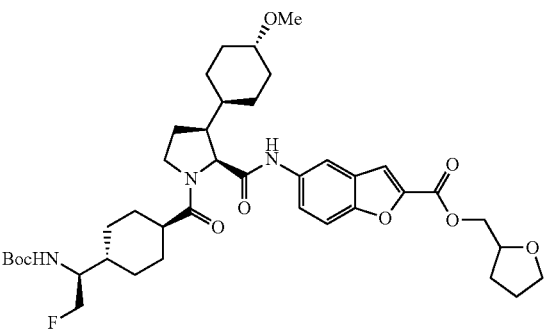

The same procedure as described in Reference Example 150 was carried out to obtain the title compound (12.2 mg, 53%) from the compound of Reference Example 174-1 (20.5 mg, 0.0312 mmol).

MS (ESI+) 742 (M+1, 52%)

Reference Example 201

3-(Morpholin-4-yl)propyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 652]

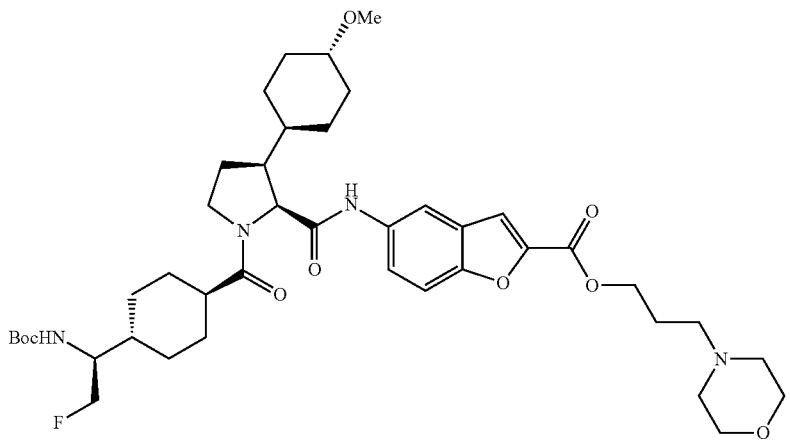

The same procedure as described in Reference Example 141 was carried out to obtain the title compound (77.6 mg, 91%) from the compound of Reference Example 174-1 (71.6 mg, 0.109 mmol) and 3-morpholinopropanol (47.4 mg, 0.327 mmol).

MS (ESI+) 785 (M+1, 100%)

Reference Example 202

4-Methoxybutyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 653]

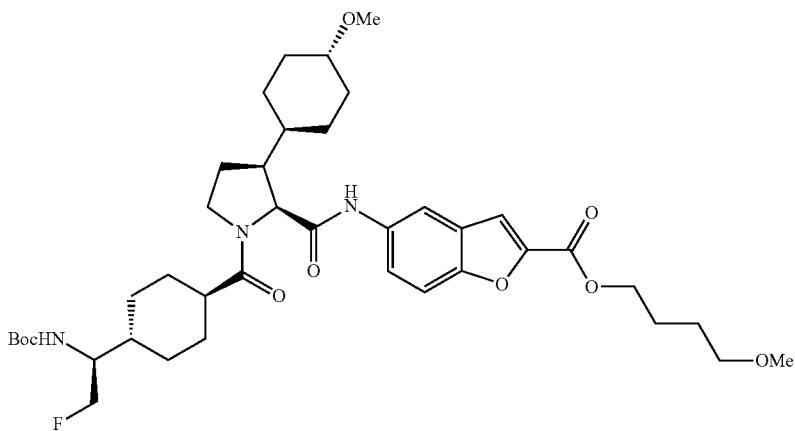

The same procedure as described in Reference Example 150 was carried out to obtain the title compound (16.0 mg, 69%) from the compound of Reference Example 174-1 (20.5 mg, 0.0312 mmol) and 1-chloro-4-methoxybutane (6.0 mg, 0.046 mmol).

MS (ESI+) 744 (M+1, 100%)

Reference Example 203

Butyl 5-{[(3S)-1-[(trans-4-{(1S)-1-[(tert-butoxycarbonyl]-2-fluoroethyl}cyclohexyl)carbonyl]-3-(trans-4-methoxycyclohexyl)-L-prolyl]amino}-1-benzofuran-2-carboxylate

[Formula 654]

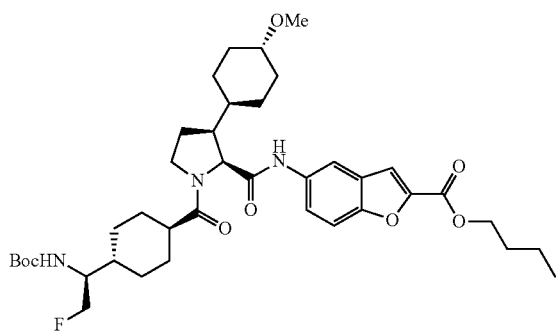

The same procedure as described in Reference Example 150 was carried out to obtain the title compound (16.4 mg, 74%) from the compound of Reference Example 174-1 (20.2 mg, 0.031 mmol) and butyl iodide (8.5 mg, 0.046 mmol).

MS (ESI+) 714 (M+1, 100%)

Reference Example 204

(5-Methyl-2-oxo-1,3-dioxol-4-yl)methyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 655]

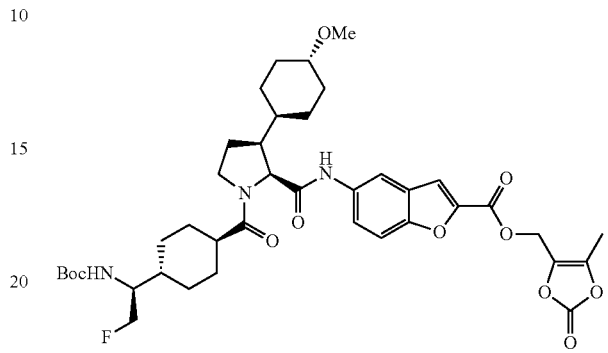

To a solution of the compound of Reference Example 174-1 (20.2 mg, 0.031 mmol) in DMF (2 mL), potassium carbonate (12.8 mg, 0.093 mmol), potassium iodide (1.0 mg, 0.003 mmol), and 4-chloromethyl-5-methyl-1,3-dioxol-2-one (6.8 mg, 0.046 mmol) were added, and the mixture was stirred at room temperature overnight. A saturated aqueous solution of ammonium chloride was added to the reaction mixture, followed by extraction with ethyl acetate. The organic layer was washed with a saturated aqueous solution of ammonium chloride twice and with a saturated saline solution, then dried over sodium sulfate and filtered, and the filtrate was concentrated under reduced pressure. The obtained residue was purified by silica gel column chromatography to obtain the title compound (19.0 mg, 82%).

MS (ESI+) 771 (M+1, 75%)

Reference Example 205

Hexyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 656]

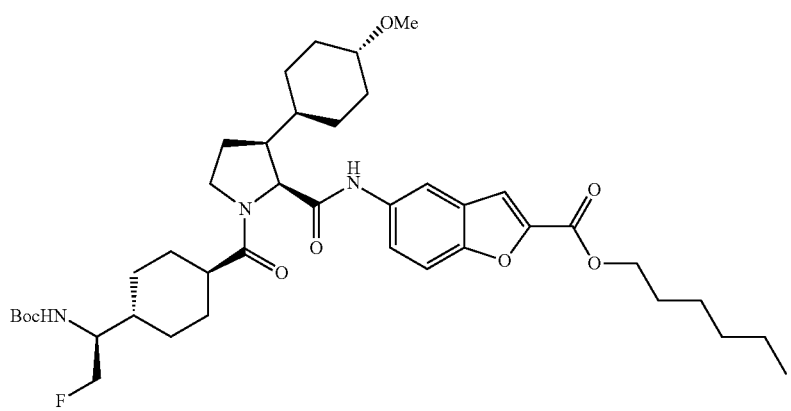

The same procedure as described in Reference Example 150 was carried out to obtain the title compound (15.8 mg, 69%) from the compound of Reference Example 174-1 (20.2 mg, 0.0307 mmol).

MS (ESI+) 742 (M+1, 92%)

Reference Example 206

Cyclobutylmethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 657]

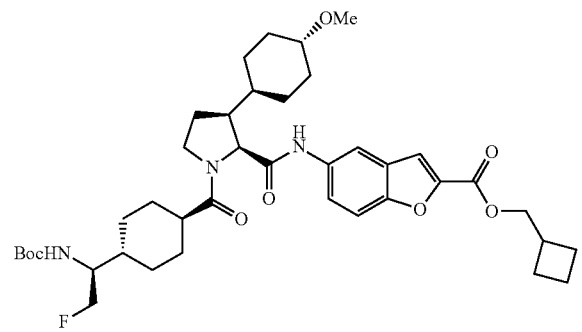

The same procedure as described in Reference Example 150 was carried out to obtain the title compound (18.3 mg, 79%) from the compound of Reference Example 174-1 (20.8 mg, 0.0316 mmol).

MS (ESI+) 726 (M+1, 100%)

Reference Example 207

[(2,2-Dimethylpropanoyl)oxo]methyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 658]

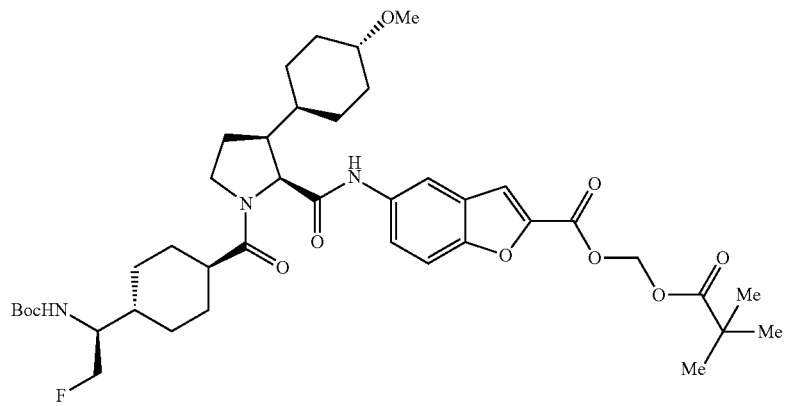

The same procedure as described in Reference Example 150 was carried out to obtain the title compound (17.5 mg, 71%) from the compound of Reference Example 174-1 (20.9 mg, 0.0318 mmol).

MS (ESI+) 772 (M+1, 28%)

Reference Example 208

Propyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 659]

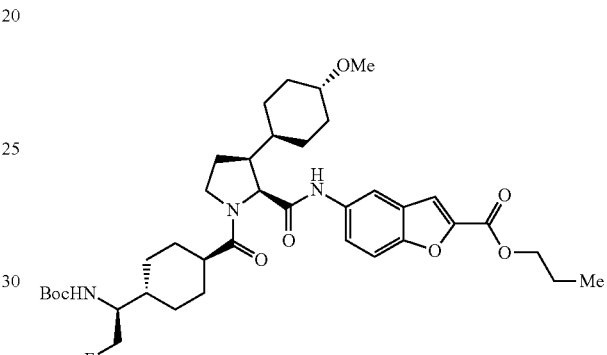

The same procedure as described in Reference Example 150 was carried out to obtain the title compound (19.1 mg, 86%) from the compound of Reference Example 174-1 (20.8 mg, 0.0316 mmol).

MS (ESI+) 700 (M+1, 86%)

Reference Example 209

Methyl 5-{[(3S)-1-[(trans-4-{(1S)-1-[(tert-butoxy-carbonyl)amino]-2-fluoroethyl}cyclohexyl)carbonyl]-3-(trans-4-methoxycyclohexyl)-L-prolyl]amino}-1-benzofuran-2-carboxylate

[Formula 660]

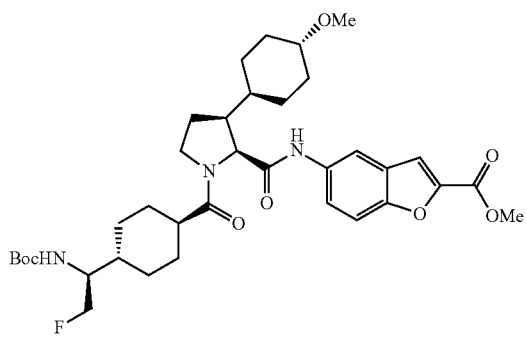

The same procedure as described in Reference Example 150 was carried out to obtain the title compound (18.7 mg, 90%) from the compound of Reference Example 174-1 (20.1 mg, 0.031 mmol) and methyl iodide (2.5 μL, 0.04 mmol).

MS (ESI+) 672 (M+1, 100%)

Reference Example 210

2-(Morpholin-4-yl)ethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate The same procedure as described in Reference Example 150 was carried out to obtain the title compound (18.9 mg, 79%) from the compound of Reference Example 174-1 (20.2 mg, 0.031 mmol) and 4-(2-chloroethyl)morpholine hydrochloride (7.4 mg, 0.04 mmol).

MS (ESI+) 771 (M+1, 100%)

Reference Example 211

Tetrahydro-2H-pyran-4-ylmethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 662]

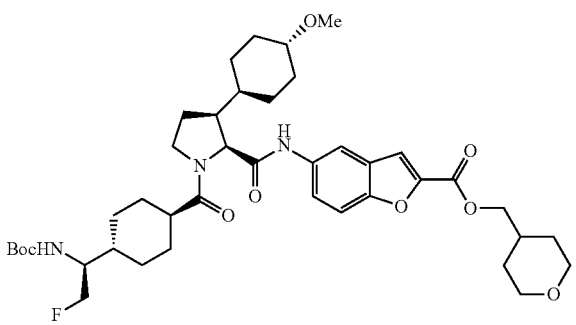

The same procedure as described in Reference Example 150 was carried out to obtain the title compound (12.5 mg, 54%) from the compound of Reference Example 174-1 (20.1 mg, 0.0306 mmol) and 4-(bromomethyl)tetrahydro-2H-pyran (6.03 mg, 0.034 mmol).

MS (ESI+) 756 (M+1, 71%)

[Formula 661]

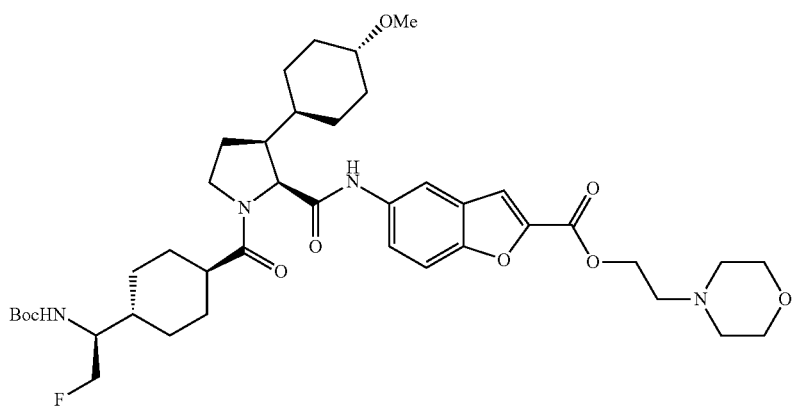

Reference Example 212

Pentyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 663]

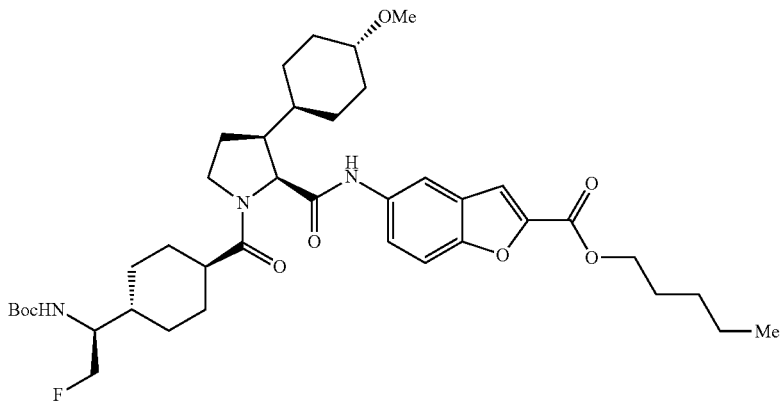

The same procedure as described in Reference Example 150 was carried out to obtain the title compound (15.4 mg, 69%) from the compound of Reference Example 174-1 (20.1 mg, 0.0306 mmol) and 1-iodopentane (6.67 mg, 0.034 mmol).
MS (ESI+) 728 (M+1, 98%)

Reference Example 213

Cyclopropylmethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 664]

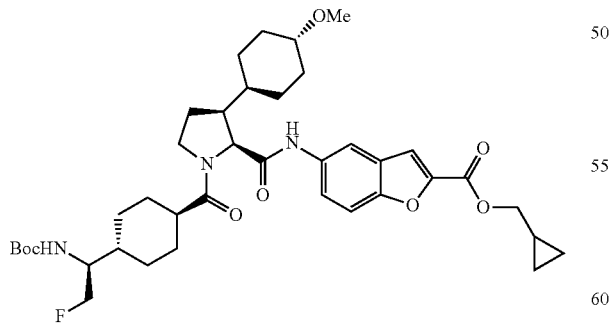

The same procedure as described in Reference Example 150 was carried out to obtain the title compound (15.5 mg, 69%) from the compound of Reference Example 174-1 (20.9 mg, 0.0318 mmol).
MS (ESI+) 712 (M+1, 100%)

Reference Example 214

1-{[(Cyclohexyloxy)carbonyl]oxy}ethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 665]

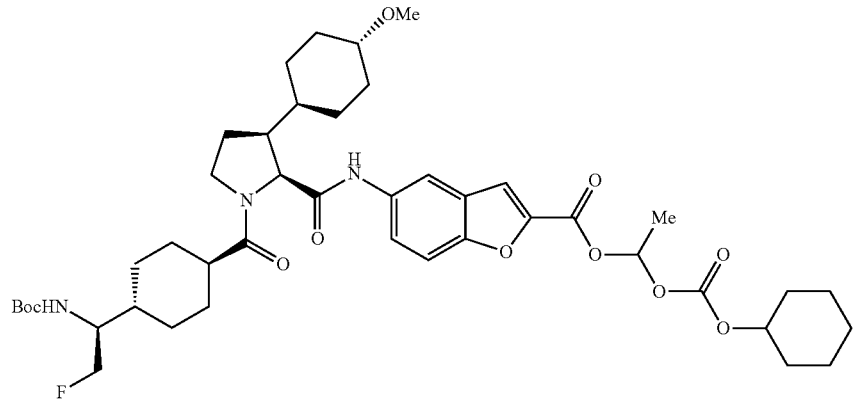

The same procedure as described in Reference Example 150 was carried out to obtain the title compound (16.6 mg, 65%) from the compound of Reference Example 174-1 (20.1 mg, 0.0306 mmol) and 1-chloroethyl cyclohexyl carbonate (7.0 mg, 0.034 mmol).

MS (ESI+) 828 (M+1, 25%)

Reference Example 215

1-{[(Propan-2-yloxy)carbonyl]oxy}ethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 666]

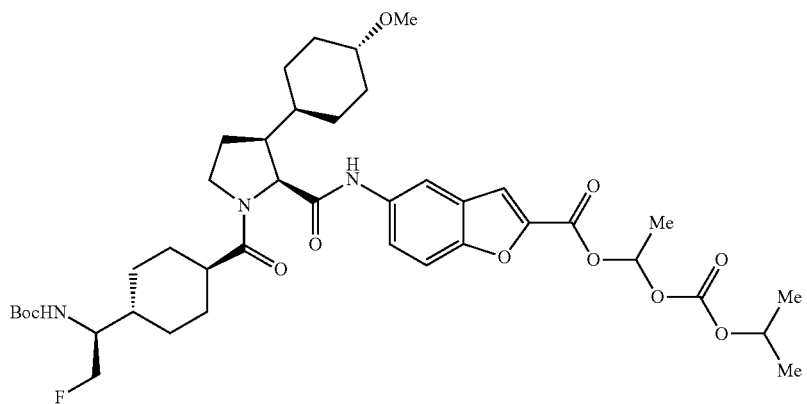

The same procedure as described in Reference Example 150 was carried out to obtain the title compound (67.1 mg, 55%) from the compound of Reference Example 174-1 (82.2 mg, 0.125 mmol) and 1-chloroethyl propan-2-yl carbonate (27.1 mg, 0.163 mmol).

MS (ESI+) 788 (M+1, 20%)

Reference Example 216

3-[(2R,6S)-2,6-Dimethylmorpholin-4-yl]propyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 667]

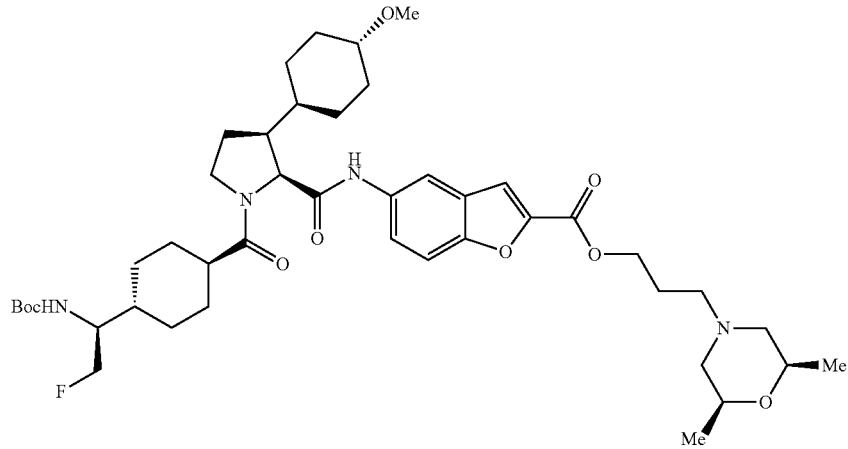

The same procedure as described in Reference Example 150 was carried out to obtain the title compound (18.3 mg, 68%) from the compound of Reference Example 174-1 (21.8 mg, 0.0331 mmol) and the compound of Reference Example 216-1 (11.7 mg, 0.0495 mmol).

MS (ESI+) 813 (M+1, 100%)

Reference Example 216-1

(2R,6S)-4-(3-Bromopropyl)-2,6-dimethylmorpholine

[Formula 668]

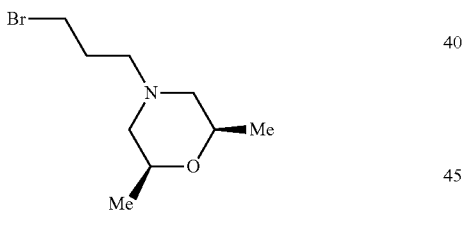

A solution of cis-2,6-dimethylmorpholine (312 mg, 2.71 mmol) and 1-bromo-3-chloropropane (213.3 mg, 1.35 mmol) in toluene (1 ml) was stirred at 70° C. for 8 hours. The reaction solution was allowed to cool and then concentrated under reduced pressure. The obtained residue was purified by silica gel column chromatography to obtain the title compound (141.2 mg, 44%).

MS (ESI+) 236, 238 (M+1, 100%)

Reference Example 217

3-(2,2-Dimethylmorpholin-4-yl)propyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 669]

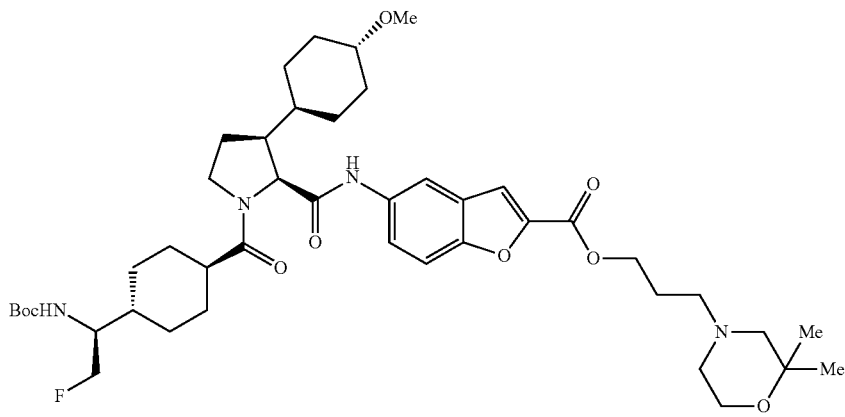

The same procedure as described in Reference Example 150 was carried out to obtain the title compound (21.7 mg, 78%) from the compound of Reference Example 174-1 (22.5 mg, 0.0342 mmol) and the compound of Reference Example 217-1 (12.1 mg, 0.0512 mmol).

MS (ESI+) 813 (M+1, 100%)

Reference Example 217-1

4-(3-Bromopropyl)-2,2-dimethylmorpholine

[Formula 670]

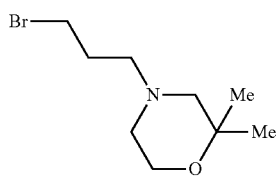

The same procedure as described in Reference Example 216-1 was carried out to obtain the title compound (131.6 mg, 32%) from 2,2-dimethylmorpholine (309 mg, 2.68 mmol) and 1-bromo-3-chloropropane (270.7 mg, 1.72 mmol).

MS (ESI+) 236, 238 (M+1, 100%)

Reference Example 218

3-(3,3-Dimethylmorpholin-4-yl)propyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate The same procedure as described in Reference Example 150 was carried out to obtain the title compound (22.3 mg, 66%) from the compound of Reference Example 174-1 (27.4 mg, 0.0417 mmol) and the compound of Reference Example 218-1 (12.8 mg, 0.0542 mmol).

MS (ESI+) 813 (M+1, 100%)

Reference Example 218-1

4-(3-Bromopropyl)-3,3-dimethylmorpholine

[Formula 672]

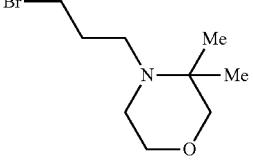

The same procedure as described in Reference Example 216-1 was carried out to obtain the title compound (33.1 mg, 15%) from 3,3-dimethylmorpholine (222 mg, 1.93 mmol) and 1,3-dibromopropane (195 mg, 0.964 mmol).

MS (ESI+) 236, 238 (M+1, 100%)

[Formula 671]

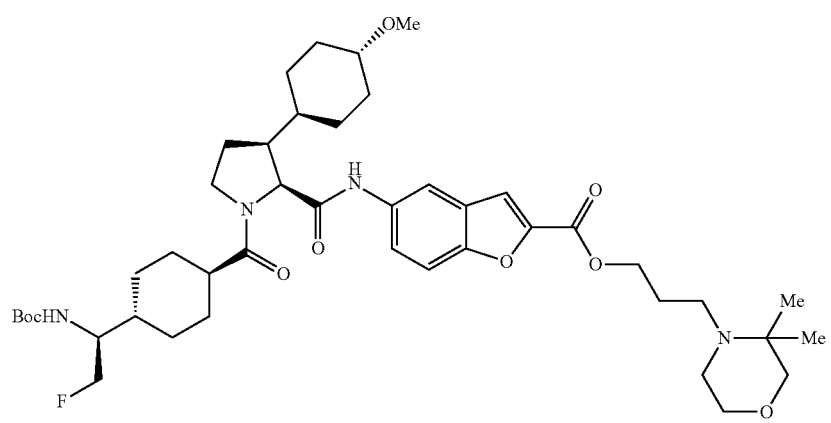

Reference Example 219

4-(Morpholin-4-yl)butyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 673]

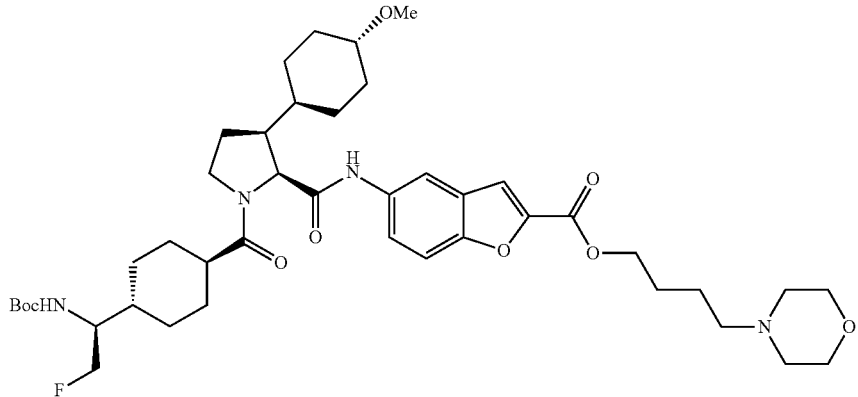

The same procedure as described in Reference Example 150 was carried out to obtain the title compound (26 mg, 76%) from the compound of Reference Example 174-1 (30.0 mg, 0.046 mmol) and commercially available 2-chloro-N,N-dimethyl acetamido (8.4 mg, 0.068 mmol).
MS (ESI+) 744 (M+1, 100%)

The same procedure as described in Reference Example 141 was carried out to obtain the title compound (17.5 mg, 73%) from the compound of Reference Example 174-1 (20.0 mg, 0.03 mmol) and commercially available 4-morpholino butan-1-ol (7.0 mg, 0.046 mmol).
MS (ESI+) 800 (M+1, 100%)

Reference Example 220

2-(Dimethylamino)-2-oxoethyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 674]

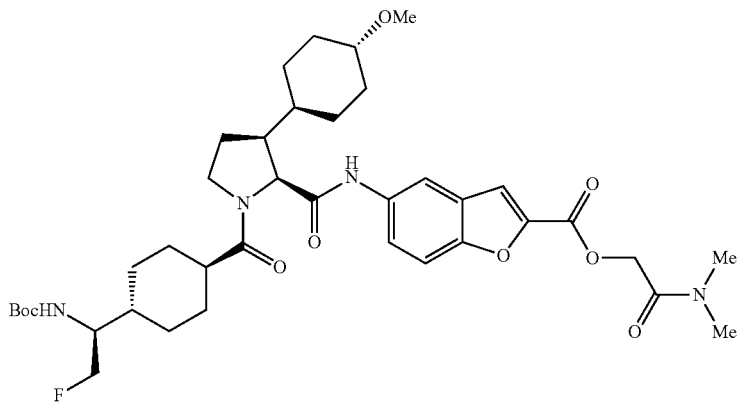

Reference Example 221

Tetrahydrofuran-3-yl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino)-}1-benzofuran-2-carboxylate

[Formula 675]

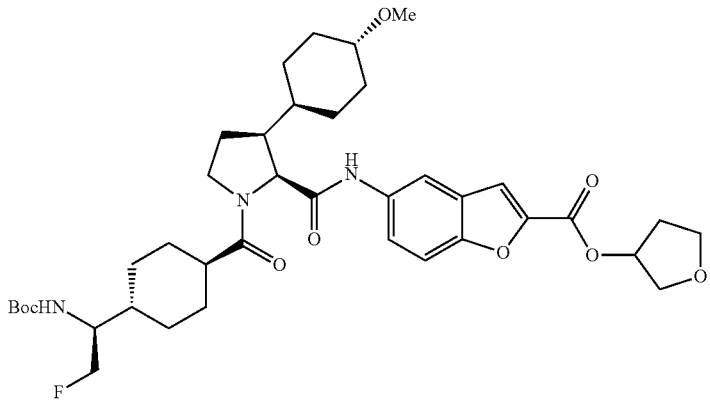

The same procedure as described in Reference Example 141 was carried out to obtain the title compound (12.0 mg, 54%) from the compound of Reference Example 174-1 (20.0 mg, 0.0304 mmol).
MS (ESI+) 728 (M+1, 100%)

Reference Example 222

(3-Methoxycyclobutyl)methyl 5-{[(3S)-1-[(trans-4-{(1S)-1-[(tert-butoxycarbonyl)amino]-2-fluoroethyl}cyclohexyl)carbonyl]-3-(trans-4-methoxycyclohexyl)-L-prolyl]amino}-1-benzofuran-2-carboxylate

[Formula 676]

The same procedure as described in Reference Example 141 was carried out to obtain the title compound (73.2 mg, 73%) from the compound of Reference Example 174-1 (87.7 mg, 0.133 mmol) and the compound of Reference Example 222-3 (17.0 mg, 0.146 mmol).
MS (ESI+) 756 (M+1, 100%)

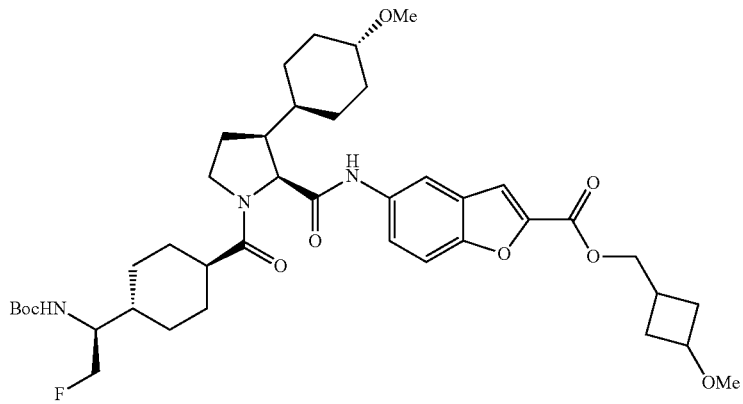

Reference Example 222-1

Benzyl 3-hydroxycyclobutanecarboxylate

[Formula 677]

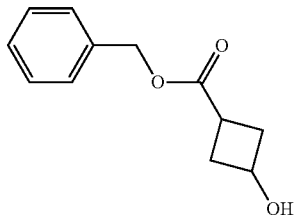

To a solution of 3-hydrxycyclobutanecarboxylic acid (1.03 g, 8.87 mmol) in tetrahydrofuran (15 ml), triethylamine (1.79 g, 17.7 mmol) and benzyl bromide (1.05 ml, 8.83 mmol) were added, and the mixture was stirred at room temperature for 4 days. A saturated aqueous solution of ammonium chloride was added to the reaction mixture, followed by extraction with ethyl acetate. The organic layer was washed with a saturated aqueous solution of sodium bicarbonate and a saturated saline solution, then dried over sodium sulfate and filtered, and the filtrate was concentrated under reduced pressure. The obtained residue was purified by silica gel column chromatography to obtain the title compound (516.9 mg, 28%).

$^1$H NMR (CDCl$_3$, 400 MHz) δ 7.39-7.31 (m, 5H), 5.12 (s, 2H), 4.22-4.15 (m, 1H), 2.71-2.57 (m, 3H), 2.24-2.15 (m, 2H), 2.09-2.06 (m, 1H).

Reference Example 222-2

Benzyl 3-methoxycyclobutanecarboxylate

[Formula 678]

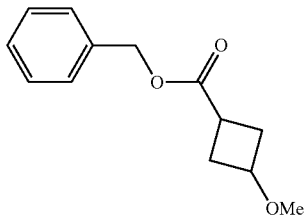

To a solution of the compound of Reference Example 222-1 (516.9 mg, 2.51 mmol) in DMF (5 ml), silver oxide (1.1 g, 4.75 mmol) and methyl iodide (1.3 ml, 20.88 mmol) were added, and the mixture was stirred at room temperature for 2 days. A saturated aqueous solution of ammonium chloride was added to the reaction mixture before filtration through Celite, followed by extraction with ethyl acetate. The organic layer was washed with a saturated aqueous solution of sodium bicarbonate and a saturated saline solution, then dried over sodium sulfate and filtered, and the filtrate was concentrated under reduced pressure. The obtained residue was purified by silica gel column chromatography to obtain the title compound (240.8 mg, 44%).

$^1$H NMR (CDCl$_3$, 300 MHz) δ 7.37-7.31 (m, 5H), 5.12 (s, 2H), 3.84-3.75 (m, 1H), 3.23 (s, 3H), 2.72-2.63 (m, 1H), 2.56-2.47 (m, 2H), 2.26-2.16 (m, 2H).

Reference Example 222-3

(3-Methoxycyclobutyl)methanol

[Formula 679]

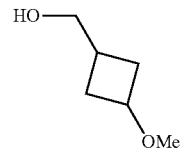

To a solution of the compound of Reference Example 222-2 (224.5 mg, 1.02 mmol) in tetrahydrofuran (3 ml), diisobutylaluminum hydride (1.02 mol/L in hexane, 3 ml, 3.06 mmol) was added dropwise at −78° C. The mixture was stirred at −78° C. for 1 hour, then sodium sulfate decahydrate (9.92 g) was added to the reaction solution, the mixture was gradually heated up to room temperature, then ethyl acetate was added, and the mixture was stirred for 1 hour. The reaction mixture was filtered through Celite, and the filtrate was concentrated under reduced pressure. The obtained residue was purified by silica gel column chromatography to obtain the title compound (81.6 mg, 69%).

$^1$H NMR (CDCl$_3$, 300 MHz) δ 3.83-3.73 (m, 1H), 3.60 (d, J=6.0 Hz, 2H), 3.23 (s, 3H), 2.40-2.31 (m, 2H), 2.08-2.04 (m, 1H), 1.70-1.60 (m, 2H), 1.51 (brs, 1H).

Example 1

4-{cis-1-[trans-4-(Aminomethyl)cyclohexanecarbonyl]-3-phenylpyrrolidine-2-carboxamide}benzoic acid trifluoroacetate

[Formula 680]

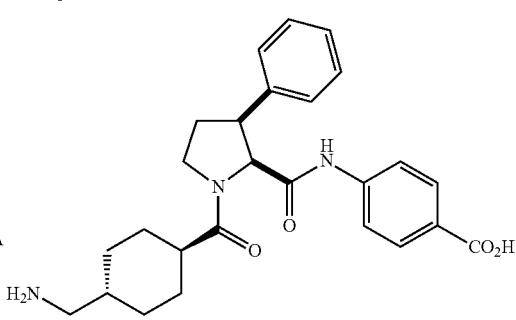

To a solution of the compound of Reference Example 1 (90.6 mg, 0.15 mmol) in chloroform (3 mL), trifluoroacetic acid (0.5 mL) was added, and the mixture was stirred for 3 hours. After the mixture was concentrated under reduced pressure, toluene (2 mL) was added to the residue for concentration under reduced pressure. Chloroform (3 mL) and hexane (3 mL) were further added for concentration under reduced pressure twice to obtain the title compound (81.7 mg, 97%).

RT 2.717 min (Shim-pack XR-ODS, 0.1% trifluoroacetic acid in water/acetonitrile, acetonitrile 1-99%, 7.0 min, 0.9 mL/min (condition A)).

MS (ESI+) 450 (M+1, 100%)

Example 2

Ethyl 5-{cis-1-[trans-4-(aminomethyl)cyclohexanecarbonyl]-3-phenylpyrrolidine-2-carboxamide}-1H-indole-2-carboxylate hydrochloride

[Formula 681]

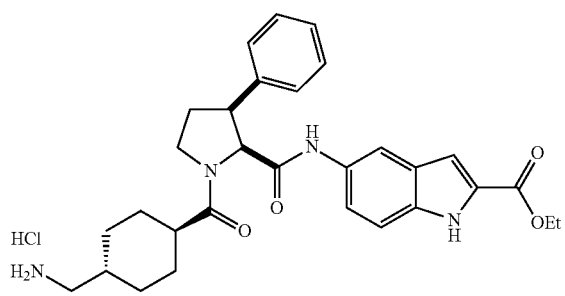

To a solution of the compound of Reference Example 2 (37.9 mg, 0.061 mmol) in 1,4-dioxane (2 mL), a 4 mol/L solution of hydrochloric acid/1,4-dioxane (1 mL) was added, and the mixture was stirred at room temperature for 4 hours. After the mixture was concentrated under reduced pressure, toluene (2 mL) was added to the residue, and the mixture was concentrated under reduced pressure. Chloroform (3 mL) and hexane (3 mL) were further added for concentration of the solvent under reduced pressure twice to obtain the title compound (34.1 mg, 100%).

RT 3.168 min (condition A). MS (ESI+) 517 (M+1, 100%)

Example 3

5-{cis-1-[trans-4-(Aminomethyl)cyclohexanecarbonyl]-3-phenylpyrrolidine-2-carboxamide}-1H-indole-2-carboxylic acid trifluoroacetate

[Formula 682]

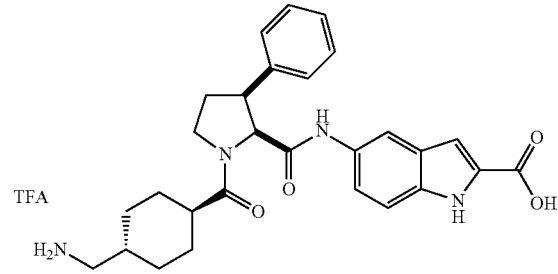

The same procedure as described in Example 1 was carried out to obtain the title compound (28.0 mg, 100%) from the compound of Reference Example 3 (30.0 mg, 0.051 mmol).

RT 2.739 min (condition A). MS (ESI+) 489 (M+1, 100%)

Example 4

5-{cis-1-[trans-4-(Aminomethyl)cyclohexanecarbonyl]-3-phenylpyrrolidine-2-carboxamide}-1H-indole-2-carboxamide hydrochloride

[Formula 683]

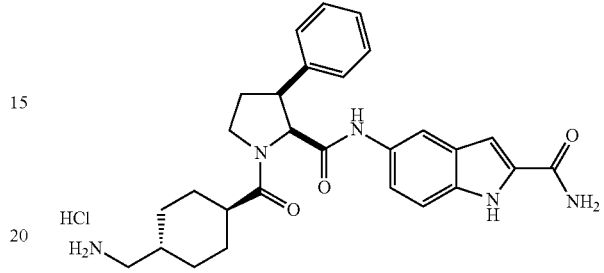

The same procedure as described in Example 2 was carried out to obtain the title compound (50.9 mg, 86%) from the compound of Reference Example 4 (68.7 mg, 0.114 mmol).

RT 2.640 min (condition A). MS (ESI+) 488 (M+1, 100%)

Example 5

5-{cis-1-[trans-4-(Aminomethyl)cyclohexanecarbonyl]-N-methyl-3-phenylpyrrolidine-2-carboxamide}-1H-indole-2-carboxylic acid trifluoroacetate

[Formula 684]

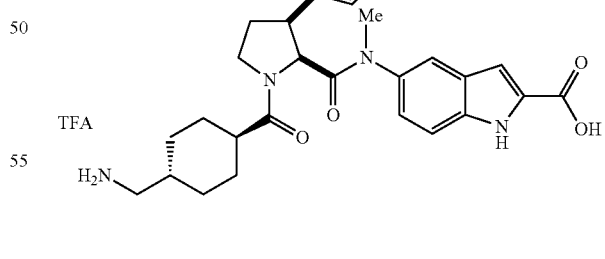

The same procedure as described in Example 1 was carried out to obtain the title compound (20.0 mg, 100%) from the compound of Reference Example 5 (22.8 mg, 0.038 mmol).

RT 2.928 min (condition A). MS (ESI+) 503 (M+1, 100%)

Example 6

4-{(2S,3S)-1-[trans-4-(Aminomethyl)cyclohexanecarbonyl]-3-phenylpyrrolidine-2-carboxamide}benzoic acid trifluoroacetate

[Formula 685]

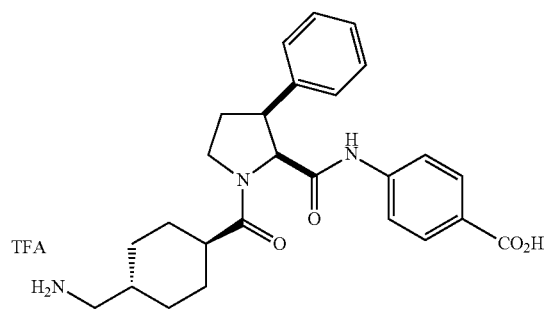

The same procedure as described in Example 1 was carried out to obtain the title compound (61.6 mg, 100%) from the compound of Reference Example 6 (62.0 mg, 0.102 mmol).

RT 2.717 min (condition A). MS (ESI+) 450 (M+1, 100%)

Example 7

Methyl 4-{(2S,3S)-1-[trans-4-(1-aminoethyl)cyclohexanecarbonyl]-3-phenylpyrrolidine-2-carboxamide}-2-fluorobenzoate trifluoroacetate

[Formula 686]

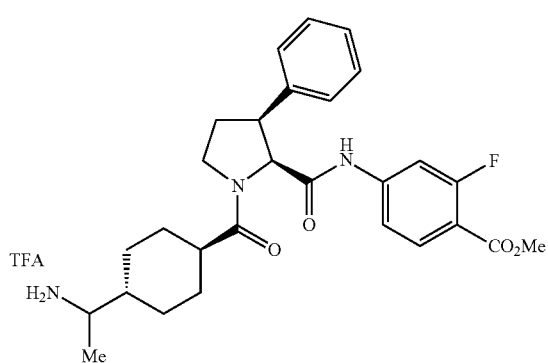

The same procedure as described in Example 1 was carried out to obtain the title compound (74.6 mg, 94%) from the compound of Reference Example 7 (88.5 mg, 0.149 mmol).

RT 3.214 min (condition A). MS (ESI+) 496 (M+1, 100%)

Example 8

4-{(2S,3S)-1-[trans-4-(1-Aminoethyl)cyclohexanecarbonyl]-3-phenylpyrrolidine-2-carboxamide}-2-fluorobenzoate hydrochloride

[Formula 687]

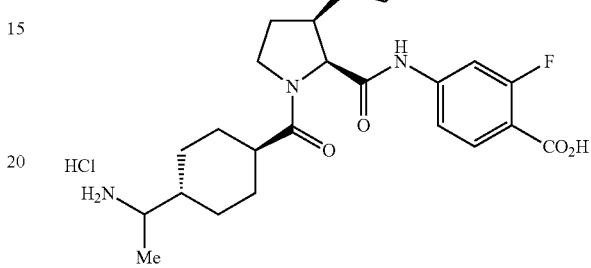

The same procedure as described in Example 2 was carried out to obtain the title compound (34.8 mg, 100%) from the compound of Reference Example 8 (32.1 mg, 0.0552 mmol).

RT 2.885 min (condition A). MS (ESI+) 482 (M+1, 100%)

Example 9

Methyl 4-{(2S,3S)-1-[trans-4-(1-aminoethyl)cyclohexanecarbonyl]-3-phenylpyrrolidine-2-carboxamide}-3-methylbenzoate trifluoroacetate

[Formula 688]

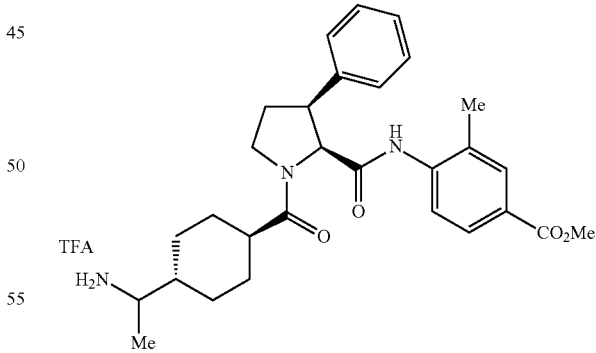

The same procedure as described in Example 1 was carried out to obtain the title compound (32.7 mg, 85%) from the compound of Reference Example 9 (37.4 mg, 0.0632 mmol).

RT 3.201 min (condition A). MS (ESI+) 492 (M+1, 100%)

Example 10

4-{(2S,3S)-1-[trans-4-(1-Aminoethyl)cyclohexanecarbonyl]-3-phenylpyrrolidine-2-carboxamide}-3-methylbenzoic acid hydrochloride

[Formula 689]

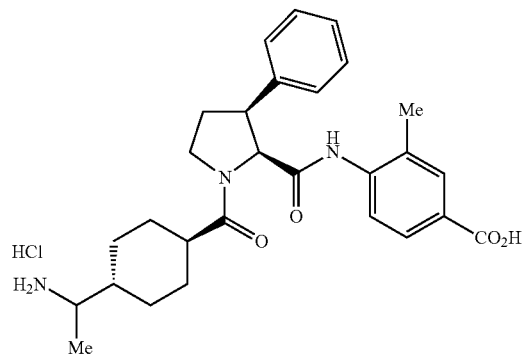

The same procedure as described in Example 2 was carried out to obtain the title compound (32.3 mg, 100%) from the compound of Reference Example 10 (30.9 mg, 0.0535 mmol).

RT 2.889 min (condition A). MS (ESI+) 478 (M+1, 100%)

Example 11

(2S,3S)-1-[trans-4-(1-Aminoethyl)cyclohexanecarbonyl]-3-cyclohexyl-N-(quinolin-6-yl)pyrrolidine-2-carboxamide

[Formula 690]

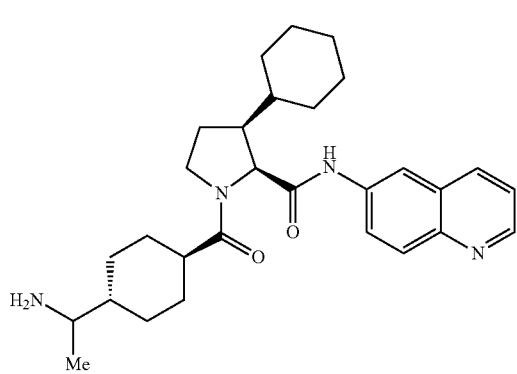

To a solution of the compound of Reference Example 11 (40.5 mg, 0.0702 mmol) in chloroform (1 mL), trifluoroacetic acid (0.5 mL) was added, and the mixture was stirred for 3 hours. After the mixture was concentrated under reduced pressure, then toluene (2 mL) was added for concentration under reduced pressure. A saturated aqueous solution of sodium bicarbonate was added to the residue, followed by extraction with chloroform. The organic layer was washed with a saturated saline solution, then dried over sodium sulfate and filtered, and the filtrate was concentrated under reduced pressure to obtain the title compound (30.2 mg, 90%).

RT 2.957 min (condition A). MS (ESI+) 477 (M+1, 69%)

Examples 12 to 18

According to the procedure described in Example 1, the compounds of Examples 12 to 18 were obtained from the compounds of Reference Examples 12 to 18.

[Formula 691]

Example 12

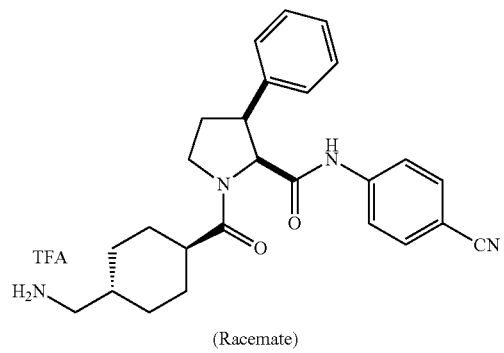

(Racemate)

Example 13

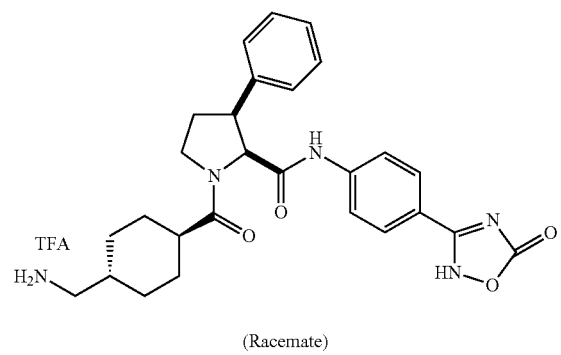

(Racemate)

Example 14

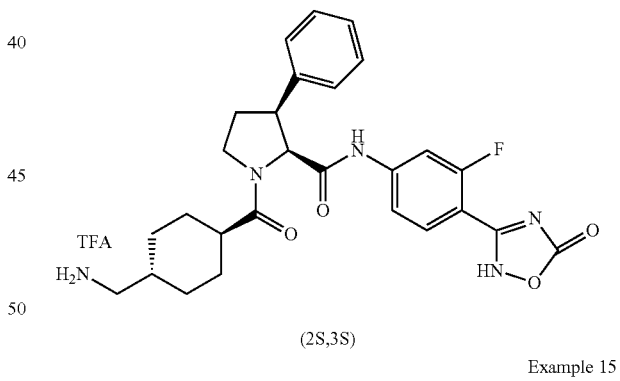

(2S,3S)

Example 15

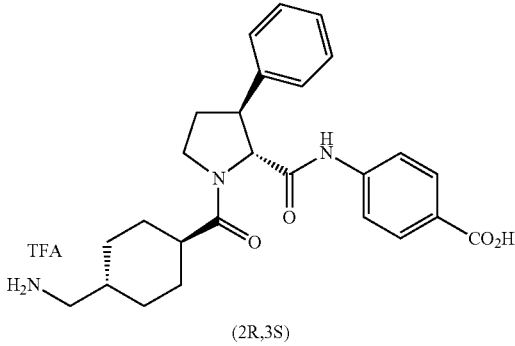

(2R,3S)

-continued

[Formula 692]

Example 16

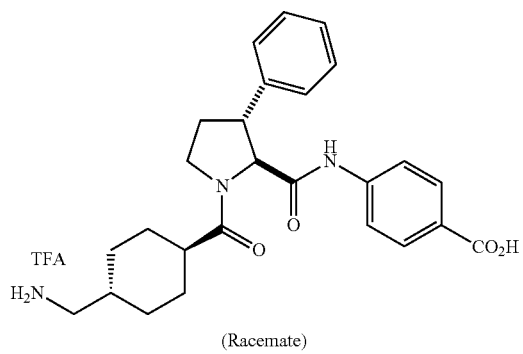

(Racemate)

Example 17

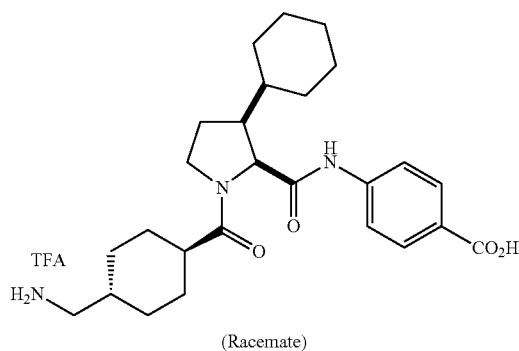

(Racemate)

Example 18

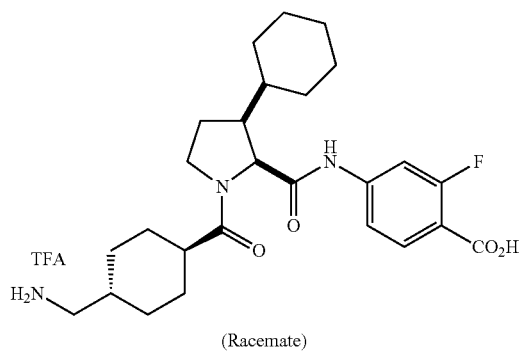

(Racemate)

TABLE 1

| Example | Instrumental analysis data |
|---|---|
| 12 | RT 3.163 min (Condition A). MS (ESI+) 431 (M + 1, 100%) |
| 13 | RT 3.037 min (Condition A). MS (ESI+) 490 (M + 1, 100%) |
| 14 | RT 3.096 min (Condition A). MS (ESI+) 508 (M + 1, 100%) |
| 15 | RT 2.963 min (Condition A). MS (ESI+) 450 (M + 1, 100%) |
| 16 | RT 2.963 min (Condition A). MS (ESI+) 450 (M + 1, 100%) |
| 17 | RT 3.365 min (Condition A). MS (ESI+) 456 (M + 1, 100%) |
| 18 | RT 3.424 min (Condition A). MS (ESI+) 474 (M + 1, 100%) |

Examples 19 to 24

According to the procedure described in Example 2, the compounds of Examples 19 to 24 were obtained from the compounds of Reference Examples 19 to 24.

Example 19

(Racemate)

Example 20

(Racemate)

Example 21

(Racemate)

Example 22

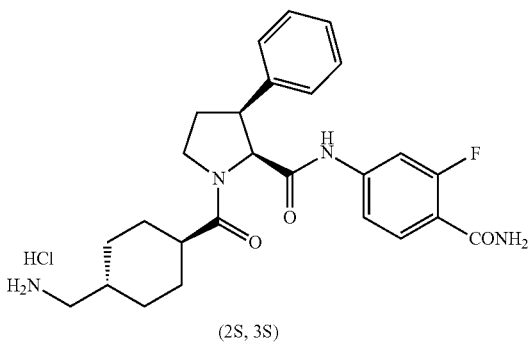

(2S, 3S)

Example 23

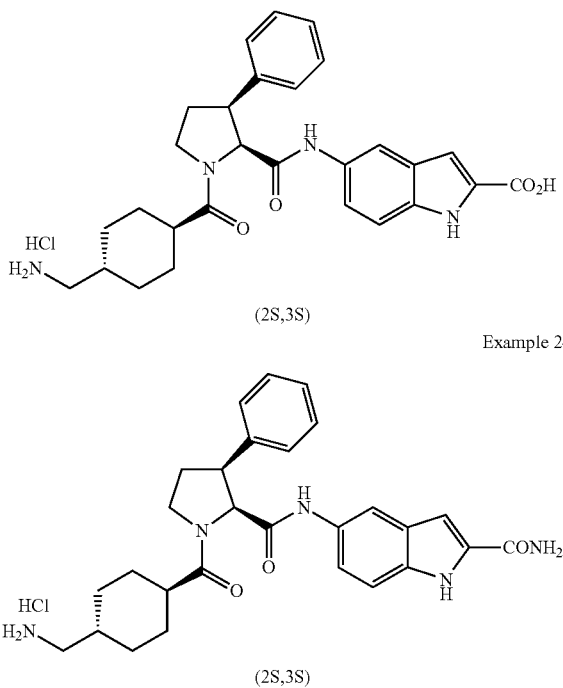

Example 25

4-{cis-1-[trans-4-(Hydroxymethyl)cyclohexanecarbonyl]-3-phenylpyrrolidine-2-carboxamide}benzoic acid

[Formula 693]

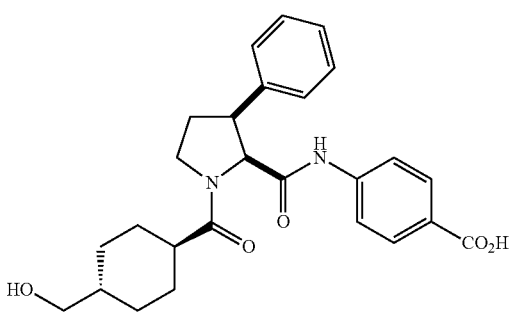

The same procedure as described in Reference Example 19 was carried out to obtain the title compound (25 mg, 83%) from the compound of Reference Example 25 (31 mg, 0.043 mmol).

RT 3.439 min (condition A). MS (ESI+) 451 (M+1, 100%)

Example 26

(2S,3S)-1-[trans-4-(1-Aminopropyl)cyclohexanecarbonyl]-3-cyclohexyl-N-(quinolin-6-yl)pyrrolidine-2-carboxamide bis(trifluoroacetate)

[Formula 694]

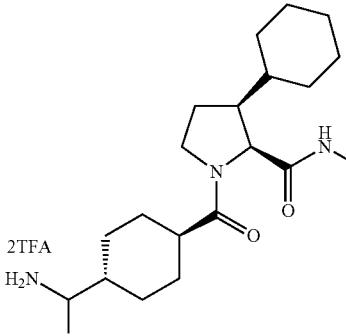

The same procedure as described in Example 1 was carried out to obtain the title compound (52.0 mg, 71%) from the compound of Reference Example 26 (60.0 mg, 0.102 mmol).

RT 3.171 min (condition A). MS (ESI+) 491 (M+1, 78%)

Example 27

4-{(2S,3S)-1-[trans-4-(1-Aminoethyl)cyclohexanecarbonyl]-3-cyclohexylpyrrolidine-2-carboxamide}-2-fluorobenzoate hydrochloride

[Formula 695]

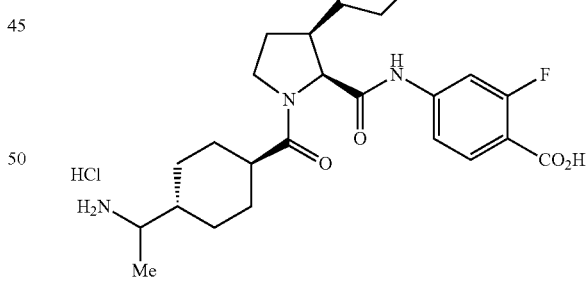

The same procedure as described in Example 2 was carried out to obtain the title compound (21.4 mg, 100%) from the compound of Reference Example 27 (19.0 mg, 0.0323 mmol).

RT 3.547 min (condition A). MS (ESI+) 488 (M+1, 100%)

Examples 28 to 40

The same procedure as described in Example 1 was carried out to obtain the compounds of Examples 28 to 40 from the compounds of Reference Examples 28 to 40.

TABLE 2

| Example | Instrumental analysis data |
| --- | --- |
| 19 | RT 3.017 min (Condition A). MS (ESI+) 480 (M + 1, 100%) |
| 20 | RT 3.139 min (Condition A). MS (ESI+) 484 (M + 1, 100%) |
| 21 | RT 2.693 min (Condition A). MS (ESI+) 457 (M + 1, 100%) |
| 22 | RT 2.965 min (Condition A). MS (ESI+) 467 (M + 1, 100%) |
| 23 | RT 3.274 min (Condition A). MS (ESI+) 489 (M + 1, 100%) |
| 24 | RT 2.883 min (Condition A). MS (ESI+) 488 (M + 1, 100%) |

[Formula 696]
Example 28
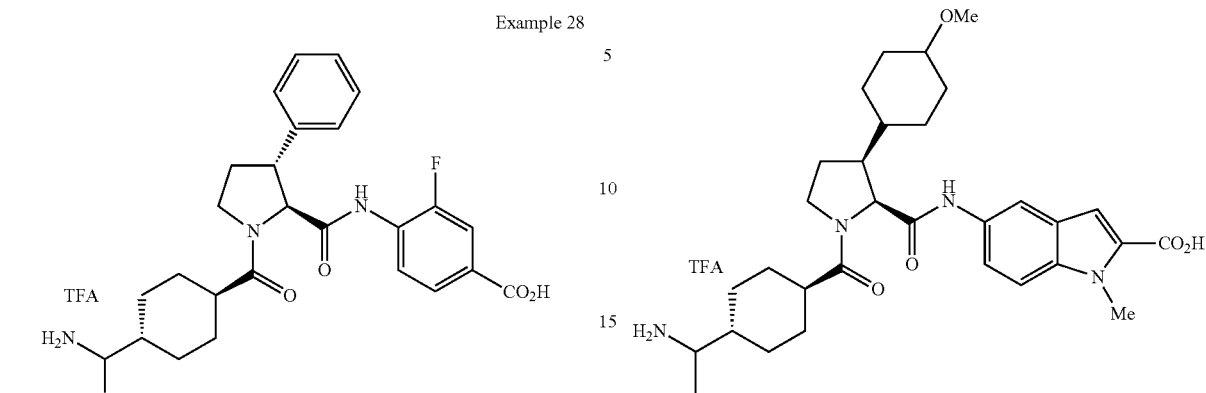
Example 29
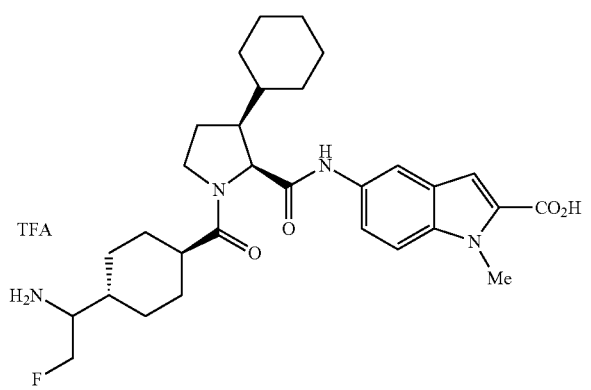
Example 30
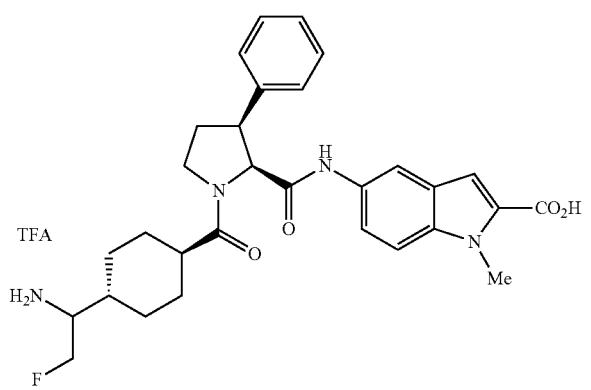
Example 31
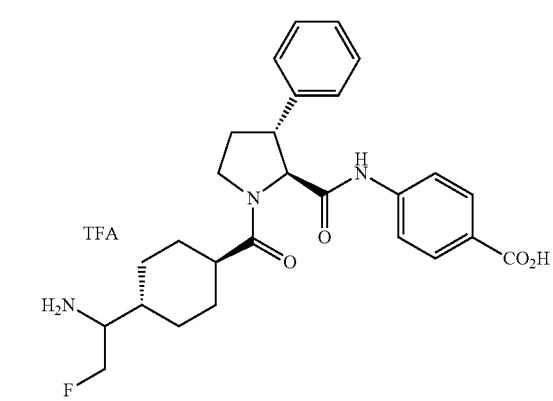
-continued
Example 32
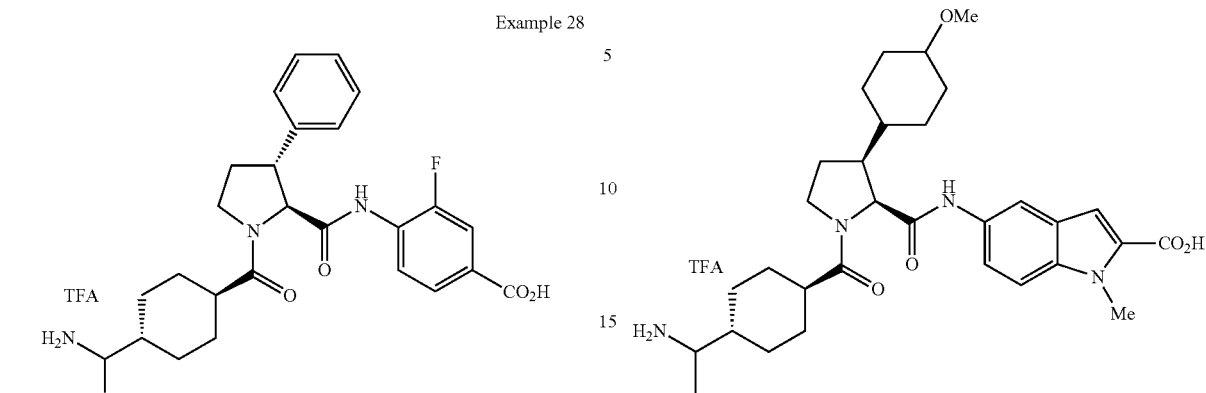
Example 33
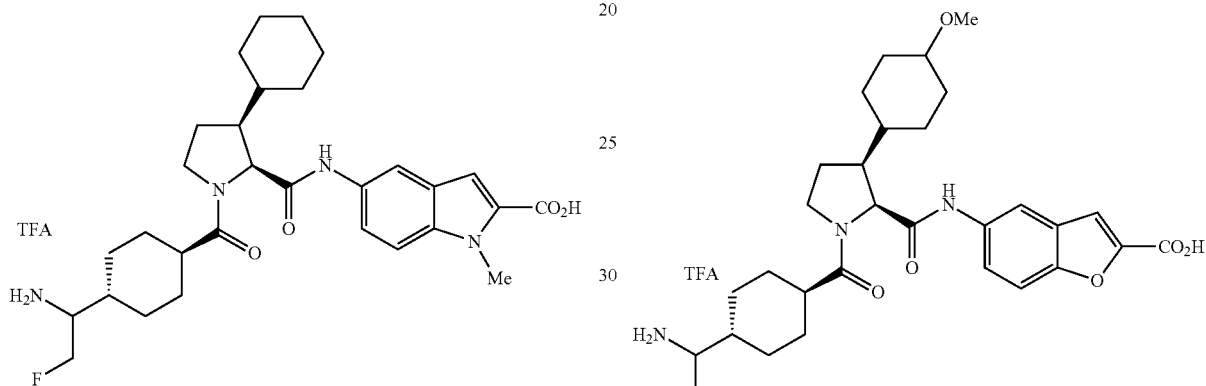
Example 34
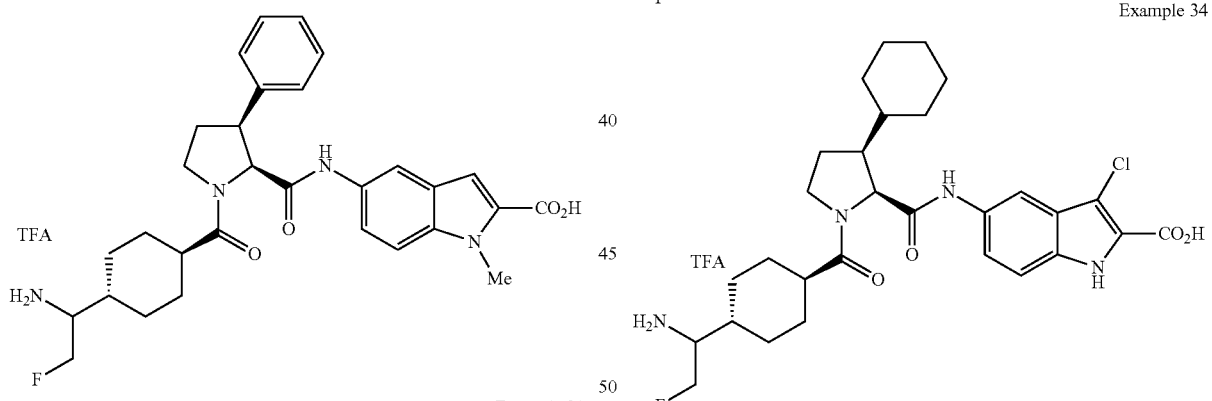
Example 35
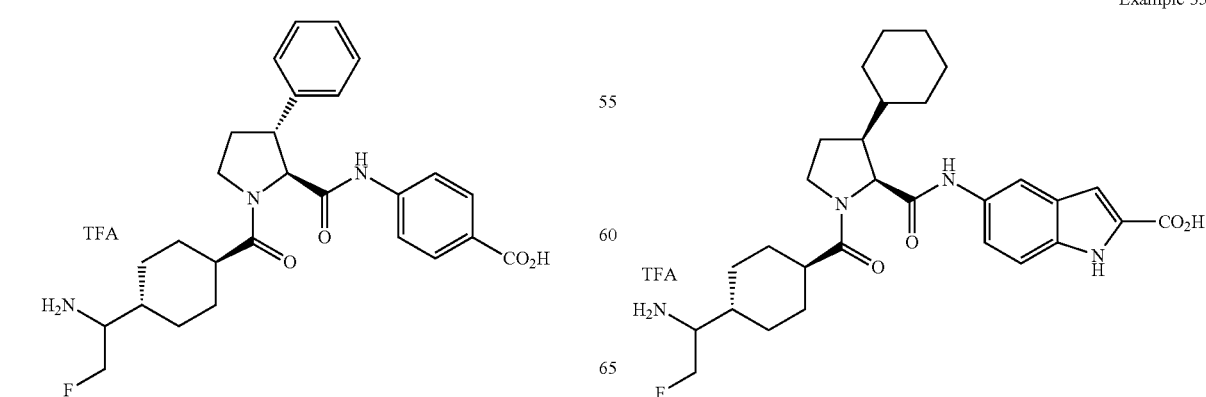

Example 36

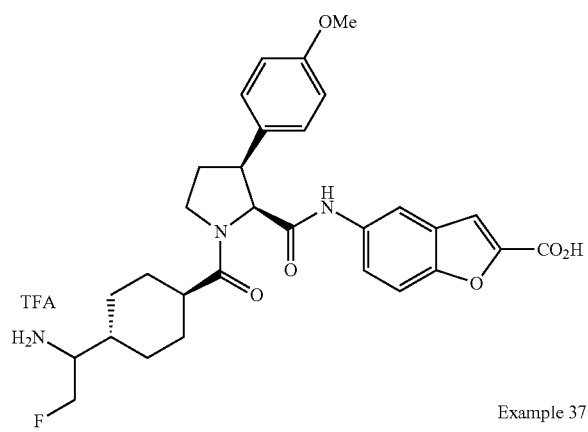

Example 37

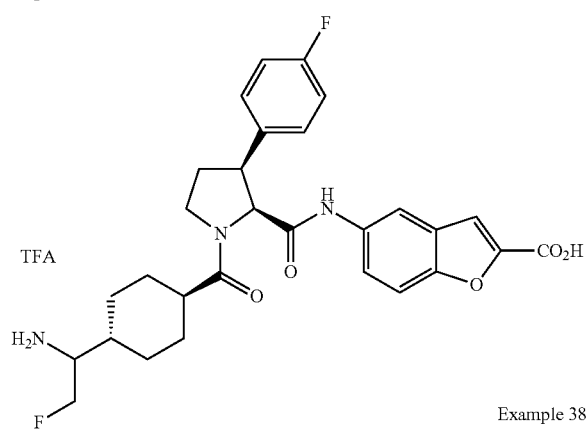

Example 38

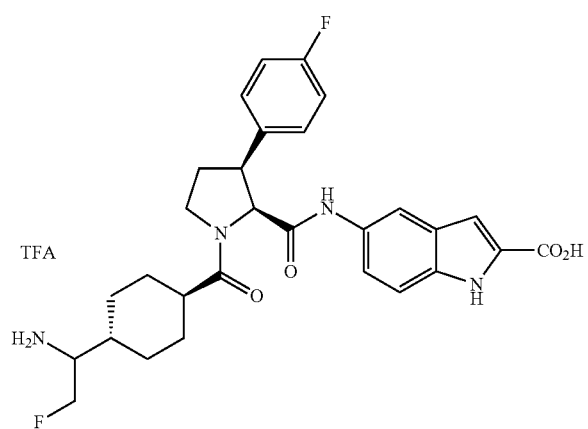

Example 39

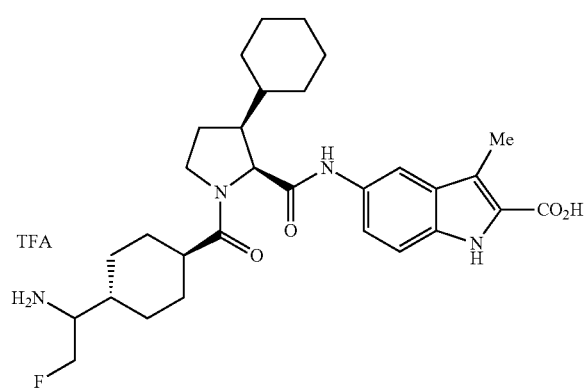

Example 40

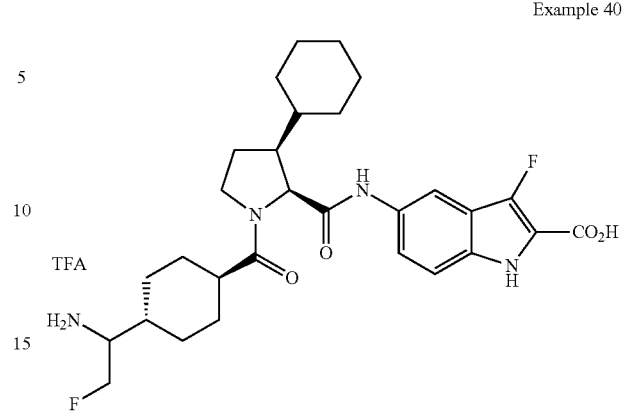

TABLE 3

| Example | Instrumental analysis data |
|---|---|
| 28 | RT 3.280 min (Condition A). MS (ESI+) 496 (M + 1, 100%) |
| 29 | RT 3.613 min (Condition A). MS (ESI+) 541 (M + 1, 100%) |
| 30 | RT 3.208 min (Condition A). MS (ESI+) 535 (M + 1, 100%) |
| 31 | RT 3.133 min (Condition A). MS (ESI+) 482 (M + 1, 100%) |
| 32 | RT 3.306 min (Condition A). MS (ESI+) 571 (M + 1, 100%) |
| 33 | RT 3.094, 3.213 min (Condition A). MS (ESI+) 558 (M + 1, 100%) |
| 34 | RT 3.635 min (Condition A). MS (ESI+) 561 (M + 1, 100%) |
| 35 | RT 3.501 min (Condition A). MS (ESI+) 527 (M + 1, 100%) |
| 36 | RT 3.133 min (Condition A). MS (ESI+) 552 (M + 1, 100%) |
| 37 | RT 3.224 min (Condition A). MS (ESI+) 540 (M + 1, 100%) |
| 38 | RT 3.165 min (Condition A). MS (ESI+) 539 (M + 1, 100%) |
| 39 | RT 3.643 min (Condition A). MS (ESI+) 541 (M + 1, 100%) |
| 40 | RT 3.609 min (Condition A). MS (ESI+) 545 (M + 1, 100%) |

Examples 41 to 57

The same procedure as described in Example 2 was carried out to obtain the compounds of Examples 41 to 57 from the compounds of Reference Examples 41 to 55.

[Formula 697]

Example 41

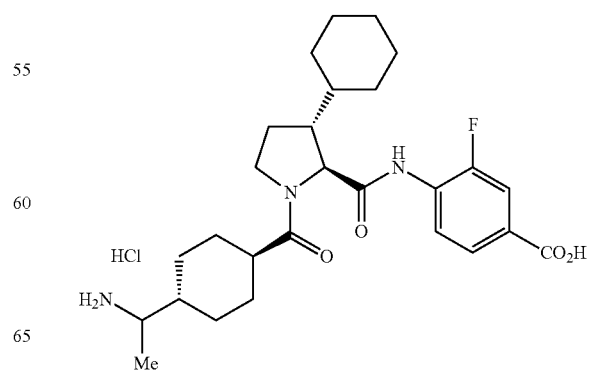

Example 42
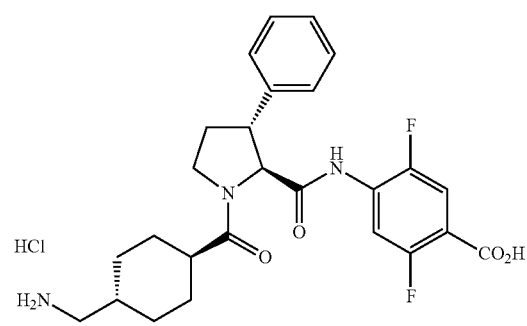
Example 43
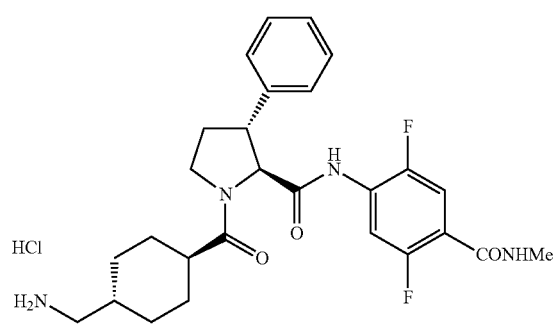
Example 44
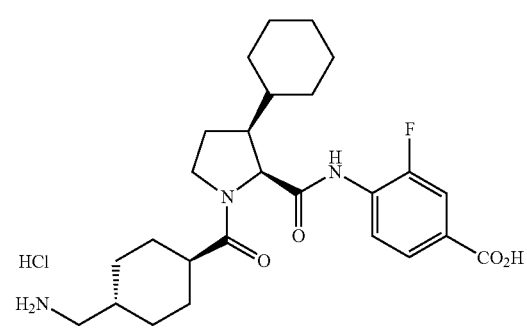
Example 45
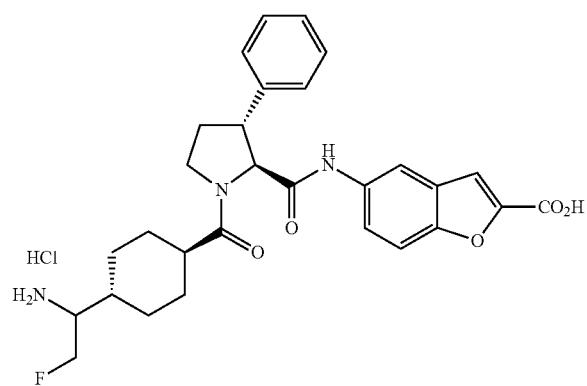
Example 46
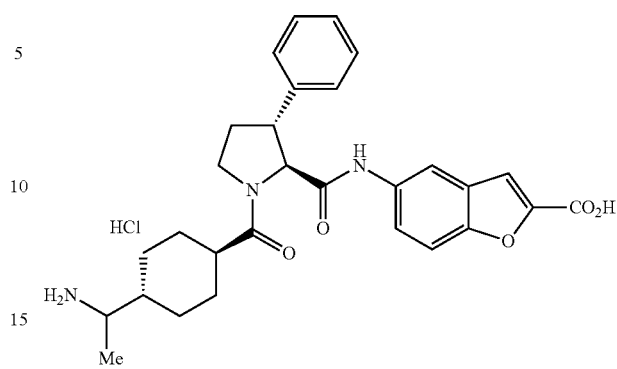
Example 47
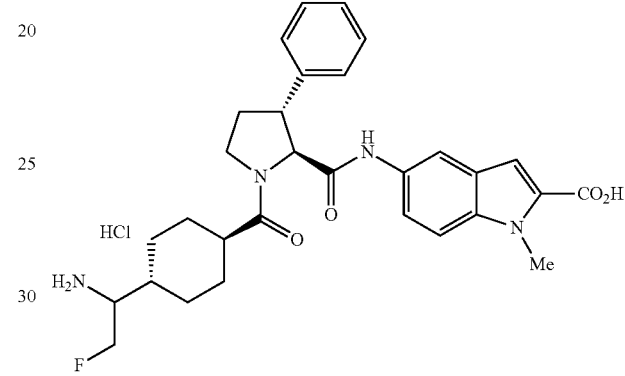
Example 48
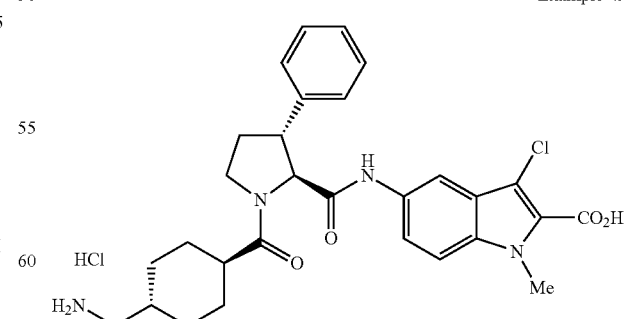
Example 49

Example 50
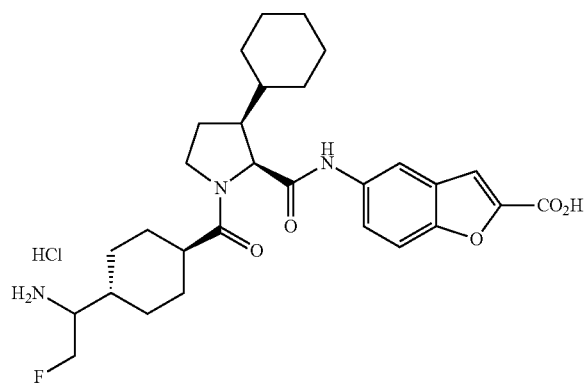
Example 51
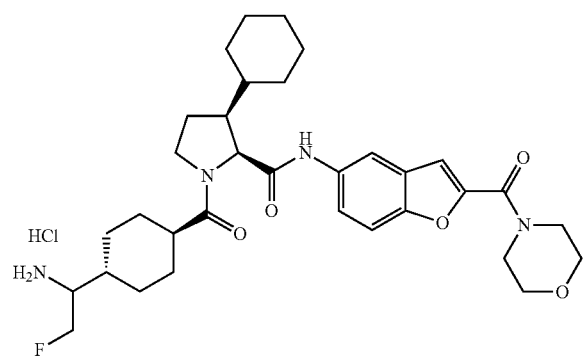
Example 52
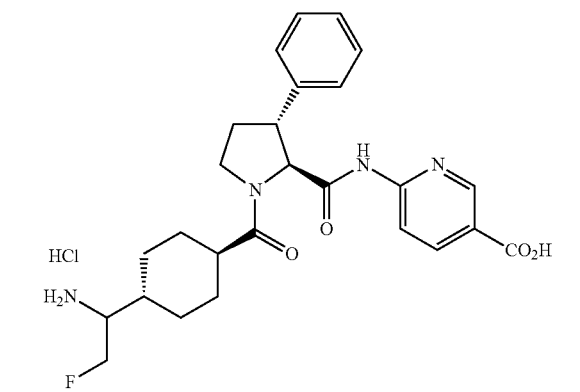
Example 53
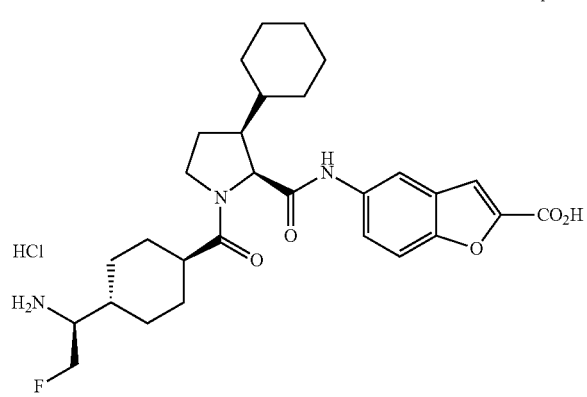
Example 54
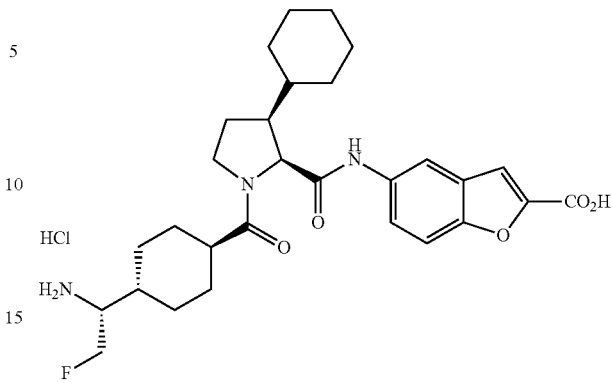
Example 55
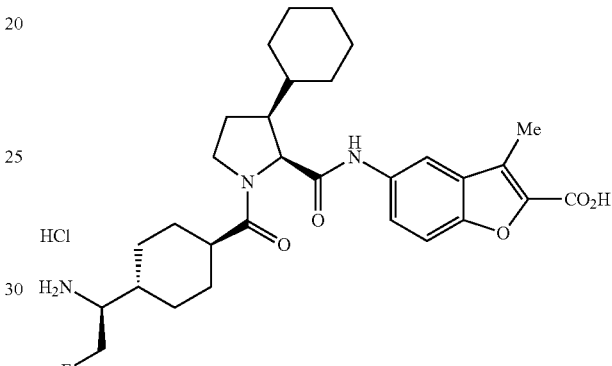
Example 56
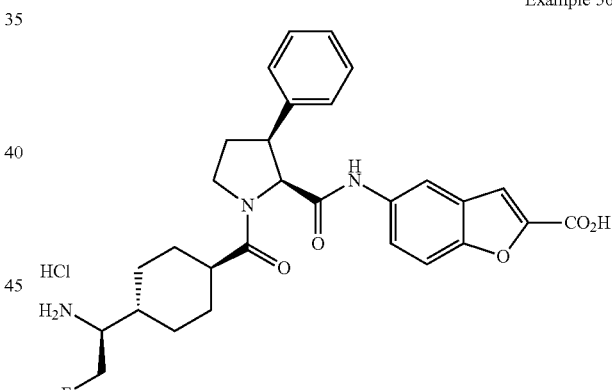
Example 57
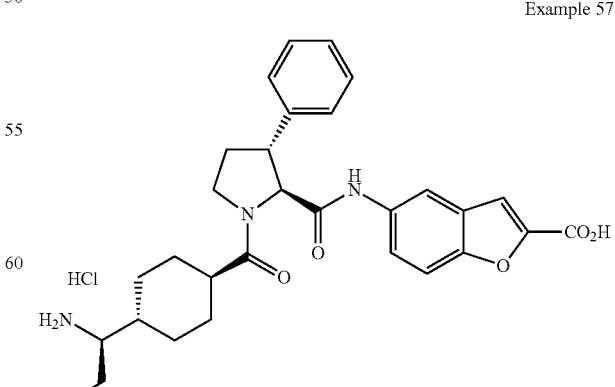

TABLE 4

| Example | Instrumental analysis data |
|---|---|
| 41 | RT 3.723 min (Condition A). MS (ESI+) 488 (M + 1, 100%) |
| 42 | RT 3.379 min (Condition A). MS (ESI+) 486 (M + 1, 100%) |
| 43 | RT 3.360 min (Condition A). MS (ESI+) 499 (M + 1, 100%) |
| 44 | RT 3.675 min (Condition A). MS (ESI+) 474 (M + 1, 100%) |
| 45 | RT 3.357 min (Condition A). MS (ESI+) 522 (M + 1, 72%) |
| 46 | RT 3.382 min (Condition A). MS (ESI+) 504 (M + 1, 100%) |
| 47 | RT 3.483 min (Condition A). MS (ESI+) 535 (M + 1, 100%) |
| 48 | RT 3.323 min (Condition A). MS (ESI+) 522 (M + 1, 100%) |
| 49 | RT 3.637 min (Condition A). MS (ESI+) 528 (M + 1, 100%) |
| 50 | RT 3.832 min (Condition A). MS (ESI+) 528 (M + 1, 100%) |
| 51 | RT 3.899 min (Condition A). MS (ESI+) 597 (M + 1, 100%) |
| 52 | RT 3.373 min (Condition A). MS (ESI+) 583 (M + 1, 100%) |
| 53 | $^1$H NMR (400 MHz, DMSO-$d_6$) δ 10.74 (s, 0.31H), 10.23 (s, 0.69H), 8.60-8.00 (br, 2H), 8.15 (s, 0.64H), 8.14 (s, 0.36H), 7.69-7.61 (m, 2H), 7.58-7.50 (m, 1H), 4.80-4.66 (m, 1H), 4.66-4.46 (m, 2H), 4.36 (br, 0.34H), 3.76 (m, 0.66H), 3.51-3.38 (m, 2H), 3.30-3.10 (m, 1H), 2.69-2.30 (m, 2H), 2.21-2.08 (m, 1H), 2.08-1.87 (m, 3H), 1.87-1.34 (m, 6H), 1.34-1.25 (m, 2H), 1.25-1.04 (m, 4H), 1.04-0.88 (m, 3H). RT 3.832 min (Condition A). MS (ESI+) 528 (M + 1, 100%) |
| 54 | RT 3.839 min (Condition A). MS (ESI+) 528 (M + 1, 100%) |
| 55 | RT 3.933 min (Condition A). MS (ESI+) 542 (M + 1, 100%) |
| 56 | RT 3.451 min (Condition A). MS (ESI+) 522 (M + 1, 100%) |
| 57 | RT 3.552 min (Condition A). MS (ESI+) 522 (M + 1, 72%) |

Example 58

(2S,3R)-1-[trans-4-(1-Aminoethyl)cyclohexanecarbonyl]-3-cyclohexyl-N-(quinolin-6-yl)pyrrolidine-2-carboxamide

[Formula 698]

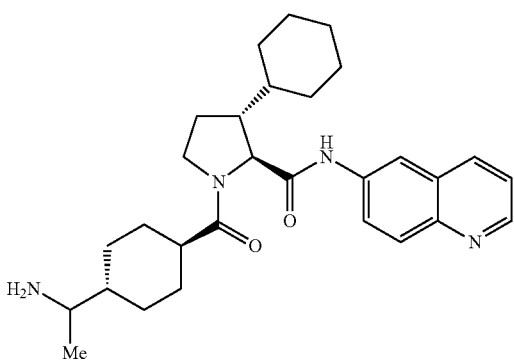

The same procedure as described in Example 11 was carried out to obtain the title compound (9.2 mg, 90%) from the compound of Reference Example 58 (12.4 mg, 0.0215 mmol).

RT 3.541 min (condition A). MS (ESI+) 477 (M+1, 64%)

Example 59

(2S,3S)-1-[trans-4-(1-Amino-2-fluoroethyl)cyclohexanecarbonyl]-3-cyclohexyl-N-(2-hydroxymethyl-1-benzofuran-5-yl)pyrrolidine-2-carboxamide

[Formula 699]

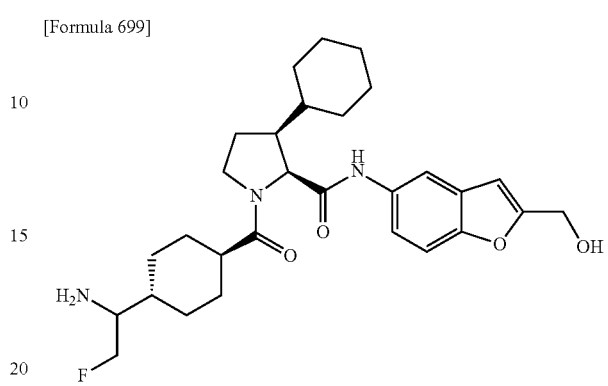

To a solution of the compound of Reference Example 59 (29.2 mg, 0.0476 mmol) in chloroform (2 mL), trifluoroacetic acid (0.5 mL) was added in an ice bath. After stirring at room temperature for 1 hour, the reaction solution was concentrated under reduced pressure. Toluene (2 mL) was added to the residue, and the solvent was concentrated under reduced pressure. Chloroform (2 mL) and hexane (2 mL) were further added and the solvent was concentrated under reduced pressure twice. The residue was dissolved in methanol (2 mL), potassium carbonate (13.1 mg, 0.0948 mmol) was added, and the mixture was stirred. After 2 hours, a saturated aqueous solution of sodium bicarbonate was added to the reaction solution, followed by extraction with chloroform twice, then the organic layer was dried over sodium sulfate and filtered, and then the solvent was concentrated under reduced pressure. The obtained residue was purified by silica gel column chromatography to obtain the title compound (10.7 mg, 44%).

RT 3.858 min (condition A). MS (ESI+) 514 (M+1, 64%)

Examples 60 to 68

The same procedure as described in Example 2 was carried out to obtain the compounds of Examples 60 to 68 from the compounds of Reference Examples 41-4, 42-4, 44-3, 46-1, 45-3, 47-5, 48-2, 50-3, and 52-3.

[Formula 700]

Example 60

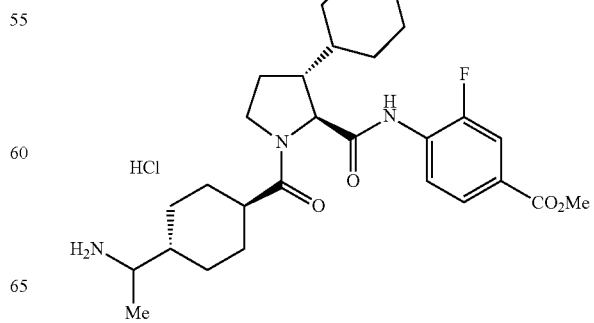

Example 61
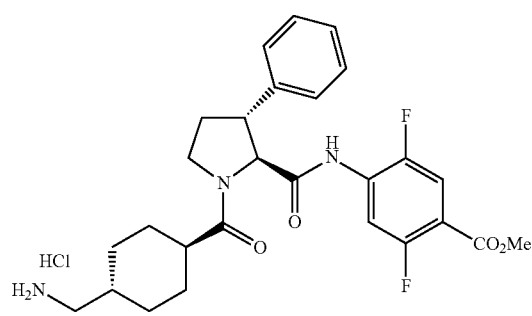
Example 62
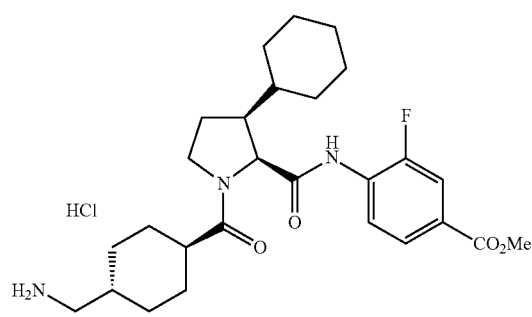
Example 63
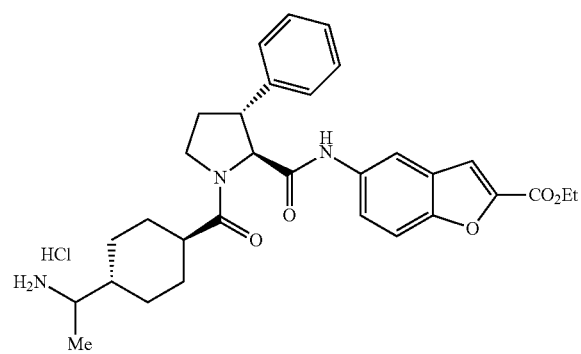
Example 64
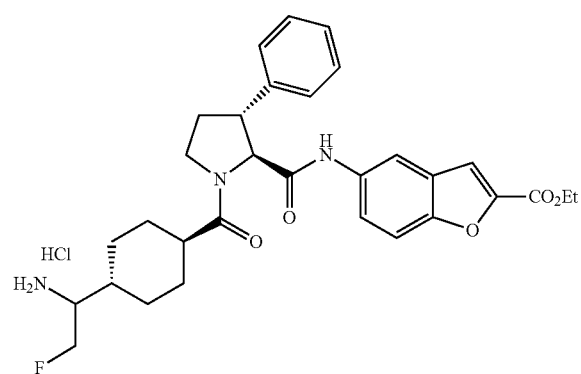
Example 65
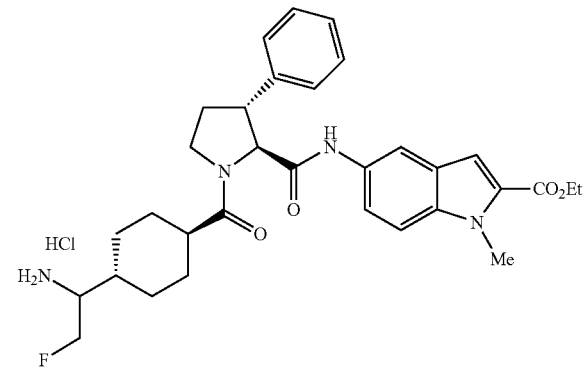
Example 66
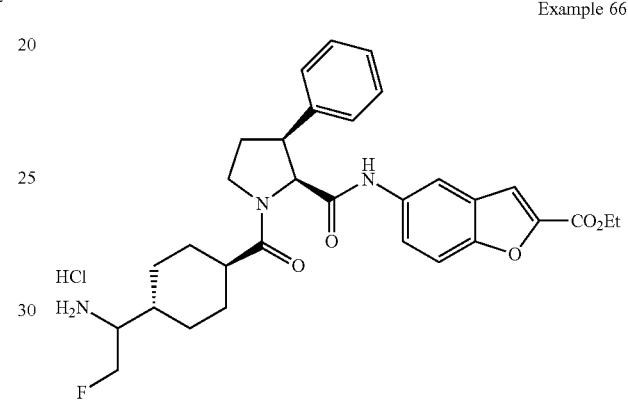
Example 67
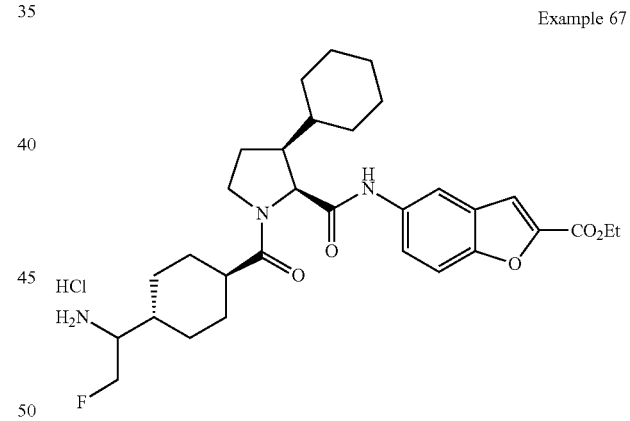
Example 68
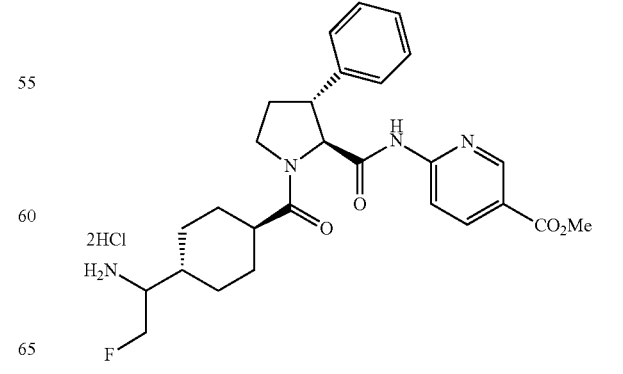

TABLE 5

| Example | Instrumental analysis data |
|---|---|
| 60 | RT 4.302 min (Condition A). MS (ESI+) 502 (M + 1, 100%) |
| 61 | RT 3.968 min (Condition A). MS (ESI+) 500 (M + 1, 89%) |
| 62 | RT 4.264 min (Condition A). MS (ESI+) 488 (M + 1, 100%) |
| 63 | RT 4.096 min (Condition A). MS (ESI+) 532 (M + 1, 100%) |
| 64 | RT 4.0617 min (Condition A). MS (ESI+) 550 (M + 1, 72%) |
| 65 | RT 4.173 min (Condition A). MS (ESI+) 563 (M + 1, 100%) |
| 66 | RT 4.021 min (Condition A). MS (ESI+) 550 (M + 1, 100%) |
| 67 | RT 4.421 min (Condition A). MS (ESI+) 556 (M + 1, 100%) |
| 68 | RT 3.832 min (Condition A). MS (ESI+) 497 (M + 1, 100%) |

Examples 69 to 82

The same procedure as described in Example 2 was carried out to obtain the compounds of Examples 69 to 82 from the compounds of Reference Examples 60 to 73.

[Formula 701]

Example 69

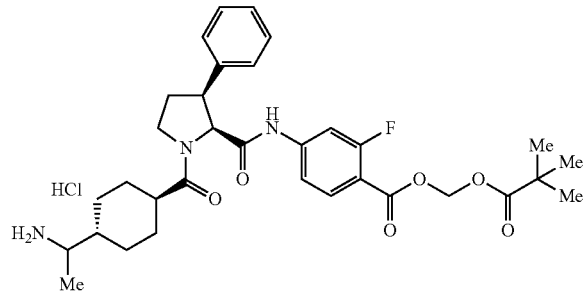

Example 70

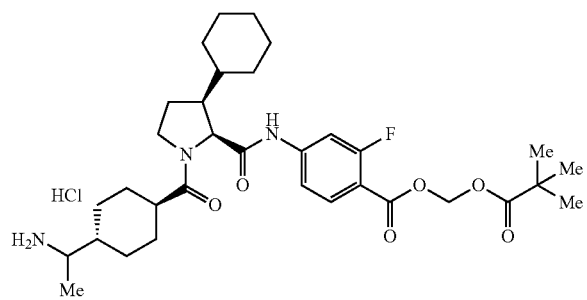

Example 71

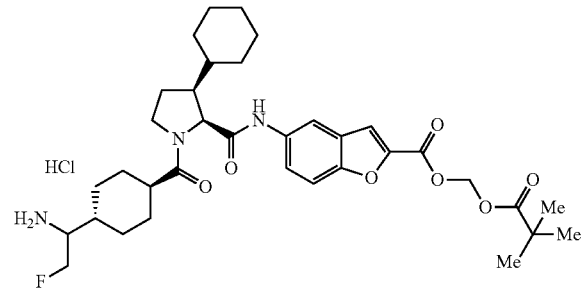

Example 72

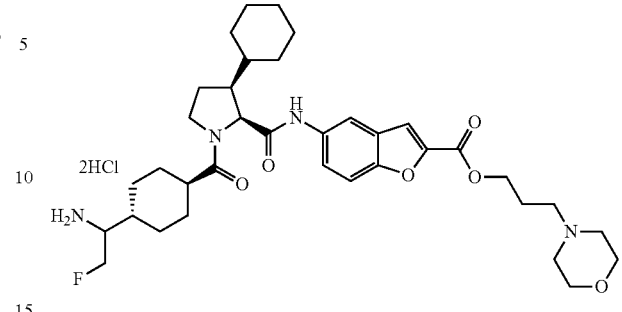

Example 73

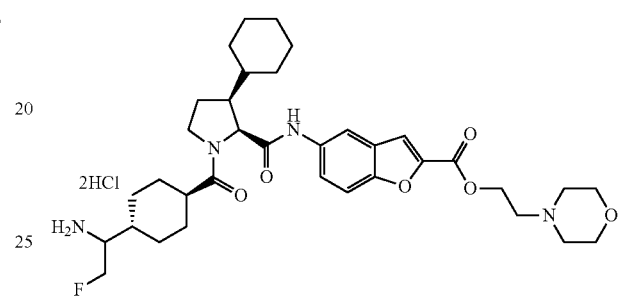

Example 74

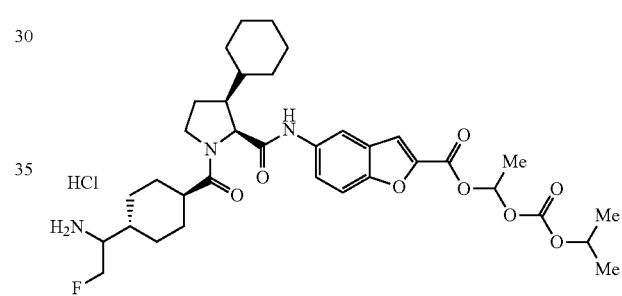

Example 75

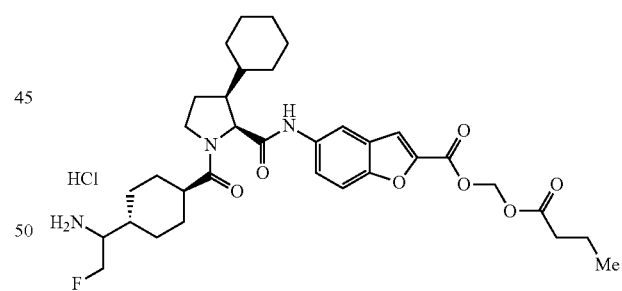

Example 76

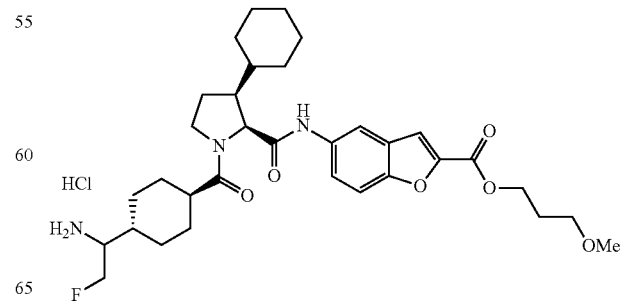

Example 77

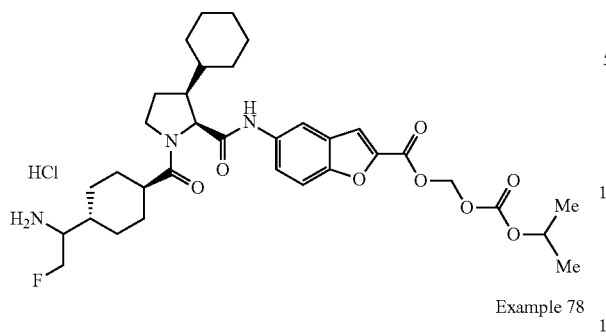

Example 78

Example 79

Example 80

Example 81

Example 82

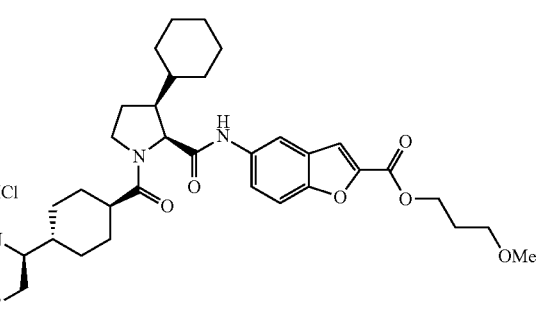

TABLE 6

| Example | Instrumental analysis data |
|---|---|
| 69 | RT 4.403 min (Condition A). MS (ESI+) 595 (M + 1, 100%) |
| 70 | RT 4.810 min (Condition A). MS (ESI+) 602 (M + 1, 100%) |
| 71 | RT 4.765 min (Condition A). MS (ESI+) 642 (M + 1, 100%) |
| 72 | RT 3.803 min (Condition A). MS (ESI+) 655 (M + 1, 100%) |
| 73 | RT 3.771 min (Condition A). MS (ESI+) 641 (M + 1, 72%) |
| 74 | RT 4.741 min (Condition A). MS (ESI+) 658 (M + 1, 100%) |
| 75 | RT 4.685 min (Condition A). MS (ESI+) 628 (M + 1, 100%) |
| 76 | RT 4.504 min (Condition A). MS (ESI+) 600 (M + 1, 100%) |
| 77 | RT 4.680 min (Condition A). MS (ESI+) 644 (M + 1, 100%) |
| 78 | RT 4.621 min (Condition A). MS (ESI+) 614 (M + 1, 100%) |
| 79 | RT 4.520 min (Condition A). MS (ESI+) 612 (M + 1, 100%) |
| 80 | RT 4.155 min (Condition A). MS (ESI+) 594 (M + 1, 100%) |
| 81 | RT 4.229 min (Condition A). MS (ESI+) 594 (M + 1, 100%) |
| 82 | RT 4.552 min (Condition A). MS (ESI+) 600 (M + 1, 100%) |

Examples 83 to 95

The same procedure as described in Example 1 was carried out to obtain the compounds of Examples 83 to 95 from the compounds of Reference Examples 74, 28-3, 75, 29-3, 30-3, 32-6, 35-2, 34-4, 37-6, 38-3, 39-5, 76, and 77.

[Formula 702]

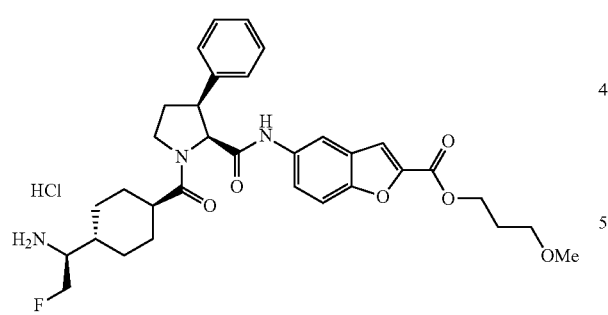

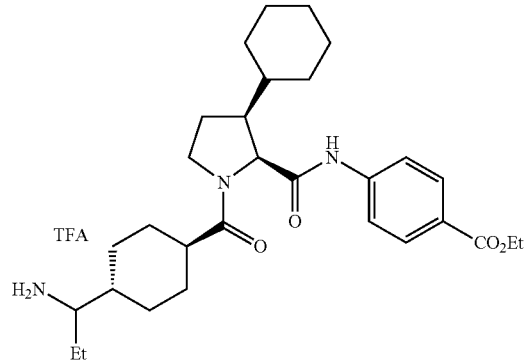

Example 83

Example 84
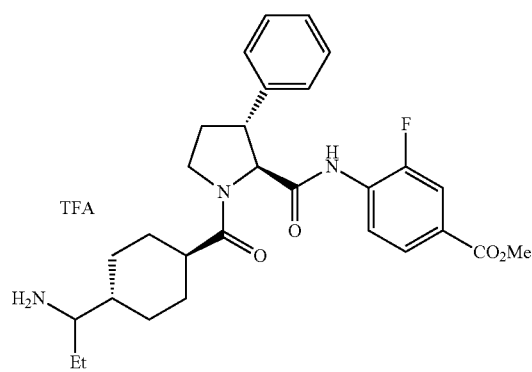
Example 85
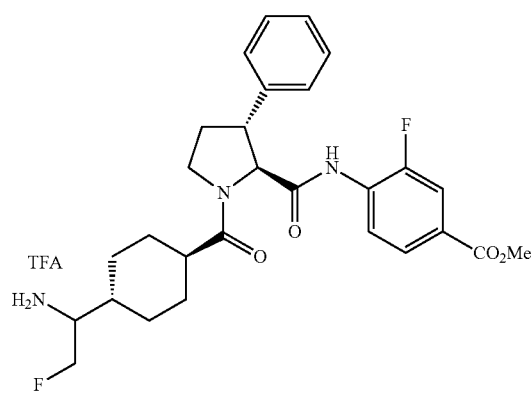
Example 86
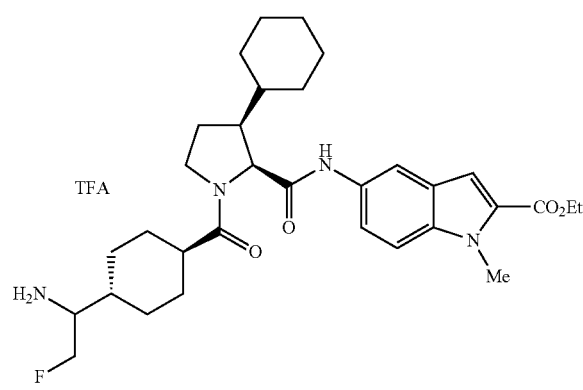
Example 87
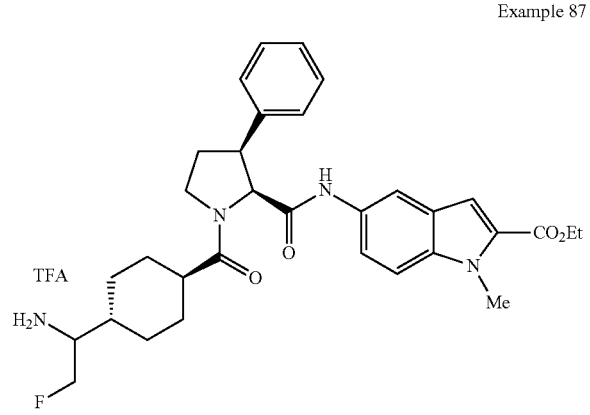
Example 88
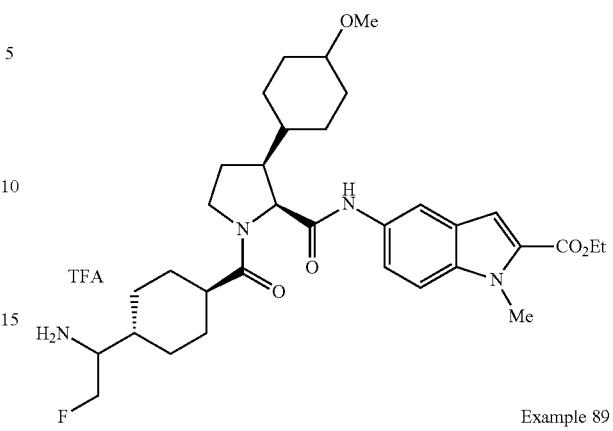
Example 89
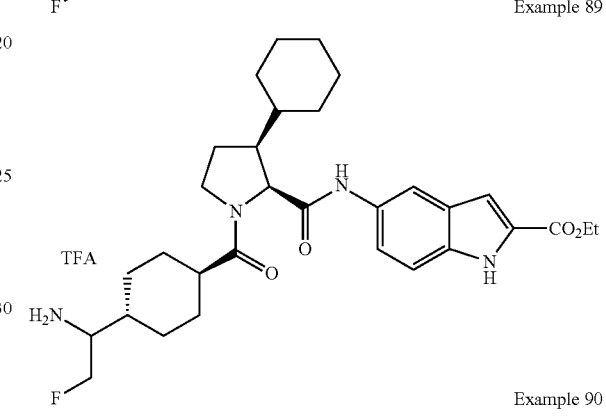
Example 90
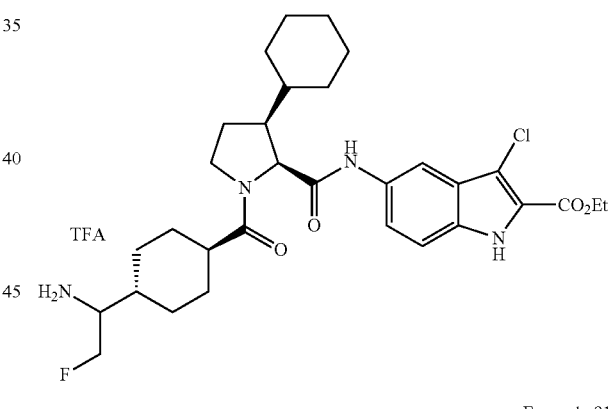
Example 91
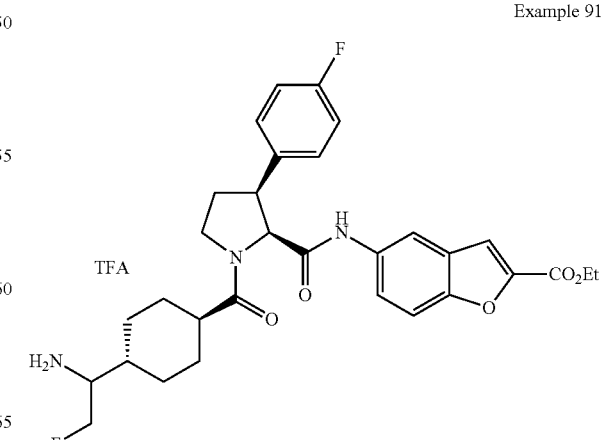

Example 92

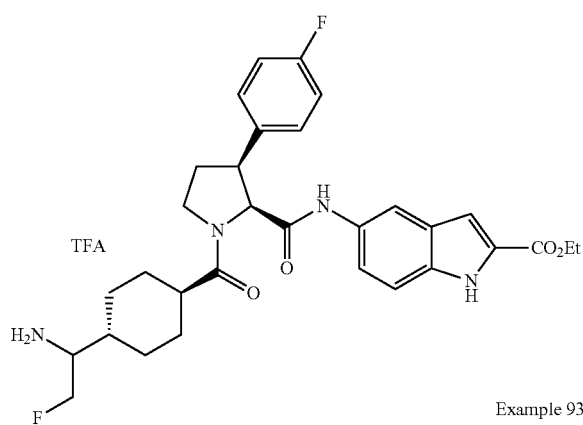

Example 93

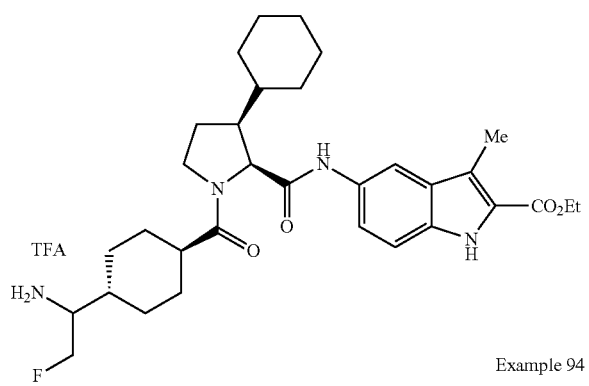

Example 94

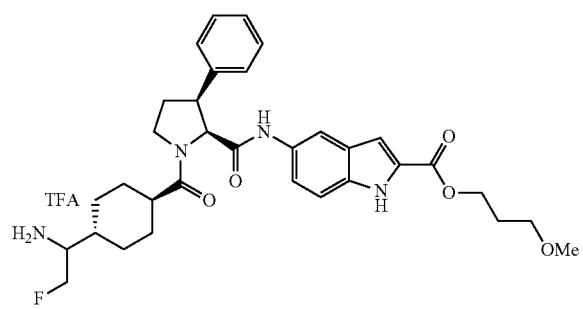

[Formula 703]

Example 96

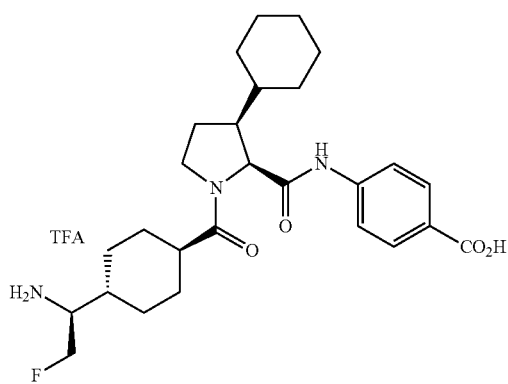

Example 95

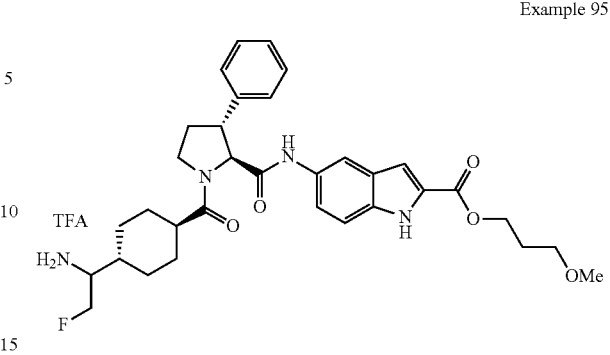

TABLE 7

| Example | Instrumental analysis data |
|---|---|
| 83 | RT 4.630 min (Condition A). MS (ESI+) 512 (M + 1, 100%) |
| 84 | RT 4.192 min (Condition A). MS (ESI+) 510 (M + 1, 100%) |
| 85 | RT 4.133 min (Condition A). MS (ESI+) 514 (M + 1, 100%) |
| 86 | RT 4.684 min (Condition A). MS (ESI+) 569 (M + 1, 60%) |
| 87 | RT 4.331 min (Condition A). MS (ESI+) 563 (M + 1, 70%) |
| 88 | RT 4.267, 4.440 min (Condition A). MS (ESI+) 599 (M + 1, 60%) |
| 89 | RT 4.488 min (Condition A). MS (ESI+) 555 (M + 1, 100%) |
| 90 | RT 4.640 min (Condition A). MS (ESI+) 589 (M + 1, 100%) |
| 91 | RT 4.296 min (Condition A). MS (ESI+) 568 (M + 1, 100%) |
| 92 | RT 4.184 min (Condition A). MS (ESI+) 567 (M + 1, 100%) |
| 93 | RT 4.640 min (Condition A). MS (ESI+) 569 (M + 1, 100%) |
| 94 | RT 4.157 min (Condition A). MS (ESI+) 593 (M + 1, 100%) |
| 95 | RT 4.229 min (Condition A). MS (ESI+) 593 (M + 1, 100%) |

Examples 96 to 116

The same procedure as described in Example 1 was carried out to obtain the compounds of Examples 96 to 116 from the compounds of Reference Examples 78 to 96 and Reference Example 140.

Example 97

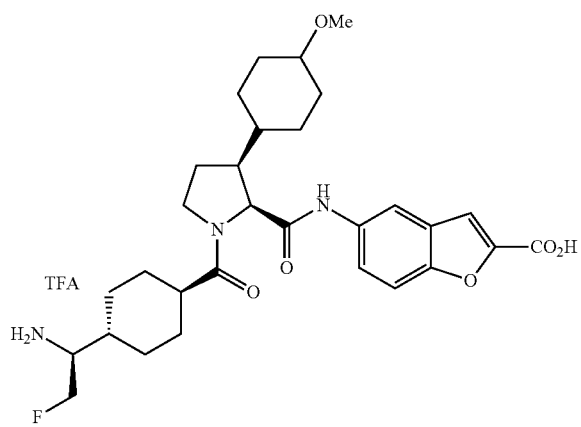

Example 98
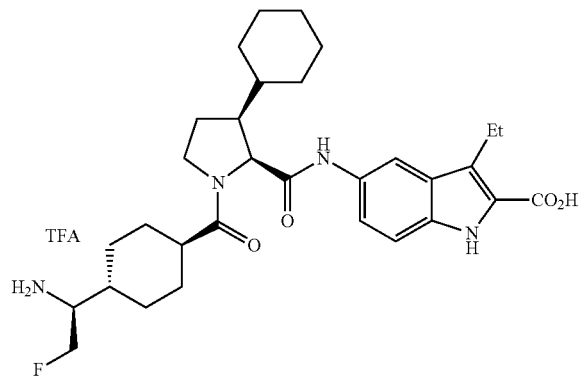
Example 99
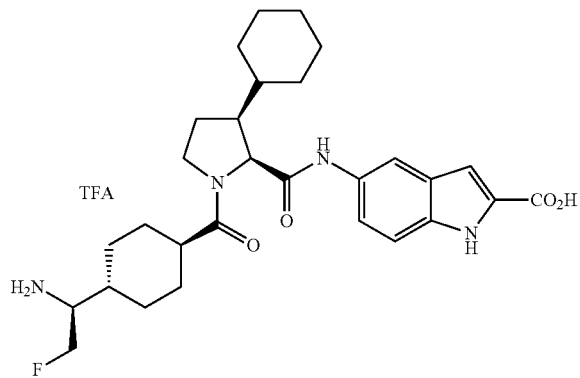
Example 100
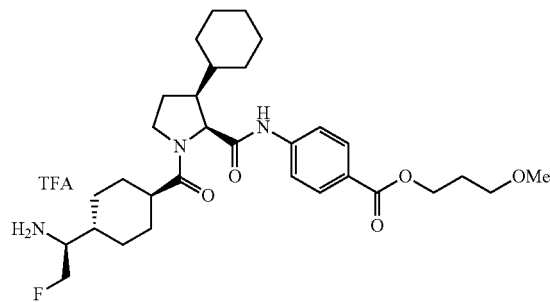
Example 101
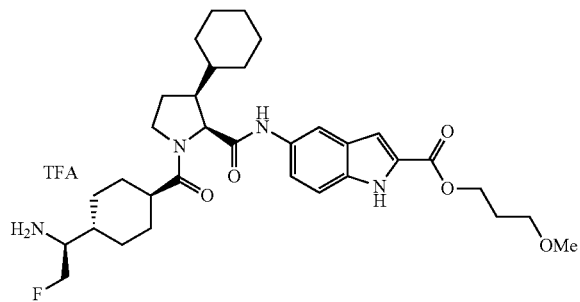
Example 102
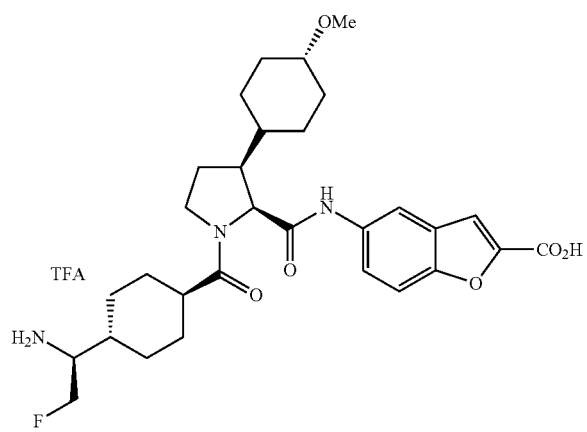
Example 103
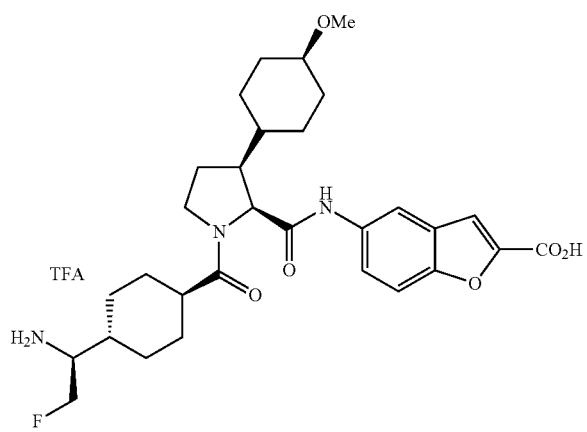
Example 104
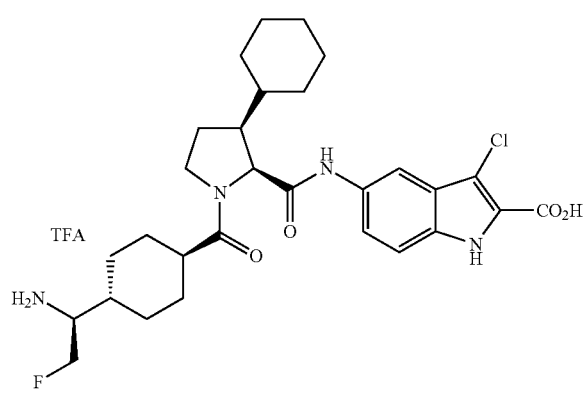
Example 105
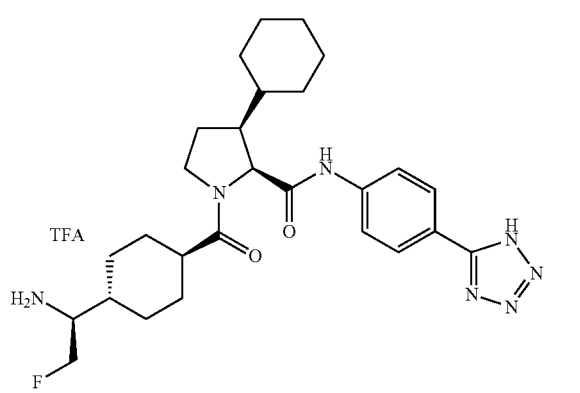

-continued
Example 106
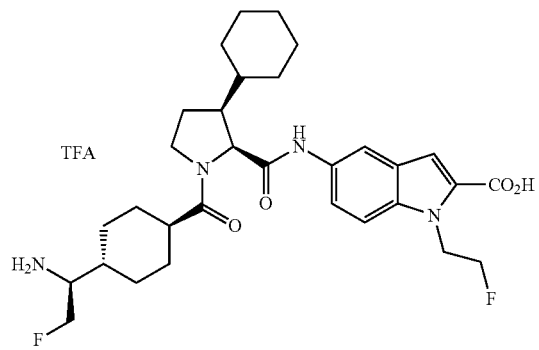
Example 107
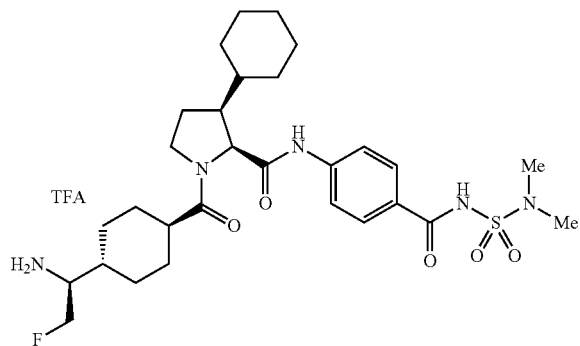
Example 108
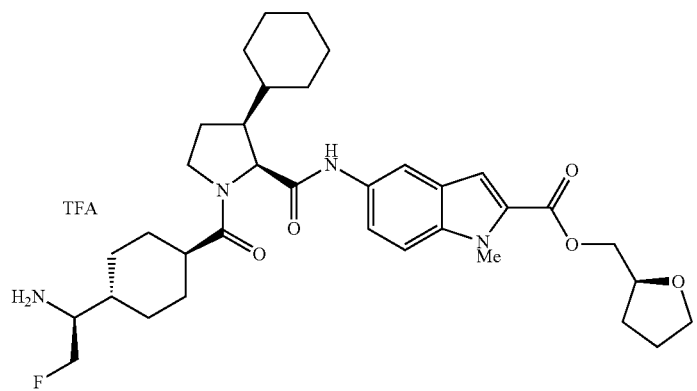
Example 109
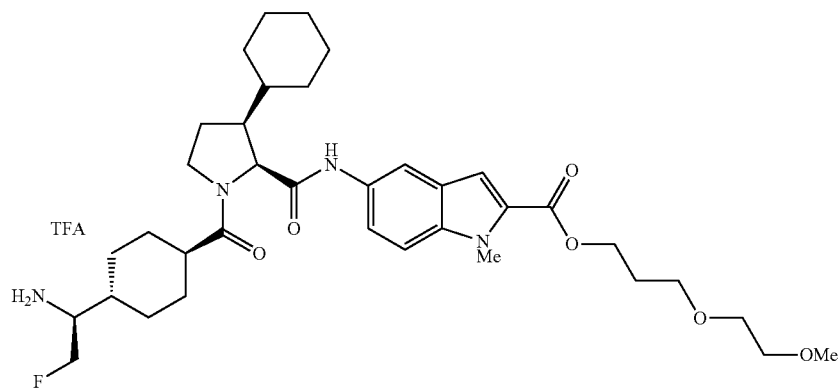
Example 110
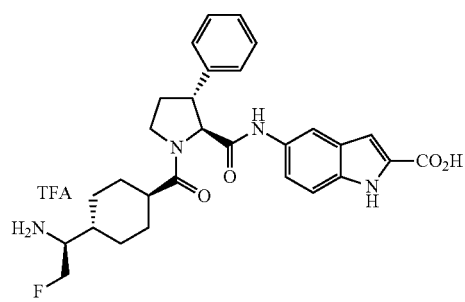
Example 111
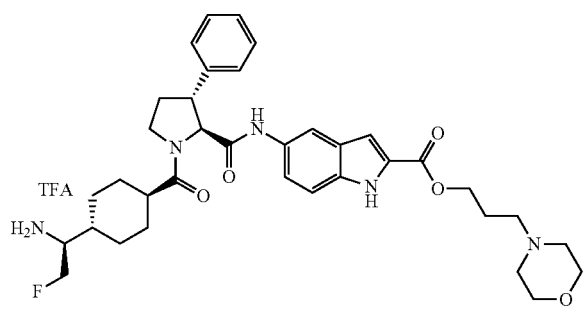

-continued

Example 112

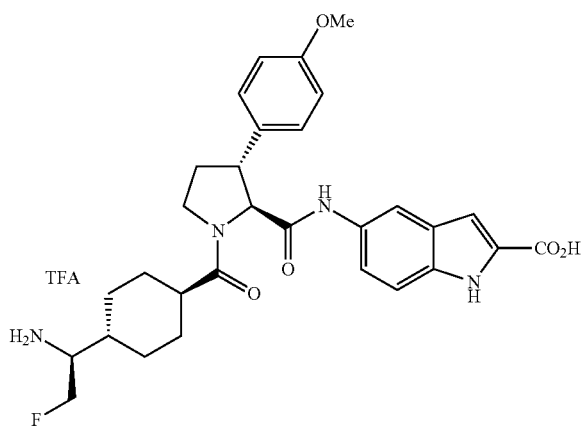

Example 113

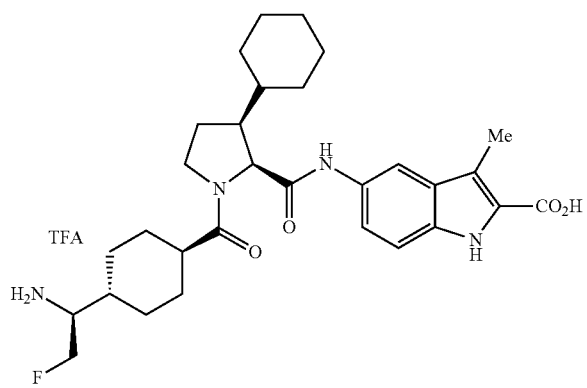

Example 114

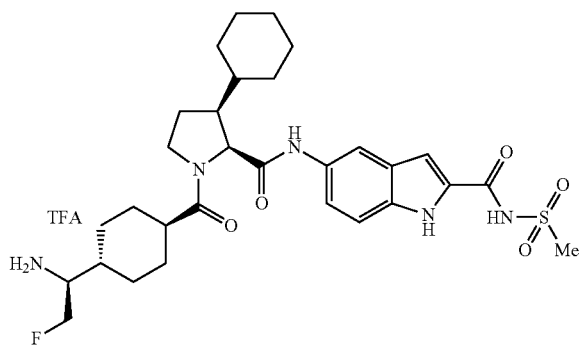

Example 115

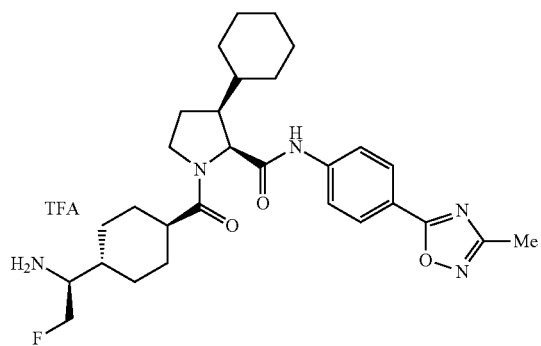

Example 116

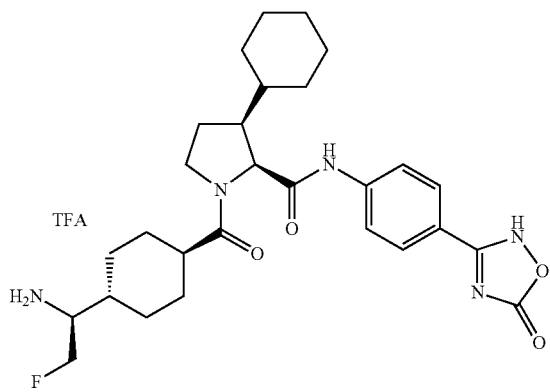

TABLE 8

| Example | Instrumental analysis data |
|---|---|
| 96 | RT 3.977 min (Kinetex 1.7μ C18 100A, 0.1% trifluoro acetic acid in water/acetonitrile, acetonitrile 1-99% 7.0 min, 0.9 mL/min (Condition B)). MS (ESI+) 488 (M + 1, 100%) |
| 97 | RT 3.618 min (Condition B). MS (ESI+) 588 (M + 1, 100%) |
| 98 | RT 4.134 min (Condition B). MS (ESI+) 555 (M + 1, 100%) |
| 99 | RT 3.917 min (Condition B). MS (ESI+) 527 (M + 1, 100%) |
| 100 | RT 4.557 min (Condition B). MS (ESI+) 560 (M + 1, 100%) |
| 101 | RT 4.403 min (Condition B). MS (ESI+) 599 (M + 1, 100%) |
| 102 | $^1$H NMR (400 MHz, DMSO-$d_6$) δ 10.77 (s, 0.27H), 10.24 (s, 0.63H), 8.12-8.08 (m, 1H), 7.67-7.62 (m, 2H), 7.55-7.49 (m, 1H), 4.77-4.66 (m, 1H), 4.63-4.55 (m, 1H), 4.51-4.50 (m, 1H), 3.77-3.73 (m, 1H), 3.20-3.16 (m, 2H), 3.14 (s, 3H), 3.04-2.97 (m, 2H), 2.42-2.36 (m, 1H), 2.19-2.17 (m, 1H), 1.98-1.90 (m, 4H), 1.81-1.57 (m, 6H), 1.31-0.75 (m, 9H). RT 3.527 min (Condition B). MS (ESI+) 558 (M + 1, 100%) |

TABLE 8-continued

| Example | Instrumental analysis data |
|---|---|
| 103 | RT 3.581 min (Condition B). MS (ESI+) 558 (M + 1, 100%) |
| 104 | RT 4.080 min (Condition B). MS (ESI+) 561 (M + 1, 100%) |
| 105 | RT 3.934 min (Condition B). MS (ESI+) 670 (M + 1, 100%) |
| 106 | RT 4.174 min (Condition B). MS (ESI+) 573 (M + 1, 100%) |
| 107 | RT 4.207 min (Condition B). MS (ESI+) 594 (M + 1, 100%) |
| 108 | RT 4.683 min (Condition B). MS (ESI+) 625 (M + 1, 100%) |
| 109 | RT 4.659 min (Condition B). MS (ESI+) 657 (M + 1, 100%) |
| 110 | RT 3.595 min (Condition B). MS (ESI+) 521 (M + 1, 100%) |
| 111 | RT 3.325 min (Condition B). MS (ESI+) 648 (M + 1, 100%) |
| 112 | RT 3.571 min (Condition B). MS (ESI+) 551 (M + 1, 100%) |
| 113 | RT 4.028 min (Condition B). MS (ESI+) 541 (M + 1, 100%) |
| 114 | RT 3.972 min (Condition B). MS (ESI+) 604 (M + 1, 100%) |
| 115 | RT 4.455 min (Condition B). MS (ESI+) 526 (M + 1, 100%) |
| 116 | RT 4.036 min (Condition B). MS (ESI+) 528 (M + 1, 100%) |

Examples 117 to 130
The same procedure as described in Example 1 was carried out to obtain the compounds of Examples 117 to 130 from the compounds of Reference Examples 97 to 110.
[Formula 704]
Example 117
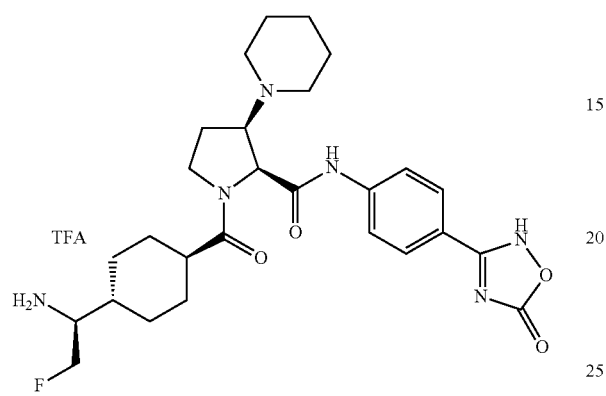
Example 118
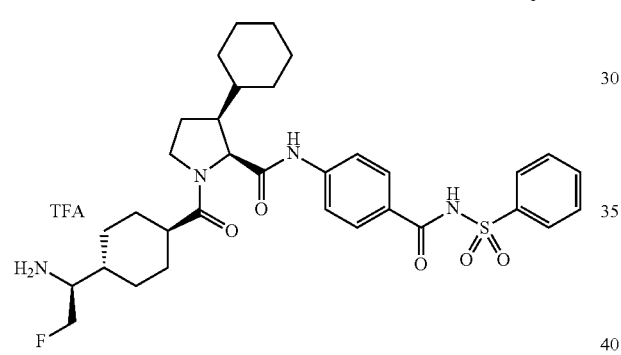
Example 119
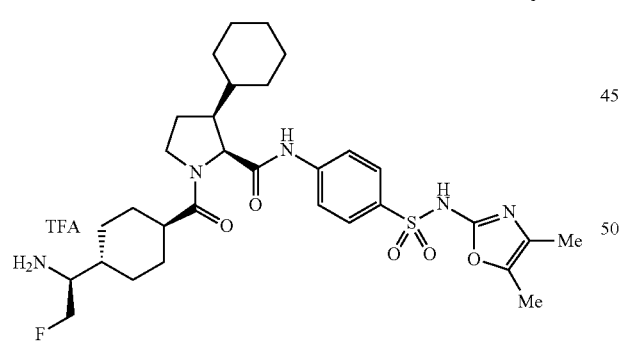
Example 120
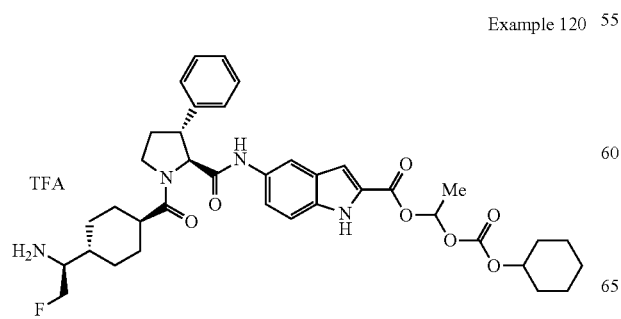
Example 121
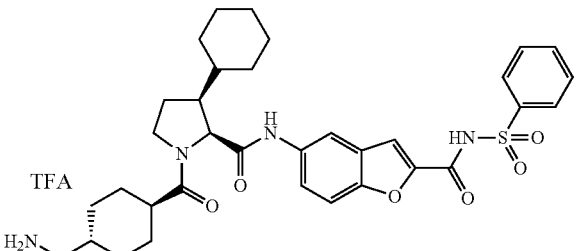
Example 122
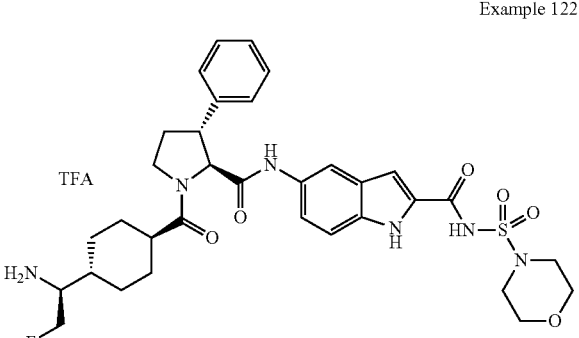
Example 123
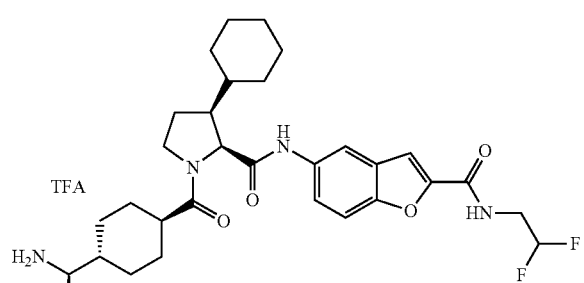
Example 124
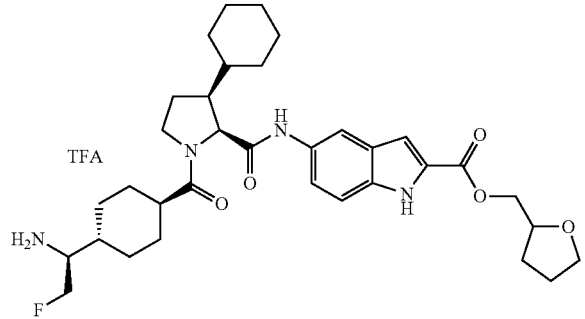

Example 125

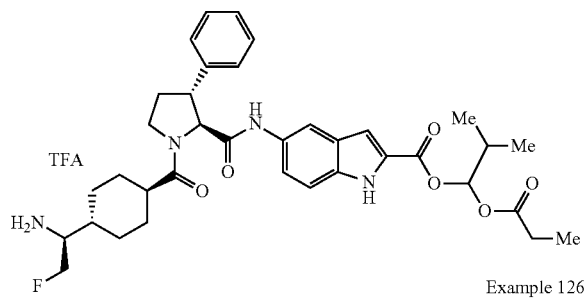

Example 126

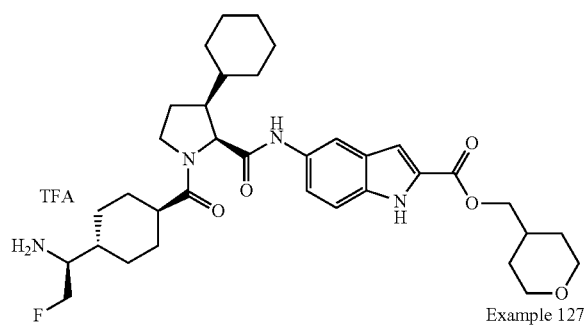

Example 127

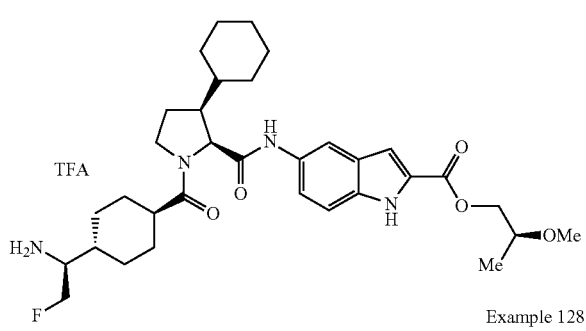

Example 128

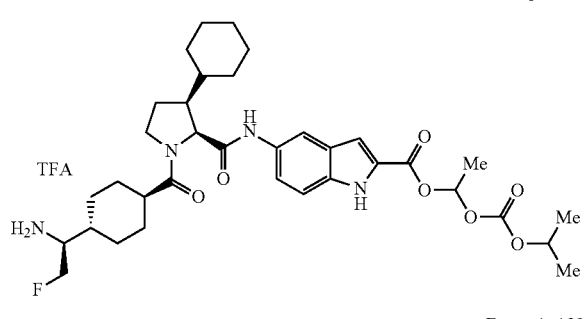

Example 129

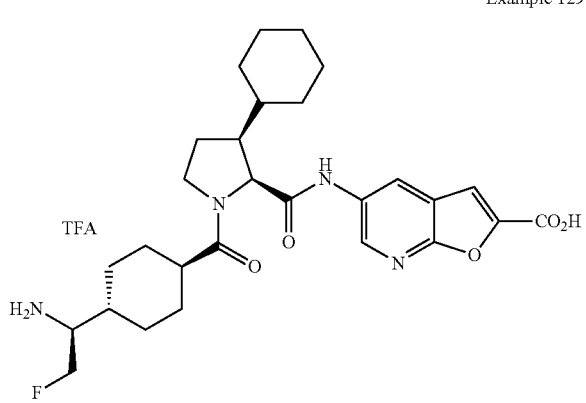

Example 130

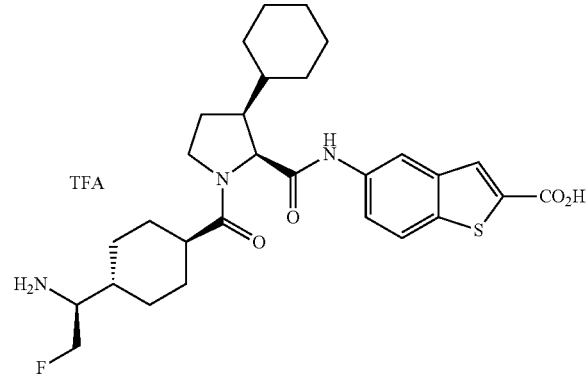

TABLE 9

| Example | Instrumental analysis data |
|---|---|
| 117 | RT 1.250 min (Kinetex 1.7μ C18 100A, 0.1% trifluoro acetic acid in water/acetonitrile, acetonitrile 10-99% 3.0 min, 0.5 mL/min (Condition C)). MS (ESI+) 529 (M + 1, 100%) |
| 118 | RT 4.386 min (Condition B). MS (ESI+) 627 (M + 1, 100%) |
| 119 | RT 4.011 min (Condition B). MS (ESI+) 618 (M + 1, 100%) |
| 120 | RT 4.826 min (Condition B). MS (ESI+) 691 (M + 1, 100%) |
| 121 | RT 4.484 min (Condition B). MS (ESI+) 667 (M + 1, 100%) |
| 122 | RT 3.813 min (Condition B). MS (ESI+) 669 (M + 1, 100%) |
| 123 | RT 4.219 min (Condition B). MS (ESI+) 591 (M + 1, 100%) |
| 124 | RT 4.381 min (Condition B). MS (ESI+) 611 (M + 1, 100%) |
| 125 | RT 4.639 min (Condition B). MS (ESI+) 649 (M + 1, 100%) |
| 126 | RT 4.437 min (Condition B). MS (ESI+) 625 (M + 1, 100%) |
| 127 | RT 4.432 min (Condition B). MS (ESI+) 599 (M + 1, 100%) |
| 128 | RT 4.795 min (Condition B). MS (ESI+) 657 (M + 1, 100%) |
| 129 | RT 3.854 min (Condition B). MS (ESI+) 529 (M + 1, 100%) |
| 130 | RT 4.228 min (Condition B). MS (ESI+) 544 (M + 1, 100%) |

Examples 131 to 139

The same procedure as described in Example 1 was carried out to obtain the compounds of Examples 131 to 139 from the compounds of Reference Examples 111 to 118 and Reference Example 157.

[Formula 705]

Example 131

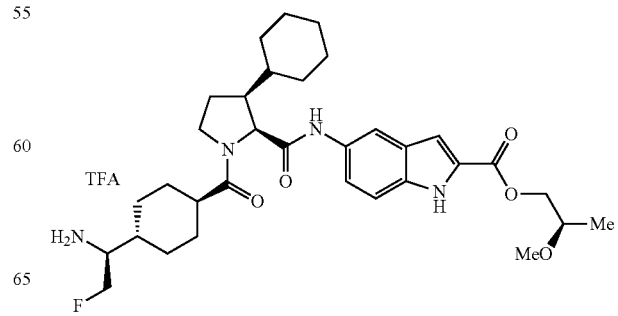

Example 132
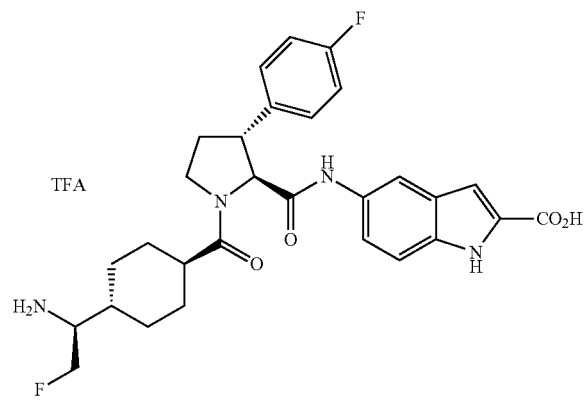
Example 136
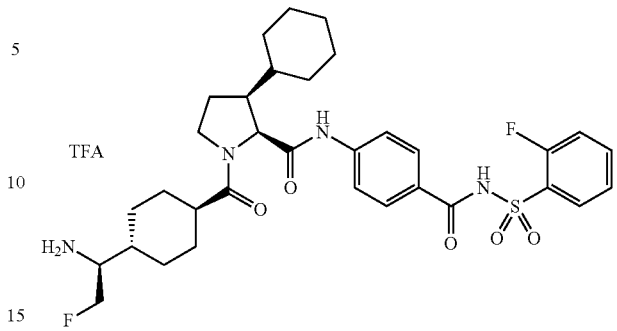
Example 133
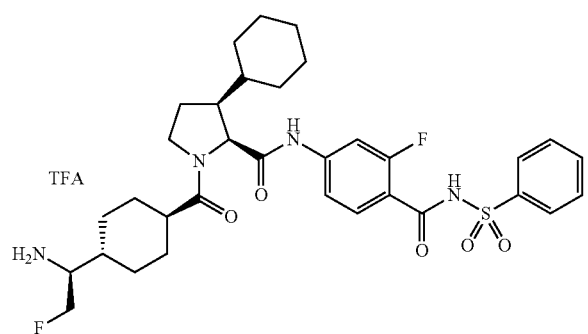
Example 137
Example 134
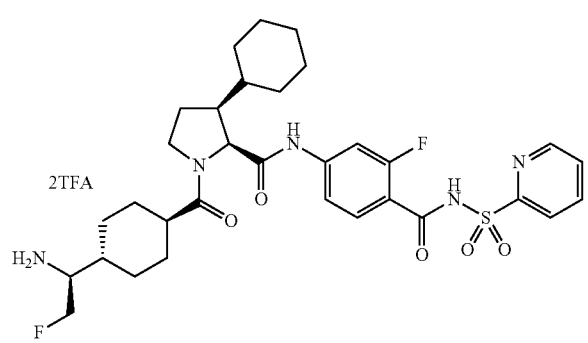
Example 138
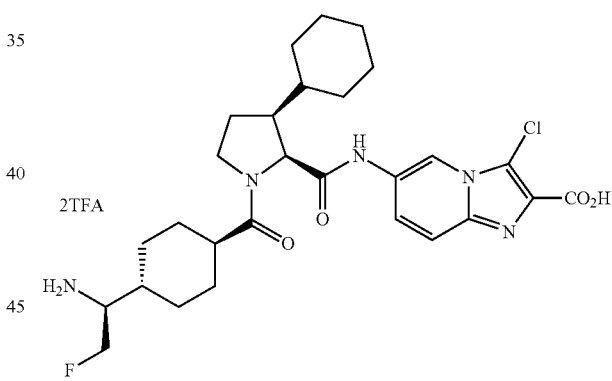
Example 135
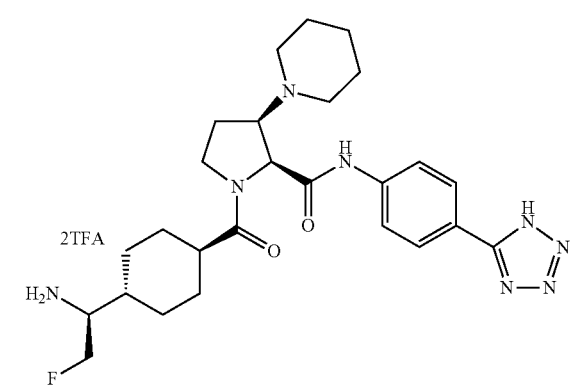
Example 139

TABLE 10

| Example | Instrumental analysis data |
|---|---|
| 131 | RT 4.414 min (Condition B). MS (ESI+) 599 (M + 1, 100%) |
| 132 | RT 3.645 min (Condition B). MS (ESI+) 539 (M + 1, 100%) |
| 133 | RT 4.509 min (Condition B). MS (ESI+) 645 (M + 1, 100%) |
| 134 | RT 4.151 min (Condition B). MS (ESI+) 628 (M + 1, 100%) |
| 135 | RT 0.500 min (Condition C). MS (ESI+) 513 (M + 1, 100%) |
| 136 | RT 4.423 min (Condition B). MS (ESI+) 645 (M + 1, 100%) |
| 137 | RT 3.514 min (Condition B). MS (ESI+) 578 (M + 1, 100%) |

TABLE 10-continued

| Example | Instrumental analysis data |
|---|---|
| 138 | RT 3.756 min (Condition B). MS (ESI+) 526 (M + 1, 100%) |
| 139 | RT 3.072 min (Condition B). MS (ESI+) 542 (M + 1, 100%) |

Examples 140 to 153

The same procedure as described in Example 1 was carried out to obtain the compounds of Examples 140 to 153 from the compounds of Reference Examples 119 to 132.

[Formula 706]

Example 140

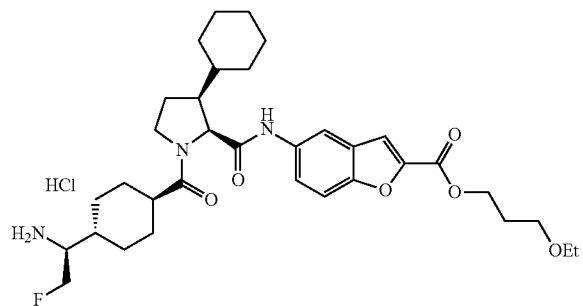

Example 141

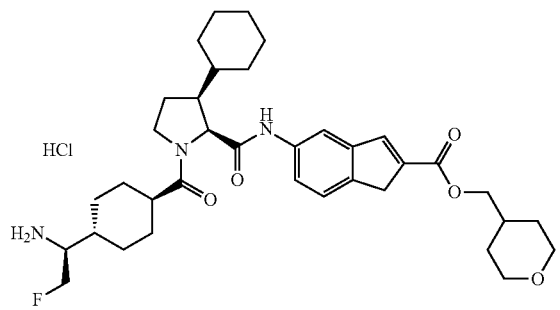

Example 142

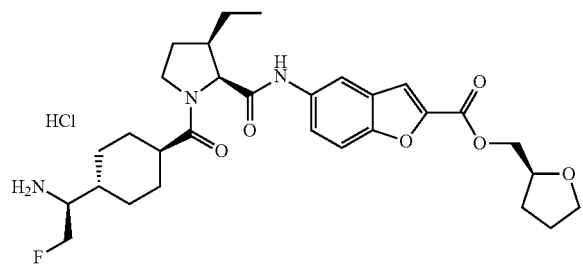

Example 143

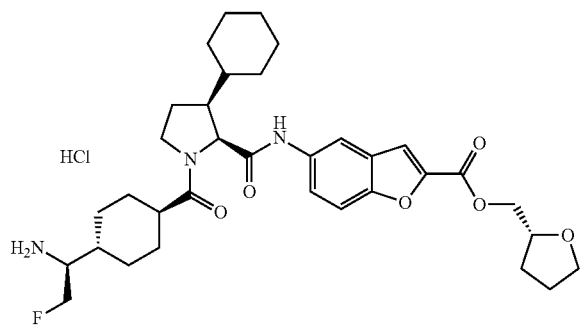

Example 144

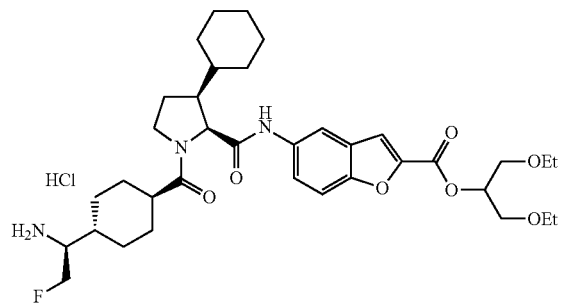

Example 145

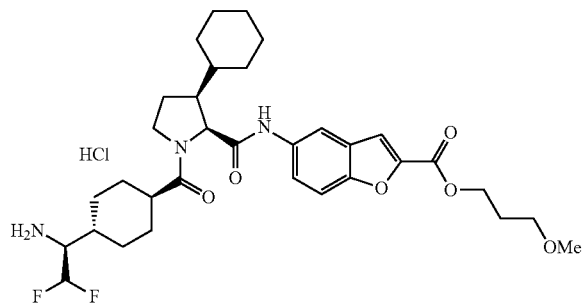

-continued
Example 146
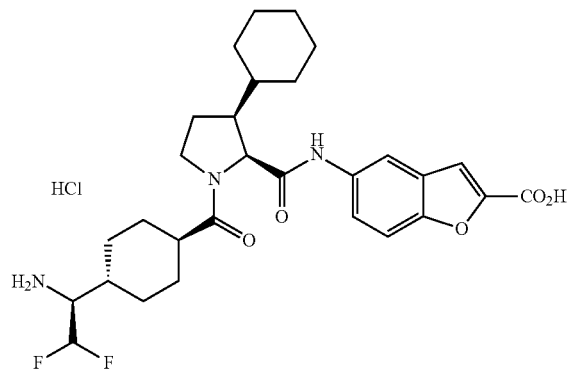
Example 147
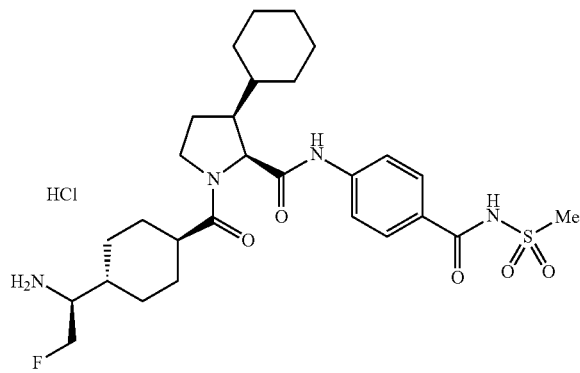
Example 148
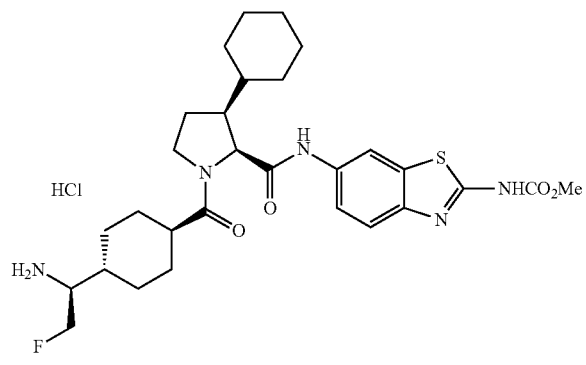
Example 149
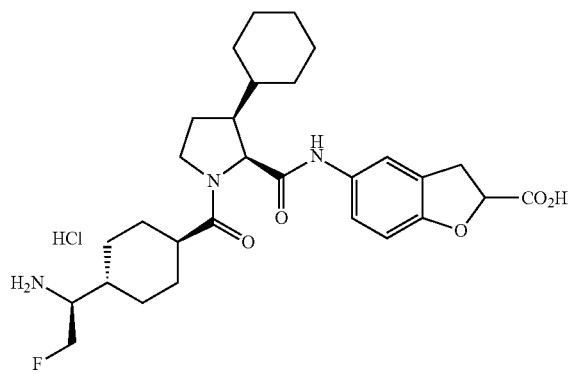
Example 150
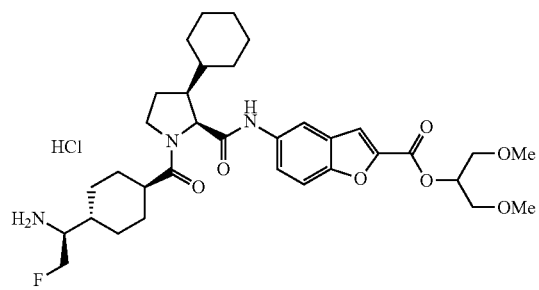
Example 151
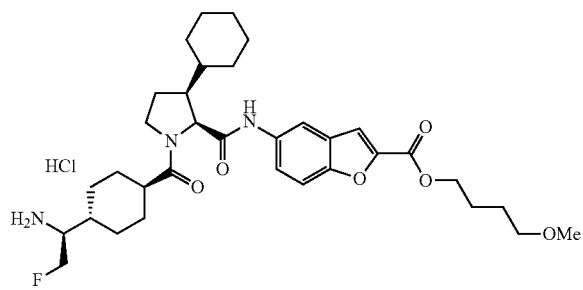
Example 152
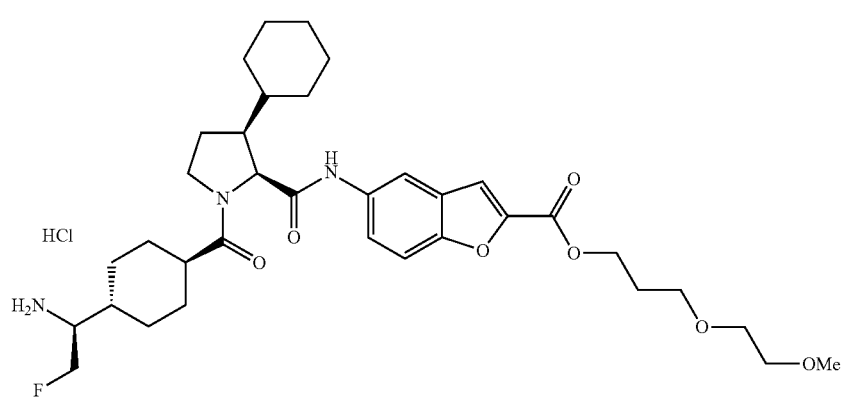

-continued

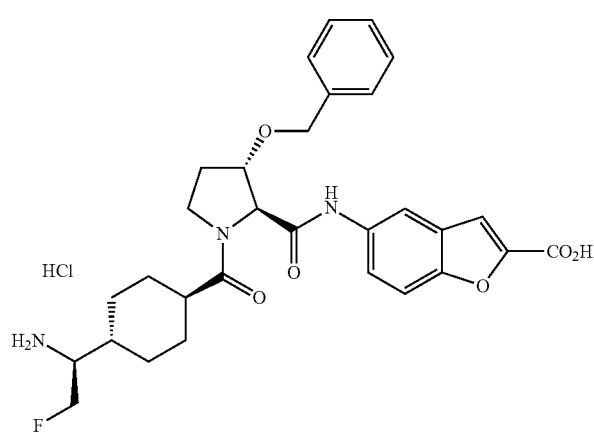

TABLE 11

| Example | Instrumental analysis data |
|---|---|
| 140 | RT 4.818 min (Condition B). MS (ESI+) 614 (M + 1, 100%) |
| 141 | RT 4.678 min (Condition B). MS (ESI+) 626 (M + 1, 100%) |
| 142 | RT 4.598 min (Condition B). MS (ESI+) 612 (M + 1, 100%) |
| 143 | RT 4.630 min (Condition B). MS (ESI+) 612 (M + 1, 100%) |
| 144 | RT 4.811 min (Condition B). MS (ESI+) 658 (M + 1, 100%) |
| 145 | RT 4.645 min (Condition B). MS (ESI+) 617 (M + 1, 60%) |
| 146 | RT 3.944 min (Condition B). MS (ESI+) 546 (M + 1, 100%) |
| 147 | RT 3.991 min (Condition B). MS (ESI+) 565 (M + 1, 100%) |
| 148 | RT 4.210 min (Condition B). MS (ESI+) 574 (M + 1, 100%) |
| 149 | RT 4.576 min (Condition B). MS (ESI+) 530 (M + 1, 100%) |
| 150 | RT 4.576 min (Condition B). MS (ESI+) 630 (M + 1, 100%) |
| 151 | RT 4.758 min (Condition B). MS (ESI+) 614 (M + 1, 100%) |
| 152 | RT 4.578 min (Condition B). MS (ESI+) 644 (M + 1, 100%) |
| 153 | RT 3.796 min (Condition B). MS (ESI+) 552 (M + 1, 100%) |

Examples 154 to 167

The same procedure as described in Example 1 was carried out to obtain the compounds of Examples 154 to 167 from the compounds of Reference Examples 133 to 146.

[Formula 707]

Example 154

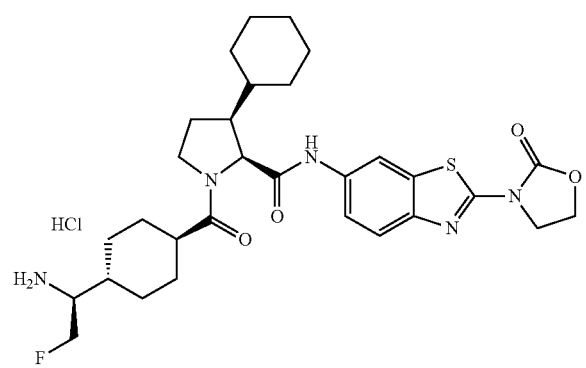

Example 153

(shown above)

-continued

Example 155

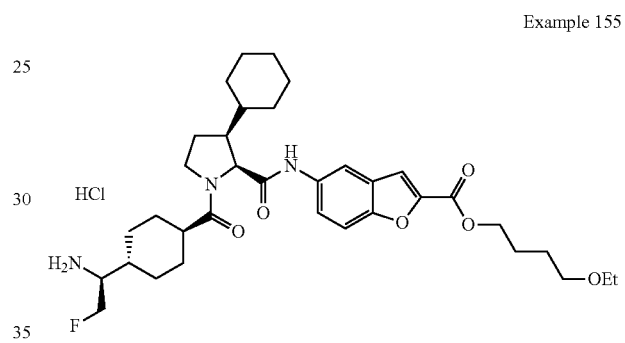

Example 156

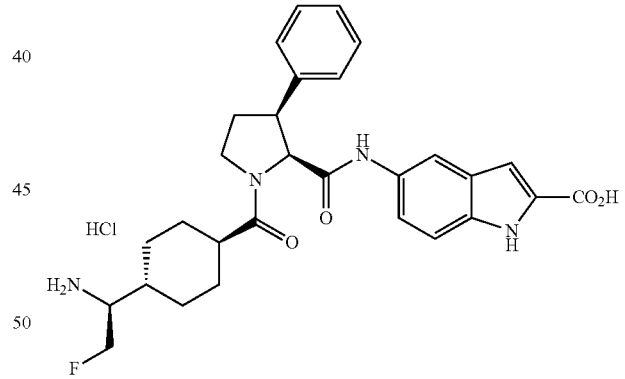

Example 157

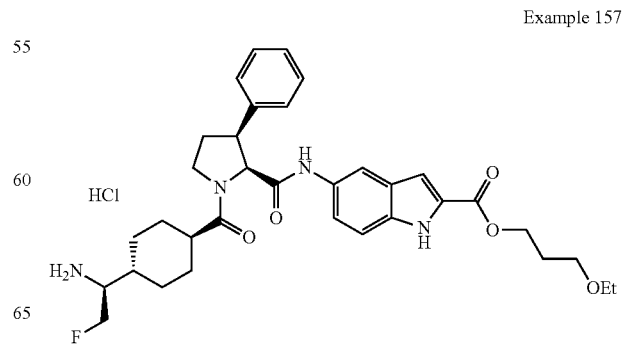

Example 158
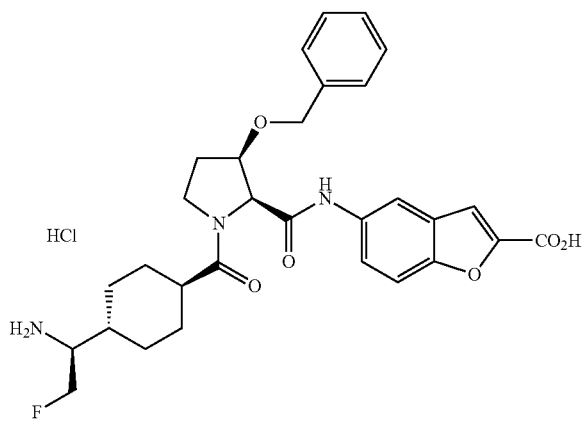
Example 159
Example 160
Example 161
Example 162
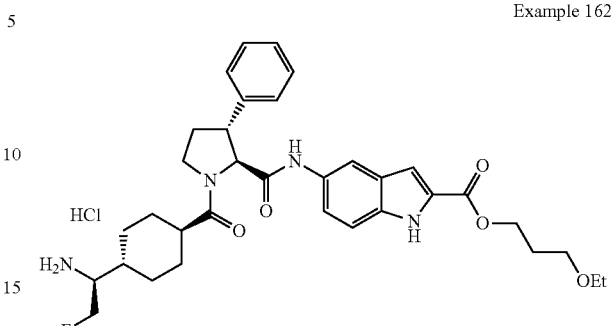
Example 163
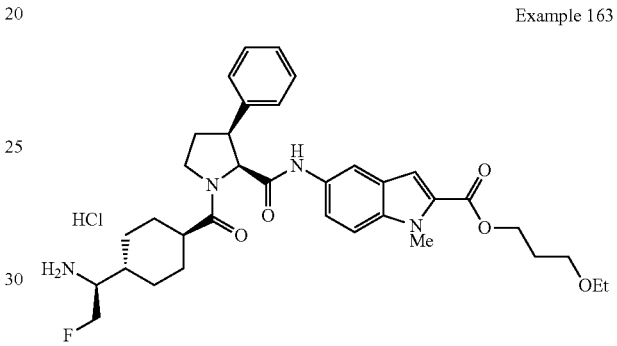
Example 164
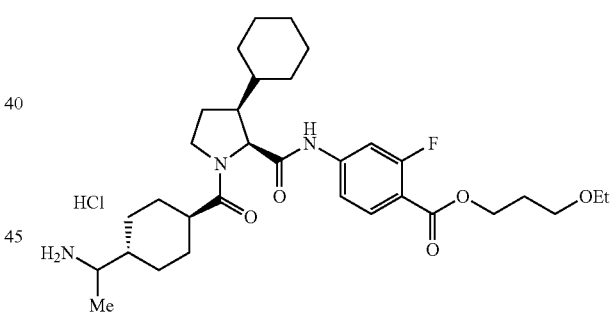
Example 165
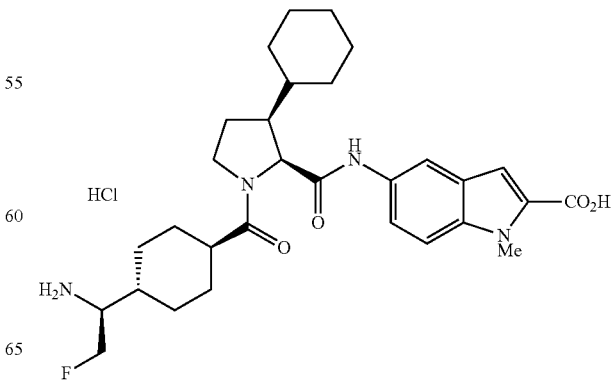

Example 166

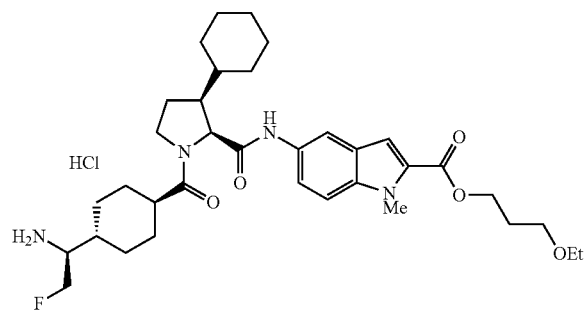

Example 167

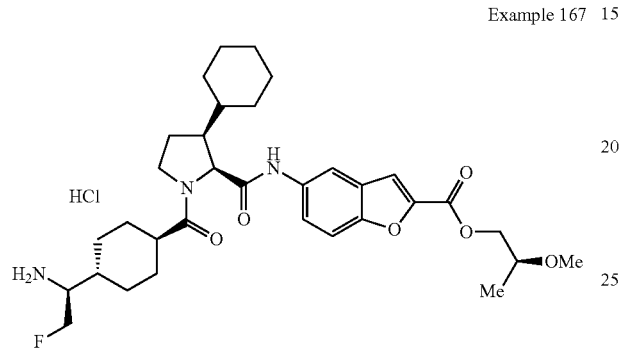

TABLE 12

| Example | Instrumental analysis data |
|---|---|
| 154 | RT 4.252 min (Condition B). MS (ESI+) 586 (M + 1, 100%) |
| 155 | RT 4.937 min (Condition B). MS (ESI+) 628 (M + 1, 100%) |
| 156 | RT 3.560 min (Condition B). MS (ESI+) 521 (M + 1, 100%) |
| 157 | RT 4.133 min (Condition B). MS (ESI+) 607 (M + 1, 60%) |
| 158 | RT 3.632 min (Condition B). MS (ESI+) 552 (M + 1, 100%) |
| 159 | RT 3.707 min (Condition B). MS (ESI+) 536 (M + 1, 60%) |
| 160 | RT 3.683 min (Condition B). MS (ESI+) 535 (M + 1, 100%) |
| 161 | RT 3.595 min (Condition B). MS (ESI+) 521 (M + 1, 100%) |
| 162 | RT 4.204 min (Condition B). MS (ESI+) 607 (M + 1, 100%) |
| 163 | RT 4.384 min (Condition B). MS (ESI+) 621 (M + 1, 100%) |
| 164 | RT 4.901 min (Condition B). MS (ESI+) 574 (M + 1, 100%) |
| 165 | RT 4.122 min (Condition B). MS (ESI+) 541 (M + 1, 100%) |
| 166 | RT 4.843 min (Condition B). MS (ESI+) 627 (M + 1, 100%) |
| 167 | RT 4.637 min (Condition B). MS (ESI+) 600 (M + 1, 100%) |

Examples 168 to 181

The same procedure as described in Example 1 was carried out to obtain the compounds of Examples 168 to 181 from the compounds of Reference Examples 147 to 160.

[Formula 708]

Example 168

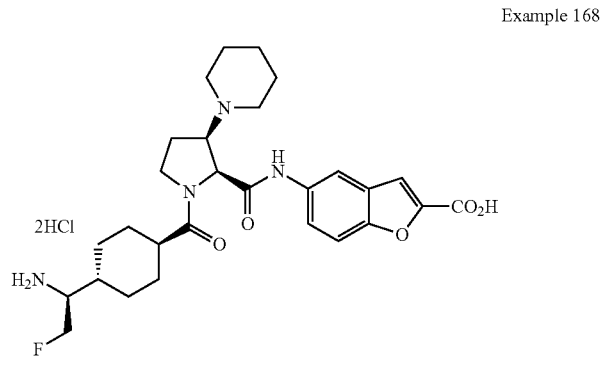

Example 169

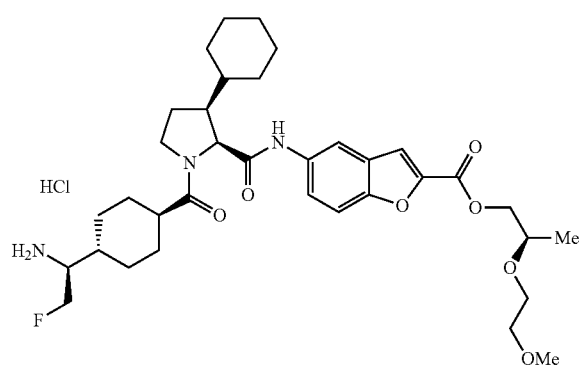

Example 170

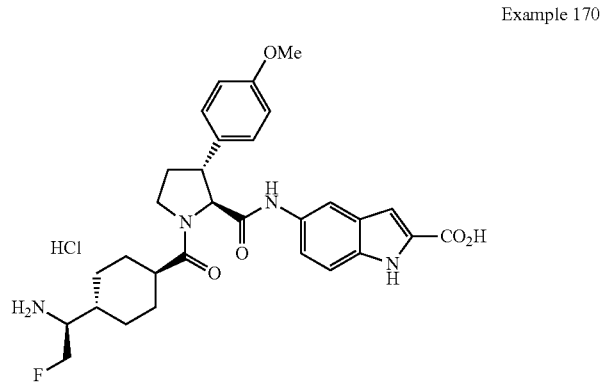

Example 171

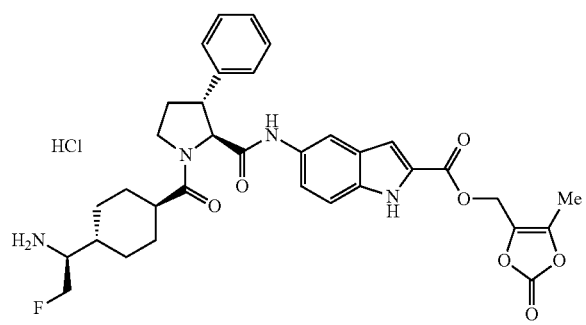

-continued
Example 172
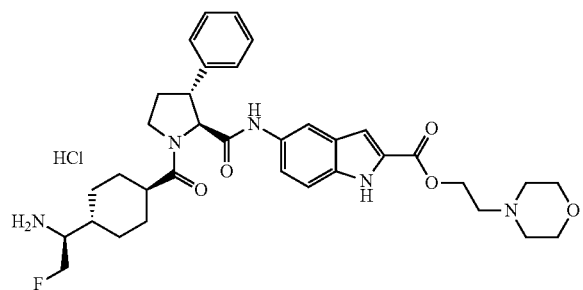
Example 173
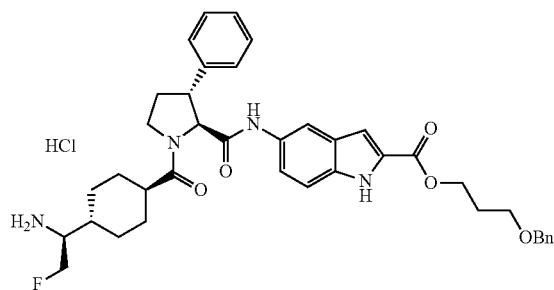
Example 174
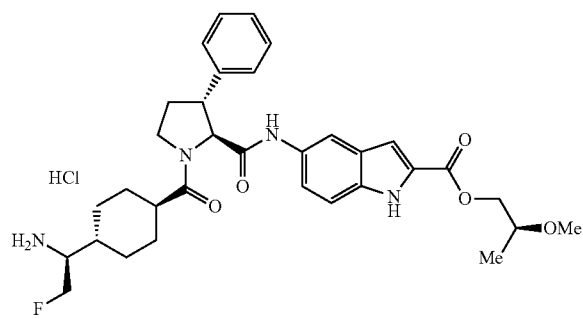
Example 175
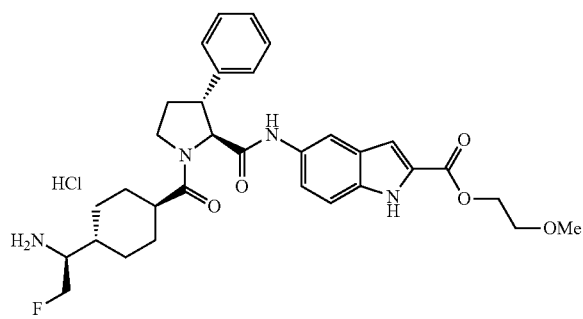
Example 176
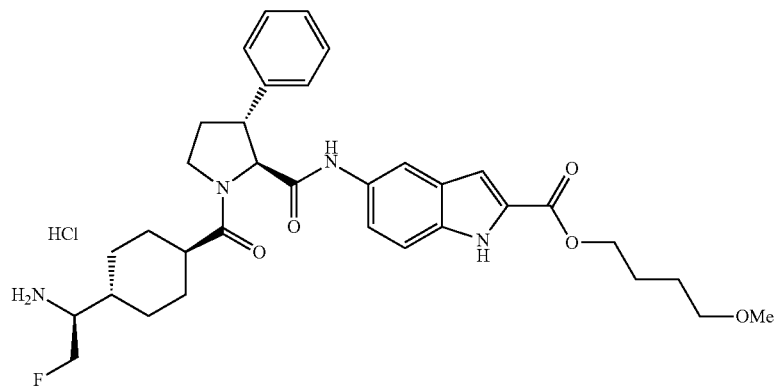
Example 177
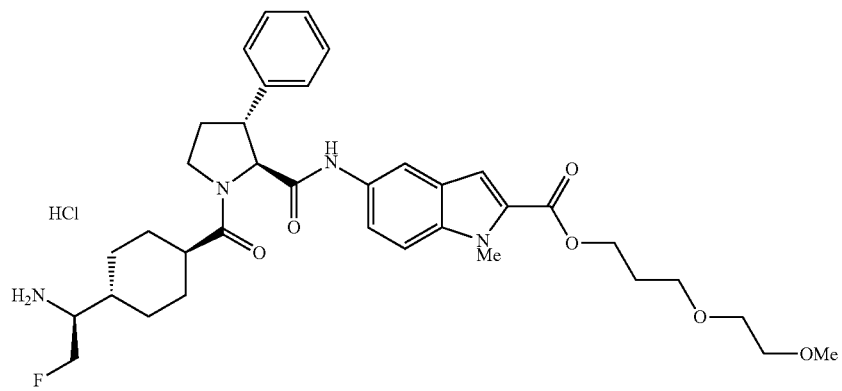

Example 178

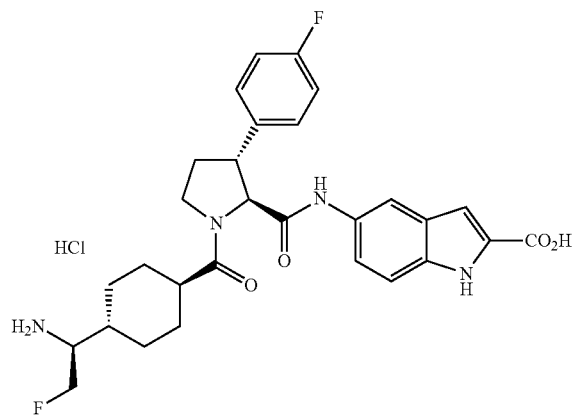

Example 179

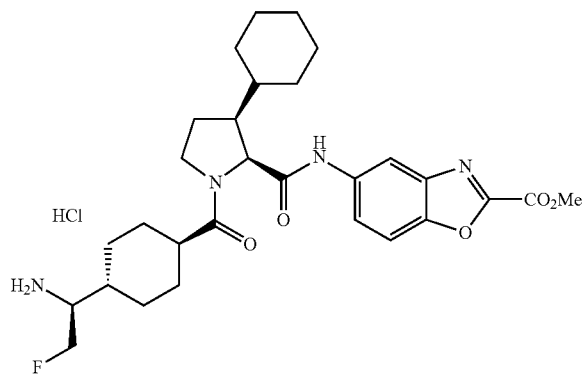

Example 180

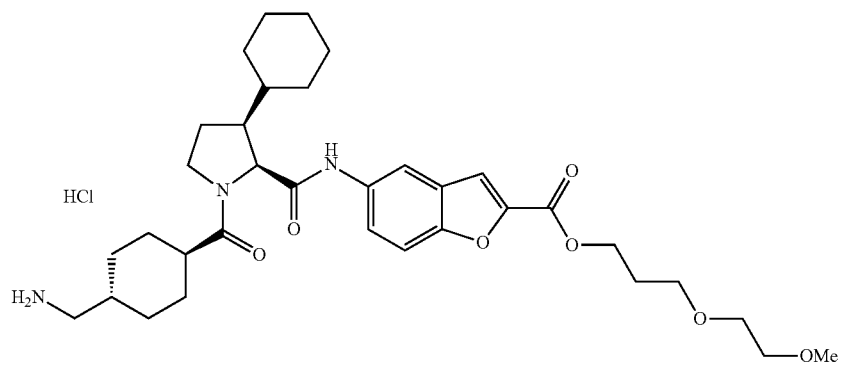

Example 181

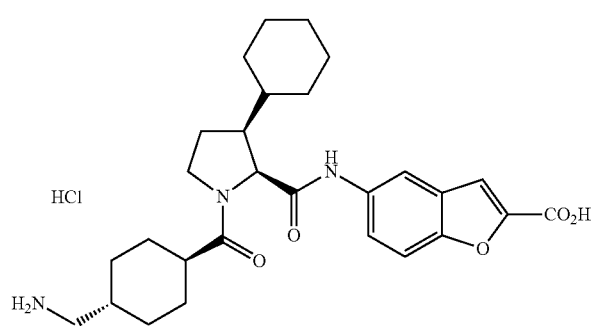

TABLE 13

| Example | Instrumental analysis data |
|---|---|
| 168 | RT 2.760 min (Condition B). MS (ESI+) 529 (M + 1, 100%) |
| 169 | RT 4.669 min (Condition B). MS (ESI+) 644 (M + 1, 100%) |
| 170 | RT 3.560 min (Condition B). MS (ESI+) 551 (M + 1, 100%) |
| 171 | RT 4.112 min (Condition B). MS (ESI+) 633 (M + 1, 60%) |
| 172 | RT 3.332 min (Condition B). MS (ESI+) 634 (M + 1, 100%) |
| 173 | RT 4.597 min (Condition B). MS (ESI+) 669 (M + 1, 100%) |
| 174 | RT 4.066 min (Condition B). MS (ESI+) 693 (M + 1, 100%) |
| 175 | RT 3.923 min (Condition B). MS (ESI+) 579 (M + 1, 100%) |
| 176 | RT 4.165 min (Condition B). MS (ESI+) 607 (M + 1, 100%) |

TABLE 13-continued

| Example | Instrumental analysis data |
|---|---|
| 177 | RT 4.035 min (Condition B). MS (ESI+) 637 (M + 1, 100%) |
| 178 | RT 3.645 min (Condition B). MS (ESI+) 539 (M + 1, 100%) |
| 179 | RT 4.251 min (Condition B). MS (ESI+) 543 (M + 1, 100%) |
| 180 | RT 4.545 min (Condition B). MS (ESI+) 612 (M + 1, 100%) |
| 181 | RT 3.999 min (Condition B). MS (ESI+) 496 (M + 1, 100%) |

Examples 182 to 193
The same procedure as described in Example 1 was carried out to obtain the compounds of Examples 182 to 193 from the compounds of Reference Examples 161 to 172.
[Formula 709]
Example 182
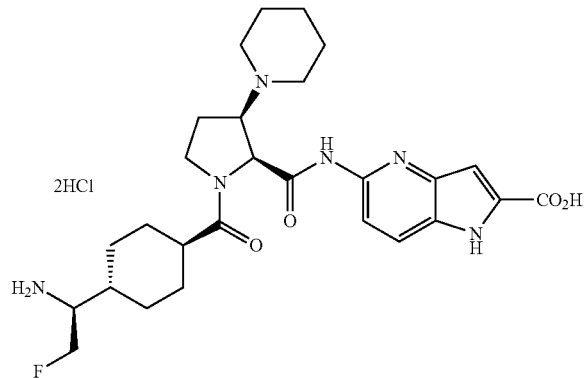
Example 183
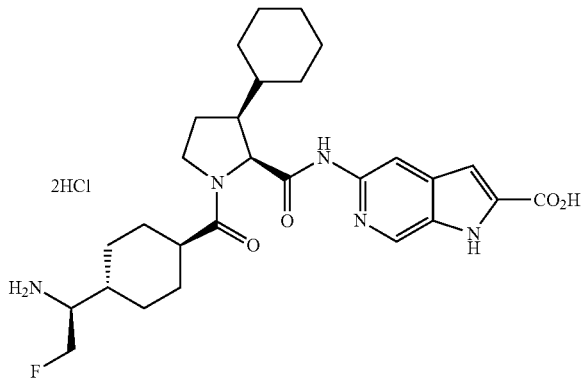
Example 184
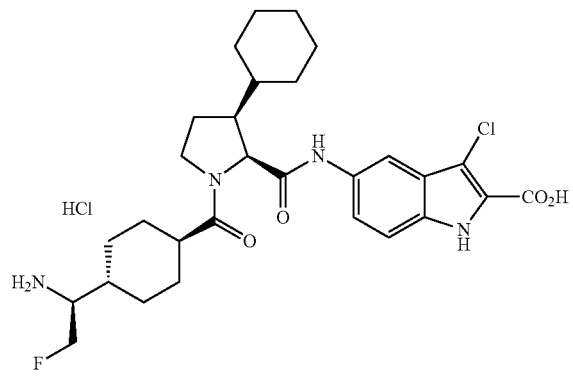
Example 185
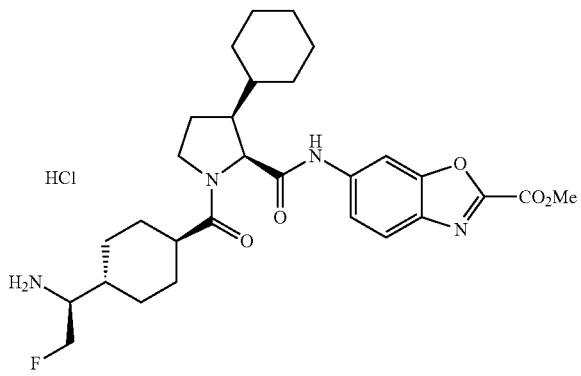
Example 186
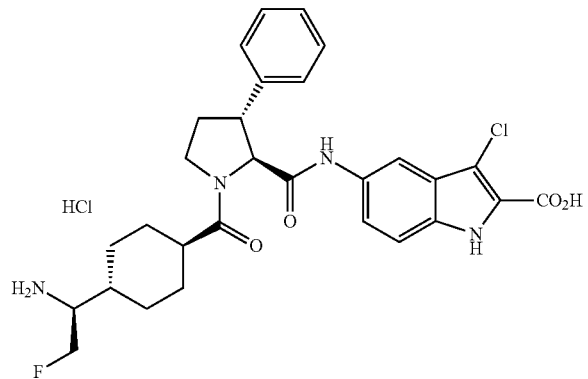
Example 187
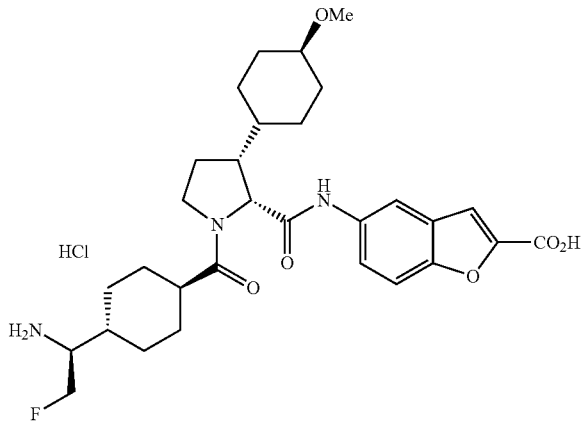

-continued
Example 188
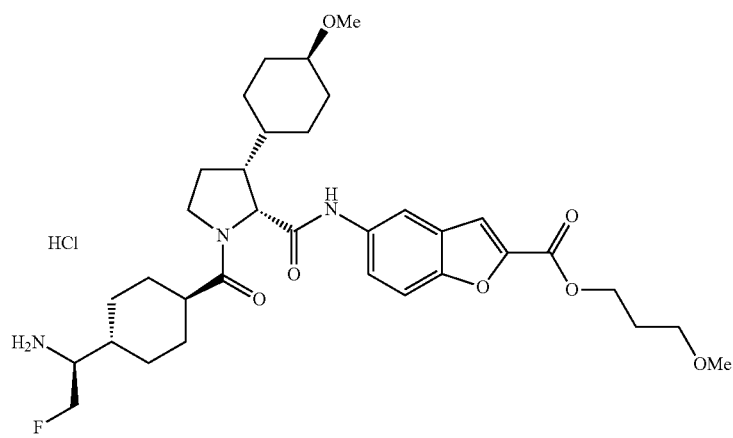
Example 189
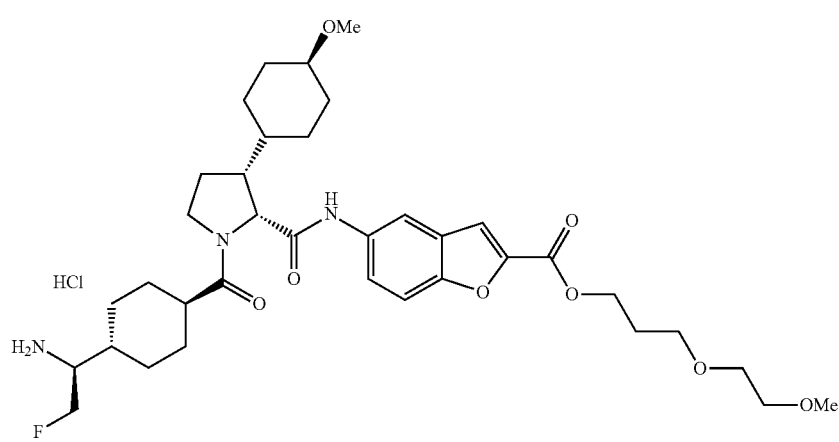
Example 190
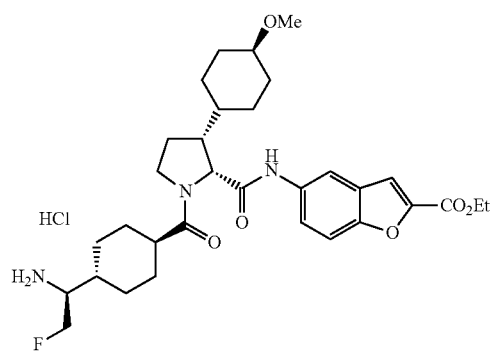
Example 191
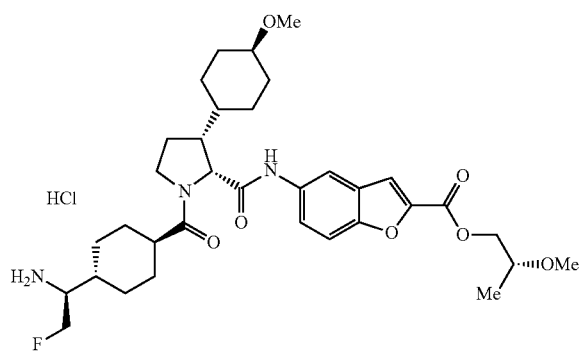
Example 192
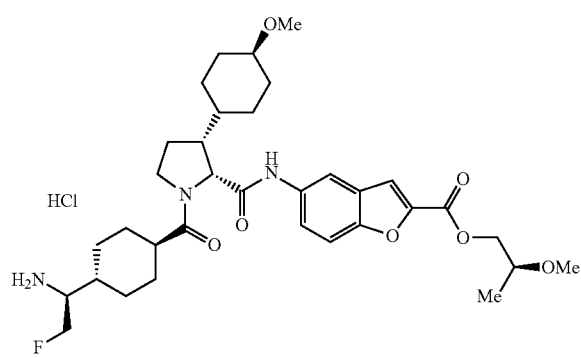
Example 193
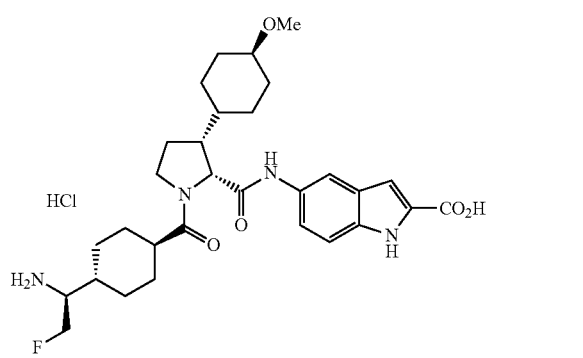

TABLE 14

| Example | Instrumental analysis data |
|---|---|
| 182 | RT 3.580 min (Condition B). MS (ESI+) 528 (M + 1, 100%) |
| 183 | RT 3.461 min (Condition A). MS (ESI+) 528 (M + 1, 100%) |
| 184 | RT 4.066 min (Condition A). MS (ESI+) 561 (M + 1, 100%) |
| 185 | RT 4.275 min (Condition B). MS (ESI+) 543 (M + 1, 100%) |
| 186 | RT 3.644 min (Condition A). MS (ESI+) 555 (M + 1, 100%) |
| 187 | RT 3.427 min (Condition B). MS (ESI+) 558 (M + 1, 100%) |
| 188 | RT 4.014 min (Condition B). MS (ESI+) 630 (M + 1, 100%) |
| 189 | RT 3.940 min (Condition B). MS (ESI+) 674 (M + 1, 100%) |
| 190 | RT 4.018 min (Condition B). MS (ESI+) 558 (M + 1, 100%) |
| 191 | RT 4.109 min (Condition B). MS (ESI+) 630 (M + 1, 100%) |

TABLE 14-continued

| Example | Instrumental analysis data |
|---|---|
| 192 | RT 3.987 min (Condition B). MS (ESI+) 630 (M + 1, 100%) |
| 193 | RT 3.273 min (Condition B). MS (ESI+) 557 (M + 1, 100%) |

Examples 194 to 203

The same procedure as described in Example 1 was carried out to obtain the compounds of Examples 194 to 203 from the compounds of Reference Examples 173 to 182.

[Formula 710]

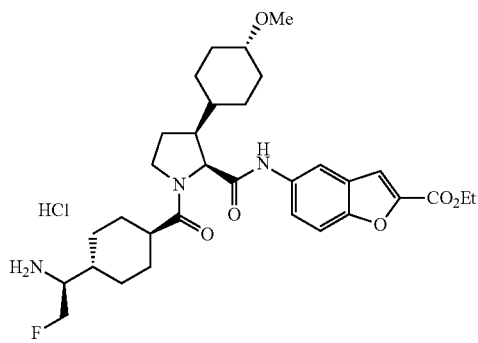

Example 194

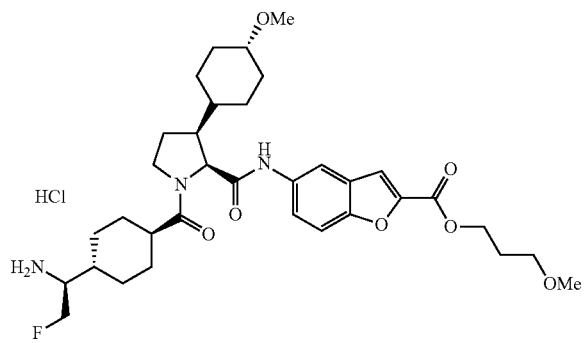

Example 195

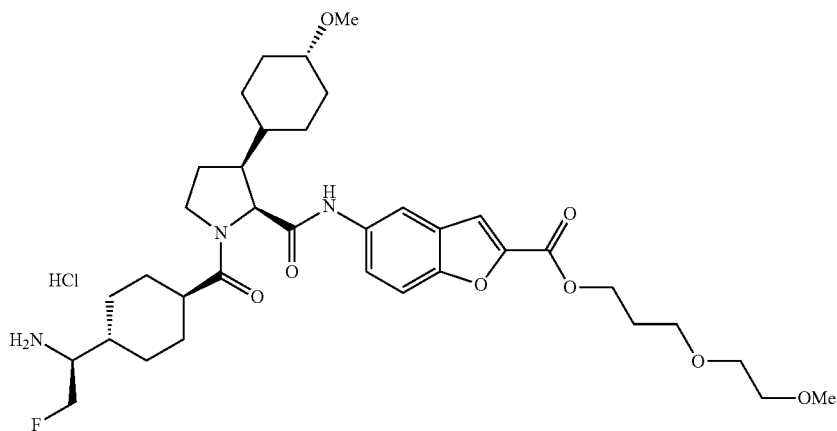

Example 196

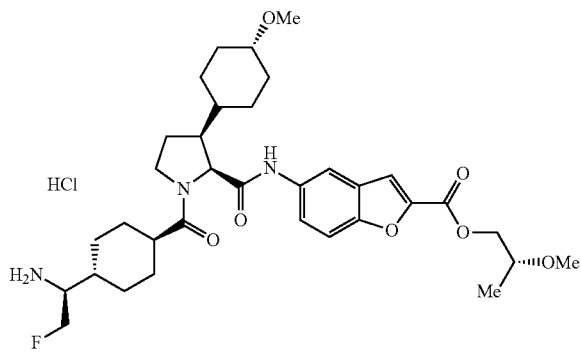

Example 197

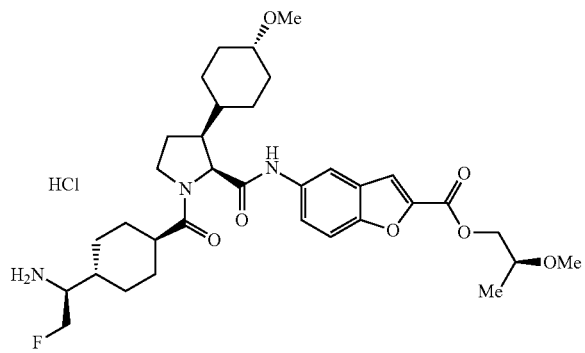

Example 198

Example 199

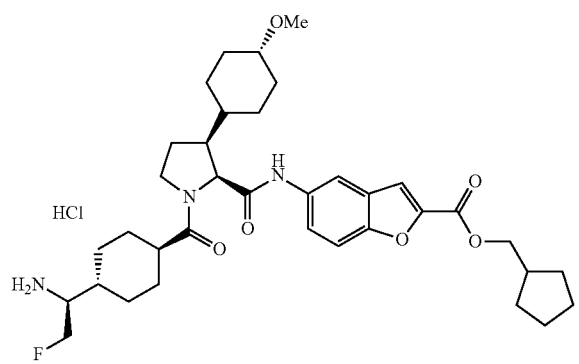

Example 200

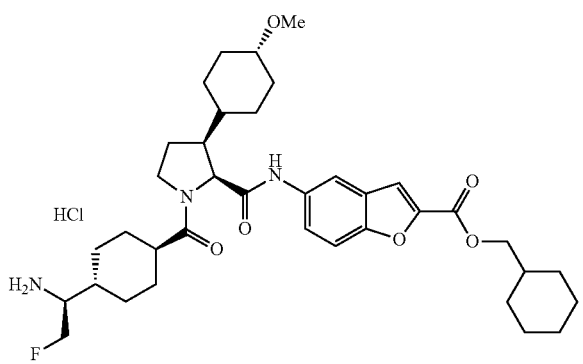

Example 201

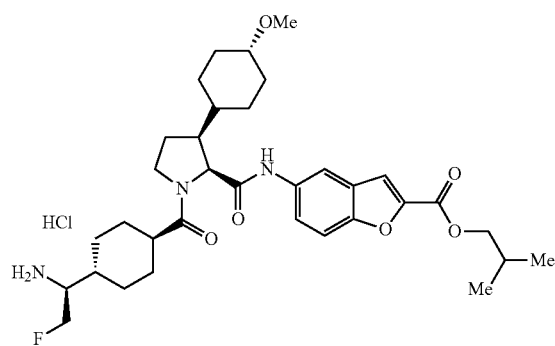

Example 202

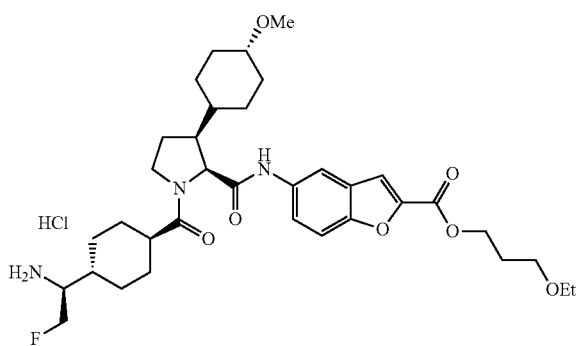

Example 203

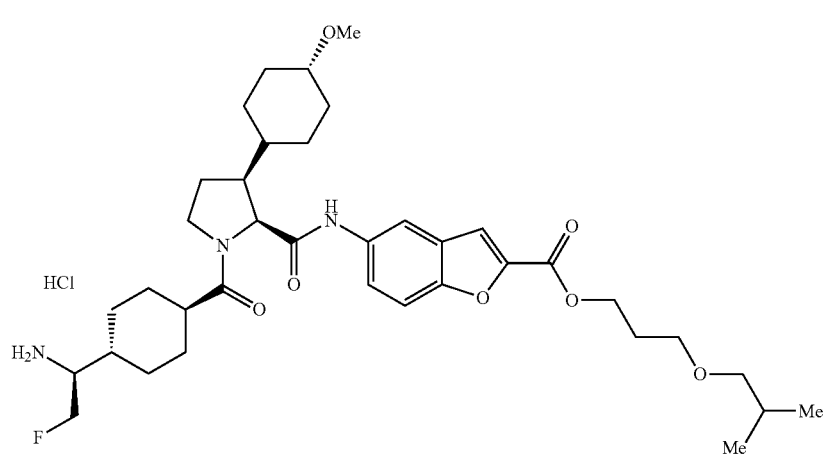

TABLE 15

| Example | Instrumental analysis data |
|---|---|
| 194 | RT 4.236 min (Condition B). MS (ESI+) 586 (M + 1, 100%) |
| 195 | RT 4.102 min (Condition B). MS (ESI+) 630 (M + 1, 100%) |
| 196 | RT 4.0673 min (Condition B). MS (ESI+) 674 (M + 1, 100%) |
| 197 | RT 4.103 min (Condition B). MS (ESI+) 630 (M + 1, 100%) |
| 198 | RT 4.099 min (Condition B). MS (ESI+) 630 (M + 1, 100%) |
| 199 | RT 4.786 min (Condition B). MS (ESI+) 640 (M + 1, 100%) |
| 200 | RT 4.786 min (Condition B). MS (ESI+) 640 (M + 1, 100%) |

TABLE 15-continued

| Example | Instrumental analysis data |
|---|---|
| 201 | RT 4.540 min (Condition B). MS (ESI+) 614 (M + 1, 100%) |
| 202 | RT 4.266 min (Condition B). MS (ESI+) 644 (M + 1, 100%) |
| 203 | RT 4.757 min (Condition B). MS (ESI+) 672 (M + 1, 100%) |

Example 204

3-Hydroxypropyl 5-[(2S,3S)-1-({trans-4-[(1S)-1-amino-2-fluoroethyl]cyclohexyl}carbonyl)-3-cyclohexylpyrrolidine-2-carboxamide]-1-benzofuran-2-carboxylate

[Formula 711]

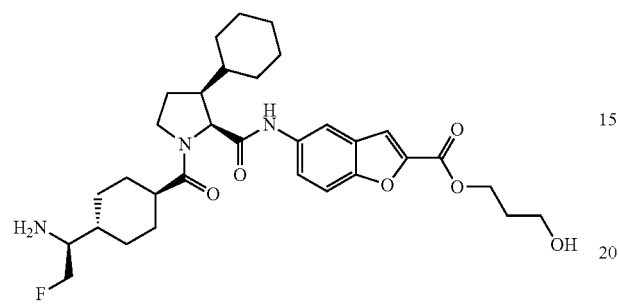

To a solution of the compound of Reference Example 183 (33.7 mg, 0.0491 mmol) in chloroform (1 mL), trifluoroacetic acid (57 μL) was added in an ice bath. After stirring for 2 hours in an ice bath, the reaction solution was concentrated under reduced pressure. A saturated aqueous solution of sodium bicarbonate was added to the residue, followed by extraction with chloroform. The organic layer was washed with a saturated saline solution, then dried over sodium sulfate and filtered, and the filtrate was concentrated under reduced pressure. The obtained residue was purified by silica gel column chromatography to obtain the title compound (10.8 mg, 38%).

RT 4.167 min (condition B). MS (ESI+) 586 (M+I, 100%)

Example 205

(1R)-1-({[(1S)-1-(trans-4-{[(2S,3S)-3-Cyclohexyl-2-{[4-(1H-tetrazol-5-yl)phenyl]carbamoyl}pyrrolidin-1-yl]carbonyl}cyclohexyl)-2-fluoroethyl]carbamoyl}oxy)ethyl 2-methylpropanoate

[Formula 712]

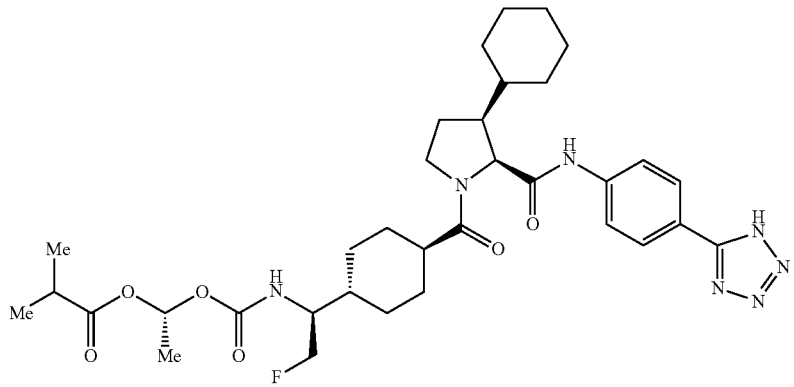

To a solution of the compound of Example 105 (15.0 mg, 0.0239 mmol) in tetrahydrofuran (1 mL), triethylamine (3.3 μL, 0.0239 mmol) and (3S,4S)-1-[({(1R)-1-[(2-methylpropanoyl)oxy]ethoxy}carbonyl)oxy]-2,5-dioxopyrrolidine-3,4-diyl dibenzoate (12.3 mg, 0.0239 mmol) known from literature (e.g., JP2012107006, WO 2010150840) were added. After stirring for 1 hour, the reaction solution was concentrated under reduced pressure. The obtained residue was purified by silica gel column chromatography to obtain the title compound (10.9 mg, 68%).

RT 5.452 min (condition B). MS (ESI+) 670 (M+1, 100%)

Example 206

3-Hydroxypropyl 5-[(2S,3R)-1-({trans-4-[(1S)-1-amino-2-fluoroethyl]cyclohexyl}carbonyl)-3-phenylpyrrolidine-2-carboxamide]-1-benzofuran-2-carboxylate

[Formula 713]

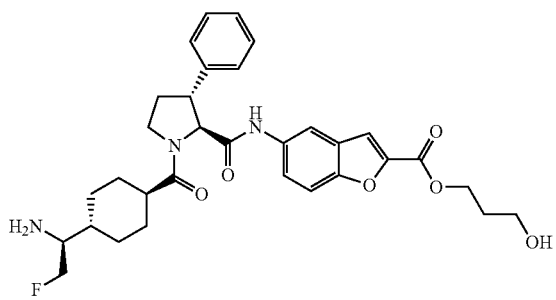

A saturated aqueous solution of sodium bicarbonate was added to the compound of Example 173 (72.1 mg, 0.102 mmol), followed by extraction with chloroform. The organic layer was washed with a saturated saline solution, then dried over sodium sulfate and filtered, and the filtrate was concentrated under reduced pressure. The obtained residue was dissolved in methanol (5 ml), then palladium hydroxide (70 mg) was added, and the mixture was heated to reflux under hydrogen atmosphere. The reaction solution was allowed to cool and filtered through Celite, then the filtrate was concentrated under reduced pressure to obtain the title compound (49.0 mg, 83%).

RT 3.700 min (condition B). MS (ESI+) 579 (M+1, 100%)

Example 207

5-[(2S,3S)-1-({trans-4-[(1S)-1-Amino-2-fluoroethyl]cyclohexyl}carbonyl)-3-cyclohexylpyrrolidine-2-carboxamide]-1,3-benzoxazole-2-carboxylic acid

[Formula 714]

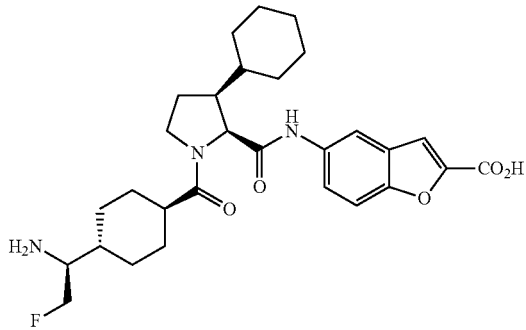

The compound of Example 179 (24.7 mg, 0.0427 mmol) was dissolved in methanol (1 mL) and tetrahydrofuran (1 mL), then a 1 mol/L aqueous solution of sodium hydroxide (0.5 mL) was added. The reaction solution was stirred at room temperature for 4 hours, then a pH 6.8 phosphate buffer was added to the reaction solution, followed by extraction with chloroform/methanol (1:1) twice. The organic layer was dried over anhydrous sodium sulfate and filtered, and then the solvent was concentrated under reduced pressure to obtain the title compound (5.0 mg, 22%).

RT 3.767 min (condition B). MS (ESI+) 529 (M+I, 100%)

Examples 208 to 214

The same procedure as described in Example 1 was carried out to obtain the compounds of Examples 208 to 215 from the compounds of Reference Examples 184 to 190.

[Formula 715]

Example 208

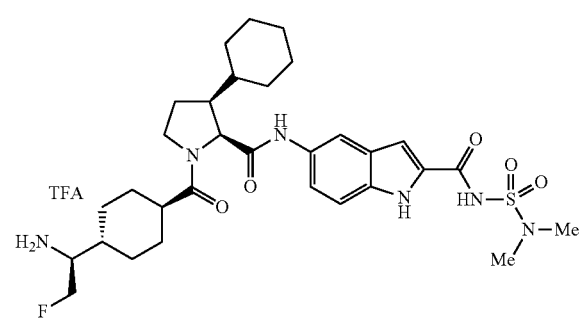

Example 209

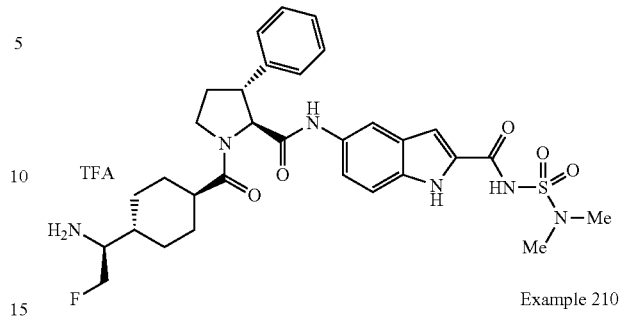

Example 210

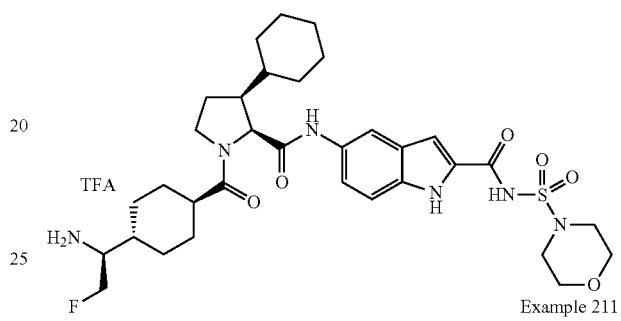

Example 211

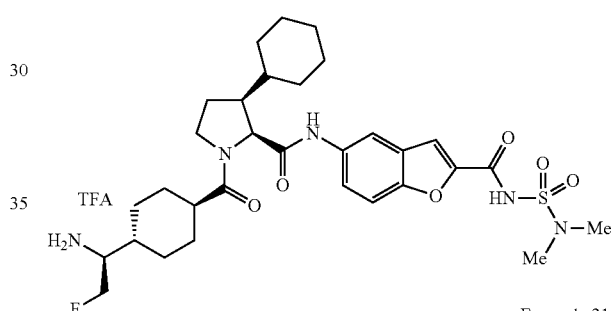

Example 212

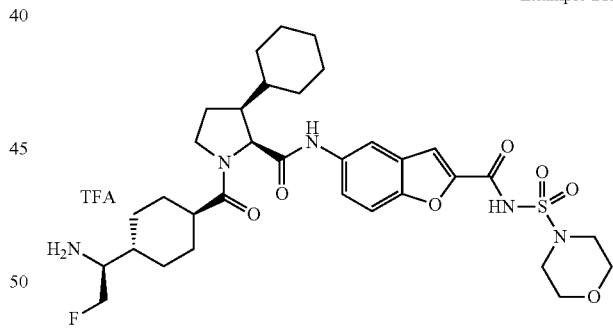

Example 213

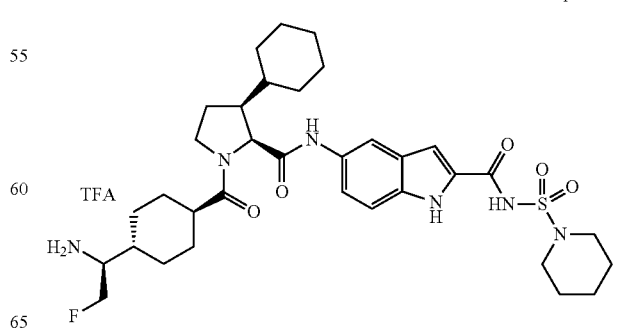

Example 214

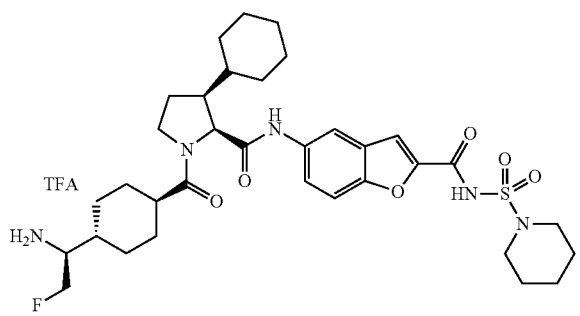

TABLE 16

| Example | Instrumental analysis data |
| --- | --- |
| 208 | RT 4.146 min (Condition B). MS (ESI+) 633 (M + 1, 100%) |
| 209 | RT 3.802 min (Condition B). MS (ESI+) 627 (M + 1, 100%) |
| 210 | RT 4.056 min (Condition B). MS (ESI+) 675 (M + 1, 100%) |
| 211 | RT 4.270 min (Condition B). MS (ESI+) 634 (M + 1, 100%) |
| 212 | RT 4.251 min (Condition B). MS (ESI+) 676 (M + 1, 100%) |
| 213 | RT 4.438 min (Condition B). MS (ESI+) 673 (M + 1, 100%) |
| 214 | RT 4.638 min (Condition B). MS (ESI+) 674 (M + 1, 100%) |

Examples 215 to 222

The same procedure as described in Example 1 was carried out to obtain the compounds of Examples 215 to 222 from the compounds of Reference Examples 191 to 198.

TABLE 17

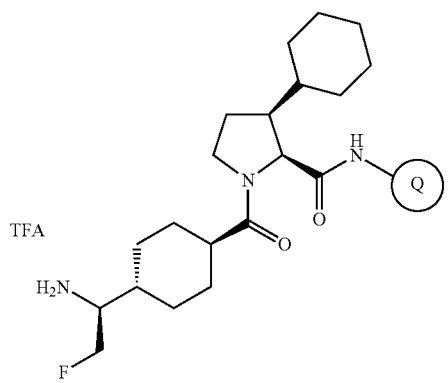

Q

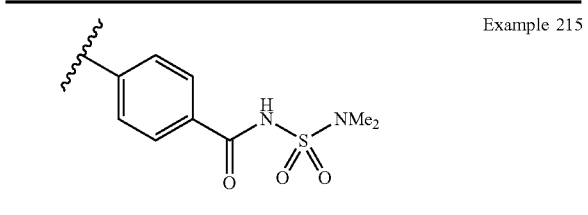

Example 215

TABLE 17-continued

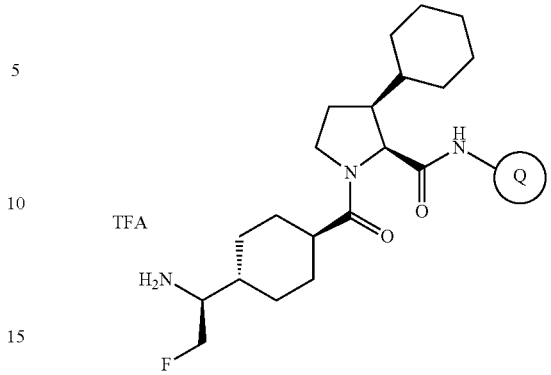

Q

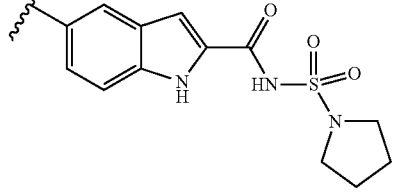

Example 216

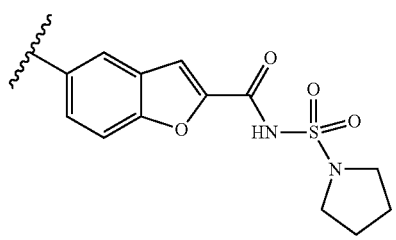 [SMILES: *c1ccc2oc(C(=O)NS(=O)(=O)N3CCCC3)cc2c1]

Example 217

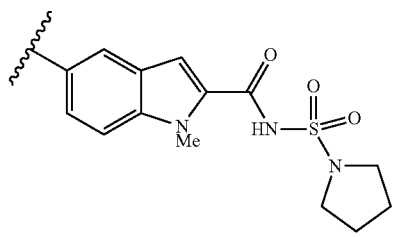 [SMILES: *c1ccc2c(c1)cc(C(=O)NS(=O)(=O)N1CCCC1)n2C]

Example 218

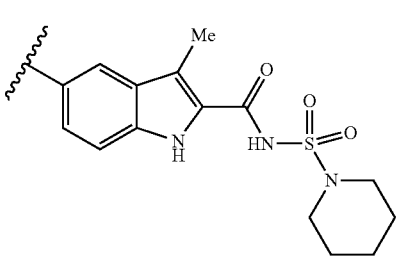 [SMILES: *c1ccc2[nH]c(C(=O)NS(=O)(=O)N3CCCCC3)c(C)c2c1]

Example 219

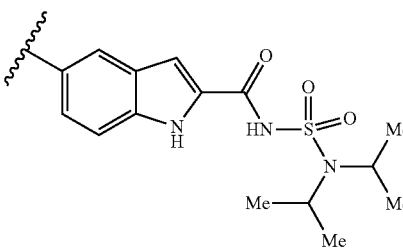

Example 220

TABLE 17-continued

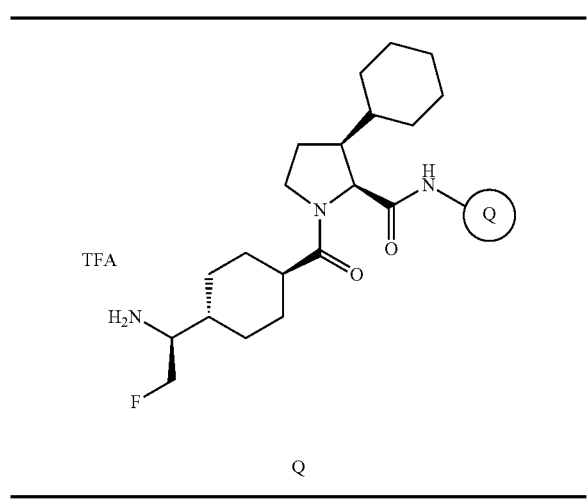

TFA

| Q | |
|---|---|
| 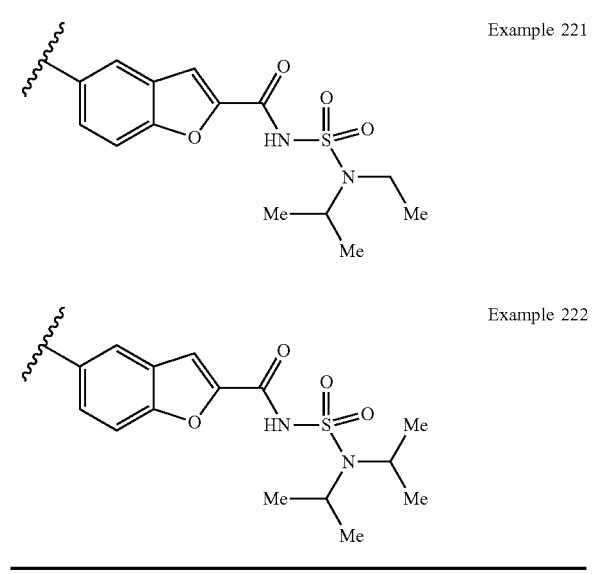 | Example 221 |
| | Example 222 |

TABLE 18

| Example | Instrumental analysis data |
|---|---|
| 215 | RT 4.207 min (Condition B). MS (ESI+) 594 (M + 1, 100%) |
| 216 | RT 3.267 min (Condition B). MS (ESI+) 659 (M + 1, 100%) |
| 217 | RT 3.312 min (Condition B). MS (ESI+) 660 (M + 1, 100%) |
| 218 | RT 4.536 min (Condition B). MS (ESI+) 673 (M + 1, 100%) |
| 219 | RT 3.369 min (Condition B). MS (ESI+) 687 (M + 1, 100%) |
| 220 | RT 4.612 min (Condition B). MS (ESI+) 689 (M + 1, 100%) |
| 221 | RT 3.054 min (Condition B). MS (ESI+) 676 (M + 1, 100%) |
| 222 | RT 2.972 min (Condition B). MS (ESI+) 690 (M + 1, 100%) |

Examples 223 to 239

The same procedure as described in Example 2 was carried out to obtain the compounds of Examples 223 to 239 from the compounds of Reference Examples 199 to 215.

TABLE 19

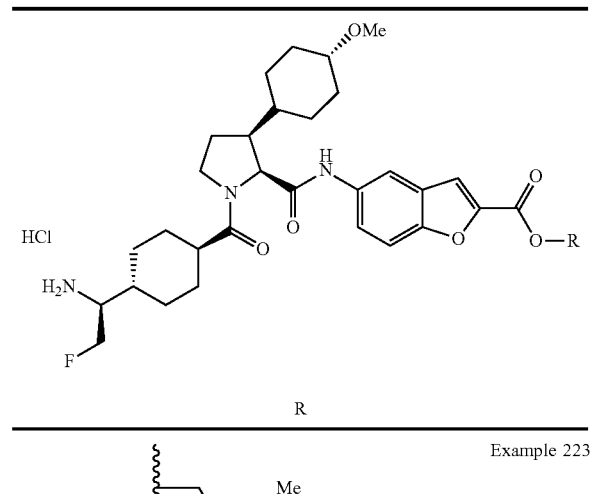

HCl

| R | |
|---|---|
|  | Example 223 |
| 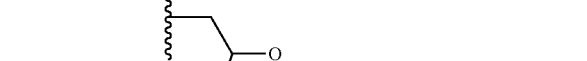 | Example 224 |
| 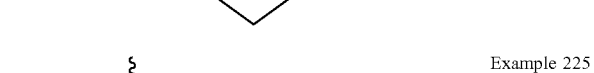 | Example 225 |
|  | Example 226 |
| 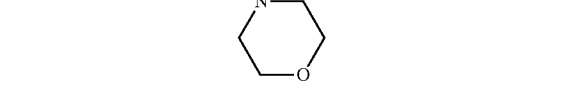 | Example 227 |
|  | Example 228 |
| | Example 229 |

TABLE 19-continued

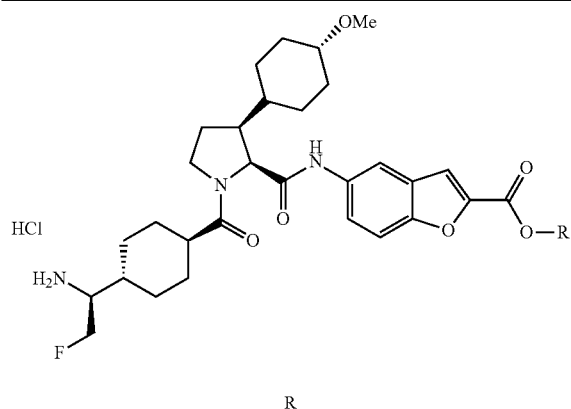

| R | |
|---|---|
| 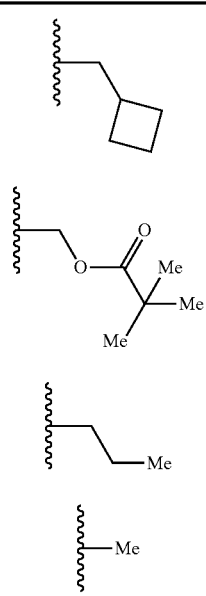 | Example 230<br><br>Example 231<br><br>Example 232<br><br>Example 233<br><br>Example 234<br><br>Example 235<br><br>Example 236<br><br>Example 237 |

TABLE 19-continued

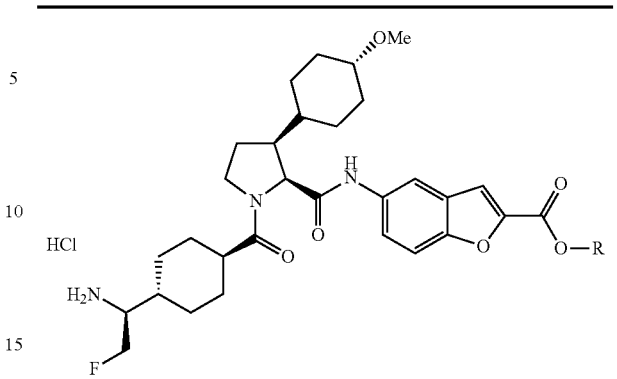

| R | |
|---|---|
| 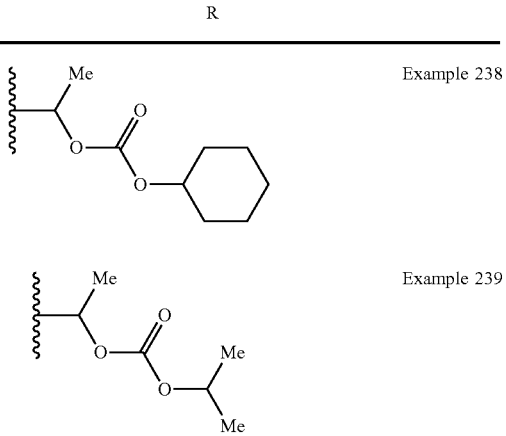 | Example 238<br><br>Example 239 |

TABLE 20

| Example | Instrumental analysis data |
|---|---|
| 223 | RT 4.744 min (Condition B). MS (ESI+) 628 (M + 1, 100%) |
| 224 | RT 4.070 min (Condition B). MS (ESI+) 642 (M + 1, 100%) |
| 225 | RT 3.339 min (Condition B). MS (ESI+) 685 (M + 1, 100%) |
| 226 | RT 4.190 min (Condition B). MS (ESI+) 644 (M + 1, 100%) |
| 227 | RT 4.533 min (Condition B). MS (ESI+) 614 (M + 1, 100%) |
| 228 | RT 4.077 min (Condition B). MS (ESI+) 670 (M + 1, 100%) |
| 229 | RT 4.907 min (Condition B). MS (ESI+) 642 (M + 1, 100%) |
| 230 | RT 4.581 min (Condition B). MS (ESI+) 626 (M + 1, 100%) |
| 231 | RT 4.544 min (Condition B). MS (ESI+) 672 (M + 1, 100%) |
| 232 | RT 4.298 min (Condition B). MS (ESI+) 600 (M + 1, 100%) |
| 233 | RT 3.924 min (Condition B). MS (ESI+) 572 (M + 1, 100%) |
| 234 | RT 3.283 min (Condition B). MS (ESI+) 671 (M + 1, 100%) |
| 235 | RT 4.085 min (Condition B). MS (ESI+) 656 (M + 1, 100%) |
| 236 | RT 4.697 min (Condition B). MS (ESI+) 628 (M + 1, 100%) |
| 237 | RT 4.333 min (Condition B). MS (ESI+) 612 (M + 1, 100%) |
| 238 | RT 4.909 min (Condition B). MS (ESI+) 728 (M + 1, 100%) |
| 239 | RT 4.199 min (Condition B). MS (ESI+) 688 (M + 1, 100%) |

Examples 240 to 246

The same procedure as described in Example 2 was carried out to obtain the compounds of Examples 240 to 246 from the compounds of Reference Examples 216 to 222.

TABLE 21

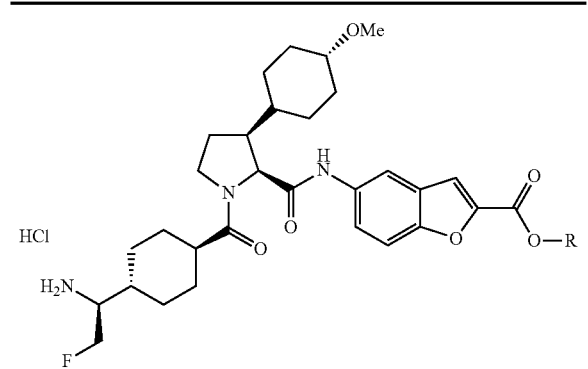

| R | |
|---|---|
| 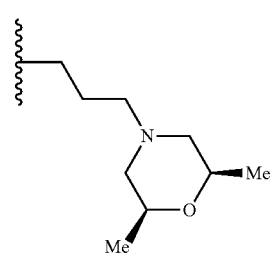 [SMILES: *CCCN1C[C@@H](C)O[C@@H](C)C1] | Example 240 |
| 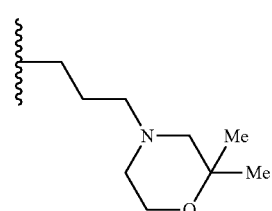 | Example 241 |
| 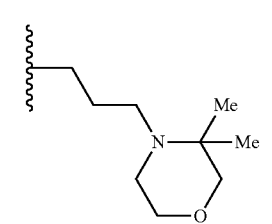 [SMILES: *CCCN1CCOCC1(C)C] | Example 242 |
| 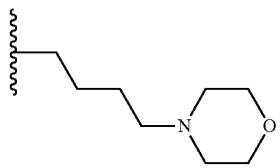 [SMILES: *CCCCN1CCOCC1] | Example 243 |
| 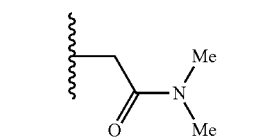 [SMILES: *CC(=O)N(C)C] | Example 244 |
| 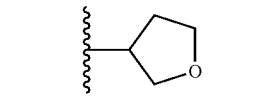 | Example 245 |

TABLE 21-continued

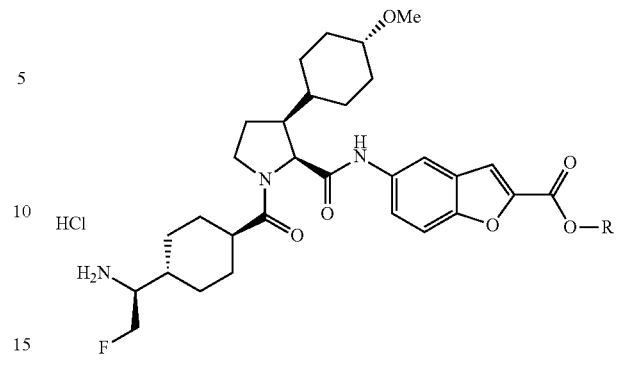

| R | |
|---|---|
| | Example 246 |

TABLE 22

| Example | Instrumental analysis data |
|---|---|
| 240 | RT 2.859 min (Kinetex 1.7μ C18 100A, 0.1% trifluoro acetic acid in water/acetonitrile, acetonitrile 1-99% 5.5 min, 0.8 mL/min(Condition D)). MS (ESI+) 713 (M + 1, 100%) |
| 241 | RT 2.863 min (Condition D). MS (ESI+) 713 (M + 1, 100%) |
| 242 | RT 2.851 min (Condition D). MS (ESI+) 713 (M + 1, 100%) |
| 243 | RT 2.839 min (Condition D). MS (ESI+) 700 (M + 1, 100%) |
| 244 | RT 2.987 min (Condition D). MS (ESI+) 644 (M + 1, 100%) |
| 245 | RT 2.905 min (Condition D). MS (ESI+) 628 (M + 1, 100%) |
| 246 | RT 3.197 min (Condition D). MS (ESI+) 656 (M + 1, 100%) |

Test Example 1

In Vitro Activated Factor XI (FXIa) Inhibition Test 0.35 μg/mL human FXIa was allowed to react with a substrate and a test compound in a 30 mmol/L HEPES buffer solution (pH 7.4) that contained 145 mmol/L NaCl, 5 mmol/L KCl, and 1 mg/mL PEG8000 (manufactured by QIAGEN) at 37° C. for 10 minutes. To the substrate, S-2366 (pyroGlu-Pro-Arg-pNA.HCl) was added to a final concentration of 300 μmol/L. After the reaction had progressed, the absorbance at OD 405 nm was measured. A change in OD without addition of the test compound was set at 100%, and a concentration at which an increase in the OD value is suppressed by 50% was calculated as an $IC_{50}$ value (nmol/L).

TABLE 23

| Example No. | FXIa inhibitory activity $IC_{50}$ (nM) |
|---|---|
| 5 | 125 |
| 14 | 130 |
| 23 | 9 |
| 24 | 34 |
| 29 | 82 |

TABLE 23-continued

| Example No. | FXIa inhibitory activity IC$_{50}$ (nM) |
|---|---|
| 34 | 28 |
| 35 | 14 |
| 38 | 30 |
| 39 | 63 |
| 40 | 45 |
| 46 | 90 |
| 50 | 84 |
| 53 | 34 |
| 55 | 220 |
| 96 | 98 |
| 99 | 6 |
| 102 | 93 |
| 103 | 2350 |
| 113 | 145 |
| 114 | 7 |
| 115 | 1500 |
| 118 | 65 |
| 121 | 43 |
| 122 | 690 |
| 130 | 195 |
| 133 | 99 |
| 134 | 54 |
| 137 | 380 |
| 138 | 72 |
| 141 | 3450 |
| 146 | 916 |
| 147 | 205 |
| 148 | 140 |
| 170 | 76 |
| 171 | 300 |
| 178 | 33 |
| 184 | 30 |
| 186 | 60 |
| 187 | 285 |
| 196 | 3500 |
| 201 | 4100 |
| 211 | 29 |
| 212 | 8 |
| 213 | 10 |

Test Example 2

Rabbit In Vivo Antithrombotic Action Evaluation Test

A rabbit model with venous thrombus was produced by modifying the report of Wienen et al. (Wienen W. et al., J. Thromb. Haemost. 5:1237-1242 (2007)). A male rabbit (JW, 2-4 kg) was narcotized by inhalation of isoflurane (ISO-FLU®, manufactured by DS Pharma Animal Health) (inductive anesthesia: 4%, continuous anesthesia: 1.5% to 2.5%). For intravenous administration of a test agent and blood collection, catheters were inserted into the left femoral vein and the left femoral artery. The left external jugular vein was exposed (2 cm) from a branch of the facial vein, the microvascular branch was then ligated, and a catheter was then inserted into the posterior facial vein. The external jugular vein (2 cm) exposed from each of an anterior facial vein branch and a facial vein branch was ligated with an artery clamp, and blood was then removed from a catheter left in the posterior facial vein. Blood in the blood vessel was washed with a normal saline, and 0.5% polidocanol (manufactured by Sigma) was injected into the blood vessel. It was then left for 5 minutes, so that the occurrence of a disorder in vascular endothelium was provoked. Thereafter, 0.5% polidocanol was removed, the inside of the blood vessel was then washed with a normal saline, and the artery clamp was then removed. The external jugular vein (2 cm) exposed from the facial vein branch, together with an injection needle 21G (manufactured by Terumo), was ligated with a silk thread, so that the inner diameter of the blood vessel was reduced to 0.8 mm. Twenty-five minutes after recirculation of the blood flow, the external jugular vein (2 cm) exposed from the facial vein branch was excised, and the wet weight and dry weight of a thrombus formed in the blood vessel were measured. A test agent or a vehicle was administered to the rabbit 2 minutes before recirculation of the blood flow.

In order to measure the activated partial thromboplastin time (aPTT) of the blood sample, which was to be used as an indicator of an endogenous coagulation pathway, 2 minutes after the administration of the test agent or the vehicle, blood was collected, and plasma was then prepared using 3.2% sodium citrate. The prepared plasma was incubated at 37° C. for 7 minutes, and an STA reagent Cephascreen (used for aPTT measurement; manufactured by Roche Diagnostics) was added in an equal amount to the resulting plasma, and the obtained mixture was further incubated for 3 minutes. Thereafter, STA calcium chloride (manufactured by Roche Diagnostics) was added in an equal amount to the resultant, and the time required until coagulation was then measured.

Figure 2:
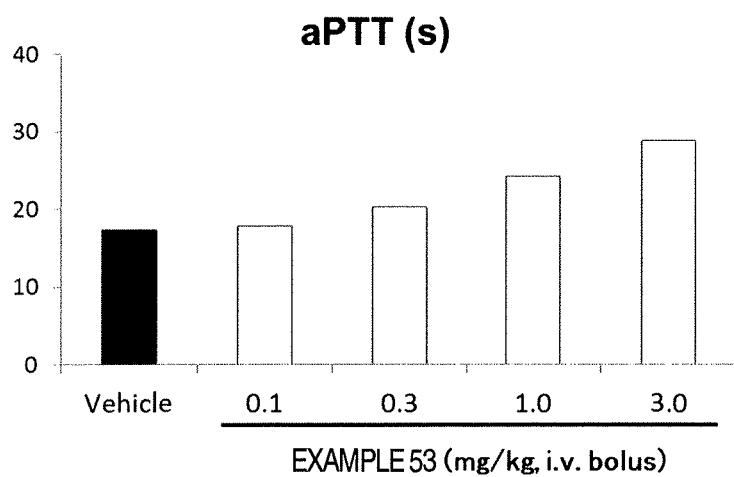
FIG. 2 is a view showing a change in the activated partial thromboplastin time (aPTT) of a blood sample by administration of the compound of Example 53 (Test Example 2).

In the present test, the compound of the present invention extended the aPTT. Thus, the present compound is considered to reduce the weight of a thrombus via inhibition of FXIa as one of endogenous coagulation factors (see Table 24 and FIGS. 1 and 2). Accordingly, the present compound is expected to become a novel anticoagulant agent.

TABLE 24

| Compound | Vehicle | Example 53 | | | |
|---|---|---|---|---|---|
| Dose (mg/kg, i.v.) | 0 | 0.1 | 0.3 | 1.0 | 3.0 |
| Thrombus weight (mg) | 68.8 | 51.3 | 30.3 | 14.7 | 14.0 |
| Thrombus (% inhibition) | 0 | 25 | 56 | 79 | 80 |
| aPTT (s) | 17.3 | 17.8 | 20.3 | 24.2 | 28.8 |
| aPTT (% vehicle) | 100 | 103 | 117 | 140 | 166 |

Test Example 3

Ester Metabolism Stabilization Test (1) Human Liver Stabilization Test

A reaction solution prepared by mixing 5 μL of human liver S9 (manufactured by Xenotech, 20 mg/mL), 20 μL of 500 mmol/L Kpi (pH7.4), 40 μL of 5 mmol/L NADPH (manufactured by Oriental Yeast Co., Ltd.) aqueous solution, and 133 μL of ion exchange water was added to 2 μL of a DMSO solution containing 100 μmol/L test substance, and the thus obtained mixture was then incubated at 37° C. for 30 minutes. After completion of the incubation, 600 μL of acetonitrile was added to the reaction solution, so that the metabolic reaction was terminated. The residual percentage of the test substance was measured using LC (LC-20A manufactured by Shimadzu Corporation) and -MS (API4000 manufactured by AB Sciex).

(2) Stabilization in Human Plasma Test

198 μL of human plasma (manufactured by Cosmo Bio) was added to 2 μL of a DMSO solution containing 100 μmol/L test substance, and the obtained mixture was then incubated at 37° C. for 30 minutes. After completion of the incubation, 600 μL of acetonitrile was added to the reaction solution, so that the metabolic reaction was terminated. The residual percentage of the test substance was measured using LC (LC-20A manufactured by Shimadzu Corporation) and -MS (API4000 manufactured by AB Sciex).

In these tests, the compound of the present invention was found to be excellent in terms of drug metabolizing property, and thus, it is anticipated that the present compound will effectively exhibit an intended FXIa inhibitory activity and the like.

TABLE 25

| Example No. | Residual percentage (%) | |
| --- | --- | --- |
| | Human liver S9 | Human plasma |
| 82 | 5.8 | 92 |
| 120 | 4.9 | 65 |
| 125 | 5.6 | 86 |
| 128 | 47 | 82 |
| 141 | 17 | 94 |
| 143 | 1.3 | 92 |
| 171 | 18 | <1 |
| 179 | 4.7 | 20 |
| 180 | 33 | 81 |
| 189 | 85 | 41 |
| 201 | 45 | 85 |
| 202 | 82 | 44 |
| 203 | 74 | 45 |
| 205 | 3.5 | 60 |
| 225 | 74 | 7.4 |
| 226 | 79 | 62 |
| 228 | 1.3 | <1 |
| 230 | 28 | 73 |
| 234 | 66 | 54 |
| 238 | 1.0 | 88 |

Industrial Applicability

Since the compound of the present invention has FXIa inhibitory activity and anticoagulant action, it is useful for the treatment of thromboembolism and the like.

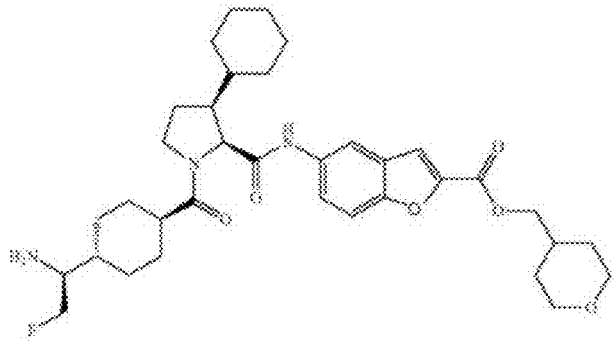

The invention claimed is:

1. A compound represented by formula (1) or a pharmaceutically acceptable salt thereof:

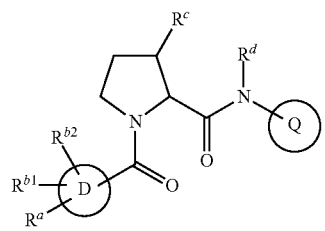

(1)

wherein
ring D represents a 3- to 8-membered hydrocarbon ring;
$R^a$ represents an optionally substituted amino group, an optionally substituted amidino group, an optionally substituted guanidino group, an optionally substituted aminocarbonyl group, an optionally substituted aminosulfonyl group, an optionally substituted $C_{1-6}$ alkoxycarbonylamino group, an optionally substituted amino $C_{1-6}$ alkyl group, an optionally substituted amidino $C_{1-6}$ alkyl group, an optionally substituted imino $C_{1-6}$ alkyl group, an optionally substituted amino $C_{3-10}$ cycloalkyl group, an optionally substituted amidino $C_{3-10}$ cycloalkyl group, an optionally substituted imino $C_{3-10}$ cycloalkyl group, an optionally substituted $C_{1-6}$ alkoxy $C_{1-6}$ alkyl group, an optionally substituted $C_{1-6}$ alkylthio $C_{1-6}$ alkyl group, an optionally substituted mercapto $C_{1-6}$ alkyl group, an optionally substituted hydroxy $C_{1-6}$ alkyl group, an optionally substituted carboxyl $C_{1-6}$ alkyl group, an optionally substituted alkoxycarbonylamino $C_{1-6}$ alkyl group or a carboxyl group;
$R^{b1}$ and $R^{b2}$ each independently represent a hydrogen atom, a halogen atom, a hydroxy group, an optionally substituted $C_{1-6}$ alkyl group or an optionally substituted $C_{1-6}$ alkoxy group;
$R^c$ represents a halogen atom, a cyano group, a carboxyl group, a hydroxy group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{3-10}$ cycloalkyl group, an optionally substituted $C_{3-10}$ cycloalkoxy group, an optionally substituted $C_{1-6}$ alkylthio group, an optionally substituted $C_{1-6}$ alkoxycarbonyl group, an optionally substituted $C_{6-10}$ aryl group, an optionally substituted 5- to 10-membered heteroaryl group, an optionally substituted 4- to 10-membered saturated heterocyclic group, an optionally substituted $C_{6-10}$ aryloxy group, an optionally substituted 5- to 10-membered heteroaryloxy group, an optionally substituted 4- to 10-membered saturated heterocyclic oxy group, an optionally substituted amino group, an optionally substituted 4- to 10-membered cyclic amino group, an optionally substituted $C_{1-6}$ alkylcarbonylamino group, an optionally substituted $C_{3-10}$ cycloalkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted aminocarbonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered saturated heterocyclic oxycarbonylamino group or an optionally substituted 4- to 10-membered cyclic aminocarbonyl group;
$R^d$ represents a hydrogen atom, an optionally substituted $C_{1-6}$ alkyl group, or an optionally substituted $C_{3-10}$ cycloalkyl group; and
ring Q is a group represented by any one of formulae (2a) to (2d):

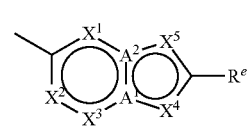

(2a)

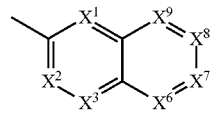

(2b)

-continued

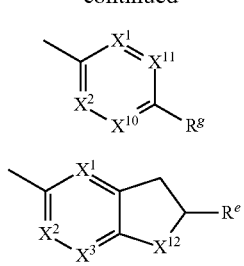

(2c)

(2d)

wherein
$X^1$, $X^2$, and $X^3$ each independently represent N or $CR^1$;
$X^4$ and $X^5$ each independently represent $CR^2$, O, S, N or $NR^3$;
$A^1$ and $A^2$ each independently represent N or C; wherein $X^1$, $X^2$, $X^3$, $X^4$, $X^5$, $A^1$, and $A^2$ are selected in such a manner that a ring containing these can form a bicyclic aromatic heterocyclic group;
$X^6$ and $X^9$ each independently represent N or $CR^4$;
$X^7$ and $X^8$ each independently represent N or $CR^f$;
$X^{10}$ and $X^{11}$ each independently represent N or $CR^5$;
$X^{12}$ represents O, S or $NR^3$;
$R^1$ represents a hydrogen atom, a halogen atom, a cyano group, an optionally substituted $C_{1-6}$ alkyl group, an optionally substituted $C_{1-6}$ alkoxy group or an optionally substituted $C_{3-10}$ cycloalkyl group wherein when two or three $R^1$ are present in the formula, these $R^1$ groups represent groups identical to or different from each other;
$R^2$ represents a hydrogen atom, a halogen atom, a cyano group, a hydroxy group, an optionally substituted $C_{2-6}$ alkenyl group, an optionally substituted $C_{2-6}$ alkynyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group, an optionally substituted $C_{1-6}$ alkoxy group or a carboxyl group wherein when two $R^2$ are present in the formula, these $R^2$ groups represent groups identical to or different from each other;
$R^3$ represents a hydrogen atom, an optionally substituted $C_{1-6}$ alkyl group, an optionally substituted $C_{3-10}$ cycloalkyl group, an optionally substituted $C_{2-6}$ alkenyl group, an optionally substituted $C_{2-6}$ alkynyl group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkylcarbonyl group, an optionally substituted $C_{3-10}$ cycloalkylcarbonyl group, an optionally substituted $C_{1-6}$ alkoxycarbonyl group, an optionally substituted aminocarbonyl group, an optionally substituted 4- to 10-membered cyclic aminocarbonyl group, an optionally substituted aminosulfonyl group, an optionally substituted 4- to 10-membered cyclic aminosulfonyl group, an optionally substituted $C_{3-10}$ cycloalkylsulfonyl group or an optionally substituted $C_{1-6}$ alkylsulfonyl group;
$R^4$ represents a hydrogen atom, a halogen atom, a cyano group, a carboxyl group, a 4- to 10-membered saturated heterocyclic oxycarbonyl group, a $C_{1-6}$ alkoxycarbonyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted aminocarbonyl group, an optionally substituted 4- to 10-membered cyclic aminocarbonyl group or an optionally substituted $C_{1-6}$ alkoxy group, wherein when two $R^4$ are present in the formula, these $R^4$ groups represent groups identical to or different from each other;
$R^5$ represents a hydrogen atom, a halogen atom, a cyano group, a hydroxy group, an optionally substituted $C_{1-6}$ alkyl group, an optionally substituted $C_{3-10}$ cycloalkyl group, an optionally substituted $C_{1-6}$ alkoxy group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group or a carboxyl group wherein when two $R^5$ are present in the formula, these $R^5$ groups represent groups identical to or different from each other;
$R^e$ and $R^f$ each independently represent a hydrogen atom, a halogen atom, a cyano group, a carboxyl group, a hydroxy group, an optionally substituted $C_{3-10}$ cycloalkyl group, an optionally substituted $C_{1-6}$ alkoxy group, an optionally substituted $C_{3-10}$ cycloalkoxy group, an optionally substituted $C_{6-10}$ aryloxy group, an optionally substituted 5- to 10-membered heteroaryloxy group, an optionally substituted 4- to 10-membered saturated heterocyclic oxy group, an optionally substituted $C_{1-6}$ alkylthio group, an optionally substituted $C_{3-10}$ cycloalkylthio group, an optionally substituted $C_{6-10}$ arylthio group, an optionally substituted 5- to 10-membered heteroarylthio group, an optionally substituted 4- to 10-membered saturated heterocyclic thio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted C$_{1-6}$ alkylcarbonylamino group, an optionally substituted C$_{3-10}$ cycloalkylcarbonylamino group, an optionally substituted C$_{6-10}$ arylcarbonylamino group, an optionally substituted 5- to 10-membered heteroarylcarbonylamino group, an optionally substituted 4- to 10-membered saturated heterocyclic carbonylamino group, an optionally substituted C$_{1-6}$ alkylsulfonylamino group, an optionally substituted C$_{3-10}$ cycloalkylsulfonylamino group, an optionally substituted C$_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted C$_{1-6}$ alkylsulfonyl group, an optionally substituted C$_{3-10}$ cycloalkylsulfonyl group, an optionally substituted C$_{6-10}$ arylsulfonyl group, an optionally substituted C$_{6-10}$ aryl group, an optionally substituted 5- to 10-membered heteroaryl group, an optionally substituted 4- to 10-membered saturated heterocyclic group, an optionally substituted C$_{1-6}$ alkyl group, an optionally substituted C$_{2-6}$ alkenyl group, an optionally substituted C$_{2-6}$ alkenyloxy group, an optionally substituted C$_{2-6}$ alkynyl group, an optionally substituted C$_{1-6}$ alkylsulfonylaminocarbonyl group, an optionally substituted C$_{3-10}$ cycloalkylsulfonylaminocarbonyl group, an optionally substituted C$_{6-10}$ arylsulfonylaminocarbonyl group, an optionally substituted 4- to 10-membered saturated heterocyclic sulfonylaminocarbonyl group, an optionally substituted 5- to 10-membered heteroarylsulfonylaminocarbonyl group, an optionally substituted aminosulfonylaminocarbonyl group, an optionally substituted 4- to 7-membered cyclic aminosulfonylaminocarbonyl group, an optionally substituted C$_{4-7}$ cycloalkoxycarbonyl group, an optionally substituted 4- to 10-membered saturated heterocyclic oxycarbonyl group or an optionally substituted C$_{1-6}$ alkoxycarbonyl group wherein when two R$^f$ are present in the formula, these R$^f$ groups represent groups identical to or different from each other; and R$^g$ represents a hydrogen atom, a halogen atom, a cyano group, a carboxyl group, a hydroxy group, an optionally substituted C$_{3-10}$ cycloalkyl group, an optionally substituted C$_{1-6}$ alkoxy group, an optionally substituted C$_{3-10}$ cycloalkoxy group, an optionally substituted C$_{6-10}$ aryloxy group, an optionally substituted 4- to 10-membered heteroaryloxy group, an optionally substituted 4- to 10-membered saturated heterocyclic oxy group, an optionally substituted C$_{1-6}$ alkylthio group, an optionally substituted C$_{3-10}$ cycloalkylthio group, an optionally substituted 5- to 10-membered heteroarylthio group, an optionally substituted 4- to 10-membered saturated heterocyclic thio group, an optionally substituted C$_{6-10}$ arylthio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted C$_{1-6}$ alkoxycarbonylamino group, an optionally substituted C$_{3-10}$ cycloalkoxycarbonylamino group, an optionally substituted C$_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted C$_{1-6}$ alkylcarbonylamino group, an optionally substituted C$_{6-10}$ arylcarbonylamino group, an optionally substituted 5- to 10-membered heteroarylcarbonylamino group, an optionally substituted 4- to 10-membered saturated heterocyclic carbonylamino group, an optionally substituted C$_{1-6}$ alkylsulfonylamino group, an optionally substituted C$_{3-10}$ cycloalkylsulfonylamino group, an optionally substituted C$_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted C$_{1-6}$ alkylsulfonyl group, an optionally substituted C$_{3-10}$ cycloalkylsulfonyl group, an optionally substituted C$_{6-10}$ arylsulfonyl group, an optionally substituted 4- to 10-membered saturated heterocyclic group, an optionally substituted C$_{1-6}$ alkyl group, an optionally substituted C$_{2-6}$ alkenyl group, an optionally substituted C$_{2-6}$ alkenyloxy group, an optionally substituted C$_{2-6}$ alkynyl group, an optionally substituted C$_{1-6}$ alkylsulfonylaminocarbonyl group, an optionally substituted C$_{3-10}$ cycloalkylsulfonylaminocarbonyl group, an optionally substituted C$_{6-10}$ arylsulfonylaminocarbonyl group, an optionally substituted 5- to 10-membered heteroarylsulfonylaminocarbonyl group, an optionally substituted 4- to 10-membered saturated heterocyclic sulfonylaminocarbonyl group, an optionally substituted aminosulfonylaminocarbonyl group, an optionally substituted 4- to 7-membered cyclic aminosulfonylaminocarbonyl group, an optionally substituted C$_{4-7}$ cycloalkoxycarbonyl group, an optionally substituted saturated heterocyclic oxycarbonyl group or an optionally substituted C$_{1-6}$ alkoxycarbonyl group.

2. The compound according to claim 1 or a pharmaceutically acceptable salt thereof, wherein ring D represents a cyclobutane ring, a cyclopentane ring, a cyclohexane ring, or a cycloheptane ring;

R$^a$ represents (1) an amino C$_{1-6}$ alkyl group wherein the amino may be optionally substituted with one or two, same or different C$_{1-6}$ alkyl groups which may be optionally substituted with one to three halogen atoms, and the C$_{1-6}$ alkyl may be optionally substituted with one to three halogen atoms, (2) a hydroxy C$_{1-6}$ alkyl group wherein the C$_{1-6}$ alkyl may be optionally substituted with one to three halogen atoms, (3) a group represented by formula (2e):

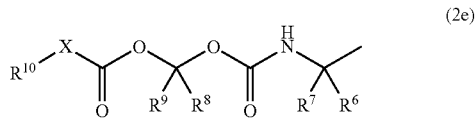

(2e)

wherein X represents a single bond or an oxygen atom; R$^6$, R$^7$, R$^8$ and R$^9$ each independently represent a hydrogen atom or a C$_{1-4}$ alkyl group which may be optionally substituted with one to three halogen atoms, and R$^{10}$ represents a C$_{1-4}$ alkyl group or a C$_{4-7}$ cycloalkyl group, (4) an amino C$_{3-10}$ cycloalkyl group wherein the amino may be optionally substituted with one or two, same or different C$_{1-6}$ alkyl groups which may be optionally substituted with one to three halogen atoms, and the $C_{3-10}$ cycloalkyl may be optionally substituted with one to three halogen atoms, or (5) an amidino group which may be optionally substituted with one or two, same or different $C_{1-6}$ alkyl groups which may be optionally substituted with one to three halogen atoms;

$R^{b1}$ and $R^{b2}$ each independently represent a hydrogen atom, a halogen atom, a hydroxy group, a $C_{1-6}$ alkyl group which may be optionally substituted with one to three halogen atoms or a $C_{1-6}$ alkoxy group, or a $C_{1-6}$ alkoxy group which may be optionally substituted with one to three halogen atoms or a $C_{1-6}$ alkoxy group; and $R^d$ represents a hydrogen atom, a $C_{1-6}$ alkyl group which may be optionally substituted with one to three halogen atoms or a $C_{1-6}$ alkoxy group, or a $C_{3-10}$ cycloalkyl group which may be optionally substituted with one to three halogen atoms or a $C_{1-6}$ alkoxy group.

3. The compound according to claim 1, or a pharmaceutically acceptable salt thereof, wherein ring D represents a cyclohexane ring;

$R^a$ represents (1) an amino $C_{1-4}$ alkyl group wherein the $C_{1-4}$ alkyl may be optionally substituted with one to three halogen atoms, (2) a hydroxy $C_{1-4}$ alkyl group wherein the $C_{1-4}$ alkyl may be optionally substituted with one to three halogen atoms, or (3) a group represented by formula (2e):

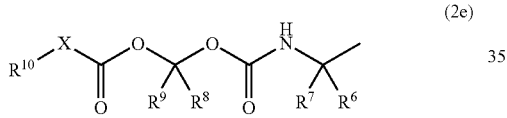

wherein X represents a single bond or an oxygen atom;

$R^6$, $R^7$, $R^8$, and $R^9$ each independently represent a hydrogen atom or a $C_{1-4}$ alkyl group which may be optionally substituted with one to three halogen atoms; and $R^{10}$ represents a $C_{1-4}$ alkyl group or a $C_{4-7}$ cycloalkyl group;

$R^{b1}$ and $R^{b2}$ each represent a hydrogen atom; and $R^d$ represents a hydrogen atom or a $C_{1-4}$ alkyl group.

4. The compound according to claim 1, or a pharmaceutically acceptable salt thereof, wherein $R^c$ represents (1) a $C_{1-6}$ alkyl group which may be optionally substituted with one to three halogen atoms, a phenyl group, a $C_{3-10}$ cycloalkyl group, or a $C_{1-6}$ alkoxy group, (2) a $C_{1-6}$ alkoxy group which may be optionally substituted with one to three halogen atoms, a phenyl group, a $C_{3-10}$ cycloalkyl group, or a $C_{1-6}$ alkoxy group, (3) a $C_{3-10}$ cycloalkyl group which may be optionally substituted with one or two, same or different groups selected from the group consisting of:

(a) a halogen atom, (b) a $C_{1-6}$ alkyl group which may be optionally substituted with one to three halogen atoms, (c) a $C_{1-6}$ alkoxy group which may be optionally substituted with one to three halogen atoms, (d) a hydroxyl group, (e) an amino group which may be optionally substituted with one or two groups selected from the group consisting of a $C_{1-6}$ alkyl group which may be optionally substituted with one to three halogen atoms, and a $C_{3-7}$ cycloalkyl group, and (f) an oxo group, (4) a $C_{3-10}$ cycloalkoxy group which may be optionally substituted with one to four, same or different groups selected from the group consisting of (a) to (f) in (3) above, (5) a phenyl group which may be optionally substituted with (a) a halogen atom, (b) a cyano group, (c) a hydroxy group, (d) a carboxyl group, (e) a $C_{1-6}$ alkyl group which may be optionally substituted with one to three halogen atoms, (f) a $C_{1-6}$ alkoxy group which may be optionally substituted with one to three halogen atoms or a $C_{1-6}$ alkoxy group, (g) a $C_{1-6}$ alkoxycarbonylamino group, (h) a $C_{1-6}$ alkylsulfonylamino group, wherein the alkyl may be optionally substituted with one to three halogen atoms, (i) a $C_{3-10}$ cycloalkyl group which may be optionally substituted with one to three halogen atoms, a $C_{1-6}$ alkoxy group, or a $C_{1-6}$ alkyl group, (j) a $C_{1-6}$ alkylcarbonylamino group, wherein the alkyl may be optionally substituted with one to three halogen atoms, (k) an amino group which may be optionally substituted with one or two, same or different groups selected from the group consisting of:

(i) a $C_{1-6}$ alkyl group which may be optionally substituted with one to three halogen atoms, a cyano group, a hydroxy group, a $C_{1-6}$ alkoxy group, a $C_{3-10}$ cycloalkyl group, or a $C_{1-6}$ alkoxycarbonylamino group, (ii) a $C_{3-10}$ cycloalkyl group which may be optionally substituted with one to three halogen atoms, a $C_{1-6}$ alkoxy group, or a $C_{1-6}$ alkyl group, and (iii) a phenyl group which may be optionally substituted with one to four, same or different groups selected from the group consisting of a halogen atom, a cyano group, a $C_{1-6}$ alkyl group, a $C_{3-10}$ cycloalkyl group, a $C_{1-6}$ alkoxycarbonylamino group, and a $C_{1-6}$ alkoxy group, (l) an aminocarbonyl group which may be optionally substituted with one or two, same or different groups selected from the group consisting of (i) to (iii) in (k) above, (m) a 4- to 10-membered cyclic amino group which may be optionally substituted with one to four, same or different groups selected from the group consisting of:

(i) a halogen atom, (ii) a $C_{1-6}$ alkyl group which may be optionally substituted with a $C_{1-6}$ alkoxy group, a hydroxy group, or one to three halogen atoms, (iii) a $C_{1-6}$ alkoxy group which may be optionally substituted with one to three halogen atoms, and (iv) a $C_{1-6}$ alkoxycarbonylamino group, and (n) a 4- to 10-membered cyclic aminocarbonyl group which may be optionally substituted with one to four, same or different groups selected from the group consisting of (i) to (iv) in (m) above, (6) a 5- or 6-membered heteroaryl group which may be optionally substituted with one to four, same or different groups selected from the group consisting of (a) to (n) in (5) above, (7) a 4- to 10-membered saturated heterocyclic group which may be optionally substituted with one to four, same or different groups selected from the group consisting of:
(a) a halogen atom,
(b) a $C_{1-6}$ alkyl group which may be optionally substituted with one to three halogen atoms or a $C_{1-6}$ alkoxy group,
(c) a $C_{1-6}$ alkoxy group which may be optionally substituted with one to three halogen atoms,
(d) a $C_{1-6}$ alkoxycarbonyl group which may be optionally substituted with one to three halogen atoms, and
(e) a $C_{3-10}$ cycloalkyl group which may be optionally substituted with one to three halogen atoms, a $C_{1-6}$ alkyl group, or a $C_{1-6}$ alkoxy group, (8) a phenoxy group which may be optionally substituted with one to four, same or different groups selected from the group consisting of (a) to (n) in (5) above, (9) a 5- or 6-membered heteroaryloxy group which may be optionally substituted with one to four, same or different groups selected from the group consisting of (a) to (n) in (5) above,

(10) a 4- to 10-membered saturated heterocyclic oxy group which may be optionally substituted with one to four, same or different groups selected from the group consisting of (a) to (e) in (7) above,

(11) an amino group which may be optionally substituted with one or two, same or different groups selected from the group consisting of:
(a) a $C_{1-6}$ alkyl group which may be optionally substituted with one to three halogen atoms, a cyano group, a hydroxy group, a $C_{1-6}$ alkoxy group, a $C_{3-10}$ cycloalkyl group, a phenyl group, a 5- or 6-membered heteroaryl group, a 4- to 7-membered saturated heterocyclic group or a $C_{1-6}$ alkoxycarbonylamino group,
(b) a $C_{3-10}$ cycloalkyl group which may be optionally substituted with one to three halogen atoms, a $C_{1-6}$ alkoxy group or a $C_{1-6}$ alkyl group, and
(c) a phenyl group which may be optionally substituted with one to four, same or different groups selected from the group consisting of a halogen atom, a cyano group, a $C_{1-6}$ alkyl group, a $C_{1-6}$ alkoxycarbonylamino group and a $C_{1-6}$ alkoxy group, or

(12) a 4- to 10-membered cyclic amino group which may be optionally substituted with one to four, same or different groups selected from the group consisting of (i) to (iv) in (m) of (5) above.

5. The compound according to claim 1, or a pharmaceutically acceptable salt thereof, wherein
$R^c$ represents
(1) a cyclohexyl group which may be optionally substituted with one or two, same or different groups selected from the group consisting of:
(a) a halogen atom,
(b) a $C_{1-6}$ alkyl group which may be optionally substituted with one to three halogen atoms or a $C_{1-6}$ alkoxy group,
(c) a $C_{1-6}$ alkoxy group which may be optionally substituted with one to three halogen atoms or a $C_{1-6}$ alkoxy group,
(d) a hydroxyl group, and
(e) an oxo group, (2) a phenyl group which may be optionally substituted with one to four, same or different groups selected from the group consisting of (a) to (d) in (1) above, (3) a pyridyl group which may be optionally substituted with one to four, same or different groups selected from the group consisting of (a) to (d) in (1) above, or (4) a 4- to 7-membered cyclic amino group which may be optionally substituted with one or two, same or different groups selected from the group consisting of (a) to (e) in (1) above.

6. The compound according to claim 1, or a pharmaceutically acceptable salt thereof, wherein
ring Q is a group represented by any one of formulae (3a) to (3v):

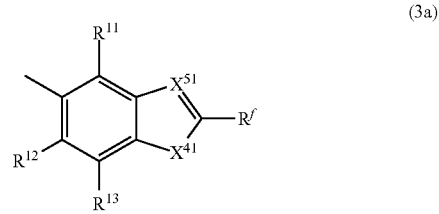

(3a)

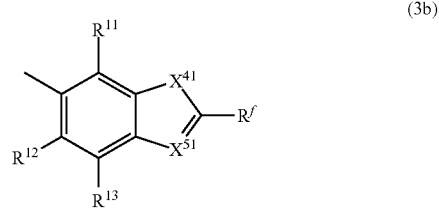

(3b)

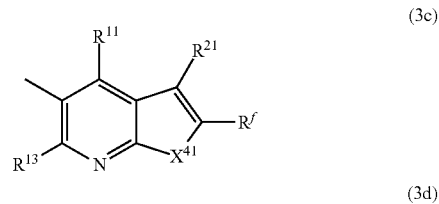

(3c)

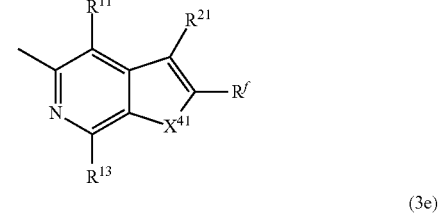

(3d)

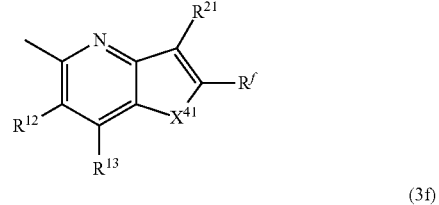

(3e)

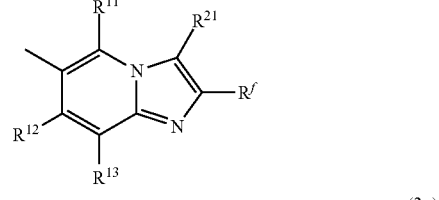

(3f)

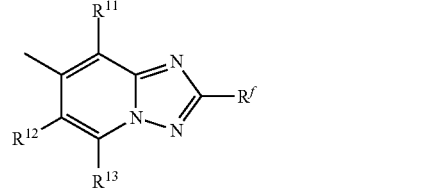

(3g)

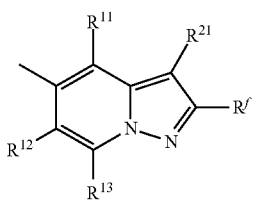 (3h)

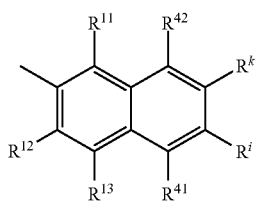 (3i)

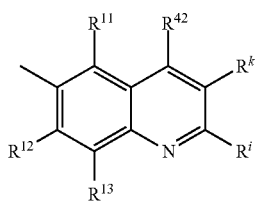 (3j)

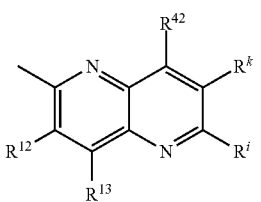 (3k)

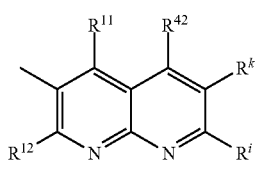 (3l)

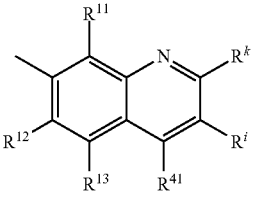 (3m)

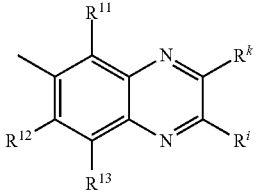 (3n)

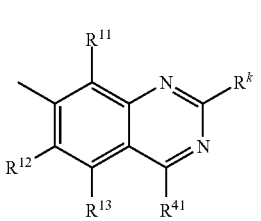 (3o)

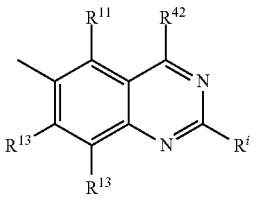 (3p)

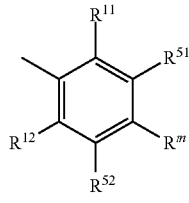 (3q)

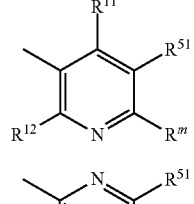 (3r)

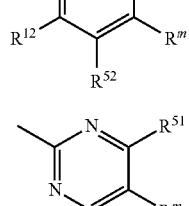 (3s)

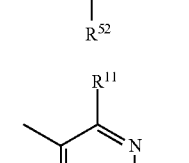 (3t)

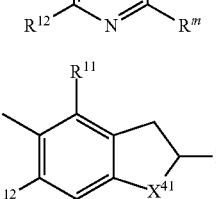 (3u)

(3v)

wherein
$X^{51}$ represents $CR^{21}$ or N;
$X^{41}$ represents $NR^{31}$, O or S;
$R^{11}$, $R^{12}$ and $R^{13}$ each independently represent a hydrogen atom, a halogen atom, a cyano group, an optionally substituted $C_{1-6}$ alkyl group, an optionally substituted $C_{1-6}$ alkoxy group or an optionally substituted $C_{3-10}$ cycloalkyl group;
$R^{21}$ represents a hydrogen atom, a halogen atom, a cyano group, a hydroxy group, an optionally substituted $C_{2-6}$ alkenyl group, an optionally substituted $C_{2-6}$ alkynyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group or a carboxyl group;

$R^{31}$ represents a hydrogen atom, an optionally substituted $C_{1-6}$ alkyl group, an optionally substituted $C_{3-10}$ cycloalkyl group, an optionally substituted $C_{2-6}$ alkenyl group, an optionally substituted $C_{2-6}$ alkynyl group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkylcarbonyl group, an optionally substituted $C_{1-6}$ alkoxycarbonyl group, an optionally substituted aminocarbonyl group, an optionally substituted 4- to 10-membered cyclic aminocarbonyl group, an optionally substituted aminosulfonyl group, an optionally substituted 4- to 10-membered cyclic aminosulfonyl group, an optionally substituted $C_{3-10}$ cycloalkylsulfonyl group or an optionally substituted $C_{1-6}$ alkylsulfonyl group;

$R^{41}$ and $R^{42}$ each independently represent a hydrogen atom, a halogen atom, a cyano group, a carboxyl group, an optionally substituted 4- to 10-membered saturated heterocyclic oxycarbonyl group, an optionally substituted $C_{1-6}$ alkoxycarbonyl group, an optionally substituted $C_{1-6}$ alkyl group, an optionally substituted $C_{3-10}$ cycloalkyl group, an optionally substituted amino group, an optionally substituted 4- to 10-membered cyclic amino group, an optionally substituted aminocarbonyl group, an optionally substituted 4- to 10-membered cyclic aminocarbonyl group or an optionally substituted $C_{1-6}$ alkoxy group;

$R^{51}$ and $R^{52}$ each independently represent a hydrogen atom, a halogen atom, a cyano group, an optionally substituted $C_{1-6}$ alkyl group, an optionally substituted $C_{3-10}$ cycloalkyl group, an optionally substituted $C_{1-6}$ alkoxy group, an optionally substituted amino group, an optionally substituted 4- to 10-membered cyclic amino group, an optionally substituted $C_{1-6}$ alkylcarbonyl group, an optionally substituted aminocarbonyl group, an optionally substituted 4- to 10-membered cyclic aminocarbonyl group, an optionally substituted $C_{1-6}$ alkylsulfonylamino group, an optionally substituted $C_{1-6}$ alkylcarbonylamino group, an optionally substituted $C_{1-6}$ alkoxycarbonylamino group, an optionally substituted 4- to 10-membered saturated heterocyclic group, an optionally substituted $C_{1-6}$ alkoxycarbonyl group, an optionally substituted 4- to 10-membered saturated heterocyclic oxycarbonyl group or a carboxyl group;

$R^f$, $R^i$, and $R^k$ each independently represent a hydrogen atom, a halogen atom, a cyano group, a carboxyl group, a hydroxy group, an optionally substituted $C_{3-10}$ cycloalkyl group, an optionally substituted $C_{1-6}$ alkoxy group, an optionally substituted $C_{3-10}$ cycloalkoxy group, an optionally substituted $C_{6-10}$ aryloxy group, an optionally substituted 5- to 10-membered heteroaryloxy group, an optionally substituted 4- to 10-membered saturated heterocyclic oxy group, an optionally substituted $C_{1-6}$ alkylthio group, an optionally substituted $C_{3-10}$ cycloalkylthio group, an optionally substituted $C_{6-10}$ arylthio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted $C_{1-6}$ alkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted $C_{1-6}$ alkylsulfonyl group, an optionally substituted $C_{3-10}$ cycloalkylsulfonyl group, an optionally substituted $C_{6-10}$ arylsulfonyl group, an optionally substituted $C_{6-10}$ aryl group, an optionally substituted 5- to 10-membered heteroaryl group, an optionally substituted 4- to 10-membered saturated heterocyclic group, an optionally substituted $C_{1-6}$ alkyl group, an optionally substituted $C_{2-6}$ alkenyl group, an optionally substituted $C_{2-6}$ alkenyloxy group, an optionally substituted $C_{2-6}$ alkynyl group, an optionally substituted $C_{1-6}$ alkylsulfonylaminocarbonyl group, an optionally substituted $C_{3-10}$ cycloalkylsulfonylaminocarbonyl group, an optionally substituted $C_{6-10}$ arylsulfonylaminocarbonyl group, an optionally substituted 4- to 10-membered saturated heterocyclic sulfonylaminocarbonyl group, an optionally substituted $C_{6-10}$ heteroarylsulfonylaminocarbonyl group, an optionally substituted aminosulfonylaminocarbonyl group, an optionally substituted 4- to 7-membered cyclic aminosulfonylaminocarbonyl group, an optionally substituted $C_{4-7}$ cycloalkoxycarbonyl group, an optionally substituted 4- to 10-membered saturated heterocyclic oxycarbonyl group or an optionally substituted $C_{1-6}$ alkoxycarbonyl group; and $R^m$ represents a hydrogen atom, a halogen atom, a cyano group, a carboxyl group, a hydroxy group, an optionally substituted $C_{3-10}$ cycloalkyl group, an optionally substituted $C_{1-6}$ alkoxy group, an optionally substituted $C_{3-10}$ cycloalkoxy group, an optionally substituted $C_{6-10}$ aryloxy group, an optionally substituted 4- to 10-membered heteroaryloxy group, an optionally substituted 4- to 10-membered saturated heterocyclic oxy group, an optionally substituted $C_{1-6}$ alkylthio group, an optionally substituted $C_{3-10}$ cycloalkylthio group, an optionally substituted $C_{6-10}$ arylthio group, an optionally substituted amino group, an optionally substituted aminocarbonyl group, an optionally substituted aminosulfonyl group, an optionally substituted 4- to 10-membered cyclic amino group, an optionally substituted 4- to 10-membered cyclic aminocarbonyl group, an optionally substituted 4- to 10-membered cyclic aminosulfonyl group, an optionally substituted $C_{1-6}$ alkoxycarbonylamino group, an optionally substituted $C_{3-10}$ cycloalkoxycarbonylamino group, an optionally substituted $C_{6-10}$ aryloxycarbonylamino group, an optionally substituted 5- to 10-membered heteroaryloxycarbonylamino group, an optionally substituted 4- to 10-membered heterocyclic oxycarbonylamino group, an optionally substituted $C_{1-6}$ alkylcarbonylamino group, an optionally substituted $C_{6-10}$ arylcarbonylamino group, an optionally substituted 5- to 10-membered heteroarylcarbonylamino group, an optionally substituted 4- to 10-membered saturated heterocyclic carbonylamino group, an optionally substituted $C_{1-6}$ alkylsulfonylamino group, an optionally substituted $C_{3-10}$ cycloalkylsulfonylamino group, an optionally substituted $C_{6-10}$ arylsulfonylamino group, an optionally substituted 5- to 10-membered heteroarylsulfonylamino group, an optionally substituted 4- to 10-membered saturated heterocyclic sulfonylamino group, an optionally substituted $C_{1-6}$ alkylsulfonyl group, an optionally substituted $C_{3-10}$ cycloalkylsulfonyl group, an optionally substituted $C_{6-10}$ arylsulfonyl group, or an optionally substituted 4- to 10-membered saturated heterocyclic group, an optionally substituted $C_{1-6}$ alkyl group, an optionally substituted $C_{2-6}$ alkenyl group, an optionally substituted $C_{2-6}$ alkenyloxy group, an optionally substituted $C_{2-6}$ alkynyl group, an optionally substituted $C_{1-6}$ alkylsulfonylaminocarbonyl group, an optionally substituted $C_{3-10}$ cycloalkylsulfonylaminocarbonyl group, an optionally substituted $C_{6-10}$ arylsulfonylaminocarbonyl group, an optionally substituted 4- to 10-membered saturated heterocyclic sulfonylaminocarbonyl group, an optionally substituted $C_{6-10}$ heteroarylsulfonylaminocarbonyl group, an optionally substituted aminosulfonylaminocarbonyl group, an optionally substituted 4- to 7-membered cyclic aminosulfonylaminocarbonyl group, an optionally substituted $C_{4-7}$ cycloalkoxycarbonyl group, an optionally substituted 4- to 10-membered saturated heterocyclic oxycarbonyl group or an optionally substituted $C_{1-6}$ alkoxycarbonyl group.

7. The compound according to claim 6 or a pharmaceutically acceptable salt thereof, wherein
ring Q is a group represented by formula (3a), (3b), (3c), (3d), (3e), (3f), (3j), (3q), (3r), (3s) or (3v).

8. The compound according to claim 7 or a pharmaceutically acceptable salt thereof, wherein ring Q is a group represented by formula (3a), (3b), (3f), (3j), (3q), (3r) or (3s).

9. The compound according to claim 8 or a pharmaceutically acceptable salt thereof, wherein ring Q is a group represented by formula (3a), (3j), (3q) or (3s), and $X^{51}$ is $CR^{21}$.

10. The compound according to claim 9 or a pharmaceutically acceptable salt thereof, wherein ring Q is a group represented by formula (3a) or (3q).

11. The compound according to claim 1, or a pharmaceutically acceptable salt thereof, wherein
$R^{11}$, $R^{12}$, $R^{13}$, $R^{41}$ and $R^{42}$ each independently represent a hydrogen atom, a halogen atom, a cyano group, a $C_{1-6}$ alkyl group which may be optionally substituted with one to three halogen atoms, a $C_{1-6}$ alkoxy group which may be optionally substituted with one to three halogen atoms, or a $C_{3-10}$ cycloalkyl group which may be optionally substituted with one to three halogen atoms;

$R^{21}$ K represents
(1) a hydrogen atom,
(2) a halogen atom,
(3) a cyano group,
(4) a $C_{1-6}$ alkyl group which may be optionally substituted with one to three halogen atoms or a $C_{1-6}$ alkoxy group,
(5) a $C_{3-10}$ cycloalkyl group which may be optionally substituted with one to three halogen atoms or a $C_{1-6}$ alkoxy group,
(6) an amino group which may be optionally substituted with one or two, same or different $C_{1-6}$ alkyl groups which may be optionally substituted with one to three halogen atoms,
(7) a $C_{1-6}$ alkylcarbonyl group which may be optionally substituted with one to three halogen atoms,
(8) a $C_{1-6}$ alkylcarbonylamino group which may be optionally substituted with one to three halogen atoms,
(9) a $C_{1-6}$ alkoxycarbonylamino group,
(10) a phenyl group which may be optionally substituted with
  (a) a halogen atom,
  (b) a cyano group,
  (c) a hydroxy group,
  (d) a carboxyl group,
  (e) a $C_{1-6}$ alkyl group which may be optionally substituted with one to three halogen atoms,
  (f) a $C_{1-6}$ alkoxy group which may be optionally substituted with one to three halogen atoms,
  (g) a $C_{1-6}$ alkoxycarbonylamino group which may be optionally substituted with one to three halogen atoms,
  (h) a $C_{1-6}$ alkylsulfonylamino group which may be optionally substituted with one to three halogen atoms,
  (i) a $C_{3-10}$ cycloalkyl group which may be optionally substituted with one to three halogen atoms or a $C_{1-6}$ alkyl group,
  (j) a $C_{1-6}$ alkylcarbonylamino group which may be optionally substituted with one to three halogen atoms,
  (k) an amino group which may be optionally substituted with one or two, same or different groups selected from the group consisting of:
    (i) a $C_{1-6}$ alkyl group which may be optionally substituted with one to three halogen atoms, a cyano group, a hydroxy group, a $C_{1-6}$ alkoxy group, a $C_{3-10}$ cycloalkyl group or a $C_{1-6}$ alkoxycarbonylamino group,
    (ii) a $C_{3-10}$ cycloalkyl group which may be optionally substituted with one to three halogen atoms or a $C_{1-6}$ alkyl group,
    (iii) a phenyl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group,
    (iv) a 5- or 6-membered heteroaryl group which may be optionally substituted with one to four, same or different groups selected from the group consisting of a halogen atom, a cyano group, a $C_{1-6}$ alkyl group, a $C_{1-6}$ alkoxycarbonylamino group, and a $C_{1-6}$ alkoxy group, and (v) a 5- or 6-membered saturated heterocyclic group which may be optionally substituted with one to three halogen atoms, a $C_{1-6}$ alkyl group or a $C_{1-6}$ alkoxy group,
(l) an aminocarbonyl group which may be optionally substituted with one or two, same or different groups selected from the group consisting of (i) to (v) in (k) above,
(m) a 4- to 10-membered cyclic amino group which may be optionally substituted with one to four, same or different groups selected from the group consisting of:
  (i) a $C_{1-6}$ alkyl group which may be optionally substituted with a hydroxy group, a $C_{1-6}$ alkoxy group or one to three halogen atoms,
  (ii) a $C_{1-6}$ alkoxy group which may be optionally substituted with one to three halogen atoms or a $C_{1-6}$ alkoxy group,
  (iii) a $C_{1-6}$ alkoxycarbonylamino group, and
  (iv) a halogen atom, or
(n) a 4- to 10-membered cyclic aminocarbonyl group which may be optionally substituted with one to four, same or different groups selected from the group consisting of (i) to (iv) in (m) above,
(11) a 5- or 6-membered heteroaryl group which may be optionally substituted with one to four, same or different groups selected from the group consisting of (a) to (n) in (10) above,
(12) a 5- or 6-membered saturated heterocyclic group which may be optionally substituted with one to four, same or different groups selected from the group consisting of (a) to (n) in (10) above,
(13) a $C_{1-6}$ alkoxycarbonyl group,
(14) an aminocarbonyl group which may be optionally substituted with one or two, same or different groups selected from the group consisting of (i) to (v) in (k) of (10) above,
(15) a 4- to 10-membered cyclic aminocarbonyl group which may be optionally substituted with one to four, same or different groups selected from the group consisting of (i) to (iv) in (m) of (10) above, or
(16) a carboxyl group;
$R^{31}$ represents
(1) a hydrogen atom,
(2) a $C_{1-6}$ alkyl group which may be optionally substituted with
  (a) a carboxyl group,
  (b) an aminocarbonyl group, wherein the amino may be optionally substituted with one or two, same or different groups selected from the group consisting of:
    (i) a $C_{1-6}$ alkyl group which may be optionally substituted with one to three halogen atoms, a cyano group, a hydroxy group, a $C_{1-6}$ alkoxy group, a $C_{3-10}$ cycloalkyl group or a $C_{1-6}$ alkoxycarbonylamino group, and
    (ii) a $C_{3-10}$ cycloalkyl group which may be optionally substituted with one to three halogen atoms or a $C_{1-6}$ alkyl group,
  (c) a $C_{1-6}$ alkoxy group which may be optionally substituted with one to three halogen atoms,
  (d) a 4- to 10-membered cyclic aminocarbonyl group which may be optionally substituted with one to four, same or different groups selected from the group consisting of:
    (i) a $C_{1-6}$ alkyl group which may be optionally substituted with a halogen atom, a hydroxy group, a $C_{1-6}$ alkoxy group, or one to three halogen atoms,
    (ii) a $C_{1-6}$ alkoxy group which may be optionally substituted with one to three halogen atoms, and
    (iii) a $C_{1-6}$ alkoxycarbonylamino,
  (e) a $C_{3-10}$ cycloalkyl group which may be optionally substituted with one to three halogen atoms, a $C_{1-6}$ alkoxy group or a $C_{1-6}$ alkyl group, or
  (f) one to three halogen atoms,
(3) a $C_{3-10}$ cycloalkyl group which may be optionally substituted with one to three halogen atoms or a $C_{1-6}$ alkyl group,
(4) a $C_{1-6}$ alkylcarbonyl group which may be optionally substituted with one to three halogen atoms, or
(5) a $C_{1-6}$ alkylsulfonyl group which may be optionally substituted with one to three halogen atoms; and
$R^{51}$, and $R^{52}$ each independently represent
(1) a hydrogen atom,
(2) a halogen atom,
(3) a cyano group,
(4) a $C_{1-6}$ alkyl group which may be optionally substituted with
  (a) a halogen atom,
  (b) a cyano group,
  (c) a hydroxy group,
  (d) a carboxyl group,
  (e) a $C_{1-6}$ alkoxy group which may be optionally substituted with one to three halogen atoms,
  (f) a $C_{1-6}$ alkoxycarbonylamino group,
  (g) a $C_{1-6}$ alkylsulfonylamino group which may be optionally substituted with one to three halogen atoms,
  (h) a $C_{3-10}$ cycloalkyl group which may be optionally substituted with one to three halogen atoms or a $C_{1-6}$ alkyl group,
  (i) a $C_{1-6}$ alkylcarbonylamino group which may be optionally substituted with one to three halogen atoms,
  (j) an amino group which may be optionally substituted with one or two, same or different $C_{1-6}$ alkyl groups which may be optionally substituted with one to three halogen atoms,
  (k) an aminocarbonyl group which may be optionally substituted with one or two, same or different $C_{1-6}$ alkyl groups which may be optionally substituted with one to three halogen atoms,
  (l) a 4- to 10-membered cyclic amino group which may be optionally substituted with one to four, same or different groups selected from the group consisting of:
    (i) a $C_{1-6}$ alkyl group which may be optionally substituted with a hydroxy group, a $C_{1-6}$ alkoxy group, or one to three halogen atoms,
    (ii) a $C_{1-6}$ alkoxy group which may be optionally substituted with one to three halogen atoms,
    (iii) a $C_{1-6}$ alkoxycarbonylamino group, and
    (iv) a halogen atom, or
  (m) a 4- to 10-membered cyclic aminocarbonyl group which may be optionally substituted with one to four, same or different groups selected from the group consisting of:
    (i) a $C_{1-6}$ alkyl group which may be optionally substituted with a $C_{1-6}$ alkoxy group, a hydroxy group, or one to three halogen atoms),
    (ii) a $C_{1-6}$ alkoxy group which may be optionally substituted with one to three halogen atoms,
    (iii) a $C_{1-6}$ alkoxycarbonylamino group, and
    (iv) a halogen atom,
  (5) a $C_{3-10}$ cycloalkyl group which may be optionally substituted with one to three halogen atoms or a $C_{1-6}$ alkyl group, (6) an amino group which may be optionally substituted with one or two, same or different $C_{1-6}$ alkyl groups which may be optionally substituted with one to three halogen atoms,
(7) a $C_{1-6}$ alkylcarbonyl group which may be optionally substituted with one to three halogen atoms,
(8) an aminocarbonyl group which may be optionally substituted with one or two, same or different $C_{1-6}$ alkyl groups,
(9) a 4- to 10-membered cyclic aminocarbonyl group which may be optionally substituted with one to four, same or different groups selected from the group consisting of:
(a) a $C_{1-6}$ alkyl group which may be optionally substituted with a $C_{1-6}$ alkoxy group, a hydroxy group, or one to three halogen atoms,
(b) a $C_{1-6}$ alkoxy group which may be optionally substituted with one to three halogen atoms,
(c) a $C_{1-6}$ alkoxycarbonylamino group, and
(d) a halogen atom,
(10) a $C_{1-6}$ alkylcarbonylamino group which may be optionally substituted with one to four, same or different groups selected from the group consisting of:
(a) a halogen atom,
(b) a cyano group,
(c) a hydroxy group,
(d) a carboxyl group,
(e) a $C_{1-6}$ alkoxy group which may be optionally substituted with one to three halogen atoms,
(f) a $C_{1-6}$ alkoxycarbonylamino group,
(g) a $C_{1-6}$ alkylsulfonylamino group which may be optionally substituted with one to three halogen atoms,
(h) a $C_{3-10}$ cycloalkyl group which may be optionally substituted with one to three halogen atoms or a $C_{1-6}$ alkyl group,
(i) a $C_{1-6}$ alkylcarbonylamino group which may be optionally substituted with one to three halogen atoms,
(j) an amino group which may be optionally substituted with one or two, same or different $C_{1-6}$ alkyl groups,
(k) an aminocarbonyl group which may be optionally substituted with one or two, same or different $C_{1-6}$ alkyl groups,
(l) a 4- to 10-membered cyclic amino group which may be optionally substituted with one to four, same or different groups selected from the group consisting of:
  (i) a $C_{1-6}$ alkyl group which may be optionally substituted with a $C_{1-6}$ alkoxy group, a hydroxy group, or one to three halogen atoms,
  (ii) a $C_{1-6}$ alkoxy group which may be optionally substituted with one to three halogen atoms,
  (iii) a $C_{1-6}$ alkoxycarbonylamino group, and
  (iv) a halogen atom, and
(m) a 4- to 10-membered cyclic aminocarbonyl group which may be optionally substituted with (a) to (d) in (9) above,
(11) a $C_{1-6}$ alkoxycarbonylamino group,
(12) a saturated heterocyclic oxycarbonyl group which may be optionally substituted with one to four, same or different groups selected from the group consisting of (a) to (m) in (10) above,
(13) a 5- or 6-membered saturated heterocyclic group which may be optionally substituted with one to four, same or different groups selected from the group consisting of (a) to (m) in (10) above,
(14) a $C_{1-6}$ alkoxy group which may be optionally substituted with one to three halogen atoms, or
(15) a carboxyl group.

12. The compound according to claim 1, or a pharmaceutically acceptable salt thereof, wherein
$R^{11}$, $R^{12}$, $R^{13}$, $R^{41}$ and $R^{42}$ each independently represent a hydrogen atom, a halogen atom, a $C_{1-6}$ alkyl group which may be optionally substituted with one to three halogen atoms, or a $C_{1-6}$ alkoxy group which may be optionally substituted with one to three halogen atoms;
$R^{21}$ represents a hydrogen atom, a halogen atom, a cyano group or a $C_{1-6}$ alkyl group which may be optionally substituted with one to three halogen atoms;
$R^{31}$ represents a hydrogen atom, a $C_{1-6}$ alkyl group which may be optionally substituted with one to three halogen atoms, a $C_{1-6}$ alkoxy group or a carboxyl group, a $C_{3-10}$ cycloalkyl group which may be optionally substituted with one to three halogen atoms or a $C_{1-6}$ alkyl group, a $C_{1-6}$ alkylsulfonyl group, or a $C_{1-6}$ alkylcarbonyl group; and
$R^{51}$, and $R^{52}$ each independently represent a hydrogen atom, a halogen atom, a cyano group, a $C_{1-6}$ alkyl group which may be optionally substituted with one to three halogen atoms, a $C_{1-6}$ alkoxy group which may be optionally substituted with one to three halogen atoms, or a carboxyl group.

13. The compound according to claim 1, or a pharmaceutically acceptable salt thereof, wherein
$R^{11}$, $R^{12}$, $R^{13}$, $R^{41}$, $R^{42}$, $R^{51}$ and $R^{52}$ each independently represent a hydrogen atom, a halogen atom, a $C_{1-6}$ alkyl group or a $C_{1-6}$ alkoxy group;
$R^{21}$ represents a hydrogen atom, a halogen atom or a $C_{1-6}$ alkyl group; and
$R^{31}$ represents a hydrogen atom or a $C_{1-6}$ alkyl group which may be optionally substituted with one to three halogen atoms.

14. The compound according to claim 1, or a pharmaceutically acceptable salt thereof, wherein
$R^f$, $R^i$ and $R^k$ each independently represent
(1) a hydrogen atom,
(2) a cyano group,
(3) a carboxyl group,
(4) an amino group which may be optionally substituted with one or two, same or different groups selected from the group consisting of:
(a) a $C_{1-6}$ alkyl group which may be optionally substituted with one to three halogen atoms, a cyano group, a hydroxy group, a carboxyl group, a $C_{1-6}$ alkoxy group, a $C_{3-10}$ cycloalkyl group, or a $C_{1-6}$ alkoxycarbonylamino group,
(b) a $C_{3-10}$ cycloalkyl group which may be optionally substituted with one to three halogen atoms or a $C_{1-6}$ alkyl group,
(c) a phenyl group which may be optionally substituted with one to four, same or different groups selected from the group consisting of a halogen atom, a cyano group, a $C_{1-6}$ alkyl group, a $C_{1-6}$ alkoxycarbonylamino group and a $C_{1-6}$ alkoxy group,
(d) a 5- or 6-membered heteroaryl group which may be optionally substituted with one to four, same or different groups selected from the group consisting of a halogen atom, a cyano group, a $C_{1-6}$ alkyl group, a $C_{1-6}$ alkoxycarbonylamino group and a $C_{1-6}$ alkoxy group, and
(e) a 4- to 6-membered saturated heterocyclic group which may be optionally substituted with one to four, same or different groups selected from the group consisting of a halogen atom, a cyano group, a $C_{1-6}$ alkyl group, a $C_{1-6}$ alkoxycarbonylamino group and a $C_{1-6}$ alkoxy group, (5) an aminocarbonyl group, wherein the amino may be optionally substituted with one to two, same or different groups selected from the group consisting of (a) to (e) in (4) above,
(6) a 4- to 10-membered cyclic amino group which may be optionally substituted with one to four, same or different groups selected from the group consisting of:
(a) a halogen atom,
(b) a cyano group,
(c) a hydroxy group,
(d) a $C_{1-6}$ alkyl group which may be optionally substituted with
  (i) one to three halogen atoms,
  (ii) a carboxyl group,
  (iii) an aminocarbonyl group wherein the amino may be optionally substituted with one or two, same or different groups selected from the group consisting of (a) to (e) in (4) above,
  (iv) a 4- to 10-membered cyclic aminocarbonyl group which may be optionally substituted with one to four, same or different groups selected from the group consisting of a halogen atom, a cyano group, a hydroxy group, a $C_{1-6}$ alkyl group, a $C_{1-6}$ alkoxy group and a $C_{1-6}$ alkoxycarbonylamino group, or
  (v) a $C_{1-6}$ alkoxycarbonylamino group,
(e) a $C_{1-6}$ alkoxy group which may be optionally substituted with
  (i) one to three halogen atoms,
  (ii) a carboxyl group,
  (iii) an aminocarbonyl group wherein the amino may be optionally substituted with one or two, same or different groups selected from the group consisting of (a) to (e) in (4) above,
  (iv) a 4- to 10-membered cyclic aminocarbonyl group which may be optionally substituted with one to four, same or different groups selected from the group consisting of a halogen atom, a cyano group, a hydroxy group, a $C_{1-6}$ alkyl group, a $C_{1-6}$ alkoxy group and a $C_{1-6}$ alkoxycarbonylamino group,
  (v) a $C_{1-6}$ alkoxycarbonylamino group, or
  (vi) a $C_{1-6}$ alkoxycarbonyl group, and
(f) a $C_{1-6}$ alkoxycarbonylamino group,
(7) a 4- to 10-membered cyclic aminocarbonyl group which may be optionally substituted with one to four, same or different groups selected from the group consisting of (a) to (f) in (6) above,
(8) a phenyl group which may be optionally substituted with one to four, same or different groups selected from the group consisting of:
(a) a halogen atom,
(b) a cyano group,
(c) a hydroxy group,
(d) a carboxyl group,
(e) a $C_{1-6}$ alkyl group which may be optionally substituted with
  (i) one to three halogen atoms,
  (ii) a carboxyl group,
  (iii) an aminocarbonyl group, wherein the amino may be optionally substituted with one or two, same or different groups selected from the group consisting of (a) to (e) in (4) above,
  (iv) a 4- to 10-membered cyclic aminocarbonyl group which may be optionally substituted with one to four, same or different groups selected from the group consisting of a halogen atom, a cyano group, a hydroxy group, a $C_{1-6}$ alkyl group, a $C_{1-6}$ alkoxy group and a $C_{1-6}$ alkoxycarbonylamino group, or
  (v) a $C_{1-6}$ alkoxycarbonylamino group,
(f) a $C_{1-6}$ alkoxy group which may be optionally substituted with
  (i) one to three halogen atoms,
  (ii) a carboxyl group,
  (iii) an aminocarbonyl group, wherein the amino may be optionally substituted with one or two, same or different groups selected from the group consisting of (a) to (e) in (4) above,
  (iv) a 4- to 10-membered cyclic aminocarbonyl group which may be optionally substituted with one to four, same or different groups selected from the group consisting of (a) to (f) in (6) above, or
  (v) a $C_{1-6}$ alkoxycarbonylamino group,
(g) a $C_{1-6}$ alkoxycarbonylamino group which may be optionally substituted with one to three halogen atoms,
(h) a $C_{1-6}$ alkylsulfonylamino group which may be optionally substituted with one to three halogen atoms,
(i) a $C_{3-10}$ cycloalkyl group which may be optionally substituted with one to three halogen atoms or a $C_{1-6}$ alkyl group,
(j) a $C_{1-6}$ alkylcarbonylamino group which may be optionally substituted with one to three halogen atoms,
(k) an amino group which may be optionally substituted with one or two different groups selected from the group consisting of (a) to (e) in (4) above,
(l) an aminocarbonyl group, wherein the amino which may be optionally substituted with one or two different groups selected from the group consisting of (a) to (e) in (4) above,
(m) a 4- to 10-membered cyclic amino group which may be optionally substituted with one to four, same or different groups selected from the group consisting of (a) to (f) in (6) above,
(n) a 4- to 10-membered cyclic aminocarbonyl group which may be optionally substituted with one to four, same or different groups selected from the group consisting of (a) to (f) in (6) above, and
(o) a $C_{1-6}$ alkoxycarbonyl group,
(9) a 5- or 6-membered heteroaryl group which may be optionally substituted with one to four, same or different groups selected from the group consisting of (a) to (o) in (8) above,
(10) a 4- to 10-membered saturated heterocyclic group which may be optionally substituted with one to four, same or different groups selected from the group consisting of (a) to (o) in (8) above,
(11) a $C_{1-6}$ alkyl group which may be optionally substituted with
(a) one to three halogen atoms,
(b) a carboxyl group,
(c) a cyano group,
(d) a $C_{1-6}$ alkoxy group,
(e) a phenyl group which may be optionally substituted with one to four, same or different groups selected from the group consisting of (a) to (o) in (8) above,
(f) a 5- or 6-membered heteroaryl group which may be optionally substituted with one to four, same or different groups selected from the group consisting of (a) to (o) in (8) above,
(g) a 4- to 10-membered saturated heterocyclic group which may be optionally substituted with one to four, same or different groups selected from the group consisting of (a) to (o) in (8) above,
(h) a hydroxy group,
(i) an aminocarbonyl group, wherein the amino may be optionally substituted with one or two different groups selected from the group consisting of (a) to (e) in (4) above,
(j) a 4- to 10-membered cyclic aminocarbonyl group which may be optionally substituted with one to four, same or different groups selected from the group consisting of (a) to (f) in (6) above,
(k) a $C_{1-6}$ alkoxycarbonylamino group,
(l) a $C_{1-6}$ alkoxycarbonyl group which may be optionally substituted with one or two, same or different groups selected from the group consisting of:
  (l1) a $C_{1-6}$ alkoxy group which may be optionally substituted with one to three halogen atoms,
  (l2) a $C_{3-7}$ cycloalkoxy group which may be optionally substituted with one to three halogen atoms,
  (l3) a mono- or di-$C_{1-6}$ alkylamino group, wherein the alkyl may be optionally substituted with one to three halogen atoms,
  (l4) a 4- to 7-membered cyclic amino group which may be optionally substituted with one to three halogen atoms, a $C_{1-6}$ alkyl group, or a $C_{1-6}$ alkoxy group,
  (l5) a mono- or di-$C_{1-6}$ alkylaminocarbonyl group, wherein the alkyl may be optionally substituted with one to three halogen atoms,
  (l6) a 4- to 7-membered cyclic aminocarbonyl group which may be optionally substituted with one to three halogen atoms, a $C_{1-6}$ alkyl group or a $C_{1-6}$ alkoxy group, and
  (l7) a $C_{3-7}$ cycloalkyl group which may be optionally substituted with one to three halogen atoms,
(m) a group represented by the following formula (4a):

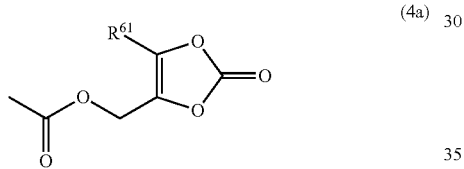

(4a)

wherein $R^{61}$ represents
  (m1) a hydrogen atom,
  (m2) a $C_{1-4}$ alkyl group which may be optionally substituted with one to three halogen atoms or a $C_{1-4}$ alkoxy group,
  (m3) a $C_{3-6}$ cycloalkyl group which may be optionally substituted with a $C_{1-4}$ alkoxy group, or
  (m4) a $C_{6-10}$ aryl group which may be optionally substituted with a $C_{1-4}$ alkyl group, one to three halogen atoms, or a $C_{1-4}$ alkoxy group, or
(n) a group represented by the following formula (5a):

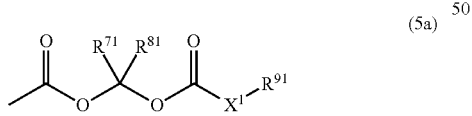

(5a)

wherein $X^1$ represents a single bond or an oxygen atom; $R^{71}$ and $R^{81}$ each independently represent
  (n11) a hydrogen atom,
  (n12) a $C_{1-4}$ alkyl group which may be optionally substituted with one to three halogen atoms, a $C_{3-6}$ cycloalkyl group which may be optionally substituted with a $C_{1-4}$ alkoxy group, a 5- or 6-membered saturated heterocyclic group or a 5- or 6-membered saturated heterocyclic oxy group,
  (n13) a $C_{3-10}$ cycloalkyl group which may be optionally substituted with one to three halogen atoms or a $C_{1-4}$ alkoxy group,
  (n14) a $C_{6-10}$ aryl group which may be optionally substituted with one to four, same or different groups selected from the group consisting of a halogen atom and a $C_{6-10}$ aryl group which may be optionally substituted with one to four, same or different groups selected from the group consisting of a halogen atom and a $C_{1-4}$ alkoxy group,
  (n15) a 5- or 6-membered saturated heterocyclic group which may be optionally substituted with one to three halogen atoms, or
  (n16) a 5- to 10-membered heteroaryl group which may be optionally substituted with one to four, same or different groups selected from the group consisting of a $C_{1-4}$ alkyl group and a $C_{1-4}$ alkoxy group; and
$R^{91}$ represents
  (n21) a $C_{1-6}$ alkyl group which may be optionally substituted with one to three halogen atoms, a hydroxy group, a $C_{1-4}$ alkoxy group, a carboxyl group, a 5- or 6-membered saturated heterocyclic group, a $C_{3-6}$ cycloalkyl group, a $C_{1-4}$ alkoxycarbonyl group, a $C_{1-4}$ alkoxycarbonylamino group, an amino group, a mono- or di-$C_{1-6}$ alkylamino group, a 4- to 7-membered cyclic amine group, one or two nitrooxy groups, an aminocarbonyl group or a 4- to 7-membered cyclic aminocarbonyl group,
  (n22) a $C_{3-10}$ cycloalkyl group which may be optionally substituted with a hydroxy group,
  (n23) a $C_{6-10}$ aryl group which may be optionally substituted with a halogen atom, a $C_{1-4}$ alkyl group, a $C_{1-4}$ alkoxy group, or a $C_{1-4}$ alkylcarbonyloxy group,
  (n24) a 5- to 10-membered heteroaryl group, or
  (n25) a 5- or 6-membered saturated heterocyclic group which may be optionally substituted with a $C_{1-4}$ alkyl group or a $C_{1-4}$ alkoxy group,
(12) a $C_{2-6}$ alkenyl group which may be optionally substituted with (a) to (n) in (11) above,
(13) a $C_{1-6}$ alkoxy group which may be optionally substituted with (a) to (n) in (11) above,
(14) a $C_{1-6}$ alkoxycarbonylamino group which may be optionally substituted with one to three halogen atoms,
(15) a $C_{1-6}$ alkylsulfonylamino group which may be optionally substituted with one to three halogen atoms,
(16) a $C_{1-6}$ alkylsulfonylaminocarbonyl group which may be optionally substituted with one to three halogen atoms,
(17) a $C_{3-10}$ cycloalkylsulfonylaminocarbonyl group which may be optionally substituted with one to three halogen atoms,
(18) a phenylsulfonylaminocarbonyl group which may be optionally substituted with one to four, same or different groups selected from the group consisting of (a) to (o) in (8) above,
(19) a 5- or 6-membered heteroarylsulfonylaminocarbonyl group which may be optionally substituted with one to four, same or different groups selected from the group consisting of (a) to (o) in (8) above,
(20) a 4- to 10-membered saturated heterocyclic sulfonylaminocarbonyl group which may be optionally substituted with one to four, same or different groups selected from the group consisting of (a) to (o) in (8) above,
(21) an aminosulfonylaminocarbonyl group, wherein the amino may be optionally substituted with one or two, same or different $C_{1-6}$ alkyl groups which may be optionally substituted with one to three halogen atoms,

(22) a 4- to 7-membered cyclic aminosulfonylaminocarbonyl group which may be optionally substituted with one to four, same or different groups selected from the group consisting of (a) to (o) in (8) above,
(23) a $C_{4-7}$ cycloalkoxycarbonyl group which may be optionally substituted with one to four, same or different groups selected from the group consisting of (a) to (o) in (8) above,
(24) a 4- to 10-membered saturated heterocyclic oxycarbonyl group which may be optionally substituted with one to four, same or different groups selected from the group consisting of (a) to (o) in (8) above,
(25) a $C_{1-6}$ alkoxycarbonyl group which may be optionally substituted with
(a) a $C_{1-6}$ alkoxy group which may be optionally substituted with one to three halogen atoms or a $C_{1-6}$ alkoxy group,
(b) a $C_{3-7}$ cycloalkoxy group which may be optionally substituted with one to three halogen atoms,
(c) a mono- or di-$C_{1-6}$ alkylamino group, wherein the alkyl may be optionally substituted with one to three halogen atoms,
(d) a 4- to 7-membered cyclic amino group which may be optionally substituted with one to three halogen atoms, a $C_{1-6}$ alkyl group or a $C_{1-6}$ alkoxy group,
(e) a mono- or di-$C_{1-6}$ alkylaminocarbonyl group wherein the alkyl may be optionally substituted with one to three halogen atoms,
(f) a 4- to 7-membered cyclic aminocarbonyl group which may be optionally substituted with one to three halogen atoms, a $C_{1-6}$ alkyl group or a $C_{1-6}$ alkoxy group,
(g) a $C_{3-7}$ cycloalkyl group which may be optionally substituted with one to three halogen atoms, or
(h) a 4- to 10-membered saturated heterocyclic group which may be optionally substituted with one to four, same or different groups selected from the group consisting of (a) to (o) in (8) above,
(26) a group represented by the following formula (4a):

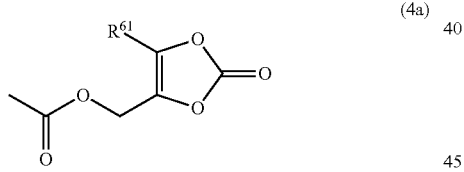

(4a)

wherein $R^{61}$ represents
(a) a hydrogen atom,
(b) a $C_{1-4}$ alkyl group which may be optionally substituted with one to three halogen atoms or a $C_{1-4}$ alkoxy group,
(c) a $C_{3-6}$ cycloalkyl group which may be optionally substituted with a $C_{1-4}$ alkoxy group, or
(d) a $C_{6-10}$ aryl group which may be optionally substituted with a $C_{1-4}$ alkoxy group, or
(27) a group represented by formula (5a):

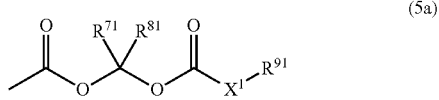

(5a)

wherein X represents a single bond or an oxygen atom; $R^{71}$ and $R^{81}$ each independently represent
(a) a hydrogen atom,
(b) a $C_{1-4}$ alkyl group which may be optionally substituted with one to three halogen atoms, a $C_{3-6}$ cycloalkyl group which may be optionally substituted with a $C_{1-4}$ alkoxy group, a 5- or 6-membered saturated heterocyclic group, or 5- or 6-membered saturated heterocyclic oxy group,
(c) a $C_{3-10}$ cycloalkyl group which may be optionally substituted with one to three halogen atoms or a $C_{1-4}$ alkoxy group,
(d) a $C_{6-10}$ aryl group which may be optionally substituted with one to four, same or different groups selected from the group consisting of a halogen atom and a $C_{6-10}$ aryl group which may be optionally substituted with one to four, same or different groups selected from the group consisting of a halogen atom and a $C_{1-4}$ alkoxy group,
(e) a 5- or 6-membered saturated heterocyclic group which may be optionally substituted with one to three halogen atoms, or
(f) a 5- to 10-membered heteroaryl group which may be optionally substituted with one to four, same or different groups selected from the group consisting of a $C_{1-4}$ alkyl group and a $C_{1-4}$ alkoxy group; and $R^{91}$ represents
(a) a $C_{1-6}$ alkyl group which may be optionally substituted with one to three halogen atoms, a hydroxyl group, a $C_{1-4}$ alkoxy group, a carboxyl group, a 5- or 6-membered saturated heterocyclic group, a $C_{3-6}$ cycloalkyl group, a $C_{1-4}$ alkoxycarbonyl group, a $C_{1-4}$ alkoxycarbonylamino group, an amino group, a mono- or di-$C_{1-6}$ alkylamino group, a 4- to 7-membered cyclic amine group, one or two nitrooxy groups, an aminocarbonyl group or a 4- to 7-membered cyclic aminocarbonyl group,
(b) a $C_{3-10}$ cycloalkyl group which may be optionally substituted with a hydroxy group,
(c) a $C_{6-10}$ aryl group which may be optionally substituted with a halogen atom, a $C_{1-4}$ alkyl group, a $C_{1-4}$ alkoxy group or a $C_{1-4}$ alkylcarbonyloxy group,
(d) a 5- to 10-membered heteroaryl group, or
(e) a 5- or 6-membered saturated heterocyclic group which may be optionally substituted with a $C_{1-4}$ alkyl group or a $C_{1-4}$ alkoxy group.

15. The compound according to claim 1, or a pharmaceutically acceptable salt thereof, wherein
$R^f$, $R^i$ and $R^k$ each independently represent
(1) a hydrogen atom,
(2) a cyano group,
(3) a carboxyl group,
(4) an aminocarbonyl group which may be optionally substituted with one or two, same or different $C_{1-6}$ alkyl groups which may be optionally substituted with one to three halogen atoms or a $C_{1-6}$ alkoxy group,
(5) a 4- to 6-membered cyclic aminocarbonyl group which may be optionally substituted with one to four, same or different groups selected from the group consisting of one to three halogen atoms, a $C_{1-6}$ alkyl group, a $C_{1-6}$ alkoxy group, a $C_{1-6}$ alkoxycarbonyl group and a $C_{1-6}$ alkoxycarbonylamino group,
(6) a tetrazolyl group,
(7) a 5-oxo-1,2,4-oxadiazol-3-yl group,
(8) a $C_{1-6}$ alkyl group which may be optionally substituted with
(a) a hydroxy group,
(b) a carboxyl group,
(c) a $C_{1-6}$ alkoxycarbonyl group, (d) a group represented by formula (4b):

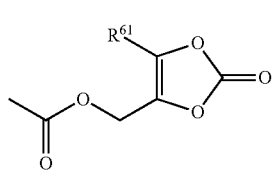

(4b)

wherein R$^{62}$ represents a hydrogen atom or a C$_{1-4}$ alkyl group, or, (e) a group represented by formula (5b):

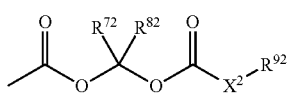

(5b)

wherein X$^2$ represents a single bond or an oxygen atom; R$^{72}$ and R$^{82}$ each independently represent a hydrogen atom or a C$_{1-4}$ alkyl group; and
R$^{92}$ represents a C$_{1-4}$ alkyl group or a C$_{4-7}$ cycloalkyl group, (9) a C$_{1-6}$ alkoxycarbonylamino group,

(10) a C$_{1-6}$ alkylsulfonylamino group,

(11) a C$_{1-6}$ alkylsulfonylaminocarbonyl group which may be optionally substituted with one to three halogen atoms,

(12) a pyridylsulfonylaminocarbonyl group,

(13) a mono- or di-C$_{1-6}$ alkylaminosulfonylaminocarbonyl group,

(14) a 4- to 7-membered cyclic aminosulfonylaminocarbonyl group,

(15) a 4- to 10-membered saturated heterocyclic oxycarbonyl group,

(16) a C$_{1-6}$ alkoxycarbonyl group which may be optionally substituted with (a) a C$_{1-6}$ alkoxy group which may be optionally substituted with a C$_{1-6}$ alkoxy group, (b) a C$_{3-7}$ cycloalkoxy group, (c) a mono- or di-C$_{1-6}$ alkylamino group, (d) a 4- to 7-membered cyclic amino group, (e) a mono- or di-C$_{1-6}$ alkylaminocarbonyl group, or (f) a 4- to 7-membered cyclic amino group, (g) a C$_{3-7}$ cycloalkyl group which may be optionally substituted with one to three halogen atoms, or (h) a 4- to 7-membered saturated heterocyclic group which may be optionally substituted with one to four, same or different groups selected from the group consisting of a halogen atom and a C$_{1-6}$ alkyl group,

(17) a group represented by formula (4b):

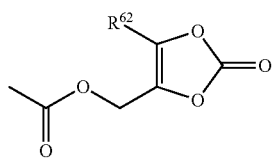

(4b)

wherein R$^{62}$ represents a hydrogen atom or a C$_{1-4}$ alkyl group, or

(18) a group represented by formula (5b):

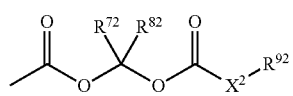

(5b)

wherein X$^2$ represents a single bond or an oxygen atom; R$^{72}$ and R$^{82}$ each independently represent a hydrogen atom or a C$_{1-4}$ alkyl group; and
R$^{92}$ represents a C$_{1-4}$ alkyl group or a C$_{4-7}$ cycloalkyl group.

16. The compound according to claim 1 or a pharmaceutically acceptable salt thereof, represented by formula (6):

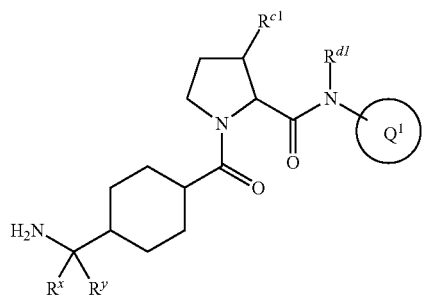

(6)

wherein

R$^x$ and R$^y$ each independently represent a hydrogen atom or an optionally substituted C$_{1-6}$ alkyl group, or these groups may together form an optionally substituted 3- to 6-membered cycloalkane ring;

R$^{c1}$ represents an optionally substituted 4- to 7-membered cycloalkyl group, an optionally substituted phenyl group, an optionally substituted pyridyl group, an optionally substituted phenoxy group, an optionally substituted 4- to 7-membered cyclic amino group or an optionally substituted C$_{1-6}$ alkoxy group;

R$^{d1}$ represents a hydrogen atom or an optionally substituted C$_{1-6}$ alkyl group; and ring Q$^1$ is a group represented by any one of formulae (7a) to (7i):

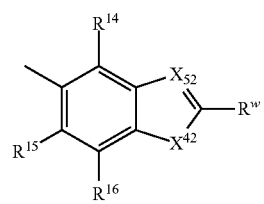

(7a)

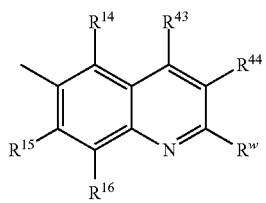

(7b)

-continued

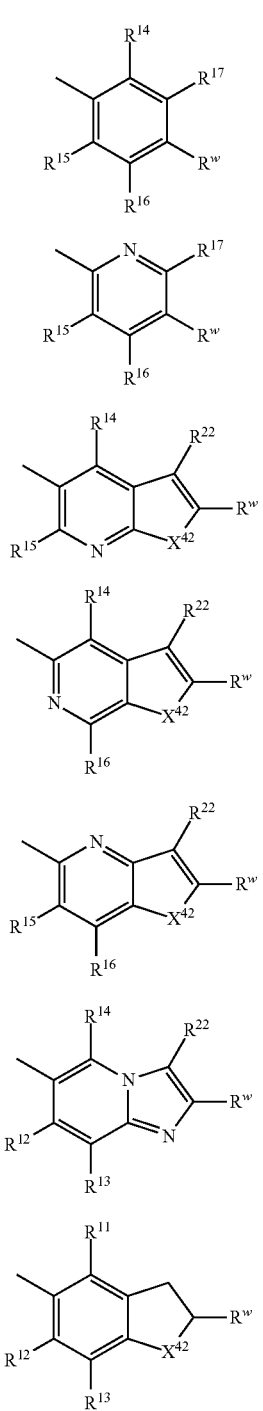

wherein X⁵² represents $CR^{22}$ or N;
X⁴² represents $NR^{32}$, O or S;
$R^{11}$, $R^{12}$, $R^{13}$, $R^{14}$, $R^{15}$, $R^{16}$, $R^{17}$, $R^{43}$ and $R^{44}$ each independently represent a hydrogen atom, a halogen atom, an optionally substituted $C_{1-6}$ alkyl group or an optionally substituted $C_{1-6}$ alkoxy group;
$R^{22}$ represents a hydrogen atom, a halogen atom, a cyano group or an optionally substituted $C_{1-6}$ alkyl group;
$R^{32}$ represents a hydrogen atom or an optionally substituted $C_{1-6}$ alkyl group;

$R^w$ represents a hydrogen atom, a carboxyl group, a cyano group, an optionally substituted aminocarbonyl group, an optionally substituted 4- to 7-membered cyclic aminocarbonyl group, a tetrazolyl group, a 5-oxo-1,2,4-oxadiazol-3-yl group, an optionally substituted $C_{1-6}$ alkylsulfonylaminocarbonyl group, an optionally substituted 5- to 10-membered heteroarylsulfonylaminocarbonyl group, an optionally substituted aminosulfonylaminocarbonyl group, an optionally substituted 4- to 7-membered cyclic aminosulfonylaminocarbonyl group, an optionally substituted 4- to 7-membered saturated heterocyclic oxycarbonyl group or an optionally substituted $C_{1-6}$ alkoxycarbonyl group.

17. The compound according to claim 16 or a pharmaceutically acceptable salt thereof, wherein
$R^x$ and $R^y$ each independently represent a hydrogen atom or a $C_{1-6}$ alkyl group which may be optionally substituted with one to three halogen atoms, or these groups may together form a 3- to 6-membered cycloalkane ring which may be optionally substituted with one to three halogen atoms;
$R^{c1}$ represents
(1) a cyclohexyl group which may be optionally substituted with one to four, same or different groups selected from the group consisting of:
(a) a halogen atom,
(b) a $C_{1-6}$ alkyl group which may be optionally substituted with one to three halogen atoms, and
(c) a $C_{1-6}$ alkoxy group which may be optionally substituted with one to three halogen atoms,
(2) a phenyl group which may be optionally substituted with one to four, same or different groups selected from the group consisting of (a) to (c) in (1) above,
(3) a pyridyl group which may be optionally substituted with one to four, same or different groups selected from the group consisting of (a) to (c) in (1) above,
(4) a 4- to 7-membered cyclic amino group which may be optionally substituted with one to four, same or different groups selected from the group consisting of (a) to (c) in (1) above, or
(5) a benzyloxy group which may be optionally substituted with one to four, same or different groups selected from the group consisting of (a) to (c) in (1) above;
$R^{d1}$ represents a hydrogen atom or a $C_{1-6}$ alkyl group;
$X^{52}$ represents $CR^{22}$;
$X^{42}$ represents $NR^{32}$, S, or O;
$R^{14}$, $R^{15}$, $R^{16}$, $R^{17}$, $R^{43}$ and $R^{44}$ each independently represent a hydrogen atom, a halogen atom, a $C_{1-6}$ alkyl group which may be optionally substituted with one to three halogen atoms, or a $C_{1-6}$ alkoxy group which may be optionally substituted with one to three halogen atoms;
$R^{22}$ represents a hydrogen atom, a halogen atom, or a $C_{1-6}$ alkyl group;
$R^{32}$ represents a hydrogen atom or a $C_{1-6}$ alkyl group which may be optionally substituted with one to three halogen atoms; and
$R^w$ represents
(1) a hydrogen atom,
(2) a carboxyl group,
(3) a cyano group,
(4) an aminocarbonyl group which may be optionally substituted with one or two, same or different $C_{1-6}$ alkyl groups which may be optionally substituted with one to three halogen atoms, (5) a 4- to 7-membered cyclic aminocarbonyl group which may be optionally substituted with one to four, same or different groups selected from the group consisting of:
(a) a halogen atom,
(b) a $C_{1-6}$ alkyl group which may be optionally substituted with one to three halogen atoms, and
(c) a $C_{1-6}$ alkoxy group which may be optionally substituted with one to three halogen atoms,
(6) a tetrazolyl group,
(7) a 5-oxo-1,2,4-oxadiazol-3-yl group,
(8) a $C_{1-6}$ alkylsulfonylaminocarbonyl group which may be optionally substituted with one to three halogen atoms,
(9) a pyridylsulfonylaminocarbonyl group,
(10) a mono- or di-$C_{1-6}$ alkylaminosulfonylaminocarbonyl group,
(11) a 4- to 7-membered cyclic aminosulfonylaminocarbonyl group,
(12) a 4- to 7-membered saturated heterocyclic oxycarbonyl group,
(13) a $C_{1-6}$ alkoxycarbonyl group which may be optionally substituted with
(a) a $C_{1-6}$ alkoxy group which may be optionally substituted with a $C_{1-6}$ alkoxy group,
(b) a $C_{3-7}$ cycloalkoxy group,
(c) a mono- or di-$C_{1-6}$ alkylamino group,
(d) a 4- to 7-membered cyclic amino group,
(e) a mono- or di-$C_{1-6}$ alkylaminocarbonyl group,
(f) a 4- to 7-membered cyclic aminocarbonyl group,
(g) a $C_{3-7}$ cycloalkyl group, or
(h) a 4- to 7-membered saturated heterocyclic group which may be optionally substituted with one to four, same or different groups selected from the group consisting of a halogen atom and a $C_{1-6}$ alkyl group,
(14) a group represented by formula (4e):

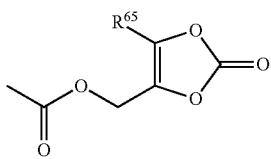

(4e)

wherein $R^{65}$ represents a hydrogen atom or a $C_{1-4}$ alkyl group, or
(15) a group represented by formula (5e):

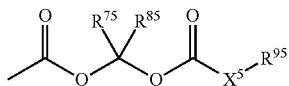

(5e)

wherein $X^5$ represents a single bond or an oxygen atom; $R^{75}$ and $R^{85}$ each independently represent a hydrogen atom or a $C_{1-4}$ alkyl group; and
$R^{95}$ represents a $C_{1-4}$ alkyl group or a $C_{4-7}$ cycloalkyl group.

18. The compound according to claim 16, or a pharmaceutically acceptable salt thereof, wherein
ring $Q^1$ is a group represented by formula (7a) or (7c).
19. The compound according to claim 18 or a pharmaceutically acceptable salt thereof, wherein ring $Q^1$ is a group represented by formula (7a); $X^{52}$ represents $CR^{22}$; $X^{42}$ represents NH or O; and $R^{14}$, $R^{15}$, $R^{16}$ and $R^{22}$ each independently represent a hydrogen atom or a halogen atom.

20. The compound according to claim 16, or a pharmaceutically acceptable salt thereof, wherein
$R^x$ and $R^y$ each independently represent a hydrogen atom or a methyl group which may be optionally substituted with one to three fluorine atoms.

21. The compound according to claim 16, or a pharmaceutically acceptable salt thereof, wherein
$R^{c1}$ represents
(1) a cyclohexyl group which may be optionally substituted with one to four, same or different groups selected from the group consisting of:
(a) a halogen atom,
(b) a $C_{1-6}$ alkyl group which may be optionally substituted with one to three halogen atoms, and
(c) a $C_{1-6}$ alkoxy group which may be optionally substituted with one to three halogen atoms,
(2) a phenyl group which may be optionally substituted with one to four, same or different groups selected from the group consisting of (a) to (c) in (1) above, or
(3) a 4- to 7-membered cyclic amino group which may be optionally substituted with one to four, same or different groups selected from the group consisting of (a) to (c) in (1) above.

22. The compound according to claim 21 or a pharmaceutically acceptable salt thereof, wherein $R^{c1}$ represents a cyclohexyl group which may be optionally substituted with one to four, same or different groups selected from the group consisting of:
(a) a halogen atom,
(b) a $C_{1-6}$ alkyl group which may be optionally substituted with one to three halogen atoms, and
(c) a $C_{1-6}$ alkoxy group which may be optionally substituted with one to three halogen atoms.

23. The compound according to claim 16, or a pharmaceutically acceptable salt thereof, wherein
$R^w$ represents
(1) a carboxyl group,
(2) a tetrazolyl group,
(3) a 5-oxo-1,2,4-oxadiazol-3-yl group,
(4) a $C_{1-6}$ alkylsulfonylaminocarbonyl group which may be optionally substituted with one to three halogen atoms,
(5) a pyridylsulfonylaminocarbonyl group,
(6) a mono- or di-$C_{1-6}$ alkylaminosulfonylaminocarbonyl group,
(7) a 4- to 7-membered cyclic aminosulfonylaminocarbonyl group,
(8) a $C_{1-6}$ alkoxycarbonyl group which may be optionally substituted with
(a) a $C_{1-6}$ alkoxy group which may be optionally substituted with a $C_{1-6}$ alkoxy group,
(b) a $C_{3-7}$ cycloalkoxy group,
(c) a mono- or di-$C_{1-6}$ alkylamino group,
(d) a 4- to 7-membered cyclic amino group,
(e) a mono- or di-$C_{1-6}$ alkylaminocarbonyl group,
(f) a 4- to 7-membered cyclic aminocarbonyl group,
(g) a $C_{3-7}$ cycloalkyl group, or
(h) a 4- to 7-membered saturated heterocyclic group which may be optionally substituted with one to four, same or different groups selected from the group consisting of a halogen atom and a $C_{1-6}$ alkyl group, (9) a group represented by formula (4e):

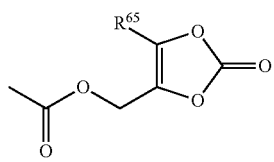

wherein R⁶⁵ represents a hydrogen atom or a $C_{1-4}$ alkyl group, or

(10) a group represented by formula (5e):

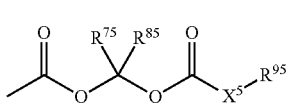

wherein $X^5$ represents a single bond or an oxygen atom; $R^{75}$ and $R^{85}$ each independently represent a hydrogen atom or a $C_{1-4}$ alkyl group; and $R^{95}$ represents a $C_{1-4}$ alkyl group or a $C_{4-7}$ cycloalkyl group.

24. The compound according to claim 16, which is represented by any one of the following formulae, or a pharmaceutically acceptable salt thereof:

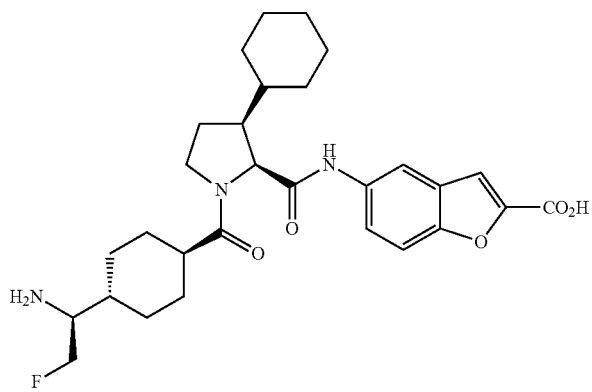

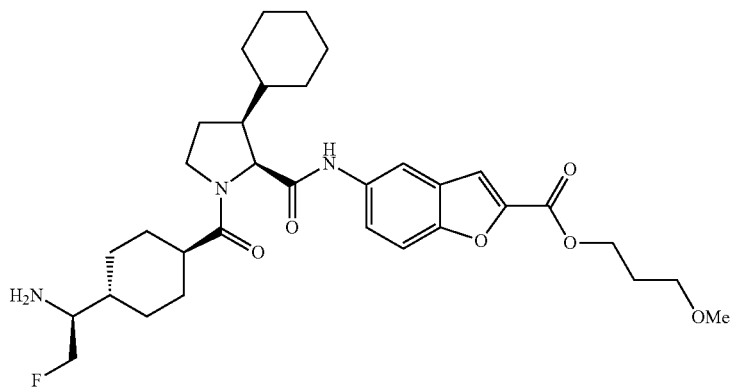

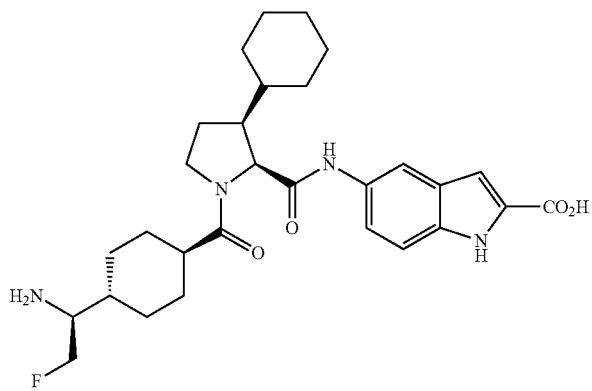

561
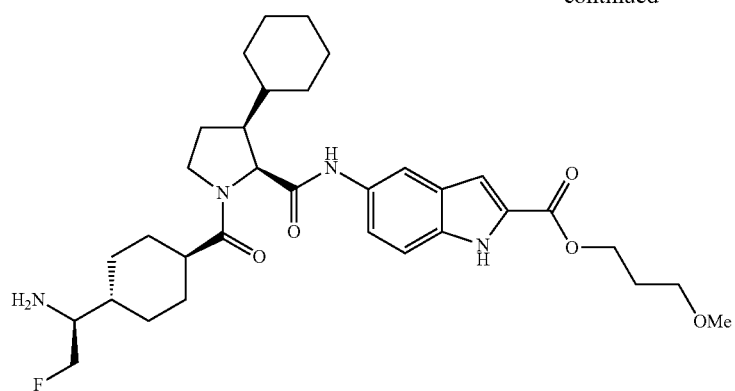
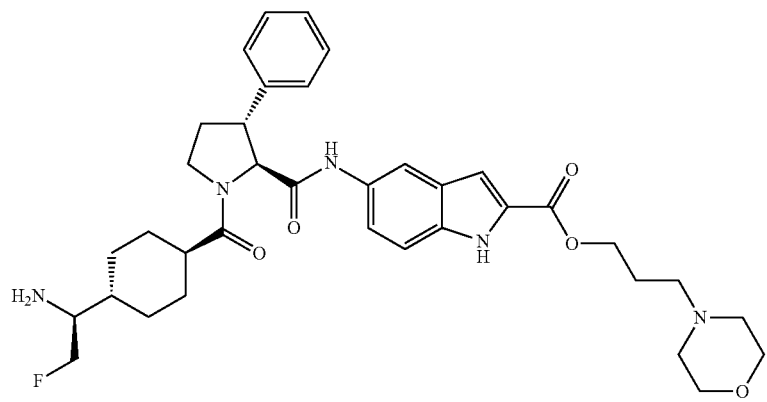
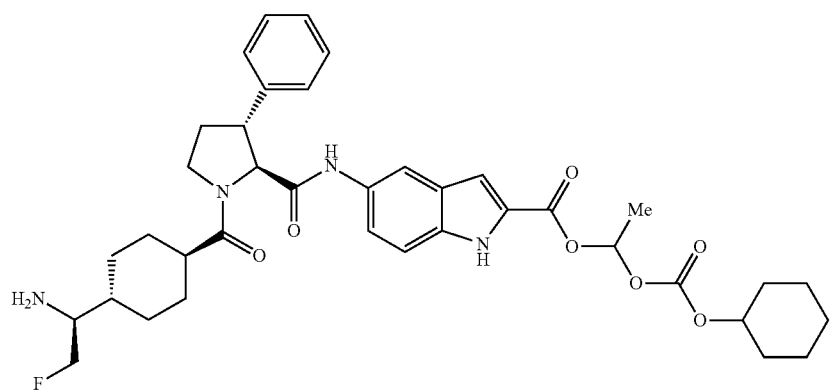
562
-continued
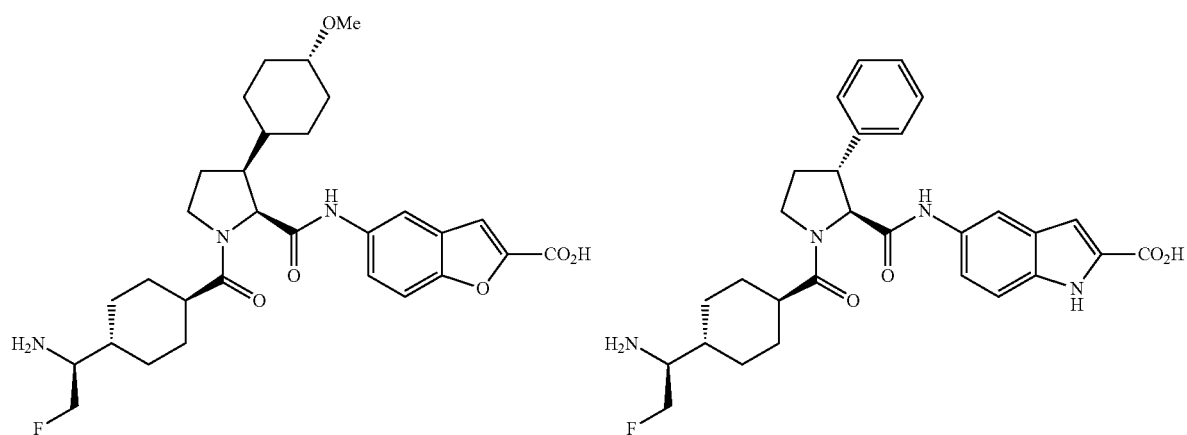

563
564
-continued
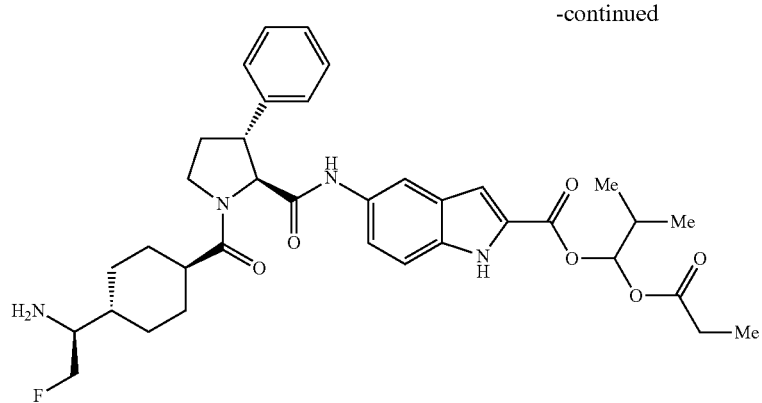
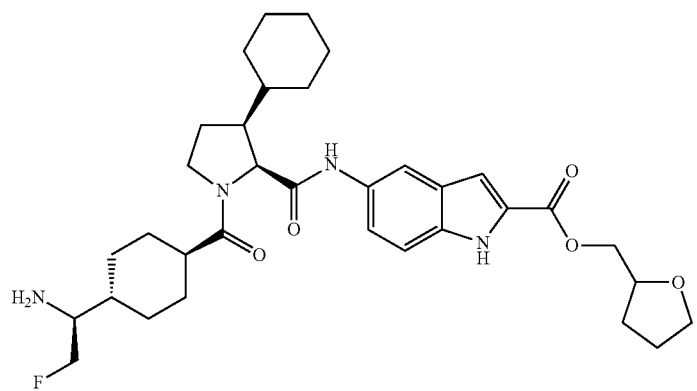
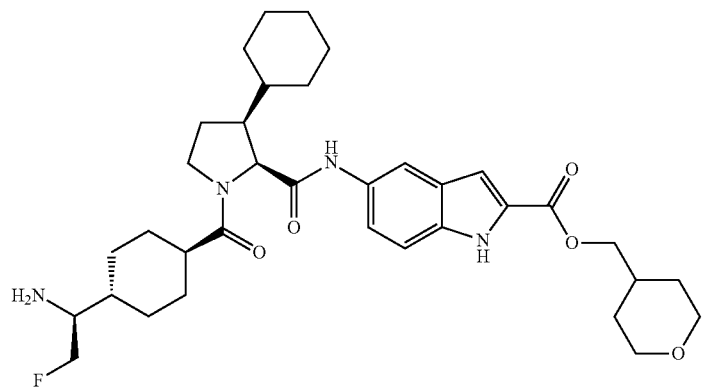
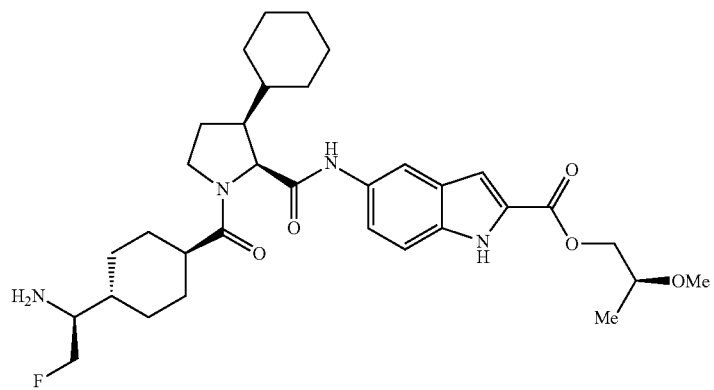

565
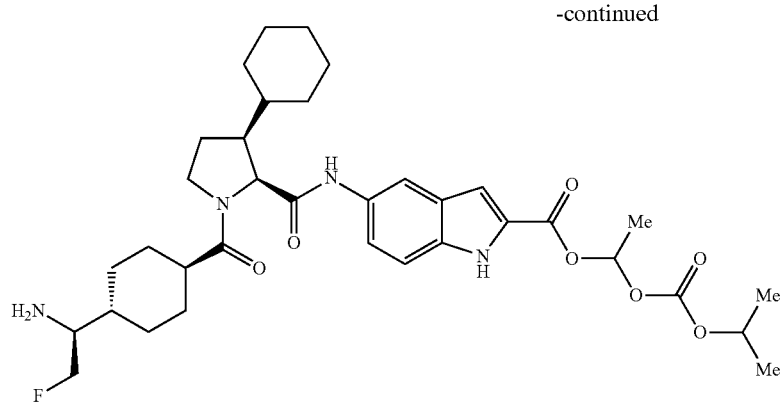
566
-continued
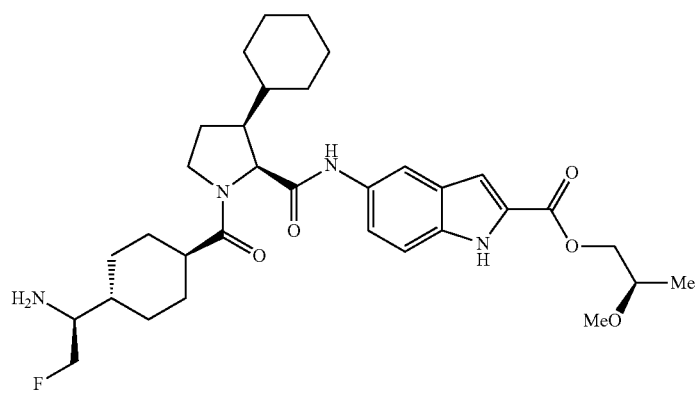
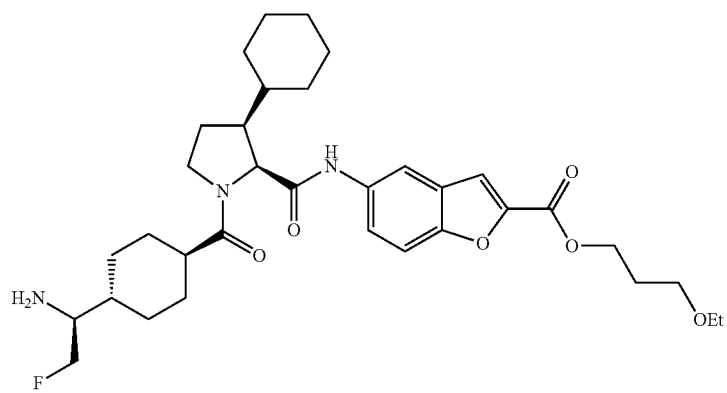
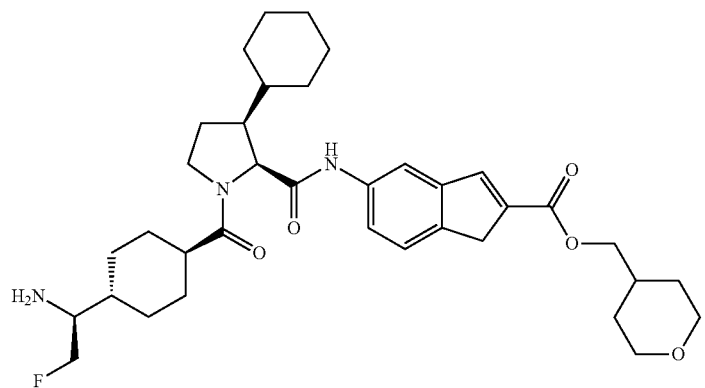

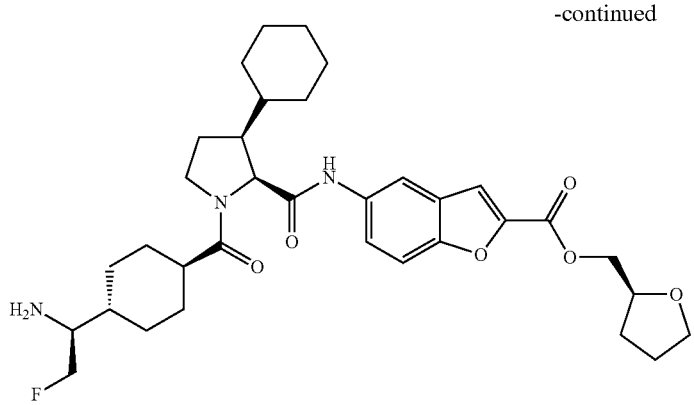
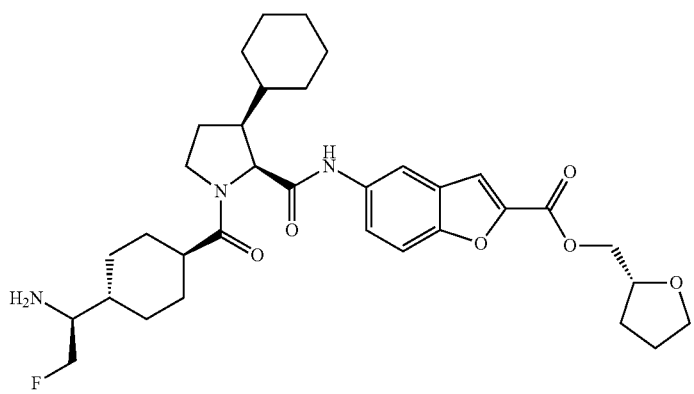
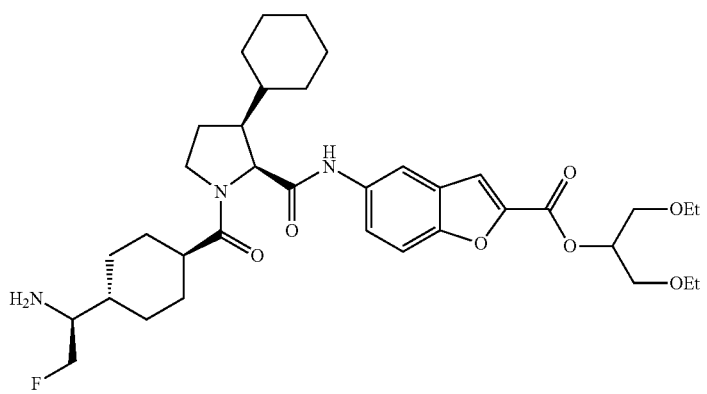
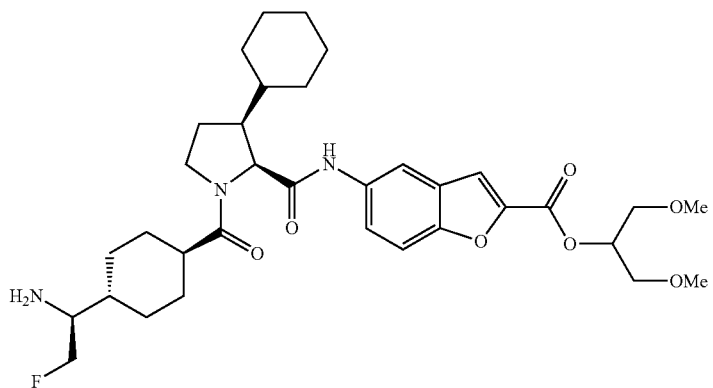

-continued
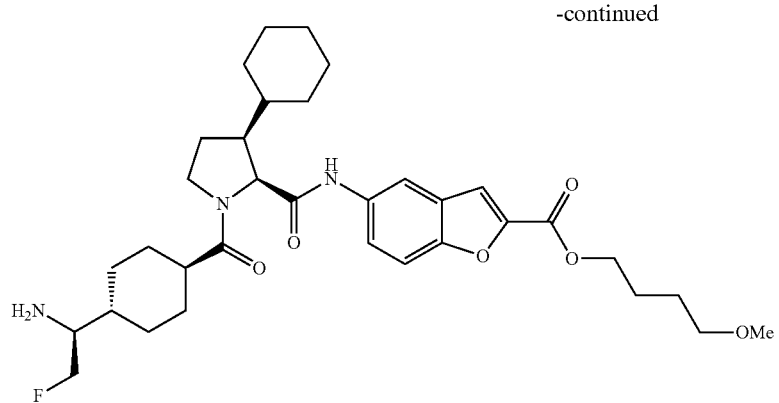
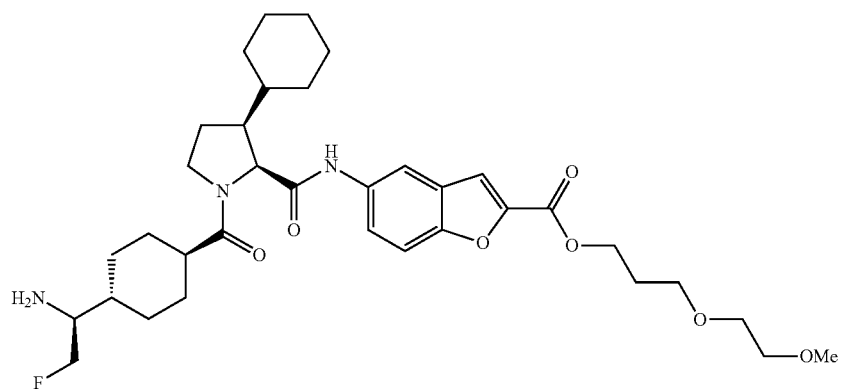
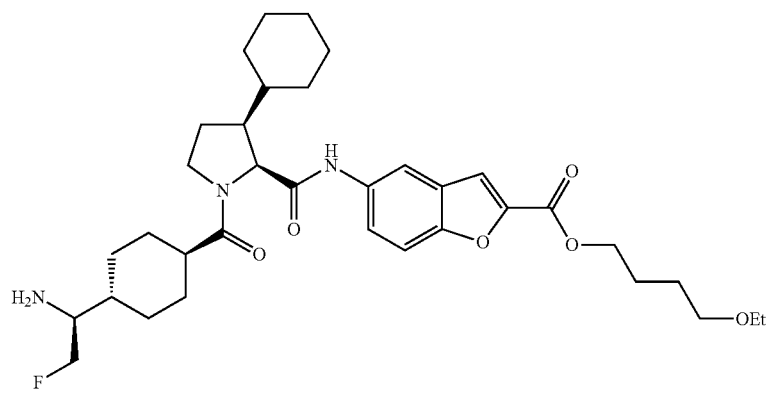
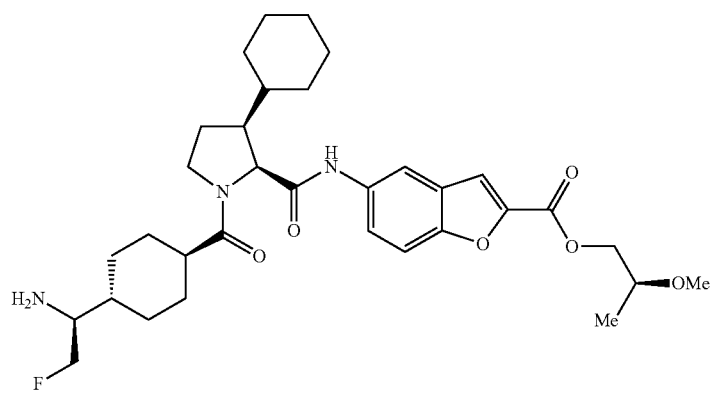

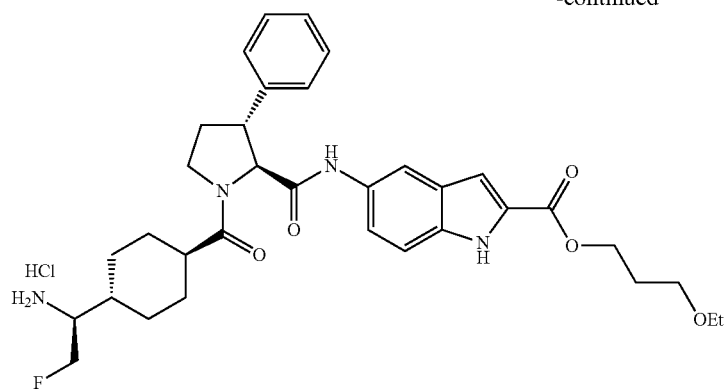
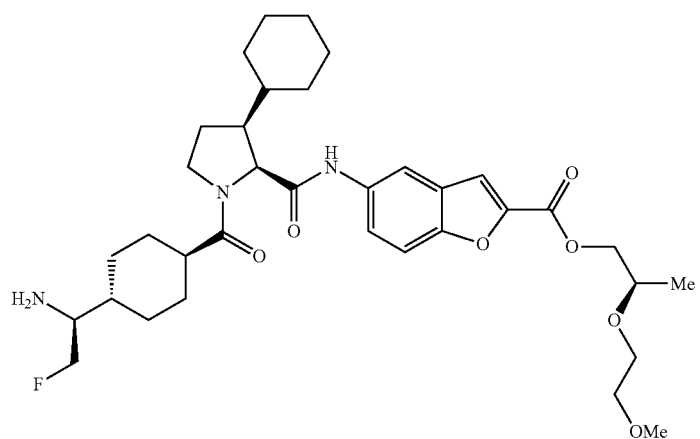
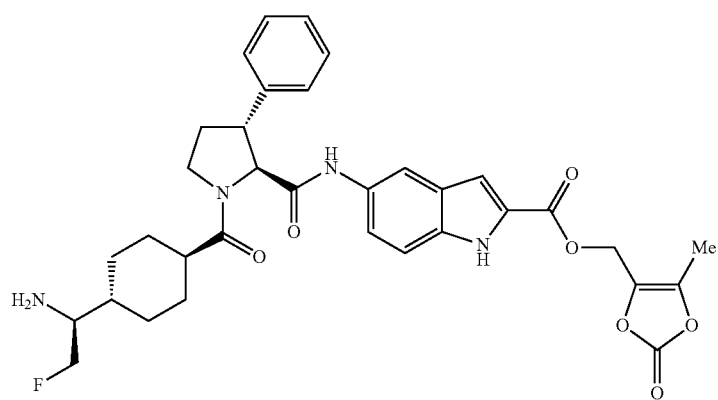
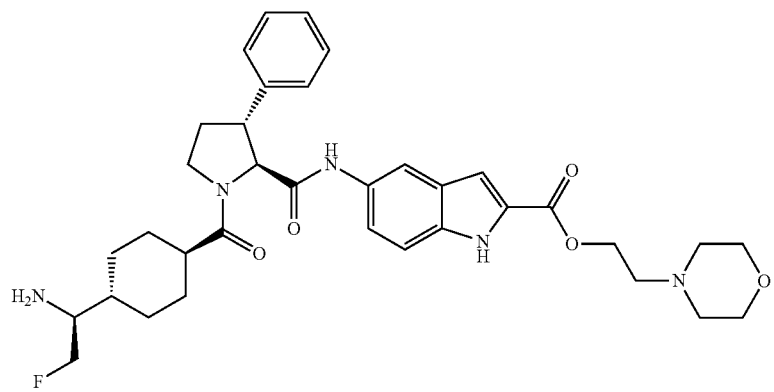

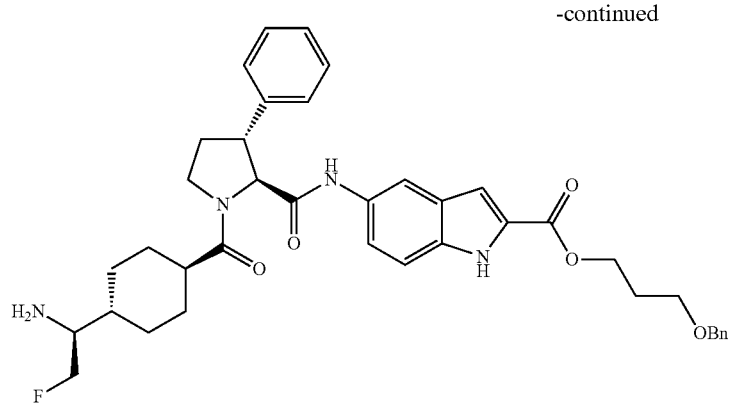
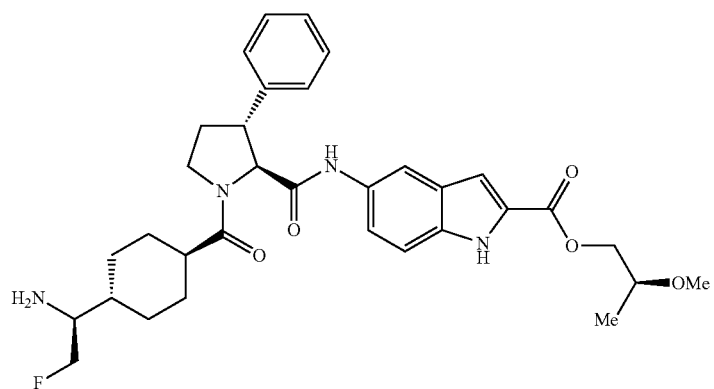
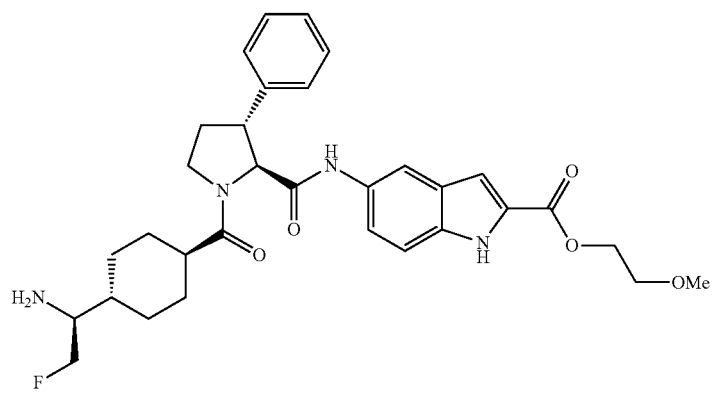
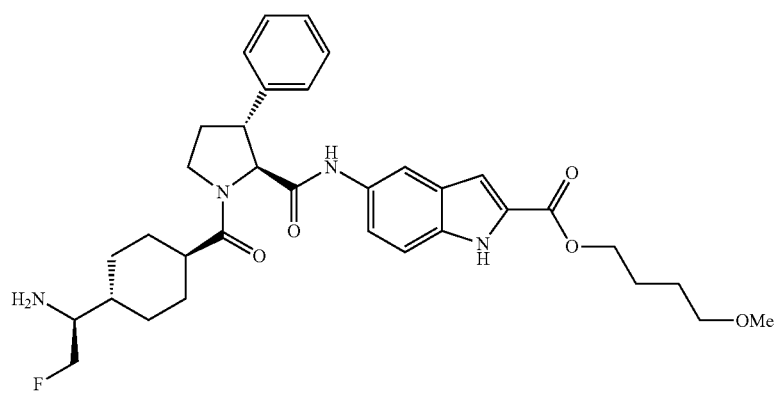

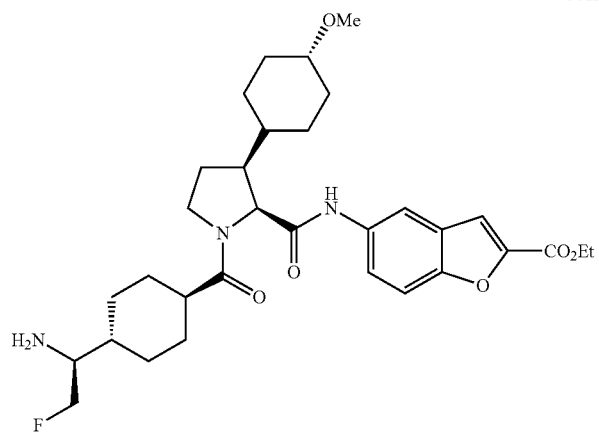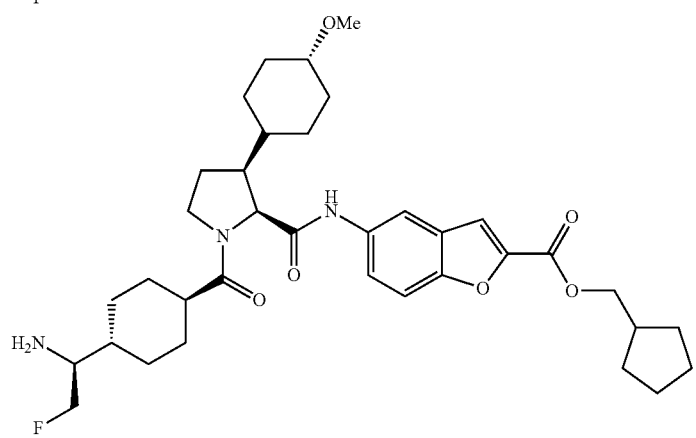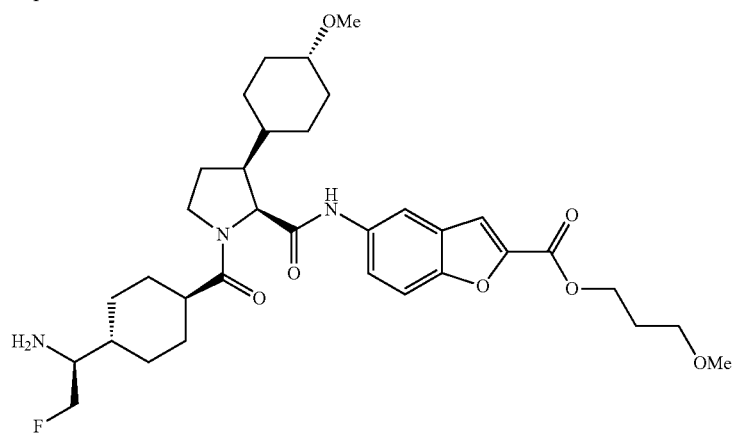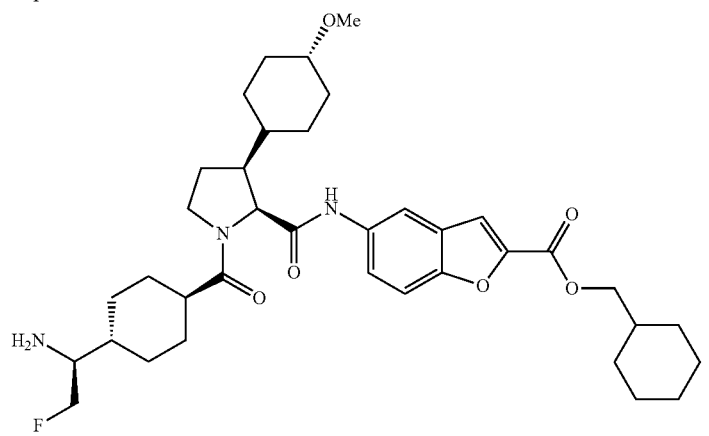

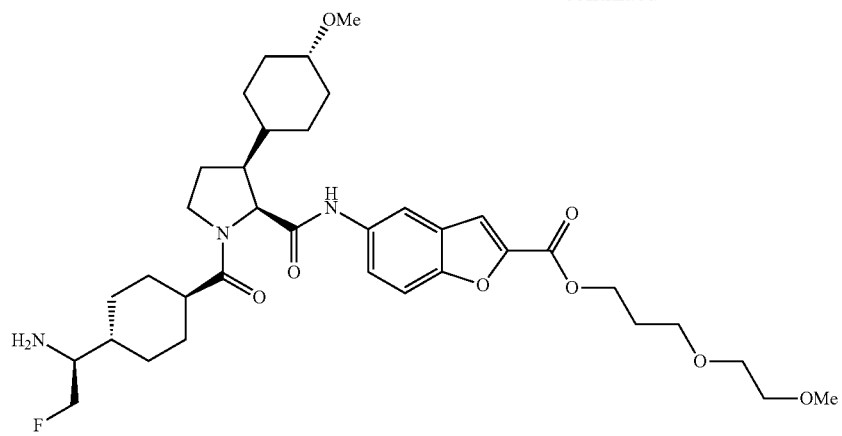
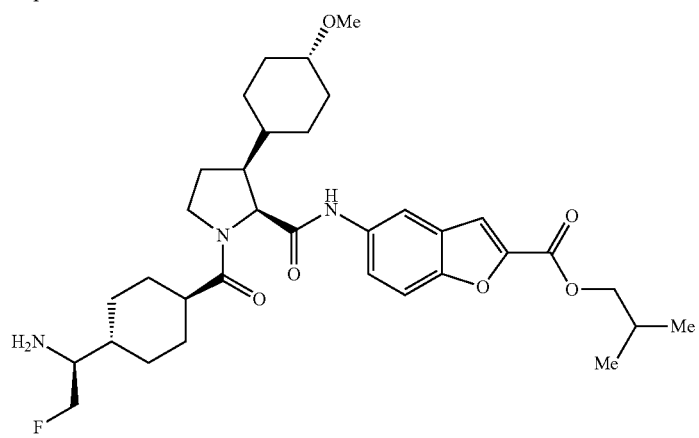
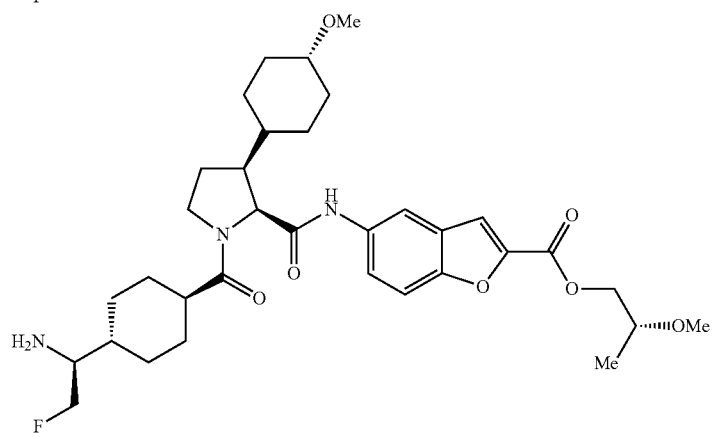
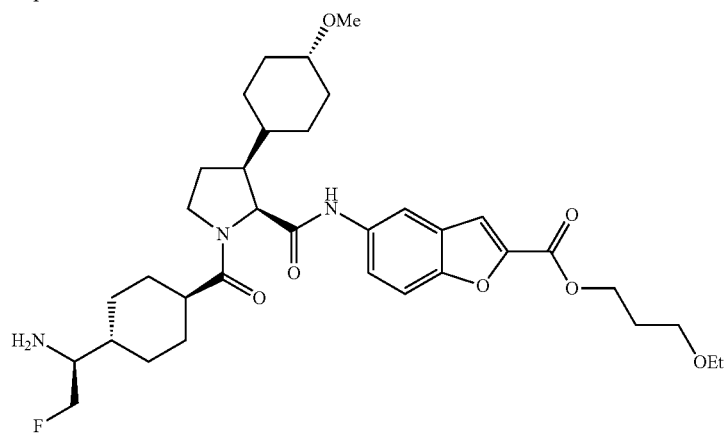

-continued
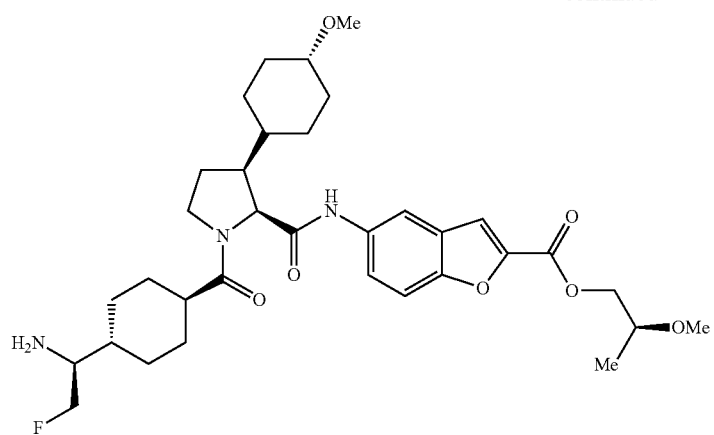
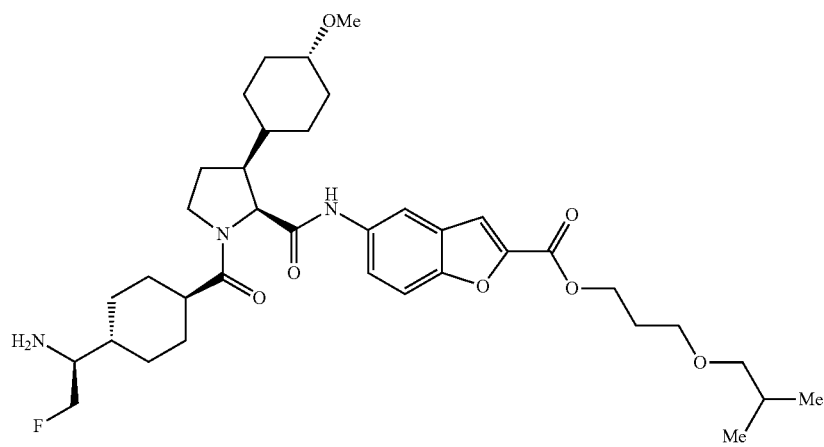
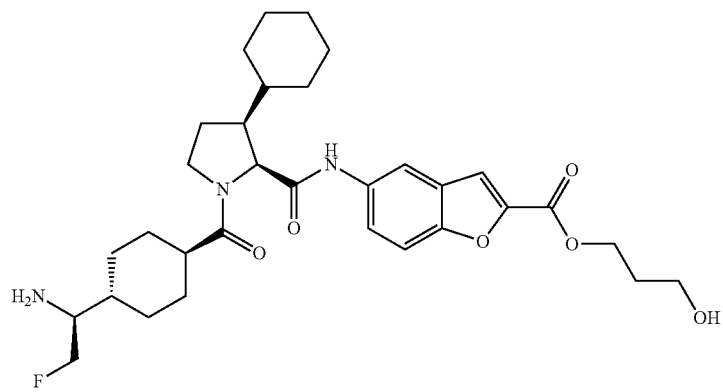
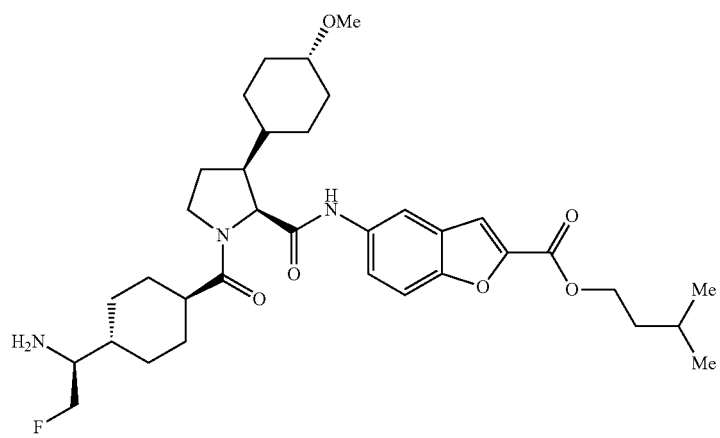

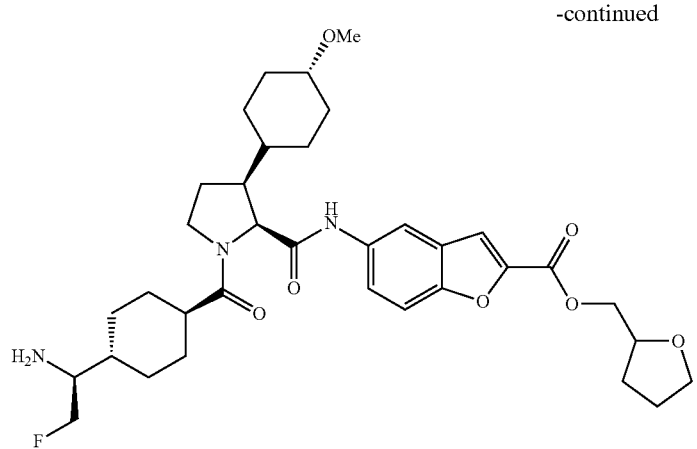
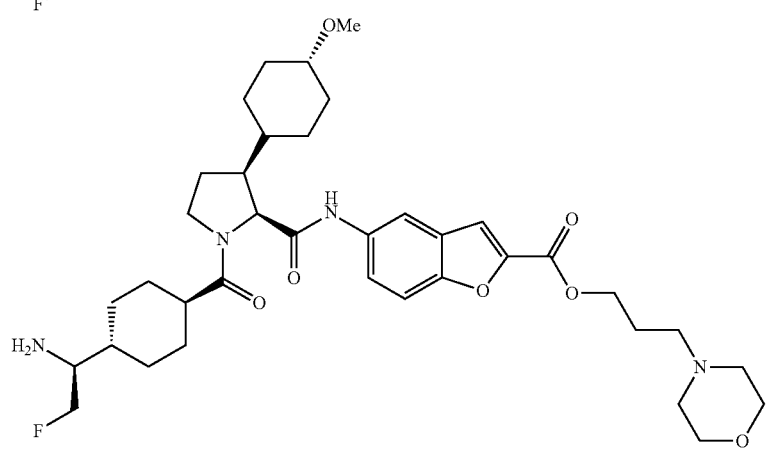
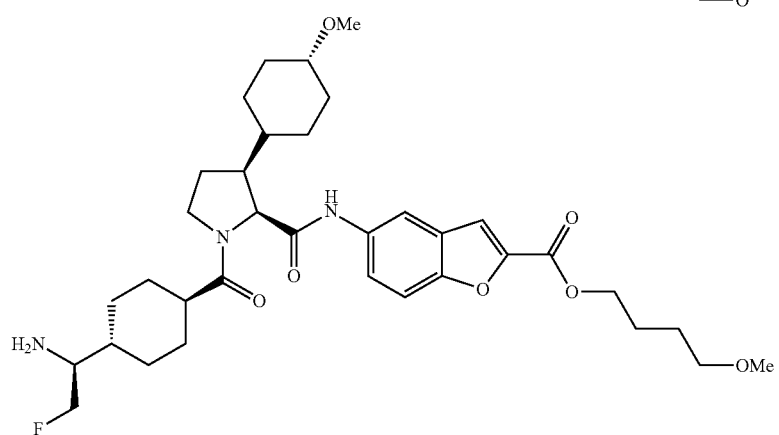
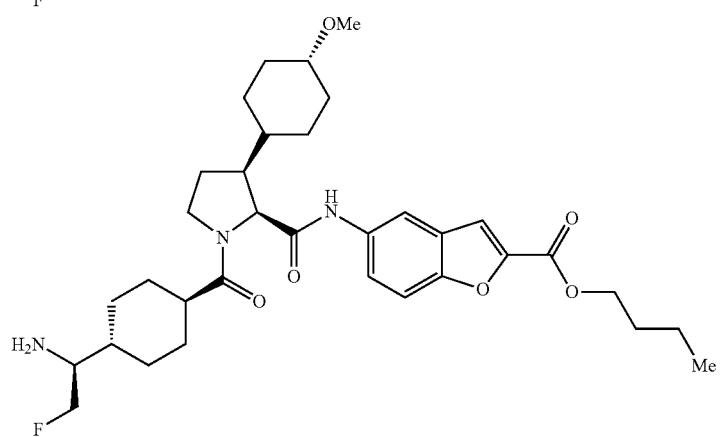

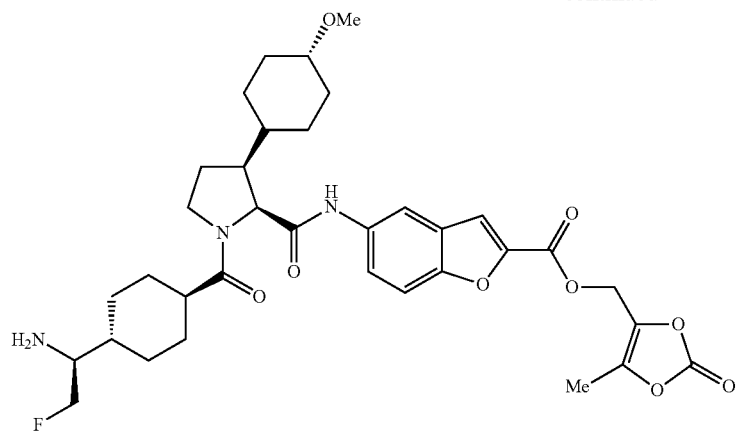
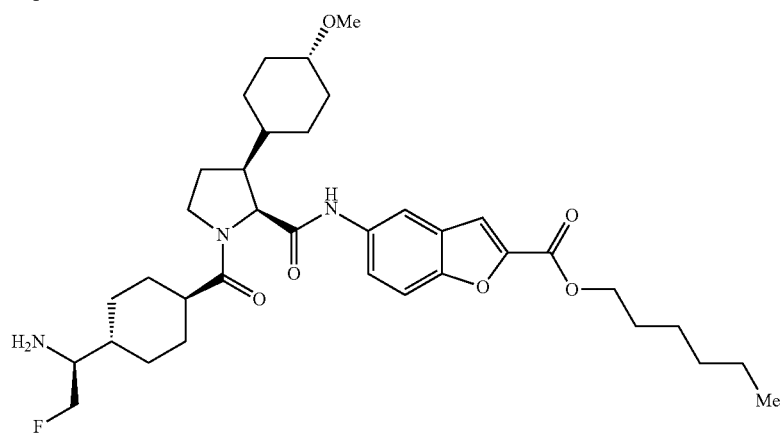
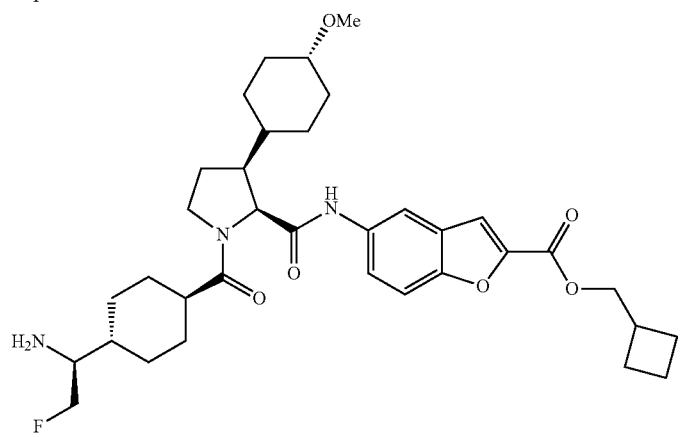
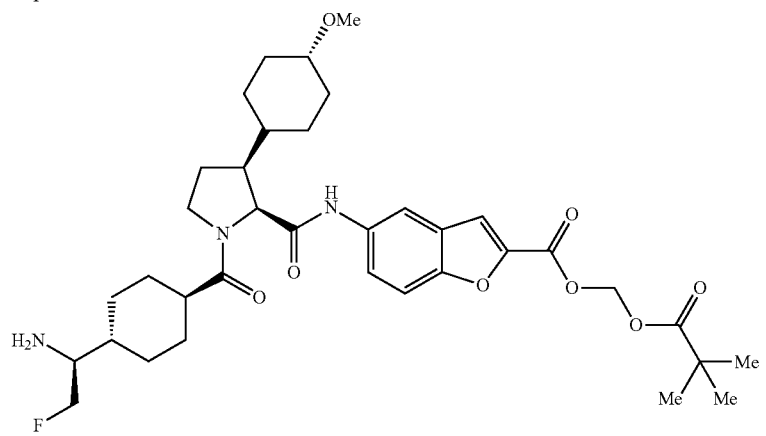

-continued
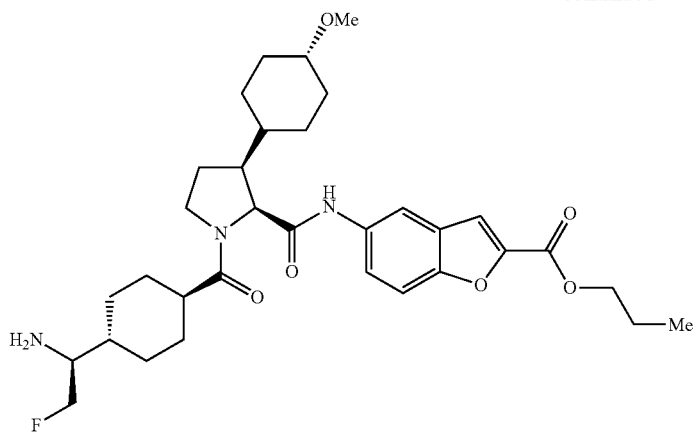
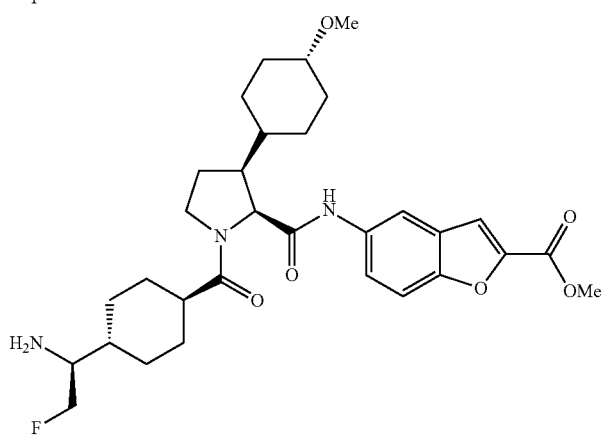
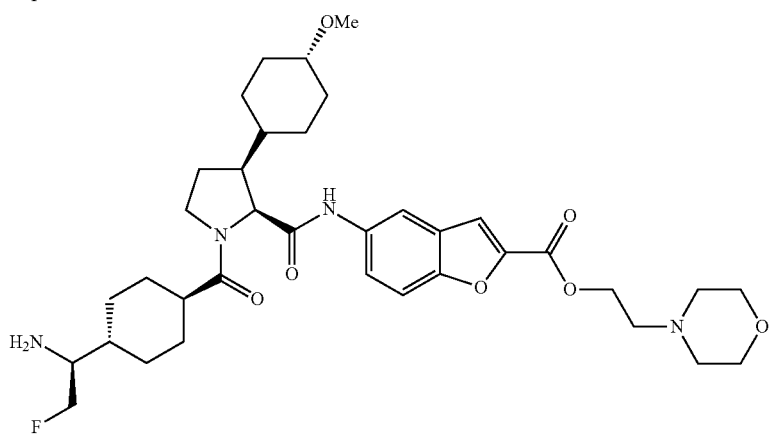
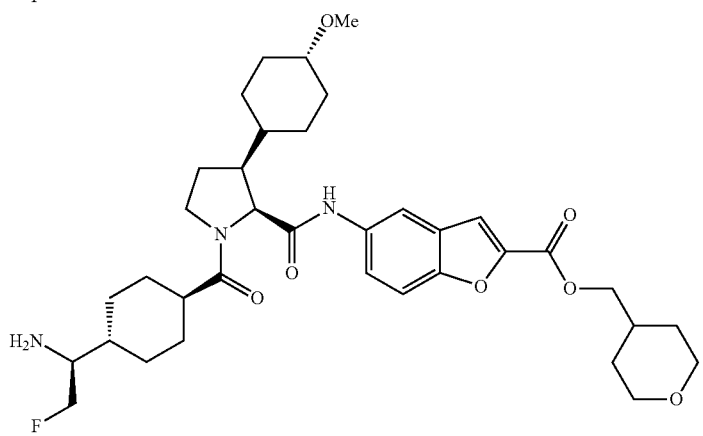

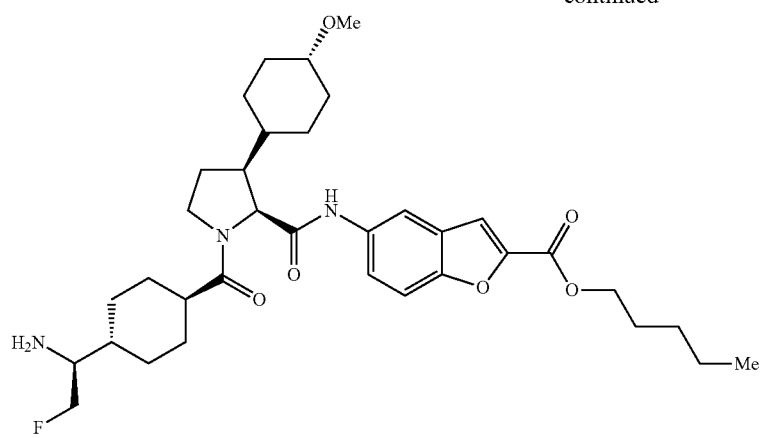
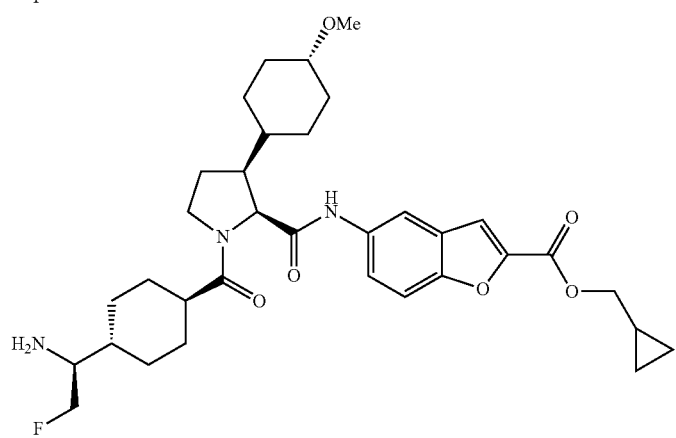
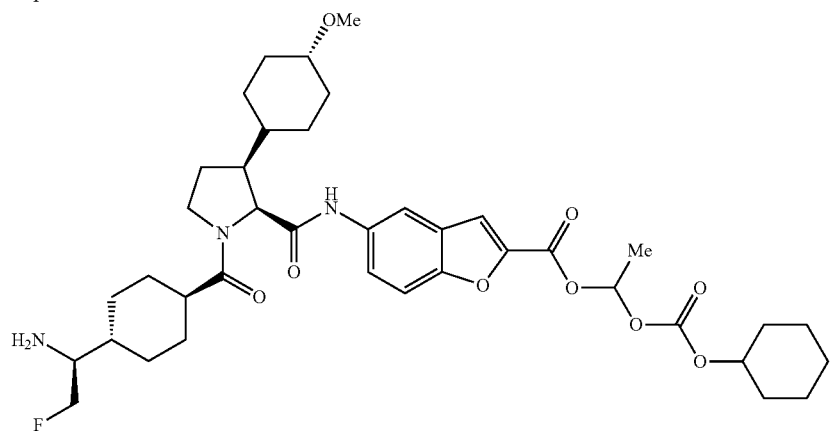
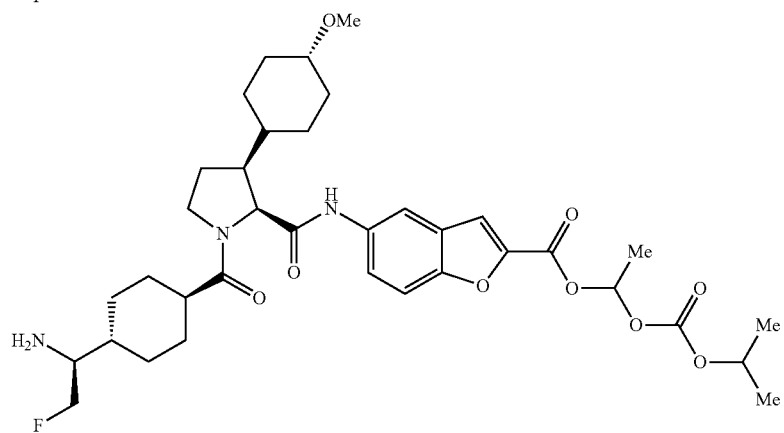

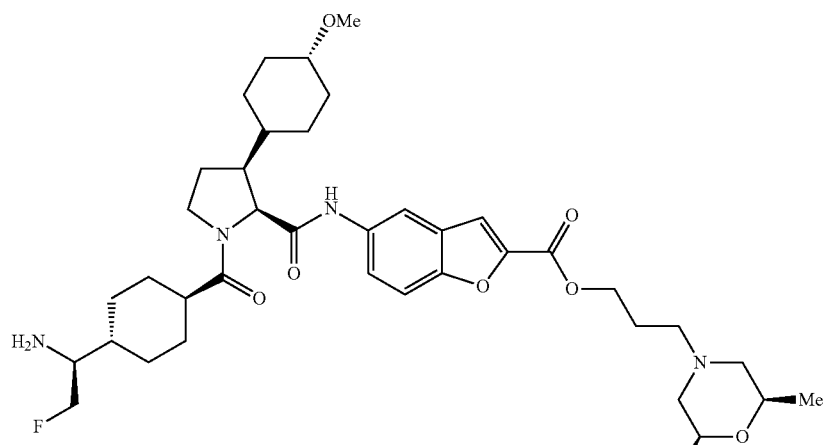
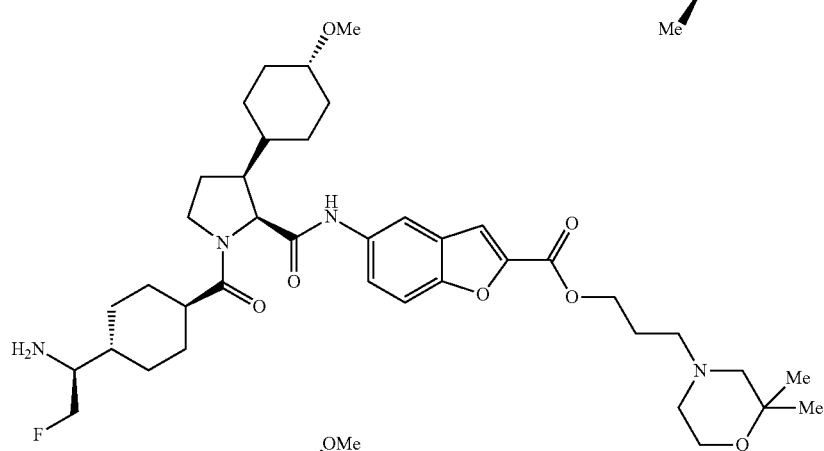
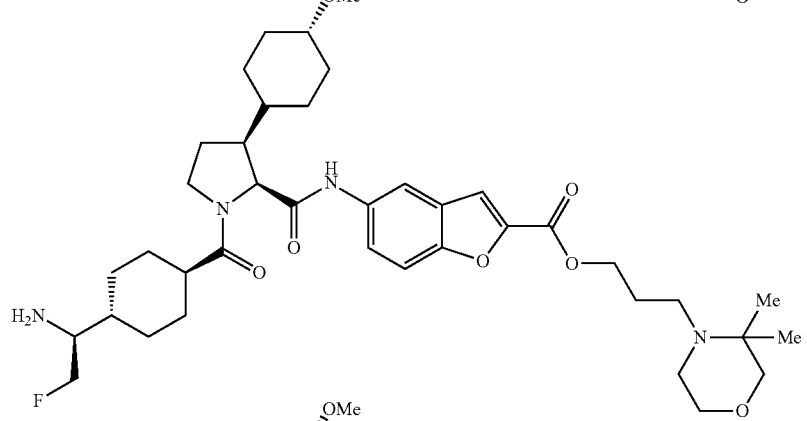
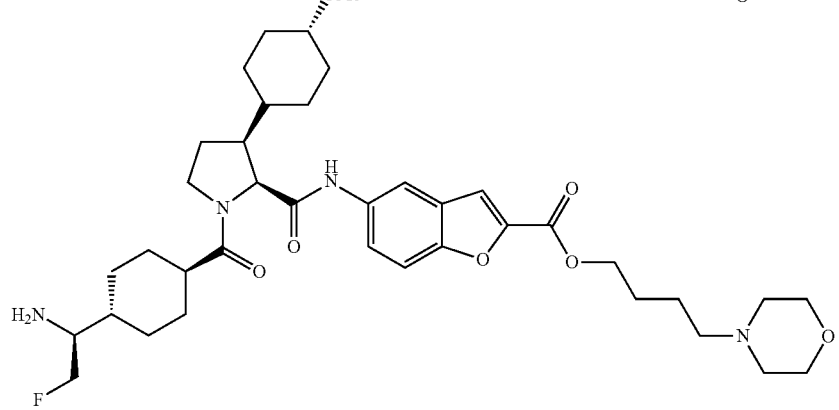

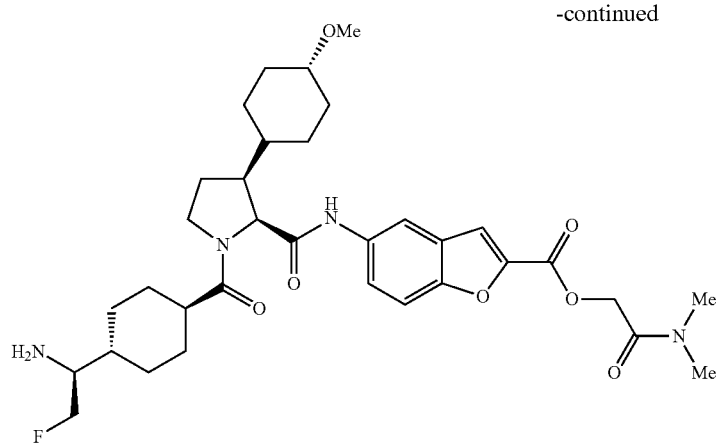
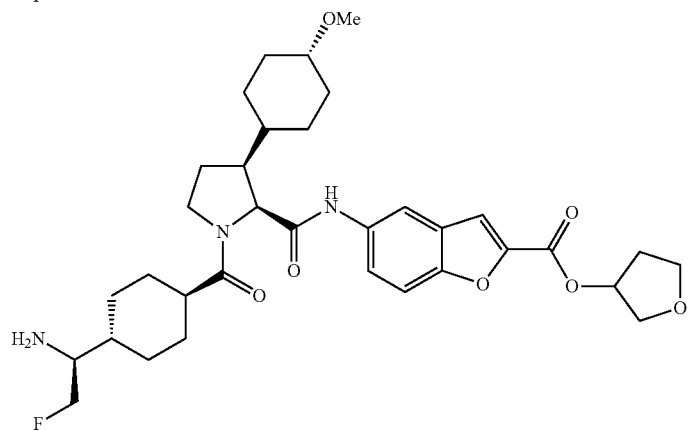
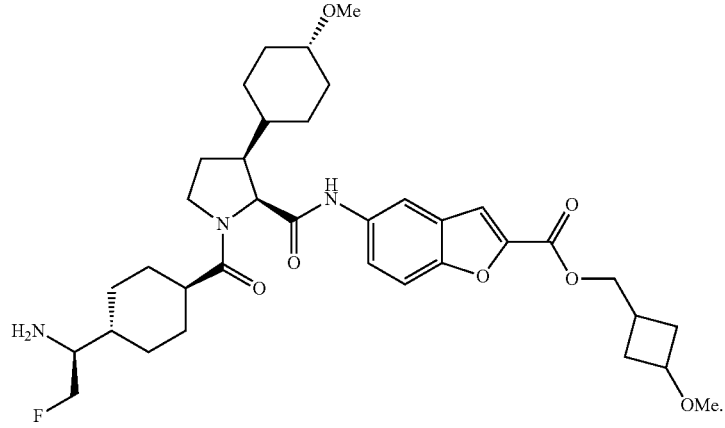

25. A medicament comprising, as an active ingredient, the compound according to claim 1 or a pharmaceutically acceptable salt thereof.

26. An FXIa inhibitor comprising, as an active ingredient, the compound according to claim 1 or a pharmaceutically acceptable salt thereof.

27. An anticoagulant agent comprising, as an active ingredient, the compound according to claim 1 or a pharmaceutically acceptable salt thereof.

28. A therapeutic agent for thrombosis comprising, as an active ingredient, the compound according to claim 1 or a pharmaceutically acceptable salt thereof.

29. A therapeutic agent for thromboembolism comprising, as an active ingredient, the compound according to claim 1 or a pharmaceutically acceptable salt thereof.

30. A method for inhibiting FXIa, which comprises administering the compound according to claim 1 or a pharmaceutically acceptable salt thereof to a subject in need thereof.

31. A method for suppressing blood coagulation, which comprises administering the compound according to claim 1 or a pharmaceutically acceptable salt thereof to a subject in need thereof.

32. A method for treating thrombosis, which comprises administering the compound according to claim 1 or a pharmaceutically acceptable salt thereof to a subject in need thereof.

33. A method for treating thromboembolism, which comprises administering the compound according to claim 1 or a pharmaceutically acceptable salt thereof to a subject in need thereof.

34. The compound according to claim 23, or a pharmaceutically acceptable salt thereof, wherein $R^w$ represents a carboxyl group.

35. The compound represented by the following formula, or a pharmaceutically acceptable salt thereof,

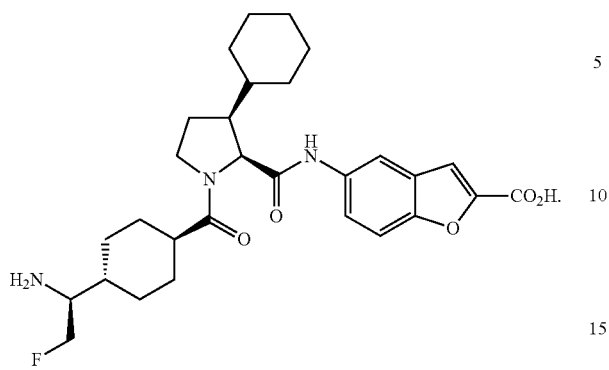

36. The compound represented by the following formula, or a pharmaceutically acceptable salt thereof,

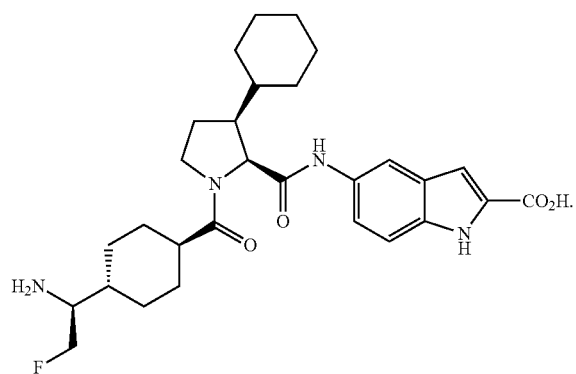 [SMILES: N[C@H](CF)[C@H]1CC[C@H](C(=O)N2CC[C@@H](C3CCCCC3)[C@H]2C(=O)Nc2ccc3[nH]c(C(=O)O)cc3c2)CC1]

37. The compound represented by the following formula, or a pharmaceutically acceptable salt thereof,

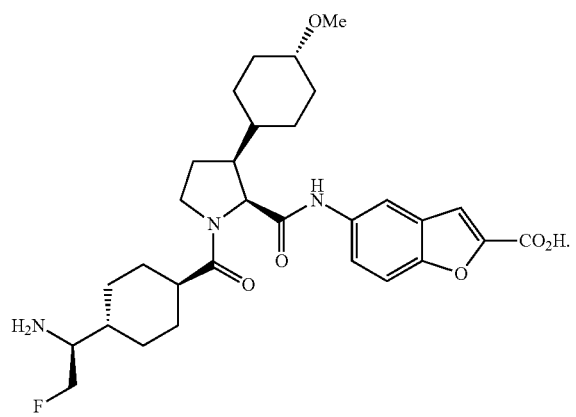

38. The compound represented by the following formula, or a pharmaceutically acceptable salt thereof,

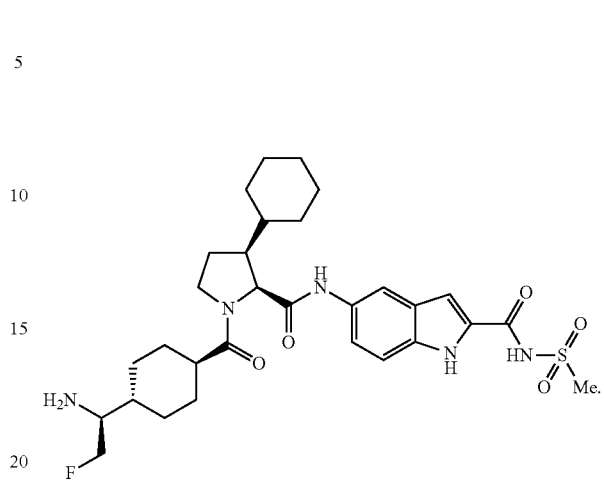

39. The compound represented by the following formula, or a pharmaceutically acceptable salt thereof,

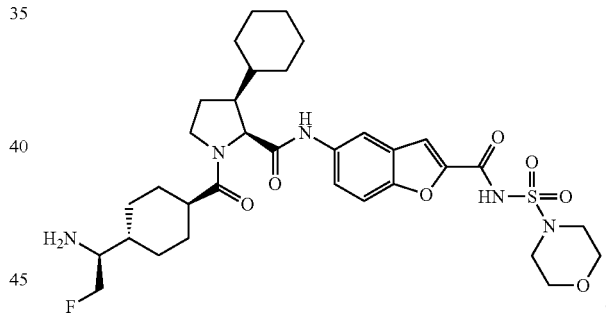

* * * * *

UNITED STATES PATENT AND TRADEMARK OFFICE
CERTIFICATE OF CORRECTION

PATENT NO.         : 9,758,480 B2
APPLICATION NO.    : 14/414838
DATED              : September 12, 2017
INVENTOR(S)        : Yohei Ikuma et al.

It is certified that error appears in the above-identified patent and that said Letters Patent is hereby corrected as shown below:

Column 49, first formula should appear as follows:

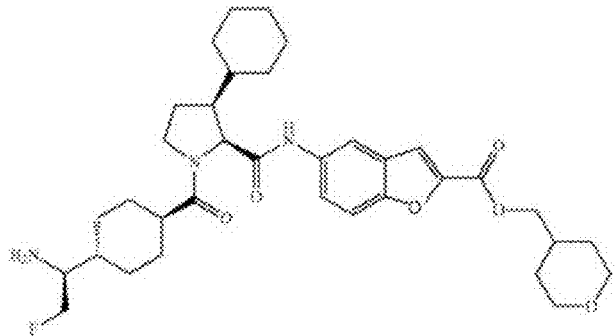

Column 492, first formula (Example 141) should appear as follows:

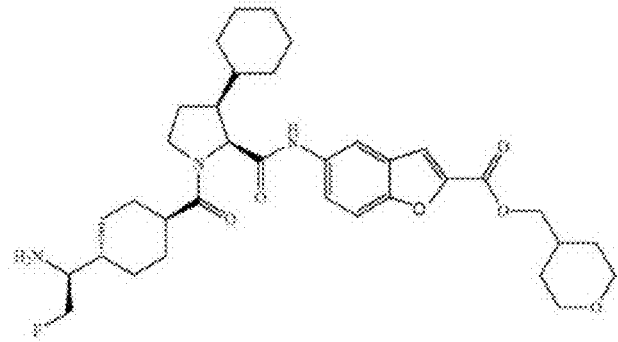

Column 542, Line 6, delete "K"

Signed and Sealed this
Second Day of January, 2018

Joseph Matal
*Performing the Functions and Duties of the
Under Secretary of Commerce for Intellectual Property and
Director of the United States Patent and Trademark Office*

CERTIFICATE OF CORRECTION (continued)

U.S. Pat. No. 9,758,480 B2

Column 565, last formula should appear as follows: